(12) United States Patent
Malik et al.

(10) Patent No.: US 12,305,179 B2
(45) Date of Patent: May 20, 2025

(54) TRANSGENIC LAND PLANTS THAT EXPRESS A POLYHYDROXYALKANOATE SYNTHASE SEED SPECIFICALLY WITH CYTOSOLIC LOCALIZATION

(71) Applicant: NUSEED NUTRITIONAL US INC., West Sacramento, CA (US)

(72) Inventors: Meghna Malik, Saskatoon (CA); Nii Patterson, Saskatoon (CA); Jihong Tang, West Roxbury, MA (US); Matthew Martino, Cortland, NY (US); Nirmala Sharma, Saskatoon (CA); Oliver P. Peoples, Arlington, MA (US); Kristi D. Snell, Belmont, MA (US); Frank Anthony Skraly, Woburn, MA (US)

(73) Assignee: NUSEED NUTRITIONAL US INC., West Sacramento, CA (US)

( * ) Notice: Subject to any disclaimer, the term of this patent is extended or adjusted under 35 U.S.C. 154(b) by 339 days.

(21) Appl. No.: 17/596,110

(22) PCT Filed: Jun. 9, 2020

(86) PCT No.: PCT/US2020/036786
§ 371 (c)(1),
(2) Date: Dec. 3, 2021

(87) PCT Pub. No.: WO2020/251932
PCT Pub. Date: Dec. 17, 2020

(65) Prior Publication Data
US 2022/0235365 A1 Jul. 28, 2022

Related U.S. Application Data

(60) Provisional application No. 62/859,244, filed on Jun. 10, 2019.

(51) Int. Cl.
*C12N 15/82* (2006.01)
*C12N 9/10* (2006.01)

(52) U.S. Cl.
CPC ....... *C12N 15/8243* (2013.01); *C12N 9/1029* (2013.01); *C12N 15/8234* (2013.01); *C12N 15/8257* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 5,849,894 A | 12/1998 | Clemente et al. | |
| 6,011,144 A | 1/2000 | Steinbüechel et al. | |
| 6,316,262 B1 | 11/2001 | Huisman et al. | |
| 6,835,820 B2 | 12/2004 | Cannon et al. | |
| 9,096,861 B2 | 8/2015 | Bohmert-Tatarev et al. | |
| 9,181,559 B2 | 11/2015 | Patterson et al. | |
| 2003/0017576 A1* | 1/2003 | Aquin | C12N 9/1029 800/278 |
| 2007/0214517 A1 | 9/2007 | Alexandrov et al. | |
| 2012/0159672 A1* | 6/2012 | Alexandrov | C07K 14/415 536/23.6 |
| 2012/0180162 A1 | 7/2012 | Patterson et al. | |

FOREIGN PATENT DOCUMENTS

| | | |
|---|---|---|
| JP | 2010286513 A | 12/2010 |
| WO | 9219747 A1 | 11/1992 |
| WO | 2010102217 A1 | 9/2010 |
| WO | 2011034946 A9 | 5/2011 |
| WO | 2014058655 A1 | 4/2014 |

OTHER PUBLICATIONS

Gou, Mingyue, et al. "Cytochrome b 5 is an obligate electron shuttle protein for syringyl lignin biosynthesis in *Arabidopsis*." The Plant Cell 31.6 (2019): 1344-1366. (Year: 2019).*
Barbante, Alessandra, et al. "Anchorage to the cytosolic face of the endoplasmic reticulum membrane: a new strategy to stabilize a cytosolic recombinant antigen in plants." Plant biotechnology journal 6.6 (2008): 560-575. (Year: 2008).*
Pieper et al., "Identification, cloning and sequence analysis of the poly(3-hydroxyalkanoic acid) synthase gene of the Gram-positive bacterium *Rhodococcus ruber*", FEMS Microbiology Letters, vol. 96, pp. 73-79 (1992).
Poirier et al., "Polyhydroxybutyrate, a Biodegradable Thermoplastic, Produced in Transgenic Plants", Science, vol. 256, pp. 520-523 (1992).
Poirier et al., "Production of Polyhydroxyalkanoates, a Family of Biodegradable Plastics and Elastomers, in Bacteria and Plants", Bio/Technology, vol. 13, pp. 142-150 (1995).
Rapoport, "Protein translocation across the eukaryotic endoplasmic reticulum and bacterial plasma membranes" Nature, vol. 450, pp. 663-669, Nov. 29, 2007.
Rowley, et al., "The upstream domain of soybean oleosin genes contains regulatory elements similar to those of legume storage proteins", Biochimica et Biophysica Acta, vol. 1345, pp. 1-4 (1997).

(Continued)

*Primary Examiner* — Charles Logsdon
*Assistant Examiner* — Kelsey L McWilliams
(74) *Attorney, Agent, or Firm* — EVENTIDE LAW LLC

(57) ABSTRACT

A transgenic land plant that expresses a polyhydroxy alkanoate synthase seed specifically, with cytosolic localization is disclosed. The plant includes a nucleic acid encoding the polyhydroxy alkanoate synthase and a seed-specific promoter operably linked to the nucleic acid. The seed-specific promoter drives expression of the polyhydroxy alkanoate synthase in cytosol of cells of seeds of the plant. The polyhydroxy alkanoate synthase includes a catalytic domain. The polyhydroxy alkanoate synthase does not include any sequence positioned to mediate translocation of the catalytic domain across any membrane of the cells, thereby resulting in the polyhydroxy alkanoate synthase being expressed seed specifically, with cytosolic localization.

22 Claims, 29 Drawing Sheets
Specification includes a Sequence Listing.

(56) References Cited

OTHER PUBLICATIONS

Schirmer et al., "Degradation of Poly(3-Hydroxyoctanoic Acid) [P(3HO)] by Bacteria: Purification and Properties of a P(3HO) Depolymerase from Pseudomonas fluorescens GK13", Applied and Environmental Microbiology, vol. 59, No. 4, pp. 1220-1227 (1993).
Slater et al., "Multiple B-Ketothiolases Mediate Poly(b-Hydroxyalkanoate) Copolymer Synthesis in Ralstonia eutropha", Journal of Bacteriology, vol. 180, No. 8, pp. 1979-1987 (1998).
Snell et al., "Polyhydroxyalkanoate Polymers and Their Production in Transgenic Plants", Metabolic Engineering, vol. 4, pp. 29-40 (2002).
Snell et al., "PHA bioplastic: A value-added coproduct for biomass biorefineries", Biofuels, Bioproducts & Biorefining, vol. 3, pp. 456-467 (2009).
Snell et al., "Production of novel biopolymers in plants: recent technological advances and future prospects", Current Opinion in Biotechnology, vol. 32, pp. 68-75 (2015).
Someleva et al., "PHA Bioplastics, Biochemicals, and Energy from Crops", Plant Biotechnology Journal, vol. 11, pp. 233-252 (2013).
Song et al., "Overexpression of AtHsp90.2, AtHsp90.5 and AtHsp90.7 in *Arabidopsis thaliana* enhances plant sensitivity to salt and drought stresses", Planta, vol. 229, pp. 955-964 (2009).
Suriyamongkol et al., "Biotechnological approaches for the production of polyhydroxyalkanoates in microorganisms and plants—A review", Biotechnology Advances, vol. 25, pp. 148-175 (2007).
Suzuki et al., "Enzyme Inhibitors to Increase Poly-hyroxybutyrate Production by Transgenic Tobacco", Biosci. Biotechnol. Biochem., vol. 66, No. 12, pp. 2537-2542 (2002).
Taroncher-Oldenburg et al., "Identification and Analysis of the Polyhydroxyalkanoate-Specific B-Ketothiolase and Acetoacetyl Coenzyme A Reductase Genes in the *Cyanobacterium synechocystis* sp. Strain PCC6803", Applied and Environmental Microbiology, vol. 66, No. 10, pp. 4440-4448 (2000).
Thompson et al., "Structural elements regulating zein gene expression", BioEssays, vol. 10, No. 4, pp. 108-113 (1989).
Tsuge et al., "Molecular cloning of two (R)-specific enoyl-CoA hydratase genes from Pseudomonas aeruginosa and their use for polyhydroxyalkanoate synthesis", FEMS Microbiology Letters, vol. 184, pp. 193-198, (1999).
Udaondo et al., "Regulation of carbohydrate degradation pathways in Pseudomonas involves a versatile set of transcriptional regulators", Microbial Biotechnology, vol. 11, pp. 442-454 (2018).
Valentin et al., "PHA production, from bacteria to plants", International Journal of Biological Macromolecules, vol. 25, pp. 303-306 (1999).
Van Beilen et al., "Production of renewable polymers from crop plants", The Plant Journal, vol. 54, pp. 684-701 (2008).
Wang et al., "Development of a New Strategy for Production of Medium-Chain-Length Polyhydroxyalkanoates by Recombinant *Escherichia coli* via Inexpensive Non-Fatty Acid Feedstocks", Applied and Environmental Microbiology, pp. 519-527 (2011).
Wittenborn et al., "Structure of the Catalytic Domain of the Class I Polyhydroxybutyrate Synthase from Cupriavidus necator*", Journal of Bilogical Chemistry, vol. 291, No. 48, pp. 25264-25277 (2016).
Xing et al., "ATP citrate lyase activity is post-translationally regulated by sink strength and impacts the wax, cutin and rubber biosynthetic pathways", The Plant Journal, vol. 79, pp. 270-284 (2014).
Yabe et al., "Enzyme reactions and genes in aflatoxin biosynthesis", Appl. Microbiol. Biotechnol., vol. 64, pp. 745-755 (2004).
Yokoo et al., "Enhanced poly(3-hydroxybutyrate) production in transgenic tobacco BY-2 cells using engineered acetoacetyl-CoA reductase", Bioscience, Biotechnology, and Biochemistry, vol. 79, No. 6, pp. 986-988 (2015).
Yoshizumi et al., "Sucrose supplementation suppressed the growth inhibition in polyhydroxyalkanoate-producing plants", Plant Biotechnology, DOI: 10.5511/plantbiotechnology.16.1121a, pp. 1-5 (2017), Galley Proof.

Search Report for International Application No. PCT/US2020/036786, mailed Nov. 13, 2020.
Abell et al., "Tail-anchored membrane proteins: exploring the complex diversity of tail-anchored-protein targeting in plant cells", Plant Cell Rep, vol. 30, pp. 137-151 (2011).
Anderson et al., "Synthesis of Short-Chain-Length/Medium-Chain Length Polyhydroxyalkanoate (PHA) Copolymers in Peroxisomes of Transgenic Sugarcane Plants", Tropical Plant Biol., vol. 4, pp. 170-184 (2011).
Arai et al., "Plastid Targeting of Polyhydroxybutyrate Biosynthetic Pathway in Tobacco", Plant Biotechnology, vol. 18, No. 4, pp. 289-293 (2001).
Barbante et al., "Anchorage to the cytosolic face of the endoplasmic reticulum membrane: a new strategy to stabilize a cytosolic recombinant antigen in plants", Plant Biotechnology Journal, vol. 6, pp. 560-575 (2008).
Bevan et al., "Structure and transcription of the nopaline synthase gene region of T-DNA", Nucleic Acids Research, vol. 11, Issue 2, pp. 369-385 (1983), Abstract Only.
Bohmert et al., "Constitutive Expression of the B-Ketothiolase Gene in Transgenic Plants. A Major Obstacle for Obtaining Polyhydroxybutyrate-Producing Plants", Plant Physiol., vol. 128, pp. 1282-1290 (2002).
Bohmert et al., "Metabolic Engineering: Plastids as Bioreactors," Chapter 21 in Molecular Biology and Biotechnology of Plant Organelles, editors Henry Daniell & Christine Chase, Springer, pages: cover, i-xxvi, 565-591 (2004).
Carey et al., "High Flux Through the Oxidative Pentose Phosphate Pathway Lowers Efficiency in Developing Camelina Seeds", Plant Physiology, vol. 182, pp. 493-506 (Jan. 2020).
Chek et al., "Structure of polyhydroxyalkanoate (PHA) synthase PhaC from *Chromobacterium* sp. USM2, producing biodegradable plastics". Scientific Reports, vol. 7, No. 5312, pp. 1-15 (Jul. 2017).
Chowdhury et al., "Thermal evaluation of transgenic cotton containing polyhydroxybutyrate", Thermochimica Acta, vol. 313, Issue 1, pp. 45-53 (Mar. 1998), Abstract Only.
Davis, et al., "Biosynthetic Thiolase from Zoogloea ramigera", The Journal of Biological Chemistry, vol. 262, No. 1 pp. 82-89, (1987).
Denecke et al., "Plant and mammalian sorting signals for protein retention in the endoplasmic reticulum contain a conserved epitope", The EMBO Journal, vol. 11, No. 6, pp. 2345-2355 (1992).
Endo et al., "Hybrid fiber production: a wood and plastic combination in transgenic rice and Tamarix made by accumulating poly-3-hydroxybutyrate", Plant Biotechnology, vol. 23, pp. 99-109 (2006).
Fukui et al., "Cloning and Analysis of the Poly(3-Hydroxybutyrate-co-3-Hydroxyhexanoate) Biosynthesis Genes of Aeromonas caviae", Journal of Bacteriology, vol. 179, No. 15, pp. 4821-4830 (1997).
Fukui et al., "Expression and Characterization of (R)-Specific Enoyl Coenzyme A Hydratase Involved in Polyhydroxyalkanoate Biosynthesis by Aeromonas caviae", Journal of Bacteriology, vol. 180, No. 3, pp. 667-673 (1998).
Gagat et al., "How protein targeting to primary plastids via the endomembrane system could have evolved? A new hypothesis based on phylogenetic studies," Biology Direct, 8, 18, pp. 1-22 (2013).
Gajewski et al., "Engineering fungal de novo fatty acid synthesis for short chain fatty acid production", Nature Communications, 8:14650 | DOI: 10.1038/ncomms14650, pp. 1-8 (2017).
Gerngross et al., "Immunocytochemical Analysis of Poly-B-Hydroxybutyrate (PHB) Synthase in Alcaligenes eutrophus H16: Localization of the Synthase Enzyme at the Surface of PHB Granules", Journal of Bacteriology, vol. 175, No. 16, pp. 5289-5293 (1993).
Gomord, et al., "Signals and mechanisms involved in intracellular transport of secreted proteins in plants: Targeting and glycosylation of plant secretory proteins" Plant Physiology and Biochemistry, vol. 34, pp. 165-181 (1996), Index Information Only.
Gou, et al., "Cytochrome b5 Is an Obligate Electron Shuttle Protein for Syringyl Lignin Biosynthesis in *Arabidopsis*", The Plant Cell, vol. 31, pp. 1344-1366 (Jun. 2019, originally published online Apr. 8, 2019).
Hall et al., "Cloning of the Nocardia corallina polyhydroxyalkanoate sythase gene and production of poly-(3-hydroxybutyrate-co-

(56) References Cited

OTHER PUBLICATIONS hydroxyhe . . . ", Can. J. Microbiol. 44, 687-91 (1998), Abstract Only (English abstract included).
Haywood et al., "The role of NADH- and NADPH-linked acetoacetyl-CoA reductases in the poly-3-hydroxybutyrate synthesizing organism Alcaligenes eutrophus", FEMS Microbiology Letters 52, pp. 259-264 (1988).
Hein et al., "*Synechocystis* sp. PCC6803 possesses a two-component polyhydroxyalkanoic acid synthase similar to that of anoxygenic purple sulfur bacteria", Arch Microbiol, vol. 170, pp. 162-170 (1998).
Hirakawa et al., "Internal plastid-targeting signal found in a RubisCO small subunit protein of a chlorarachniophyte alga", The Plant Journal, vol. 64, pp. 402-410 (2010).
Hitchman et al., "Hexanoate Synthase, a Specialized Type I Fatty Acid Synthase in Aflatoxin B1 Biosynthesis", Bioorganic Chemistry, vol. 29, Issue 5, pp. 293-307 (Oct. 2001), Abstract Only.
Houmiel et al., "Poly(b-hydroxybutyrate) production in oilseed leukoplasts of Brassica napus", Planta, vol. 209, pp. 547-550 (1999).
Iida et al., "Positive and negative cis-regulatory regions in the soybean glycinin promoter identified by quantitative transient gene expression", Plant Cell Reports, vol. 14, pp. 539-544 (1995).
Ishiguro et al., "Shepherd is the *Arabidopsis* GRP94 responsible for the formation of functional CLAVATA proteins", The EMBO Journal, vol. 21, No. 5, pp. 898-908 (2002).
Jahns et al., "Tolerance of the Ralstonia eutropha Class I Polyhydroxyalkanoate Synthase for Translational Fusions to Its C Terminus Reveals a New Mode of Functional Display", Applied and Enviornmental Microbiology, vol. 75, No. 17, pp. 5461-5466 (Sep. 2009).
Jing et al., "Two distinct domains contribute to the substrate acyl chain length selectivity of plant acyl-ACP thioesterase", Nature Communications, 9, 860, DOI: 10.1038/s41467-018-03310-z (2018).
John et al., "Metabolic pathway engineering in cotton: Biosynthesis of polyhydroxybutyrate in fiber cells", Proc. Natl. Acad. Sci. USA, vol. 93, pp. 12768-12773 (1996).
John, "Cotton Crop Improvement Through Genetic Engineering", Critical reviews in Biotechnology, vol. 17, Issue 3, pp. 185-208 (1997), Abstract Only.
Kato et al., "Production of a novel copolyester of 3-hydroxybutryic acid and medium-chain-length 3-hydroxyalkanoic acids by *Pseudomonas* sp. 61-3 from sugars", Appl Microbiol Biotechnol, vol. 45, pp. 363-370 (1996).
Kolibachuk et al., "Cloning, Molecular Analysis, and Expression of the Polyhydroxyalkanoic Acid Synthase (phaC) Gene from Chromobacterium violaceum", Applied and Environmental Microbiology, vol. 65, No. 8, pp. 3561-3565 (1999).
Kourtz et al., "A novel thiolase-reductase gene fusion promotes the production of polyhydroxybutyrate in *Arabidopsis*", Plant Biotechnology Journal, 3, pp. 435-447 (2005).
Kourtz et al., "Chemically inducible expression of the PHB biosynthetic pathway in Arabidopsis", Transgenic Res, vol. 16, pp. 759-769 (2007).
Kriechbaumer et al., "Subcellular Distribution of Tail-Anchored Proteins in Arabidopsis", Traffic, vol. 10, pp. 1753-1764 (2009).
Lee et al., "Biosynthesis of copolyesters consisting of 3-hydroxybutyric acid and medium-chain-length 3-hydroxyalkanoic acids from 1,3-butanediol or from 3-hydroxybutyrate by *Pseudomonas* sp A33", Appl Microbiol Biotechnol, vol. 42, pp. 901-909 (1995).
Lee et al., "Functional Characterization of Sequence Motifs in the Transit Peptide of Arabidopsis Small Subunit of Rubisco", Plant Physiology, vol. 140, pp. 466-483 (2006).
Li-Beisson et al., "Acyl-Lipid Metabolism", The Arabidopsis Book, 2010: e0133, pp. 1-65 (2010).
Liebergesell et al., "Cloning and nucleotide sequences of genes relevant for biosynthesis of poly(3-hydroxybutyric acid) in Chromatium vinosum strain D", Eur. J Biochem., vol. 209, pp. 135-150 (1992).

Lu et al., "Generation of transgenic plants of a potential oilseed crop *Camelina sativa* by Agrobacterium-mediated transformation", Plant Cell Rep, vol. 27, pp. 273-278 (2008).
Malik et al., "Production of high levels of poly-3-hydroxybutyrate in plastids of Camelina sativa seeds", Plant Biotechnology Journal, vol. 13, pp. 675-688 (2015).
Matsumoto et al., "Enhancement of Poly(3-hydroxybutyrate-co-3-hydroxyvalerate) Production in the Transgenic *Arabidopsis thaliana* by the Vitro Evolved Highly Active Mutants of Polyhydroxyalkanoate (PHA) Synthase from Aeromonas caviae", Biomacromolecules, vol. 6, Issue. 4, pp. 2126-2130 (2005), Abstract Only.
Matsumoto et al., "Improved polyhydroxybutyrate (PHB) production in transgenic tobacco by enhancing translation efficiency of bacterial PHB biosynthetic genes", Journal of Bioscience and Bioengineering, vol. 111, Issue 4, pp. 485-488 (2011), Abstract Only.
Matsumoto et al., "Directed Evolution and Structural Analysis of NADPH-Dependent Acetoacetyl Coenzyme A (Acetoacetyl-CoA) Reductase from Ralstonia europha Reveals Two Mutations Responsible for Enhanced Kinetics", Applied and Environmental Microbiology, vol. 79, No. 19, pp. 6134-6139 (2013).
Matz et al., "Fluorescent proteins from nonbioluminescent *Anthozoa* species", Nature Biotechnology, vol. 17, pp. 969-973 (1999).
McBride et al., "Global Analysis of Membrane-associated Protein Oligomerization Using Protein Correlation Profiling", Molecular & Cellular Proteomics, 16.11, pp. 1972-1989 (2017).
McQualter et al., "The use of an acetoacetyl-CoA synthase in place of a β-ketothiolase enhances poly-3-hydroxybutyrate production in sugarcane mesophyll cells", Plant Biotechnology Journal, vol. 13, pp. 700-707 (2015).
Mezzolla et al., "Role of PhaC Type I and Type II Enzymes during PHA Biosynthesis", Polymers, vol. 10, 910, doi:10.3390/polym10080910, pp. 1-12 (2018).
Nakashita et al., "Production of Biodegradable Polyester by a Transgenic Tobacco", Biosc., Biotechnol. Biochem., vol. 63, No. 5, pp. 870-874 (1999).
Odell et al., "Identification of DNA sequences required for activity of the cauliflower mosaic virus 35S promoter", Nature, vol. 313, pp. 810-812 (1985).
Oeding et al., "β-Ketothiolase from Hydrogenomonas eutropha H16 and its significance in the regulation of poly-β-hydroxybutyrate metabolism", Biochemical J, vol. 134(1), pp. 239-248 (1973), Abstract Only.
Okamura et al., "Unprecedented acetoacetyl-coenzyme A synthesizing enzyme of the thiolase superfamily involved in the mevalonate pathway", Proceedings of the National Academy of Sciences USA, vol. 107, No. 25, pp. 11265-11270 (2010).
Pagny et al., "Signals and mechanisms for protein retention in the endoplasmic reticulum", Journal of Experimental Botany, vol. 50, No. 331, pp. 157-164 (1999).
Parveez et al., "Production of polyhydroxybutyrate in oil palm (*Elaeis guineensis* Jacq.) mediated by microprojectile bombardment of PHB biosynthesis genes into embryogenic calli", Frontiers in Plant Science, vol. 6, Article 598, pp. 1-12 (2015).
Pedrazzini, "Tail-Anchored Proteins in Plants", J. Plant Biol., vol. 52, pp. 88-101 (2009).
Peoples et al., "Poly-β-hydroxybutyrate (PHB) Biosynthesis in Alcaligenes eutrophus H16", The Journal of Biological Chemistry, vol. 264, No. 26, pp. 15298-15303 (1989).
Peoples et al., "Fine structural analysis of the Zoogloea ramigera phbA-phbB locus encoding β-ketothiolase and acetoacetyl-CoA reductase: nucleotide sequence of phbB", Molecular Microbiology, vol. 3, Issue 3, pp. 349-357 (1989), Abstract Only.
Petrasovits et al., "Production of polyhydroxybutyrate in sugarcane", Plant Biotechnology Journal, vol. 5, pp. 162-172 (2007).
Suriyamongkol, "Polyhydroxybutyrate (PHB) production in transgenic *Arabidopsis thaliana* seeds," Thesis, University of Alberta, Department of Agricultural, Food and Nutritional Science, pp. i-xv, 1-191 (2006).

* cited by examiner

| Organism | Sequence | |
|---|---|---|
| Nocardia_corallina | ------------------------------------------------------------ | 0 |
| Pseudomonas_putida | ------------------------------------------------------------ | 0 |
| Pseudomonas_oleovorans | ------------------------------------------------------------ | 0 |
| Rhodococcus_ruber | ------------------------------------------------------------ | 0 |
| Aeromonas_caviae | ------------------------------------------------------------ | 0 |
| Acinetobacter_sp. | ------------------------------------------------------------ | 0 |
| Caulobacter_vibrioides | ------------------------------------------------------------ | 0 |
| Rhodospirillum_rubrum | MFTTTNPTFIRPTAACPMFSCCPTWAARRSKPEPPWASWPWIILTPISAAASRPTGSPDR | 60 |
| Chromobacterium_violaceum | ------------------------------------------------------------ | 0 |
| Pseudomonas_sp_61-3 | ------------------------------------------------------------ | 0 |
| Zoogloea_ramigera | ------------------------------------------------------------ | 0 |
| Cupriavidus_necator | ------------------------------------------------MATGKGAAASTQEG | 14 |
| Delftia_acidovorans | ------------------------------------------------------------ | 0 |
| Azohydromonas_lata | ------------------------------------------------------------ | 0 |
| Burkholderia_sp. | ------------------------------------------------MTASKNSSTSAQAD | 14 |
| Allochromatium_vinosum | ------------------------------------------------------------ | 0 |
| Thiocapsa_pfennigii | ------------------------------------------------------------ | 0 |
| Synechosystis_sp._PCC_6803 | ------------------------------------------------------------ | 0 |
| Arthrospira_sp._PCC_8005 | ------------------------------------------------------------ | 0 |
| Cyanothece_sp._PCC_7425 | ------------------------------------------------------------ | 0 |
| Bacillus_bataviensis | ------------------------------------------------------------ | 0 |
| Bacillus_cereus | ------------------------------------------------------------ | 0 |
| Bacillus_megaterium | ------------------------------------------------------------ | 0 |

FIG. 2A

| | | | |
|---|---|---|---|
| Nocardia_corallina | ------------------------------- | ----------------MMAQARTVIG------ | 10 |
| Pseudomonas_putida | ------------------------------- | ----------------MTDKPAKGS------- | 9 |
| Pseudomonas_oleovorans | ------------------------------- | ----------------MSNKNNDEL------- | 9 |
| Rhodococcus_ruber | ------------------------------- | ----------------MLDHVHKKL------- | 9 |
| Aeromonas_caviae | --MSQPSY---------GP------ | LFEALAHY----NDKLLAMAKA---- | 26 |
| Acinetobacter_sp. | --MNPNSF-------QFKENILQFFSVHDDI | ----WKKLQEFY-Y----------- | 31 |
| Caulobacter_vibrioides | ------------------------------- | -------MVETLSANLARAA------ | 13 |
| Rhodospirillum_rubrum | PWSGRPSEREGKTMTD-TRAEADLTEVWRAWAAWGEKSRTMWATALGGAAPPSSPS--- | | 115 |
| Chromobacterium_violaceum | ------------------------------- | -------------------------- | 0 |
| Pseudomonas_sp_61-3 | ---------------MDNNAHTFK- | -TY----WSG--------------- | 14 |
| Zoogloea_ramigera | -----MNLPDPQAIANAWMSQVGDPSQWQSWF | ---SK----AP--------------- | 31 |
| Cupriavidus_necator | ----KSQPFK---V-----TPGPFDPATWLEWS | ---RQ----WQGTEGNGH-------- | 46 |
| Delftia_acidovorans | -----MNFDPLAG------LSGQ---SVQQFWN | ---EQ----WSRTLQTLQOMGQP--- | 35 |
| Azohydromonas_lata | ------------------------------- | -------------------------- | 0 |
| Burkholderia_sp. | TFAGQQAFAQAAQ-------QAAQPMQQMFEAWL | ---SA----WRGFADPARAATASAATNP | 62 |
| Allochromatium_vinosum | ------------------------------- | -------------------------- | 0 |
| Thiocapsa_pfennigii | ------------------------------- | -------------------------- | 0 |
| Synechosystis_sp._PCC_6803 | ------------------------------- | -------------------------- | 0 |
| Arthrospira_sp._PCC_8005 | ------------------------------- | -------------------------- | 0 |
| Cyanothece_sp._PCC_7425 | ------------------------------- | -------------------------- | 0 |
| Bacillus_bataviensis | ------------------------------- | -------------------------- | 0 |
| Bacillus_cereus | ------------------------------- | -------------------------- | 0 |
| Bacillus_megaterium | ------------------------------- | -------------------------- | 0 |

FIG. 2B

```
Nocardia_corallina         ------------ESVEESIGGGE-----DVAPPRLGP--------------AVGALADVFGHGRAVAR    47
Pseudomonas_putida         ------------TTLPGTRM--------NVQNAILGLRGRDL----LSTLRNVGRHGLRHPLHTAH    51
Pseudomonas_oleovorans     ------------QRQASENT--------LGLNPVIGIRRKDL----LSSARTVLRQAVRQPLHSAK    51
Rhodococcus_ruber          ------------KSTL------------DPIGWGPA----------VTSVAGRAVRNPQAVTA    38
Aeromonas_caviae           ------------QTERTAQA--------L---LQTN----------LDDLGQVLEQGSQQPWQLIQ    59
Acinetobacter_sp.          ------------GQSPINEA--------L---AQLN----------KEDMSLFFEALSKNPARMME    64
Caulobacter_vibrioides     ------------VTAQGAIAEAA-----LRQADRPAALTPDFHVAPALNEVMTRLAAQPDRLMR    61
Rhodospirillum_rubrum      ------------PSGPDPAV--------GGGPAVGGDAARAF----------LEGVLRPSQPVLD   150
Chromobacterium_violaceum  ------------MQQFVNSLSQPPAP--DGAAHPF-----------AGAW--AQLMNQTNQLFA    37
Pseudomonas_sp_61-3        ------------QVPFIASFAV------QQLRL-WVSTNPWF----SGHEHGAWFELPRETLDS    55
Zoogloea_ramigera          ------------TTEANPM---------------------------ATMLQDIGVALKPEAMEQ    56
Cupriavidus_necator        ------------AAAASGI---------------------------PGLDALAGVKIAPAQLGD    70
Delftia_acidovorans        -----GLPG--IQGMPGMPDM-------AQA-WKAAVPE-------PGALPENALSLDPEKLLE    77
Azohydromonas_lata         ----------------------------M---S-GLNL--------PMQAMTK    13
Burkholderia_sp.           FATFQFPKSFPFQMPSMADF--------GGAASPF-----------A-GLKLPAAAIPPERLQK   106
Allochromatium_vinosum     ----------------------------------------------------     0
Thiocapsa_pfennigii        ----------------------------------------------------     0
Synechosystis_sp._PCC_6803 ----------------------------------------------------     0
Arthrospira_sp._PCC_8005   ----------------------------------------------------     0
Cyanothece_sp._PCC_7425    ----------------------------------------------------     0
Bacillus_bataviensis       ----------------------------------------------------     0
Bacillus_cereus            ----------------------------------------------------     0
Bacillus_megaterium        ----------------------------------------------------     0
```

FIG. 2C

| | | |
|---|---|---|
| Nocardia_corallina | HGVSFGRE----LAKIAVG--------RSTVAPAKGDRRFADSAWSANPAYRRLGQTYLAAT | 97 |
| Pseudomonas_putida | HLLALGGQ----LGRVMLG--------DTPYQPNPRDARFSDPTWSQNPFYRRGLQAYLAWQ | 101 |
| Pseudomonas_oleovorans | HVAHFGLE----LKNVLLG--------KSSLAPESDDRRFNDPAWSNNPLYRRYLQTYLAWR | 101 |
| Rhodococcus_ruber | ATAEYAGRLAKIPAAATRVFNANDPDAPMPVDPRDRRFSDTAWQENPAYFSLLQSYLATR | 98 |
| Aeromonas_caviae | AQMNWWQDQLKLMQHTLLKSAGQPSEPVITPERSDRRFKAEAWSEQPIYDYLKQSYLLTA | 119 |
| Acinetobacter_sp. | MQWSWWQGQIQIYQNVLMRSVAKDVAPFIQPESGDRRFNSPLWQEHPNFDLLSQSYLLFS | 124 |
| Caulobacter_vibrioides | AQADLFGQYMELWQTAARRAAGEDVAPVVAPAAGDKRFNDPDWASNPMFDLMKQSYLLSS | 121 |
| Rhodospirillum_rubrum | AQAAWARDIAALCQAAAKRLRGEEAAPVIEPAGDDNRFKDDAWTKDPLFDTLKQGYLLTA | 210 |
| Chromobacterium_violaceum | LQSSLYQQQLNLWSQFLGQAAGQEAAAEAGAKPADRRFASPEWNEHPFYNFLKQSYLQTS | 97 |
| Pseudomonas_sp_61-3 | LQADYQVQWGQLGQKLLTG--------QPFSFDDRRFASGNWSE-PLFGSLAAFYLLNS | 105 |
| Zoogloea_ramigera | LKNDYLRDFTALWQDFLAG--------KAPAVQRPRFSSAAWQGNPMSAFNAASYLLNA | 107 |
| Cupriavidus_necator | IQQRYMKDFSALWQAMAEG--------KAEATGPLHDRRFAGDAWRTNLPYRFAAAFYLLNA | 124 |
| Delftia_acidovorans | LQRQYLDGAKAMA-----------EQGGAQALLAKDKRFNTESWAGNPLTAATAATYLLNS | 127 |
| Azohydromonas_lata | LQGEYLNEATALWNQTLGRLQ--PDGSAQPAKLGDRRFSAEDWAKNPAAAYLAQVYLLNA | 71 |
| Burkholderia_sp. | LQADYARDCVTLMQQA---------SAAKLEAPELKDRRFSGDAWKASPAHAFAAAWYLLNA | 159 |
| Allochromatium_vinosum | ------------------------------------------------------------ | 0 |
| Thiocapsa_pfennigii | ------------------------------------------------------------ | 0 |
| Synechosystis_sp._PCC_6803 | ------------------------------------------------------------ | 0 |
| Arthrospira_sp._PCC_8005 | ------------------------------------------------------------ | 0 |
| Cyanothece_sp._PCC_7425 | ------------------------------------------------------------ | 0 |
| Bacillus_bataviensis | ------------------------------------------------------------ | 0 |
| Bacillus_cereus | ------------------------------------------------------------ | 0 |
| Bacillus_megaterium | ------------------------------------------------------------ | 0 |

FIG. 2D

```
Nocardia_corallina           EAVDGVVDEVGRAIG-PRRTAEARFAADILTAALAPTNYLWTNPAALKEAFDTAGLSLAR  156
Pseudomonas_putida           KQTRQWIDES---HLN-DDDRARAHFLFNLINDALAPSNSL-LNPLAVKELFNTGGQSLVR  157
Pseudomonas_oleovorans       KELQDWIGNS---DLS-PQDISRGQFVINLMTEAMAPTNTL-SNPAAVKRFFETGGKSLLD  157
Rhodococcus_ruber            AYVEELTEAG--SGD-PLQDGKARQFANLMFDALAPSNFLW-NPGVLTRAFETGGASLLR  154
Aeromonas_caviae             RHLLASVDAL--EGVPQKSRERLRFFTRQYVNAMAPSNFLATNPELLKLTLESDGQNLVR  177
Acinetobacter_sp.            QLVQNMVDVV--EGVPDKVRYRIHFFTRQMINALSPSNFLWTNPEVIQQTVAEQGENLVR  182
Caulobacter_vibrioides       NWLNGLIAEV--DGVDPATKRRVEFFTKMLTDAFSPSNFLISNPAALREVVQTQGQSLVR  179
Rhodospirillum_rubrum        RLVATTLENS--GGD-PACRQRLAFYGRQVVDALAPTNFAATNPLVRRTALESGGKSLLN  267
Chromobacterium_violaceum    KWMMELVDKT--QLD-EDAKDKLAFATRQYLDAMSPSNFMLTNPDVVKRAIETKGESLVE  154
Pseudomonas_sp_61-3          SFLLKLLDML--LIDEKKPRQRLRYLVEQAIAASAPSNFLVSNPDALQRVVETQGASLVT  163
Zoogloea_ramigera            KFLSAMVEAV--DTA-PQQKQKIRFAVQQVIDAMSPANFLATNPEAQQKLIETKGESLTR  164
Cupriavidus_necator          RALTELADAV--EAD-AKTRQRIRFAISQWVDAMSPANFLATNPEAQRLLIESGGESLRA  181
Delftia_acidovorans          RMLMGLADAV--QAD-DKTRNRVRFAIEQWLAAMAPSNFLALNAEAQKKAIETQGESLAQ  184
Azohydromonas_lata           RTLMQMAESI--EGD-AKAKARVRFAVQQWIDAAAPSNFLALNPEAQRKALETKGESISQ  128
Burkholderia_sp.             RYLQELADAL--ETD-PKTRERIRFAVQQWTAAAAPSNFLAFNPDAQKSILETQGESLRQ  216
Allochromatium_vinosum       ----------------------MFPID-IRPDKLTQEMLDYSRKLGQ  24
Thiocapsa_pfennigii          ----------------------MSPFPID-IRPDKLTEEMLEYSRKLGE  26
Synechosystis_sp._PCC_6803   -----------MFLLFFIVHWLKIMLPFFAQ-VGLEENLHETLDFTEKFLS  39
Arthrospira_sp._PCC_8005     -----------------MSLLGGHQAMLPFALQ-MGLEDLTQEYADLTEKIVH  35
Cyanothece_sp._PCC_7425      ----------------------MLPFLLQ-IHLEEAAHESAQLTHKLVK  26
Bacillus_bataviensis         -------------------MAIESPFKEYIQE-LDVEKEKK-----RWEQ  25
Bacillus_cereus              -----------------MTTFATEWEKQLELYPEE--YRKAYR-----RVKR  28
Bacillus_megaterium          -------------------MQEWEKLIKSMPSE---YKSSSAR-----RFKR  24

FIG. 2E
```

```
Nocardia_corallina            GTKHFV------SDLIENRG---MPSMVQRGAFTVGKDLAVTPGAVISRDEVAEVLQYTPT   208
Pseudomonas_putida            GVAHLL------DDLRHNDG---LPRQVDERAFEVGANLAATPGAVVFRNELLELIQYSPM   209
Pseudomonas_oleovorans        GLSNLA------KDLVNNGG---MPSQVNMDAFEVGKNLGTSEGAVVYRNDVLELIQYKPI   209
Rhodococcus_ruber             GARYAA------HDILNRGG---LPLKVDSDAFTVGENLAATPGKVVFRNDLIELIQYAPQ   206
Aeromonas_caviae              GLALLA------EDLERSADQLNIRLTDESAFELGRDLALTPGRVVQRTELYELIQYSPT   231
Acinetobacter_sp.             GMQVFH------DDVMNSGKYLSIRMVNSDSFSLGKDLAYTPGAVVFENDIFQLLQYEAT   236
Caulobacter_vibrioides        GMENFA------ADLERGGGQLAISQTDLAKFKVGENVATAPGKVVYQNDILQLLQFDPT   233
Rhodospirillum_rubrum         GLENLL------RDLERGGGRLRPTMSDETAFEVGRTLAMTPGKVVFQNALMQLILYAPT   321
Chromobacterium_violaceum     GMKNML------DDFQKG----HISMSDESKFEIGKNLVVTPGQVVFRNELIELIQYTPT   204
Pseudomonas_sp_61-3           GMQHLA------SDMNEG----KMRQCDSGAFKVGIDLANTPGEIVFENHLFQLIHYPPQ   213
Zoogloea_ramigera             GLVNMLGDINMLGDINNG----HISLSDESAFEVGRNLAITPGTVIYENPLFQLIQYTPT   220
Cupriavidus_necator           GVRNMM------EDLTRG----KISQTDESAFEVGRNVAVTEGAVVFENEYFQLLQYKPL   231
Delftia_acidovorans           GVANLL------ADMRQG----HVSMTDESLFTVGKNVATTEGAVVFENELFQLIEYKPL   234
Azohydromonas_lata            GLQQLW------HDIQQG----HVSQTDESVFFEVGKNVATTEGAVVYENDLFQLIEYKPL   178
Burkholderia_sp.              GMMNLL------GDLQRG----KISQTDESQFVVGKNLGCTEGAVVYENDLIQLIQYKPT   266
Allochromatium_vinosum        GMENL-------------LNAEA----IDTGVSPKQAVYSEDKLVLYRYDRP           59
Thiocapsa_pfennigii           GMQNL-------------LKADQ----IDTGVTPKDVVHREDKLVLYRYRRP           61
Synechosystis_sp._PCC_6803    GLENLQ------------GLNEDD---IQVGFTPKEAVYQEDKVILYRFQPV           76
Arthrospira_sp._PCC_8005      GMDNLS------------SLREEE---IIVGVTPKEAVYQEDKVTLYRFEPK           72
Cyanothece_sp._PCC_7425       GMENLS------------QLREED---IEVGSTPREVVYQEDKVKLYRFKAP           63
Bacillus_bataviensis          L-F--K------------VFSEPE---PKIGHTPRTEVWRKNKSVLWHYPAK           59
Bacillus_cereus               ASE--I------------LLREPE---PQVGLTPKEVIWTKNKTKLYRYIPK           63
Bacillus_megaterium           AYE--I------------MTAEAE---PEVGLTPKEVIWKKNKAKLYRYTPV           59
```

FIG. 2F

```
Nocardia_corallina          DTYA-GRVIRAIDEVREITGSDDVNLIGFCAGGIIATTVLNHLAAQGD---------------  313
Pseudomonas_putida          SSYV-QALEEALNACRSISGNRAPNLMGACAGGLTMAALQGHIQAKKQL---------------  315
Pseudomonas_oleovorans      STYI-DALKEAVDAVLAITGSKDLNMLGACSGGITCTALVGHYAALGE---------------  314
Rhodococcus_ruber           DDYYVDGIATALDVVEEITGSPKIEVLSICLGGAMAAMAAARAFAVGD---------------  312
Aeromonas_caviae            DDYVVDGVIAALDGVEAATGEREVHGIGYCIGGTALSLAMGWLAARRQK---------------  338
Acinetobacter_sp.           ADLITQGSVEALRVIEEITGEKEANCIGYCIGGTLLAATQAYYVAKRLK---------------  343
Caulobacter_vibrioides      EDYMIEGIYDAAQQVMTQCGVDRVNTVGYCIGGTLLSVALAHMAARGD---------------  339
Rhodospirillum_rubrum       EDYLSQGPLAAMEVMTEITGQRALGLVGYCIGGTLTACTLAVLAARRD---------------  427
Chromobacterium_violaceum   ETYIEKGVFAAAEAVQKITKQPTMNVLGFCVGGVILTTALCVAQAKGL---------------  310
Pseudomonas_sp_61-3         DDLIELGVIDGLQVAREISGEQRLNCVGFCIGGTLLSTALAVLAARGD---------------  319
Zoogloea_ramigera           DDYVEQGVIEAIRIVQDVSGQDKLNMFGFCVGGTIVATALAVLAARGQ---------------  326
Cupriavidus_necator         DDYIEHAAIRAIEVARDISGQDKINVLGFCVGGTIVSTALAVLAARGE---------------  337
Delftia_acidovorans         DNYIEDGVLTGIRVAREIAGAEQINVLGFCVGGTMLSTALAVLQARHDREHGAVAAPAAK     352
Azohydromonas_lata          DDYVEQGVIRAIRVMQQITGHEKVNALGFCVGGTILSTALAVLAARGE---------------  284
Burkholderia_sp.            DDYMNEGLLAAIDAVQQVSGREQINTLGFCVGGTMLSTALAVLAARGE---------------  372
Allochromatium_vinosum      DDYINGYIDRCVDYLREAHGVDKVNLLGICQGGAFSLMYSALH---PD---------------  164
Thiocapsa_pfennigii         DDYINGYIDRCVDYLRETHGVDQVNLLGICQGGAFSLCYTALH---SE---------------  165
Synechosystis_sp._PCC_6803  EDYLSGYLNNCVDIICQRSQQEKITLLGVCQGGTFSLCYASLF---PD---------------  179
Arthrospira_sp._PCC_8005    DDYINGYINNCVDFLRDHYELDKINLLGVCQGGTFSLCYSSLY---PE---------------  175
Cyanothece_sp._PCC_7425     DDYINGYLNNCVDFIRASHQLDKVNLLGICQGGTFSLCYSSLY---PD---------------  168
Bacillus_bataviensis        DTYIEKYLRTAVKRAIRHSGAEEITLIGYCLGGTIASIYASIA---D----------------  160
Bacillus_cereus             DDFVFDYITRAVKKVMRTAKSDEISLLGYCMGGTLTSIYAALH---PH---------------  166
Bacillus_megaterium         DDYIVDYIPKAAKKVLRTSKSPDLSVLGYCMGGTMTSIFAALN---ED---------------  162
                                               :  *   **

FIG. 2H
```

| Organism | Sequence | # |
|---|---|---|
| Nocardia_corallina | ----------TRVHSMAYAVTMLDFGDPALLGA------FARP | 340 |
| Pseudomonas_putida | ----------RRVRSATYLVSLLDSKFESPASL------FADE | 342 |
| Pseudomonas_oleovorans | ----------NKVNALTLLVSVLDTTMDNQVAL------FVDE | 341 |
| Rhodococcus_ruber | ----------KRVSAFTMINTLLDYSQVGELGL------LTDP | 339 |
| Aeromonas_caviae | ----------QRVRTATLFTTLLDFSQPGELGI------FIHE | 365 |
| Acinetobacter_sp. | ----------NHVKSATYMATIIDFENPGSLGV------FINE | 370 |
| Caulobacter_vibrioides | ----------KRINSATFFAAQQDFAEAGDLLL------FTNE | 366 |
| Rhodospirillum_rubrum | ----------HRVKSATLLTTLVDFSEPGELGV------FIDP | 454 |
| Chromobacterium_violaceum | ----------KYFDSATFMTSLIDHAEPGEISF------FIDE | 337 |
| Pseudomonas_sp_61-3 | ----------REIASVSLFTTFLDYHDTGPIDI------FVDE | 346 |
| Zoogloea_ramigera | ----------HPAASLTLLTTFLDFSDTGCSTS------C-RE | 352 |
| Cupriavidus_necator | ----------HPAASVTLLTTLLDFADTGILDV------FVDE | 364 |
| Delftia_acidovorans | APAAKRAAGSRSAARTSTARATAPAGVPFPVASVTLLTTFIDFSDTGILDV------FIDE | 407 |
| Azohydromonas_lata | ----------QPAASLTLLTTLLDFSNTGVLDL------FIDE | 311 |
| Burkholderia_sp. | ----------HPAASMTLLTAMLDFSDTGVVDV------FVDR | 399 |
| Allochromatium_vinosum | ----------KVRNLVTMVTPVDFKTPDNLLSAW-------V | 189 |
| Thiocapsa_pfennigii | ----------KVKNLVTMVTPVDFQTPGNLLSAW-------V | 190 |
| Synechosystis_sp._PCC_6803 | ----------KVKNLVVMVAPVDFEQPGTLLNARGGCTLGA | 210 |
| Arthrospira_sp._PCC_8005 | ----------KVQNLITMVAPVNFDMPNTLLNARGGCTLGP | 206 |
| Cyanothece_sp._PCC_7425 | ----------KVNNLVVMVAPVDFHQPETLLNMRGGCTLGA | 199 |
| Bacillus_bataviensis | ----------EPIKNLVATVPIDFKPFI--GPDQWAEGMRQ | 190 |
| Bacillus_cereus | ----------MPIRNLIFMTSPFDFSET-----GLYGPLLDE | 193 |
| Bacillus_megaterium | ----------LPIKNLIFMTSPFDFSDT-----GLYGAFLDD | 189 |

FIG. 2I

```
Nocardia_corallina           GLIRFAKGRSRR-----KGIISARDMGSAFTWMRPNDLVFNYVVNNYLMGRTPPAF----  391
Pseudomonas_putida           QTIEAAKRRSYQ-----RGVLDGGEVARIFAWMRPNDLIWNYWVNNYLLGKTPPAF----  393
Pseudomonas_oleovorans       QTLEAAKRHSYQ-----AGVLEGSEMAKVFAWMRPNDLIWNYWVNNYLLGNEPPVF----  392
Rhodococcus_ruber            ATLDLVEFRMRQ-----QGFLSGKEMAGSFDMIRAKDLVFNYWVSRWMKGEKPAAF----  390
Aeromonas_caviae             PIIAALEAQNEA-----KGIMDGRQLAVSFSLLRENSLYWNYYIDSYLKGQSPVAF----  416
Acinetobacter_sp.            PVVSGLENLNNQ-----LGYFDGRQLAVTFSLLRENTLYWNYYIDNYLKGKEPSDF----  421
Caulobacter_vibrioides       EWLQSIEQQMDQ-----AGGFLPSQSMADTFNALRGNDLIWSFFVSNYLMGKEPRPF----  418
Rhodospirillum_rubrum        PLLDALDDQMAR-----DGGLDGDLLSMAFNMLRDNDLIWSVFINNYLLGKTPAAF----  505
Chromobacterium_violaceum    SVVAGREAKMAS-----GGIISGKEIGRTFASLRANDLVWNYVVNNYLLGKTPAPF----  388
Pseudomonas_sp_61-3          ELVAHRERTIGGVN-GPIGLFRGEDMGNTFSLLRPNDLWWNYNVDKYLKGQKPIPL----  401
Zoogloea_ramigera            TQVALREQQLRD-----GGLMPGRDLASTFSSLRPNDLVWNYVQSNYLKGNEPAAF----  403
Cupriavidus_necator          GHVQLREATLGGGAGAPCALLRGLELELANTFSFLRPNDLVWNYLKGNTPVPF----  420
Delftia_acidovorans          SVVRFREMQMGE-----GGLMKGQDLASTFSFLRPNDLVWNYLKGETPPPF----  458
Azohydromonas_lata           AGVRLREMTIGEKAPNGPGLLNGKELATTFSFLRPNDLVWNYVVGNYLKGEAPPPF----  367
Burkholderia_sp.             AHVQMREQTIGGKSGTPPGLMRGVEFANTFSFLRPNDLVWNYVVDNYLKGRTPAPF----  455
Allochromatium_vinosum       QNVDIDL----------AVDTMGNIPGELLNWTFLSLKPFSLITGQKYVNMVDLLDDPDKVKNFL  243
Thiocapsa_pfennigii          QNVDVDL----------AVDTMGNIPGELLNWTFLSLKPFSLITGQKYVNMVDLLDDEDKVKNFL  244
Synechocystis_sp._PCC_6803   EAVDIDL----------MVDAMGNIPGDYLNLEFLMLKPLQLGYQKYLDVPDIMGDEAKLLNFL  264
Arthrospira_sp._PCC_8005     EAIDVDL----------MVEALGNIPGDYLNIEFLMLKPLQLGYQKYLDLPEIMGSRDKLLNFL  260
Cyanothece_sp._PCC_7425      EAIDVDL----------MVDALGNIPGDFINLEFLMLKPQQLGIQKYLDVPDIMDSPEKLLNFL  253
Bacillus_bataviensis         GDINIDR----------FIDAYGVVPPQLVEGMFRAI-GAPIYFTNYTMLLSRAHDQRYVDKWR  243
Bacillus_cereus              KYFNLDK----------AVDTFGNIPPEMIDFGNKMLKPITNFVGPYVALVDRSENERFVESWR  247
Bacillus_megaterium          RYFNLDK----------AVDTFGNIPPEMIDFGNKMLKPITNFYGPYVTLVDRSENQRFVESWK  243
```

FIG. 2J

| | | |
|---|---|---|
| Nocardia_corallina | DILAWNDDGTNLPGALHGQFL-DIFRDNVLVEPGRLAVLGTPVDLKSITVPTFVSGAIAD | 450 |
| Pseudomonas_putida | DILYWNADSTRLPAALHGDLL-EFFKLNPLTYASGLEVCGTPIDLQQVNIDSFTVAGSND | 452 |
| Pseudomonas_oleovorans | DILFWNNDTTRLPAAFHGDLI-EMFKSNPLITRPDALEVCGTPIDLKQVKCDIYSLAGTND | 451 |
| Rhodococcus_ruber | DILAWNEDSTSMPAEMHSHYLRSLYGRNELA-EGLYVLDGQPLNLHDIACDTYVVGAIND | 449 |
| Aeromonas_caviae | DLLHWNSDSTNVAGKTHNSLLRRLYLENQLVKG-ELKIRNTRIDLGKVKTPVLLVSAVDD | 475 |
| Acinetobacter_sp. | DILYWNSDGTNIPAKIHNFLLRNLYLNNELISPNAVKVNGVGLNLSRVKTPSFFIATQED | 481 |
| Caulobacter_vibrioides | DLLFWNADQTRMPKALHLFYLRNFYKDNALT-TGKLSLSGGERLDLSKVKIPIYVQSSKDD | 477 |
| Rhodospirillum_rubrum | DLLYWNGDSTRMPAAMQRYYLREMYQKNKLVQPGGLTVLGHALDLRRIRTPVYLLSARDD | 565 |
| Chromobacterium_violaceum | DLLFWNNDAVDLPLPMHTFLLRQFYMNNALVRPGAITLCGVPIDIAKIDVPVYMFAARDD | 448 |
| Pseudomonas_sp_61-3 | DLLFWNNDSTNLPGPMYCWYLRHTYLQNDLK-SGELECCGNKLDRAIDAPAYILATHDD | 460 |
| Zoogloea_ramigera | DLLFWNSDSTNLPGPMFCWYLRNTYLENSLKVPGKLTVAGEKIDLGLIDAPAFIYGSRED | 463 |
| Cupriavidus_necator | DLLFWNGDATNLPGPWYCWYLRHTYLQNELKVPGKLTVCGVPVDLASIDVPTYIYGSRED | 480 |
| Delftia_acidovorans | DLLYWNSDSTNLPGPYYAWYLRNLYLENRLAQPGALTVCGERIDMHQLRLPAYIYGSRED | 518 |
| Azohydromonas_lata | DLLYWNSDSTNMAGPMFCWYLRNTYLENKLRVPGALTICGEKVDLSRIEAPVYFYGSRED | 427 |
| Burkholderia_sp. | DLLYWNSDSTNLPGPMYAWYLRNTYLENRLREPGALTVCGEAVDLSRIDVPTFIYGSRED | 515 |
| Allochromatium_vinosum | RMEKWIFDSPDQAGETFRQFIKDFYQNNGFL-NGGVVLGGQEVDLKDITCPVLNIFALQD | 302 |
| Thiocapsa_pfennigii | RMEKWIFDSPDQAGETFRQFIKDFYQRNGFI-NGGVLIGDQEVDLRNIRCPVLNIYPMQD | 303 |
| Synechosystis_sp._PCC_6803 | RMEKWIFDSPDQAGETYRQFLKDFYQQNKLI-KGEVMIGDRLVDLHNLTMPILNLYAEKD | 323 |
| Arthrospira_sp._PCC_8005 | RMEKWIFDSPDQAGETYRQFLKDFYQENKLI-KGEVMIGDSRVDLSNITMPVLNLYAEKD | 319 |
| Cyanothece_sp._PCC_7425 | RMEKWIFDSPDQAGETYRQFMKDFYQGNKLI-KNQVKIGDQLVNLLNLTMPILNLYAEKD | 312 |
| Bacillus_bataviensis | RMNRWTRDQVPFAGEAYKQLANDLFKENKIV-KGELMIGNKKVDLKNITANLYVVSGSRD | 302 |
| Bacillus_cereus | LVQKWVGDGIPFPGESYRQWIRDFYQNNKIV-KGELVIRGQKVDLANIKANVLNISGKRD | 306 |
| Bacillus_megaterium | LMQKWVADGIPFAGEAYRQWIRDFYQQNKLI-NGELEVRGRKVDLKNIKANILNIAASRD | 302 |
| | : * * . * .. : . : :: .: * | |

FIG. 2K

```
Nocardia_corallina          HLTAWRNCYRTTQLLG----GETEFALSFSGHIASLVNPPGNPKAHYWT-----GG--TP   499
Pseudomonas_putida          HITPWDAVYRSALLLG----GERRFVLANSGHIQSIINPPGNPKAYYLA-----NP--KL   501
Pseudomonas_oleovorans      HITPWQSCYRSAHLFG----GKIEFVLSNSGHIQSILNPPGNPKARFMT-----GA--DR   500
Rhodococcus_ruber           HIVPWTSSYQAVNLLG----GDVRYVLTNGHVAGAVNPPGKRVWFKAVGAPDAESGTPL   505
Aeromonas_caviae            HIALWQGTWQGMKLFG----GEQRFLLAESGHIAGIINPPAANKYGFWH-----NG--AE   524
Acinetobacter_sp.           HIALWDTCFRGADYLG----GESTLVLGESGHVAGIVNPPSRNKYGCYT-----NA--AK   530
Caulobacter_vibrioides      HIAPYRSVYRGARAFG----GPVTFTMAGSGHIAGVINHPDARKYQHWT-----NS--EL   526
Rhodospirillum_rubrum       HIAPWTSTFKATGLYG----GPLRFVLAGSGHIAGVINPPAKARYGYWT-----NAD--T   614
Chromobacterium_violaceum   HIVLWSSAFSGLKYLQG-APSRRFVLGASGHIAGSINPVTKDKRNYWA-----ND--TL   499
Pseudomonas_sp_61-3         HIVPWKSAYASTNLLS----GSKRFVLGASGHIAGVINPPAKQKRHYWT-----NN--RV   509
Zoogloea_ramigera           HIVPWMSAYGSLDILNQGKPGANRFVLGASGHIAGVINSVAKNKRTYWI-----NDGG--   516
Cupriavidus_necator         HIVPWTAAYASTALLA----NKLRFVLGASGHIAGVINPPAKNKRSHWT-----ND--AL   529
Delftia_acidovorans         HIVPVGGSYASTQVLG----GDKRFVMGASGHIAGVINPPAKKKRSYWL-----REDGQL   569
Azohydromonas_lata          HIVPWESAYAGTQMLS----GPKRYVLGASGHIAGVINPPQKKKRSYWT-----NE-Q-L   476
Burkholderia_sp.            HIVPWQTAYASTSIIT----GPLKFVLGASGHIAGVINPPAKKKRSFWV-----ND-NDL   565
Allochromatium_vinosum      HLVPPDASRALKGLTS----SPDYTELAFPGGHIGIYVSGKAQK---------EV       344
Thiocapsa_pfennigii         HLVPPDASKALAGLTS----SEDYTELAFPGGHIGIYVSGKAQE---------GV       345
Synechosystis_sp._PCC_6803  HLVAPASSLALGDYLP--ENCDYTVQSFPVGHIGMYVSGKVQR---------DL       366
Arthrospira_sp._PCC_8005    HLVPPSSSLALEEYIS----SEDYTAKSFPVGHIGMYVSGKVQR---------DL       361
Cyanothece_sp._PCC_7425     HLVPPASSVALAKYIG----TQDYTAKGFPVGHIGMYVSGKVQQ---------DL       354
Bacillus_bataviensis        NLILEEQSKPLMDLAS----SEDKTYVSVEAGHVSLALSGLFAK---------          342
Bacillus_cereus             HIALPCQVEALLDHIS----STDKQYVCLPTGHMSIVYGGTAVK---------QT       348
Bacillus_megaterium         HIAMPHQVAALMDAVS----SEDKEYKLLQTGHVSVVFGPKAVK---------ET       344
                            ::                    :                         **:.        .

FIG. 2L
```

| Organism | Sequence | Position |
|---|---|---|
| Nocardia_corallina | GPDPDAWLENAERQQGSWWQAWADWVLARGGEETAAPDAPGS-AHDRALDAAPGRYVRDL | 558 |
| Pseudomonas_putida | SSDPRAWFHDAKRSEGSWWPLMLEWITARSGLLKTPRTELGN-ATYPPLGPAPGTYVLTR | 560 |
| Pseudomonas_oleovorans | PGDPVAWQENATKHADSWWLHWQSWLGERAGELEKAPTRLGN-RAYAAGEASPGTYVHER | 559 |
| Rhodococcus_ruber | PADPQVWDEAATRYEHSWWEDWTAWSNKRAGELVAPPAMGS--TAHPPLEDAPGTYVFS- | 562 |
| Aeromonas_caviae | AESPESWLAGATHQGGSWWPEMMGFIQNRDEGSEPVPARV----PEEGLAPAPGHYVKVR | 580 |
| Acinetobacter_sp. | FENTKQWLDGAEYHPESWWLRWQAWVTPYTGE--QVPARNLGNAQYPSIEAAPGRYVLVN | 588 |
| Caulobacter_vibrioides | PADVSEWIAGAQEHPGSWWPHWAAWLKARSGDQVPARDPAK--GKLKPLEDAPGSFVLVK | 584 |
| Rhodospirillum_rubrum | SLEAESWLEGATPHGGSWWPDWAAWAAGYAGPKVAARDPTK--GPRPPLEDAPGSYVKVR | 672 |
| Chromobacterium_violaceum | PLHAEEWLESAESRPGSWWKDWDAWLAPQSGKQVAAPKSLGN-KEFPPLLAAPGSYVLAK | 558 |
| Pseudomonas_sp_61-3 | TKNPETWFKNAEQHPGSWWNDWFTWLAGHSGERQPAVAHTGN-NKYPPLEPAPGRYVKL- | 567 |
| Zoogloea_ramigera | AADAQAWFDGAQEVPGSWWPQWAGFLTQHGGKKVKPKAKPGN-ARYTAIEAAPGRYVKAK | 575 |
| Cupriavidus_necator | PESPQQWLAGAIEHHGSWWPDWTAWLAGQAGAKRAAPANYGN-ARYRAIEPAPGRYVKAK | 588 |
| Delftia_acidovorans | PATLKEWQAGADEYPGSWWADWSPWLAEHGGKLVAAPKQYGKGREYTAIEPAPGRYVLVK | 629 |
| Azohydromonas_lata | DGDFNQWLEGSTEHPGSWWTDWSDWLKQHAGKEIAAPKTPGN-KTHKPIEPAPGRYVKQK | 535 |
| Burkholderia_sp. | PDAADDWFAGAAEQPGSWWPTWTEWLGQYGGRKVAPPAQAGS-AQFPVIEPAPGRYVLQR | 624 |
| Allochromatium_vinosum | TPAIGKWLNER------------------------------------------------ | 355 |
| Thiocapsa_pfennigii | TPAIGRWLNERG----------------------------------------------- | 357 |
| Synechosystis_sp._PCC_6803 | PPAIAHWLSERQ----------------------------------------------- | 378 |
| Arthrospira_sp._PCC_8005 | PPTIVDWLKVRE----------------------------------------------- | 373 |
| Cyanothece_sp._PCC_7425 | PPVIADWLRNRD----------------------------------------------- | 366 |
| Bacillus_bataviensis | --IVDQWASSRSNQL-------------------------------------------- | 355 |
| Bacillus_cereus | YPTIGNWLEERSN---------------------------------------------- | 361 |
| Bacillus_megaterium | YPSIGDWLEKRSK---------------------------------------------- | 357 |
|  | *                                                          |  |

FIG. 2M

| Species | Seq | Num | SEQ ID NO |
|---|---|---|---|
| Nocardia_corallina | PAG--------------- | 561 | (SEQ ID NO: 41) |
| Pseudomonas_putida | ------------------ | 560 | (SEQ ID NO: 45) |
| Pseudomonas_oleovorans | ------------------ | 559 | (SEQ ID NO: 44) |
| Rhodococcus_ruber | ------------------ | 562 | (SEQ ID NO: 42) |
| Aeromonas_caviae | LNPVFACPTEEDAA | 594 | (SEQ ID NO: 35) |
| Acinetobacter_sp. | LF---------------- | 590 | (SEQ ID NO: 39) |
| Caulobacter_vibrioides | SQP--------------- | 587 | (SEQ ID NO: 36) |
| Rhodospirillum_rubrum | I----------------- | 673 | (SEQ ID NO: 43) |
| Chromobacterium_violaceum | AMPSVAASLQ-------- | 568 | (SEQ ID NO: 33) |
| Pseudomonas_sp_61-3 | ------------------ | 567 | (SEQ ID NO: 46) |
| Zoogloea_ramigera | G----------------- | 576 | (SEQ ID NO: 37) |
| Cupriavidus_necator | A----------------- | 589 | (SEQ ID NO: 32) |
| Delftia_acidovorans | A----------------- | 630 | (SEQ ID NO: 34) |
| Azohydromonas_lata | A----------------- | 536 | (SEQ ID NO: 38) |
| Burkholderia_sp. | D----------------- | 625 | (SEQ ID NO: 40) |
| Allochromatium_vinosum | ------------------ | 355 | (SEQ ID NO: 47) |
| Thiocapsa_pfennigii | ------------------ | 357 | (SEQ ID NO: 48) |
| Synechosystis_sp._PCC_6803 | ------------------ | 378 | (SEQ ID NO: 51) |
| Arthrospira_sp._PCC_8005 | ------------------ | 373 | (SEQ ID NO: 49) |
| Cyanothece_sp._PCC_7425 | ------------------ | 366 | (SEQ ID NO: 50) |
| Bacillus_bataviensis | ------------------ | 355 | (SEQ ID NO: 54) |
| Bacillus_cereus | ------------------ | 361 | (SEQ ID NO: 52) |
| Bacillus_megaterium | ------------------ | 357 | (SEQ ID NO: 53) |

SEQUENCE LISTING

```
<160> NUMBER OF SEQ ID NOS: 158

<210> SEQ ID NO 1
<211> LENGTH: 1094
<212> TYPE: DNA
<213> ORGANISM: Glycine max

<400> SEQUENCE: 1
```

```
tgtgtcaatg ttgtttctgg tgaattgaca taatgaattc tacctgtacg gagtagagaa      60
taactattta cccaacaaga atgattatct cattaatttt tgaagtagac gcaataacga     120
atatattata cattcagaaa aatttcacca tattattctc aaatcacaac aataatttgt     180
tttttttttg cttgatataa aaccaatact ctatactttt taaggttaat ttaaacttaa     240
agagtatttt taagatgcat gtactttaag gaataataga acatgacaa catcataaaa      300 gaatgaagaa actgaatcat aacgtagttt gttacgcctt ccatttggtg gttgatttgg     360
atacaatcta gattggtttg ctaaatggtt tataagttat gtagacgttt ttattactac     420
tattttagac aaatcaaata cacaccttca ctttattcta ttcaaataac atgattttc      480 ctaacatttt ttaaaaaaat tactttttaa atataaacta attattttag aaatagtttt     540
ataaaaatcc acgccaaaaa aattaagttg ttttttataaa tataaacatc gggcttcaat    600
cttaaattta taaatgtacg aaataatttg acagttaaat ggaaattgct agcatggaag     660 tgttttatc atttatcaaa ctcaaccaaa ctgaacatca gaataattat tagtgacaaa      720
ttttgcagca tatgaagtgg cttgcatagc tccaaggctg gcgatcatat gtcagattag     780
agcaggctct ctttggtact atgatacatt tcaagcaaat aacaaccgta aaaattcacg     840
ccaaaatttt tggaacgaat ctatatatta ttatttttatt tcttttgatt tcatgtacgt    900
acagtgcccg taattgacat gtctttgttc cttaatgcct ttcccacgtg aacaggcac      960 ctagaaactt ggactaagta gggaattgag ggccatggac tatagtgcca aaccaacatc    1020
attttatata tatatatata tatatatata tatatgctat tgttttctat agttttgga    1080 aattaatact tatc                                                      1094

<210> SEQ ID NO 2
<211> LENGTH: 1449
<212> TYPE: DNA
<213> ORGANISM: Glycine max

<400> SEQUENCE: 2
atttgtacta aaaaaaaata tgtagattaa attaaactcc aattttaatt ggagaacaat      60
acaaacaaca cttaaaaacct gtaattaatt tttcttcttt ttaaaagtgg ttcaacaaca    120
caagcttcaa gttttaaaag gaaaaatgtc agccaaaaac tttaaataaa atggtaacaa    180
ggaaattatt caaaaattac aaacctcgtc aaaataggaa agaaaaaaag tttagggatt    240
tagaaaaaac atcaatctag ttccaccta ttttatagag agaagaaact aatatataag      300
aactaaaaaa cagaagaata gaaaaaaaaa gtattgacag gaaagaaaaa gtagctgtat    360
gcttataagt actttgagga tttgaattct ctcttataaa acacaaacac aattttttaga   420 tttttatttaa ataatcatca atccgattat aattatttat atatttttct attttcaaag   480
aagtaaatca tgagcttttc caactcaaca tctattttt ttctctcaac cttttttcaca    540 tcttaagtag tctcaccctt tatatatata acttatttct tacctttttac attatgtaac   600 ttttatcacc aaaaccaaca actttaaaat tttattaaat agactccaca agtaacttga    660
cactcttaca ttcatcgaca ttaacttta tctgttttat aaatattatt gtgatataat     720
ttaatcaaaa taaccacaaa cttttcataaa aggttcttat taagcatggc atttaataag   780
caaaaacaac tcaatcactt tcatataggaa ggtagcctaa gtacgtactc aaaatgccaa   840
caaataaaaa aaaagttgct ttaataatgc caaaacaaat taataaaaca cttacaacac    900
cggatttttt ttaattaaaa tgtgccattt aggataaata gttaatatt ttaataatta     960 tttaaaaagc cgtatctact aaaatgattt ttatttggtt gaaaatatta atatgtttaa   1020
```

| | | | |
|---|---|---|---|
| atcaacacaa | tctatcaaaa ttaaactaaa | aaaaaaataa gtgtacgtgg | ttaacattag | 1080 |
| tacagtaata | taagaggaaa atgagaaatt | aagaaattga aagcgagtct | aattttaaa | 1140 |
| ttatgaacct | gcatatataa aaggaaagaa | agaatccagg aagaaaagaa | atgaaaccat | 1200 |
| gcatggtccc | ctcgtcatca cgagtttctg | ccatttgcaa tagaaacact | gaaacacctt | 1260 |
| tctctttgtc | acttaattga gatgccgaag | ccacctcaca ccatgaactt | catgaggtgt | 1320 |
| agcacccaag | gcttccatag ccatgcatac | tgaagaatgt ctcaagctca | gcaccctact | 1380 |
| tctgtgacgt | gtccctcatt caccttcctc | tcttccctat aaataaccac | gcctcaggtt | 1440 |
| ctccgcttc | | | 1449 |

<210> SEQ ID NO 3
<211> LENGTH: 1321
<212> TYPE: DNA
<213> ORGANISM: Glycine max

<400> SEQUENCE: 3

| | | | |
|---|---|---|---|
| aaaaacacaa | aaaaaaatta tacaaaaatg | tttctcacaa catgagaagt | aaaatccctc | 60 |
| aaagaatttc | acatcatcat atcagaatca | aaggaatcaa aatcataggt | caaaaataca | 120 |
| aaaacaccaa | gaacactcaa tttattaact | aatttgcatc atgacatcaa | ttggtccatc | 180 |
| aaacacaaca | atcttgtaat tataatcgta | acgaaagaat tacaatgcaa | taaacatccc | 240 |
| aaaataaacc | tcaatttaat cctctaagga | tccctataca tgttcattct | aaccccaatt | 300 |
| gtgataaatt | catcccttac ctctaagcag | gctcacgtgt gtagtctggc | agtgatagag | 360 |
| gcatctctag | tggttttcta atagtcctca | agcttgtttt tcctctagtt | gttctgttag | 420 |
| gattttcaag | cgttagagag aagaagaaga | gattggagcc tctatttcac | tgttaccgta | 480 |
| caagggatat | ttttctcacc ataaacatta | ttttgcaaat cccaacgaag | gagatgtccg | 540 |
| tacataagtt | cgaaacctgg tgctcgaatt | tcacgacgat tcaatggtta | acaagtccaa | 600 |
| gattgtattt | ttactgtgac agatttgagt | gtatacaaga aaaagagagc | tccatgcgag | 660 |
| gaatatttct | ctcacagtag acattatttc | ataaatccca atggtaaaaa | tatgcaaaaa | 720 |
| tgagtttcaa | acctgctttt aaaatttcat | gacgactcaa cggttaacgt | gtccgggatt | 780 |
| atattttcac | tggaacaagt ttgagtgcat | gcgggaaaag agagggtttt | gggagaggaa | 840 |
| aaaaggaaaa | caaatttaag aggaagagag | agcgtaaaaa tttatcgtaa | atgtaaaaaa | 900 |
| tgacctaata | tatctctatt tataactagg | gtactctcaa tctattattt | actcattttt | 960 |
| ttatttatt | attttataaa aaagaatttt | attttacttc ctatcaaatt | aataaataaa | 1020 |
| acattcttct | tattttctaa gatcacatat | ttattttatt taccttaaaa | tcatcatttt | 1080 |
| aattaataaa | attatttctt cttatttatt | taattacaaa aatcttatta | ttttttaaa | 1140 |
| attttattta | tttttaaata aaatattttt | taatttattt tataaaaaat | gagatgttac | 1200 |
| attgaattat | aaaataaata gccaacaata | aatagccgac ttgcttttgc | attgactaag | 1260 |
| gaagtcaagt | catcaataaa tataatttcc | agttggcaat attctcaaag | ttggtctata | 1320 |
| t | | | 1321 |

<210> SEQ ID NO 4
<211> LENGTH: 702
<212> TYPE: DNA
<213> ORGANISM: Glycine max

<400> SEQUENCE: 4

| | |
|---|---|
| cgcgccgtac gtaagtacgt actcaaaatg ccaacaaata aaaaaaaagt tgctttaata | 60 |
| atgccaaaac aaattaataa aacacttaca acaccggatt tttttttaatt aaaatgtgcc | 120 |
| atttaggata aatagttaat attttttaata attatttaaa aagccgtatc tactaaaatg | 180 |
| atttttattt ggttgaaaat attaatatgt ttaaatcaac acaatctatc aaaattaaac | 240 |
| taaaaaaaaa ataagtgtac gtggttaaca ttagtacagt aatataagag gaaaatgaga | 300 |
| aattaagaaa ttgaaagcga gtctaatttt taaattatga acctgcatat ataaaaggaa | 360 |
| agaaagaatc caggaagaaa agaaatgaaa ccatgcatgg tccccctcgtc atcacgagtt | 420 |
| tctgccattt gcaatagaaa cactgaaaca cctttctctt tgtcacttaa ttgagatgcc | 480 |
| gaagccacct cacaccatga acttcatgag gtgtagcacc caaggcttcc atagccatgc | 540 |
| atactgaaga atgtctcaag ctcagcaccc tacttctgtg acgtgtccct cattcacctt | 600 |
| cctctcttcc ctataaataa ccacgcctca ggttctccgc ttcacaactc aaacattctc | 660 |
| tccattggtc cttaaacact catcagtcat caccgcggcc gc | 702 |

<210> SEQ ID NO 5
<211> LENGTH: 579
<212> TYPE: DNA
<213> ORGANISM: Glycine max

<400> SEQUENCE: 5

| | |
|---|---|
| acgcgccgta cgtagtgttt atctttgttg cttttctgaa caatttattt actatgtaaa | 60 |
| tatattatca atgtttaatc tattttaatt tgcacatgaa ttttcatttt attttttactt | 120 |
| tacaaaacaa ataatatat atgcaaaaaa atttacaaac gatgcacggg ttacaaacta | 180 |
| atttcattaa atgctaatgc agattttgtg aagtaaaact ccaattatga tgaaaaatac | 240 |
| caccaacacc acctgcgaaa ctgtatccca actgtcctta ataaaaatgt taaaaagtat | 300 |
| attattctca tttgtctgtc ataatttatg taccccactt taattttttct gatgtactaa | 360 |
| accgagggca aactgaaacc tgttcctcat gcaaagcccc tactcaccat gtatcatgta | 420 |
| cgtgtcatca cccaacaact ccacttttgc tatataacaa caccccgtc acactctccc | 480 |
| tctctaacac acacccccact aacaattcct tcacttgcag cactgttgca tcatcatctt | 540 |
| cattgcaaaa ccctaaactt caccttcaac cgcggccgc | 579 |

<210> SEQ ID NO 6
<211> LENGTH: 1945
<212> TYPE: DNA
<213> ORGANISM: Oryza sativa

<400> SEQUENCE: 6

| | |
|---|---|
| aaggtttcat gcgtatcgtg acagatgtta cataatgaca aattcccccag ctggagcacc | 60 |
| tttatccctg ctgtttgcat gaaattagct tgtcttgtag ttccctccag caaaaagaag | 120 |
| tctgaaacaa aacaacattt cgaaaaaaag gcatccatga gttagcattt ctacagttgt | 180 |
| ctatagaggg gaaggctgca cgacaaagtt tccaggcttg gaaacaacct cttatgtaaa | 240 |
| atttttcgta tgtatcagat gatttgtttg cgttacggca tctccaccta acatcacctt | 300 |
| catcatgcgc ctatggtctt tctcttgcct gttttatacg taaaattgga aacgacagaa | 360 |
| acttttgcca tctttattaa aggaaggcaa atatgcaaat ataggcatca agatcacagt | 420 |
| tagtggatta tcatctttgt aggttaacat gtcctacccc aggggagctt atactcaagt | 480 |
| actccatgca ttttcatgaa atgagaaaaa acgatttttta agagaaatgt actttcttgt | 540 |
| atttatgcca aatggcaagg actgaaaggg aaaaactaag aaagggaacg ttacagtaag | 600 |

```
gctctgtggg gactgggac ttcagagaaa cgtgaaccct gcttccttcc tctgcatgaa      660
cataacacca gaggtttcca gcctttcaca cagttgttga tggcttcaca caattcatct      720
ctacctcctg actctttata aggaccccca gcatcaccac aattgcacaa gtacaggcat      780
tagatccaca agaacacttg ggcaggcaag cacctctttg atctttaagc cgttgttatg      840
ttctatttct gagcatatgg tttctagtta tattctttt cttcattcgt ttcatatctt      900
tgaagtgttg atgcaaatgc ggtgaacaac tatcaactgt gtactctcca agtgaatgcg      960
aataatcatt tcctgtgaga attgtgggct agataaacga atgaaatgct gttttatcta     1020
tgtcatgtgt ggaaatttag ttaatttcc ggtctttta tgcattgaga tgggtatgct     1080 gttttttag ttgggtccca tcatcttgag aattctttca aatttccttt tctttatcct     1140
atataaagga tagagaaggc gtatgcctag gtgcaccaac cctgaaagtt ttattctaat     1200
tgcgggaatg gtttgtaatt tttgcttgtt caggttcttt ttcgtggcct ttctttttt     1260 tccccttatt ttgcttagtc tttcacagtc caattttttgg gaagtagtat atcttagttt     1320
ggtcctaagg caccatgttg tactgcagga aaaaaagag taattgtatt ctgtttttc     1380 cttgattact atatccctgt tttaattaat tttgtgcctt tgttgtttga tgttggaact     1440
tcaatgccca taattagtca tttgacttgt tttgggtttt gacgctatct tgagtgccat     1500
aggaaactgg tagaatttag taataatttt atatagactg aatgttgagc ccaccacaaa     1560
tggtttcctt ctgtacaagt atttaataac tcaagcacag gaaacatcag atctctaatc     1620
taaaggttaa caatgggctc aagcaggagc agtagttcag ctctatctgt atatttagaa     1680
gggctggatc tacctgtcca ccagctttta attttacct ggcagctgga taacttcttg     1740
tctgttaatt tcatttagtg ctgtgttatt ttcttcttgt tgttcaggat ggatgctttt     1800
gaatttctgg aatttcgtat tttgttctat ctctttatga aatgacgtta tggcacactt     1860
tttctgcata ttcttgatga aaataattac ctagtcattt ttttagttgc aggtttgtct     1920
gggactttga gtacccatgc aattc                                          1945

<210> SEQ ID NO 7
<211> LENGTH: 1500
<212> TYPE: DNA
<213> ORGANISM: Zea mays

<400> SEQUENCE: 7
tttaaatttg gaacgtcgat ccaacatcta acagaagcac caatttttaca aagaacccct       60 ttcaccttcc tcacttggtg ggacggttct taatcaaatt aactgcagcc gctggtatac      120
atgtacatgt gggcccgcct agcccggcac ggcacaggcc cacaaaaaca cggtccacaa      180
aagcacgacc cacaaaagca catatctaat tatgggccgt gccgtgccag cacgtgtgcc      240
cagtcatcgg cccacaatta gttatgtgtg ccaggccgac ccaaatagcc caaaatacct      300
taatatgcca gaccggctca tatacataca acagtaatac atcaacaaaa cgtataaaat      360
atatatatga ccaaaataaa actaagatgt tttgtggatg cacattataa accttttggtc      420 agaaagaaaa aaatattaca actagctcac aaaaaatatc cagttctctg tttagtgttt      480
aattgagtac tatacatcca tacagaataa atatacaatg atcatcatca ctattcacta      540
tccatatcta ggtattggtt ctcgatggct tattaaagct ctagattctc caagttatgc      600
tagtcatgtg ggcttgaca gaccttagtt aaatactgag tctatatttt gtgggcctta      660
gttaaatggg tcgtggcagg ccggcccgtg ggcttgactt gaggcccagg cacggcccac      720
```

```
aatgtgggcc gtgccggccc atgcccacaa ttaggttggg cagtgccaga tatgggccgt    780
gccagaaatt gtgtgctttg ggccggccta ttaggcacaa cataaatgta cacctatagc    840
cgcatagccg ctggatgtga gatgaatgtc tcagatttaa aatgtgcact tgagcaccgt    900
acctctttga caacagata tgttccttta agattgatgg tggaaaaaaa ttagtcagta     960
cctcactgta tggcggcatt gtttgattat ttcagttcgc acccgttgga ccttgctcat   1020
taaaaaagtt tataccatgg agtctttgca tgtagttgtg tagtagggga agagtggcat   1080
aggaggaatc acaacttcag ctagcttctc tagccttagg gtattttgt cttttgcag    1140 ttcggtctt tcgcagccct cgctgcccc cctgtccgc ctgtccctag acctgttttg    1200
cgtcggcggg aagacagtt gacaggaagg acacgatctt cgtgtccgat gccgatcttc    1260
atgcgagcag cgagccacta cgttgcgctg ccagtgtcgg ctatggtatc caggcattcg   1320
ttgtgcacgt tgacgatgag ctcgaagccg gtccgggtga acgcgagcag cacggtgagg   1380
tcaacgtcgt acatccgcac gtcgatgctg aggccagcca gcagcggcat gacagattgc   1440
ggcgtcagga gattgtgcca gtaggtggcg gggctgggg cagaccggca ggcgaggcct    1500

<210> SEQ ID NO 8
<211> LENGTH: 2315
<212> TYPE: DNA
<213> ORGANISM: Oryza sativa

<400> SEQUENCE: 8
gttcaagatt tattttggt atttaattta cttgcttaag tcagatatat tcccatcgtt     60
gcaggtttgt cacttagtat tattattaag cgctctagca ctaggactct ggataaataa   120
gaaagtttat tcacgaggct agagtagtaa tcaataacat aagcgtggtg tctaggtcag   180
cggttatctt catatgtagt gtgctccatg gaaagtgagg taggaggaag gtggtgacag   240
tcccgtccgt cctttgtatc cctccatgtt cgggtatatc atagagctac aggctagact   300
tagcttggca gactagggga gagccggtgc tcgaagcaat ccatgaggct ttacatttaa   360
cataagttag taaattaacc cataggaatc atctctagac tgaacctacc agtagttgtg   420
cttggatata attatattcc tacatataca tacacgttcc ctgcgattag ataccctgg   480 aatactctaa ggtgaagtgc tacagcggta tccgtgcgct tgcggattta tctgtgaccg   540
tatcaaatac caacaggtag atacaaggaa tcatctctcc tatccattgg tttatcatct   600
tttaaaatta tctcttgctc tcctattgcc tctgcaactg cggataggtg tttctcaaca   660
atgaaggttg tgaagaatgc tttgtgcaac aagatggatg acaagtatct cagccatagc   720
ctcatttgct ttgtagaaaa ggatatgtcg gacacaatca ctaagtatca ccgtggaaag   780
gatgcactgt atgccctatc tatatttacc atttagtaat atttatatgg cttgtgctaa   840
ctttatgttg tctttacagg caataacatt atttggaagg catatctata tattactatt   900
taagataatg taatatctca aagttttat aagctgcaat gaggtgagtt tcacttagct    960
ttctaacttg ttatgagtta tagatgcatg ccaccagtca tttttatct tgcatcagcc   1020 cctgcctgtt agaatatgtt tctttgtctg ggagtccatg tcaactagcc aatttccaaa   1080
tatatgaaca aaactatgtg gccttttgtaa cccaaatgag ataaagacta ctctccatag   1140
aaatttagca acatggcac tcaaagaaaa tgtgttggat agtttcatca tgcatacaaa    1200
agcaacactt ttgaactacc attccaaatc ctttttgtaa attatctttg cttaacacta   1260 ccccttttgag caaatgtggc tttgtgcgga aaaaactcaa acttggtagg gtagacatcc   1320
atttatataa ttggatccat gtacataagt tgttgagtac ttcaagtact taccccttgtg   1380
```

| | |
|---|---|
| atatacatct caaatatatt gaagaagaga agttcttttt ttgagagagg ttgaagaaga | 1440 |
| gaagtttgtc catagctgaa gaggagtttt atagtgtcta gcttaccttg ctgctgattg | 1500 |
| catgtctaaa atgtcgttta atttgggcta taatgaaata ttcaccaata tttctgctgg | 1560 |
| tctattaaag tttaatagtt actcgtaact catttatttt gggctataat ttaatattca | 1620 |
| cctatgtttt tgttagtcta ttttatttcc ctagtgtgca ctagcttaac cccaaattag | 1680 |
| ttttgaacac ttaacctaaa tgtgtctatt atggtcagac actctctcac ggcactctaa | 1740 |
| caaaaagtga attttgttgt tatgttttg tcatgatctc acaagcaatg tacatgtacg | 1800 |
| tttctagagt gcaatcttat gctagcctga ttgtgaattt agtgtagttt gttttctctt | 1860 |
| tttgtagcta cactaccaat aacctattgt cctctagtca taccacgtaa tcacaaggca | 1920 |
| aatccctaac tctcaccttt aaaagcatgt ctttatttc ttgggtggca ctaatacaaa | 1980 |
| atcttttca gcattcctat gtgcgatagc aagaaaacat ggcataactc ttgcttcact | 2040 |
| ctaacaaaaa aaacactttt ccaactttaa aacaatggta tctatgtgtt taatgatcaa | 2100 |
| tcaagcatat aatgacttac aagttttac ctatgccctt tttgcatcat cttgtttgca | 2160 |
| acagacaaac tagatattcc tttaggctat aaacacatca gcatgataaa gagattaggt | 2220 |
| aagtttgtta tccctttttg catatattct cgtctactcc gtgtatataa gcccctctcc | 2280 |
| tccaactcgt ccatccatca ccaagagcag tggga | 2315 |

<210> SEQ ID NO 9
<211> LENGTH: 1194
<212> TYPE: DNA
<213> ORGANISM: Oryza sativa

<400> SEQUENCE: 9

| | |
|---|---|
| ttgcatgccg tcgtcttaag cgtccgcgtg tgaaaatcgg attttcgcat acggttgaac | 60 |
| cggtcgcatg caaagatcgc gatcttcgca gacgatttgg cacatgcggt tgcaccaacc | 120 |
| gtatgcgaaa acccttctcg cccgtatgca aaaccatct ttgttgtagt gtacggttca | 180 |
| caatggtttg gatgggaaat cattgtgaac caaaagtgat agactgattt cgacgagtgt | 240 |
| ttttttttaa gtagtgccac aattttggtc atcatacgtc gtgtctaaaa ttgtaacttt | 300 |
| tgaaaaccaa tttacattaa attaaattta taagactaaa taaagacgat ggtcattgaa | 360 |
| caattgttga gaaaaatcta cacacatgtg tgtccaacac aaatgtttac acatatacta | 420 |
| ctatgttcat agtcgaagtt agattttttt tttccttaaa gggaaagtct gttttcaaat | 480 |
| tttagacctc actccttccg tttcaaatat atcgtgtatt ttttttcta gggcaagctt | 540 |
| ttgaccaatg attactctat tatgacacaa tgttaaaggg atagattcat attcaaaatt | 600 |
| actattataa ttataatttt gtcatataaa taatatttta agcaattgtt agccaaaatc | 660 |
| tcgtcctaac gaaacaaaat acgccttatt tttaaaaaca cggagtatat ccttaaatat | 720 |
| ttctctatcc aatataaaag gtcaatcttt taaaattccg atcatcaata atttctcaaa | 780 |
| taattacttt gaaataaaaa aacatatgca aatttgtgtc gtcataatat ccaatgaact | 840 |
| tattcaaatt tataaactta ttttaattca aaatttgatc attaattttt tttttaaaaa | 900 |
| aaaaccaaat cttatcataa acgtcaaata tattttgat agtggggggcg ataataccat | 960 |
| aaaactaaca acagaagaga catgatacta ctactgtaat cctaatacgt acgtacgtat | 1020 |
| acttctacgc cggatgcata acttcagcct tgtgagacac aacagttgct gcctagctcg | 1080 |
| tggtcgttgg ttttttcgct cgagaaacca ctacgcgtaa accgtgaagt atattatata | 1140 |

```
tagccaactg gtcttctcgc aaatccgcac atccctttct gcccctcgtc ttct            1194
```

<210> SEQ ID NO 10
<211> LENGTH: 1500
<212> TYPE: DNA
<213> ORGANISM: Zea mays

<400> SEQUENCE: 10

```
caaaattttc tattttttaa aaaatatgaa ttctagattt gggattgaac acatctaggc      60
tacaacgttg aattgatgaa caatagtgct tgttaataaa ttgctcacat tcacattgtc     120
gctcttactt caaccatcat acatccatct acagtggtca cccatattta atcctatgga    180
ctaaagatga cagatgaact tctctcgtta tatatatcac tgtcctacat atatgagaaa    240
tgatatgtcc taaactcacc taaaaacaac aacatagttt aaatttaatc atagatgagc    300
ctacagaggt cgaacgtgat ttggaaacat agctctattg ttctctatct catgcataaa    360
tatggtgcaa tgaagaatat tagggttatg atgtcgaaat ctcactcgaa ctcgtgcctc    420
atcataaata gcacactatc aattgttcta tggctgttca aatagggaca atcttgaaac    480
aacatttctc acatgtaaaa cgttgtgaag tatgccaact gaaacggatg acacatacac    540
ttcgtgaacc aatcgatatt ttacttgctt ctatgttaaa taatgttata atacaatatt    600
ttattcaaat gctaaaactt attactagat aaaaataaaa tttaattatc ttcaaaaact    660
aaccaataga tattccatca taactacatt taccaaacta atatactaaa aaatatagga    720
taattactaa attaatcgtg caataatcag tatttatgag attgataatt ttaaattttg    780
tgggctacaa acaaaaatta aaacttactt ttcaagttgg agataagaac aatggtagac    840
gtagctcggg atggtatggc gtcggtgcag acggttaccc tttgtgcgaa gtggcgcggg    900
cacgagggtg gggacttggt acatgcatga gagagaggaa gaacgaaaca acttctcaaa    960
ttaaagcata tgaaaatcac ctaattttg tctgtcggtg gaaactaata actagttttt   1020
attatctttt ttaataagga tccacgaaaa ttatttttga ccgatgaaaa tcctggatct   1080
tcgtattatg tttcgccttt tcccgactct ttgcatgcta gatttccatg cttggactaa   1140
aacgaagata ataaaaccaa tctatcattt tcacacgatg tattcatact tgcaatagat   1200
aaaccactac tccgacggga tttgcttctc gacctctgaa atcttggaag gattatgtgt   1260
ctacacttct cgatcgaggg gaaaaagtcg tagtaccaag ttgtagttaa atttgtttct   1320
tcgatgacaa acaaaggag aggggcccgc gcggcgcagc gcagcgcagt tggctggttc   1380
cggaacacga aaaccaagca cactccacca gctgccatcc accgggttgg atggagatta   1440
caatactcga atagtcagcc agccagccgg cttgaacgtg cagttttccc ctataaaacg   1500
```

<210> SEQ ID NO 11
<211> LENGTH: 1500
<212> TYPE: DNA
<213> ORGANISM: Zea mays

<400> SEQUENCE: 11

```
gattcgcgcg tgctggaact cgggattgga ttcatgcgtg ctggaacttg aagtctgga     60
gtggactttg gaagcctgga ttccagaaca agaactcaag aagtctagga gccgccgagc    120
aggtagggaa ttagggaaat aaagagaaga ggcggctggc gttcgacgtt ccatcttcag    180
tagaggcggc tggcgtttca actccctgta gtcgggccgc ctgccaaaaa agcccacgaa    240
ggcaggaaat caaaaaatct aggtcctaaa cctagtcgcg cagaaccggc taatcgagcg    300
actaatcgac cctaatcgtc gactagtcgg acggccaggg cgattaggta ctctaatcga    360
```

```
gtcggttgtg ctaatcgagc tctgctaacc gactagcccg accgcgatta gtcagatgac        420
ttgaaaacaa agatagagac atactttttt atattctttg cattgttttg tttctatcca        480
aaactgctat ttagaaattg gaaaatctgc acattgaaaa atctaatgga ttagatatgt        540
tgatttgttt ttattcacga gcataatcaa ataaattaga tttagaattg gactgcacgc        600
agtgaactac tgaactgaac tgtgttcaat aatttaaata ctcacggctg agccgtgagc        660
tgtaggctgg agcacaagca cgagccagca ccgagcggcg gagcactgga gcagcaggcg        720
agcagggagg cggccaggcg ggagcagcca gccagcaagc aggcagcagc ggagcagccc        780
acagccgagc gcccaagctg gagctgctgc agagcctgca gcgtgccgct gcgcgccggc        840
aggacaggag cggccgagcg ggagtgcagg actgtggcct gcgggacgcg gggatgggcg        900
gacggcgtag cgcttacagt ccgcggacag cggactcacg gtggcggcta agatagtgag        960
accgatgacc taatctctat ttggaccggt tcaaggtttt gcccagttaa tattggacca       1020
tattgggcct tccgcccctg ctcgcaagac acactgaaca aagaatccac acggctctcc       1080
aaaagataga gagataattc acatgcttct ctctctctga aaaaaaggaa cttgcatggt       1140
tgacacggaa aacgtcatta aacgcgcacg tggctgcaaa tgcaacgtaa cagatccatc       1200
atctatccat ccatagaatc agacggccac agaaggcaac gaccgtgtgc ctgtccaccg       1260
gcgcaggtgg cccacagacg cccgtgcgat tcatccgtct cggccaccaa accacgggag       1320
gggccccagg gccctcctta gtccttacaa ataccggcag cagcatcacc cggccaccac       1380
cacccacccg ttttatccac gcacggcgtc gaacaccccg cggtcgctca cgtgaggcgc       1440
caccccgcgc acccagtcag cgcccgcctc caccacccac ccacacgaca aaaatccgcc       1500

<210> SEQ ID NO 12
<211> LENGTH: 770
<212> TYPE: DNA
<213> ORGANISM: Cauliflower mosaic virus

<400> SEQUENCE: 12
agagatagat tgtagagag agactggtga tttcagcgtg tcctctccaa atgaaatgaa         60
cttccttata tagaggaagg tcttgcgaag gatagtggga ttgtgcgtca tcccttacgt        120
cagtggagat atcacatcaa tccacttgct tgaagacgt ggttggaacg tcttcttttt        180
ccacgatgct cctcgtgggt gggggtccat ctttgggacc actgtcggca gaggcatctt        240
gaacgatagc ctttcctta tcgcaatgat ggcatttgta ggtgccacct tccttttcta        300
ctgtcctttt gatgaagtga cagatagctg gcaatggaa tccgaggagg tttcccgata        360
ttaccctttg ttgaaaagtc tcaatagccc tttggtcttc tgagactgta tctttgatat        420
tcttggagta gacgagagtg tcgtgctcca ccatgttatc acatcaatcc acttgctttg        480
aagacgtggt tggaacgtct tctttttcca cgatgctcct cgtgggtggg ggtccatctt        540
tgggaccact gtcggcagag gcatcttgaa cgatagcctt tcctttatcg caatgatggc        600
atttgtaggt gccaccttcc ttttctactg tccttttgat gaagtgacag atagctgggc        660
aatggaatcc gaggaggttt cccgatatta cccttttgttg aaaagtctca atagcccttt       720
ggtcttctga gactgtatct ttgatattct tggagtagac gagagtgtcg                   770

<210> SEQ ID NO 13
<211> LENGTH: 1148
<212> TYPE: DNA
<213> ORGANISM: Glycine max
```

<400> SEQUENCE: 13

```
gcaacagaag acccaaaact caaaaaagtt agtttcgggc caacatttcc tcttgaggga      60
tgacacgtga cctgctactc tggcccttat ctggcatgtc catccttctt ggcgcgacat     120
ttaattcgtc gtcagaaata actgaaggac accttgcttg tttctctttt ggccgccacc     180
ggtcttgtca tcgtcgaagg cgcccttgcg cttgtcggca gaaccttttt cggcgacctc     240
cttgcctttt cctttggcct tgttcgtcat ttctacagag aatgcaatga gaccaacgcc     300
aattgcatgg ttagagttag agaaatggag agaggaagaa gtgcgtgact agagtgtgtg     360
taactgtgaa gaacgacgag tccaaaatga attttactgt aaataatttg aggaaaaaag     420
tgatcaatac atatcatgcg gtgcatacaa gaatcggcca ttggtcaact tgtgagagga     480
aaaaatcatt taactaatac caaataatct taaaattaat aaaataattt aactaattaa     540
cccacggaag aaccttcttc cgttgactct ggcggaagaa gttcttccgc atagttccat     600
ggaagatggt tcttccgcag ttcttctttc gttgacactc gcggaagaaa tgttccacgg     660
gcgtccgcgg aagaactttc ttccgcaaag ctaaagagca ttttgccat gtcgaaatca      720
tcgccaatga ccagggtaac agaaccacgc cctcttatgt tggtttcacc gattcagagc     780
gtttgatcgg tgatgccgcc aagaatcagg tcgccatgaa ccccgtcaac accgtcttcg     840
gtaagatccc tagccgacac ttcgcctttt caggatttgc attgttccta gattttggga    900
tctgttgttt gaaactccac ttttctattt tggtaatttt tagttttatt ttgtaatcct    960
gctgtttata tgtcttattg ttattattaa tcgttgcatg gtctgaactg gtttagaact   1020
ctacttgtat tgtttgttaa aatcttattt gaaatcgaat agtaatataa ttttaatcga   1080
atggtgatat gcataaacat cgtatttgtt cgtcgaattc tggttttgaa ttgaataata   1140
ttgttatg                                                           1148
```

<210> SEQ ID NO 14
<211> LENGTH: 1378
<212> TYPE: DNA
<213> ORGANISM: Glycine max

<400> SEQUENCE: 14

```
ctagaaatta aatgttttta acaggtaatt tgagaaaaat gtacttcaaa ataattagtt      60
ttaccagttt atgtcttctt tttctctttt ttatctttat tctatgtttc aaattctaat     120
aatacatcat ttaaatattt ttaatttaaa agtgcttact aaattttaaa aaaatcatat     180
ttatcaaata acttctactt taaatttaaa cttcattatt tttaacttaa aataaacttt     240
taaattaaaa aaatgaaaac aaacactacc taaaccctaa acactatcta tctaagtcac     300
attacttaat gattcttaat ttatgttctt tgtaaacttt catttcttcc tccttttggc     360
tatacatgtt catttctgtg tactttacta tattattagt aaaagccttt tatataggta     420
tatcaaatca ataattaat ataatatata attctcttaa tttcatttct tcatataaat      480
gtatttcaaa agtatttctt ctagaataaa ctaaagctat tacagatgaa aaattcttaa     540
aaaattattt gaccttcata tatgggtcct tttctaatta ataattaact atataggtgc     600
attctaaatg ctcctatatt atctgctttc tcctcttctt tccttttttc ctagtcgctc     660
acgaaaatct cctataatcc tctgcagttt tcgaaatcaa taaccgactc ctagaacctg     720
tccatgtcta acttaataaa tcgtgagggt gtgattgtga ttactttgaa tctttaattt     780
ttgacattaa aacaagacca aacaaaaacc ttcaggttac gtgagactcc aacctaccca     840
agttatgtat tagttttcc tggtccagaa gaaaagagcc atgcattagt ttattacaac     900
```

| | | | | |
|---|---|---|---|---|
| taactatatt | tcaatttcat | gtaagtgtgc | cccctcatta | aaatcgacct gtgtaaccat | 960 |
| caacctgtag | ttcgctcttt | tcaccatttg | tctctctgtc | tttatcttcc ctcccccatt | 1020 |
| gccaatattt | gttgcaatac | aacatctctc | cgttgcaatc | actcatttca aattttgtgg | 1080 |
| ttctcatttg | ccctagtaca | acattagatg | tggacccaaa | aatatctcac attgaaagca | 1140 |
| tatcagtcac | acaattcaat | caattttttc | cacatcacct | cctaaattga ataacatgag | 1200 |
| aaaaaaatag | ctaagtgcac | atacatatct | actggaatcc | catagtccta cgtggaagac | 1260 |
| ccacattggc | cacaaaacca | tacgaagaat | ctaacccatt | tagtggatta tgggggtgcc | 1320 |
| aagtgtacca | aacaaaatct | caaaccccca | atgagattgt | agcaatagat agcccaag | 1378 |

<210> SEQ ID NO 15
<211> LENGTH: 1500
<212> TYPE: DNA
<213> ORGANISM: Glycine max

<400> SEQUENCE: 15

| | | | | |
|---|---|---|---|---|
| gatcctcaca | aacctcactt | ggagacatag | gtgtgagggt | aaccttttc cctttatgta | 60 |
| caaatgaaaa | tttgtttgtg | acaccattat | ggacaacatc | cttacactac taaaaaagct | 120 |
| ttttttacg | acatcatatt | tacgacagtc | atacaaaaac | gtcttagtat gtataaggat | 180 |
| ggcaatttcg | taaatatttc | aaacatttca | aaggcagttt | cagaaaaccg tctttgaatg | 240 |
| cggccatttt | aattttaac | gcgcccctcg | catccgttcc | tcttctttcc gcaaatgtgg | 300 |
| tgctcgttcc | ttttctttcc | cagctggcat | ctgttcctct | ccccactcgc tagctatctt | 360 |
| ctgcttctcc | tcttctctcc | tcttcccatt | acatttctcc | accttctccc tggtaccacc | 420 |
| accgcccccc | actccacatt | cgtcctccgc | cccattccc | ctatcctcca gtaaaattac | 480 |
| aaaaaaccct | aacaccaaaa | aaacccaaac | ccctgtcgca | atgaaatctc cacccccaaa | 540 |
| tagctctttg | gaatagaatc | aaggaactta | ccaaatccat | tatatgctat tggggttttg | 600 |
| gcatgtttcc | ggtgtgaaag | aaggaaaaag | aaatgcgtat | gcgatggtga tgtacgtagg | 660 |
| tacgccgaag | gactacgaat | tctacatagc | catactcgtg | cttctcaaat cgctggctac | 720 |
| gctcgacgtt | gaaattgatc | ttgctgtgat | tgcttccctt | gatgttcctc ctcgatggat | 780 |
| tcgagctctg | taagtctcac | tccttcacca | tcatttgcca | ctttatttt atgtactttt | 840 |
| actttattat | tatttgtaac | ctgtattttt | atttggtttc | ggatatctgt tgctttatta | 900 |
| ttcaccctgg | aatttggttg | attttattat | ttttgaaaaa | taaggaaaga gatttatttg | 960 |
| ttagcttaat | tgttttaatt | ggcgaatatg | ttttctttt | cccttttttg cacagagtga | 1020 |
| agctttgttc | ttagggtaat | ggattcccttt | ttttgtgatg | ctagtggatg atttgactga | 1080 |
| ttagtgttta | gtggaatgaa | gaaccagaac | tagtagtagg | tagagggaat cacttttggt | 1140 |
| tttggatgta | aacttagaaa | tgtgcagcac | tgcacagaat | tgatatttga tcgtgggtca | 1200 |
| aattgtcaaa | atgtgcaaag | aatacaaagg | cacaggtgat | atcattccat tttacgtttt | 1260 |
| ttaacgaagc | tgttagtttc | aattcaatta | tttacatata | taataaatat attgatactt | 1320 |
| gctttagttt | catgaattaa | aagaatttga | ttttgtaaat | ttcatttgaa tttgtttttg | 1380 |
| tacaagctct | caacttttat | tatatgaacg | agaagtttct | ttttccttt ttgagtttat | 1440 |
| ttgaacttgt | ggtgttctaa | ttgtatatat | ttttgtgcag | gtgtcaatcg gtactactac | 1500 |

<210> SEQ ID NO 16
<211> LENGTH: 1261
<212> TYPE: DNA

<213> ORGANISM: Glycine max

<400> SEQUENCE: 16

```
atctctcgac agttgcgaac tgaacgctga gttggtaatg ctatgcccta tcgctttttg        60
caccgtccca tgatcatttc ccccacacca ccccatcaac ctctaaaaag ttaagagtga       120
aaattacaca cacccgagga aagaaaagc tgcttcttct aagcatcaca acctagttac        180
tttacttgta gggccttttc catttccct aaattacccc tcttttcatc atatgataat        240
aatatccagc tcagactata gtatgatatt atgatgtcag cataataggt tggcactaaa       300
gtcttaaagg gcattgtaca tgttgcacct ggcattcaaa ttcataaata ctaacactgt       360
gaaatagatt ataaatcctc aaataaatgt cacacggttg gggttcgaat ccactcaaaa       420
aggctaatgg gatgggattt aagtgccaag gaatatacca tggactttaa cagcaacaca       480
atttacaatc taaaatgtat tactttttt tttcaaaaaa gatatacaaa ataaggtacc        540
aagaataaaa ggagtattta gaaacagtgg caccaattta ataaattatt tatataaaat       600
gacacttatt taatttatca atgataaaag taatattgat ttattctctg attaactgtt       660
caattaatag tgttattatc ataatctgtc gcaaaagtta ttttttatcaa caacaataat      720
tgatacaagt agtataaaat taagcctctt agttaatata gactacttga tactaaaacc       780
atgttacacc aaaaagtaat ttttatgtca cttgtctata taataattac gactaaatta       840
ataatttta aaaatattac tgaatccatt aaccgaactt ttataatgaa agtatttta        900
tgctttaaaa tcacaaacat tgaataaact aaaaatgata ccacggaatt ggaacaagag       960
acgttccaca caaagaaaa aaatatgttg aataattgaa acggtgacaa gaaaagtgga      1020
ataataatac aaagatggca gatggggtta ttgttattgg aggagatgag tgaaataatg      1080
agtgaggggg gtgtaactgg aaagcaagaa aaagcgcaag agtgccagct atttccaaca      1140
acaaacgtgg cccgtgggat gcgatattcg taacgaacgg cgaggatgga aggacgtgca      1200
atttgcgctt catttgaggc gaatttcatt tggccagacc ttccttttt aaaccacagg      1260
g                                                                     1261
```

<210> SEQ ID NO 17
<211> LENGTH: 1500
<212> TYPE: DNA
<213> ORGANISM: Oryza sativa

<400> SEQUENCE: 17

```
gcagctgttt tcgcggtaca gggtgcaaca aaagcccatg acggcccaca cctgcctctc        60
tccgctccaa acaccgaaac aagggggtgg gtgcaatggg ccggcgctcg aagaccgcga       120
actctttcca acagcccagc gcattagccc ctcctcctac tctctctacc ttctttttaa       180
catgcgactt tctttctgtg gacgacggca tcaacgacgg gagcaggagc gggggctgaa       240
gcacggtgcg tgggctcctg gagtggcgac ggcctctccg gcgagcttcc tctggcgaac       300
tccctccgct cctcctatgg cgaaatccaa acaagggtca gtttcgactc caaccttctc       360
ccaccaccac ctcctgaccg tgccaccacc cggccttgtc ggcactgaaa ggcgtcaact       420
tgtcagcgcg ggcctgctcg gtcggtctcc tcctccccta tttcgtttag ctttgccccc       480
gccaccaaca ccggcccacg gcccatggcc gacccgcgg ctttggcgcc gccatcgcta       540
tctcgccgct gtccttttt catgaccttc ggtgccatcc ctctaaattc gatgcacctc       600
cctggctcta tctcccttta cctccgaaat cctaaccta cccataatct ctagtgagtc       660
ttgtctttat ttatggcctc tttgaatcgc aggattgata aaacgtagga ttttgatagg       720
```

```
aatgtaagtg taaaacacat gattgtaaaa tagaggaaaa acataggaat ggccgtttga    780
ttgaaccgca gaaaaacac aggaattaga tgagagagat agactcaaag ttactaagag    840
attgaagctt tgctaaatt tcctccaaaa tctctatagg attggccatt ccatagaaat    900
ttcaaaagat ttaataggat tcaatccttt gtttcaaaaa acttcataga aaattttttct  960
atagaattaa aatcctctaa aattcctatg ttttttctcc aattcaaagg ggcccttagg   1020
ttggaatttg gaaagtgttc gcgagaaatc aagcggtcgc acgttagcga attaggattt   1080
ccggaaacaa aggaccgact ccgcctatcc atcgtcacga gcacagtgta gaacctccca   1140
gacctcaaga gaccgttcaa aaagcgcgcg cccaagcggg gcccaccaac gcgtccccac   1200
cgtgtcgcct cctgattggt tgtcccctct tcctttcacg cgaaccggca ccctcccgac   1260
ccttccagaa cccccaatcc gacggccagg atcgcccgcg cgcgaacgtt ctagaccccc   1320
gccacctccg ccacaaaacc tctgcccctc ccctctcccc ccgcttcgtc tcgttcgaga   1380
aatcagaaag agagagaaat tcccacgcag cagcaagcaa tccaatccga gagcgcgcgt   1440
ttgcgattat tcgctttcga ttccgcgagg ttttttggaga gggaggagaa ggaggaggag   1500
```

<210> SEQ ID NO 18
<211> LENGTH: 1500
<212> TYPE: DNA
<213> ORGANISM: Zea mays

<400> SEQUENCE: 18

```
agttttcgct tgtctattca ccctctatag gcaactttca attatgtaat cacttttttt    60
ttcttttttc tgtttaaaat ctcagtttca aacttccaat tgattttgaa tacgaggttt   120
gggtttaaat tcatattgga ggcaaaaatc gaaagttcca cgtgatgcta ggttttattt   180
cggttttcta tctcctattg ttttttcacgt ttcaacttga ttcaaattct agtttttttt   240
aacttaagca caattaaata caacataaaa acaacatgga ttcaagttct atttcaattt   300
ttattaacta ttatgttgtc tagtctgttc aagcacataa tacttataaa tataaaatta   360
aacgaaatca catatttcca caaatcttgg gtactacact cggagacgac gatggattcc   420
atctcaattt ggatgttgat tatagctcta tttcagttgt cactgttgtc ctaacacgcc   480
ctattgtgca tgatagtgca cgtgctcaac gtaaaagaaa agagatcagt aacaagtagc   540
agcactgtac aaggtaagcc gtgattcaat taaaactgtt tgagcaattc agttgctaga   600
tcgttccacc atcgataatt cgatatgtac gatgatataa aaagagccca taagtttgtc   660
ttgaaaaggt tgatcaaata atttaaatta gatgataaaa acatggaag atgtgggagt   720
ggacgacggc tatgaagaat agtactatat caggtttata cgtaaaattt attttttgaaa  780
tgtttttata atctgtttga attgtatttt ttgcttaatt atgtgattgg atgttttttc    840
atgaaatgtc gagttttatt ttaaataaaa ttctgtaaag agaagttgct gcgctgagaa    900
aactataaat cgatagtaaa ggctgtacgc aacgtttaag tccttgtttg aatgcgtatg    960
aatctgagaa agttcagaat gattaaatct ttttattta attttaattt gagagagatt   1020
aagttctctc caattctctt taatttagac gtaatcgaac aagctggttg ccaaactaga   1080
tgagtacatt ttgtccactg ccatagagcc atcgactaca aaagtctaga acacagtgga   1140
aagcaccaga caacgcgcga ccaaaagggc ccaggcccca gcgcccagt ccggggttg    1200
tgttcgccga cctgtgcgtg cctgctcgtc acgtcacgtc cctatttgcc cgtcttcctc   1260
ccctccagac ccttctcgaa cgccccttcg ttctggatcc aacggtcggt ctctgccggg   1320
```

| ctcgaacgtt ctcgaaacca cgtcacccc gataaaaccc cacgcacagc ctcctcccctt | 1380 |
| cctcaaccat cattgcaaaa gcgaagcaag caatccgaat tctctgcgat ttctctagat | 1440 |
| ctcgaccacc cctactagtt ttggttcctc ctttcgttcg agagagcgtt tctagtggca | 1500 |

<210> SEQ ID NO 19
<211> LENGTH: 1500
<212> TYPE: DNA
<213> ORGANISM: Oryza sativa

<400> SEQUENCE: 19

| acagcattta ttgtagtctg gtcaagcgtg tcacgctgca tgcaacgcag tacagcgcgt | 60 |
| tcctttaccc ggtctgtgac cagtcacaga ccggtcagat cacgggttag gtggcgactg | 120 |
| gcggtctgac gcacgccttg ccccatcccg tcaagacgaa agcctctagg cactcgtctc | 180 |
| aagccggagc tagcgtgtta tctcttagag atggcacgtt agccctggtt agatttatac | 240 |
| caggcttcat cctaaccatt acaggcaagg tgttacacga agaagggcaa acatgcacg | 300 |
| ttgttaaact gacgcgtggg ggacaagaat gaccggtctg acactggtcg catcagcaac | 360 |
| gggcagccac gatcccgcgt catctccgtc tccgccggga gtggaggtag tgtgggctg | 420 |
| tcccatcaga agggctcccg gatggaaacc gtaccgatct ccgcccatta aagagaaaaa | 480 |
| gaacagtcca gtttggaaag agaagggtgc atgtggtatc cccttgaagt ataaaaggag | 540 |
| gaccttgccc atagaaagg gggttgattc tttccagatt cagagcctag aacgagggag | 600 |
| aggtgggctc acactttgta acttgtccat acacaaatcc acaaaaacac aggagtaggg | 660 |
| tattacgctt ccgagcggcc cgaacctgta tagatcgtcc gtgtctcgcg tttcttgctg | 720 |
| gctgacgatc cttccacata cagagagaga gagagcttgg gatctcaccc taagcccccg | 780 |
| gccgaaccgg caaagggggg cctgcgcggt ctcccggtga ggagcctcga gctccgtcag | 840 |
| acatgttcag tttcattata ttatgaaatg tcacgtactg tttgttctag ttagtgaatt | 900 |
| gtcatatggt aagaatatat aaaaattagg ttttctggac tctatcttcc aatgtatttt | 960 |
| tggatcctat aacaaaatat tttcataaat atattttta agaatctaaa cttttttgaa | 1020 |
| ataaaagagc aacaaagaaa ataaaaacgc tctctcgtaa gtaactcgtg aagatccatc | 1080 |
| gagagccact cgtttgaatc gtcgacacaa agaacacttt cattgattgc ttttcgtcaa | 1140 |
| ttagccgcac agcacagtac tctccaatct gctaaaccaa aaccaatctc atccatccat | 1200 |
| acccttcttg acaccaagtg gcaactcctg attggacgcg ccctatccta catggcaccc | 1260 |
| ccaagattct ctcgatagcc tacaggggcc acaccgaccc tccacgtcat cgtccacgtc | 1320 |
| accctcatcc cggcccatcc agccaatccc agcccagcaa aaaatcttcc caagtggcca | 1380 |
| ccagataagc ctctccacgt attaatacgc caagtgttcg tcgccatgac acagcacgca | 1440 |
| cacacacccc accagcagca gcagcagtag ctgagcttga agcagcagag cgaggtagac | 1500 |

<210> SEQ ID NO 20
<211> LENGTH: 1500
<212> TYPE: DNA
<213> ORGANISM: Zea mays

<400> SEQUENCE: 20

| caacttacaa gcgatgaggc caagacgatt agacgaatag ctacagaaca agacaatgag | 60 |
| agttcagcac tcacttttg ccagttcctt ctccttggca gcagccaggc gcttgagttt | 120 |
| agcagcttgt gcaaatgtgg acggcctaca gcagacatac aggcaaagaa gcgaggagta | 180 |
| atttgcagtt ggaaatcatt cttcgatcaa tagggaaact ctgagtcaca gcgaaaggaa | 240 |

```
ggttaattgc ctacgttgac aactgatcag cctccttgag aagttgcttg atttcaagcc    300
gcactttgat ctgctcatca ctaagtcctc cgctctggat gacaaaagca cagaacgcat    360
gagtggcaag tggaaacact agagcgaaat aaatacaaaa ccgcagacta caggctaaca    420
gatagggaga ccgggaagac aaagactcga gcctgcattc aacagttaca gtcgcctcgg    480
ccaaaggttg agaaatttgc atcaaaatcc aaactgtcta gggccatggg aaatagttcc    540
tcggaatcag agttcaattc atggacgaaa tagatggaac tgatggtagg ctactcttcc    600
gcccaatcag aattcacgga agatccaggt ctcgagacta ggagacggat gggaggcgca    660
acgcgcgatg ggaggggggg cggcgctgac ctttctggcg aggtcgaggt agcggtagag    720
cagctgcagc gcggacacga tgaggaagac gaagatagcc gccagggaca tggtcgccgg    780
cggcggcgga gcgaggctga gccggtctct ccggcctccg atcggcgtta agttggggat    840
cgtaacgtga cgtgtctcct ctccacagat cgacacaacc ggcctactcg ggtgcacgac    900
gccgcgacaa gggtgagatg tccgtgcacg cagcccgttt ggagtcctcg ttgcccacga    960
accgaccct tacagaacaa ggcctagccc aaaactattc tgagttgagc ttttgagcct   1020
agcccaccta agccgagcgt catgaactga tgaacccact accactagtc aaggcaaacc   1080
acaaccacaa atggatcaat tgatctagaa caatccgaag gaggggaggc cacgtcacac   1140
tcacaccaac cgaaatatct gccagtatca gatcaaccgg ccaataggac gccagcgagc   1200
ccaacaccta gcgacgccgc aaaattcacc gcgaggggca ccgggcacgg caaaaacaaa   1260
agcccggcgc ggtgagaata tctggcgact ggcggagacc tggtggccag cgcgcggcca   1320
catcagccac cccatccgcc cacctcacct ccggcgagcc aatggcaact cgtcttaaga   1380
ttccacgaga taaggacccg atcgccggcg acgctattta gccaggtgcg ccccccacgg   1440
tacactccac cagcggcatc tatagcaacc ggtccaacac tttcacgctc agcttcagca   1500

<210> SEQ ID NO 21
<211> LENGTH: 1500
<212> TYPE: DNA
<213> ORGANISM: Zea mays

<400> SEQUENCE: 21
tctcataaaa gcaataaaac aatatctcac aaaatacaag tggcaaacat tatacaaaca     60
tacacatagt cagaaagtca caactcagga ccttaaaaaa tgaaactatc cgattgaaaa    120
tacattgata acaattgaac actagaaaat aatatcacaa atcaaactat ggagcatata    180
actagccata taactcttat aatacaataa taaaatcatc atatatttaa ataaaacact    240
agcaagtcta ataacatatg actatagaat caagatgtgt atgatgacat gacacttgca    300
attttatcat ctcctactac tcgacatagt caatataatt gatgtcctcc ttatctttaa    360
agtttccatg cgaattataa atatatgtat gaagagtaat gattgataag aaactataaa    420
taagagtcac aatagttcaa acaactctaa actatatatc attagataga tcttgatttt    480
agaaaaataa cgaaatcagt ttcataattt tctaagttaa gatgaattta caaagattag    540
tttagattta atatttttc tgaaaaaata ccgatttcgg aaacgggcaa agagatcca    600
aactatttct gttttttttt accgatttca tttccgtatt ttcggtaacg gtttccggtt    660
tcgtatgacc ctaaattttg gtaaagtttc gaaaaaaat attttaagaa ctgaaaatta    720
acgttcctgt tttcatccat actaatggct ctttaccgct aaaatgttgc ccacaatcat    780
tgagtaggtt tagacgtgag agcaaacagt acaacattac gattcgccct tgcccaaatt    840
```

| | |
|---|---|
| tacatgcctt ttccctacgg aaacaacata gaatcaagtt gacggggtta cttacattga | 900 |
| agtggccaaa ctgatggtag ctgtagattt ggatgtatgt tttctataaa ttagtcaaaa | 960 |
| ttgagacaaa ataaactgca atttaaaact gaggaaatag taaaaaaaag gtgaagaagg | 1020 |
| gaggaagagg aaatcagaag caaaaaatgg gcaactttag gcccattatc tcgatggtct | 1080 |
| cgtcggagtc cagatatgtg attgacggat tggattgggc cgtacatctt gcatgagagt | 1140 |
| tcgccaagat ttcattgttt aacaagaagc gcgtgacaac aaaaccaagc ctatctcatc | 1200 |
| cactctttt ttcccttccc acaatggcaa gtggcagctc ctgattcgct ctggccattc | 1260 |
| ctacgtggca cacaccagga ttcttgtgtg ataggccact gggtcccacc caccaggtgc | 1320 |
| cacatcagac gccaagccat cccggcagaa ccaatcccag cccagcaaca gatggtctgc | 1380 |
| tatccagttc caactgtata aaagcagctg ctgtgttctg ttaatggcac agccatcaca | 1440 |
| cgcacgcata cacagcacag agtgaggtaa gcatccgaaa aaagctgtga tctgatcgac | 1500 |

<210> SEQ ID NO 22
<211> LENGTH: 1507
<212> TYPE: DNA
<213> ORGANISM: Artificial Sequence
<220> FEATURE:
<223> OTHER INFORMATION: Synthetic construct hybrid promoter/intron

<400> SEQUENCE: 22

| | |
|---|---|
| ctgcagtgca gcgtgacccg gtcgtgcccc tctctagaga taatgagcat tgcatgtcta | 60 |
| agttataaaa aattaccaca tattttttt gtcacacttg tttgaagtgc agtttatcta | 120 |
| tctttataca tatatttaaa ctttactcta cgaataatat aatctatagt actacaataa | 180 |
| tatcagtgtt ttagagaatc atataaatga acagttagac atggtctaaa ggacaattga | 240 |
| gtattttgac aacaggactc tacagtttta tcttttagt gtgcatgtgt tctccttttt | 300 |
| ttttgcaaat agcttcacct atataatact tcatccattt tattagtaca tccatttagg | 360 |
| gtttagggtt aatggttttt atagactaat ttttttagta catctatttt attctatttt | 420 |
| agcctctaaa ttaagaaaac taaaactcta ttttagtttt tttatttaat aatttagata | 480 |
| taaaatagaa taaaataaag tgactaaaaa ttaaacaaat acccttttaag aaattaaaaa | 540 |
| aactaaggaa acatttttct tgtttcgagt agataatgcc agcctgttaa acgccgtcga | 600 |
| tcgacgagtc taacggacac caaccagcga accagcagcg tcgcgtcggg ccaagcgaag | 660 |
| cagacggcac ggcatctctg tcgctgcctc tggacccctc tcgagagttc cgctccaccg | 720 |
| ttggacttgc tccgctgtcg gcatccagaa attgcgtggc ggagcggcag acgtgagccg | 780 |
| gcacggcagg cggcctcctc ctcctctcac ggcaccggca gctacggggg attcctttcc | 840 |
| caccgctcct tcgctttccc ttcctcgccc gccgtaataa atagacaccc cctccacacc | 900 |
| ctctttcccc aacctcgtgt tgttcggagc gcacacacac acaaccagat ctcccccaaa | 960 |
| tccacccgtc ggcacctccg cttcaaggta cgccgctcgt cctccccccc ccccctctc | 1020 |
| taccttctct agatcggcgt tccggtccat ggttagggcc cggtagttct acttctgttc | 1080 |
| atgtttgtgt tagatccgtg tttgtgttag atccgtgctg ctagcgttcg tacacggatg | 1140 |
| cgacctgtac gtcagacacg ttctgattgc taacttgcca gtgtttctct ttggggaatc | 1200 |
| ctgggatggc tctagccgtt ccgcagacgg gatcgatcta ggataggtat acatgttgat | 1260 |
| gtgggttta ctgatgcata tacatgatgg catatgcagc atctattcat atgctctaac | 1320 |
| cttgagtacc tatctattat aataaacaag tatgttttat aattatttg atcttgatat | 1380 |
| acttggatga tggcatatgc agcagctata tgtggatttt tttagccctg ccttcatacg | 1440 |

```
ctatttattt gcttggtact gtttcttttg tcgatgctca ccctgttgtt tggtgttact    1500
tctgcag                                                              1507

<210> SEQ ID NO 23
<211> LENGTH: 1996
<212> TYPE: DNA
<213> ORGANISM: Zea mays

<400> SEQUENCE: 23
ctgcagtgca gcgtgacccg gtcgtgcccc tctctagaga taatgagcat tgcatgtcta     60
agttataaaa aattaccaca tattttttt gtcacacttg tttgaagtgc agtttatcta    120
tctttataca tatatttaaa ctttactcta cgaataatat aatctataaa gtactacaat    180
aatatcagtg tttagagaaa tcatataaat gaacagttag acatggtcta aaggacaatt    240
gagtattttg acaacaggac tctacagttt tatcttttta gtgtgcatgt gttctccttt    300
ttttttgcaa atagcttcac ctatataata cttcatccat tttattagta catccattta    360
gggtttaggg ttaatggttt ttatagacta attttttag tacatctatt ttattctatt    420
ttagcctcta aattaagaaa actaaaactc tattttagtt tttttattta ataatttaga    480
tataaaatag aataaaataa agtgactaaa aattaaacaa ataccettta agaaattaaa    540 aaaactaagg aaacattttt cttgtttcga gtagataatg ccagcctgtt aaacgccgtc    600
gacgagtcta acggacacca accagcgaac cagcagcgtc gcgtcgggcc aagcgaagca    660
gacggcacgg catctctgtc gctgcctctg gaccectctc gagagttccg ctccaccgtt    720
ggacttgctc cgctgtcggc atccagaaat tgcgtggcgg agcggcagac gtgagccggc    780
acggcaggcg gcctcctcct cctctcacgg caccggcagc tacggggat tccttccca    840 ccgctccttc gctttccctt cctcgcccgc cgtaataaat agacacccce tccacaccct    900 ctttccccaa cctcgtgttg ttcggagcgc acacacacac aaccagatct ccccaaatc    960 cacccgtcgg cacctccgct tcaaggtacg ccgctcgtcc tccccccccc ccctctcta    1020 ccttctctag atcggcgttc cggtccatgg ttagggcccg gtagttctac ttctgttcat    1080
gtttgtgtta gatccgtgtt tgtgttagat ccgtgctgct agcgttcgta cacggatgcg    1140
acctgtacgt cagacacgtt ctgattgcta acttgccagt gtttctcttt ggggaatcct    1200
gggatggctc tagccgttcc gcagacggga tcgatttcat gatttttttt gtttcgttgc    1260
ataggggttg gtttgccctt ttcctttatt tcaatatatg ccgtgcactt gtttgtcggg    1320
tcatcttttc atgcttttttt ttgtcttggt tgtgatgatg tggtctggtt gggcggtcgt    1380
tctagatcgg agtagaaatc tgtttcaaac tacctggtgg atttattaat tttggatctg    1440
tatgtgtgtg ccatacatat tcatagttac gaattgaaga tgatggatgg aaatatcgat    1500
ctaggatagg tatacatgtt gatgcgggtt ttactgatgc atatacagag atgcttttg    1560 ttcgcttggt tgtgatgatg tggtgtggtt gggcggtcgt tcattcgttc tagatcggag    1620
tagaatactg tttcaaacta cctggtgtat ttattaattt tggaactgta tgtgtgtgtc    1680
atacatcttc atagttacga gtttaagatg gatggaaata tcgatctagg ataggtatac    1740
atgttgatgt gggtttttact gatgcatata catgatggca tatgcagcat ctattcatat    1800
gctctaacct tgagtaccta tctattataa taaacaagta tgttttataa ttattttgat    1860
cttgatatac ttggatgatg gcatatgcag cagctatatg tggattttttt tagccctgcc    1920 ttcatacgct atttatttgc ttggtactgt ttcttttgtc gatgctcacc ctgttgtttg    1980
```

```
gtgttacttc tgcagg                                                      1996
```

<210> SEQ ID NO 24
<211> LENGTH: 1500
<212> TYPE: DNA
<213> ORGANISM: Oryza sativa

<400> SEQUENCE: 24

```
tccacctctg ttggttgcat cgacgtcgct tccctagctc ccgtctctag tccggatcct       60
attcctcctt ggagaccgaa gctaccgcaa ccattgctcg gtggttagcg agcgtggagc      120
tgtcctcccc actttcgcgt cctcgttcgc caccacagcc atacttcgca tggtgatgtc      180
ttctccttca ctcaccgcta aactcagtgc aaccgtttct accctagccc cggccgccgc      240
tctcatagag gtgaaagttc atttacatgt aggtcccaca tgttttatgt ttttttatttt     300
tcttttactg attagcatgc cacgtaaatc aaaacaacaa tccatagtgt tttaagtatt      360
tttatttaat acgtgagatg gagtacaaaa acgagagatg caaagtgaac ttgctaaaac      420
acatttctg gttgattaca gtcgcttgtt gagccattgg atcggtcata ggattcgtgc       480
tagcatactt aattacgcgt aactagttgt gctttatagg ttacaggtcg ctaattagcg      540
gtctactgga gaactttgct actattttt tcttcactgc atgcactcga tcaagtatga      600
gtatttgtac cgaccagcga acacatatg taattaaagt ataaatatgt aattagtata      660
tattagtagt atatttagac agtagttaca ccctacatac acaccactta catatataat      720
tagtatgtaa ttttgtaact tacatatgta attttagtac ttacatatgt aattttgaga      780
cttacattgt aaatacacta aaattacata tgtaatttag taacctacaa tgtaaataca      840
tgccgactaa cttttgatga aaaatatggt gttataaata tagctactcc cgaactttat      900
tccttctctg tgagatatca gtggaaacgc tcggtggaat cggggagta tttgggagca      960
cgcgccgacg cgcgcgtcgt gcgtgccgtc gtctttgtcg cggtggagcg gagcgcgccc     1020
acttgcgcgc ctgggccgga ggcgggcgcg ccggggttc gggaatcccc tggagccaca     1080
cgtaaaggcg cgggcgggag ggagggaggg gccagctagg ataaggcacg cgcggccgct     1140
gcgattgggg cgcttgtgaa caccggggcg ccacgtggag aggacgttac actccagccg     1200
ccaaatttcc actcccacac ccgcgctccc ctcccctctc ttttccgtga tcgcacctcg     1260
cccacgcgcc ccccgccaca cacaatctct gcagctctcc agcttcgttg gaactcgcga     1320
atctctctcc gatcccaggt aaagcagcga acgacgtcac gcacgacgct gctcggtgga     1380
tttcgttcct tgctggggaa aaccatgcag agacgaaggt gaatgatctg ctttttgtgta    1440
cttgcgttta ccaggtgaag cgcgagcttg gagttggagg ggagatcgat cagggccagg     1500
```

<210> SEQ ID NO 25
<211> LENGTH: 1500
<212> TYPE: DNA
<213> ORGANISM: Zea mays

<400> SEQUENCE: 25

```
cgagaatata tgttatcttc gtcgttagag aaatctagac agtatacaac aagatccacg       60
tactacaggt aaacttttag gggtattgtg aacaagagga tgagtaaact ctaaaagaac      120
aaagctccaa tgaaaattta ggttttatg tggttagtca tagggcaagt tgcaaacagg      180
tgttgatcta aaaaggaagt agtagggaaa tgtgaagtgt ctttgcgagg aattggaaaa     240
tgaagatcac atttttctttg ggtgcatcat gggaagaacc atttgggact cttttaagga    300
ggcctaagaa tgccataaag tttgcaagat ctttttgaag agtgtctacc tataaacaat     360
```

```
agtaaatatc atgtcaaaat tttcatcttc gccattattc tttaggagaa tttagaatgt      420
tccgaataaa atatggatag aaaagaagtt cccaaagtca tccaatttc tacaaaatct       480 tcaactttaa gattgagagt gggtgttgta aagttcttgg aagatgagtt gaaccccatg      540
gaggcgttgg ctaaagtact gaaagcaatc taaagacatg gaggtggaag gcctgacgta     600
gatagagaag atgctcttag ctttcattgt ctttcttttg tagtcatctg atttacctct      660
ctcgtttata caactggttt tttaaacact ccttaacttt tcaaattgtc tcttcttta       720 ccctagacta gataatttta atggtgattt tgctaatgtg gcgccatgtt agatagaggt      780
aaaatgaact agttaaaagc tcagagtgat aaatcaggct ctcaaaaatt cataaactgt      840
tttttaaata tccaaatatt tttacatgga aaataataaa atttagttta gtattaaaaa      900
attcagttga atatagtttt gtcttcaaaa attatgaaac tgatcttaat tatttttcct      960
taaaaccgtg ctctatcttt gatgtctagt ttgagacgat tatataattt tttttgtgct     1020
taactacgac gagctgaagt acgtagaaat actagtggag tcgtgccgcg tgtgcctgta     1080
gccactcgta cgctacagcc caagcgctag agcccaagag gccggaggtg aaggcgtcg      1140 cggcactata gccactcgcc gcaagagccc aagaggccgg agctggaagg atgagggtct     1200
gggtgttcac gaattgcctg gaggcaggag gctcgtcgtc cggagccaca ggcgtggaga     1260
cgtccgggat aaggtgagca gccgctgcga taggggcgcg tgtgaacccc gtcgcgcccc     1320
acggatggta taagaataaa ggcattccgc gtgcaggatt cacccgttcg cctctcacct    1380
tttcgctgta ctcactcgcc acacacaccc cctctccagc tccgttggag ctccggacag    1440
cagcaggcgc ggggcggtca cgtagtaagc agctctcggc tccctctccc cttgctccat    1500

<210> SEQ ID NO 26
<211> LENGTH: 1500
<212> TYPE: DNA
<213> ORGANISM: Oryza sativa

<400> SEQUENCE: 26
ataattaatt aattaatcaa tcacttttcg tgctgtaaaa aatctcaccc gatttgctga       60
aacgaactga gccgggcgac tgtgatattc tttcacgatt tctgtttgtg gcagtgggac     120
attgctgttt attcgaaaca attttcaagt aaaaaaaaat actcaatggt aaggttgcta     180
gtaatagttt aacagtttgt ttgcagctca gcaaatttcg tttcctcaca gatgacacat     240
aactgaaagc actcaatgta atgttgtgct tagctgctaa agcatgtcac gtcttagaaa     300
acaactactc caccatggag aatttttcct cctacttact cctcacatac ttaccatctc     360
catataagtt cccttgtcgt atcatatgtc ttattcttct tgagcacagt tattacagca     420
gattttgtag aatagttatc gcatcaaaat tttcctatgt caccttttgat catgtgttat   480 gtgtgcctct tgagtcttag ggttaatgtg gttgtaatgt gtttaaaaaa ctatatgaaa     540
gctcgtgtgt tgctacggga gagagatacc tcgaatgaat gtgagagatc tccatttgag    600
ttgtgtacct tgagagagtg aaagatcaca ctatttatag acggttaata atggttactg      660
aggtcgattc accacatcgt cttaaacatt taatgagcat cctccacgtg aaaagtagag     720
atgatagcgt gtaagagtgg ttcggccgat atccctcagc cgccttcac tatcttttt       780 gcccgagtca ttgtcatgtg aaccttggca tgtataatcg gtgaattgcg tcgattttcc     840
tcttataggt gggccaatga atccgtgtga tcgcgtctga ttggctagag atatgtttct     900
tccttgttgg atgtatttc atacataatc atatgcatac aaatatttca ttacacttta      960
```

| | |
|---|---:|
| tagaaatggt cagtaataaa ccctatcact atgtctggtg tttcatttta tttgctttta | 1020 |
| aacgaaaatt gacttcctga ttcaatattt aaggatcgtc aacggtgtgc agttactaaa | 1080 |
| ttctggtttg taggaactat agtaaactat tcaagtcttc acttattgtg cactcacctc | 1140 |
| tcgccacatc accacagatg ttattcacgt cttaaatttg aactacacat catattgaca | 1200 |
| caatattttt tttaaataag cgattaaaac ctagcctcta tgtcaacaat ggtgtacata | 1260 |
| accagcgaag tttagggagt aaaaaacatc gccttacaca aagttcgctt taaaaaataa | 1320 |
| agagtaaatt ttactttgga ccaccccttca accaatgttt cactttagaa cgagtaattt | 1380 |
| tattattgtc actttggacc accctcaaat ctttttttcca tctacatcca atttatcatg | 1440 |
| tcaaagaaat ggtctacata cagctaagga gatttatcga cgaatagtag ctagcataag | 1500 |

<210> SEQ ID NO 27
<211> LENGTH: 1500
<212> TYPE: DNA
<213> ORGANISM: Zea mays

<400> SEQUENCE: 27

| | |
|---|---:|
| cgataagaac aatgttggac acaacttaag tctgttttac aacaatgtct ctcaaaacta | 60 |
| tagttttaca atattatact ttgcaattat catgacaata atgtagtttc ggtagctcca | 120 |
| aaaatacagt agttttgaga acattgtttt agatacaata ttataaatca tgtattagac | 180 |
| aaaagatagc catgccatta aaactttgaa ttggactgta gttttttcaa tactccaaaa | 240 |
| atattatggt acctagaata cgatgtctag aaaacatatt ttttaaaatg caaccaaaca | 300 |
| tcatatgaca taaataatat agtatttttt tgaaaaccat ggtattacct aaaaaactaca | 360 |
| gaatacttca ttctgaaata ggtcctaaca agttgcagca gctaggtcgt acatcagcaa | 420 |
| atagctactt catcaatctc agaataaaca tattttatag atgagttaaa ctaaaaatat | 480 |
| agaagaacaa cgtacacgcg ttgaatcaca acgtagcgcg atatccattc aacttttttgg | 540 |
| aagttttttac tgagcacaaa ttcgaaaatg ggaagcgcca cgtaacacga gcgctgggcc | 600 |
| aatttctgcc agtgccagtt atcccggccc acatccaatc ctggggaaga cgcgaacccg | 660 |
| gctccgcggc acgagttgtc cgcacgtacg gcacgtcggg gctggctcgt ccgcccgcga | 720 |
| gtgggaggcc actgtttcct ctgcctcacc gggtcgtgtg gcggaggggc gtgggccat | 780 |
| ggttcgcagc gcggggcgac gagcgcgctc ctcctctcgc gcagcgccag cgccaccccg | 840 |
| caccgtggct ttatatacac ccctcctccc aaccctaccg aatcatcact accaccgctc | 900 |
| tctcttcctc tcctccatct ctcaacgcct gaagctcacc gcacctcccc tcctcgccgc | 960 |
| ggatccccca ctactccggt aaccgtctct ccattcaccc tgcctgctgt ctcgctagaa | 1020 |
| tcgcctgcct ctgccagcgc cgtgacgcgg gggcgcggta tggctctccc agatccgcct | 1080 |
| ggcattgctc gctcgggtcg tgccaggccg atctgatctc gcatttgctg cgcgctcctc | 1140 |
| ctgctgcgga tcccaccgga tctcgctgga atcggagcgc gcgtctcttt gaaatgccgc | 1200 |
| agatctgcgt gcttgcgcgc gtgatctaag tccgggcctt tcgttaacga aatggtccga | 1260 |
| tctgtggttt ggtggaggca atgccatggt ttttcccgt gaatttttt tgctgatttt | 1320 |
| aggagctttt ttctactgtc ctatgttagt aggacaaaaa aaagaaaca tagattagct | 1380 |
| tcaataggcg ccttttagaa cagattctgt acagcaactc gtggaaacaa atctgcttcc | 1440 |
| ttaatgatgt tgcttgtttt aacaaatgcg gcatcgggcg agcttttctg taggtagaaa | 1500 |

<210> SEQ ID NO 28
<211> LENGTH: 1694

```
<212> TYPE: DNA
<213> ORGANISM: Artificial Sequence
<220> FEATURE:
<223> OTHER INFORMATION: Synthetic construct hybrid cab5/hsp70 intron
      promoter

<400> SEQUENCE: 28
cacggaagat ccaggtctcg agactaggag acggatggga ggcgcaacgc gcgatgggga      60 gggggcggc gctgaccttt ctggcgaggt cgaggtagcg atcgagcagc tgcagcgcgg     120
acacgatgag gaagacgaag atagccgcca tggacatgtt cgccagcggc ggcggagcga    180
ggctgagccg gtctctccgg cctccggtcg gcgttaagtt ggggatcgta acgtgacgtg    240
tctcgtctcc acggatcgac acaaccggcc tactcgggtg cacgacgccg cgataagggc    300
gagatgtccg tgcacgcagc ccgtttggag tcctcgttgc ccacgaaccg accccttaca    360
gaacaaggcc tagcccaaaa ctattctgag ttgagctttt gagcctagcc cacctaagcc    420
gagcgtcatg aactgatgaa cccactacca ctagtcaagg caaaccacaa ccacaaatgg    480
atcaattgat ctagaacaat ccgaaggagg ggaggccacg tcacactcac accaaccgaa    540
atatctgcca gaatcagatc aaccggccaa taggacgcca gcgagcccaa cacctggcga    600
cgccgcaaaa ttcaccgcga ggggcaccgg gcacggcaaa aacaaaagcc cggcgcggtg    660
agaatatctg gcgactggcg gagacctggt ggccagcgcg cggccacatc agccacccca    720
tccgcccacc tcacctccgg cgagccaatg gcaactcgtc ttaagattcc acgagataag    780
gacccgatcg ccggcgacgc tatttagcca ggtgcgcccc ccacggtaca ctccaccagc    840
ggcatctata gcaaccggtc cagcactttc acgctcagct tcagcaagat ctaccgtctt    900
cggtacgcgc tcactccgcc ctctgccttt gttactgcca cgtttctctg aatgctctct    960
tgtatggtga ttgctgagag tggtttagct ggatctagaa ttcacactctg aaatcgtgtt   1020 ctgcctgtgc tgattacttg ccgtccttg tagcagcaaa atatagggac atggtagtac    1080
gaaacgaaga tagaacctac acagcaatac gagaaatgtg taatttggtg catacggtat    1140
ttatttaagc acctgttgct gctatagggc acttgtattc agaagtttgc tgttaattta    1200
ggcacaggct tcatactaca tgggtcaata gtatagggat tcatattata ggcgatacta    1260
taataatttg ttcgtctgca gagcttatta tttgccaaaa ttagatattc ctattctgtt    1320
tttgtttgtg tgctgttaaa ttgttaacgc ctgaaggaat aaatataaat gacgaaattt    1380
tgatgtttat ctctgctcct ttattgtgac gataagtcaa gatcagatgc acttgtttta    1440
aatattgttg tctgaagaaa taagtactga cagtttttg atgcattgat ctgcttgttt     1500
gttgtaacaa aattttaaaa taaagagttc ccttttttgtt gctctcctta cctcctgatg   1560
gtatctagta tctaccaact gatactatat tgcttctctt tacatacgta tcttgctcga    1620
tgccttctcc tagtgttgac cagtgttact cacatagtct ttgctcattt cattgtaatg    1680
cagataccaa gcgg                                                      1694

<210> SEQ ID NO 29
<211> LENGTH: 15629
<212> TYPE: DNA
<213> ORGANISM: Artificial Sequence
<220> FEATURE:
<223> OTHER INFORMATION: Synthetic construct pMBXS394 transformation
      vector

<400> SEQUENCE: 29
ggggatccgt acgtaagtac gtactcaaaa tgccaacaaa taaaaaaaaa gttgctttaa      60
```

```
taatgccaaa acaaattaat aaaacactta caacaccgga ttttttttaa ttaaaatgtg    120
ccatttagga taaatagtta atatttttaa taattattta aaaagccgta tctactaaaa    180
tgatttttat ttggttgaaa atattaatat gtttaaatca acacaatcta tcaaaattaa    240
actaaaaaaa aaataagtgt acgtggttaa cattagtaca gtaatataag aggaaaatga    300
gaaattaaga aattgaaagc gagtctaatt tttaaattat gaacctgcat atataaaagg    360
aaagaaagaa tccaggaaga aaagaaatga aaccatgcat ggtcccctcg tcatcacgag    420
tttctgccat ttgcaataga aacactgaaa cacctttctc tttgtcactt aattgagatg    480
ccgaagccac ctcacaccat gaacttcatg aggtgtagca cccaaggctt ccatagccat    540
gcatactgaa gaatgtctca agctcagcac cctacttctg tgacgtgtcc ctcattcacc    600
ttcctctctt ccctataaat aaccacgcct caggttctcc gcttcacaac tcaaacattc    660
tctccattgg tccttaaaca ctcatcagtc atcaccgcgg ccgcgaaaat gactgacgtt    720
gtcatcgtat ccgccgcccg caccgcggtc ggcaagtttg gcggctcgct ggccaagatc    780
ccggcaccgg aactgggtgc cgtggtcatc aaggccgcgc tggagcgcgc cggcgtcaag    840
ccggagcagg tgagcgaagt catcatgggc caggtgctga ccgccggttc gggccagaac    900
cccgcacgcc aggccgcgat caaggccggc ctgccggcga tggtgccggc catgaccatc    960
aacaaggtgt gcggctcggg cctgaaggcc gtgatgctgg ccgccaacgc gatcatggcg   1020
ggcgacgccg agatcgtggt ggccggcggc caggaaaaca tgagcgccgc cccgcacgtg   1080
ctgccgggct cgcgcgatgg tttccgcatg ggcgatgcca agctggtcga caccatgatc   1140
gtcgacggcc tgtgggacgt gtacaaccag taccacatgg gcatcaccgc cgagaacgtg   1200
gccaaggaat acggcatcac acgcgaggcg caggatgagt cgccgtcgg ctcgcagaac   1260 aaggccgaag ccgcgcagaa ggccggcaag tttgacgaag atcgtcccc ggtgctgatc   1320 ccgcagcgca agggcgaccc ggtggccttc aagaccgacg agttcgtgcg ccagggcgcc   1380
acgctggaca gcatgtccgg cctcaagccc gccttcgaca aggccggcac ggtgactgcg   1440
gccaacgcct cgggcctgaa cgacggcgcc gccgcggtgg tggtgatgtc ggcggccaag   1500
gccaaggaac tgggcctgac cccgctggcc acgatcaaga gctatgccaa cgccggtgtc   1560
gatcccaagg tgatgggcat gggcccggtg ccggcctcca gcgcgccct gtcgcgcgcc   1620 gagtggaccc cgcaagacct ggacctgatg gagatcaacg aggcctttgc gcgcaggcg   1680 ctggcggtgc accagcagat gggctgggac acctccaagg tcaatgtgaa cggcggcgcc   1740
atcgccatcg gccacccgat cggcgcgtcg ggctgccgta tcctggtgac gctgctgcac   1800
gagatgaagc gccgtgacgc gaagaagggc ctggcctcgc tgtgcatcgg cggcggcatg   1860
ggcgtggcgc tggcagtcga gcgcaaataa ctcgaggcgg ccgcagccct ttttgtatgt   1920
gctaccccac ttttgtcttt ttggcaatag tgctagcaac caataaataa taataataat   1980
aatgaataag aaaacaaagg ctttagcttg ccttttgttc actgtaaaat aataatgtaa   2040
gtactctcta taatgagtca cgaaactttt gcgggaataa aaggagaaat tccaatgagt   2100
tttctgtcaa atcttctttt gtctctctct ctctctcttt ttttttttc tttcttctga   2160 gcttcttgca aaacaaaagg caaacaataa cgattggtcc aatgatagtt agcttgatcg   2220
atgatatctt taggaagtgt tggcaggaca ggacatgatg tagaagacta aaattgaaag   2280
tattgcagac ccaatagttg aagattaact ttaagaatga agacgtctta tcaggttctt   2340
catgacttaa gctttaagag gagtccacca tggtagatct gactagaaat gaattcgtaa   2400
tcatgtcata gctgtttcct gtgtgaaatt gttatccgct cacaattcca cacaacatac   2460
```

```
gagccggaag cataaagtgt aaagcctggg gtgcctaatg agtgagctaa ctcacattaa    2520
ttgcgttgcg ctcactgccc gctttccagt cgggaaacct gtcgtgccag ctgcattaat    2580
gaatcggcca acgcgcgggg agaggcggtt tgcgtattgg ctagagcagc ttgccaacat    2640
ggtggagcac gacactctcg tctactccaa gaatatcaaa gatacagtct cagaagacca    2700
aagggctatt gagactttc aacaaagggt aatatcggga aacctcctcg gattccattg     2760
cccagctatc tgtcacttca tcaaaaggac agtagaaaag gaaggtggca cctacaaatg    2820
ccatcattgc gataaaggaa aggctatcgt tcaagatgcc tctgccgaca gtggtcccaa    2880
agatggaccc ccaccacga ggagcatcgt ggaaaaagaa gacgttccaa ccacgtcttc     2940
aaagcaagtg gattgatgtg aacatggtgg agcacgacac tctcgtctac tccaagaata   3000
tcaaagatac agtctcagaa gaccaaaggg ctattgagac ttttcaacaa agggtaatat   3060
cgggaaacct cctcggattc cattgcccag ctatctgtca cttcatcaaa aggacagtag   3120
aaaaggaagg tggcacctac aaatgccatc attgcgataa aggaaaggct atcgttcaag   3180
atgcctctgc cgacagtggt cccaaagatg gacccccacc cacgaggagc atcgtggaaa   3240
aagaagacgt tccaaccacg tcttcaaagc aagtggattg atgtgatatc tccactgacg   3300
taagggatga cgcacaatcc cactatcctt cgcaagaccc ttcctctata taggaagtt    3360
catttcattt ggagaggaca cgctgaaatc accagtctct ctctacaaat ctatctctct   3420
cgagaaaatg gcctcctccg agaacgtcat caccgagttc atgcgcttca aggtgcgcat   3480
ggagggcacc gtgaacggcc acgagttcga gatcgagggc gagggcgagg ccgcccccta   3540
cgagggccac aacaccgtga agctgaaggt gaccaagggc ggccccctgc cttcgcctg    3600
ggacatcctg tccccccagt tccagtacgg ctccaaggtg tacgtgaagc accccgccga   3660
catccccgac tacaagaagc tgtccttccc cgagggcttc aagtgggagc gcgtgatgaa   3720
cttcgaggac ggcggcgtgg cgaccgtgac ccaggactcc tccctgcagg acggctgctt   3780
catctacaag gtgaagttca tcggcgtgaa cttcccctcc gacggccccg tgatgcagaa   3840
gaagaccatg ggctgggagg cctccaccga gcgcctgtac cccgcgacg gcgtgctgaa    3900
gggcgagacc cacaaggccc tgaagctgaa ggacggcggc cactacctgg tggagttcaa   3960
gtccatctac atggccaaga gcccgtgca gctgccggc tactactacg tggacgccaa     4020
gctggacatc acctcccaca acgaggacta caccatcgtg gagcagtacg agcgcaccga   4080
gggccgccac cacctgttcc tggtaccctg agctcggtca cctgtccaac agtctcaggg   4140
ttaatgtcta tgtatcttaa ataatgttgt cggcgatcgt tcaaacattt ggcaataaag   4200
tttcttaaga ttgaatcctg ttgccggtct tgcgatgatt atcatataat ttctgttgaa   4260
ttacgttaag catgtaataa ttaacatgta atgcatgacg ttatttatga gatgggtttt   4320
tatgattaga gtcccgcaat tatacattta atacgcgata gaaaacaaaa tatagcgcgc   4380
aaactaggat aaattatcgc gcgcggtgtc atctatgtta ctagatcggg aattaaacta   4440
tcagtgtttg acaggatata ttggcgggta aacctaagag aaaagagcgt ttattagaat   4500
aatcggatat ttaaaagggc gtgaaaaggt ttatccgttc gtccatttgt atgtgcatgc   4560
caaccacagg gttcccctcg ggatcaaagt actttgatcc aaccccctcc gctgctatagt  4620
gcagtcggct tctgacgttc agtgcagccg tcttctgaaa acgacatgtc gcacaagtcc   4680
taagttacgc gacaggctgc cgccctgccc ttttcctggc gttttcttgt cgcgtgtttt   4740
agtcgcataa agtagaatac ttgcgactag aaccggagac attacgccat gaacaagagc   4800
```

```
gccgccgctg gcctgctggg ctatgcccgc gtcagcaccg acgaccagga cttgaccaac    4860 caacgggcc  aactgcacgc ggccggctgc accaagctgt tttccgagaa gatcaccggc    4920
accaggcgcg accgcccgga gctggccagg atgcttgacc acctacgccc tggcgacgtt    4980
gtgacagtga ccaggctaga ccgcctggcc cgcagcaccc gcgacctact ggacattgcc    5040
gagcgcatcc aggaggccgg cgcgggcctg cgtagcctgg cagagccgtg ggccgacacc    5100
accacgccgg ccggccgcat ggtgttgacc gtgttcgccg gcattgccga gttcgagcgt    5160
tccctaatca tcgaccgcac ccggagcggg cgcgaggccg ccaaggcccg aggcgtgaag    5220
tttggccccc gccctaccct caccccggca cagatcgcgc acgcccgcga gctgatcgac    5280
caggaaggcc gcaccgtgaa agaggcggct gcactgcttg gcgtgcatcg ctcgaccctg    5340
taccgcgcac ttgagcgcag cgaggaagtg acgcccaccg aggccaggcg gcgcggtgcc    5400
ttccgtgagg acgcattgac cgaggccgac gccctggcgg ccgccgagaa tgaacgccaa    5460
gaggaacaag catgaaaccg caccaggacg gccaggacga accgtttttc attaccgaag    5520
agatcgaggc ggagatgatc gcggccgggt acgtgttcga gccgcccgcg cacgtctcaa    5580
ccgtgcggct gcatgaaaatc ctggccggtt tgtctgatgc caagctggcg gcctggccgg    5640
ccagcttggc cgctgaagaa accgagcgcc gccgtctaaa aaggtgatgt gtatttgagt    5700
aaaacagctt gcgtcatgcg gtcgctgcgt atatgatgcg atgagtaaat aaacaaatac    5760
gcaaggggaa cgcatgaagg ttatcgctgt acttaaccag aaaggcgggt caggcaagac    5820
gaccatcgca acccatctag cccgcgccct gcaactcgcc ggggccgatg ttctgttagt    5880
cgattccgat ccccagggca gtgcccgcga ttgggcggcc gtgcgggaag atcaaccgct    5940
aaccgttgtc ggcatcgacc gcccgacgat tgaccgcgac gtgaaggcca tcggccggcg    6000
cgacttcgta gtgatcgacg gagcgcccca ggcggcggac ttggctgtgt ccgcgatcaa    6060
ggcagccgac ttcgtgctga ttccggtgca gccaagccct tacgacatat gggccaccgc    6120
cgacctggtg gagctggtta agcagcgcat tgaggtcacg gatggaaggc tacaagcggc    6180
ctttgtcgtg tcgcgggcga tcaaaggcac gcgcatcggc ggtgaggttg ccgaggcgct    6240
ggccgggtac gagctgccca ttcttgagtc ccgtatcacg cagcgcgtga gctacccagg    6300
cactgccgcc gccggcacaa ccgttcttga atcagaaccc gagggcgacg ctgcccgcga    6360
ggtccaggcg ctggccgctg aaattaaatc aaaactcatt tgagttaatg aggtaaagag    6420
aaaatgagca aaagcacaaa cacgctaagt gccggccgtc cgagcgcacg cagcagcaag    6480
gctgcaacgt tggccagcct ggcagacacg ccagccatga agcgggtcaa ctttcagttg    6540
ccggcggagg atcacaccaa gctgaagatg tacgcggtac gccaaggcaa gaccattacc    6600
gagctgctat ctgaatacat cgcgcagcta ccagagtaaa tgagcaaatg aataaatgag    6660
tagatgaatt ttagcggcta aaggaggcgg catggaaaat caagaacaac caggcaccga    6720
cgccgtggaa tgccccatgt gtggaggaac gggcggttgg ccaggcgtaa gcggctgggt    6780
tgtctgccgg ccctgcaatg gcactggaac ccccaagccc gaggaatcgg cgtgacggtc    6840
gcaaaccatc cggcccggta caaatcggcg cggcgctggg tgatgacctg gtggagaagt    6900
tgaaggccgc gcaggccgcc cagcggcaac gcatcgaggc agaagcacgc cccggtgaat    6960
cgtggcaagc ggccgctgat cgaatccgca aagaatcccg gcaaccgccg cagccggtg    7020 cgccgtcgat taggaagccg cccaagggcg acgagcaacc agattttttc gttccgatgc    7080
tctatgacgt gggcacccgc gatagtcgca gcatcatgga cgtggccgtt ttccgtctgt    7140
cgaagcgtga ccgacgagct ggcgaggtga tccgctacga gcttccagac gggcacgtag    7200
```

```
aggtttccgc agggccggcc ggcatggcca gtgtgtggga ttacgacctg gtactgatgg    7260
cggtttccca tctaaccgaa tccatgaacc gataccggga agggaaggga gacaagcccg    7320
gccgcgtgtt ccgtccacac gttgcggacg tactcaagtt ctgccggcga gccgatggcg    7380
gaaagcagaa agacgacctg gtagaaacct gcattcggtt aaacaccacg cacgttgcca    7440
tgcagcgtac gaagaaggcc aagaacggcc gcctggtgac ggtatccgag ggtgaagcct    7500
tgattagccg ctacaagatc gtaaagagcg aaaccgggcg gccggagtac atcgagatcg    7560
agctagctga ttggatgtac cgcgagatca cagaaggcaa gaacccggac gtgctgacgg    7620
ttcaccccga ttacttttg atcgatcccg gcatcggccg ttttctctac cgcctggcac    7680
gccgcgccgc aggcaaggca gaagccagat ggttgttcaa gacgatctac gaacgcagtg    7740
gcagcgccga gagttcaag aagttctgtt tcaccgtgcg caagctgatc gggtcaaatg    7800
acctgccgga gtacgatttg aaggaggagg cggggcaggc tggcccgatc ctagtcatgc    7860
gctaccgcaa cctgatcgag ggcgaagcat ccgccggttc ctaatgtacg gagcagatgc    7920
tagggcaaat tgccctagca ggggaaaaag gtcgaaaagg tctctttcct gtggatagca    7980
cgtacattgg gaacccaaag ccgtacattg gaaccggaa cccgtacatt gggaacccaa    8040
agccgtacat tgggaaccgg tcacacatgt aagtgactga tataaaagag aaaaaaggcg    8100
attttccgc ctaaaactct ttaaaactta ttaaaactct taaaacccgc ctggcctgtg    8160
cataactgtc tggccagcgc acagccgaag agctgcaaaa agcgcctacc cttcggtcgc    8220
tgcgctccct acgccccgcc gcttcgcgtc ggcctatcgc ggccgctggc cgctcaaaaa    8280
tggctggcct acggccaggc aatctaccag ggcgcggaca agccgcgccg tcgccactcg    8340
accgccggcg cccacatcaa ggcaccctgc ctcgcgcgtt tcggtgatga cggtgaaaac    8400
ctctgacaca tgcagctccc ggagacggtc acagcttgtc tgtaagcgga tgccgggagc    8460
agacaagccc gtcagggcgc gtcagcgggt gttggcgggt gtcggggcgc agccatgacc    8520
cagtcacgta gcgatagcgg agtgtatact ggcttaacta tgcggcatca gagcagattg    8580
tactgagagt gcaccatatg cggtgtgaaa taccgcacag atgcgtaagg agaaaatacc    8640
gcatcaggcg ctcttccgct tcctcgctca ctgactcgct gcgctcggtc gttcggctgc    8700
ggcgagcggt atcagctcac tcaaaggcgg taatacggtt atccacagaa tcaggggata    8760
acgcaggaaa gaacatgtga gcaaaaggcc agcaaaaggc caggaaccgt aaaaaggccg    8820
cgttgctggc gtttttccat aggctccgcc cccctgacga gcatcacaaa aatcgacgct    8880
caagtcagag gtggcgaaac ccgacaggac tataaagata ccaggcgttt ccccctggaa    8940
gctccctcgt gcgctctcct gttccgaccc tgccgcttac cggatacctg tccgcctttc    9000
tcccttcggg aagcgtggcg ctttctcata gctcacgctg taggtatctc agttcggtgt    9060
aggtcgttcg ctccaagctg ggctgtgtgc acgaaccccc cgttcagccc gaccgctgcg    9120
ccttatccgg taactatcgt cttgagtcca acccggtaag acacgactta tcgccactgg    9180
cagcagccac tggtaacagg attagcagag cgaggtatgt aggcggtgct acagagttct    9240
tgaagtggtg gcctaactac ggctacacta aaggacagt atttggtatc tgcgctctgc    9300
tgaagccagt taccttcgga aaaagagttg gtagctcttg atccggcaaa caaaccaccg    9360
ctggtagcgg tggttttttt gtttgcaagc agcagattac gcgcagaaaa aaaggatctc    9420
aagaagatcc tttgatcttt tctacggggt ctgacgctca gtggaacgaa aactcacgtt    9480
aagggatttt ggtcatgcat tctaggtact aaaacaattc atccagtaaa atataatatt    9540
```

```
ttattttctc ccaatcaggc ttgatcccca gtaagtcaaa aaatagctcg acatactgtt    9600
cttccccgat atcctccctg atcgaccgga cgcagaaggc aatgtcatac cacttgtccg    9660
ccctgccgct tctcccaaga tcaataaagc cacttacttt gccatcttcc acaaagatgt    9720
tgctgtctcc caggtcgccg tgggaaaaga caagttcctc ttcgggcttt tccgtcttta    9780
aaaaatcata cagctcgcgc ggatctttaa atggagtgtc ttcttcccag ttttcgcaat    9840
ccacatcggc cagatcgtta ttcagtaagt aatccaattc ggctaagcgg ctgtctaagc    9900
tattcgtata gggacaatcc gatatgtcga tggagtgaaa gagcctgatg cactccgcat    9960
acagctcgat aatctttcca gggctttgtt catcttcata ctcttccgag caaaggacgc   10020
catcggcctc actcatgagc agattgctcc agccatcatg ccgttcaaag tgcaggacct   10080
ttggaacagg cagcttccct tccagccata gcatcatgtc cttttcccgt tccacatcat   10140
aggtggtccc tttataccgg ctgtccgtca ttttttaaata taggttttca ttttctccca   10200
ccagcttata taccttagca ggagacattc cttccgtatc ttttacgcag cggtattttt   10260
cgatcagttt tttcaattcc ggtgatattc tcattttagc catttattat ttccttcctc   10320
ttttctacag tatttaaaga tacccccaaga agctaattat aacaagacga actccaattc   10380
actgttcctt gcattctaaa accttaaata ccagaaaaca gcttttcaa agttgttttc   10440
aaagttggcg tataacatag tatcgacgga gccgattttg aaaccgcggt gatcacaggc   10500
agcaacgctc tgtcatcgtt acaatcaaca tgctaccctc cgcgagatca tccgtgtttc   10560
aaacccggca gcttagttgc cgttcttccg aatagcatcg gtaacatgag caaagtctgc   10620
cgccttacaa cggctctccc gctgacgccg tcccggactg atgggctgcc tgtatcgagt   10680
ggtgattttg tgccgagctg ccggtcgggg agctgttggc tggctggtgg caggatatat   10740
tgtggtgtaa acaaattgac gcttagacaa cttaataaca cattgcggac gttttttaatg   10800
tactgaatta acgccgaatt aattcctagg gtacgtagtg tttatctttg ttgcttttct   10860
gaacaattta tttactatgt aaatatatta tcaatgttta atctatttta atttgcacat   10920
gaattttcat tttatttttta ctttacaaaa caaataaata tatatgcaaa aaaatttaca   10980
aacgatgcac gggttacaaa ctaatttcat taaatgctaa tgcagatttt gtgaagtaaa   11040
actccaatta tgatgaaaaa taccaccaac accacctgcg aaactgtatc ccaactgtcc   11100
ttaataaaaa tgttaaaaag tatattattc tcatttgtct gtcataattt atgtaccccca   11160
cttttaatttt tctgatgtac taaaccgagg gcaaactgaa acctgttcct catgcaaagc   11220
ccctactcac catgtatcat gtacgtgtca tcacccaaca actccacttt tgctatataa   11280
caacaccccc gtcacactct ccctctctaa cacacacccc actaacaatt ccttcacttg   11340
cagcactgtt gcatcatcat cttcattgca aaaccctaaa cttcaccttc aaccgcggcc   11400
gcatgagtaa caagaacaac gatgagctgc agtggcaatc ctggttcagc aaggcgccca   11460
ccaccgaggc gaacccgatg gccaccatgt tgcaggatat cggcgttgcg ctcaaaccgg   11520
aagcgatgga gcagctgaaa aacgattatc tgcgtgactt caccgcgttg tggcaggatt   11580
ttttggctgg caaggcgcca gccgtcagcg accgccgctt cagctcggca gcctggcagg   11640
gcaatccgat gtcggccttc aatgccgcat cttacctgct caacgccaaa ttcctcagtg   11700
ccatggtgga ggcggtggac accgcacccc agcaaaagca gaaaatacgc tttgccgtgc   11760
agcaggtgat tgatgccatg tcgcccgcga acttcctcgc caccaacccg gaagcgcagc   11820
aaaaactgat tgaaaccaag ggcgagagcc tgacgcgtgg cctggtcaat atgctgggcg   11880
atatcaacaa gggccatatc tcgctgtcgg acgaatcggc ctttgaagtg ggccgcaacc   11940
```

```
tggccattac cccgggcacc gtgatttacg aaaatccgct gttccagctg atccagtaca   12000
cgccgaccac gccgacggtc agccagcgcc cgctgttgat ggtgccgccg tgcatcaaca   12060
agttctacat cctcgacctg caaccggaaa attcgctggt gcgctacgcg gtggagcagg   12120
gcaacaccgt gttcctgatc tcgtggagca atccggacaa gtcgctggcc ggcaccacct   12180
gggacgacta cgtggagcag ggcgtgatcg aagcgatccg catcgtccag gacgtcagcg   12240
gccaggacaa gctgaacatg ttcggcttct gcgtgggcgg caccatcgtt gccaccgcac   12300
tggcggtact ggcggcgcgt ggccagcacc cggcggccag cctgaccctg ctgaccacct   12360
tcctcgactt cagcgacacc ggcgtgctcg acgtcttcgt cgatgaaacc caggtcgcgc   12420
tgcgtgaaca gcaattgcgc gatggcggcc tgatgccggg ccgtgacctg gcctcgacct   12480
tctcgagcct cgctccgaac gacctggtat ggaactatgt gcagtcgaac tacctcaaag   12540
gcaatgagcc ggcggcgttt gacctgctgt tctggaattc ggacagcacc aatttgccgg   12600
gcccgatgtt ctgctggtac ctgcgcaaca cctacctgga aaacagcctg aaagtgccgg   12660
gcaagctgac ggtggccggc gaaaagatcg acctcggcct gatcgacgcc ccggccttca   12720
tctacggttc gcgcgaagac cacatcgtgc cgtggatgtc ggcgtacggt tcgctcgaca   12780
tcctcaacca gggcaagccg ggcgccaacc gcttcgtgct gggcgcgtcc ggccatatcg   12840
ccggcgtgat caactcggtg gccaagaaca agcgcagcta ctggatcaac gacggtggcg   12900
ccgccgatgc ccaggcctgg ttcgatggcg cgcaggaagt gccgggcagc tggtggccgc   12960
aatgggccgg gttcctgacc cagcatggcg gcaagaaggt caagcccaag gccaagcccg   13020
gcaacgcccg ctacaccgcg atcgaggcgg cgcccggccg ttacgtcaaa gccaagggct   13080
gagcggccgc tgagtaattc tgatattaga gggagcatta atgtgttgtt gtgatgtggt   13140
ttatatgggg aaattaaata aatgatgtat gtacctcttg cctatgtagg tttgtgtgtt   13200
ttgttttgtt gtctagcttt ggttattaag tagtagggac gttcgttcgt gtctcaaaaa   13260
aagggtact accactctgt agtgtatatg gatgctggaa atcaatgtgt tttgtatttg   13320
ttcacctcca ttgttgaatt caatgtcaaa tgtgttttgc gttggttatg tgtaaaatta   13380
ctatctttct cgtccgatga tcaaagtttt aagcaacaaa accaagggtg aaatttaaac   13440
tgtgctttgt tgaagattct tttatcatat tgaaaatcaa attactagca gcagatttta   13500
cctagcatga aattttatca acagtacagc actcactaac caagttccaa actaagatgc   13560
gccattaaca tcagccaata ggcattttca gcaaggcgcg ccgatgtatg tgacaaccct   13620
cgggattgtt gatttatttc aaaactaaga gttttgctt attgttctcg tctatttgg    13680
atatcaatct tagtttttata tcttttctag ttctctacgt gttaaatgtt caacacacta   13740
gcaatttggc tgcagcgtat ggattatgga actatcaagt ctgtgacgcg ccgtacgtag   13800
tgtttatctt tcttgctttt ctgaacaatt tatttactat gtaaatatat tatcaatgtt   13860
taatctattt taatttgcac attaattttc attttatttt tacttacaa aacaaataaa    13920
tatatatgca aaaaaattta caaacgatgc acgggttaca aactaatttc attaaatgct   13980
aatgcagatt ttgtgaagta aaactccaat tatgatgaaa aataccacca acaccacctg   14040
cgaaactgta tcccaactgt ccttaataaa atgttaaaa agtatattat tctcatttgt    14100
ctgtcataat ttatgtaccc cactttaatt tttctgatgt actaaaccga gggcaaactg   14160
aaacctgttc ctcatgcaaa gcccctactc accatgtatc atgtacgtgt catcacccaa   14220
caactccact tttgctatat aacaacaccc ccgtcacact ctccctctct aacacacacc   14280
```

```
ccactaacaa ttccttcact tgcagcactg ttgcatcatc atcttcattg caaacccta    14340
aacttcacct tcaaccgcgg ccgcaaaatg actcagcgca ttgcgtatgt gaccggcggc    14400
atgggtggta tcggaaccgc catttgccag cggctggcca aggatggctt tcgtgtggtg    14460
gccggttgcg gccccaactc gccgcgccgc gaaaagtggc tggagcagca gaaggccctg    14520
ggcttcgatt tcattgcctc ggaaggcaat gtggctgact gggactcgac caagaccgca    14580
ttcgacaagg tcaagtccga ggtcggcgag gttgatgtgc tgatcaacaa cgccggtatc    14640
acccgcgacg tggtgttccg caagatgacc cgcgccgact gggatgcggt gatcgacacc    14700
aacctgacct cgctgttcaa cgtcaccaag caggtgatcg acggcatggc cgaccgtggc    14760
tggggccgca tcgtcaacat ctcgtcggtg aacgggcaga agggccagtt cggccagacc    14820
aactactcca ccgccaaggc cggcctgcat ggcttcacca tggcactggc gcaggaagtg    14880
gcgaccaagg gcgtgaccgt caacacggtc tctccgggct atatcgccac cgacatggtc    14940
aaggcgatcc gccaggacgt gctcgacaag atcgtcgcga cgatcccggt caagcgcctg    15000
ggcctgccgg aagagatcgc ctcgatctgc gcctggttgt cgtcggagga gtccggtttc    15060
tcgaccggcg ccgacttctc gctcaacggc ggcctgcata tgggctgagc ggccgctgag    15120
taattctgat attagaggga gcattaatgt gttgttgtga tgtggtttat atggggaaat    15180
taaataaatg atgtatgtac ctcttgccta tgtaggtttg tgtgttttgt tttgttgtct    15240
agctttggtt attaagtagt agggacgttc gttcgtgtct caaaaaagg ggtactacca    15300
ctctgtagtg tatatggatg ctggaaatca atgtgttttg tatttgttca cctccattgt    15360
tgaattcaat gtcaaatgtg ttttgcgttg gttatgtgta aaattactat ctttctcgtc    15420
cgatgatcaa agttttaagc aacaaaacca agggtgaaat ttaaactgtg ctttgttgaa    15480
gattctttta tcatattgaa aatcaaatta ctagcagcag attttaccta gcatgaaatt    15540
ttatcaacag tacagcactc actaaccaag ttccaaacta agatgcgcca ttaacatcag    15600
ccaataggca ttttcagcaa ggcgcgtaa                                      15629
```

<210> SEQ ID NO 30
<211> LENGTH: 15818
<212> TYPE: DNA
<213> ORGANISM: Artificial Sequence
<220> FEATURE:
<223> OTHER INFORMATION: Synthetic construct pMBXS763 transformation vector

<400> SEQUENCE: 30

```
ggggatccgt acgtaagtac gtactcaaaa tgccaacaaa taaaaaaaaa gttgctttaa      60
taatgccaaa acaaattaat aaaacactta caacaccgga ttttttttaa ttaaaatgtg     120
ccatttagga taaatagtta atatttttaa taattattta aaaagccgta tctactaaaa     180
tgattttat ttggttgaaa atattaatat gtttaaatca acacaatcta tcaaaattaa      240
actaaaaaa aaataagtgt acgtggttaa cattagtaca gtaatataag aggaaaatga      300
gaaattaaga aattgaaagc gagtctaatt tttaaattat gaacctgcat atataaagg      360
aaagaaagaa tccaggaaga aaagaaatga accatgcat ggtcccctcg tcatcacgag      420
tttctgccat ttgcaataga aacactgaaa cacctttctc tttgtcactt aattgagatg      480
ccgaagccac ctcacaccat gaacttcatg aggtgtagca cccaaggctt ccatagccat     540
gcatactgaa gaatgtctca agctcagcac cctacttctg tgacgtgtcc ctcattcacc    600
ttcctctctt ccctataaat aaccacgcct caggttctcc gcttcacaac tcaaacattc    660
```

```
tctccattgg tccttaaaca ctcatcagtc atcaccgcgg ccgcgaaaat gactgacgtt    720
gtcatcgtat ccgccgcccg caccgcggtc ggcaagtttg gcggctcgct ggccaagatc    780
ccggcaccgg aactgggtgc cgtggtcatc aaggccgcgc tggagcgcgc cggcgtcaag    840
ccggagcagg tgagcgaagt catcatgggc caggtgctga ccgccggttc gggccagaac    900
cccgcacgcc aggccgcgat caaggccggc ctgccggcga tggtgccggc catgaccatc    960
aacaaggtgt gcggctcggg cctgaaggcc gtgatgctgg ccgccaacgc gatcatggcg   1020
ggcgacgccg agatcgtggt ggccggcggc caggaaaaca tgagcgccgc cccgcacgtg   1080
ctgccgggct cgcgcgatgg tttccgcatg ggcgatgcca agctggtcga ccatgatc    1140 gtcgacggcc tgtgggacgt gtacaaccag taccacatgg gcatcaccgc cgagaacgtg   1200
gccaaggaat acggcatcac acgcgaggcg caggatgagt cgccgtcgg ctcgcagaac    1260 aaggccgaag ccgcgcagaa ggccggcaag tttgacgaag agatcgtccc ggtgctgatc   1320
ccgcagcgca agggcgaccc ggtggccttc aagaccgacg agttcgtgcg ccagggcgcc   1380
acgctggaca gcatgtccgg cctcaagccc gccttcgaca aggccggcac ggtgactgcg   1440
gccaacgcct cgggcctgaa cgacggcgcc gccgcggtgg tggtgatgtc ggcggccaag   1500
gccaaggaac tgggcctgac cccgctggcc acgatcaaga gctatgccaa cgccggtgtc   1560
gatcccaagg tgatgggcat gggcccggtg ccggcctcca agcgcgccct gtcgcgcgcc   1620
gagtggaccc cgcaagacct ggacctgatg gagatcaacg aggcctttgc cgcgcaggcg   1680
ctggcggtgc accagcagat gggctgggac acctccaagg tcaatgtgaa cggcggcgcc   1740
atcgccatcg gccacccgat cggcgcgtcg ggctgccgta cctggtgac gctgctgcac   1800 gagatgaagc gccgtgacgc gaagaagggc ctggcctcgc tgtgcatcgg cggcggcatg   1860
ggcgtggcgc tggcagtcga gcgcaaataa ctcgaggcgg ccgcagccct ttttgtatgt   1920
gctaccccac ttttgtcttt ttggcaatag tgctagcaac caataaataa taataataat   1980
aatgaataag aaaacaaagg ctttagcttg ccttttgttc actgtaaaat aataatgtaa   2040
gtactctcta taatgagtca cgaaactttt gcgggaataa aaggagaaat tccaatgagt   2100
tttctgtcaa atcttctttt gtctctctct ctctctcttt ttttttttc tttcttctga    2160 gcttcttgca aaacaaaagg caaacaataa cgattggtcc aatgatagtt agcttgatcg   2220
atgatatctt taggaagtgt tggcaggaca ggacatgatg tagaagacta aaattgaaag   2280
tattgcagac ccaatagttg aagattaact ttaagaatga agacgtctta tcaggttctt   2340
catgacttaa gctttaagag gagtccacca tggtagatct gactagaaat gaattcgtaa   2400
tcatgtcata gctgtttcct gtgtgaaatt gttatccgct cacaattcca cacaacatac   2460
gagccggaag cataaagtgt aaagcctggg gtgcctaatg agtgagctaa ctcacattaa   2520
ttgcgttgcg ctcactgccc gctttccagt cgggaaacct gtcgtgccag ctgcattaat   2580
gaatcggcca acgcgcgggg agaggcggtt tgcgtattgg ctagagcagc ttgccaacat   2640
ggtggagcac gacactctcg tctactccaa gaatatcaaa gatacagtct cagaagacca   2700
aagggctatt gagacttttc aacaagggt aatatcggga aacctcctcg gattccattg    2760
cccagctatc tgtcacttca tcaaaaggac agtagaaaag gaaggtggca cctacaaatg   2820
ccatcattgc gataaaggaa aggctatcgt tcaagatgcc tctgccgaca gtggtcccaa   2880
agatggaccc ccacccacga ggagcatcgt ggaaaaagaa gacgttccaa ccacgtcttc   2940
aaagcaagtg gattgatgtg aacatggtgg agcacgacac tctcgtctac tccaagaata   3000
tcaaagatac agtctcagaa gaccaaaggg ctattgagac ttttcaacaa agggtaatat   3060
```

-continued

```
cgggaaacct cctcggattc cattgcccag ctatctgtca cttcatcaaa aggacagtag    3120
aaaaggaagg tggcacctac aaatgccatc attgcgataa aggaaaggct atcgttcaag    3180
atgcctctgc cgacagtggt cccaaagatg acccccacc cacgaggagc atcgtggaaa    3240
aagaagacgt tccaaccacg tcttcaaagc aagtggattg atgtgatatc tccactgacg    3300
taagggatga cgcacaatcc cactatcctt cgcaagaccc ttcctctata taaggaagtt    3360
catttcattt ggagaggaca cgctgaaatc accagtctct ctctacaaat ctatctctct    3420
cgagaaaatg gcctcctccg agaacgtcat caccgagttc atgcgcttca aggtgcgcat    3480
ggagggcacc gtgaacggcc acgagttcga gatcgagggc gagggcgagg ccgccccta    3540 cgagggccac aacaccgtga agctgaaggt gaccaagggc ggccccctgc cttcgcctg    3600 ggacatcctg tccccccagt tccagtacgg ctccaaggtg tacgtgaagc accccgccga    3660
catccccgac tacaagaagc tgtccttccc cgagggcttc aagtgggagc gcgtgatgaa    3720
cttcgaggac ggcggcgtgg cgaccgtgac ccaggactcc tccctgcagg acggctgctt    3780
catctacaag gtgaagttca tcggcgtgaa cttccctcc gacggccccg tgatgcagaa    3840
gaagaccatg ggctgggagg cctccaccga gcgcctgtac ccccgcgacg gcgtgctgaa    3900
gggcgagacc cacaaggccc tgaagctgaa ggacggcggc cactacctgg tggagttcaa    3960
gtccatctac atggccaaga gcccgtgca gctgccccgc tactactacg tggacgccaa    4020
gctggacatc acctcccaca cgaggacta caccatcgtg gagcagtacg agcgcaccga    4080
gggccgccac cacctgttcc tggtaccctg agctcggtca cctgtccaac agtctcaggg    4140
ttaatgtcta tgtatcttaa ataatgttgt cggcgatcgt tcaaacattt ggcaataaag    4200
tttcttaaga ttgaatcctg ttgccggtct tgcgatgatt atcatataat ttctgttgaa    4260
ttacgttaag catgtaataa ttaacatgta atgcatgacg ttatttatga gatgggtttt    4320
tatgattaga gtcccgcaat tatacattta atacgcgata gaaaacaaaa tatagcgcgc    4380
aaactaggat aaattatcgc gcgcggtgtc atctatgtta ctagatcggg aattaaacta    4440
tcagtgtttg acaggatata ttggcgggta aacctaagag aaaagagcgt ttattagaat    4500
aatcggatat ttaaagggc gtgaaaaggt ttatccgttc gtccatttgt atgtgcatgc    4560
caaccacagg gttcccctcg ggatcaaagt actttgatcc aaccccctccg ctgctatagt    4620 gcagtcggct tctgacgttc agtgcagccg tcttctgaaa cgacatgtc gcacaagtcc    4680 taagttacgc gacaggctgc cgccctgccc ttttcctggc gttttcttgt cgcgtgtttt    4740
agtcgcataa agtagaatac ttgcgactag aaccggagac attacgccat gaacaagagc    4800
gccgccgctg gcctgctggg ctatgcccgc gtcagcaccg acgaccagga cttgaccaac    4860
caacgggccc aactgcacgc ggccggctgc accaagctgt tttccgagaa gatcaccggc    4920
accaggcgcg accgcccgga gctggccagg atgcttgacc acctacgccc tggcgacgtt    4980
gtgacagtga ccaggctaga ccgcctggcc cgcagcaccc gcgacctact ggacattgcc    5040
gagcgcatcc aggaggccgg cgcgggcctg cgtagcctgg cagagccgtg ggccgacacc    5100
accacgccgg ccggccgcat ggtgttgacc gtgttcgccg gcattgccga gttcgagcgt    5160
tccctaatca tcgaccgcac ccggagcggg cgcgaggccg ccaaggcccg aggcgtgaag    5220
tttggccccc gccctaccct caccccggca cagatcgcgc acgcccgcga gctgatcgac    5280
caggaaggcc gcaccgtgaa agaggcggct gcactgcttg gcgtgcatcg ctcgaccctg    5340
taccgcgcac ttgagcgcag cgaggaagtg acgcccaccg aggccaggcg gcgcggtgcc    5400
```

```
ttccgtgagg acgcattgac cgaggccgac gccctggcgg ccgccgagaa tgaacgccaa    5460
gaggaacaag catgaaaccg caccaggacg gccaggacga accgttttc attaccgaag     5520 agatcgaggc ggagatgatc gcggccgggt acgtgttcga gccgcccgcg cacgtctcaa    5580
ccgtgcggct gcatgaaatc ctggccggtt tgtctgatgc caagctggcg gcctggccgg    5640
ccagcttggc cgctgaagaa accgagcgcc gccgtctaaa aaggtgatgt gtatttgagt    5700
aaaacagctt gcgtcatgcg gtcgctgcgt atatgatgcg atgagtaaat aaacaaatac    5760
gcaaggggaa cgcatgaagg ttatcgctgt acttaaccag aaaggcgggt caggcaagac    5820
gaccatcgca acccatctag cccgcgccct gcaactcgcc ggggccgatg ttctgttagt    5880
cgattccgat ccccagggca gtgcccgcga ttgggcggcc gtgcgggaag atcaaccgct    5940
aaccgttgtc ggcatcgacc gcccgacgat tgaccgcgac gtgaaggcca tcggccggcg    6000
cgacttcgta gtgatcgacg gagcgcccca ggcggcggac ttggctgtgt ccgcgatcaa    6060
ggcagccgac ttcgtgctga ttccggtgca gccaagccct tacgacatat gggccaccgc    6120
cgacctggtg gagctggtta agcagcgcat tgaggtcacg gatggaaggc tacaagcggc    6180 cttttgtcgtg tcgcgggcga tcaaaggcac gcgcatcggc ggtgaggttg ccgaggcgct    6240
ggccgggtac gagctgccca ttcttgagtc ccgtatcacg cagcgcgtga gctacccagg    6300
cactgccgcc gccggcacaa ccgttcttga atcagaaccc gagggcgacg ctgcccgcga    6360
ggtccaggcg ctggccgctg aaattaaatc aaaactcatt tgagttaatg aggtaaagag    6420
aaaatgagca aaagcacaaa cacgctaagt gccggccgtc cgagcgcacg cagcagcaag    6480
gctgcaacgt tggccagcct ggcagacacg ccagccatga gcgggtcaa ctttcagttg    6540 ccggcggagg atcacaccaa gctgaagatg tacgcggtac gccaaggcaa gaccattacc    6600
gagctgctat ctgaatacat cgcgcagcta ccagagtaaa tgagcaaatg aataaatgag    6660
tagatgaatt ttagcggcta aaggaggcgg catggaaaat caagaacaac caggcaccga    6720
cgccgtggaa tgccccatgt gtggaggaac gggcggttgg ccaggcgtaa gcggctgggt    6780
tgtctgccgg ccctgcaatg gcactggaac ccccaagccc gaggaatcgg cgtgacggtc    6840
gcaaaccatc cggcccggta caaatcgcg cggcgctggg tgatgacctg gtggagaagt    6900
tgaaggccgc gcaggccgcc cagcggcaac gcatcgaggc agaagcacgc cccggtgaat    6960
cgtggcaagc ggccgctgat cgaatccgca aagaatcccg gcaaccgccg gcagccggtg    7020
cgccgtcgat taggaagccg cccaagggcg acgagcaacc agattttttc gttccgatgc    7080
tctatgacgt gggcacccgc gatagtcgca gcatcatgga cgtggccgtt ttccgtctgt    7140
cgaagcgtga ccgacgagct ggcgaggtga tccgctacga gcttccagac gggcacgtag    7200
aggtttccgc agggccggcc ggcatggcca gtgtgtggga ttacgacctg gtactgatgg    7260
cggtttccca tctaaccgaa tccatgaacc gataccggga agggaaggga gacaagcccg    7320
gccgcgtgtt ccgtccacac gttgcggacg tactcaagtt ctgccggcga gccgatggcg    7380
gaaagcagaa agacgacctg gtagaaacct gcattcggtt aaacaccacg cacgttgcca    7440
tgcagcgtac gaagaaggcc aagaacggcc gcctggtgac ggtatccgag ggtgaagcct    7500
tgattagccg ctacaagatc gtaaagagcg aaaccgggcg gccggagtac atcgagatcg    7560
agctagctga ttgatgtac cgcgagatca cagaaggcaa gaacccggac gtgctgacgg    7620
ttcaccccga ttactttttg atcgatcccg gcatcggccg ttttctctac cgcctggcac    7680
gccgcgccgc aggcaaggca gaagccagat ggttgttcaa gacgatctac gaacgcagtg    7740
gcagcgccgg agagttcaag aagttctgtt tcaccgtgcg caagctgatc gggtcaaatg    7800
```

```
acctgccgga gtacgatttg aaggaggagg cggggcaggc tggcccgatc ctagtcatgc   7860
gctaccgcaa cctgatcgag ggcgaagcat ccgccggttc ctaatgtacg gagcagatgc   7920
tagggcaaat tgccctagca ggggaaaaag gtcgaaaagg tctctttcct gtggatagca   7980
cgtacattgg gaacccaaag ccgtacattg ggaaccggaa cccgtacatt gggaacccaa   8040
agccgtacat tgggaaccgg tcacacatgt aagtgactga tataaagag aaaaaaggcg    8100
attttttccgc ctaaaactct ttaaaactta ttaaaactct taaaacccgc ctggcctgtg  8160
cataactgtc tggccagcgc acagccgaag agctgcaaaa agcgcctacc cttcggtcgc   8220
tgcgctccct acgccccgcc gcttcgcgtc ggcctatcgc ggccgctggc cgctcaaaaa   8280
tggctggcct acggccaggc aatctaccag ggcgcggaca agccgcgccg tcgccactcg   8340
accgccggcg cccacatcaa ggcaccctgc ctcgcgcgtt tcggtgatga cggtgaaaac   8400
ctctgacaca tgcagctccc ggagacggtc acagcttgtc tgtaagcgga tgccgggagc   8460
agacaagccc gtcagggcgc gtcagcgggt gttggcgggt gtcggggcgc agccatgacc   8520
cagtcacgta gcgatagcgg agtgtatact ggcttaacta tgcggcatca gagcagattg   8580
tactgagagt gcaccatatg cggtgtgaaa taccgcacag atgcgtaagg agaaaatacc   8640
gcatcaggcg ctcttccgct tcctcgctca ctgactcgct gcgctcggtc gttcggctgc   8700
ggcgagcgg atcagctcac tcaaaggcgg taatacggtt atccacagaa tcaggggata    8760
acgcaggaaa gaacatgtga gcaaaaggcc agcaaaaggc caggaaccgt aaaaaggccg   8820
cgttgctggc gtttttccat aggctccgcc cccctgacga gcatcacaaa aatcgacgct   8880
caagtcagag gtggcgaaac ccgacaggac tataaagata ccaggcgttt ccccctggaa   8940
gctccctcgt gcgctctcct gttccgaccc tgccgcttac cggatacctg tccgcctttc   9000
tcccttcggg aagcgtggcg ctttctcata gctcacgctg taggtatctc agttcggtgt   9060
aggtcgttcg ctccaagctg ggctgtgtgc acgaaccccc cgttcagccc gaccgctgcg   9120
ccttatccgg taactatcgt cttgagtcca acccggtaag acacgactta tcgccactgg   9180
cagcagccac tggtaacagg attagcagag cgaggtatgt aggcggtgct acagagttct   9240
tgaagtggtg gcctaactac ggctacacta gaaggacagt atttggtatc tgcgctctgc   9300
tgaagccagt taccttcgga aaaagagttg gtagctcttg atccggcaaa caaaccaccg   9360
ctggtagcgg tggttttttt gtttgcaagc agcagattac gcgcagaaaa aaggatctc    9420
aagaagatcc tttgatcttt tctacggggt ctgacgctca gtggaacgaa aactcacgtt   9480
aagggatttt ggtcatgcat tctaggtact aaaacaattc atccagtaaa atataatatt   9540
ttatttctc ccaatcaggc ttgatcccca gtaagtcaaa aaatagctcg acatactgtt    9600
cttcccgat atcctccctg atcgaccgga cgcagaaggc aatgtcatac cacttgtccg    9660
ccctgccgct tctcccaaga tcaataaagc cacttacttt gccatctttc acaaagatgt   9720
tgctgtctcc caggtcgccg tgggaaaaga caagttcctc ttcgggcttt tccgtctttta  9780
aaaaatcata cagctcgcgc ggatctttaa atggagtgtc ttcttcccag ttttcgcaat   9840
ccacatcggc cagatcgtta ttcagtaagt aatccaattc ggctaagcgg ctgtctaagc   9900
tattcgtata gggacaatcc gatatgtcga tggagtgaaa gagcctgatg cactccgcat   9960
acagctcgat aatctttttca gggctttgtt catcttcata ctcttccgag caaaggacgc  10020
catcggcctc actcatgagc agattgctcc agccatcatg ccgttcaaag tgcaggacct   10080
ttggaacagg cagctttcct tccagccata gcatcatgtc cttttcccgt tccacatcat   10140
```

```
aggtggtccc tttataccgg ctgtccgtca ttttaaata taggttttca ttttctccca    10200
ccagcttata taccttagca ggagacattc cttccgtatc ttttacgcag cggtatttt    10260
cgatcagttt tttcaattcc ggtgatattc tcattttagc catttattat ttccttcctc    10320
ttttctacag tatttaaaga taccccaaga agctaattat aacaagacga actccaattc    10380
actgttcctt gcattctaaa accttaaata ccagaaaaca gcttttcaa agttgtttc     10440
aaagttggcg tataacatag tatcgacgga gccgattttg aaaccgcggt gatcacaggc    10500
agcaacgctc tgtcatcgtt acaatcaaca tgctaccctc cgcgagatca tccgtgttc     10560
aaacccggca gcttagttgc cgttcttccg aatagcatcg gtaacatgag caaagtctgc    10620
cgccttacaa cggctctccc gctgacgccg tcccggactg atgggctgcc tgtatcgagt    10680
ggtgattttg tgccgagctg ccggtcgggg agctgttggc tggctggtgg caggatatat    10740
tgtggtgtaa acaaattgac gcttagacaa cttaataaca cattgcggac gttttaatg     10800
tactgaatta acgccgaatt aattcctagg gtacgtagtg tttatcttg ttgcttttct     10860
gaacaattta tttactatgt aaatatatta tcaatgttta atctatttta atttgcacat    10920
taatttcat tttatttta ctttacaaaa caaataaata tatatgcaaa aaaatttaca     10980
aacgatgcac gggttacaaa ctaatttcat taaatgctaa tgcagatttt gtgaagtaaa    11040
actccaatta tgatgaaaaa taccaccaac accacctgcg aaactgtatc ccaactgtcc    11100
ttaataaaaa tgttaaaaag tatattattc tcatttgtct gtcataattt atgtacccca    11160
ctttaatttt tctgatgtac taaaccgagg gcaaactgaa acctgttcct catgcaaagc    11220
ccctactcac catgtatcat gtacgtgtca tcacccaaca actccacttt tgctatataa    11280
caacaccccc gtcacactct ccctctctaa cacacacccc actaacaatt ccttcacttg    11340
cagcactgtt gcatcatcat cttcattgca aaaccctaaa cttcaccttc aaccgcggcc    11400
gcatgagtaa caagaacaac gatgagctgc agtggcaatc ctggttcagc aaggcgccca    11460
ccaccgaggc gaacccgatg ccaccatgt tgcaggatat cggcgttgcg ctcaaaccgg     11520
aagcgatgga gcagctgaaa acgattatc tgcgtgactt caccgcgttg tggcaggatt     11580
ttttggctgg caaggcgcca gccgtcagcg accgccgctt cagctcggca gcctggcagg    11640
gcaatccgat gtcggccttc aatgccgcat cttacctgct caacgccaaa ttcctcagtg    11700
ccatggtgga ggcggtggac accgcacccc agcaaaagca gaaaatacgc tttgccgtgc    11760
agcaggtgat tgatgccatg tcgcccgcga acttcctcgc caccaaccg gaagcgcagc     11820
aaaaactgat tgaaaccaag ggcgagagcc tgacgcgtgg cctggtcaat atgctgggcg    11880
atatcaacaa gggccatatc tcgctgtcgg acgaatcggc ctttgaagtg ggccgcaacc    11940
tggccattac cccgggcacc gtgatttacg aaaatccgct gttccagctg atccagtaca    12000
cgccgaccac gccgacggtc agccagcgcc cgctgttgat ggtgccgccg tgcatcaaca    12060
agttctacat cctcgacctg caaccggaaa attcgctggt gcgctacgcg gtggagcagg    12120
gcaacaccgt gttcctgatc tcgtggagca atccggacaa gtcgctggcc ggcaccacct    12180
gggacgacta cgtggagcag ggcgtgatcg aagcgatccg catcgtccag gacgtcagcg    12240
gccaggacaa gctgaacatg ttcggcttct gcgtgggcgg caccatcgtt gccaccgcac    12300
tggcggtact ggcggcgcgt ggccagcacc cggcggccag cctgaccctg ctgaccacct    12360
tcctcgactt cagcgacacc ggcgtgctcg acgtcttcgt cgatgaaacc caggtcgcgc    12420
tgcgtgaaca gcaattgcgc gatggcgcc tgatgccggg ccgtgacctg gcctcgacct     12480
tctcgagcct gcgtccgaac gacctggtat ggaactatgt gcagtcgaac tacctcaaag    12540
```

```
gcaatgagcc ggcggcgttt gacctgctgt tctggaattc ggacagcacc aatttgccgg    12600
gcccgatgtt ctgctggtac ctgcgcaaca cctacctgga aaacagcctg aaagtgccgg    12660
gcaagctgac ggtggccggc gaaaagatcg acctcggcct gatcgacgcc ccggccttca    12720
tctacggttc gcgcgaagac cacatcgtgc cgtggatgtc ggcgtacggt tcgctcgaca    12780
tcctcaacca gggcaagccg ggcgccaacc gcttcgtgct gggcgcgtcc ggccatatcg    12840
ccggcgtgat caactcggtg gccaagaaca agcgcagcta ctggatcaac gacggtggcg    12900
ccgccgatgc ccaggcctgg ttcgatggcg cgcaggaagt gccgggcagc tggtggccgc    12960
aatgggccgg gttcctgacc cagcatgccg gcaagaaggt caagcccaag gccaagcccg    13020
gcaacgcccg ctacaccgcg atcgaggcgg cgcccggccg ttacgtcaaa gccaagggcg    13080
tgctggcggt ggcgattgat aaacgcgag gcggtggagg cagcggcggt ggcggtagcg    13140
gtggcggtgg cagcggcggt ggcggtagcg attttgttat taagctcctt cagttccttg    13200
ttccacttct aatcttaggc ttggctttcg gcattcggta ctacactaag accaaggctc    13260
cttcttctta agcggccgct gagtaattct gatattagag ggagcattaa tgtgttgttg    13320
tgatgtggtt tatatgggga aattaaataa atgatgtatg tacctcttgc ctatgtaggt    13380
ttgtgtgttt tgttttgttg tctagctttg gttattaagt agtagggacg ttcgttcgtg    13440
tctcaaaaaa aggggtacta ccactctgta gtgtatatgg atgctggaaa tcaatgtgtt    13500
ttgtatttgt tcacctccat tgttgaattc aatgtcaaat gtgttttgcg ttggttatgt    13560
gtaaaattac tatctttctc gtccgatgat caaagtttta agcaacaaaa ccaagggtga    13620
aatttaaact gtgctttgtt gaagattctt ttatcatatt gaaaatcaaa ttactagcag    13680
cagattttac ctagcatgaa attttatcaa cagtacagca ctcactaacc aagttccaaa    13740
ctaagatgcg ccattaacat cagccaatag gcattttcag caaggcgcgc cgatgtatgt    13800
gacaaccctc gggattgttg atttatttca aaactaagag ttttgctta ttgttctcgt    13860 ctattttgga tatcaatctt agtttatat cttttctagt tctctacgtg ttaaatgttc    13920
aacacactag caatttggct gcagcgtatg gattatggaa ctatcaagtc tgtgacgcgc    13980
cgtacgtagt gtttatcttt cttgcttttc tgaacaattt atttactatg taaatatatt    14040
atcaatgttt aatctatttt aatttgcaca ttaattttca ttttattttt actttacaaa    14100
acaaataaat atatatgcaa aaaaatttac aaacgatgca cgggttacaa actaatttca    14160
ttaaatgcta atgcagattt tgtgaagtaa aactccaatt atgatgaaaa ataccaccaa    14220
caccacctgc gaaactgtat cccaactgtc cttaataaaa atgttaaaaa gtatattatt    14280
ctcatttgtc tgtcataatt tatgtacccc actttaattt ttctgatgta ctaaaccgag    14340
ggcaaactga aacctgttcc tcatgcaaag cccctactca ccatgtatca tgtacgtgtc    14400
atcacccaac aactccactt ttgctatata acaacacccc cgtcacactc tccctctcta    14460
acacacaccc cactaacaat tccttcactt gcagcactgt tgcatcatca tcttcattgc    14520
aaaaccctaa acttcacctt caaccgcggc cgcaaaatga ctcagcgcat tgcgtatgtg    14580
accggcggca tggtggtat cggaaccgcc atttgccagc ggctggccaa ggatggcttt    14640
cgtgtggtgg ccggttgcgg ccccaactcg ccgcgccgcg aaaagtggct ggagcagcag    14700
aaggccctgg gcttcgattt cattgcctcg gaaggcaatg tggctgactg ggactcgacc    14760
aagaccgcat tcgacaaggt caagtccgag gtcggcgagg ttgatgtgct gatcaacaac    14820
gccggtatca cccgcgacgt ggtgttccgc aagatgaccc gcgccgactg ggatgcggtg    14880
```

| | |
|---|---|
| atcgacacca acctgacctc gctgttcaac gtcaccaagc aggtgatcga cggcatggcc | 14940 |
| gaccgtggct ggggccgcat cgtcaacatc tcgtcggtga acgggcagaa gggccagttc | 15000 |
| ggccagacca actactccac cgccaaggcc ggcctgcatg gcttcaccat ggcactggcg | 15060 |
| caggaagtgg cgaccaaggg cgtgaccgtc aacacggtct ctccgggcta tatcgccacc | 15120 |
| gacatggtca aggcgatccg ccaggacgtg ctcgacaaga tcgtcgcgac gatcccggtc | 15180 |
| aagcgcctgg gcctgccgga agagatcgcc tcgatctgcg cctggttgtc gtcggaggag | 15240 |
| tccggtttct cgaccggcgc cgacttctcg ctcaacggcg gcctgcatat gggctgagcg | 15300 |
| gccgctgagt aattctgata ttagagggag cattaatgtg ttgttgtgat gtggtttata | 15360 |
| tggggaaatt aaataaatga tgtatgtacc tcttgcctat gtaggtttgt gtgttttgtt | 15420 |
| ttgttgtcta gctttggtta ttaagtagta gggacgttcg ttcgtgtctc aaaaaaaggg | 15480 |
| gtactaccac tctgtagtgt atatggatgc tggaaatcaa tgtgttttgt atttgttcac | 15540 |
| ctccattgtt gaattcaatg tcaaatgtgt tttgcgttgg ttatgtgtaa aattactatc | 15600 |
| tttctcgtcc gatgatcaaa gttttaagca acaaaaccaa gggtgaaatt taaactgtgc | 15660 |
| tttgttgaag attcttttat catattgaaa atcaaattac tagcagcaga ttttacctag | 15720 |
| catgaaattt tatcaacagt acagcactca ctaaccaagt tccaaactaa gatgcgccat | 15780 |
| taacatcagc caataggcat tttcagcaag gcgcgtaa | 15818 |

<210> SEQ ID NO 31
<211> LENGTH: 1470
<212> TYPE: DNA
<213> ORGANISM: Arabidopsis thaliana

<400> SEQUENCE: 31

| | |
|---|---|
| gaactaaagg ggatcgctct ccctgagggt tcagataaac tcttttcagt cagtattgat | 60 |
| ggtacattgc gagtttggga ctgcaattct ggtcagtgtg tacattccat caaccttgac | 120 |
| gcagaagcag ggtctctaat cagtgaaggc ccttgggttt tccttggctt gccaaacgct | 180 |
| ataaaggctt ttaacgttca aaccagtcaa gatttgcatc ttcaagcagc aggggtggtt | 240 |
| ggtcaggtga atgcaatgac tattgcaaac ggaatgcttt tgctggaaac aagttctggt | 300 |
| agtatcttag tctggaaagc tactacagac tctgagtctg atccattcaa atacttgaca | 360 |
| tctcttgagg gacatagtgg tgaagtcact tgttttgctg ttggaggtca aatgctatac | 420 |
| tctggttctg tcgataaaac aatcaagatg tgggatctca cacccctgca atgtataatg | 480 |
| accctgaagc aacataccgg cactgtcact tcactcttat gttgggataa atgtttgata | 540 |
| tcgtcttcct tggatgggac cataaaagtt tgggcttatt ctgaaaacgg aatcttgaaa | 600 |
| gttgttcaaa ctcgcagaca agaacagagt agtgttcatg ctctttctgg tatgcatgat | 660 |
| gcagaagcca aaccgataat attctgctct taccaaaacg gaaccgttgg cattttcgac | 720 |
| ctaccatctt ttcaagaaag aggaaggatg ttctctacgc acacgatcgc cacactcaca | 780 |
| attggtcctc aaggattgtt attcagtgga gacgagagtg gtaacttgcg tgtatggacc | 840 |
| ttagctgctg gcaacaaagt ttagtctttt cgactaaaga attctgattt aatttttgtgg | 900 |
| tttatatgtt gagttaactg ttaagagagt tttattttgt aataggtgta tcagtcaata | 960 |
| aacaatcttt gtatcaacca aatgtaattt ttctcgttaa ttcgatttca gagtttttac | 1020 |
| tttaagataa acaaactctt tcacacatca tttaatgaaa gtggagaagc ttaaaaaaca | 1080 |
| aacaaagaaa ctgatccatt tttggcgggt cttcttctac tcttattcat atgtgttaac | 1140 |
| gaactatagc gtaaaattca gagcaagcga tctccgattt gaacgtggct atcaccggag | 1200 |

```
gcccaccact acgggcgata cgctctaagt gaggattaaa gtgctctggt ggtgacgttg    1260
aagaaactcg cccatggttt ttgttatctc tgcagccaag tgtcgttctt tcttcgccac    1320
ttctcatcaa gctacagtga atttaaaaat ggcgtctttc tttgatctcg tatacataag    1380
ctggattggt ttcttaaaca aattcctctc cttttgggtc ttctgggttt gccttgtaag    1440
tgtttgtgtt tttgcctctg agaaaaaatc                                     1470
```

<210> SEQ ID NO 32
<211> LENGTH: 589
<212> TYPE: PRT
<213> ORGANISM: Cupriavidus necator

<400> SEQUENCE: 32

Met Ala Thr Gly Lys Gly Ala Ala Ser Thr Gln Glu Gly Lys Ser
1               5                   10                  15

Gln Pro Phe Lys Val Thr Pro Gly Pro Phe Asp Pro Ala Thr Trp Leu
            20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
    290                 295                 300

Arg Asp Ile Ser Gly Gln Asp Lys Ile Asn Val Leu Gly Phe Cys Val
305                 310                 315                 320

```
Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
        435                 440                 445

Glu Leu Lys Val Pro Gly Lys Leu Thr Val Cys Gly Val Pro Val Asp
    450                 455                 460

Leu Ala Ser Ile Asp Val Pro Thr Tyr Ile Tyr Gly Ser Arg Glu Asp
465                 470                 475                 480

His Ile Val Pro Trp Thr Ala Ala Tyr Ala Ser Thr Ala Leu Leu Ala
                485                 490                 495

Asn Lys Leu Arg Phe Val Leu Gly Ala Ser Gly His Ile Ala Gly Val
            500                 505                 510

Ile Asn Pro Pro Ala Lys Asn Lys Arg Ser His Trp Thr Asn Asp Ala
        515                 520                 525

Leu Pro Glu Ser Pro Gln Gln Trp Leu Ala Gly Ala Ile Glu His His
    530                 535                 540

Gly Ser Trp Trp Pro Asp Trp Thr Ala Trp Leu Ala Gly Gln Ala Gly
545                 550                 555                 560

Ala Lys Arg Ala Ala Pro Ala Asn Tyr Gly Asn Ala Arg Tyr Arg Ala
                565                 570                 575

Ile Glu Pro Ala Pro Gly Arg Tyr Val Lys Ala Lys Ala
            580                 585

<210> SEQ ID NO 33
<211> LENGTH: 568
<212> TYPE: PRT
<213> ORGANISM: Chromobacterium violaceum

<400> SEQUENCE: 33

Met Gln Gln Phe Val Asn Ser Leu Ser Gln Pro Pro Ala Pro Asp Gly
1               5                   10                  15

Ala Ala His Pro Phe Ala Gly Ala Trp Ala Gln Leu Met Asn Gln Thr
            20                  25                  30

Asn Gln Leu Phe Ala Leu Gln Ser Ser Leu Tyr Gln Gln Gln Leu Asn
        35                  40                  45

Leu Trp Ser Gln Phe Leu Gly Gln Ala Ala Gly Gln Glu Ala Ala Ala
    50                  55                  60

Glu Ala Gly Ala Lys Pro Ala Asp Arg Arg Phe Ala Ser Pro Glu Trp
65                  70                  75                  80

Asn Glu His Pro Phe Tyr Asn Phe Leu Lys Gln Ser Tyr Leu Gln Thr
                85                  90                  95

Ser Lys Trp Met Met Glu Leu Val Asp Lys Thr Gln Leu Asp Glu Asp
            100                 105                 110
```

Ala Lys Asp Lys Leu Ala Phe Ala Thr Arg Gln Tyr Leu Asp Ala Met
            115                 120                 125

Ser Pro Ser Asn Phe Met Leu Thr Asn Pro Asp Val Val Lys Arg Ala
        130                 135                 140

Ile Glu Thr Lys Gly Glu Ser Leu Val Glu Gly Met Lys Asn Met Leu
145                 150                 155                 160

Asp Asp Phe Gln Lys Gly His Ile Ser Met Ser Asp Glu Ser Lys Phe
                165                 170                 175

Glu Ile Gly Lys Asn Leu Val Val Thr Pro Gly Gln Val Val Phe Arg
                180                 185                 190

Asn Glu Leu Ile Glu Leu Ile Gln Tyr Thr Pro Thr Thr Asp Lys Val
            195                 200                 205

Tyr Glu Lys Pro Leu Leu Phe Val Pro Pro Cys Ile Asn Lys Tyr Tyr
        210                 215                 220

Leu Met Asp Leu Gln Pro Asp Asn Ser Met Val Arg His Phe Val Ala
225                 230                 235                 240

Gln Gly Tyr Arg Val Phe Leu Ile Ser Trp Arg Ser Ala Val Ala Glu
                245                 250                 255

Met Lys His Phe Thr Trp Glu Thr Tyr Ile Glu Lys Gly Val Phe Ala
            260                 265                 270

Ala Ala Glu Ala Val Gln Lys Ile Thr Lys Gln Pro Thr Met Asn Val
        275                 280                 285

Leu Gly Phe Cys Val Gly Gly Val Ile Leu Thr Thr Ala Leu Cys Val
        290                 295                 300

Ala Gln Ala Lys Gly Leu Lys Tyr Phe Asp Ser Ala Thr Phe Met Thr
305                 310                 315                 320

Ser Leu Ile Asp His Ala Glu Pro Gly Glu Ile Ser Phe Phe Ile Asp
                325                 330                 335

Glu Ser Val Val Ala Gly Arg Glu Ala Lys Met Ala Ser Gly Gly Ile
            340                 345                 350

Ile Ser Gly Lys Glu Ile Gly Arg Thr Phe Ala Ser Leu Arg Ala Asn
        355                 360                 365

Asp Leu Val Trp Asn Tyr Val Val Asn Asn Tyr Leu Leu Gly Lys Thr
        370                 375                 380

Pro Ala Pro Phe Asp Leu Leu Phe Trp Asn Asn Asp Ala Val Asp Leu
385                 390                 395                 400

Pro Leu Pro Met His Thr Phe Leu Leu Arg Gln Phe Tyr Met Asn Asn
                405                 410                 415

Ala Leu Val Arg Pro Gly Ala Ile Thr Leu Cys Gly Val Pro Ile Asp
            420                 425                 430

Ile Ala Lys Ile Asp Val Pro Val Tyr Met Phe Ala Ala Arg Asp Asp
        435                 440                 445

His Ile Val Leu Trp Ser Ser Ala Phe Ser Gly Leu Lys Tyr Leu Gln
        450                 455                 460

Gly Ala Pro Ser Arg Arg Phe Val Leu Gly Ala Ser Gly His Ile Ala
465                 470                 475                 480

Gly Ser Ile Asn Pro Val Thr Lys Asp Lys Arg Asn Tyr Trp Ala Asn
                485                 490                 495

Asp Thr Leu Pro Leu His Ala Glu Glu Trp Leu Glu Ser Ala Glu Ser
            500                 505                 510

Arg Pro Gly Ser Trp Trp Lys Asp Trp Asp Ala Trp Leu Ala Pro Gln
        515                 520                 525

-continued

Ser Gly Lys Gln Val Ala Ala Pro Lys Ser Leu Gly Asn Lys Glu Phe
    530                 535                 540

Pro Pro Leu Leu Ala Ala Pro Gly Ser Tyr Val Leu Ala Lys Ala Met
545                 550                 555                 560

Pro Ser Val Ala Ala Ser Leu Gln
                565

<210> SEQ ID NO 34
<211> LENGTH: 630
<212> TYPE: PRT
<213> ORGANISM: Delftia acidovorans

<400> SEQUENCE: 34

Met Asn Phe Asp Pro Leu Ala Gly Leu Ser Gly Gln Ser Val Gln Gln
1               5                   10                  15

Phe Trp Asn Glu Gln Trp Ser Arg Thr Leu Gln Thr Leu Gln Gln Met
            20                  25                  30

Gly Gln Pro Gly Leu Pro Gly Ile Gln Gly Met Pro Gly Met Pro Asp
        35                  40                  45

Met Ala Gln Ala Trp Lys Ala Val Pro Glu Pro Gly Ala Leu Pro
50                  55                  60

Glu Asn Ala Leu Ser Leu Asp Pro Glu Lys Leu Glu Leu Gln Arg
65                  70                  75                  80

Gln Tyr Leu Asp Gly Ala Lys Ala Met Ala Glu Gln Gly Gly Ala Gln
                85                  90                  95

Ala Leu Leu Ala Lys Asp Lys Arg Phe Asn Thr Glu Ser Trp Ala Gly
            100                 105                 110

Asn Pro Leu Thr Ala Ala Thr Ala Ala Thr Tyr Leu Leu Asn Ser Arg
        115                 120                 125

Met Leu Met Gly Leu Ala Asp Ala Val Gln Ala Asp Asp Lys Thr Arg
    130                 135                 140

Asn Arg Val Arg Phe Ala Ile Glu Gln Trp Leu Ala Ala Met Ala Pro
145                 150                 155                 160

Ser Asn Phe Leu Ala Leu Asn Ala Glu Ala Gln Lys Lys Ala Ile Glu
                165                 170                 175

Thr Gln Gly Glu Ser Leu Ala Gln Gly Val Ala Asn Leu Leu Ala Asp
            180                 185                 190

Met Arg Gln Gly His Val Ser Met Thr Asp Glu Ser Leu Phe Thr Val
        195                 200                 205

Gly Lys Asn Val Ala Thr Thr Glu Gly Ala Val Val Phe Glu Asn Glu
    210                 215                 220

Leu Phe Gln Leu Ile Glu Tyr Lys Pro Leu Thr Asp Lys Val His Glu
225                 230                 235                 240

Arg Pro Phe Leu Met Val Pro Pro Cys Ile Asn Lys Phe Tyr Ile Leu
                245                 250                 255

Asp Leu Gln Pro Asp Asn Ser Leu Ile Arg Tyr Ala Val Ser Gln Gly
            260                 265                 270

His Arg Thr Phe Val Met Ser Trp Arg Asn Pro Asp Glu Ser Leu Ala
        275                 280                 285

Arg Lys Thr Trp Asp Asn Tyr Ile Glu Asp Gly Val Leu Thr Gly Ile
    290                 295                 300

Arg Val Ala Arg Glu Ile Ala Gly Ala Glu Gln Ile Asn Val Leu Gly
305                 310                 315                 320

Phe Cys Val Gly Gly Thr Met Leu Ser Thr Ala Leu Ala Val Leu Gln
                325                 330                 335

Ala Arg His Asp Arg Glu His Gly Ala Val Ala Ala Pro Ala Ala Lys
                340                 345                 350

Ala Pro Ala Ala Lys Arg Ala Ala Gly Ser Arg Ser Ala Ala Arg Thr
            355                 360                 365

Ser Thr Ala Arg Ala Thr Ala Pro Ala Gly Val Pro Phe Pro Val Ala
370                 375                 380

Ser Val Thr Leu Leu Thr Thr Phe Ile Asp Phe Ser Asp Thr Gly Ile
385                 390                 395                 400

Leu Asp Val Phe Ile Asp Glu Ser Val Val Arg Phe Arg Glu Met Gln
                405                 410                 415

Met Gly Glu Gly Gly Leu Met Lys Gly Gln Asp Leu Ala Ser Thr Phe
            420                 425                 430

Ser Phe Leu Arg Pro Asn Asp Leu Val Trp Asn Tyr Val Val Gly Asn
        435                 440                 445

Tyr Leu Lys Gly Glu Thr Pro Pro Phe Asp Leu Leu Tyr Trp Asn
    450                 455                 460

Ser Asp Ser Thr Asn Leu Pro Gly Pro Tyr Tyr Ala Trp Tyr Leu Arg
465                 470                 475                 480

Asn Leu Tyr Leu Glu Asn Arg Leu Ala Gln Pro Gly Ala Leu Thr Val
                485                 490                 495

Cys Gly Glu Arg Ile Asp Met His Gln Leu Arg Leu Pro Ala Tyr Ile
            500                 505                 510

Tyr Gly Ser Arg Glu Asp His Ile Val Pro Val Gly Ser Tyr Ala
        515                 520                 525

Ser Thr Gln Val Leu Gly Gly Asp Lys Arg Phe Val Met Gly Ala Ser
    530                 535                 540

Gly His Ile Ala Gly Val Ile Asn Pro Pro Ala Lys Lys Lys Arg Ser
545                 550                 555                 560

Tyr Trp Leu Arg Glu Asp Gly Gln Leu Pro Ala Thr Leu Lys Glu Trp
                565                 570                 575

Gln Ala Gly Ala Asp Glu Tyr Pro Gly Ser Trp Trp Ala Asp Trp Ser
            580                 585                 590

Pro Trp Leu Ala Glu His Gly Gly Lys Leu Val Ala Ala Pro Lys Gln
        595                 600                 605

Tyr Gly Lys Gly Arg Glu Tyr Thr Ala Ile Glu Pro Ala Pro Gly Arg
    610                 615                 620

Tyr Val Leu Val Lys Ala
625                 630

<210> SEQ ID NO 35
<211> LENGTH: 594
<212> TYPE: PRT
<213> ORGANISM: Aeromonas caviae

<400> SEQUENCE: 35

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala

```
         65                  70                  75                  80
Gly Gln Pro Ser Glu Pro Val Ile Thr Pro Glu Arg Ser Asp Arg Arg
                 85                  90                  95

Phe Lys Ala Glu Ala Trp Ser Glu Gln Pro Ile Tyr Asp Tyr Leu Lys
                100                 105                 110

Gln Ser Tyr Leu Leu Thr Ala Arg His Leu Leu Ala Ser Val Asp Ala
                115                 120                 125

Leu Glu Gly Val Pro Gln Lys Ser Arg Glu Arg Leu Arg Phe Phe Thr
        130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
                180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
        210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
        290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
                340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
        370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
                420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
        450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495
```

```
Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
            515                 520                 525

Glu Ser Trp Leu Ala Gly Ala Thr His Gln Gly Gly Ser Trp Trp Pro
            530                 535                 540

Glu Met Met Gly Phe Ile Gln Asn Arg Asp Glu Gly Ser Glu Pro Val
545                 550                 555                 560

Pro Ala Arg Val Pro Glu Gly Leu Ala Pro Ala Pro Gly His Tyr
            565                 570                 575

Val Lys Val Arg Leu Asn Pro Val Phe Ala Cys Pro Thr Glu Glu Asp
            580                 585                 590

Ala Ala

<210> SEQ ID NO 36
<211> LENGTH: 587
<212> TYPE: PRT
<213> ORGANISM: Caulobacter vibrioides

<400> SEQUENCE: 36

Met Val Glu Thr Leu Ser Ala Asn Leu Ala Arg Ala Ala Val Thr Ala
1               5                   10                  15

Gln Gly Ala Ile Ala Glu Ala Ala Leu Arg Gln Ala Asp Arg Pro Ala
            20                  25                  30

Ala Leu Thr Pro Asp Pro Phe His Val Ala Pro Ala Leu Asn Glu Val
            35                  40                  45

Met Thr Arg Leu Ala Ala Gln Pro Asp Arg Leu Met Arg Ala Gln Ala
    50                  55                  60

Asp Leu Phe Gly Gln Tyr Met Glu Leu Trp Gln Thr Ala Ala Arg Arg
65                  70                  75                  80

Ala Ala Gly Glu Asp Val Ala Pro Val Ala Pro Ala Ala Gly Asp
            85                  90                  95

Lys Arg Phe Asn Asp Pro Asp Trp Ala Ser Asn Pro Met Phe Asp Leu
            100                 105                 110

Met Lys Gln Ser Tyr Leu Leu Ser Ser Asn Trp Leu Asn Gly Leu Ile
            115                 120                 125

Ala Glu Val Asp Gly Val Asp Pro Ala Thr Lys Arg Arg Val Glu Phe
            130                 135                 140

Phe Thr Lys Met Leu Thr Asp Ala Phe Ser Pro Ser Asn Phe Leu Ile
145                 150                 155                 160

Ser Asn Pro Ala Ala Leu Arg Glu Val Val Gln Thr Gly Gln Ser
            165                 170                 175

Leu Val Arg Gly Met Glu Asn Phe Ala Ala Asp Leu Glu Arg Gly Gly
            180                 185                 190

Gly Gln Leu Ala Ile Ser Gln Thr Asp Leu Ala Lys Phe Lys Val Gly
            195                 200                 205

Glu Asn Val Ala Thr Ala Pro Gly Lys Val Val Tyr Gln Asn Asp Ile
            210                 215                 220

Leu Gln Leu Leu Gln Phe Asp Pro Thr Thr Asp Thr Val Cys Glu Ile
225                 230                 235                 240

Pro Leu Leu Ile Phe Pro Pro Trp Ile Asn Lys Phe Tyr Ile Met Asp
            245                 250                 255

Leu Arg Pro Glu Asn Ser Met Ile Arg Trp Leu Thr Ala Gln Gly Phe
            260                 265                 270
```

Thr Val Phe Val Ala Ser Trp Val Asn Pro Asp Gln Thr Leu Ala Ala
              275                 280                 285

Lys Thr Phe Glu Asp Tyr Met Ile Glu Gly Ile Tyr Asp Ala Ala Gln
          290                 295                 300

Gln Val Met Thr Gln Cys Gly Val Asp Arg Val Asn Thr Val Gly Tyr
305                 310                 315                 320

Cys Ile Gly Gly Thr Leu Leu Ser Val Ala Leu Ala His Met Ala Ala
                  325                 330                 335

Arg Gly Asp Lys Arg Ile Asn Ser Ala Thr Phe Phe Ala Ala Gln Gln
              340                 345                 350

Asp Phe Ala Glu Ala Gly Asp Leu Leu Leu Phe Thr Asn Glu Glu Trp
              355                 360                 365

Leu Gln Ser Ile Glu Gln Gln Met Asp Gln Ala Gly Gly Phe Leu Pro
          370                 375                 380

Ser Gln Ser Met Ala Asp Thr Phe Asn Ala Leu Arg Gly Asn Asp Leu
385                 390                 395                 400

Ile Trp Ser Phe Phe Val Ser Asn Tyr Leu Met Gly Lys Glu Pro Arg
                  405                 410                 415

Pro Phe Asp Leu Leu Phe Trp Asn Ala Asp Gln Thr Arg Met Pro Lys
              420                 425                 430

Ala Leu His Leu Phe Tyr Leu Arg Asn Phe Tyr Lys Asp Asn Ala Leu
              435                 440                 445

Thr Thr Gly Lys Leu Ser Leu Gly Gly Glu Arg Leu Asp Leu Ser Lys
          450                 455                 460

Val Lys Ile Pro Ile Tyr Val Gln Ser Ser Lys Asp Asp His Ile Ala
465                 470                 475                 480

Pro Tyr Arg Ser Val Tyr Arg Gly Ala Arg Ala Phe Gly Gly Pro Val
                  485                 490                 495

Thr Phe Thr Met Ala Gly Ser Gly His Ile Ala Gly Val Ile Asn His
              500                 505                 510

Pro Asp Ala Arg Lys Tyr Gln His Trp Thr Asn Ser Glu Leu Pro Ala
          515                 520                 525

Asp Val Ser Glu Trp Ile Ala Gly Ala Gln His Pro Gly Ser Trp
530                 535                 540

Trp Pro His Trp Ala Ala Trp Leu Lys Ala Arg Ser Gly Asp Gln Val
545                 550                 555                 560

Pro Ala Arg Asp Pro Ala Lys Gly Lys Leu Lys Pro Leu Glu Asp Ala
              565                 570                 575

Pro Gly Ser Phe Val Leu Val Lys Ser Gln Pro
          580                 585

<210> SEQ ID NO 37
<211> LENGTH: 576
<212> TYPE: PRT
<213> ORGANISM: Zoogloea ramigera

<400> SEQUENCE: 37

Met Asn Leu Pro Asp Pro Gln Ala Ile Ala Asn Ala Trp Met Ser Gln
1               5                   10                  15

Val Gly Asp Pro Ser Gln Trp Gln Ser Trp Phe Ser Lys Ala Pro Thr
            20                  25                  30

Thr Glu Ala Asn Pro Met Ala Thr Met Leu Gln Asp Ile Gly Val Ala
        35                  40                  45

Leu Lys Pro Glu Ala Met Glu Gln Leu Lys Asn Asp Tyr Leu Arg Asp

```
                50                  55                  60
Phe Thr Ala Leu Trp Gln Asp Phe Leu Ala Gly Lys Ala Pro Ala Val
 65                  70                  75                  80

Gln Arg Pro Arg Phe Ser Ser Ala Ala Trp Gln Gly Asn Pro Met Ser
                     85                  90                  95

Ala Phe Asn Ala Ala Ser Tyr Leu Leu Asn Ala Lys Phe Leu Ser Ala
                    100                 105                 110

Met Val Glu Ala Val Asp Thr Ala Pro Gln Gln Lys Gln Lys Ile Arg
                    115                 120                 125

Phe Ala Val Gln Gln Val Ile Asp Ala Met Ser Pro Ala Asn Phe Leu
                    130                 135                 140

Ala Thr Asn Pro Glu Ala Gln Gln Lys Leu Ile Glu Thr Lys Gly Glu
145                 150                 155                 160

Ser Leu Thr Arg Gly Leu Val Asn Met Leu Gly Asp Ile Asn Met Leu
                    165                 170                 175

Gly Asp Ile Asn Asn Gly His Ile Ser Leu Ser Asp Glu Ser Ala Phe
                    180                 185                 190

Glu Val Gly Arg Asn Leu Ala Ile Thr Pro Gly Thr Val Ile Tyr Glu
                    195                 200                 205

Asn Pro Leu Phe Gln Leu Ile Gln Tyr Thr Pro Thr Thr Pro Thr Val
                    210                 215                 220

Ser Gln Arg Pro Leu Leu Met Val Pro Pro Cys Ile Asn Lys Phe Tyr
225                 230                 235                 240

Ile Leu Asp Leu Gln Pro Glu Asn Ser Leu Val Arg Tyr Ala Val Glu
                    245                 250                 255

Gln Gly Asn Thr Val Phe Leu Ile Ser Trp Ser Asn Pro Asp Lys Ser
                    260                 265                 270

Leu Ala Gly Thr Thr Trp Asp Asp Tyr Val Glu Gln Val Ile Glu
                    275                 280                 285

Ala Ile Arg Ile Val Gln Asp Val Ser Gly Gln Asp Lys Leu Asn Met
                    290                 295                 300

Phe Gly Phe Cys Val Gly Gly Thr Ile Val Ala Thr Ala Leu Ala Val
305                 310                 315                 320

Leu Ala Ala Arg Gly Gln His Pro Ala Ala Ser Leu Thr Leu Leu Thr
                    325                 330                 335

Thr Phe Leu Asp Phe Ser Asp Thr Gly Cys Ser Thr Ser Cys Arg Glu
                    340                 345                 350

Thr Gln Val Ala Leu Arg Glu Gln Gln Leu Arg Asp Gly Gly Leu Met
                    355                 360                 365

Pro Gly Arg Asp Leu Ala Ser Thr Phe Ser Ser Leu Arg Pro Asn Asp
                    370                 375                 380

Leu Val Trp Asn Tyr Val Gln Ser Asn Tyr Leu Lys Gly Asn Glu Pro
385                 390                 395                 400

Ala Ala Phe Asp Leu Leu Phe Trp Asn Ser Asp Ser Thr Asn Leu Pro
                    405                 410                 415

Gly Pro Met Phe Cys Trp Tyr Leu Arg Asn Thr Tyr Leu Glu Asn Ser
                    420                 425                 430

Leu Lys Val Pro Gly Lys Leu Thr Val Ala Gly Glu Lys Ile Asp Leu
                    435                 440                 445

Gly Leu Ile Asp Ala Pro Ala Phe Ile Tyr Gly Ser Arg Glu Asp His
                    450                 455                 460

Ile Val Pro Trp Met Ser Ala Tyr Gly Ser Leu Asp Ile Leu Asn Gln
465                 470                 475                 480
```

```
Gly Lys Pro Gly Ala Asn Arg Phe Val Leu Gly Ala Ser Gly His Ile
                485                 490                 495
Ala Gly Val Ile Asn Ser Val Ala Lys Asn Lys Arg Thr Tyr Trp Ile
            500                 505                 510
Asn Asp Gly Gly Ala Ala Asp Ala Gln Ala Trp Phe Asp Gly Ala Gln
        515                 520                 525
Glu Val Pro Gly Ser Trp Trp Pro Gln Trp Ala Gly Phe Leu Thr Gln
    530                 535                 540
His Gly Gly Lys Lys Val Lys Pro Lys Ala Lys Pro Gly Asn Ala Arg
545                 550                 555                 560
Tyr Thr Ala Ile Glu Ala Ala Pro Gly Arg Tyr Val Lys Ala Lys Gly
                565                 570                 575

<210> SEQ ID NO 38
<211> LENGTH: 536
<212> TYPE: PRT
<213> ORGANISM: Azohydromonas latus

<400> SEQUENCE: 38

Met Ser Gly Leu Asn Leu Pro Met Gln Ala Met Thr Lys Leu Gln Gly
1               5                   10                  15
Glu Tyr Leu Asn Glu Ala Thr Ala Leu Trp Asn Gln Thr Leu Gly Arg
                20                  25                  30
Leu Gln Pro Asp Gly Ser Ala Gln Pro Ala Lys Leu Gly Asp Arg Arg
            35                  40                  45
Phe Ser Ala Glu Asp Trp Ala Lys Asn Pro Ala Ala Ala Tyr Leu Ala
    50                  55                  60
Gln Val Tyr Leu Leu Asn Ala Arg Thr Leu Met Gln Met Ala Glu Ser
65                  70                  75                  80
Ile Glu Gly Asp Ala Lys Ala Lys Ala Arg Val Arg Phe Ala Val Gln
                85                  90                  95
Gln Trp Ile Asp Ala Ala Ala Pro Ser Asn Phe Leu Ala Leu Asn Pro
                100                 105                 110
Glu Ala Gln Arg Lys Ala Leu Glu Thr Lys Gly Glu Ser Ile Ser Gln
            115                 120                 125
Gly Leu Gln Gln Leu Trp His Asp Ile Gln Gln Gly His Val Ser Gln
    130                 135                 140
Thr Asp Glu Ser Val Phe Glu Val Gly Lys Asn Val Ala Thr Thr Glu
145                 150                 155                 160
Gly Ala Val Val Tyr Glu Asn Asp Leu Phe Gln Leu Ile Glu Tyr Lys
                165                 170                 175
Pro Leu Thr Pro Lys Val His Glu Lys Pro Met Leu Phe Val Pro Pro
                180                 185                 190
Cys Ile Asn Lys Tyr Tyr Ile Leu Asp Leu Gln Pro Asp Asn Ser Leu
            195                 200                 205
Ile Arg Tyr Thr Val Ala Gln Gly His Arg Val Phe Val Val Ser Trp
    210                 215                 220
Arg Asn Pro Asp Ala Ser Val Ala Gly Lys Thr Trp Asp Asp Tyr Val
225                 230                 235                 240
Glu Gln Gly Val Ile Arg Ala Ile Arg Val Met Gln Gln Ile Thr Gly
                245                 250                 255
His Glu Lys Val Asn Ala Leu Gly Phe Cys Val Gly Gly Thr Ile Leu
                260                 265                 270
Ser Thr Ala Leu Ala Val Leu Ala Ala Arg Gly Glu Gln Pro Ala Ala
```

```
                275                 280                 285
Ser Leu Thr Leu Leu Thr Thr Leu Leu Asp Phe Ser Asn Thr Gly Val
    290                 295                 300

Leu Asp Leu Phe Ile Asp Glu Ala Gly Val Arg Leu Arg Glu Met Thr
305                 310                 315                 320

Ile Gly Glu Lys Ala Pro Asn Gly Pro Gly Leu Leu Asn Gly Lys Glu
                325                 330                 335

Leu Ala Thr Thr Phe Ser Phe Leu Arg Pro Asn Asp Leu Val Trp Asn
            340                 345                 350

Tyr Val Val Gly Asn Tyr Leu Lys Gly Glu Ala Pro Pro Phe Asp
        355                 360                 365

Leu Leu Tyr Trp Asn Ser Asp Ser Thr Asn Met Ala Gly Pro Met Phe
    370                 375                 380

Cys Trp Tyr Leu Arg Asn Thr Tyr Leu Glu Asn Lys Leu Arg Val Pro
385                 390                 395                 400

Gly Ala Leu Thr Ile Cys Gly Glu Lys Val Asp Leu Ser Arg Ile Glu
                405                 410                 415

Ala Pro Val Tyr Phe Tyr Gly Ser Arg Glu Asp His Ile Val Pro Trp
            420                 425                 430

Glu Ser Ala Tyr Ala Gly Thr Gln Met Leu Ser Gly Pro Lys Arg Tyr
        435                 440                 445

Val Leu Gly Ala Ser Gly His Ile Ala Gly Val Ile Asn Pro Pro Gln
    450                 455                 460

Lys Lys Lys Arg Ser Tyr Trp Thr Asn Glu Gln Leu Asp Gly Asp Phe
465                 470                 475                 480

Asn Gln Trp Leu Glu Gly Ser Thr Glu His Pro Gly Ser Trp Trp Thr
                485                 490                 495

Asp Trp Ser Asp Trp Leu Lys Gln His Ala Gly Lys Glu Ile Ala Ala
            500                 505                 510

Pro Lys Thr Pro Gly Asn Lys Thr His Lys Pro Ile Glu Pro Ala Pro
        515                 520                 525

Gly Arg Tyr Val Lys Gln Lys Ala
    530                 535

<210> SEQ ID NO 39
<211> LENGTH: 590
<212> TYPE: PRT
<213> ORGANISM: Acinetobacter sp. RA3849

<400> SEQUENCE: 39

Met Asn Pro Asn Ser Phe Gln Phe Lys Glu Asn Ile Leu Gln Phe Phe
1               5                   10                  15

Ser Val His Asp Asp Ile Trp Lys Lys Leu Gln Glu Phe Tyr Tyr Gly
            20                  25                  30

Gln Ser Pro Ile Asn Glu Ala Leu Ala Gln Leu Asn Lys Glu Asp Met
        35                  40                  45

Ser Leu Phe Phe Glu Ala Leu Ser Lys Asn Pro Ala Arg Met Met Glu
    50                  55                  60

Met Gln Trp Ser Trp Trp Gln Gly Gln Ile Gln Ile Tyr Gln Asn Val
65                  70                  75                  80

Leu Met Arg Ser Val Ala Lys Asp Val Ala Pro Phe Ile Gln Pro Glu
                85                  90                  95

Ser Gly Asp Arg Arg Phe Asn Ser Pro Leu Trp Gln Glu His Pro Asn
            100                 105                 110
```

```
Phe Asp Leu Leu Ser Gln Ser Tyr Leu Leu Phe Ser Gln Leu Val Gln
            115                 120                 125

Asn Met Val Asp Val Val Glu Gly Val Pro Asp Lys Val Arg Tyr Arg
130                 135                 140

Ile His Phe Phe Thr Arg Gln Met Ile Asn Ala Leu Ser Pro Ser Asn
145                 150                 155                 160

Phe Leu Trp Thr Asn Pro Glu Val Ile Gln Gln Thr Val Ala Glu Gln
                165                 170                 175

Gly Glu Asn Leu Val Arg Gly Met Gln Val Phe His Asp Asp Val Met
            180                 185                 190

Asn Ser Gly Lys Tyr Leu Ser Ile Arg Met Val Asn Ser Asp Ser Phe
195                 200                 205

Ser Leu Gly Lys Asp Leu Ala Tyr Thr Pro Gly Ala Val Val Phe Glu
    210                 215                 220

Asn Asp Ile Phe Gln Leu Leu Gln Tyr Glu Ala Thr Thr Glu Asn Val
225                 230                 235                 240

Tyr Gln Thr Pro Ile Leu Val Val Pro Pro Phe Ile Asn Lys Tyr Tyr
                245                 250                 255

Val Leu Asp Leu Arg Glu Gln Asn Ser Leu Val Asn Trp Leu Arg Gln
            260                 265                 270

Gln Gly His Thr Val Phe Leu Met Ser Trp Arg Asn Pro Asn Ala Glu
        275                 280                 285

Gln Lys Glu Leu Thr Phe Ala Asp Leu Ile Thr Gln Gly Ser Val Glu
    290                 295                 300

Ala Leu Arg Val Ile Glu Glu Ile Thr Gly Glu Lys Glu Ala Asn Cys
305                 310                 315                 320

Ile Gly Tyr Cys Ile Gly Gly Thr Leu Leu Ala Ala Thr Gln Ala Tyr
                325                 330                 335

Tyr Val Ala Lys Arg Leu Lys Asn His Val Lys Ser Ala Thr Tyr Met
            340                 345                 350

Ala Thr Ile Ile Asp Phe Glu Asn Pro Gly Ser Leu Gly Val Phe Ile
        355                 360                 365

Asn Glu Pro Val Val Ser Gly Leu Glu Asn Leu Asn Asn Gln Leu Gly
    370                 375                 380

Tyr Phe Asp Gly Arg Gln Leu Ala Val Thr Phe Ser Leu Leu Arg Glu
385                 390                 395                 400

Asn Thr Leu Tyr Trp Asn Tyr Tyr Ile Asp Asn Tyr Leu Lys Gly Lys
                405                 410                 415

Glu Pro Ser Asp Phe Asp Ile Leu Tyr Trp Asn Ser Asp Gly Thr Asn
            420                 425                 430

Ile Pro Ala Lys Ile His Asn Phe Leu Leu Arg Asn Leu Tyr Leu Asn
        435                 440                 445

Asn Glu Leu Ile Ser Pro Asn Ala Val Lys Val Asn Gly Val Gly Leu
    450                 455                 460

Asn Leu Ser Arg Val Lys Thr Pro Ser Phe Phe Ile Ala Thr Gln Glu
465                 470                 475                 480

Asp His Ile Ala Leu Trp Asp Thr Cys Phe Arg Gly Ala Asp Tyr Leu
                485                 490                 495

Gly Gly Glu Ser Thr Leu Val Leu Gly Glu Ser Gly His Val Ala Gly
            500                 505                 510

Ile Val Asn Pro Pro Ser Arg Asn Lys Tyr Gly Cys Tyr Thr Asn Ala
        515                 520                 525

Ala Lys Phe Glu Asn Thr Lys Gln Trp Leu Asp Gly Ala Glu Tyr His
```

```
                530             535             540
Pro Glu Ser Trp Trp Leu Arg Trp Gln Ala Trp Val Thr Pro Tyr Thr
545                 550             555                 560

Gly Glu Gln Val Pro Ala Arg Asn Leu Gly Asn Ala Gln Tyr Pro Ser
                565             570             575

Ile Glu Ala Ala Pro Gly Arg Tyr Val Leu Val Asn Leu Phe
            580             585             590
```

<210> SEQ ID NO 40
<211> LENGTH: 625
<212> TYPE: PRT
<213> ORGANISM: Burkholderia sp. DSMZ 9242

<400> SEQUENCE: 40

```
Met Thr Ala Ser Lys Asn Ser Ser Thr Ser Ala Gln Ala Asp Thr Phe
1               5                   10                  15

Ala Gly Gln Gln Ala Phe Ala Gln Ala Ala Gln Ala Ala Gln Pro
            20                  25                  30

Met Gln Gln Met Phe Glu Ala Trp Leu Ser Ala Trp Arg Gly Phe Ala
            35                  40                  45

Asp Pro Ala Arg Ala Ala Thr Ala Ser Ala Ala Thr Asn Pro Phe Ala
50                  55                  60

Thr Phe Gln Phe Pro Lys Ser Phe Pro Phe Gln Met Pro Ser Met Ala
65                  70                  75                  80

Asp Phe Gly Gly Ala Ala Ser Pro Phe Ala Gly Leu Lys Leu Pro Ala
                85                  90                  95

Ala Ala Ile Pro Pro Glu Arg Leu Gln Lys Leu Gln Ala Asp Tyr Ala
            100                 105                 110

Arg Asp Cys Val Thr Leu Met Gln Gln Ala Ser Ala Ala Lys Leu Glu
        115                 120                 125

Ala Pro Glu Leu Lys Asp Arg Arg Phe Ser Gly Asp Ala Trp Lys Ala
130                 135                 140

Ser Pro Ala His Ala Phe Ala Ala Ala Trp Tyr Leu Leu Asn Ala Arg
145                 150                 155                 160

Tyr Leu Gln Glu Leu Ala Asp Ala Leu Glu Thr Asp Pro Lys Thr Arg
                165                 170                 175

Glu Arg Ile Arg Phe Ala Val Gln Gln Trp Thr Ala Ala Ala Pro
            180                 185                 190

Ser Asn Phe Leu Ala Phe Asn Pro Asp Ala Gln Lys Ser Ile Leu Glu
        195                 200                 205

Thr Gln Gly Glu Ser Leu Arg Gln Gly Met Met Asn Leu Leu Gly Asp
210                 215                 220

Leu Gln Arg Gly Lys Ile Ser Gln Thr Asp Glu Ser Gln Phe Val Val
225                 230                 235                 240

Gly Lys Asn Leu Gly Cys Thr Glu Gly Ala Val Val Tyr Glu Asn Asp
                245                 250                 255

Leu Ile Gln Leu Ile Gln Tyr Lys Pro Thr Thr Glu Thr Val Phe Glu
            260                 265                 270

Arg Pro Leu Leu Ile Val Pro Pro Cys Ile Asn Lys Phe Tyr Ile Leu
        275                 280                 285

Asp Leu Gln Pro Glu Asn Ser Leu Val Ala His Ala Leu Ser Cys Gly
        290                 295                 300

His Gln Val Phe Leu Val Ser Trp Arg Asn Ala Asp Ala Ser Val Ala
305                 310                 315                 320
```

-continued

```
His Lys Thr Trp Asp Asp Tyr Met Asn Glu Gly Leu Leu Ala Ala Ile
                325                 330                 335

Asp Ala Val Gln Gln Val Ser Gly Arg Glu Gln Ile Asn Thr Leu Gly
            340                 345                 350

Phe Cys Val Gly Gly Thr Met Leu Ser Thr Ala Leu Ala Val Leu Ala
        355                 360                 365

Ala Arg Gly Glu His Pro Ala Ala Ser Met Thr Leu Leu Thr Ala Met
370                 375                 380

Leu Asp Phe Ser Asp Thr Gly Val Val Asp Val Phe Val Asp Arg Ala
385                 390                 395                 400

His Val Gln Met Arg Glu Gln Thr Ile Gly Gly Lys Ser Gly Thr Pro
                405                 410                 415

Pro Gly Leu Met Arg Gly Val Glu Phe Ala Asn Thr Phe Ser Phe Leu
            420                 425                 430

Arg Pro Asn Asp Leu Val Trp Asn Tyr Val Val Asp Asn Tyr Leu Lys
        435                 440                 445

Gly Arg Thr Pro Ala Pro Phe Asp Leu Leu Tyr Trp Asn Ser Asp Ser
450                 455                 460

Thr Asn Leu Pro Gly Pro Met Tyr Ala Trp Tyr Leu Arg Asn Thr Tyr
465                 470                 475                 480

Leu Glu Asn Arg Leu Arg Glu Pro Gly Ala Leu Thr Val Cys Gly Glu
                485                 490                 495

Ala Val Asp Leu Ser Arg Ile Asp Val Pro Thr Phe Ile Tyr Gly Ser
            500                 505                 510

Arg Glu Asp His Ile Val Pro Trp Gln Thr Ala Tyr Ala Ser Thr Ser
        515                 520                 525

Ile Leu Thr Gly Pro Leu Lys Phe Val Leu Gly Ala Ser Gly His Ile
530                 535                 540

Ala Gly Val Ile Asn Pro Pro Ala Lys Lys Lys Arg Ser Phe Trp Val
545                 550                 555                 560

Asn Asp Asn Asp Leu Pro Asp Ala Ala Asp Asp Trp Phe Ala Gly Ala
                565                 570                 575

Ala Glu Gln Pro Gly Ser Trp Trp Pro Thr Trp Thr Glu Trp Leu Gly
            580                 585                 590

Gln Tyr Gly Gly Arg Lys Val Ala Pro Pro Ala Gln Ala Gly Ser Ala
        595                 600                 605

Gln Phe Pro Val Ile Glu Pro Ala Pro Gly Arg Tyr Val Leu Gln Arg
610                 615                 620

Asp
625

<210> SEQ ID NO 41
<211> LENGTH: 561
<212> TYPE: PRT
<213> ORGANISM: Nocardia corallina

<400> SEQUENCE: 41

Met Met Ala Gln Ala Arg Thr Val Ile Gly Glu Ser Val Glu Glu Ser
1               5                   10                  15

Ile Gly Gly Gly Glu Asp Val Ala Pro Pro Arg Leu Gly Pro Ala Val
            20                  25                  30

Gly Ala Leu Ala Asp Val Phe Gly His Gly Arg Ala Val Ala Arg His
        35                  40                  45

Gly Val Ser Phe Gly Arg Glu Leu Ala Lys Ile Ala Val Gly Arg Ser
    50                  55                  60
```

```
Thr Val Ala Pro Ala Lys Gly Asp Arg Arg Phe Ala Asp Ser Ala Trp
 65                  70                  75                  80

Ser Ala Asn Pro Ala Tyr Arg Arg Leu Gly Gln Thr Tyr Leu Ala Ala
                 85                  90                  95

Thr Glu Ala Val Asp Gly Val Val Asp Glu Val Gly Arg Ala Ile Gly
            100                 105                 110

Pro Arg Arg Thr Ala Glu Ala Arg Phe Ala Ala Asp Ile Leu Thr Ala
        115                 120                 125

Ala Leu Ala Pro Thr Asn Tyr Leu Trp Thr Asn Pro Ala Ala Leu Lys
130                 135                 140

Glu Ala Phe Asp Thr Ala Gly Leu Ser Leu Ala Arg Gly Thr Lys His
145                 150                 155                 160

Phe Val Ser Asp Leu Ile Glu Asn Arg Gly Met Pro Ser Met Val Gln
                165                 170                 175

Arg Gly Ala Phe Thr Val Gly Lys Asp Leu Ala Val Thr Pro Gly Ala
            180                 185                 190

Val Ile Ser Arg Asp Glu Val Ala Glu Val Leu Gln Tyr Thr Pro Thr
        195                 200                 205

Thr Glu Thr Val Arg Arg Pro Val Leu Val Pro Pro Ile
210                 215                 220

Gly Arg Tyr Tyr Phe Leu Asp Leu Arg Pro Gly Arg Ser Phe Val Glu
225                 230                 235                 240

Tyr Ser Val Gly Arg Gly Leu Gln Thr Phe Leu Leu Ser Trp Arg Asn
                245                 250                 255

Pro Thr Ala Glu Gln Gly Asp Trp Asp Phe Asp Thr Tyr Ala Gly Arg
            260                 265                 270

Val Ile Arg Ala Ile Asp Glu Val Arg Glu Ile Thr Gly Ser Asp Asp
        275                 280                 285

Val Asn Leu Ile Gly Phe Cys Ala Gly Gly Ile Ile Ala Thr Thr Val
290                 295                 300

Leu Asn His Leu Ala Ala Gln Gly Asp Thr Arg Val His Ser Met Ala
305                 310                 315                 320

Tyr Ala Val Thr Met Leu Asp Phe Gly Asp Pro Ala Leu Leu Gly Ala
                325                 330                 335

Phe Ala Arg Pro Gly Leu Ile Arg Phe Ala Lys Gly Arg Ser Arg Arg
            340                 345                 350

Lys Gly Ile Ile Ser Ala Arg Asp Met Gly Ser Ala Phe Thr Trp Met
        355                 360                 365

Arg Pro Asn Asp Leu Val Phe Asn Tyr Val Val Asn Asn Tyr Leu Met
370                 375                 380

Gly Arg Thr Pro Pro Ala Phe Asp Ile Leu Ala Trp Asn Asp Asp Gly
385                 390                 395                 400

Thr Asn Leu Pro Gly Ala Leu His Gly Gln Phe Leu Asp Ile Phe Arg
                405                 410                 415

Asp Asn Val Leu Val Glu Pro Gly Arg Leu Ala Val Leu Gly Thr Pro
            420                 425                 430

Val Asp Leu Lys Ser Ile Thr Val Pro Thr Phe Val Ser Gly Ala Ile
        435                 440                 445

Ala Asp His Leu Thr Ala Trp Arg Asn Cys Tyr Arg Thr Thr Gln Leu
450                 455                 460

Leu Gly Gly Glu Thr Glu Phe Ala Leu Ser Phe Ser Gly His Ile Ala
465                 470                 475                 480
```

```
Ser Leu Val Asn Pro Pro Gly Asn Pro Lys Ala His Tyr Trp Thr Gly
                485                 490                 495

Gly Thr Pro Gly Pro Asp Pro Asp Ala Trp Leu Glu Asn Ala Glu Arg
            500                 505                 510

Gln Gln Gly Ser Trp Trp Gln Ala Trp Ala Asp Trp Val Leu Ala Arg
            515                 520                 525

Gly Gly Glu Glu Thr Ala Ala Pro Asp Ala Pro Gly Ser Ala His Asp
            530                 535                 540

Arg Ala Leu Asp Ala Ala Pro Gly Arg Tyr Val Arg Asp Leu Pro Ala
545                 550                 555                 560

Gly

<210> SEQ ID NO 42
<211> LENGTH: 562
<212> TYPE: PRT
<213> ORGANISM: Rhodococcus ruber

<400> SEQUENCE: 42

Met Leu Asp His Val His Lys Lys Leu Lys Ser Thr Leu Asp Pro Ile
1               5                   10                  15

Gly Trp Gly Pro Ala Val Thr Ser Val Ala Gly Arg Ala Val Arg Asn
            20                  25                  30

Pro Gln Ala Val Thr Ala Ala Thr Ala Glu Tyr Ala Gly Arg Leu Ala
        35                  40                  45

Lys Ile Pro Ala Ala Thr Arg Val Phe Asn Ala Asn Asp Pro Asp
    50                  55                  60

Ala Pro Met Pro Val Asp Pro Arg Asp Arg Arg Phe Ser Asp Thr Ala
65                  70                  75                  80

Trp Gln Glu Asn Pro Ala Tyr Phe Ser Leu Leu Gln Ser Tyr Leu Ala
                85                  90                  95

Thr Arg Ala Tyr Val Glu Glu Leu Thr Glu Ala Gly Ser Gly Asp Pro
            100                 105                 110

Leu Gln Asp Gly Lys Ala Arg Gln Phe Ala Asn Leu Met Phe Asp Ala
        115                 120                 125

Leu Ala Pro Ser Asn Phe Leu Trp Asn Pro Gly Val Leu Thr Arg Ala
    130                 135                 140

Phe Glu Thr Gly Gly Ala Ser Leu Leu Arg Gly Ala Arg Tyr Ala Ala
145                 150                 155                 160

His Asp Ile Leu Asn Arg Gly Gly Leu Pro Leu Lys Val Asp Ser Asp
                165                 170                 175

Ala Phe Thr Val Gly Glu Asn Leu Ala Ala Thr Pro Gly Lys Val Val
            180                 185                 190

Phe Arg Asn Asp Leu Ile Glu Leu Ile Gln Tyr Ala Pro Gln Thr Glu
        195                 200                 205

Gln Val His Ala Val Pro Ile Leu Ala Ala Pro Trp Ile Asn Lys
    210                 215                 220

Tyr Tyr Ile Leu Asp Leu Ala Pro Gly Arg Ser Leu Ala Glu Trp Ala
225                 230                 235                 240

Val Gln His Gly Arg Thr Val Phe Met Ile Ser Tyr Arg Asn Pro Asp
                245                 250                 255

Glu Ser Met Arg His Ile Thr Met Asp Asp Tyr Tyr Val Asp Gly Ile
            260                 265                 270

Ala Thr Ala Leu Asp Val Val Glu Glu Ile Thr Gly Ser Pro Lys Ile
        275                 280                 285
```

Glu Val Leu Ser Ile Cys Leu Gly Gly Ala Met Ala Met Ala Ala
        290                 295                 300

Ala Arg Ala Phe Ala Val Gly Asp Lys Arg Val Ser Ala Phe Thr Met
305                 310                 315                 320

Leu Asn Thr Leu Leu Asp Tyr Ser Gln Val Gly Glu Leu Gly Leu Leu
                325                 330                 335

Thr Asp Pro Ala Thr Leu Asp Leu Val Glu Phe Arg Met Arg Gln Gln
            340                 345                 350

Gly Phe Leu Ser Gly Lys Glu Met Ala Gly Ser Phe Asp Met Ile Arg
        355                 360                 365

Ala Lys Asp Leu Val Phe Asn Tyr Trp Val Ser Arg Trp Met Lys Gly
370                 375                 380

Glu Lys Pro Ala Ala Phe Asp Ile Leu Ala Trp Asn Glu Asp Ser Thr
385                 390                 395                 400

Ser Met Pro Ala Glu Met His Ser His Tyr Leu Arg Ser Leu Tyr Gly
                405                 410                 415

Arg Asn Glu Leu Ala Glu Gly Leu Tyr Val Leu Asp Gly Gln Pro Leu
            420                 425                 430

Asn Leu His Asp Ile Ala Cys Asp Thr Tyr Val Val Gly Ala Ile Asn
        435                 440                 445

Asp His Ile Val Pro Trp Thr Ser Ser Tyr Gln Ala Val Asn Leu Leu
450                 455                 460

Gly Gly Asp Val Arg Tyr Val Leu Thr Asn Gly His Val Ala Gly
465                 470                 475                 480

Ala Val Asn Pro Pro Gly Lys Arg Val Trp Phe Lys Ala Val Gly Ala
                485                 490                 495

Pro Asp Ala Glu Ser Gly Thr Pro Leu Pro Ala Asp Pro Gln Val Trp
            500                 505                 510

Asp Glu Ala Ala Thr Arg Tyr Glu His Ser Trp Trp Glu Asp Trp Thr
        515                 520                 525

Ala Trp Ser Asn Lys Arg Ala Gly Glu Leu Val Ala Pro Pro Ala Met
530                 535                 540

Gly Ser Thr Ala His Pro Pro Leu Glu Asp Ala Pro Gly Thr Tyr Val
545                 550                 555                 560

Phe Ser

<210> SEQ ID NO 43
<211> LENGTH: 673
<212> TYPE: PRT
<213> ORGANISM: Rhodospirillum rubrum

<400> SEQUENCE: 43

Met Phe Thr Thr Thr Asn Pro Thr Phe Ile Arg Pro Thr Ala Ala Cys
1               5                   10                  15

Pro Met Phe Ser Cys Cys Pro Thr Trp Ala Ala Arg Arg Ser Lys Pro
                20                  25                  30

Glu Pro Pro Trp Ala Ser Trp Pro Trp Ile Ile Leu Thr Pro Ile Ser
            35                  40                  45

Ala Ala Ala Ser Arg Pro Thr Gly Ser Pro Asp Arg Pro Trp Ser Gly
        50                  55                  60

Arg Pro Ser Glu Arg Glu Gly Lys Thr Met Thr Asp Thr Arg Ala Glu
65                  70                  75                  80

Ala Asp Leu Thr Glu Val Trp Arg Ala Trp Ala Ala Trp Gly Glu Lys
                85                  90                  95

```
Ser Arg Thr Met Trp Ala Thr Ala Leu Gly Gly Ala Ala Pro Pro Ser
            100                 105                 110

Ser Pro Ser Pro Ser Gly Pro Asp Pro Ala Val Gly Gly Pro Ala
        115                 120                 125

Val Gly Gly Asp Ala Ala Arg Ala Phe Leu Glu Gly Val Leu Arg Pro
    130                 135                 140

Ser Gln Pro Val Leu Asp Ala Gln Ala Ala Trp Ala Arg Asp Ile Ala
145                 150                 155                 160

Ala Leu Cys Gln Ala Ala Lys Arg Leu Arg Gly Glu Glu Ala Ala
            165                 170                 175

Pro Val Ile Glu Pro Ala Gly Asp Asp Asn Arg Phe Lys Asp Asp Ala
            180                 185                 190

Trp Thr Lys Asp Pro Leu Phe Asp Thr Leu Lys Gln Gly Tyr Leu Leu
        195                 200                 205

Thr Ala Arg Leu Val Ala Thr Thr Leu Glu Asn Ser Gly Gly Asp Pro
        210                 215                 220

Ala Cys Arg Gln Arg Leu Ala Phe Tyr Gly Arg Gln Val Val Asp Ala
225                 230                 235                 240

Leu Ala Pro Thr Asn Phe Ala Ala Thr Asn Pro Leu Val Arg Arg Thr
            245                 250                 255

Ala Leu Glu Ser Gly Gly Lys Ser Leu Leu Asn Gly Leu Glu Asn Leu
            260                 265                 270

Leu Arg Asp Leu Glu Arg Gly Gly Arg Leu Arg Pro Thr Met Ser
        275                 280                 285

Asp Glu Thr Ala Phe Glu Val Gly Arg Thr Leu Ala Met Thr Pro Gly
        290                 295                 300

Lys Val Val Phe Gln Asn Ala Leu Met Gln Leu Ile Leu Tyr Ala Pro
305                 310                 315                 320

Thr Thr Pro Lys Val His Lys Arg Pro Leu Leu Val Val Pro Pro Trp
            325                 330                 335

Ile Asn Lys Phe Tyr Ile Leu Asp Leu Thr Glu Lys Asn Ser Leu Ile
            340                 345                 350

Lys Tyr Met Val Asp Gln Gly Phe Ser Val Phe Val Ile Ser Trp Val
        355                 360                 365

Asn Pro Asp Ala Gly Leu Ala Glu Thr Arg Phe Glu Asp Tyr Leu Ser
        370                 375                 380

Gln Gly Pro Leu Ala Ala Met Glu Val Met Thr Glu Ile Thr Gly Gln
385                 390                 395                 400

Arg Ala Leu Gly Leu Val Gly Tyr Cys Ile Gly Gly Thr Leu Thr Ala
            405                 410                 415

Cys Thr Leu Ala Val Leu Ala Ala Arg Arg Asp His Arg Val Lys Ser
            420                 425                 430

Ala Thr Leu Leu Thr Thr Leu Val Asp Phe Ser Glu Pro Gly Glu Leu
        435                 440                 445

Gly Val Phe Ile Asp Pro Pro Leu Leu Asp Ala Leu Asp Gln Met
    450                 455                 460

Ala Arg Asp Gly Gly Leu Asp Gly Asp Leu Leu Ser Met Ala Phe Asn
465                 470                 475                 480

Met Leu Arg Asp Asn Asp Leu Ile Trp Ser Val Phe Ile Asn Asn Tyr
            485                 490                 495

Leu Leu Gly Lys Thr Pro Ala Ala Phe Asp Leu Leu Tyr Trp Asn Gly
            500                 505                 510

Asp Ser Thr Arg Met Pro Ala Ala Met Gln Arg Tyr Tyr Leu Arg Glu
```

```
                515                 520                 525
Met Tyr Gln Lys Asn Lys Leu Val Gln Pro Gly Gly Leu Thr Val Leu
    530                 535                 540

Gly His Ala Leu Asp Leu Arg Arg Ile Arg Thr Pro Val Tyr Leu Leu
545                 550                 555                 560

Ser Ala Arg Asp Asp His Ile Ala Pro Trp Thr Ser Thr Phe Lys Ala
                565                 570                 575

Thr Gly Leu Tyr Gly Gly Pro Leu Arg Phe Val Leu Ala Gly Ser Gly
            580                 585                 590

His Ile Ala Gly Val Ile Asn Pro Pro Ala Lys Ala Arg Tyr Gly Tyr
        595                 600                 605

Trp Thr Asn Ala Asp Thr Ser Leu Glu Ala Glu Ser Trp Leu Glu Gly
    610                 615                 620

Ala Thr Pro His Gly Gly Ser Trp Trp Pro Asp Trp Ala Ala Trp Ala
625                 630                 635                 640

Ala Gly Tyr Ala Gly Pro Lys Val Ala Ala Arg Asp Pro Thr Lys Gly
                645                 650                 655

Pro Arg Pro Pro Leu Glu Asp Ala Pro Gly Ser Tyr Val Lys Val Arg
            660                 665                 670

Ile

<210> SEQ ID NO 44
<211> LENGTH: 559
<212> TYPE: PRT
<213> ORGANISM: Pseudomonas oleovorans

<400> SEQUENCE: 44

Met Ser Asn Lys Asn Asn Asp Glu Leu Gln Arg Gln Ala Ser Glu Asn
1               5                   10                  15

Thr Leu Gly Leu Asn Pro Val Ile Gly Ile Arg Arg Lys Asp Leu Leu
            20                  25                  30

Ser Ser Ala Arg Thr Val Leu Arg Gln Ala Val Arg Gln Pro Leu His
        35                  40                  45

Ser Ala Lys His Val Ala His Phe Gly Leu Glu Leu Lys Asn Val Leu
    50                  55                  60

Leu Gly Lys Ser Ser Leu Ala Pro Glu Ser Asp Asp Arg Arg Phe Asn
65                  70                  75                  80

Asp Pro Ala Trp Ser Asn Asn Pro Leu Tyr Arg Arg Tyr Leu Gln Thr
                85                  90                  95

Tyr Leu Ala Trp Arg Lys Glu Leu Gln Asp Trp Ile Gly Asn Ser Asp
            100                 105                 110

Leu Ser Pro Gln Asp Ile Ser Arg Gly Gln Phe Val Ile Asn Leu Met
        115                 120                 125

Thr Glu Ala Met Ala Pro Thr Asn Thr Leu Ser Asn Pro Ala Ala Val
    130                 135                 140

Lys Arg Phe Phe Glu Thr Gly Gly Lys Ser Leu Leu Asp Gly Leu Ser
145                 150                 155                 160

Asn Leu Ala Lys Asp Leu Val Asn Asn Gly Gly Met Pro Ser Gln Val
                165                 170                 175

Asn Met Asp Ala Phe Glu Val Gly Lys Asn Leu Gly Thr Ser Glu Gly
            180                 185                 190

Ala Val Val Tyr Arg Asn Asp Val Leu Glu Leu Ile Gln Tyr Lys Pro
        195                 200                 205

Ile Thr Glu Gln Val His Ala Arg Pro Leu Leu Val Val Pro Pro Gln
```

```
              210                 215                 220
Ile Asn Lys Phe Tyr Val Phe Asp Leu Ser Pro Glu Lys Ser Leu Ala
225                 230                 235                 240

Arg Tyr Cys Leu Arg Ser Gln Gln Thr Phe Ile Ile Ser Trp Arg
                245                 250                 255

Asn Pro Thr Lys Ala Gln Arg Glu Trp Gly Leu Ser Thr Tyr Ile Asp
                260                 265                 270

Ala Leu Lys Glu Ala Val Asp Ala Val Leu Ala Ile Thr Gly Ser Lys
                275                 280                 285

Asp Leu Asn Met Leu Gly Ala Cys Ser Gly Gly Ile Thr Cys Thr Ala
            290                 295                 300

Leu Val Gly His Tyr Ala Ala Leu Gly Glu Asn Lys Val Asn Ala Leu
305                 310                 315                 320

Thr Leu Leu Val Ser Val Leu Asp Thr Thr Met Asp Asn Gln Val Ala
                325                 330                 335

Leu Phe Val Asp Glu Gln Thr Leu Glu Ala Ala Lys Arg His Ser Tyr
                340                 345                 350

Gln Ala Gly Val Leu Glu Gly Ser Glu Met Ala Lys Val Phe Ala Trp
                355                 360                 365

Met Arg Pro Asn Asp Leu Ile Trp Asn Tyr Trp Val Asn Asn Tyr Leu
            370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
                405                 410                 415

Lys Ser Asn Pro Leu Thr Arg Pro Asp Ala Leu Glu Val Cys Gly Thr
                420                 425                 430

Pro Ile Asp Leu Lys Gln Val Lys Cys Asp Ile Tyr Ser Leu Ala Gly
                435                 440                 445

Thr Asn Asp His Ile Thr Pro Trp Gln Ser Cys Tyr Arg Ser Ala His
            450                 455                 460

Leu Phe Gly Gly Lys Ile Glu Phe Val Leu Ser Asn Ser Gly His Ile
465                 470                 475                 480

Gln Ser Ile Leu Asn Pro Pro Gly Asn Pro Lys Ala Arg Phe Met Thr
                485                 490                 495

Gly Ala Asp Arg Pro Gly Asp Pro Val Ala Trp Gln Glu Asn Ala Thr
                500                 505                 510

Lys His Ala Asp Ser Trp Trp Leu His Trp Gln Ser Trp Leu Gly Glu
                515                 520                 525

Arg Ala Gly Glu Leu Glu Lys Ala Pro Thr Arg Leu Gly Asn Arg Ala
            530                 535                 540

Tyr Ala Ala Gly Glu Ala Ser Pro Gly Thr Tyr Val His Glu Arg
545                 550                 555

<210> SEQ ID NO 45
<211> LENGTH: 560
<212> TYPE: PRT
<213> ORGANISM: Pseudomonas putida

<400> SEQUENCE: 45

Met Thr Asp Lys Pro Ala Lys Gly Ser Thr Thr Leu Pro Gly Thr Arg
1               5                   10                  15

Met Asn Val Gln Asn Ala Ile Leu Gly Leu Arg Gly Arg Asp Leu Leu
                20                  25                  30
```

-continued

```
Ser Thr Leu Arg Asn Val Gly Arg His Gly Leu Arg Pro Leu His
         35                  40                  45

Thr Ala His His Leu Leu Ala Leu Gly Gly Gln Leu Gly Arg Val Met
 50                  55                  60

Leu Gly Asp Thr Pro Tyr Gln Pro Asn Pro Arg Asp Ala Arg Phe Ser
 65                  70                  75                  80

Asp Pro Thr Trp Ser Gln Asn Pro Phe Tyr Arg Arg Gly Leu Gln Ala
                 85                  90                  95

Tyr Leu Ala Trp Gln Lys Gln Thr Arg Gln Trp Ile Asp Glu Ser His
             100                 105                 110

Leu Asn Asp Asp Arg Ala Arg Ala His Phe Leu Phe Asn Leu Ile
         115                 120                 125

Asn Asp Ala Leu Ala Pro Ser Asn Ser Leu Leu Asn Pro Leu Ala Val
130                 135                 140

Lys Glu Leu Phe Asn Thr Gly Gly Gln Ser Leu Val Arg Gly Val Ala
145                 150                 155                 160

His Leu Leu Asp Asp Leu Arg His Asn Asp Gly Leu Pro Arg Gln Val
                 165                 170                 175

Asp Glu Arg Ala Phe Glu Val Gly Ala Asn Leu Ala Ala Thr Pro Gly
             180                 185                 190

Ala Val Val Phe Arg Asn Glu Leu Leu Glu Leu Ile Gln Tyr Ser Pro
         195                 200                 205

Met Ser Glu Lys Gln His Ala Arg Pro Leu Leu Val Pro Pro Gln
     210                 215                 220

Ile Asn Lys Phe Tyr Ile Phe Asp Leu Ser Ala Thr Asn Ser Phe Val
225                 230                 235                 240

Gln Tyr Met Leu Lys Ser Gly Leu Gln Val Phe Met Val Ser Trp Arg
                 245                 250                 255

Asn Pro Asp Pro Arg His Arg Glu Trp Gly Leu Ser Ser Tyr Val Gln
             260                 265                 270

Ala Leu Glu Glu Ala Leu Asn Ala Cys Arg Ser Ile Ser Gly Asn Arg
         275                 280                 285

Ala Pro Asn Leu Met Gly Ala Cys Ala Gly Gly Leu Thr Met Ala Ala
     290                 295                 300

Leu Gln Gly His Leu Gln Ala Lys Lys Gln Leu Arg Arg Val Arg Ser
305                 310                 315                 320

Ala Thr Tyr Leu Val Ser Leu Leu Asp Ser Lys Phe Glu Ser Pro Ala
                 325                 330                 335

Ser Leu Phe Ala Asp Glu Gln Thr Ile Glu Ala Ala Lys Arg Arg Ser
             340                 345                 350

Tyr Gln Arg Gly Val Leu Asp Gly Gly Glu Val Ala Arg Ile Phe Ala
         355                 360                 365

Trp Met Arg Pro Asn Asp Leu Ile Trp Asn Tyr Trp Val Asn Asn Tyr
     370                 375                 380

Leu Leu Gly Lys Thr Pro Pro Ala Phe Asp Ile Leu Tyr Trp Asn Ala
385                 390                 395                 400

Asp Ser Thr Arg Leu Pro Ala Ala Leu His Gly Asp Leu Leu Glu Phe
                 405                 410                 415

Phe Lys Leu Asn Pro Leu Thr Tyr Ala Ser Gly Leu Glu Val Cys Gly
             420                 425                 430

Thr Pro Ile Asp Leu Gln Gln Val Asn Ile Asp Ser Phe Thr Val Ala
         435                 440                 445

Gly Ser Asn Asp His Ile Thr Pro Trp Asp Ala Val Tyr Arg Ser Ala
```

-continued

```
            450                 455                 460
Leu Leu Leu Gly Gly Glu Arg Arg Phe Val Leu Ala Asn Ser Gly His
465                 470                 475                 480

Ile Gln Ser Ile Ile Asn Pro Pro Gly Asn Pro Lys Ala Tyr Tyr Leu
                485                 490                 495

Ala Asn Pro Lys Leu Ser Ser Asp Pro Arg Ala Trp Phe His Asp Ala
            500                 505                 510

Lys Arg Ser Glu Gly Ser Trp Trp Pro Leu Trp Leu Glu Trp Ile Thr
        515                 520                 525

Ala Arg Ser Gly Leu Leu Lys Thr Pro Arg Thr Glu Leu Gly Asn Ala
            530                 535                 540

Thr Tyr Pro Pro Leu Gly Pro Ala Pro Gly Thr Tyr Val Leu Thr Arg
545                 550                 555                 560
```

<210> SEQ ID NO 46
<211> LENGTH: 567
<212> TYPE: PRT
<213> ORGANISM: Pseudomonas sp. 61-3

<400> SEQUENCE: 46

```
Met Asp Asn Asn Ala His Thr Phe Lys Thr Tyr Trp Ser Gly Gln Val
1               5                   10                  15

Pro Phe Ile Ala Ser Phe Ala Val Gln Gln Leu Arg Leu Trp Val Ser
                20                  25                  30

Thr Asn Pro Trp Phe Ser Gly His Glu His Gly Ala Trp Phe Glu Leu
            35                  40                  45

Pro Arg Glu Thr Leu Asp Ser Leu Gln Ala Asp Tyr Gln Val Gln Trp
        50                  55                  60

Gly Gln Leu Gly Gln Lys Leu Leu Thr Gly Gln Pro Phe Ser Phe Asp
65                  70                  75                  80

Asp Arg Arg Phe Ala Ser Gly Asn Trp Ser Glu Pro Leu Phe Gly Ser
                85                  90                  95

Leu Ala Ala Phe Tyr Leu Leu Asn Ser Ser Phe Leu Leu Lys Leu Leu
                100                 105                 110

Asp Met Leu Leu Ile Asp Glu Lys Lys Pro Arg Gln Arg Leu Arg Tyr
            115                 120                 125

Leu Val Glu Gln Ala Ile Ala Ala Ser Ala Pro Ser Asn Phe Leu Val
        130                 135                 140

Ser Asn Pro Asp Ala Leu Gln Arg Val Val Glu Thr Gln Gly Ala Ser
145                 150                 155                 160

Leu Val Thr Gly Met Gln His Leu Ala Ser Asp Met Asn Glu Gly Lys
                165                 170                 175

Met Arg Gln Cys Asp Ser Gly Ala Phe Lys Val Gly Ile Asp Leu Ala
                180                 185                 190

Asn Thr Pro Gly Glu Ile Val Phe Glu Asn His Leu Phe Gln Leu Ile
            195                 200                 205

His Tyr Tyr Pro Gln Ser Glu Thr Gln Tyr Arg His Pro Val Phe Val
        210                 215                 220

Val Pro Pro Ser Ile Asn Lys Tyr Tyr Ile Leu Asp Leu Arg Pro Asp
225                 230                 235                 240

Asn Ser Met Val Arg His Leu Leu Glu Gln Gly His Pro Val Phe Leu
                245                 250                 255

Met Ser Trp Arg Asn Phe Asp Glu Glu His Ala Gly Thr Thr Trp Asp
                260                 265                 270
```

Asp Leu Ile Glu Leu Gly Val Ile Asp Gly Leu Gln Val Ala Arg Glu
            275                 280                 285

Ile Ser Gly Glu Gln Arg Leu Asn Cys Val Gly Phe Cys Ile Gly Gly
        290                 295                 300

Thr Leu Ser Thr Ala Leu Ala Val Leu Ala Ala Arg Gly Asp Arg
305                 310                 315                 320

Glu Ile Ala Ser Val Ser Leu Phe Thr Thr Phe Leu Asp Tyr His Asp
                325                 330                 335

Thr Gly Pro Ile Asp Ile Phe Val Asp Glu Leu Val Ala His Arg
            340                 345                 350

Glu Arg Thr Ile Gly Gly Val Asn Gly Pro Ile Gly Leu Phe Arg Gly
        355                 360                 365

Glu Asp Met Gly Asn Thr Phe Ser Leu Leu Arg Pro Asn Asp Leu Trp
370                 375                 380

Trp Asn Tyr Asn Val Asp Lys Tyr Leu Lys Gly Gln Lys Pro Ile Pro
385                 390                 395                 400

Leu Asp Leu Leu Phe Trp Asn Asn Asp Ser Thr Asn Leu Pro Gly Pro
            405                 410                 415

Met Tyr Cys Trp Tyr Leu Arg His Thr Tyr Leu Gln Asn Asp Leu Lys
            420                 425                 430

Ser Gly Glu Leu Glu Cys Cys Gly Asn Lys Leu Asp Leu Arg Ala Ile
        435                 440                 445

Asp Ala Pro Ala Tyr Ile Leu Ala Thr His Asp Asp His Ile Val Pro
            450                 455                 460

Trp Lys Ser Ala Tyr Ala Ser Thr Asn Leu Leu Ser Gly Ser Lys Arg
465                 470                 475                 480

Phe Val Leu Gly Ala Ser Gly His Ile Ala Gly Val Ile Asn Pro Pro
                485                 490                 495

Ala Lys Gln Lys Arg His Tyr Trp Thr Asn Asn Arg Val Thr Lys Asn
            500                 505                 510

Pro Glu Thr Trp Phe Lys Asn Ala Glu Gln His Pro Gly Ser Trp Trp
        515                 520                 525

Asn Asp Trp Phe Thr Trp Leu Ala Gly His Ser Gly Glu Arg Gln Pro
530                 535                 540

Ala Val Ala His Thr Gly Asn Asn Lys Tyr Pro Pro Leu Glu Pro Ala
545                 550                 555                 560

Pro Gly Arg Tyr Val Lys Leu
            565

<210> SEQ ID NO 47
<211> LENGTH: 355
<212> TYPE: PRT
<213> ORGANISM: Allochromatium vinosum

<400> SEQUENCE: 47

Met Phe Pro Ile Asp Ile Arg Pro Asp Lys Leu Thr Gln Glu Met Leu
1               5                   10                  15

Asp Tyr Ser Arg Lys Leu Gly Gln Gly Met Glu Asn Leu Leu Asn Ala
            20                  25                  30

Glu Ala Ile Asp Thr Gly Val Ser Pro Lys Gln Ala Val Tyr Ser Glu
        35                  40                  45

Asp Lys Leu Val Leu Tyr Arg Tyr Asp Arg Pro Glu Gly Ala Pro Glu
    50                  55                  60

Ala Gln Pro Val Pro Leu Leu Ile Val Tyr Ala Leu Val Asn Arg Pro
65                  70                  75                  80

```
Tyr Met Thr Asp Ile Gln Glu Asp Arg Ser Thr Ile Lys Gly Leu Leu
                85                  90                  95

Ala Thr Gly Gln Asp Val Tyr Leu Ile Asp Trp Gly Tyr Pro Asp Gln
            100                 105                 110

Ala Asp Arg Ala Leu Thr Leu Asp Asp Tyr Ile Asn Gly Tyr Ile Asp
            115                 120                 125

Arg Cys Val Asp Tyr Leu Arg Glu Ala His Gly Val Asp Lys Val Asn
    130                 135                 140

Leu Leu Gly Ile Cys Gln Gly Gly Ala Phe Ser Leu Met Tyr Ser Ala
145                 150                 155                 160

Leu His Pro Asp Lys Val Arg Asn Leu Val Thr Met Val Thr Pro Val
                165                 170                 175

Asp Phe Lys Thr Pro Asp Asn Leu Leu Ser Ala Trp Val Gln Asn Val
            180                 185                 190

Asp Ile Asp Leu Ala Val Asp Thr Met Gly Asn Ile Pro Gly Glu Leu
            195                 200                 205

Leu Asn Trp Thr Phe Leu Ser Leu Lys Pro Phe Ser Leu Thr Gly Gln
            210                 215                 220

Lys Tyr Val Asn Met Val Asp Leu Leu Asp Pro Asp Lys Val Lys
225                 230                 235                 240

Asn Phe Leu Arg Met Glu Lys Trp Ile Phe Asp Ser Pro Asp Gln Ala
                245                 250                 255

Gly Glu Thr Phe Arg Gln Phe Ile Lys Asp Phe Tyr Gln Asn Asn Gly
            260                 265                 270

Phe Leu Asn Gly Gly Val Val Leu Gly Gly Gln Glu Val Asp Leu Lys
            275                 280                 285

Asp Ile Thr Cys Pro Val Leu Asn Ile Phe Ala Leu Gln Asp His Leu
            290                 295                 300

Val Pro Pro Asp Ala Ser Arg Ala Leu Lys Gly Leu Thr Ser Ser Pro
305                 310                 315                 320

Asp Tyr Thr Glu Leu Ala Phe Pro Gly Gly His Ile Gly Ile Tyr Val
                325                 330                 335

Ser Gly Lys Ala Gln Lys Glu Val Thr Pro Ala Ile Gly Lys Trp Leu
            340                 345                 350

Asn Glu Arg
        355

<210> SEQ ID NO 48
<211> LENGTH: 357
<212> TYPE: PRT
<213> ORGANISM: Thiocapsa pfennigii

<400> SEQUENCE: 48

Met Ser Pro Phe Pro Ile Asp Ile Arg Pro Asp Lys Leu Thr Glu Glu
1               5                   10                  15

Met Leu Glu Tyr Ser Arg Lys Leu Gly Glu Gly Met Gln Asn Leu Leu
                20                  25                  30

Lys Ala Asp Gln Ile Asp Thr Gly Val Thr Pro Lys Asp Val Val His
            35                  40                  45

Arg Glu Asp Lys Leu Val Leu Tyr Arg Tyr Arg Pro Ala Gln Val
        50                  55                  60

Ala Thr Gln Thr Ile Pro Leu Leu Ile Val Tyr Ala Leu Val Asn Arg
65                  70                  75                  80

Pro Tyr Met Thr Asp Ile Gln Glu Asp Arg Ser Thr Ile Lys Gly Leu
```

```
                    85                  90                  95
Leu Ala Thr Gly Gln Asp Val Tyr Leu Ile Asp Trp Gly Tyr Pro Asp
                100                 105                 110

Gln Ala Asp Arg Ala Leu Thr Leu Asp Asp Tyr Ile Asn Gly Tyr Ile
                115                 120                 125

Asp Arg Cys Val Asp Tyr Leu Arg Glu Thr His Gly Val Asp Gln Val
            130                 135                 140

Asn Leu Leu Gly Ile Cys Gln Gly Gly Ala Phe Ser Leu Cys Tyr Thr
145                 150                 155                 160

Ala Leu His Ser Glu Lys Val Lys Asn Leu Val Thr Met Val Thr Pro
                165                 170                 175

Val Asp Phe Gln Thr Pro Gly Asn Leu Leu Ser Ala Trp Val Gln Asn
                180                 185                 190

Val Asp Val Asp Leu Ala Val Asp Thr Met Gly Asn Ile Pro Gly Glu
            195                 200                 205

Leu Leu Asn Trp Thr Phe Leu Ser Leu Lys Pro Phe Ser Leu Thr Gly
                210                 215                 220

Gln Lys Tyr Val Asn Met Val Asp Leu Leu Asp Asp Glu Asp Lys Val
225                 230                 235                 240

Lys Asn Phe Leu Arg Met Glu Lys Trp Ile Phe Asp Ser Pro Asp Gln
                245                 250                 255

Ala Gly Glu Thr Phe Arg Gln Phe Ile Lys Asp Phe Tyr Gln Arg Asn
                260                 265                 270

Gly Phe Ile Asn Gly Gly Val Leu Ile Gly Asp Gln Glu Val Asp Leu
            275                 280                 285

Arg Asn Ile Arg Cys Pro Val Leu Asn Ile Tyr Pro Met Gln Asp His
            290                 295                 300

Leu Val Pro Pro Asp Ala Ser Lys Ala Leu Ala Gly Leu Thr Ser Ser
305                 310                 315                 320

Glu Asp Tyr Thr Glu Leu Ala Phe Pro Gly Gly His Ile Gly Ile Tyr
                325                 330                 335

Val Ser Gly Lys Ala Gln Glu Gly Val Thr Pro Ala Ile Gly Arg Trp
            340                 345                 350

Leu Asn Glu Arg Gly
            355

<210> SEQ ID NO 49
<211> LENGTH: 373
<212> TYPE: PRT
<213> ORGANISM: Arthrospira sp. PCC 8005

<400> SEQUENCE: 49

Met Ser Leu Leu Gly Gly His Gln Ala Met Leu Pro Phe Ala Leu Gln
1               5                   10                  15

Met Gly Leu Glu Asp Leu Thr Gln Glu Tyr Ala Asp Leu Thr Glu Lys
                20                  25                  30

Ile Val His Gly Met Asp Asn Leu Ser Ser Leu Arg Glu Glu Glu Ile
            35                  40                  45

Ile Val Gly Val Thr Pro Lys Glu Ala Val Tyr Gln Glu Asp Lys Val
        50                  55                  60

Thr Leu Tyr Arg Phe Glu Pro Lys Val Lys Lys Thr Leu Ser Val Pro
65                  70                  75                  80

Leu Leu Ile Val Tyr Ala Leu Val Asn Arg Pro Phe Met Val Asp Leu
                85                  90                  95
```

```
Gln Glu Gly Arg Ser Leu Val Ala Asn Leu Leu Ser Leu Gly Leu Asp
                100                 105                 110

Val Tyr Leu Ile Asp Trp Gly Tyr Pro Thr Arg Ser Asp Arg Trp Leu
            115                 120                 125

Thr Leu Asp Asp Tyr Ile Asn Gly Tyr Ile Asn Asn Cys Val Asp Phe
        130                 135                 140

Leu Arg Asp His Tyr Glu Leu Asp Lys Ile Asn Leu Leu Gly Val Cys
145                 150                 155                 160

Gln Gly Gly Thr Phe Ser Leu Cys Tyr Ser Ser Leu Tyr Pro Glu Lys
                165                 170                 175

Val Gln Asn Leu Ile Thr Met Val Ala Pro Val Asn Phe Asp Met Pro
            180                 185                 190

Asn Thr Leu Leu Asn Ala Arg Gly Gly Cys Thr Leu Gly Pro Glu Ala
        195                 200                 205

Ile Asp Val Asp Leu Met Val Glu Ala Leu Gly Asn Ile Pro Gly Asp
210                 215                 220

Tyr Leu Asn Ile Glu Phe Leu Met Leu Lys Pro Leu Gln Leu Gly Tyr
225                 230                 235                 240

Gln Lys Tyr Leu Asp Leu Pro Glu Ile Met Gly Ser Arg Asp Lys Leu
                245                 250                 255

Leu Asn Phe Leu Arg Met Glu Lys Trp Ile Phe Asp Ser Pro Asp Gln
            260                 265                 270

Ala Gly Glu Thr Tyr Arg Gln Phe Leu Lys Asp Phe Tyr Gln Glu Asn
        275                 280                 285

Lys Leu Ile Lys Gly Glu Val Met Ile Gly Asp Ser Arg Val Asp Leu
290                 295                 300

Ser Asn Ile Thr Met Pro Val Leu Asn Leu Tyr Ala Glu Lys Asp His
305                 310                 315                 320

Leu Val Pro Pro Ser Ser Leu Ala Leu Glu Tyr Ile Ser Ser
                325                 330                 335

Glu Asp Tyr Thr Ala Lys Ser Phe Pro Val Gly His Ile Gly Met Tyr
            340                 345                 350

Val Ser Gly Lys Val Gln Arg Asp Leu Pro Pro Thr Ile Val Asp Trp
        355                 360                 365

Leu Lys Val Arg Glu
    370

<210> SEQ ID NO 50
<211> LENGTH: 366
<212> TYPE: PRT
<213> ORGANISM: Cyanothece sp. PCC 7425

<400> SEQUENCE: 50

Met Leu Pro Phe Leu Leu Gln Ile His Leu Glu Glu Ala Ala His Glu
1               5                   10                  15

Ser Ala Gln Leu Thr His Lys Leu Val Lys Gly Met Glu Asn Leu Ser
            20                  25                  30

Gln Leu Arg Glu Glu Asp Ile Glu Val Gly Ser Thr Pro Arg Glu Val
        35                  40                  45

Val Tyr Gln Glu Asp Lys Val Lys Leu Tyr Arg Phe Lys Ala Pro Ala
    50                  55                  60

Asn Gln Gly Lys Thr Val Gln Thr Pro Ile Leu Met Val Tyr Ala Leu
65                  70                  75                  80

Val Asn Arg Pro Phe Met Val Asp Leu Gln Glu Asp Arg Ser Leu Val
                85                  90                  95
```

Ala Asn Leu Leu Lys Leu Gly Leu Asp Ile Tyr Leu Ile Asp Trp Gly
            100                 105                 110

Tyr Pro Gly Arg Gly Asp Arg Trp Leu Thr Leu Asp Asp Tyr Ile Asn
            115                 120                 125

Gly Tyr Leu Asn Asn Cys Val Asp Phe Ile Arg Ala Ser His Gln Leu
            130                 135                 140

Asp Lys Val Asn Leu Leu Gly Ile Cys Gln Gly Thr Phe Ser Leu
145                 150                 155                 160

Cys Tyr Ser Ser Leu Tyr Pro Asp Lys Val Asn Asn Leu Val Val Met
                165                 170                 175

Val Ala Pro Val Asp Phe His Gln Pro Glu Thr Leu Leu Asn Met Arg
            180                 185                 190

Gly Gly Cys Thr Leu Gly Ala Glu Ala Ile Asp Val Asp Leu Met Val
            195                 200                 205

Asp Ala Leu Gly Asn Ile Pro Gly Asp Phe Leu Asn Leu Glu Phe Leu
            210                 215                 220

Met Leu Lys Pro Gln Gln Leu Gly Ile Gln Lys Tyr Leu Asp Val Pro
225                 230                 235                 240

Asp Leu Met Asp Ser Pro Glu Lys Leu Leu Asn Phe Leu Arg Met Glu
                245                 250                 255

Lys Trp Ile Phe Asp Ser Pro Asp Gln Ala Gly Glu Thr Tyr Arg Gln
            260                 265                 270

Phe Met Lys Asp Phe Tyr Gln Gly Asn Lys Leu Ile Lys Asn Gln Val
            275                 280                 285

Lys Ile Gly Asp Gln Leu Val Asn Leu Leu Asn Leu Thr Met Pro Ile
            290                 295                 300

Leu Asn Leu Tyr Ala Glu Lys Asp His Leu Val Pro Pro Ala Ser Ser
305                 310                 315                 320

Val Ala Leu Ala Lys Tyr Ile Gly Thr Gln Asp Tyr Thr Ala Lys Gly
            325                 330                 335

Phe Pro Val Gly His Ile Gly Met Tyr Val Ser Gly Lys Val Gln Gln
            340                 345                 350

Asp Leu Pro Pro Val Ile Ala Asp Trp Leu Arg Asn Arg Asp
            355                 360                 365

<210> SEQ ID NO 51
<211> LENGTH: 378
<212> TYPE: PRT
<213> ORGANISM: Synechocystis PCC6803

<400> SEQUENCE: 51

Met Phe Leu Leu Phe Phe Ile Val His Trp Leu Lys Ile Met Leu Pro
1               5                   10                  15

Phe Phe Ala Gln Val Gly Leu Glu Glu Asn Leu His Glu Thr Leu Asp
            20                  25                  30

Phe Thr Glu Lys Phe Leu Ser Gly Leu Glu Asn Leu Gln Gly Leu Asn
            35                  40                  45

Glu Asp Asp Ile Gln Val Gly Phe Thr Pro Lys Glu Ala Val Tyr Gln
            50                  55                  60

Glu Asp Lys Val Ile Leu Tyr Arg Phe Gln Pro Val Val Glu Asn Pro
65                  70                  75                  80

Leu Pro Ile Pro Val Leu Ile Val Tyr Ala Leu Val Asn Arg Pro Tyr
                85                  90                  95

Met Val Asp Leu Gln Glu Gly Arg Ser Leu Val Ala Asn Leu Leu Lys

-continued

```
            100                 105                 110

Leu Gly Leu Asp Val Tyr Leu Ile Asp Trp Gly Tyr Pro Ser Arg Gly
        115                 120                 125

Asp Arg Trp Leu Thr Leu Glu Asp Tyr Leu Ser Gly Tyr Leu Asn Asn
    130                 135                 140

Cys Val Asp Ile Ile Cys Gln Arg Ser Gln Gln Glu Lys Ile Thr Leu
145                 150                 155                 160

Leu Gly Val Cys Gln Gly Gly Thr Phe Ser Leu Cys Tyr Ala Ser Leu
                165                 170                 175

Phe Pro Asp Lys Val Lys Asn Leu Val Val Met Val Ala Pro Val Asp
            180                 185                 190

Phe Glu Gln Pro Gly Thr Leu Leu Asn Ala Arg Gly Gly Cys Thr Leu
        195                 200                 205

Gly Ala Glu Ala Val Asp Ile Asp Leu Met Val Asp Ala Met Gly Asn
    210                 215                 220

Ile Pro Gly Asp Tyr Leu Asn Leu Glu Phe Leu Met Leu Lys Pro Leu
225                 230                 235                 240

Gln Leu Gly Tyr Gln Lys Tyr Leu Asp Val Pro Asp Ile Met Gly Asp
                245                 250                 255

Glu Ala Lys Leu Leu Asn Phe Leu Arg Met Glu Lys Trp Ile Phe Asp
            260                 265                 270

Ser Pro Asp Gln Ala Gly Glu Thr Tyr Arg Gln Phe Leu Lys Asp Phe
        275                 280                 285

Tyr Gln Gln Asn Lys Leu Ile Lys Gly Glu Val Met Ile Gly Asp Arg
    290                 295                 300

Leu Val Asp Leu His Asn Leu Thr Met Pro Ile Leu Asn Leu Tyr Ala
305                 310                 315                 320

Glu Lys Asp His Leu Val Ala Pro Ala Ser Ser Leu Ala Leu Gly Asp
                325                 330                 335

Tyr Leu Pro Glu Asn Cys Asp Tyr Thr Val Gln Ser Phe Pro Val Gly
            340                 345                 350

His Ile Gly Met Tyr Val Ser Gly Lys Val Gln Arg Asp Leu Pro Pro
        355                 360                 365

Ala Ile Ala His Trp Leu Ser Glu Arg Gln
    370                 375

<210> SEQ ID NO 52
<211> LENGTH: 361
<212> TYPE: PRT
<213> ORGANISM: Bacillus cereus

<400> SEQUENCE: 52

Met Thr Thr Phe Ala Thr Glu Trp Glu Lys Gln Leu Glu Leu Tyr Pro
1               5                   10                  15

Glu Glu Tyr Arg Lys Ala Tyr Arg Arg Val Lys Arg Ala Ser Glu Ile
            20                  25                  30

Leu Leu Arg Glu Pro Glu Pro Gln Val Gly Leu Thr Pro Lys Glu Val
        35                  40                  45

Ile Trp Thr Lys Asn Lys Thr Lys Leu Tyr Arg Tyr Ile Pro Lys Gln
    50                  55                  60

Glu Lys Thr Gln Arg Val Pro Ile Leu Leu Ile Tyr Ala Leu Ile Asn
65                  70                  75                  80

Lys Pro Tyr Ile Met Asp Leu Thr Pro Gly Asn Ser Leu Val Glu Tyr
                85                  90                  95
```

```
Leu Val Asp Arg Gly Phe Asp Val Tyr Met Leu Asp Trp Gly Thr Phe
            100                 105                 110

Gly Leu Glu Asp Ser His Leu Lys Phe Asp Asp Phe Val Phe Asp Tyr
        115                 120                 125

Ile Thr Arg Ala Val Lys Lys Val Met Arg Thr Ala Lys Ser Asp Glu
        130                 135                 140

Ile Ser Leu Leu Gly Tyr Cys Met Gly Gly Thr Leu Thr Ser Ile Tyr
145                 150                 155                 160

Ala Ala Leu His Pro His Met Pro Ile Arg Asn Leu Ile Phe Met Thr
                165                 170                 175

Ser Pro Phe Asp Phe Ser Glu Thr Gly Leu Tyr Gly Pro Leu Leu Asp
            180                 185                 190

Glu Lys Tyr Phe Asn Leu Asp Lys Ala Val Asp Thr Phe Gly Asn Ile
        195                 200                 205

Pro Pro Glu Met Ile Asp Phe Gly Asn Lys Met Leu Lys Pro Ile Thr
        210                 215                 220

Asn Phe Val Gly Pro Tyr Val Ala Leu Val Asp Arg Ser Glu Asn Glu
225                 230                 235                 240

Arg Phe Val Glu Ser Trp Arg Leu Val Gln Lys Trp Val Gly Asp Gly
            245                 250                 255

Ile Pro Phe Pro Gly Glu Ser Tyr Arg Gln Trp Ile Arg Asp Phe Tyr
            260                 265                 270

Gln Asn Asn Lys Leu Val Lys Gly Glu Leu Val Ile Arg Gly Gln Lys
        275                 280                 285

Val Asp Leu Ala Asn Ile Lys Ala Asn Val Leu Asn Ile Ser Gly Lys
        290                 295                 300

Arg Asp His Ile Ala Leu Pro Cys Gln Val Glu Ala Leu Leu Asp His
305                 310                 315                 320

Ile Ser Ser Thr Asp Lys Gln Tyr Val Cys Leu Pro Thr Gly His Met
                325                 330                 335

Ser Ile Val Tyr Gly Gly Thr Ala Val Lys Gln Thr Tyr Pro Thr Ile
            340                 345                 350

Gly Asn Trp Leu Glu Glu Arg Ser Asn
        355                 360

<210> SEQ ID NO 53
<211> LENGTH: 357
<212> TYPE: PRT
<213> ORGANISM: Bacillus megaterium

<400> SEQUENCE: 53

Met Gln Glu Trp Glu Lys Leu Ile Lys Ser Met Pro Ser Glu Tyr Lys
1               5                   10                  15

Ser Ser Ala Arg Arg Phe Lys Arg Ala Tyr Glu Ile Met Thr Ala Glu
            20                  25                  30

Ala Glu Pro Glu Val Gly Leu Thr Pro Lys Glu Val Ile Trp Lys Lys
        35                  40                  45

Asn Lys Ala Lys Leu Tyr Arg Tyr Thr Pro Val Lys Asp Asn Leu His
    50                  55                  60

Lys Thr Pro Ile Leu Leu Val Tyr Ala Leu Ile Asn Lys Pro Tyr Ile
65                  70                  75                  80

Leu Asp Leu Thr Pro Gly Asn Ser Leu Val Glu Tyr Leu Leu Asn Arg
                85                  90                  95

Gly Phe Asp Val Tyr Leu Leu Asp Trp Gly Thr Pro Gly Leu Glu Asp
            100                 105                 110
```

-continued

```
Ser Asn Met Lys Leu Asp Asp Tyr Ile Val Asp Tyr Ile Pro Lys Ala
        115                 120                 125

Ala Lys Lys Val Leu Arg Thr Ser Lys Ser Pro Asp Leu Ser Val Leu
    130                 135                 140

Gly Tyr Cys Met Gly Gly Thr Met Thr Ser Ile Phe Ala Ala Leu Asn
145                 150                 155                 160

Glu Asp Leu Pro Ile Lys Asn Leu Ile Phe Met Thr Ser Pro Phe Asp
                165                 170                 175

Phe Ser Asp Thr Gly Leu Tyr Gly Ala Phe Leu Asp Asp Arg Tyr Phe
            180                 185                 190

Asn Leu Asp Lys Ala Val Asp Thr Phe Gly Asn Ile Pro Pro Glu Met
        195                 200                 205

Ile Asp Phe Gly Asn Lys Met Leu Lys Pro Ile Thr Asn Phe Tyr Gly
    210                 215                 220

Pro Tyr Val Thr Leu Val Asp Arg Ser Glu Asn Gln Arg Phe Val Glu
225                 230                 235                 240

Ser Trp Lys Leu Met Gln Lys Trp Val Ala Asp Gly Ile Pro Phe Ala
                245                 250                 255

Gly Glu Ala Tyr Arg Gln Trp Ile Arg Asp Phe Tyr Gln Gln Asn Lys
            260                 265                 270

Leu Ile Asn Gly Glu Leu Glu Val Arg Gly Arg Lys Val Asp Leu Lys
        275                 280                 285

Asn Ile Lys Ala Asn Ile Leu Asn Ile Ala Ala Ser Arg Asp His Ile
    290                 295                 300

Ala Met Pro His Gln Val Ala Ala Leu Met Asp Ala Val Ser Ser Glu
305                 310                 315                 320

Asp Lys Glu Tyr Lys Leu Leu Gln Thr Gly His Val Ser Val Val Phe
                325                 330                 335

Gly Pro Lys Ala Val Lys Glu Thr Tyr Pro Ser Ile Gly Asp Trp Leu
            340                 345                 350

Glu Lys Arg Ser Lys
        355

<210> SEQ ID NO 54
<211> LENGTH: 355
<212> TYPE: PRT
<213> ORGANISM: Bacillus bataviensis

<400> SEQUENCE: 54

Met Ala Ile Glu Ser Pro Phe Lys Glu Tyr Ile Gln Glu Leu Asp Val
1               5                   10                  15

Glu Lys Glu Lys Lys Arg Trp Glu Gln Leu Phe Lys Val Phe Ser Glu
            20                  25                  30

Pro Glu Pro Lys Ile Gly His Thr Pro Arg Thr Glu Val Trp Arg Lys
        35                  40                  45

Asn Lys Ser Val Leu Trp His Tyr Pro Ala Lys Gln Lys Lys Tyr Glu
    50                  55                  60

Ile Pro Leu Phe Phe Val Tyr Ser Leu Phe Asn Lys Pro Tyr Ile Leu
65                  70                  75                  80

Asp Ile Ala Pro Lys Ala Ser Val Ile Glu Gly Leu Thr Asn Met Gly
                85                  90                  95

Tyr Glu Val Tyr Leu Leu Asp Trp Gly Ser Pro Gly Tyr Glu Asp Lys
            100                 105                 110

Lys Met Gly Leu Asp Thr Tyr Ile Glu Lys Tyr Leu Arg Thr Ala Val
```

```
            115                 120                 125
Lys Arg Ala Ile Arg His Ser Gly Ala Glu Ile Thr Leu Ile Gly
    130                 135                 140

Tyr Cys Leu Gly Gly Thr Ile Ala Ser Ile Tyr Ala Ser Ile Ala Asp
145                 150                 155                 160

Glu Pro Ile Lys Asn Leu Val Val Ala Thr Val Pro Ile Asp Phe Lys
                165                 170                 175

Pro Phe Ile Gly Pro Asp Gln Trp Ala Glu Gly Met Arg Gln Gly Asp
            180                 185                 190

Ile Asn Ile Asp Arg Phe Ile Asp Ala Tyr Gly Val Val Pro Pro Gln
        195                 200                 205

Leu Val Glu Gly Met Phe Arg Ala Ile Gly Ala Pro Ile Tyr Phe Thr
    210                 215                 220

Asn Tyr Thr Met Leu Leu Ser Arg Ala His Asp Gln Arg Tyr Val Asp
225                 230                 235                 240

Lys Trp Arg Arg Met Asn Arg Trp Thr Arg Asp Gln Val Pro Phe Ala
                245                 250                 255

Gly Glu Ala Tyr Lys Gln Leu Ala Asn Asp Leu Phe Lys Glu Asn Lys
            260                 265                 270

Leu Val Lys Gly Glu Leu Met Ile Gly Asn Lys Lys Val Asp Leu Lys
        275                 280                 285

Asn Ile Thr Ala Asn Leu Tyr Val Val Ser Gly Ser Arg Asp Asn Leu
    290                 295                 300

Ile Leu Glu Glu Gln Ser Lys Pro Leu Met Asp Leu Ala Ser Ser Glu
305                 310                 315                 320

Asp Lys Thr Tyr Val Ser Val Glu Ala Gly His Val Ser Leu Ala Leu
                325                 330                 335

Ser Gly Leu Phe Ala Lys Ile Val Asp Gln Trp Ala Ser Ser Arg Ser
            340                 345                 350

Asn Gln Leu
        355

<210> SEQ ID NO 55
<211> LENGTH: 559
<212> TYPE: PRT
<213> ORGANISM: Artificial Sequence
<220> FEATURE:
<223> OTHER INFORMATION: Synthetic construct hybrid PhaC of Pseudomonas
      oleovorans/Zoogloea ramigera

<400> SEQUENCE: 55

Met Ser Asn Lys Asn Asn Asp Glu Leu Gln Trp Gln Ser Trp Phe Ser
1               5                   10                  15

Lys Ala Pro Thr Thr Glu Ala Asn Pro Met Ala Thr Met Leu Gln Asp
            20                  25                  30

Ile Gly Val Ala Leu Lys Pro Glu Ala Met Glu Gln Leu Lys Asn Asp
        35                  40                  45

Tyr Leu Arg Asp Phe Thr Ala Leu Trp Gln Asp Phe Leu Ala Gly Lys
    50                  55                  60

Ala Pro Ala Val Ser Asp Arg Arg Phe Ser Ser Ala Ala Trp Gln Gly
65                  70                  75                  80

Asn Pro Met Ser Ala Phe Asn Ala Ala Ser Tyr Leu Leu Asn Ala Lys
                85                  90                  95

Phe Leu Ser Ala Met Val Glu Ala Val Asp Thr Ala Pro Gln Gln Lys
            100                 105                 110
```

-continued

```
Gln Lys Ile Arg Phe Ala Val Gln Gln Val Ile Asp Ala Met Ser Pro
            115                 120                 125
Ala Asn Phe Leu Ala Thr Asn Pro Glu Ala Gln Gln Lys Leu Ile Glu
130                 135                 140
Thr Lys Gly Glu Ser Leu Thr Arg Gly Leu Val Asn Met Leu Gly Asp
145                 150                 155                 160
Ile Asn Lys Gly His Ile Ser Leu Ser Asp Glu Ser Ala Phe Glu Val
                165                 170                 175
Gly Arg Asn Leu Ala Ile Thr Pro Gly Thr Val Ile Tyr Glu Asn Pro
            180                 185                 190
Leu Phe Gln Leu Ile Gln Tyr Thr Pro Thr Thr Pro Thr Val Ser Gln
        195                 200                 205
Arg Pro Leu Leu Met Val Pro Pro Cys Ile Asn Lys Phe Tyr Ile Leu
    210                 215                 220
Asp Leu Gln Pro Glu Asn Ser Leu Val Arg Tyr Ala Val Glu Gln Gly
225                 230                 235                 240
Asn Thr Val Phe Leu Ile Ser Trp Ser Asn Pro Asp Lys Ser Leu Ala
                245                 250                 255
Gly Thr Thr Trp Asp Asp Tyr Val Glu Gln Gly Val Ile Glu Ala Ile
            260                 265                 270
Arg Ile Val Gln Asp Val Ser Gly Gln Asp Lys Leu Asn Met Phe Gly
        275                 280                 285
Phe Cys Val Gly Gly Thr Ile Val Ala Thr Ala Leu Ala Val Leu Ala
    290                 295                 300
Ala Arg Gly Gln His Pro Ala Ala Ser Leu Thr Leu Leu Thr Thr Phe
305                 310                 315                 320
Leu Asp Phe Ser Asp Thr Gly Val Leu Asp Val Phe Val Asp Glu Thr
                325                 330                 335
Gln Val Ala Leu Arg Glu Gln Gln Leu Arg Asp Gly Gly Leu Met Pro
            340                 345                 350
Gly Arg Asp Leu Ala Ser Thr Phe Ser Ser Leu Arg Pro Asn Asp Leu
        355                 360                 365
Val Trp Asn Tyr Val Gln Ser Asn Tyr Leu Lys Gly Asn Glu Pro Ala
    370                 375                 380
Ala Phe Asp Leu Leu Phe Trp Asn Ser Asp Ser Thr Asn Leu Pro Gly
385                 390                 395                 400
Pro Met Phe Cys Trp Tyr Leu Arg Asn Thr Tyr Leu Glu Asn Ser Leu
                405                 410                 415
Lys Val Pro Gly Lys Leu Thr Val Ala Gly Glu Lys Ile Asp Leu Gly
            420                 425                 430
Leu Ile Asp Ala Pro Ala Phe Ile Tyr Gly Ser Arg Glu Asp His Ile
        435                 440                 445
Val Pro Trp Met Ser Ala Tyr Gly Ser Leu Asp Ile Leu Asn Gln Gly
    450                 455                 460
Lys Pro Gly Ala Asn Arg Phe Val Leu Gly Ala Ser Gly His Ile Ala
465                 470                 475                 480
Gly Val Ile Asn Ser Val Ala Lys Asn Lys Arg Ser Tyr Trp Ile Asn
                485                 490                 495
Asp Gly Gly Ala Ala Asp Ala Gln Ala Trp Phe Asp Gly Ala Gln Glu
            500                 505                 510
Val Pro Gly Ser Trp Trp Pro Gln Trp Ala Gly Phe Leu Thr Gln His
        515                 520                 525
Gly Gly Lys Lys Val Lys Pro Lys Ala Lys Pro Gly Asn Ala Arg Tyr
```

```
                530             535             540
Thr Ala Ile Glu Ala Ala Pro Gly Arg Tyr Val Lys Ala Lys Gly
545                 550             555

<210> SEQ ID NO 56
<211> LENGTH: 8
<212> TYPE: PRT
<213> ORGANISM: Artificial Sequence
<220> FEATURE:
<223> OTHER INFORMATION: Synthetic construct DsRed2b amino acids 226-233

<400> SEQUENCE: 56

Val Pro Met Thr Arg Val Ser Pro
1               5

<210> SEQ ID NO 57
<211> LENGTH: 30
<212> TYPE: PRT
<213> ORGANISM: Artificial Sequence
<220> FEATURE:
<223> OTHER INFORMATION: Synthetic construct linker sequence

<400> SEQUENCE: 57

Val Leu Ala Val Ala Ile Asp Lys Arg Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 58
<211> LENGTH: 140
<212> TYPE: PRT
<213> ORGANISM: Arabidopsis thaliana

<400> SEQUENCE: 58

Met Gly Gly Asp Gly Lys Val Phe Thr Leu Ser Glu Val Ser Gln His
1               5                   10                  15

Ser Ser Ala Lys Asp Cys Trp Ile Val Ile Asp Gly Lys Val Tyr Asp
                20                  25                  30

Val Thr Lys Phe Leu Asp Asp His Pro Gly Gly Asp Glu Val Ile Leu
            35                  40                  45

Thr Ser Thr Gly Lys Asp Ala Thr Asp Phe Glu Asp Val Gly His
    50                  55                  60

Ser Ser Thr Ala Lys Ala Met Leu Asp Glu Tyr Tyr Val Gly Asp Ile
65                  70                  75                  80

Asp Thr Ala Thr Val Pro Val Lys Ala Lys Phe Val Pro Pro Thr Ser
                85                  90                  95

Thr Lys Ala Val Ala Thr Gln Asp Lys Ser Ser Asp Phe Val Ile Lys
            100                 105                 110

Leu Leu Gln Phe Leu Val Pro Leu Leu Ile Leu Gly Leu Ala Phe Gly
        115                 120                 125

Ile Arg Tyr Tyr Thr Lys Thr Lys Ala Pro Ser Ser
        130                 135                 140

<210> SEQ ID NO 59
<211> LENGTH: 6
<212> TYPE: PRT
<213> ORGANISM: Artificial Sequence
<220> FEATURE:
<223> OTHER INFORMATION: Synthetic construct PhaC box consensus sequence
<220> FEATURE:
<221> NAME/KEY: VARIANT
<222> LOCATION: (1)..(1)
```

```
<223> OTHER INFORMATION: May be Ser
<220> FEATURE:
<221> NAME/KEY: VARIANT
<222> LOCATION: (2)..(2)
<223> OTHER INFORMATION: May be any amino acid
<220> FEATURE:
<221> NAME/KEY: VARIANT
<222> LOCATION: (4)..(4)
<223> OTHER INFORMATION: May be any amino acid

<400> SEQUENCE: 59

Gly Xaa Cys Xaa Gly Gly
1               5

<210> SEQ ID NO 60
<211> LENGTH: 4
<212> TYPE: PRT
<213> ORGANISM: Artificial Sequence
<220> FEATURE:
<223> OTHER INFORMATION: Synthetic construct C-terminal ER targeting
      consensus sequence

<400> SEQUENCE: 60

His Asp Glu Leu
1

<210> SEQ ID NO 61
<211> LENGTH: 4
<212> TYPE: PRT
<213> ORGANISM: Artificial Sequence
<220> FEATURE:
<223> OTHER INFORMATION: Synthetic construct C-terminal ER targeting
      consensus sequence

<400> SEQUENCE: 61

Lys Asp Glu Leu
1

<210> SEQ ID NO 62
<211> LENGTH: 514
<212> TYPE: DNA
<213> ORGANISM: Glycine max

<400> SEQUENCE: 62
agatttgatc gatacttcat taaattgaca tttattttta acacataata cattattaaa      60
aatataaata acatttaca gcgaagttat ataattaaaa gcctggtcta tgtaatggta     120
ggaaatttga aaatctaaaa gcaaacaaaa attgttgttt atggtgctaa gttgcacctg     180
gaaagatgca ttgtttagct aaaacattca cgtcgagtac ttggtttggg aaaaaaagcc     240
attcaagctt agctggtcct ctctcctgtc tctctctctc tgtctgtctc tctctgtctg     300
tctctctctc aagcacatac acaaacaaag taagggctat aaataggagg gatggaagtg     360
gaagaaagtc tatagcgaag tttcatttct ttggattaga aattttttccc aaagctgatc     420 gagaagccag ccaggccagg tctgtagttt tcttttttttc ttttttaatat taattcatta     480 ttgtgttctt catcatataa tataattaag cctt                                514

<210> SEQ ID NO 63
<211> LENGTH: 1500
<212> TYPE: DNA
<213> ORGANISM: Oryza sativa

<400> SEQUENCE: 63
gcaaagaagg ccagtggcct ttgcagctaa gctagctagc tagcccttct tcctctcttt      60
```

|  |  |  |  |  |  |
|---|---|---|---|---|---|
| cctgctttcc | ctttgccttc | tcctattaat | cctctgcacc | tcacacagca | gcagaaaacc | 120 |
| caccaactgg | agctctcctt | tcctactcca | agaaacgaag | gtagagaaag | aaagatcaga | 180 |
| tcagcttcag | gaccaatttt | agctaggtta | tatatctctt | tgcgtgctaa | tgtgttttag | 240 |
| ttatctgggt | gtgtgtagag | ttcttttgtta | aggcactgat | tcagctgcag | tttagattca | 300 |
| agtttgtatg | ttctctcttt | gaggaaaaga | aacccttttc | ctgtgcttcg | agttcttgca | 360 |
| aagagaaact | gtgatgcttg | gcttccagtt | tgatgcttct | ttgttcagat | tggaaattct | 420 |
| tcctagcttc | tttctctatt | tatgtagcaa | ggattctttc | cggcccagtg | atcctggttt | 480 |
| cttttggaag | gtttcagttt | tttcgttctt | tcttgaaatt | tctcttcttg | ccttaggcag | 540 |
| atctttgatc | ttgtgaggag | acaggagaaa | aggaagaagc | tagtttcctg | cggccgacct | 600 |
| cttgcttctc | actttgtgat | gagttttctt | tggtcaattc | ttagctagat | atgttaagat | 660 |
| agttagttaa | gcaaatcgaa | attgctagct | tttccatgct | ttcttaaaca | tgattcttca | 720 |
| gatttggttg | gttctttttt | ttcctttttg | tgggacgtg | ctgttcttgc | atcttatcct | 780 |
| tcttgattca | tctacccatc | tggttctttg | agctttcttt | ttcgcttctt | cccttcatta | 840 |
| tttcgagcaa | tctctgcaca | tctgaaagtt | ttgtttcttg | agactacttt | tgctagatct | 900 |
| tgtttactcg | atcactctat | acttgcatct | aggctccttt | ctaaataggc | gatgattgag | 960 |
| ctttgcttat | gtcaaatgat | gggatagata | ttgtcccagt | ctccaaattt | gatccatatc | 1020 |
| cgccaagtct | ttcatcatct | ttttctttct | tttttatgag | caaaaatcat | cttttctttt | 1080 |
| caaagttcag | ctttttttctc | ttgttttacc | cctctttagc | tatagctggt | ttcttattcc | 1140 |
| ttttggattt | acatgtataa | aacatgcttg | aatttgttag | atcgatcact | ttatacacat | 1200 |
| actatgtgaa | tcacgatctc | agatctctca | gtatagttga | attcattaat | ttcttagatc | 1260 |
| gatcagcgtg | tgatgtagta | ctgtaaatca | ctactagatc | tttcatcagt | ctcttttctg | 1320 |
| catctatcaa | tttctcatgc | aagttttagt | tgtttcttta | atccggtctc | tctctctttt | 1380 |
| ttaatcagct | gagagtttgt | gctgttcttt | aatcattacc | agatctttca | tcagtactct | 1440 |
| ctcttctgca | tctatcaaac | ttctcatgca | atgtttttgc | tgttctttga | tctgatctct | 1500 |

<210> SEQ ID NO 64
<211> LENGTH: 1500
<212> TYPE: DNA
<213> ORGANISM: Zea mays

<400> SEQUENCE: 64

|  |  |  |  |  |  |
|---|---|---|---|---|---|
| acacttgctc | tcttcgcgtg | gtcatttagc | ccccgaacat | tccaagaaaa | aatagcacat | 60 |
| ttttgattca | taaggtaaag | actgccactc | cacttaacac | agcacgctgc | caccacacat | 120 |
| ggattagcag | gagagcctgc | tgtaaaatcc | taacaggagg | gagaacctcc | aaacaagggt | 180 |
| tcgccgagca | aaaacacagc | ccgaccacaa | ccgacaacct | gaaagaacaa | cagagataca | 240 |
| caggcatgct | gggggaccta | gaccagcgcc | cagaagtaat | aacgccagcg | gagatacaac | 300 |
| cgctccgaga | gagcctgacc | atctgagaac | acattggtca | ccaaaagcac | caccaaccgg | 360 |
| cctagacaaa | gcagctcagt | tgaccccgc | ctcgacatct | tcgatggccg | gcatcacctt | 420 |
| tctccccttc | ttttattct | tcgctgtctt | caccttgtct | tgatttaaca | gctccatgat | 480 |
| tgcatccatt | tgcttcttgg | agagaggctt | tgtgagaagg | cttgtcatct | gctcaaatga | 540 |
| ctcatcaaag | ttagtacatt | ttgaagaact | aattattatt | atatagaatg | cactgcacat | 600 |
| atattactat | taccagttttt | cttgggcaca | gcagaaaaca | tgcacacgca | gatagaaaaa | 660 |
| ggagaggcca | taaaccaaaa | ggctttaaga | atatatgtaa | agatatgtct | aaatatatgg | 720 |

-continued

```
ctatatctgg ttaagcaaga taacagggct ctggtcatca gtagtagtgg cctttttgccc      780
ttgcccctct ctctcacctc tcttttctca gccttgcttc cgatggatcc catcccactg      840
ccatcctttc tttcccttgc gcgcattgcc tagccggccg gccggcctgc tattaaacca      900
ctttaccccgc cccctctcgc tcacgctcga cgcagctccc ttttccttgt ttgcttattg      960
caagtctctg caagaacctg ctagagagga acaaggtaga gtagtatcgc ttttttccat     1020
ctaggttatc tctttttaca tgaaaaattt cagccgtatt tcgttctcca tcagtcctgc     1080
gataatatat acgcgcgtct tgtgtgatcc ggcatatgta tagttcctgc taactgatcg     1140
agatcgctct cgtttgtact ttctcccttt gaggaaagag tttcccctttt tctgtgcttc     1200
aagttcttgt aaggaaaacc atgcctgcca gcttcttctg ctacttgtat gatgattctt     1260
atttgcttat tacttgattt ccgttttttt tcttgctttc tatatgtatg tatctgggct     1320
gtcttcccct gcgtctcgtt actgctaagc tttggaaggt ttcaactctt tgtatacgat     1380
gaggtttctg ctcctagtag cagatccgcg catatgacta gatgtttgag gaaaagaaaa     1440
gggcaagacg ctatatatat atgcagcacg cagtcgcaca tatattcagt tttccaatct     1500
```

<210> SEQ ID NO 65
<211> LENGTH: 403
<212> TYPE: PRT
<213> ORGANISM: Camelina sativa

<400> SEQUENCE: 65

```
Met Ala His Thr Ala Asp Ser Val Asn Pro Lys Asp Val Cys Ile Val
1               5                   10                  15

Gly Val Ala Arg Thr Pro Met Gly Gly Phe Leu Gly Ser Leu Ser Ser
                20                  25                  30

Leu Pro Ala Thr Lys Leu Gly Ser Leu Ala Ile Ala Ala Ala Leu Lys
            35                  40                  45

Arg Ala Asn Val Asp Pro Ser Leu Val Gln Glu Val Val Phe Gly Asn
        50                  55                  60

Val Leu Ser Ala Asn Leu Gly Gln Ala Pro Ala Arg Gln Ala Ala Leu
65                  70                  75                  80

Gly Ala Gly Ile Pro Asn Ser Val Ile Cys Thr Thr Val Asn Lys Val
                85                  90                  95

Cys Ala Ser Gly Met Lys Ala Val Met Ile Ala Ala Gln Ser Ile Gln
                100                 105                 110

Leu Gly Ile Asn Asp Val Val Val Ala Gly Gly Met Glu Ser Met Ser
            115                 120                 125

Asn Thr Pro Lys Tyr Leu Ala Glu Ala Arg Lys Gly Ser Arg Phe Gly
        130                 135                 140

His Asp Ser Val Val Asp Gly Met Leu Lys Asp Gly Leu Trp Asp Val
145                 150                 155                 160

Tyr Asn Asp Cys Gly Met Gly Ser Cys Ala Glu Leu Cys Ala Glu Lys
                165                 170                 175

Phe Glu Ile Thr Arg Glu Gln Gln Asp Asp Tyr Ala Val Gln Ser Phe
                180                 185                 190

Glu Arg Gly Ile Ala Ala Gln Glu Ala Gly Ala Phe Thr Trp Glu Ile
            195                 200                 205

Val Pro Val Glu Val Ser Gly Gly Arg Gly Arg Pro Ser Thr Ile Val
        210                 215                 220

Asp Lys Asp Glu Gly Leu Gly Lys Phe Asp Ala Ala Lys Leu Arg Lys
225                 230                 235                 240
```

```
Leu Arg Pro Ser Phe Lys Glu Asn Gly Gly Thr Val Thr Ala Gly Asn
                245                 250                 255

Ala Ser Ser Ile Ser Asp Gly Ala Ala Leu Val Leu Val Ser Gly
        260                 265                 270

Glu Lys Ala Leu Gln Leu Gly Leu Gln Val Leu Ala Lys Ile Lys Gly
            275                 280                 285

Tyr Gly Asp Ala Ala Gln Glu Pro Glu Phe Phe Thr Thr Ala Pro Ala
        290                 295                 300

Leu Ala Ile Pro Lys Ala Ile Ala His Ala Gly Leu Glu Ser Ser Gln
305                 310                 315                 320

Val Asp Tyr Tyr Glu Ile Asn Glu Ala Phe Ala Val Ala Leu Ala
                325                 330                 335

Asn Gln Lys Leu Leu Gly Ile Ser Pro Glu Lys Val Asn Val Asn Gly
            340                 345                 350

Gly Ala Val Ser Leu Gly His Pro Leu Gly Cys Ser Gly Ala Arg Ile
            355                 360                 365

Leu Ile Thr Leu Leu Gly Ile Leu Lys Lys Arg Asn Gly Lys Tyr Gly
            370                 375                 380

Val Gly Gly Val Cys Asn Gly Gly Gly Ala Ser Ala Leu Val Leu
385                 390                 395                 400

Glu Leu Leu

<210> SEQ ID NO 66
<211> LENGTH: 401
<212> TYPE: PRT
<213> ORGANISM: Oryza sativa

<400> SEQUENCE: 66

Met Ala Ser Asp Asn Ile Gly Ser Arg Asp Val Cys Val Gly Val
1               5                   10                  15

Ala Arg Thr Pro Met Gly Gly Phe Leu Gly Ala Leu Ser Ser Leu Ser
            20                  25                  30

Ala Thr Lys Leu Gly Ser Ile Ala Ile Glu Ala Ala Leu Lys Arg Ala
        35                  40                  45

Asn Val Asp Pro Ala Leu Val Gln Glu Val Phe Phe Gly Asn Val Leu
    50                  55                  60

Ser Ala Asn Leu Gly Gln Ala Pro Ala Arg Gln Ala Ala Leu Gly Ala
65                  70                  75                  80

Gly Ile Pro Asn Thr Val Val Cys Ser Ala Val Asn Lys Val Cys Ala
                85                  90                  95

Ser Gly Met Lys Ala Thr Met Phe Ala Ala Gln Ser Ile Leu Leu Gly
            100                 105                 110

Ile Asn Asp Ile Val Val Ala Gly Gly Met Glu Ser Met Ser Asn Ala
        115                 120                 125

Pro Lys Tyr Ile Ala Glu Ala Arg Lys Gly Ser Arg Phe Gly His Asp
    130                 135                 140

Thr Leu Val Asp Gly Met Leu Lys Asp Gly Leu Trp Asp Val Tyr Gly
145                 150                 155                 160

Asp Phe Ala Met Gly Asn Cys Ala Glu Leu Cys Ala Asp Asn His Ala
                165                 170                 175

Leu Thr Arg Glu Asp Gln Asp Ala Tyr Ala Ile Gln Ser Asn Glu Arg
            180                 185                 190

Gly Ile Ala Ala Arg Asn Ser Gly Ala Phe Ala Trp Glu Ile Val Pro
        195                 200                 205
```

```
Ile Glu Val Pro Val Gly Arg Gly Lys Pro Val Leu Val Asp Lys
    210                 215                 220

Asp Glu Gly Leu Asp Lys Phe Asp Pro Val Lys Leu Lys Leu Arg
225                 230                 235                 240

Pro Ser Phe Lys Glu Asn Gly Gly Thr Val Thr Ala Gly Asn Ala Ser
                    245                 250                 255

Ser Ile Ser Asp Gly Ala Ala Ala Leu Val Leu Val Ser Gly Gln Lys
                260                 265                 270

Ala Gln Glu Leu Gly Leu Gln Val Ile Ala Arg Ile Lys Gly Phe Ala
                275                 280                 285

Asp Ala Ala Gln Ala Pro Glu Leu Phe Thr Thr Ser Pro Ala Leu Ala
290                 295                 300

Ile Pro Lys Ala Leu Ala Asn Ala Gly Leu Glu Ser Ser Arg Val Asp
305                 310                 315                 320

Tyr Tyr Glu Ile Asn Glu Ala Phe Ser Ala Val Ala Leu Ala Asn Gln
                325                 330                 335

Lys Leu Leu Gly Ile Pro Ser Glu Lys Ile Asn Val His Gly Gly Ala
                340                 345                 350

Val Ser Leu Gly His Pro Leu Gly Cys Ser Gly Ala Arg Ile Leu Val
                355                 360                 365

Thr Leu Leu Gly Val Leu Arg Glu Lys Gly Lys Ile Gly Val Ala
370                 375                 380

Gly Val Cys Asn Gly Gly Gly Ala Ser Ala Leu Val Leu Glu Leu
385                 390                 395                 400

Ala

<210> SEQ ID NO 67
<211> LENGTH: 401
<212> TYPE: PRT
<213> ORGANISM: Zea mays

<400> SEQUENCE: 67

Met Ala Ser Asp Gly Ile Thr Pro Arg Asp Val Cys Val Val Gly Val
1               5                   10                  15

Ala Arg Thr Pro Ile Gly Ser Phe Leu Gly Ala Leu Ser Ser Leu Pro
                20                  25                  30

Ala Thr Lys Leu Gly Ser Ile Ala Ile Gln Ala Ala Leu Glu Arg Ala
                35                  40                  45

Asn Val Asp Pro Ala Leu Val Gln Glu Val Tyr Phe Gly Asn Val Leu
                50                  55                  60

Ser Ala Asn Leu Gly Gln Ala Pro Ala Arg Gln Ala Ala Leu Gly Ala
65                  70                  75                  80

Gly Ile Pro Asn Ser Val Val Cys Thr Thr Ile Asn Lys Val Cys Ala
                85                  90                  95

Ser Gly Met Lys Ala Thr Met Phe Ala Ala Gln Ser Ile Gln Leu Gly
                100                 105                 110

Ile Asn Asp Ile Val Val Ala Gly Gly Met Glu Ser Met Ser Asn Ala
                115                 120                 125

Pro Lys Tyr Ile Ala Glu Ala Arg Lys Gly Ser Arg Phe Gly His Asp
                130                 135                 140

Thr Leu Val Asp Ala Met Leu Lys Asp Gly Leu Trp Asp Val Tyr Asn
145                 150                 155                 160

Asp Cys Ala Met Gly Met Cys Ala Glu Leu Cys Ala Asp Asn His Ala
                165                 170                 175
```

```
Leu Thr Arg Glu Asp Gln Asp Ala Phe Ser Ile Arg Ser Asn Glu Arg
            180                 185                 190

Gly Ile Ala Ala Arg Asp Ser Gly Ala Phe Ala Trp Glu Ile Val Pro
        195                 200                 205

Val Glu Val Pro Val Gly Arg Gly Lys Pro Pro Thr Leu Val Glu Lys
    210                 215                 220

Asp Glu Ser Leu Asp Lys Phe Asp Pro Val Lys Leu Lys Lys Leu Arg
225                 230                 235                 240

Pro Ser Phe Lys Glu Asn Cys Gly Thr Val Thr Ala Gly Asn Ala Ser
                245                 250                 255

Ser Ile Ser Asp Gly Ala Ala Leu Ala Leu Val Ser Gly Gln Lys
            260                 265                 270

Ala Gln Glu Leu Gly Leu Gln Val Leu Ala Arg Ile Lys Gly Tyr Ala
            275                 280                 285

Asp Ala Ala Gln Ala Pro Glu Leu Phe Thr Thr Thr Pro Ala Leu Ala
    290                 295                 300

Ile Pro Lys Ala Ile Thr Asn Ala Gly Leu Glu Ser Ser His Val Asp
305                 310                 315                 320

Phe Tyr Glu Ile Asn Glu Ala Phe Ser Ala Val Ala Leu Ala Asn Gln
                325                 330                 335

Lys Leu Leu Gly Ile Pro Ser Glu Lys Thr Asn Val His Gly Gly Ala
            340                 345                 350

Val Ser Leu Gly His Pro Leu Gly Cys Ser Gly Ala Arg Ile Leu Val
            355                 360                 365

Thr Leu Leu Gly Val Leu Arg Ala Lys Ser Gly Lys Ile Gly Val Ala
    370                 375                 380

Gly Val Cys Asn Gly Gly Gly Ala Ser Ala Leu Val Val Glu Leu
385                 390                 395                 400

Ala

<210> SEQ ID NO 68
<211> LENGTH: 403
<212> TYPE: PRT
<213> ORGANISM: Brassica napus

<400> SEQUENCE: 68

Met Ala His Ser Ala Asp Ser Val Asn Pro Arg Asp Val Cys Ile Val
1               5                   10                  15

Gly Val Ala Arg Thr Pro Met Gly Gly Phe Leu Gly Ser Leu Ser Ser
            20                  25                  30

Leu Pro Ala Thr Lys Leu Gly Ser Val Ala Ile Ala Ala Ala Leu Lys
        35                  40                  45

Arg Ala Asn Val Asp Pro Ser Leu Val Gln Glu Val Phe Gly Asn
    50                  55                  60

Val Leu Ser Ala Asn Leu Gly Gln Ala Pro Ala Arg Gln Ala Ala Leu
65                  70                  75                  80

Gly Ala Gly Ile Ser Asn Ser Val Ile Cys Thr Thr Val Asn Lys Val
                85                  90                  95

Cys Ala Ser Gly Met Lys Ala Val Met Ile Ala Ala Gln Ser Ile Gln
            100                 105                 110

Leu Gly Ile Ser Asp Val Val Val Ala Gly Gly Met Glu Ser Met Ser
        115                 120                 125

Asn Thr Pro Lys Tyr Leu Ala Glu Ala Arg Lys Gly Ser Arg Phe Gly
    130                 135                 140
```

-continued

His Asp Ser Leu Val Asp Gly Met Leu Lys Asp Gly Leu Trp Asp Val
145                 150                 155                 160

Tyr Asn Asp Cys Gly Met Gly Ser Cys Ala Glu Leu Cys Ala Glu Lys
            165                 170                 175

Phe Glu Ile Thr Arg Glu Gln Gln Asp Asp Tyr Ala Val Gln Ser Phe
        180                 185                 190

Glu Arg Gly Ile Ala Ala Gln Glu Ala Gly Ala Phe Thr Trp Glu Ile
    195                 200                 205

Val Pro Val Glu Val Ser Gly Arg Gly Arg Pro Ser Thr Ile Val
210                 215                 220

Asp Lys Asp Glu Gly Leu Gly Lys Phe Asp Ala Ala Lys Leu Arg Lys
225                 230                 235                 240

Leu Arg Pro Ser Phe Lys Glu Asn Gly Gly Thr Val Thr Ala Gly Asn
                245                 250                 255

Ala Ser Ser Ile Ser Asp Gly Ala Ala Ala Leu Val Leu Val Ser Gly
            260                 265                 270

Glu Lys Ala Leu Gln Leu Gly Leu Gln Val Ile Ala Lys Val Lys Gly
        275                 280                 285

Tyr Gly Asp Ala Ala Gln Glu Pro Glu Phe Phe Thr Thr Ala Pro Ala
    290                 295                 300

Leu Ala Ile Pro Lys Ala Ile Ala His Ala Gly Leu Glu Ser Ser Gln
305                 310                 315                 320

Val Asp Tyr Tyr Glu Ile Asn Glu Ala Phe Ala Val Val Ala Leu Ala
                325                 330                 335

Asn Gln Lys Leu Leu Gly Ile Thr Pro Glu Lys Val Asn Val Asn Gly
            340                 345                 350

Gly Ala Val Ser Leu Gly His Pro Leu Gly Cys Ser Gly Ala Arg Ile
        355                 360                 365

Leu Ile Thr Leu Leu Gly Ile Leu Lys Asn Arg Asn Gly Lys Tyr Gly
370                 375                 380

Val Gly Gly Val Cys Asn Gly Gly Gly Gly Ala Ser Ala Ile Val Leu
385                 390                 395                 400

Glu Leu Val

<210> SEQ ID NO 69
<211> LENGTH: 407
<212> TYPE: PRT
<213> ORGANISM: Glycine max

<400> SEQUENCE: 69

Met Ala Pro Val Ala Ala Ala Ser Ser Asp Ser Ile Lys Pro Arg Asp
1               5                   10                  15

Val Cys Ile Val Gly Val Ala Arg Thr Pro Met Gly Gly Phe Leu Gly
            20                  25                  30

Thr Leu Ser Ser Leu Ser Ala Thr Lys Leu Gly Ser Ile Ala Ile Glu
        35                  40                  45

Ala Ala Leu Lys Arg Ala Asn Val Asp Pro Ser Leu Val Glu Glu Val
    50                  55                  60

Phe Phe Gly Asn Val Leu Ser Ala Asn Leu Gly Gln Ala Pro Ala Arg
65                  70                  75                  80

Gln Ala Ala Leu Gly Ala Gly Ile Ser Asn Ser Val Ile Cys Thr Thr
                85                  90                  95

Val Asn Lys Val Cys Ala Ser Gly Met Lys Ala Ala Met Leu Ala Ala
            100                 105                 110

```
Gln Ser Ile Gln Leu Ser Ile Asn Asp Val Val Ala Gly Gly Met
        115                 120                 125
Glu Ser Met Ser Asn Val Pro Lys Tyr Leu Ala Glu Ala Arg Lys Gly
    130                 135                 140
Ser Arg Leu Gly His Asp Ser Leu Val Asp Gly Met Leu Lys Asp Gly
145                 150                 155                 160
Leu Trp Asp Val Tyr Lys Asp Val Gly Met Gly Val Cys Ala Glu Leu
                165                 170                 175
Cys Ala Asp Asn His Ala Leu Thr Arg Asp Asp Gln Asp Asn Tyr Ala
            180                 185                 190
Val Gln Ser Phe Glu Arg Gly Ile Ala Ala Gln Glu Ser Gly Ala Phe
        195                 200                 205
Ser Trp Glu Ile Ala Pro Val Glu Val Ser Gly Gly Arg Gly Arg Pro
    210                 215                 220
Ser Thr Val Val Asp Lys Asp Glu Gly Leu Gly Lys Phe Asp Ala Ala
225                 230                 235                 240
Lys Leu Arg Lys Leu Arg Pro Ser Phe Lys Glu Thr Gly Gly Ser Val
                245                 250                 255
Thr Ala Gly Asn Ala Ser Ser Ile Ser Asp Gly Ala Ala Ala Leu Val
            260                 265                 270
Leu Val Ser Gly Glu Lys Ala Leu Lys Leu Gly Leu Gln Val Ile Ala
        275                 280                 285
Lys Ile Thr Gly Tyr Ala Asp Ala Ala Gln Glu Pro Glu Leu Phe Thr
    290                 295                 300
Thr Ala Pro Ser Leu Ala Ile Pro Lys Ala Ile Ala Lys Ala Gly Leu
305                 310                 315                 320
Glu Thr Ser Gln Ile Asp Phe Tyr Glu Ile Asn Glu Ala Phe Ala Val
                325                 330                 335
Val Ala Leu Ala Asn Gln Lys Leu Leu Gly Leu Asn Ser Glu Lys Val
            340                 345                 350
Asn Leu His Gly Gly Ala Val Ala Leu Gly His Pro Leu Gly Cys Ser
        355                 360                 365
Gly Ala Arg Ile Leu Val Thr Leu Leu Gly Val Leu Lys Gln Lys Asn
    370                 375                 380
Gly Lys Tyr Gly Val Gly Gly Ile Cys Asn Gly Gly Gly Gly Ala Ser
385                 390                 395                 400
Ala Leu Val Val Glu Leu Leu
                405

<210> SEQ ID NO 70
<211> LENGTH: 404
<212> TYPE: PRT
<213> ORGANISM: Solanum tuberosum

<400> SEQUENCE: 70

Met Ala Pro Ala Thr Ala Glu Ser Ile Lys Pro Arg Asp Val Cys Val
1               5                   10                  15
Val Gly Val Ala Arg Thr Pro Met Gly Gly Phe Leu Gly Ser Leu Ser
            20                  25                  30
Ser Val Ser Ala Thr Lys Leu Gly Ser Ile Ala Ile Ala Gly Ala Ile
        35                  40                  45
Lys Arg Ala Asn Val Asp Pro Ser Leu Val Glu Glu Val Phe Phe Gly
    50                  55                  60
Asn Val Leu Ser Ala Asn Leu Gly Gln Ala Pro Ala Arg Gln Ala Ala
```

```
            65                  70                  75                  80
        Leu Gly Ala Gly Leu Pro Asn Thr Val Ile Cys Thr Val Asn Lys
                        85                  90                  95

Val Cys Ala Ser Gly Met Lys Ala Thr Met Leu Ala Ala Gln Ser Ile
                        100                 105                 110

Gln Leu Gly Ile Asn Asp Val Val Ala Gly Met Glu Asn Met
                        115                 120             125

Ser Asn Val Pro Lys Tyr Phe Ala Glu Ala Arg Lys Gly Ser Arg Leu
                130                 135                 140

Gly His Asp Ser Leu Val Asp Gly Met Leu Lys Asp Gly Leu Thr Asp
        145                 150                 155                 160

Val Tyr Asn Asp Cys Gly Met Gly Val Cys Ala Glu Ile Cys Ala Glu
                        165                 170                 175

Asn His Lys Ile Thr Arg Glu Asp Gln Asp Asn Phe Ala Val Gln Ser
                        180                 185                 190

Phe Glu Arg Gly Ile Ala Ala Gln Glu Ala Gly Ala Phe Thr Trp Glu
                        195                 200                 205

Ile Val Pro Val Glu Val Pro Gly Gly Arg Gly Lys Pro Ser Thr Ile
                        210                 215                 220

Val Asp Lys Asp Glu Gly Pro Gly Lys Phe Asp Gly Ala Lys Leu Arg
        225                 230                 235                 240

Lys Leu Arg Pro Ser Phe Lys Glu Lys Asp Gly Thr Val Thr Ala Gly
                        245                 250                 255

Asn Ala Ser Ser Ile Ser Asp Gly Ala Ala Ala Leu Val Leu Val Ser
                        260                 265                 270

Gly Glu Lys Ala Val Lys Leu Gly Leu Asp Val Ile Ala Lys Ile Ser
                        275                 280                 285

Gly Tyr Ala Asp Ala Ala Gln Glu Pro Glu Leu Phe Thr Ile Ser Pro
                        290                 295                 300

Ala Lys Ala Ile Pro Lys Ala Ile Lys Ser Ala Gly Leu Glu Ala Ser
        305                 310                 315                 320

Gln Ile Asp Tyr Tyr Glu Ile Asn Glu Ala Phe Ala Val Val Ala Leu
                        325                 330                 335

Ala Asn Gln Lys Leu Leu Gly Leu Asn Pro Glu Lys Ile Asn Val His
                        340                 345                 350

Gly Gly Ala Val Ser Leu Gly His Pro Leu Gly Cys Ser Gly Ala Arg
                        355                 360                 365

Ile Leu Val Thr Leu Leu Gly Val Leu Arg Gln Lys Asn Gly Lys Tyr
                        370                 375                 380

Gly Ala Ala Gly Val Cys Asn Gly Gly Gly Ala Ser Ala Leu Val
        385                 390                 395                 400

Val Glu Leu Met

<210> SEQ ID NO 71
<211> LENGTH: 398
<212> TYPE: PRT
<213> ORGANISM: Saccharomyces cerevisiae

<400> SEQUENCE: 71

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
                20                  25                  30

Val Ala Leu Lys Gly Ala Leu Ala Lys Val Pro Glu Leu Asp Ala Ser
```

```
            35                  40                  45
Lys Asp Phe Asp Glu Ile Ile Phe Gly Asn Val Leu Ser Ala Asn Leu
 50                  55                  60

Gly Gln Ala Pro Ala Arg Gln Val Ala Leu Ala Ala Gly Leu Ser Asn
 65                  70                  75                  80

His Ile Val Ala Ser Thr Val Asn Lys Val Cys Ala Ser Ala Met Lys
                 85                  90                  95

Ala Ile Ile Leu Gly Ala Gln Ser Ile Lys Cys Gly Asn Ala Asp Val
                100                 105                 110

Val Val Ala Gly Gly Cys Glu Ser Met Thr Asn Ala Pro Tyr Tyr Met
            115                 120                 125

Pro Ala Ala Arg Ala Gly Ala Lys Phe Gly Gln Thr Val Leu Val Asp
130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
                180                 185                 190

Gln Lys Glu Gly Lys Phe Asp Asn Glu Ile Val Pro Val Thr Ile Lys
            195                 200                 205

Gly Phe Arg Gly Lys Pro Asp Thr Gln Val Thr Lys Asp Glu Glu Pro
210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
            275                 280                 285

Gln Pro Ala Asp Phe Thr Trp Ala Pro Ser Leu Ala Val Pro Lys Ala
290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
            355                 360                 365

Ser Ile Leu Gln Gln Glu Gly Gly Lys Ile Gly Val Ala Ala Ile Cys
370                 375                 380

Asn Gly Gly Gly Gly Ala Ser Ser Ile Val Ile Glu Lys Ile
385                 390                 395

<210> SEQ ID NO 72
<211> LENGTH: 393
<212> TYPE: PRT
<213> ORGANISM: Cupriavidus necator

<400> SEQUENCE: 72

Met Thr Asp Val Val Ile Val Ser Ala Ala Arg Thr Ala Val Gly Lys
  1                5                  10                  15
```

```
Phe Gly Gly Ser Leu Ala Lys Ile Pro Ala Pro Glu Leu Gly Ala Val
                20                  25                  30

Val Ile Lys Ala Ala Leu Glu Arg Ala Gly Val Lys Pro Glu Gln Val
            35                  40                  45

Ser Glu Val Ile Met Gly Gln Val Leu Thr Ala Gly Ser Gly Gln Asn
 50                  55                  60

Pro Ala Arg Gln Ala Ala Ile Lys Ala Gly Leu Pro Ala Met Val Pro
 65                  70                  75                  80

Ala Met Thr Ile Asn Lys Val Cys Gly Ser Gly Leu Lys Ala Val Met
                85                  90                  95

Leu Ala Ala Asn Ala Ile Met Ala Gly Asp Ala Glu Ile Val Val Ala
                100                 105                 110

Gly Gly Gln Glu Asn Met Ser Ala Ala Pro His Val Leu Pro Gly Ser
            115                 120                 125

Arg Asp Gly Phe Arg Met Gly Asp Ala Lys Leu Val Asp Thr Met Ile
            130                 135                 140

Val Asp Gly Leu Trp Asp Val Tyr Asn Gln Tyr His Met Gly Ile Thr
145                 150                 155                 160

Ala Glu Asn Val Ala Lys Glu Tyr Gly Ile Thr Arg Glu Ala Gln Asp
                165                 170                 175

Glu Phe Ala Val Gly Ser Gln Asn Lys Ala Glu Ala Ala Gln Lys Ala
            180                 185                 190

Gly Lys Phe Asp Glu Glu Ile Val Pro Val Leu Ile Pro Gln Arg Lys
            195                 200                 205

Gly Asp Pro Val Ala Phe Lys Thr Asp Glu Phe Val Arg Gln Gly Ala
210                 215                 220

Thr Leu Asp Ser Met Ser Gly Leu Lys Pro Ala Phe Asp Lys Ala Gly
225                 230                 235                 240

Thr Val Thr Ala Ala Asn Ala Ser Gly Leu Asn Asp Gly Ala Ala Ala
                245                 250                 255

Val Val Val Met Ser Ala Ala Lys Ala Lys Glu Leu Gly Leu Thr Pro
            260                 265                 270

Leu Ala Thr Ile Lys Ser Tyr Ala Asn Ala Gly Val Asp Pro Lys Val
            275                 280                 285

Met Gly Met Gly Pro Val Pro Ala Ser Lys Arg Ala Leu Ser Arg Ala
 290                 295                 300

Glu Trp Thr Pro Gln Asp Leu Asp Leu Met Glu Ile Asn Glu Ala Phe
305                 310                 315                 320

Ala Ala Gln Ala Leu Ala Val His Gln Gln Met Gly Trp Asp Thr Ser
                325                 330                 335

Lys Val Asn Val Asn Gly Gly Ala Ile Ala Ile Gly His Pro Ile Gly
            340                 345                 350

Ala Ser Gly Cys Arg Ile Leu Val Thr Leu Leu His Glu Met Lys Arg
            355                 360                 365

Arg Asp Ala Lys Lys Gly Leu Ala Ser Leu Cys Ile Gly Gly Gly Met
370                 375                 380

Gly Val Ala Leu Ala Val Glu Arg Lys
385                 390
```

<210> SEQ ID NO 73
<211> LENGTH: 409
<212> TYPE: PRT
<213> ORGANISM: Synechocystis PCC6803

<400> SEQUENCE: 73

-continued

```
Met Ala Ala His Pro Asn Pro Trp His Trp Lys Thr Ile Met Arg Asp
1               5                   10                  15

Val Phe Ile Val Ala Ala Lys Arg Thr Pro Leu Gly Arg Phe Gly Gly
                20                  25                  30

Ser Leu Thr Asn Phe Ser Ala Ala Asp Leu Gly Ala His Val Met Lys
            35                  40                  45

Ser Val Leu Ala Gln Ala Gly Val Gly Gly Asp Gln Leu Asp Leu Tyr
50                          55                  60

Ile Met Gly Asn Val Leu Arg Ala Gly His Gly Gln Leu Ile Pro Arg
65                      70                  75                  80

Gln Ala Ala Leu Lys Ala Glu Ile Pro Asp Thr Val Asp Gly Tyr Ala
                85                  90                  95

Val Asp Met Val Cys Ser Ser Ala Met Met Ser Val Ile Asn Ala Ala
                100                 105                 110

Leu Thr Ile Arg Ala Gly Glu Gly Asp Leu Ile Leu Ala Gly Gly Thr
            115                 120                 125

Glu Ser Met Ser Gln Thr Gly Phe Tyr Leu Ser His Arg Ala Arg Trp
130                 135                 140

Gly Tyr Lys Phe Leu Met Gly Ala Pro Glu Asn Leu Thr Asp Leu Leu
145                 150                 155                 160

Leu His Asp Gly Leu Thr Asp Ser Thr Asn Gly Glu Gly Met Gly Glu
                165                 170                 175

Gln Thr Glu Lys Leu Ala Ala Glu His Gly Phe Ser Arg Ile Glu Leu
                180                 185                 190

Asp Glu Val Ala Cys Leu Ser Gln Gln Arg Ala Ala His Ala Thr Glu
            195                 200                 205

Ser Gly Tyr Phe Asp Ser Glu Ile Ala Pro Ile Glu Ile Thr Ser Arg
210                 215                 220

Lys Gly Thr Gln Val Leu Ala Ser Asp Glu Gly Ile Arg Ser Asp Thr
225                 230                 235                 240

Thr Val Glu Ser Leu Gly Lys Leu Arg Ser Ala Phe Ala Lys Asp Gly
                245                 250                 255

Val Leu Thr Ala Gly Asn Cys Ser Gln Ile Thr Asp Gly Ala Ala Ala
            260                 265                 270

Leu Leu Leu Ala Ser Gly Glu Ala Val Glu Lys Tyr Gln Leu Lys Pro
275                 280                 285

Leu Ala Lys Ile Leu Gly Gly Ser Trp Ala Ala Gly Thr Pro Ser Arg
290                 295                 300

Phe Pro Glu Leu Pro Ile Thr Ala Ser Gln Lys Leu Leu Ala Lys Leu
305                 310                 315                 320

Asp Lys Thr Leu Ala Asp Phe Asp Leu Phe Glu Asn Asn Glu Ala Phe
                325                 330                 335

Ser Val Ser Asn Leu Leu Phe Glu Arg Arg Leu Gly Val Asp Arg Asp
            340                 345                 350

Lys Leu Asn Val Asn Gly Gly Ala Ile Ala Leu Gly His Pro Ile Gly
                355                 360                 365

Ala Ser Gly Ala Arg Ile Met Val Thr Leu Leu Tyr Ala Leu Gln Gln
370                 375                 380

Arg Asp Lys Thr Leu Gly Leu Ala Ala Leu Cys His Gly Thr Gly Gly
385                 390                 395                 400

Gly Thr Ala Ile Ala Leu Glu Arg Val
                405
```

<210> SEQ ID NO 74
<211> LENGTH: 382
<212> TYPE: PRT
<213> ORGANISM: Micrococcus luteus

<400> SEQUENCE: 74

```
Met Pro Glu Ala Tyr Ile Ile Asp Ala Val Arg Thr Pro Val Gly Arg
1               5                   10                  15

Arg Gly Lys Gly Leu Ala Gly Val His Pro Leu Asp Leu Ala Ala Ala
                20                  25                  30

Pro Leu Arg Glu Leu Val Ala Arg Gln Asp Ile Asp Ser Ala Glu Tyr
            35                  40                  45

Asp Glu Val Ile Leu Gly Cys Ile Asp Gln Leu Gly Pro Gln Ala Met
        50                  55                  60

Asp Val Ala Arg Asn Ala Trp Leu Ala Ala Gly Leu Ser Glu Asp Val
65                  70                  75                  80

Pro Gly Thr Thr Val Glu Arg Gln Cys Gly Ser Gly Gln Gln Ala Val
                85                  90                  95

His Tyr Ala Ala Gln Ala Val Met Ser Gly Thr Ala Asp Leu Val Val
            100                 105                 110

Ala Gly Gly Val Gln Ser Met Ser Ala Ile Pro Leu Ser Arg Ser Asn
        115                 120                 125

Thr Ala Ala Arg Glu Leu Gly Phe Pro Asp Pro Phe Thr Gly Ser Glu
130                 135                 140

Ser Trp Ala Ala Arg Tyr Gly Asp Glu Glu Ile Ser Gln Phe Arg Gly
145                 150                 155                 160

Ala Glu Met Met Ala Arg His Trp Asn Leu Asp Arg Asp Ala Leu Glu
                165                 170                 175

Ala Phe Ala Val Arg Ser His Glu Arg Ala Leu Ala Ala Gln Ala Asp
            180                 185                 190

Gly Arg Phe Asp Arg Glu Ile Leu Pro Leu Ala Gly Leu Thr Ala Asp
        195                 200                 205

Glu Gly Pro Arg Thr Pro Asp Ala Ala Lys Ile Ala Ser Leu Asp Pro
210                 215                 220

Ile Val Pro Gly Gly Leu His Thr Ala Ala Thr Ala Ser Gln Met Ser
225                 230                 235                 240

Asp Gly Ala Ala Ala Leu Leu Leu Ala Ser Glu Glu Ala Val Arg Arg
                245                 250                 255

His Gly Leu Thr Pro Arg Ala Arg Ile His His Leu Ser Ala Arg Gly
            260                 265                 270

Ala Asp Pro Val Met Met Leu Ser Ala Pro Ile Pro Ala Thr Ala Tyr
        275                 280                 285

Ala Leu Asp Arg Met Gly Leu Thr Ile Asp Asp Met Asp Leu Val Glu
290                 295                 300

Ile Asn Glu Ala Phe Ala Ala Val Val Leu Ala Trp Leu Thr Glu Thr
305                 310                 315                 320

Gly Ala Asp Pro Ala Lys Val Asn Val Asn Gly Gly Ala Ile Ala Leu
                325                 330                 335

Gly His Pro Ile Gly Ala Thr Gly Ala Arg Leu Met Thr Ser Leu Leu
            340                 345                 350

His Glu Leu Glu Arg Ser Gly Gly Arg Tyr Gly Leu Gln Thr Met Cys
        355                 360                 365

Glu Gly Gly Gly Gln Ala Asn Val Thr Val Ile Glu Arg Leu
370                 375                 380
```

<210> SEQ ID NO 75
<211> LENGTH: 246
<212> TYPE: PRT
<213> ORGANISM: Cupriavidus necator

<400> SEQUENCE: 75

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 76
<211> LENGTH: 240
<212> TYPE: PRT
<213> ORGANISM: Synechocystis PCC6803

<400> SEQUENCE: 76

Met Leu Ser Leu Gly Leu Glu Asp Lys Val Ile Val Thr Gly Gly
1               5                   10                  15

Asn Arg Gly Ile Gly Ala Ala Ile Val Lys Leu Leu Gln Glu Met Gly
            20                  25                  30

Ala Lys Val Ala Phe Thr Asp Leu Ala Thr Asp Gly Gly Asn Thr Glu
        35                  40                  45

Ala Leu Gly Val Val Ala Asn Val Thr Asp Leu Glu Ser Met Thr Ala
    50                  55                  60

Ala Ala Ala Glu Ile Thr Asp Lys Leu Gly Pro Val Tyr Gly Val Val
65                  70                  75                  80

```
Ala Asn Ala Gly Ile Thr Lys Asp Asn Phe Phe Pro Lys Leu Thr Pro
                85                  90                  95

Ala Asp Trp Asp Ala Val Leu Asn Val Asn Leu Lys Gly Val Ala Tyr
            100                 105                 110

Ser Ile Lys Pro Phe Ile Glu Gly Met Tyr Glu Arg Lys Ala Gly Ser
        115                 120                 125

Ile Val Ala Ile Ser Ser Ile Ser Gly Glu Arg Gly Asn Val Gly Gln
130                 135                 140

Thr Asn Tyr Ser Ala Thr Lys Ala Gly Val Ile Gly Met Met Lys Ser
145                 150                 155                 160

Leu Ala Arg Glu Gly Ala Arg Tyr Gly Val Arg Ala Asn Ala Val Ala
                165                 170                 175

Pro Gly Phe Ile Asp Thr Glu Met Thr Leu Ala Ile Arg Glu Asp Ile
            180                 185                 190

Arg Glu Lys Ile Thr Lys Glu Ile Pro Phe Arg Arg Phe Gly Lys Pro
        195                 200                 205

Glu Glu Ile Ala Trp Ala Val Ala Phe Leu Leu Ser Pro Val Ala Ser
210                 215                 220

Ser Tyr Val Thr Gly Glu Val Leu Arg Val Asn Gly Ala His His Thr
225                 230                 235                 240

<210> SEQ ID NO 77
<211> LENGTH: 247
<212> TYPE: PRT
<213> ORGANISM: Bacillus megaterium

<400> SEQUENCE: 77

Met Thr Thr Leu Gln Gly Lys Val Ala Ile Val Thr Gly Gly Ser Lys
1               5                   10                  15

Gly Ile Gly Ala Ala Ile Thr Arg Glu Leu Ala Ser Asn Gly Val Lys
                20                  25                  30

Val Ala Val Asn Tyr Asn Ser Ser Lys Glu Ser Ala Glu Ala Ile Val
            35                  40                  45

Lys Glu Ile Lys Asp Asn Gly Gly Glu Ala Ile Ala Val Gln Ala Asp
        50                  55                  60

Val Ser Tyr Val Asp Gln Ala Lys His Leu Ile Glu Glu Thr Lys Ala
65                  70                  75                  80

Ala Phe Gly Gln Leu Asp Ile Leu Val Asn Asn Ala Gly Ile Thr Arg
                85                  90                  95

Asp Arg Ser Phe Lys Lys Leu Gly Glu Glu Asp Trp Lys Lys Val Ile
            100                 105                 110

Asp Val Asn Leu His Ser Val Tyr Asn Thr Thr Ser Ala Ala Leu Thr
        115                 120                 125

His Leu Leu Glu Ser Glu Gly Gly Arg Val Ile Asn Ile Ser Ser Ile
130                 135                 140

Ile Gly Gln Ala Gly Gly Phe Gly Gln Thr Asn Tyr Ser Ala Ala Lys
145                 150                 155                 160

Ala Gly Met Leu Gly Phe Thr Lys Ser Leu Ala Leu Glu Leu Ala Lys
                165                 170                 175

Thr Gly Val Thr Val Asn Ala Ile Cys Pro Gly Phe Ile Glu Thr Glu
            180                 185                 190

Met Val Met Ala Ile Pro Glu Asp Val Arg Ala Lys Ile Val Ala Lys
        195                 200                 205

Ile Pro Thr Arg Arg Leu Gly His Ala Glu Glu Ile Ala Arg Gly Val
```

```
                210                 215                 220
Val Tyr Leu Ala Lys Asp Gly Ala Tyr Ile Thr Gly Gln Gln Leu Asn
225                 230                 235                 240

Ile Asn Gly Gly Leu Tyr Met
                245

<210> SEQ ID NO 78
<211> LENGTH: 246
<212> TYPE: PRT
<213> ORGANISM: Xanthomonas campestris

<400> SEQUENCE: 78

Met Thr Leu Arg Ile Ala Tyr Val Thr Ser Gly Met Gly Ser Val Gly
1               5                   10                  15

Thr Ala Ile Cys Gln Lys Leu Ala Arg Thr Gly His Thr Val Val Ala
                20                  25                  30

Gly Cys Gly Pro Asn Ser Pro Arg Lys Ser Ala Trp Leu Arg Glu Gln
            35                  40                  45

Arg Glu Leu Gly Phe Asp Phe Val Ala Ser Glu Gly Asn Ala Ala Asp
        50                  55                  60

Trp Asp Ser Thr Met Ala Ala Phe Ala Lys Val Lys Ala Glu Val Gly
65                  70                  75                  80

Glu Ile Asp Val Leu Val Asn Asn Ala Gly Gly Ser Arg Asp Thr Leu
                85                  90                  95

Phe Arg Gln Met Ser Arg Asp Asp Trp Asn Ala Val Ile Ala Ser Asn
                100                 105                 110

Leu His Ser Leu Phe Asn Ile Thr Lys Gln Val Val Asp Gly Met Thr
            115                 120                 125

Ser Arg Gly Trp Gly Arg Ile Val Asn Ile Gly Ser Val Ser Ala His
        130                 135                 140

Lys Gly Gln Ile Gly Gln Ile Asn Phe Ala Thr Ala Lys Ala Ala Met
145                 150                 155                 160

His Gly Phe Ser Arg Ala Leu Ala Gln Glu Val Ala Ser Arg Gly Val
                165                 170                 175

Thr Val Asn Thr Ile Ser Pro Gly Tyr Ile Ala Ser Ala Ser Ile Ser
                180                 185                 190

Asn Phe Pro Pro Asp Val Leu Asp Arg Leu Ala Thr Ser Val Pro Val
            195                 200                 205

Arg Arg Leu Gly Lys Pro Ala Glu Val Ala Gly Leu Cys Ala Trp Leu
        210                 215                 220

Ala Ser Asp Asp Ala Ala Tyr Val Thr Gly Ala Asp Tyr Ala Val Asn
225                 230                 235                 240

Gly Gly Leu Tyr Met Gly
                245

<210> SEQ ID NO 79
<211> LENGTH: 241
<212> TYPE: PRT
<213> ORGANISM: Unknown
<220> FEATURE:
<223> OTHER INFORMATION: Rhizobiales

<400> SEQUENCE: 79

Met Ser Arg Val Ala Leu Val Thr Gly Gly Ser Arg Gly Ile Gly Ala
1               5                   10                  15

Ala Ile Cys Val Ala Leu Lys Ala Ala Gly Tyr Lys Val Ala Ala Asn
                20                  25                  30
```

```
Tyr Ala Gly Asn Asp Glu Arg Ala Lys Ala Phe Glu Gln Glu Ser Gly
            35                  40                  45

Ile Pro Val Tyr Lys Trp Asp Val Ser Ser Tyr Gln Ala Cys Val Asp
 50                  55                  60

Gly Ile Ala Arg Val Glu Ala Asp Leu Gly Pro Val Asp Ile Leu Val
 65                  70                  75                  80

Asn Asn Ala Gly Ile Thr Arg Asp Ala Met Phe His Lys Met Thr Pro
                85                  90                  95

Glu Gln Trp Gly Glu Val Ile Gly Thr Asn Leu Thr Gly Val Phe Asn
            100                 105                 110

Met Thr His Pro Leu Trp Ser Gly Met Arg Asp Arg Gly Phe Gly Arg
            115                 120                 125

Ile Val Asn Ile Ser Ser Ile Asn Gly Gln Lys Gly Gln Met Gly Gln
            130                 135                 140

Val Asn Tyr Ser Ala Ala Lys Ala Gly Asp Leu Gly Leu Thr Lys Ala
145                 150                 155                 160

Leu Ala Gln Glu Gly Ala Ala Lys Gly Ile Thr Val Asn Ala Ile Cys
                165                 170                 175

Pro Gly Tyr Ile Gly Thr Glu Met Val Arg Ala Val Pro Glu Lys Val
            180                 185                 190

Leu Asn Glu Arg Ile Ile Pro Gln Ile Pro Val Gly Arg Leu Gly Glu
            195                 200                 205

Pro Glu Glu Val Ala Arg Cys Val Val Phe Leu Ala Ser Asp Asp Ala
            210                 215                 220

Gly Phe Ile Thr Gly Ser Thr Ile Ser Ala Asn Gly Gly Gln Tyr Phe
225                 230                 235                 240

Ala

<210> SEQ ID NO 80
<211> LENGTH: 241
<212> TYPE: PRT
<213> ORGANISM: Rhizobium etli

<400> SEQUENCE: 80

Met Ser Arg Val Ala Leu Val Thr Gly Gly Thr Arg Gly Ile Gly Ala
 1               5                  10                  15

Ala Ile Ser Thr Ala Leu Lys Asn Ala Gly Tyr Arg Val Ala Ala Thr
                20                  25                  30

Tyr Ala Gly Asn Asp Glu Lys Ala His Ala Phe His Asp Val Thr Gly
            35                  40                  45

Val Ala Val Phe Lys Trp Asp Val Ser Asp Tyr Ala Ala Cys Gly Glu
 50                  55                  60

Gly Ile Thr Lys Val Glu Gly Glu Ile Gly Pro Val Glu Ile Leu Val
 65                  70                  75                  80

Asn Asn Ala Gly Ile Thr Arg Asp Ala Met Phe His Lys Met Thr Pro
                85                  90                  95

Gln Gln Trp His Glu Val Ile Asn Thr Asn Leu Thr Gly Leu Phe Asn
            100                 105                 110

Met Thr His Gln Val Trp Ser Gly Met Arg Asp Arg Ser Phe Gly Arg
            115                 120                 125

Ile Val Asn Ile Ser Ser Ile Asn Gly Gln Lys Gly Gln Met Gly Gln
            130                 135                 140

Ala Asn Tyr Ser Ala Ala Lys Ala Gly Asp Leu Gly Phe Thr Lys Ala
145                 150                 155                 160
```

Leu Ala Gln Glu Gly Ala Ala Lys Asn Ile Thr Val Asn Ala Ile Cys
                165                 170                 175

Pro Gly Tyr Ile Gly Thr Glu Met Val Leu Ala Val Pro Glu Lys Val
            180                 185                 190

Leu Asn Glu Arg Ile Ile Pro Gln Ile Pro Val Gly Arg Leu Gly Glu
        195                 200                 205

Pro Glu Glu Ile Ala Arg Cys Val Thr Phe Leu Val Ser Asp Asp Ala
    210                 215                 220

Gly Phe Ile Thr Gly Ser Thr Leu Thr Ala Asn Gly Gly Gln Phe Phe
225                 230                 235                 240

Val

<210> SEQ ID NO 81
<211> LENGTH: 242
<212> TYPE: PRT
<213> ORGANISM: Rhodospirillum rubrum

<400> SEQUENCE: 81

Met Thr Lys Gly Arg Val Ala Leu Val Thr Gly Gly Thr Arg Gly Ile
1               5                   10                  15

Gly Ala Ala Ile Ser Leu Ala Leu Arg Asp Ala Gly Tyr Arg Val Ala
            20                  25                  30

Ala Asn Tyr Tyr Gly Asn Asp Ala Ala Ala Glu Arg Phe Thr Glu Glu
        35                  40                  45

Asn Lys Ile Pro Ala Phe Lys Phe Asp Val Ala Glu Tyr Ala Ala Val
    50                  55                  60

Gln Glu Gly Val Lys Gln Ile Thr Ala Glu Leu Gly Pro Ile Glu Val
65                  70                  75                  80

Leu Val Asn Asn Ala Gly Ile Thr Arg Asp Gly Thr Met His Arg Met
                85                  90                  95

Thr Pro Glu Gln Trp Glu Glu Val Ile His Thr Asn Leu Ser Ser Cys
            100                 105                 110

Phe Asn Leu Ala Arg Gly Val Ile Asp Ser Met Arg Asp Arg Gly Phe
        115                 120                 125

Gly Arg Ile Val Asn Ile Gly Ser Ile Asn Gly Gln Ala Gly Gln Tyr
    130                 135                 140

Gly Gln Val Asn Tyr Ala Ala Lys Ser Gly Ile His Gly Phe Thr
145                 150                 155                 160

Lys Ala Leu Ala Gln Glu Ala Ala Ala Lys Gly Ile Thr Val Asn Ala
                165                 170                 175

Ile Ala Pro Gly Tyr Val Asp Thr Asp Met Val Arg Ala Val Pro Tyr
            180                 185                 190

His Val Leu Glu Lys Ile Ile Ala Lys Ile Pro Met Gly Arg Leu Gly
        195                 200                 205

Arg Ala Glu Asp Ile Ala Arg Gly Val Leu Phe Leu Val Ala Asp Asp
    210                 215                 220

Ala Asp Tyr Ile Thr Gly Ala Thr Leu Ser Ile Asn Gly Gly Gln His
225                 230                 235                 240

Met Tyr

<210> SEQ ID NO 82
<211> LENGTH: 246
<212> TYPE: PRT
<213> ORGANISM: Azospirillum brasilense

<400> SEQUENCE: 82

Met Ser Gln Lys Ile Ala Leu Val Thr Gly Ala Met Gly Gly Leu Gly
1               5                   10                  15

Thr Ala Ile Cys Gln Ala Leu Ala Lys Asp Gly Tyr Ile Val Ala Ala
            20                  25                  30

Asn Cys Leu Pro Asn Phe Glu Pro Ala Ala Trp Leu Gly Gln Gln
        35                  40                  45

Glu Ala Leu Gly Phe Lys Phe Tyr Val Ala Gly Asp Val Ser Asp
    50                  55                  60

Phe Glu Ser Cys Lys Ala Met Val Ala Lys Ile Glu Ala Asp Leu Gly
65                  70                  75                  80

Pro Val Asp Ile Leu Val Asn Asn Ala Gly Ile Thr Arg Asp Lys Phe
                85                  90                  95

Phe Ala Lys Met Glu Lys Ala Gln Trp Asp Ala Val Ile Ala Thr Asn
                100                 105                 110

Leu Ser Ser Leu Phe Asn Val Thr Gln Gln Val Ser Ala Lys Met Ala
            115                 120                 125

Glu Arg Gly Trp Gly Arg Ile Ile Asn Ile Ser Ser Val Asn Gly Val
130                 135                 140

Lys Gly Gln Ala Gly Gln Thr Asn Tyr Ser Ala Ala Lys Ala Gly Val
145                 150                 155                 160

Ile Gly Phe Thr Lys Ala Leu Ala Ala Glu Leu Ala Thr Lys Gly Val
                165                 170                 175

Thr Val Asn Ala Ile Ala Pro Gly Tyr Ile Gly Thr Asp Met Val Met
            180                 185                 190

Ala Ile Arg Glu Asp Ile Arg Gln Ala Ile Thr Asp Ser Val Pro Met
        195                 200                 205

Lys Arg Leu Gly Arg Pro Asp Glu Ile Gly Gly Ala Val Ser Tyr Leu
    210                 215                 220

Ala Ser Glu Ile Ala Gly Tyr Val Thr Gly Ser Thr Leu Asn Ile Asn
225                 230                 235                 240

Gly Gly Leu Asn Tyr Gln
                245

<210> SEQ ID NO 83
<211> LENGTH: 247
<212> TYPE: PRT
<213> ORGANISM: Bacillus thuringiensis

<400> SEQUENCE: 83

Met Val Gln Leu Asn Gly Lys Val Ala Ile Val Thr Gly Gly Ala Lys
1               5                   10                  15

Gly Ile Gly Lys Ala Ile Thr Val Ala Leu Ala Gln Glu Gly Ala Lys
            20                  25                  30

Val Val Ile Asn Tyr Asn Ser Ser Lys Glu Ala Ala Glu Asn Leu Val
            35                  40                  45

Asn Glu Leu Gly Lys Glu Gly His Asp Val Tyr Ala Val Gln Ala Asp
    50                  55                  60

Val Ser Lys Val Glu Asp Ala Asn Arg Leu Val Glu Glu Ala Val Asn
65                  70                  75                  80

His Phe Gly Lys Val Asp Ile Leu Val Asn Asn Ala Gly Ile Thr Arg
                85                  90                  95

Asp Arg Thr Phe Lys Lys Leu Asn Arg Glu Asp Trp Glu Arg Val Ile
                100                 105                 110

```
Asp Val Asn Leu Ser Ser Val Phe Asn Thr Thr Ser Ala Val Leu Pro
            115                 120                 125

Tyr Ile Thr Glu Ala Glu Glu Gly Arg Ile Ile Ser Ile Ser Ser Ile
    130                 135                 140

Ile Gly Gln Ala Gly Gly Phe Gly Gln Thr Asn Tyr Ser Ala Ala Lys
145                 150                 155                 160

Ala Gly Met Leu Gly Phe Thr Lys Ser Leu Ala Leu Glu Leu Ala Lys
                165                 170                 175

Thr Asn Val Thr Val Asn Ala Ile Cys Pro Gly Phe Ile Asp Thr Glu
            180                 185                 190

Met Val Ala Glu Val Pro Glu Glu Val Arg Gln Lys Ile Val Ala Lys
        195                 200                 205

Ile Pro Lys Lys Arg Phe Gly Gln Ala Asp Glu Ile Ala Lys Gly Val
    210                 215                 220

Val Tyr Leu Cys Arg Asp Gly Ala Tyr Ile Thr Gly Gln Gln Leu Asn
225                 230                 235                 240

Ile Asn Gly Gly Leu Tyr Met
                245

<210> SEQ ID NO 84
<211> LENGTH: 240
<212> TYPE: PRT
<213> ORGANISM: Arthrospira platensis

<400> SEQUENCE: 84

Met Val Ser Leu Gly Leu Glu Asp Lys Val Ile Val Thr Gly Gly
1               5                   10                  15

Ala Arg Gly Ile Gly Ala Ala Ile Val Lys Leu Val Glu Leu Gly
                20                  25                  30

Ala Lys Val Ala Ser Ile Asp Val Ile Asp Gly Glu Thr Pro Thr Gly
            35                  40                  45

Gly Leu Ala Leu Lys Ala Asp Val Thr Lys Leu Asp Ser Met Glu Ser
    50                  55                  60

Ala Ala Lys Glu Ile Ser Glu Lys Leu Gly Thr Val Tyr Gly Val Val
65                  70                  75                  80

Ala Asn Ala Gly Ile Thr Arg Asp Asn Phe Phe Thr Lys Leu Thr Asp
                85                  90                  95

Glu Asp Trp Asp Gln Val Ile Ala Val Asn Leu Lys Gly Val Lys Asn
            100                 105                 110

Thr Ile Gln Pro Phe Met Gln Gly Met Tyr Asp Gln Asn Ala Gly Ser
        115                 120                 125

Ile Val Ala Ile Ser Ser Ile Ser Gly Asp Arg Gly Asn Ala Gly Gln
    130                 135                 140

Thr Asn Tyr Ala Ser Thr Lys Ala Ala Val Ile Gly Met Met Lys Ser
145                 150                 155                 160

Leu Ala Arg Glu Gly Ala Arg Phe Asn Val Arg Ala Asn Ala Ile Ala
                165                 170                 175

Pro Gly Phe Ile Asn Thr Glu Met Thr Gln Lys Ile Pro Glu Lys Val
            180                 185                 190

Arg Asp Lys Ile Thr Ala Glu Ile Pro Phe Arg Arg Phe Gly Glu Pro
        195                 200                 205

Glu Asp Ile Ala Trp Ala Val Ala Phe Leu Leu Ser Pro Val Ala Ser
    210                 215                 220

Asn Tyr Val Thr Gly Glu Val Leu Arg Val Asn Gly Ala His His Thr
225                 230                 235                 240
```

```
<210> SEQ ID NO 85
<211> LENGTH: 295
<212> TYPE: PRT
<213> ORGANISM: Unknown
<220> FEATURE:
<223> OTHER INFORMATION: Pseudomonas

<400> SEQUENCE: 85
```

| | | | | | | | | | | | | | | | |
|---|---|---|---|---|---|---|---|---|---|---|---|---|---|---|---|
| Met | Arg | Pro | Glu | Ile | Ala | Val | Leu | Asp | Ile | Gln | Gly | Gln | Tyr | Arg | Val |
| 1 | | | | 5 | | | | | 10 | | | | | 15 | |
| Tyr | Thr | Glu | Phe | Tyr | Arg | Ala | Asp | Ala | Ala | Glu | Asn | Thr | Ile | Ile | Leu |
| | | | 20 | | | | | 25 | | | | | 30 | | |
| Ile | Asn | Gly | Ser | Leu | Ala | Thr | Thr | Ala | Ser | Phe | Ala | Gln | Thr | Val | Arg |
| | | | 35 | | | | | 40 | | | | | 45 | | |
| Asn | Leu | His | Pro | Gln | Phe | Asn | Val | Val | Leu | Phe | Asp | Gln | Pro | Tyr | Ser |
| | | | 50 | | | | | 55 | | | | | 60 | | |
| Gly | Lys | Ser | Lys | Pro | His | Asn | Arg | Gln | Glu | Arg | Leu | Ile | Ser | Lys | Glu |
| 65 | | | | | 70 | | | | | 75 | | | | | 80 |
| Thr | Glu | Ala | His | Ile | Leu | Leu | Glu | Leu | Ile | Glu | His | Phe | Gln | Ala | Asp |
| | | | | 85 | | | | | 90 | | | | | 95 | |
| His | Val | Met | Ser | Phe | Ser | Trp | Gly | Gly | Ala | Ser | Thr | Leu | Leu | Ala | Leu |
| | | | 100 | | | | | 105 | | | | | 110 | | |
| Ala | His | Gln | Pro | Arg | Tyr | Val | Lys | Lys | Ala | Val | Val | Ser | Ser | Phe | Ser |
| | | | 115 | | | | | 120 | | | | | 125 | | |
| Pro | Val | Ile | Asn | Glu | Pro | Met | Arg | Asp | Tyr | Leu | Asp | Arg | Gly | Cys | Gln |
| | | 130 | | | | | 135 | | | | | 140 | | | |
| Tyr | Leu | Ala | Ala | Cys | Asp | Arg | Tyr | Gln | Val | Gly | Asn | Leu | Val | Asn | Asp |
| 145 | | | | | 150 | | | | | 155 | | | | | 160 |
| Thr | Ile | Gly | Lys | His | Leu | Pro | Ser | Leu | Phe | Lys | Arg | Phe | Asn | Tyr | Arg |
| | | | | 165 | | | | | 170 | | | | | 175 | |
| His | Val | Ser | Ser | Leu | Asp | Ser | His | Glu | Tyr | Ala | Gln | Met | His | Phe | His |
| | | | 180 | | | | | 185 | | | | | 190 | | |
| Ile | Asn | Gln | Val | Leu | Glu | His | Asp | Leu | Glu | Arg | Ala | Leu | Gln | Gly | Ala |
| | | | 195 | | | | | 200 | | | | | 205 | | |
| Arg | Asn | Ile | Asn | Ile | Pro | Val | Leu | Phe | Ile | Asn | Gly | Glu | Arg | Asp | Glu |
| | | 210 | | | | | 215 | | | | | 220 | | | |
| Tyr | Thr | Thr | Val | Glu | Asp | Ala | Arg | Gln | Phe | Ser | Lys | His | Val | Gly | Arg |
| 225 | | | | | 230 | | | | | 235 | | | | | 240 |
| Ser | Gln | Phe | Ser | Val | Ile | Arg | Asp | Ala | Gly | His | Phe | Leu | Asp | Met | Glu |
| | | | | 245 | | | | | 250 | | | | | 255 | |
| Asn | Lys | Thr | Ala | Cys | Glu | Asn | Thr | Arg | Asn | Val | Met | Leu | Gly | Phe | Leu |
| | | | 260 | | | | | 265 | | | | | 270 | | |
| Lys | Pro | Thr | Val | Arg | Glu | Pro | Arg | Gln | Arg | Tyr | Gln | Pro | Val | Gln | Gln |
| | | | 275 | | | | | 280 | | | | | 285 | | |
| Gly | Gln | His | Ala | Phe | Ala | Ile | | | | | | | | | |
| | | 290 | | | | 295 | | | | | | | | | |

```
<210> SEQ ID NO 86
<211> LENGTH: 560
<212> TYPE: PRT
<213> ORGANISM: Pseudomonas putida

<400> SEQUENCE: 86
```

| | | | | | | | | | | | | | | | |
|---|---|---|---|---|---|---|---|---|---|---|---|---|---|---|---|
| Met | Leu | Gln | Thr | Arg | Ile | Ile | Lys | Pro | Ala | Glu | Gly | Ala | Tyr | Ala | Tyr |
| 1 | | | | 5 | | | | | 10 | | | | | 15 | |

-continued

```
Pro Leu Leu Ile Lys Arg Leu Leu Met Ser Gly Ser Arg Tyr Glu Lys
             20                  25                  30

Thr Arg Glu Ile Val Tyr Arg Asp Gln Met Arg Leu Thr Tyr Pro Gln
         35                  40                  45

Leu Asn Glu Arg Ile Ala Arg Leu Ala Asn Val Leu Thr Glu Ala Gly
     50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                 85                  90                  95

Thr Ile Asn Val Arg Leu Ser Pro Glu Gln Ile Leu Tyr Thr Met Asn
             100                 105                 110

His Ala Glu Asp Arg Val Val Leu Val Asn Ser Asp Phe Val Gly Leu
         115                 120                 125

Tyr Gln Ala Ile Ala Gly Gln Leu Thr Thr Val Asp Lys Thr Leu Leu
     130                 135                 140

Leu Thr Asp Gly Pro Asp Lys Thr Ala Glu Leu Pro Gly Leu Val Gly
145                 150                 155                 160

Glu Tyr Glu Gln Leu Leu Ala Ala Ala Ser Pro Arg Tyr Asp Phe Pro
                 165                 170                 175

Asp Phe Asp Glu Asn Ser Val Ala Thr Thr Phe Tyr Thr Thr Gly Thr
             180                 185                 190

Thr Gly Asn Pro Lys Gly Val Tyr Phe Ser His Arg Gln Leu Val Leu
         195                 200                 205

His Thr Leu Ala Glu Ala Ser Val Thr Gly Ser Ile Asp Ser Val Arg
     210                 215                 220

Leu Leu Gly Ser Asn Asp Val Tyr Met Pro Ile Thr Pro Met Phe His
225                 230                 235                 240

Val His Ala Trp Gly Ile Pro Tyr Ala Ala Thr Met Leu Gly Met Lys
                 245                 250                 255

Gln Val Tyr Pro Gly Arg Tyr Glu Pro Asp Met Leu Val Lys Leu Trp
             260                 265                 270

Arg Glu Glu Lys Val Thr Phe Ser His Cys Val Pro Thr Ile Leu Gln
         275                 280                 285

Met Leu Leu Asn Cys Pro Asn Ala Gln Gly Gln Asp Phe Gly Gly Trp
     290                 295                 300

Lys Ile Ile Ile Gly Gly Ser Ser Leu Asn Arg Ser Leu Tyr Gln Ala
305                 310                 315                 320

Ala Leu Ala Arg Gly Ile Gln Leu Thr Ala Ala Tyr Gly Met Ser Glu
                 325                 330                 335

Thr Cys Pro Leu Ile Ser Ala Ala His Leu Asn Asp Glu Leu Gln Ala
             340                 345                 350

Gly Ser Glu Asp Glu Arg Val Thr Tyr Arg Ile Lys Ala Gly Val Pro
         355                 360                 365

Val Pro Leu Val Glu Ala Ala Ile Val Asp Gly Glu Gly Asn Phe Leu
     370                 375                 380

Pro Ala Asp Gly Glu Thr Gln Gly Glu Leu Val Leu Arg Ala Pro Trp
385                 390                 395                 400

Leu Thr Met Gly Tyr Phe Lys Glu Pro Glu Lys Ser Glu Glu Leu Trp
                 405                 410                 415

Gln Gly Gly Trp Leu His Thr Gly Asp Val Ala Thr Leu Asp Gly Met
             420                 425                 430

Gly Tyr Ile Asp Ile Arg Asp Arg Ile Lys Asp Val Ile Lys Thr Gly
```

435                 440                 445
Gly Glu Trp Val Ser Ser Leu Asp Leu Glu Asp Leu Ile Ser Arg His
    450                 455                 460

Pro Ala Val Arg Glu Val Ala Val Gly Val Ala Asp Pro Gln Trp
465                 470                 475                 480

Gly Glu Arg Pro Phe Ala Leu Leu Val Ala Arg Asp Gly His Asp Ile
                    485                 490                 495

Asp Ala Lys Ala Leu Lys Glu His Leu Lys Pro Phe Val Glu Gln Gly
                500                 505                 510

His Ile Asn Lys Trp Ala Ile Pro Ser Gln Ile Ala Leu Val Thr Glu
            515                 520                 525

Ile Pro Lys Thr Ser Val Gly Lys Leu Asp Lys Lys Arg Ile Arg Gln
        530                 535                 540

Asp Ile Val Gln Trp Gln Ala Ser Asn Ser Ala Phe Leu Ser Thr Leu
545                 550                 555                 560

<210> SEQ ID NO 87
<211> LENGTH: 295
<212> TYPE: PRT
<213> ORGANISM: Delftia acidovorans

<400> SEQUENCE: 87

Met Arg Pro Glu Ile Ala Val Leu Asp Ile Gln Gly Gln Tyr Arg Val
1               5                   10                  15

Tyr Thr Glu Phe Tyr Arg Ala Asp Ala Ala Glu Asn Thr Ile Ile Leu
                20                  25                  30

Ile Asn Gly Ser Leu Ala Thr Thr Ala Ser Phe Ala Gln Thr Val Arg
            35                  40                  45

Asn Leu Tyr Pro Gln Phe Asn Val Val Leu Phe Asp Gln Pro Tyr Ser
        50                  55                  60

Gly Lys Ser Lys Pro His Asn Arg Gln Glu Arg Leu Ile Ser Lys Glu
65                  70                  75                  80

Thr Glu Ala His Ile Leu Leu Glu Leu Ile Glu His Phe Gln Ala Asp
                85                  90                  95

His Val Leu Ser Phe Ser Trp Gly Gly Ala Ser Thr Leu Leu Ala Leu
            100                 105                 110

Ala His Gln Pro Arg Tyr Val Lys Lys Ala Val Val Ser Ser Phe Ser
        115                 120                 125

Pro Val Ile Asn Glu Pro Met Arg Asp Tyr Leu Asp Arg Gly Cys Gln
130                 135                 140

Tyr Leu Ala Ala Cys Asp Arg Tyr Gln Val Gly Asn Leu Val Asn Asp
145                 150                 155                 160

Thr Ile Gly Lys His Leu Pro Ser Leu Phe Lys Arg Phe Asn Tyr Arg
                165                 170                 175

His Val Ser Ser Leu Asp Ser His Glu Tyr Ala Gln Met His Phe His
            180                 185                 190

Ile Asn Gln Val Leu Glu His Asp Leu Glu Arg Ala Leu Gln Gly Ala
        195                 200                 205

Arg Asn Ile Asn Ile Pro Val Leu Phe Ile Asn Gly Glu Arg Asp Glu
210                 215                 220

Tyr Thr Thr Val Glu Asp Ala Arg Gln Phe Ser Lys His Val Gly Arg
225                 230                 235                 240

Ser Gln Phe Ser Val Ile Arg Asp Ala Gly His Phe Leu Asp Met Glu
                245                 250                 255

Asn Lys Thr Ala Cys Glu Asn Thr Arg Asn Val Met Leu Gly Phe Leu
            260                 265                 270

Lys Pro Thr Val Arg Glu Pro Arg Gln Arg Tyr Gln Pro Val Gln Gln
            275                 280                 285

Gly Gln His Ala Phe Ala Ile
            290             295

<210> SEQ ID NO 88
<211> LENGTH: 296
<212> TYPE: PRT
<213> ORGANISM: Pantoea sp. Ap-967

<400> SEQUENCE: 88

Met Arg Pro Glu Ile Ala Val Leu Asp Val Gln Gly Gln Tyr Arg Val
1               5                   10                  15

Tyr Thr Glu Phe Tyr Arg Ala Asp Ala Ala Glu Lys Thr Ile Ile Leu
            20                  25                  30

Ile Asn Gly Ser Leu Ala Thr Thr Ala Ser Phe Ala Gln Thr Val Arg
            35                  40                  45

Asn Leu His Pro Gln Phe Asn Val Val Leu Tyr Asp Gln Pro Tyr Ala
    50                  55                  60

Gly Lys Ser Lys Pro His Asn Arg Gln Glu Arg Leu Ile Ser Lys Glu
65                  70                  75                  80

Asp Glu Ala His Ile Leu Leu Glu Leu Ile Glu His Phe Arg Cys Asp
                85                  90                  95

His Val Met Ser Phe Ser Trp Gly Gly Ala Cys Thr Leu Leu Ala Leu
            100                 105                 110

Ala His Gln Pro Arg Leu Val Lys Lys Ala Val Val Ser Ser Phe Ser
        115                 120                 125

Pro Ile Ile Asn Glu Pro Met Arg Asp Tyr Leu Glu Arg Gly Cys Lys
    130                 135                 140

Tyr Leu Ala Ala Cys Asp Arg Tyr Gln Val Gly Asn Leu Val Asn Asp
145                 150                 155                 160

Thr Ile Gly Lys His Leu Pro Ser Leu Phe Lys Arg Phe Asn Tyr Arg
                165                 170                 175

His Val Ser Ser Leu Asp Ser His Glu Tyr Ala Gln Met His Phe His
            180                 185                 190

Ile Asn Gln Val Leu Gln His Asp Leu Glu Arg Ala Leu Lys Gly Ala
        195                 200                 205

Arg Asn Ile Asp Ile Pro Val Leu Phe Ile Asn Gly Asp Arg Asp Glu
    210                 215                 220

Tyr Thr Thr Val Glu Asp Ala Arg His Phe Gly Gln His Val Gly Lys
225                 230                 235                 240

Ser His Phe Ser Val Ile Arg Asp Ala Gly His Phe Leu Asp Met Glu
                245                 250                 255

Asn Lys Asn Ala Cys Glu Asp Thr Arg Asn Val Met Leu Asp Phe Leu
            260                 265                 270

Lys Pro Thr Val Arg Glu Ser Arg Gln Pro Tyr Ser Phe Met Gln
            275                 280                 285

Gln Gly Gln His Ala Val Ala Ile
        290                 295

<210> SEQ ID NO 89
<211> LENGTH: 296
<212> TYPE: PRT
<213> ORGANISM: Stenotrophomonas rhizophila

<400> SEQUENCE: 89

Met Arg Pro Glu Ile Ala Val Leu Asp Ile Gln Gly Gln Tyr Arg Val
1               5                   10                  15

Tyr Thr Glu Phe Tyr Arg Ala Asp Ala Ala Glu Lys Thr Ile Ile Leu
            20                  25                  30

Ile Asn Gly Ser Leu Ala Thr Thr Ala Ser Phe Ala Gln Thr Val Arg
        35                  40                  45

Asn Leu His Pro His Phe Asn Val Val Leu Tyr Asp Gln Pro Tyr Ala
    50                  55                  60

Gly Lys Ser Lys Pro His Asn Arg Gln Glu Arg Leu Ile Ser Lys Glu
65                  70                  75                  80

Asp Glu Ala Gln Ile Leu Leu Glu Leu Ile Asp Arg Phe Gln Cys Asp
                85                  90                  95

His Val Met Ser Phe Ser Trp Gly Gly Ala Cys Thr Leu Leu Ala Leu
            100                 105                 110

Ala His Gln Pro Arg Arg Val Lys Lys Ala Val Val Ser Ser Phe Ser
        115                 120                 125

Pro Ile Ile Asn Glu Pro Met Arg Asp Tyr Leu Glu Arg Gly Cys Gln
    130                 135                 140

Tyr Leu Ala Ala Cys Asp Arg Tyr Gln Val Gly Asn Leu Val Asn Asp
145                 150                 155                 160

Thr Ile Gly Lys Tyr Leu Pro Ser Leu Phe Lys Arg Phe Asn Tyr Arg
                165                 170                 175

His Val Ser Gly Leu Asp Ser His Glu Tyr Ala Gln Met His Phe His
            180                 185                 190

Ile Asn Glu Val Leu Gln Arg Asp Leu Gln Arg Ala Leu Asn Gly Ala
        195                 200                 205

Arg Asn Ile Asp Ile Pro Val Leu Phe Ile Asn Gly Glu Arg Asp Glu
210                 215                 220

Tyr Thr Thr Val Glu Asp Ala Arg Glu Phe Gly Lys His Ile Gly Asn
225                 230                 235                 240

Ser Gln Phe Ser Val Ile Arg Asp Ala Gly His Phe Leu Asp Met Glu
                245                 250                 255

His Lys Ala Ala Cys Asp Asp Thr Arg Asn Ala Met Leu Gly Phe Leu
            260                 265                 270

Lys Pro Thr Met Arg Glu Ala Arg Gln Arg Ser His Ala Tyr Ile Gln
        275                 280                 285

Gln Gly Gln His Ala Leu Ala Ile
    290                 295

<210> SEQ ID NO 90
<211> LENGTH: 294
<212> TYPE: PRT
<213> ORGANISM: Trinickia caryophylli

<400> SEQUENCE: 90

Met Arg Pro Glu Ile Ala Val Leu Asp Ile Gln Gly Gln Tyr Arg Val
1               5                   10                  15

Tyr Thr Glu Phe Tyr Arg Ala Asp Ala Ala Glu Lys Thr Ile Ile Leu
            20                  25                  30

Ile Asn Gly Ser Leu Ala Thr Thr Ala Ser Phe Ala Gln Thr Val Arg
        35                  40                  45

Asn Leu His Pro Gln Phe Asn Val Val Leu Tyr Asp Gln Pro Tyr Ser
    50                  55                  60

Gly Lys Ser Lys Pro His Asn Arg Asn Asp His Leu Leu Thr Lys Glu
65                  70                  75                  80

Ile Glu Gly Gln Ile Leu Leu Glu Leu Ile Asp His Phe Ala Ala Asp
            85                  90                  95

His Ile Met Ser Phe Ser Trp Gly Gly Ala Cys Thr Leu Leu Ala Leu
            100                 105                 110

Ala His Arg Pro Arg Arg Ile Glu Lys Ala Val Ile Ser Ser Phe Ser
            115                 120                 125

Pro Val Ile Asn Glu Pro Met Arg Asp Tyr Leu Glu Arg Gly Ser His
        130                 135                 140

Tyr Leu Ser Lys Cys Asp Arg Tyr Glu Val Gly Ala Leu Val Asn Asp
145                 150                 155                 160

Thr Ile Gly Lys His Leu Pro Ser Leu Phe Lys Arg Phe Asn Tyr Arg
                165                 170                 175

His Val Ser Ser Leu Asp Asn His Glu Tyr Lys Gln Met His Phe His
            180                 185                 190

Ile Asn Gln Val Leu Lys His Asp Leu Asp Asn Ala Leu Arg Ser Ala
            195                 200                 205

Arg Val Ile Asp Ile Pro Val Leu Phe Met Asn Gly Glu Trp Asp Glu
210                 215                 220

Tyr Thr Thr Thr Glu Asp Ala Gln Lys Phe Ser Lys His Val Arg Asn
225                 230                 235                 240

Ser His Phe Ser Arg Ile Glu Ser Ala Gly His Phe Leu Asp Met Glu
            245                 250                 255

His Lys Ala Ala Cys Arg Asp Ser Arg Asp Ala Leu Leu Ser Phe Leu
            260                 265                 270

Thr Pro Ser Pro Arg Glu His Arg Val Arg Thr Pro Phe Thr Leu Gly
            275                 280                 285

Glu His Ala Phe Ala Ile
        290

<210> SEQ ID NO 91
<211> LENGTH: 294
<212> TYPE: PRT
<213> ORGANISM: Serratia sp. 18057

<400> SEQUENCE: 91

Met Arg Pro Glu Ile Ala Val Leu Asp Ile Gln Gly Gln Tyr Arg Val
1               5                   10                  15

Tyr Thr Glu Phe Tyr Arg Ala Glu Lys Ala Glu Lys Thr Ile Ile Leu
            20                  25                  30

Val Asn Gly Ser Met Ala Thr Thr Ala Ser Phe Ala Gln Thr Val Lys
        35                  40                  45

Ser Leu His Pro Gln Phe Asn Val Val Leu Tyr Asp Gln Pro Tyr Ala
50                  55                  60

Gly Arg Ser Lys Ile His Asn Arg His Glu Gln Met Leu Thr Lys Glu
65                  70                  75                  80

Val Glu Gly Gln Ile Leu Leu Glu Leu Ile Asp His Phe Ala Ala Glu
            85                  90                  95

His Val Leu Ser Phe Ser Trp Gly Gly Ala Ala Thr Leu Val Ala Leu
            100                 105                 110

Ala His Arg Pro Arg Arg Val Glu Lys Ala Val Ile Ser Ser Phe Ser
            115                 120                 125

Pro Val Ile Asn Ala Pro Met Arg Asp Tyr Leu Glu Arg Gly Val Asp

```
                  130                 135                 140
Tyr Leu Gly Asn Leu Asp Arg Asp Arg Val Gly His Leu Val Asn Ser
145                 150                 155                 160

Thr Ile Gly Lys His Leu Pro Ser Leu Phe Lys Arg Phe Asn Tyr Lys
                165                 170                 175

His Val Ser Ser Leu Ala Glu His Glu Tyr Gly Gln Met His Phe His
                180                 185                 190

Ile Ser Gln Val Leu Tyr Ser Asp Arg Leu Cys Tyr Leu Lys Ala Ala
                195                 200                 205

Lys Gln Ile Asp Ile Pro Val Leu Phe Leu Asn Gly Glu Trp Asp Glu
                210                 215                 220

Tyr Thr Ser Ala Gln Asp Ala Lys Leu Phe Gly Gln His Val Ala Asn
225                 230                 235                 240

Ser Ser Phe Ser Thr Val Gln Ala Thr Gly His Phe Leu Asp Met Glu
                245                 250                 255

His Lys Ala Ala Cys Arg Asp Ser Arg Glu Ala Val Val Gly Phe Leu
                260                 265                 270

Lys Pro Glu Arg Gln Ala Asn Arg Leu Arg Tyr His Gln Gly Gln Thr
                275                 280                 285

His His Ala Phe Ala Ile
            290

<210> SEQ ID NO 92
<211> LENGTH: 297
<212> TYPE: PRT
<213> ORGANISM: Paucimonas lemoignei

<400> SEQUENCE: 92

Met Arg Pro Glu Ile Ala Val Leu Asp Ile Gln Gly Gln Phe Arg Val
1               5                   10                  15

Tyr Thr Glu Phe Tyr Arg Ala Glu Ala Ala Glu Lys Thr Ile Ile Leu
                20                  25                  30

Val Asn Gly Ser Leu Ala Thr Thr Ala Ser Phe Ala Gln Thr Leu Arg
            35                  40                  45

Asn Leu His Pro His Phe Asn Val Val Leu Tyr Asp Gln Pro Tyr Ala
        50                  55                  60

Gly Lys Ser Lys Pro His Asn Ile Asn Glu Arg Pro Leu Thr Lys Glu
65                  70                  75                  80

Leu Glu Gly Gln Ile Leu Leu Glu Leu Ile Asp His Phe Asn Ala Glu
                85                  90                  95

His Ile Met Ser Phe Ser Trp Gly Gly Ala Ala Ala Leu Val Ala Leu
                100                 105                 110

Ser His Arg Pro Lys Arg Ile Glu Lys Ala Val Ile Ser Ser Phe Ser
                115                 120                 125

Pro Val Ile Asn Glu His Met Arg Asp Tyr Leu Glu Arg Gly Ile Thr
            130                 135                 140

His Leu Ser Val His Asp Arg Tyr Glu Val Gly Asn Leu Val Asn Ser
145                 150                 155                 160

Thr Ile Gly Lys His Leu Pro Pro Leu Phe Lys Arg Phe Asn His Arg
                165                 170                 175

His Val Ser Asn Leu Asp Thr His Glu Tyr Asp Gln Met His Phe His
                180                 185                 190

Ile Asn Asp Val Leu Asn Leu Asp Pro His Asn Tyr Leu Ser Thr Ala
                195                 200                 205
```

```
Lys Asn Ile Asn Val Pro Val Leu Phe Leu Asn Gly Glu Trp Asp Glu
        210                 215                 220

Tyr Thr Ser Ala Ala Asp Ala Arg Leu Phe Ala Pro Val Val Gln Asn
225                 230                 235                 240

Ser Ser Phe Ser Thr Val Gln Ser Thr Gly His Phe Leu Asp Met Glu
                245                 250                 255

His Lys Ala Ala Cys Arg Asp Ser Arg Phe Ala Leu Met Asp Phe Leu
                260                 265                 270

Thr Pro Gln Thr Pro Ala Pro Ser Arg Ser Thr Tyr His Phe Lys Gln
                275                 280                 285

Val Gln Thr Val His Ala Phe Ala Leu
        290                 295

<210> SEQ ID NO 93
<211> LENGTH: 300
<212> TYPE: PRT
<213> ORGANISM: Streptococcus dysgalactiae

<400> SEQUENCE: 93

Met Arg Pro Glu Thr Ala Ile Val Glu Ile His Gly Gln His Arg Val
1               5                   10                  15

His Thr Glu Phe Tyr Gly Asn Pro Ala Ala Gln Gln Thr Ile Val Leu
                20                  25                  30

Val Asn Gly Ser Leu Ser Thr Thr Ala Ser Phe Ala Gln Thr Val Lys
            35                  40                  45

Tyr Leu Gln Pro His Phe Asn Val Val Leu Tyr Asp Gln Pro Tyr Ala
        50                  55                  60

Gly Gln Ser Lys Pro His Asn Asp Asn Arg Ala Pro Ile Ser Lys Glu
65                  70                  75                  80

Cys Glu Ala Gly Ile Leu Leu Glu Leu Leu His Phe Arg Ala Glu
                85                  90                  95

Val Val Met Ser Phe Ser Trp Gly Gly Val Ala Thr Leu Leu Ala Leu
                100                 105                 110

Ala Gln Arg Pro Gly Arg Val Arg Lys Ala Val Val Asn Ser Phe Ser
            115                 120                 125

Pro Leu Leu Asn Pro Ala Met Leu Asp Tyr Leu His Arg Gly Leu Asp
        130                 135                 140

Tyr Leu Ala Ala Cys Asp Arg Thr Gln Val Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Gly Leu Asp Glu His Glu Tyr Arg Gln Met His Phe His
            180                 185                 190

Ile Arg Glu Val Leu Arg Leu Asn Ala Gly Ser Tyr Thr Glu Ser Phe
        195                 200                 205

Ala Gly Ile Glu Ile Pro Val Leu Phe Met Asn Gly Glu Leu Asp Ile
    210                 215                 220

Tyr Thr Thr Pro His Glu Ala Arg Gln Phe Gly Gln Leu Ile Arg Ala
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
                260                 265                 270

Arg Pro Gln His Ala Lys Pro Leu Asn Pro Ile Tyr Arg Pro Leu Pro
                275                 280                 285
```

Asn Gly Ala Ser Val Pro Leu Ala Ala Leu Ala Ser
            290             295             300

<210> SEQ ID NO 94
<211> LENGTH: 300
<212> TYPE: PRT
<213> ORGANISM: Enterobacter cloacae

<400> SEQUENCE: 94

Met Arg Pro Glu Thr Ala Ile Ile Glu Ile His Gly Gln Tyr Arg Ile
1               5                   10                  15

His Thr Glu Phe Tyr Gly Asn Pro Ser Ala Gln Gln Thr Ile Ile Leu
            20                  25                  30

Val Asn Gly Ser Leu Ser Thr Thr Ala Ser Phe Ala Gln Thr Val Lys
        35                  40                  45

Tyr Leu Gln Pro His Tyr Asn Val Val Leu Tyr Asp Gln Pro Tyr Ala
    50                  55                  60

Gly Gln Ser Lys Pro His Asn Glu Asn Arg Thr Pro Ile Ser Lys Glu
65                  70                  75                  80

Cys Glu Ala Arg Ile Leu Leu Glu Leu Ile Glu Arg Phe Arg Ala Asp
                85                  90                  95

Val Val Met Ser Phe Ser Trp Gly Gly Val Ala Thr Leu Leu Ala Leu
            100                 105                 110

Ala Gln Arg Pro Gly Arg Ile Arg Arg Ala Val Val Asn Ser Phe Ser
        115                 120                 125

Pro Gln Leu Asn Pro Ala Met Leu Asp Tyr Leu His Arg Gly Leu Asp
    130                 135                 140

Tyr Leu Ala Ala Cys Asp Arg Thr Gln Val Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Ser Leu Asp Glu His Glu Tyr His Gln Met His Phe His
            180                 185                 190

Ile Arg Glu Val Leu Arg Leu Asn Ala Asp Ser Tyr Thr Glu Ser Phe
        195                 200                 205

Ala Gly Ile Glu Ile Pro Val Leu Phe Met Asn Gly Glu Leu Asp Ile
    210                 215                 220

Tyr Thr Thr Pro His Glu Ala Arg Gln Phe Gly Gln Leu Ile Arg Gly
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
            260                 265                 270

Arg Pro Gln Arg Thr Gln Pro Leu Asn Pro Ile Tyr Arg Pro Gln Pro
        275                 280                 285

Asn Gly Ala Ser Val Pro Leu Ala Ala Leu Ala Ser
    290                 295                 300

<210> SEQ ID NO 95
<211> LENGTH: 300
<212> TYPE: PRT
<213> ORGANISM: Acinetobacter baumannii

<400> SEQUENCE: 95

Met Arg Pro Glu Thr Ala Ile Ile Glu Ile His Gly Gln Tyr Arg Ile
1               5                   10                  15

His Thr Glu Phe Tyr Gly Asn Pro Ala Ala Gln Gln Thr Ile Ile Leu
            20                  25                  30

Val Asn Gly Ser Leu Ser Thr Thr Ala Ser Phe Ala Gln Thr Val Lys
        35                  40                  45

Tyr Leu Gln Pro His Tyr Asn Val Val Leu Tyr Asp Gln Pro Tyr Ala
    50                  55                  60

Gly Gln Ser Lys Pro His Asn Glu Asn His Thr Pro Ile Ser Lys Glu
65                  70                  75                  80

Cys Glu Ala Arg Ile Leu Leu Glu Leu Ile Glu Arg Phe Arg Ala Glu
                85                  90                  95

Val Val Met Ser Phe Ser Trp Gly Val Ala Thr Leu Leu Ala Leu
            100                 105                 110

Ala Gln Arg Pro Gly Arg Ile Arg Arg Ala Val Val Asn Ser Phe Ser
        115                 120                 125

Pro Gln Leu Asn Pro Ala Met Leu Asp Tyr Leu His Arg Gly Leu Asp
    130                 135                 140

Tyr Leu Ala Ala Cys Asp Arg Thr Gln Ile Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Ser Leu Asp Glu His Glu Tyr His Gln Met His Phe His
            180                 185                 190

Ile Arg Glu Val Leu Arg Leu Asn Ala Asp Ser Tyr Thr Glu Ser Phe
        195                 200                 205

Ala Gly Ile Glu Ile Pro Val Leu Phe Met Asn Gly Glu Leu Asp Ile
    210                 215                 220

Tyr Thr Thr Pro His Glu Ala Arg Gln Phe Gly Gln Leu Ile Arg Gly
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
            260                 265                 270

Arg Pro Gln Arg Thr Gln Pro Leu Asn Pro Ile Tyr Arg Pro Gln Pro
        275                 280                 285

Asn Gly Ala Ser Val Pro Leu Ala Ala Leu Ala Ser
    290                 295                 300

<210> SEQ ID NO 96
<211> LENGTH: 308
<212> TYPE: PRT
<213> ORGANISM: Nevskia soli

<400> SEQUENCE: 96

Met Glu Pro Glu Thr Leu Leu Ile Ser Val Pro Gly Gly Phe Lys Val
1               5                   10                  15

Tyr Val Glu His Tyr Arg Ile Asn Pro Ser Phe Glu Thr Val Ile Leu
            20                  25                  30

Val Asn Gly Ala Leu Ala Thr Thr Thr Ser Phe Asn Gln Thr Val Lys
        35                  40                  45

Tyr Leu Lys Glu Asn Phe Asn Val Val Leu Tyr Asp Leu Pro Tyr Ala
    50                  55                  60

Gly Gln Ser Lys Gln His Asn Ala Asn Ser Ala Leu Leu Thr Lys Asp
65                  70                  75                  80

Asp Glu Val Asp Ile Leu Ser Phe Leu Ile Gly Arg Phe Glu Pro Ser 85                  90                  95
His Leu Ile Ser Ile Ser Trp Gly Gly Val Ala Ala Leu Leu Ala Leu
                100                 105                 110

Ser Arg Ala Pro Lys Ser Val Lys Lys Ala Val Ile Gly Ser Phe Ser
            115                 120                 125

Pro Lys Leu Asn Ala Ala Met Leu Asp Tyr Leu Asp Lys Gly Gln Gln
    130                 135                 140

Tyr Leu Glu Ser Asn Asp Gln Ala Gly Ala Ser Ala Leu Leu Asn Ser
145                 150                 155                 160

Thr Val Gly Lys Tyr Leu Pro Arg Leu Leu Lys Leu Tyr Asn Tyr Arg
                165                 170                 175

Tyr Leu Ser Asn Leu Ala Glu His Glu Tyr Ala Gln Ile Ala Phe His
            180                 185                 190

Met Gln Gln Ile Arg Gln Leu Asp Ser Gln Arg Tyr Val Asn Arg Phe
    195                 200                 205

Val Gly Ile Lys Ile Pro Val Leu Phe Val Asn Gly Glu Leu Asp Glu
210                 215                 220

Tyr Thr Thr Ala Ser Asp Ile Arg Pro Leu Ser Gln Tyr Ile Arg His
225                 230                 235                 240

Ser Arg Phe Val Thr Val Pro Ala Thr Gly His Phe Leu Asp Leu Glu
                245                 250                 255

Asn Lys Arg Ser Trp Gly Glu Val Arg Arg Ile Thr Asn Glu Phe Leu
            260                 265                 270

Leu Asp Ala Ala Glu Ala Lys Ala Glu Ala Lys Ala Glu Asn Ala Ala
    275                 280                 285

Glu Thr Ala Ala Ser Ala Val Asp Val Val Arg Ser Phe Gly Pro Ala
290                 295                 300

Phe Ala Thr Ser
305

<210> SEQ ID NO 97
<211> LENGTH: 560
<212> TYPE: PRT
<213> ORGANISM: Stenotrophomonas rhizophila

<400> SEQUENCE: 97

Met Leu Gln Thr Arg Ile Ile Lys Pro Ala Glu Gly Ala Tyr Ser Phe
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Leu Arg Leu Thr Tyr Pro Gln
        35                  40                  45

Leu Asn Glu Arg Ile Ala Arg Leu Ala Asn Val Leu Thr Asp Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                85                  90                  95

Thr Ile Asn Val Arg Leu Ser Pro Glu Gln Ile Leu Tyr Thr Met Asn
                100                 105                 110

His Ala Glu Asp Arg Phe Val Leu Val Asn Ser Asp Phe Val Gly Leu
            115                 120                 125

Tyr Gln Ala Ile Ala Gly Gln Leu Thr Thr Val Asp Lys Thr Leu Leu
    130                 135                 140

```
Ile Thr Asp Gly Pro Asp Gln Thr Ala Asp Leu Pro Asn Leu Val Gly
145                 150                 155                 160

Glu Tyr Glu Gln Leu Leu Ala Ala Ala Ser Pro Arg Tyr Asp Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Thr His Arg Gln Leu Val Leu
        195                 200                 205

His Thr Leu Ala Glu Ala Ala Val Thr Gly Ser Ile Asp Ser Val Arg
210                 215                 220

Leu Leu Gly Ser Asn Asp Val Tyr Met Pro Ile Thr Pro Met Phe His
225                 230                 235                 240

Val His Ala Trp Gly Ile Pro Tyr Ala Ala Thr Met Leu Gly Met Lys
                245                 250                 255

Gln Val Tyr Pro Gly Arg Tyr Glu Pro Asp Met Leu Val Lys Leu Trp
            260                 265                 270

Arg Glu Glu Lys Val Thr Phe Ser His Cys Val Pro Thr Ile Leu Gln
        275                 280                 285

Met Leu Leu Asn Cys Pro Asn Ala Gln Gly Gln Asp Phe Gly Gly Trp
290                 295                 300

Lys Ile Ile Gly Gly Ser Ala Leu Asn Ser Ser Leu Tyr Lys Ala
305                 310                 315                 320

Ala Leu Ala Arg Gly Ile Gln Leu Thr Ala Ala Tyr Gly Met Ser Glu
                325                 330                 335

Thr Cys Pro Leu Ile Ser Ala Ala His Leu Asn Asp Glu Leu Gln Ala
            340                 345                 350

Gly Ser Glu Asp Glu Arg Val Thr Tyr Arg Ile Lys Ala Gly Val Pro
        355                 360                 365

Val Pro Leu Val Glu Ala Ala Ile Val Asp Gly Glu Gly Asn Phe Leu
370                 375                 380

Pro Ala Asp Gly Glu Thr Gln Gly Glu Leu Val Leu Arg Ala Pro Trp
385                 390                 395                 400

Leu Thr Met Gly Tyr Phe Lys Glu Pro Glu Lys Ser Glu Glu Leu Trp
                405                 410                 415

Gln Gly Gly Trp Leu His Thr Gly Asp Val Ala Thr Leu Asp Gly Met
            420                 425                 430

Gly Tyr Ile Asp Ile Arg Asp Arg Ile Lys Asp Val Ile Lys Thr Gly
        435                 440                 445

Gly Glu Trp Ile Ser Ser Leu Asp Leu Glu Asp Leu Ile Ser Arg His
450                 455                 460

Pro Ala Val Arg Glu Val Ala Val Val Gly Val Ala Asp Pro Gln Trp
465                 470                 475                 480

Gly Glu Arg Pro Phe Ala Leu Leu Val Val Arg Glu Asp Lys Ala Ile
                485                 490                 495

Asp Ala Lys Thr Leu Lys Glu His Leu Lys Pro Phe Val Glu Glu Gly
            500                 505                 510

His Ile Asn Lys Trp Ala Ile Pro Ser Gln Ile Ala Val Val Thr Glu
        515                 520                 525

Ile Pro Lys Thr Ser Val Gly Lys Leu Asp Lys Lys Arg Ile Arg Gln
530                 535                 540

Asp Ile Val Gln Trp Gln Ala Ser Asn Ser Ala Phe Leu Ser Thr Leu
545                 550                 555                 560
```

```
<210> SEQ ID NO 98
<211> LENGTH: 560
<212> TYPE: PRT
<213> ORGANISM: Pantoea sp. Cy-639

<400> SEQUENCE: 98

Met Leu Gln Thr Arg Ile Ile Lys Pro Ala Glu Gly Ala Tyr Gln Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Ile Arg Leu Ser Tyr Pro Gln
        35                  40                  45

Leu Val Glu Arg Ile Ala Arg Leu Ala Asn Val Leu Thr Ala Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                85                  90                  95

Thr Ile Asn Val Arg Leu Ser Pro Glu Gln Ile Leu Tyr Thr Met Asn
            100                 105                 110

His Ala Glu Asp Arg Phe Val Leu Val Asn Ser Asp Phe Val Gly Leu
        115                 120                 125

Tyr Gln Ala Ile Ala Gly Gln Leu Ser Thr Val Gln Gly Thr Leu Leu
    130                 135                 140

Leu Thr Asp Gly Ala Glu Lys Thr Ala Glu Leu Pro Gly Leu Ile Gly
145                 150                 155                 160

Glu Tyr Glu Gln Leu Leu Ala Ala Ala Ser Ala His Tyr Asp Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Thr His Arg Gln Leu Val Leu
        195                 200                 205

His Thr Leu Ala Glu Thr Ser Val Leu Gly Ser Leu Asp Ser Val Arg
    210                 215                 220

Leu Leu Ser Ser Asn Asp Val Tyr Met Pro Ile Thr Pro Met Phe His
225                 230                 235                 240

Val His Ala Trp Gly Ile Pro Tyr Ala Ala Thr Met Met Gly Ile Lys
                245                 250                 255

Gln Val Tyr Pro Gly Arg Tyr Glu Pro Asp Met Leu Ile Arg Leu Trp
            260                 265                 270

Arg Glu Glu Lys Val Thr Phe Ser His Cys Val Pro Thr Ile Leu Gln
        275                 280                 285

Met Leu Leu Asn Cys Pro Thr Ala Ala Gly Gln Asp Phe Gly Gly Trp
    290                 295                 300

Lys Ile Ile Ile Gly Gly Ser Ala Leu Asn Arg Ala Leu Tyr Glu Ala
305                 310                 315                 320

Ala Leu Ala Arg Gly Val Gln Leu Thr Ala Ala Tyr Gly Met Ser Glu
                325                 330                 335

Thr Cys Pro Leu Ile Ser Ala Ala His Leu Asn Asp Glu Leu Gln Ala
            340                 345                 350

Gly Ser Glu Asp Glu Arg Ile Ser Tyr Arg Ile Lys Ala Gly Val Pro
        355                 360                 365

Val Pro Leu Val Glu Ala Ala Ile Val Asp Gly Asn Gly Arg Phe Leu
    370                 375                 380
```

-continued

```
Pro Ala Asp Gly Glu Thr Gln Gly Glu Leu Val Leu Arg Ala Pro Trp
385                 390                 395                 400

Leu Thr Met Gly Tyr Phe Asn Glu Pro Glu Lys Ser Glu Glu Leu Trp
            405                 410                 415

Gln Gly Gly Trp Leu His Thr Gly Asp Val Ala Thr Leu Asp Gly Met
        420                 425                 430

Gly Phe Ile Asp Ile Arg Asp Arg Ile Lys Asp Val Ile Lys Thr Gly
    435                 440                 445

Gly Glu Trp Ile Ser Ser Leu Asp Leu Glu Asp Leu Val Ser Arg His
450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Val Arg Glu Gly Gln Ala Ile
            485                 490                 495

Asp Ala Arg Ile Leu Lys Glu His Leu Lys Pro Phe Val Glu Gln Gly
        500                 505                 510

His Ile Asn Lys Trp Ala Ile Pro Ser Gln Ile Ala Ile Val Thr Glu
    515                 520                 525

Ile Pro Lys Thr Ser Val Gly Lys Leu Asp Lys Lys Arg Ile Arg Leu
530                 535                 540

Asp Ile Ser Gln Trp Gln Ala Ser Gly Ser Gly Phe Leu Ser Thr Leu
545                 550                 555                 560
```

<210> SEQ ID NO 99
<211> LENGTH: 560
<212> TYPE: PRT
<213> ORGANISM: Lipotes vexillifer

<400> SEQUENCE: 99

```
Met Leu Gln Thr Arg Leu Leu Lys Pro Ala Asp Asp Ala Tyr Ala Tyr
1               5                   10                  15

Pro Leu Leu Ile Lys Arg Leu Leu Met Ser Ala Ser Arg Tyr Glu Lys
            20                  25                  30

Thr Arg Glu Ile Val Tyr Arg Asp Gln Val Arg Leu Thr Tyr Ala Gln
        35                  40                  45

Leu Asn Gln Arg Ile Ala Gln Leu Ala Asn Val Leu Ser Glu Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val His
            85                  90                  95

Thr Ile Asn Val Arg Leu Ser Pro Asp Gln Ile Leu Tyr Thr Met Asn
            100                 105                 110

His Ala Glu Asp Arg Leu Val Leu Val Asn Ser Asp Phe Ile Glu Leu
        115                 120                 125

Tyr Gln Ser Ile Ala Gly Gln Leu Thr Thr Val Glu Arg Thr Val Leu
    130                 135                 140

Leu Thr Asp Gly Ala Asp Thr Gln Ala Ala Leu Pro Asn Leu Val Gly
145                 150                 155                 160

Glu Tyr Glu Gln Leu Leu Ala Gly Ala Ser Thr Gln Tyr Asp Phe Pro
            165                 170                 175

Asp Phe Asp Glu His Ser Val Ala Thr Thr Phe Tyr Thr Thr Gly Thr
        180                 185                 190

Thr Gly Asn Pro Lys Gly Val Tyr Phe Thr His Arg Gln Leu Val Leu
    195                 200                 205
```

His Thr Leu Ala Glu Ala Ser Val Met Gly Ser Ile Asp Ser Val Arg
          210                 215                 220

Leu Leu Gly Ser Asp Asp Val Tyr Met Pro Ile Thr Pro Met Phe His
225                 230                 235                 240

Val His Ala Trp Gly Ile Pro Tyr Val Ala Thr Met Leu Gly Val Lys
                    245                 250                 255

Gln Val Tyr Pro Gly Arg Tyr Glu Pro Glu Met Leu Leu Lys Leu Trp
            260                 265                 270

Arg Glu Glu Arg Val Thr Phe Ser His Cys Val Pro Thr Ile Leu Gln
        275                 280                 285

Met Leu Leu Asn Cys Pro His Gly Lys Gly Val Asp Phe Gly Gly Trp
    290                 295                 300

Lys Ile Ile Ile Gly Gly Ser Ala Leu Asn Arg Ser Leu Tyr Asp Ala
305                 310                 315                 320

Ala Tyr Ala Arg Gly Ile Gln Leu Thr Ala Ala Tyr Gly Met Ser Glu
                325                 330                 335

Thr Cys Pro Leu Ile Ser Ala Ala His Leu Asn Asp Glu Leu Gln Ala
            340                 345                 350

Gly Thr Glu Asp Glu Arg Ile Ser Tyr Arg Ile Lys Ala Gly Val Pro
        355                 360                 365

Val Pro Leu Val Glu Ala Ile Ile Asp Ala Gln Gly Arg Phe Leu
    370                 375                 380

Pro Ala Asp Gly Glu Ser Gln Gly Glu Leu Val Leu Arg Ala Pro Trp
385                 390                 395                 400

Leu Thr Gln Gly Tyr Phe Lys Glu Pro Glu Lys Ser Gln Ala Leu Trp
                405                 410                 415

Glu Asn Gly Trp Leu His Thr Gly Asp Val Ala Thr Leu Asp Ser Met
            420                 425                 430

Gly Phe Ile Asp Ile Arg Asp Arg Ile Lys Asp Val Ile Lys Thr Gly
        435                 440                 445

Gly Glu Trp Leu Ser Ser Leu Asp Leu Glu Asp Met Ile Ser Ala His
    450                 455                 460

Pro Ala Val Arg Glu Val Ala Val Val Gly Ala Ala Asp Pro Gln Trp
465                 470                 475                 480

Gly Glu Arg Pro Phe Ala Leu Val Val Arg Glu Gly Gln Ala Ile
                485                 490                 495

Asp Ala Lys Ala Leu Lys Glu His Leu Lys Pro Phe Val Glu Gln Gly
            500                 505                 510

Arg Ile Asn Lys Trp Ala Ile Pro Ser Gln Val Ala Leu Val Thr Glu
        515                 520                 525

Ile Pro Lys Thr Ser Val Gly Lys Leu Asp Lys Lys Arg Ile Arg Gln
    530                 535                 540

Asp Ile Ile Glu Trp Gln Ala Gly Asn Ser Ala Phe Leu Ser Thr Leu
545                 550                 555                 560

<210> SEQ ID NO 100
<211> LENGTH: 560
<212> TYPE: PRT
<213> ORGANISM: Serratia sp. 18057

<400> SEQUENCE: 100

Met Leu Gln Thr Arg Ile Ile Pro Pro Ala Glu Gly Ala Tyr Ser Cys
1               5                   10                  15

Pro Leu Leu Ile Lys Arg Leu Leu Leu Ser Gly Thr Arg Tyr Glu Lys

```
                   20                  25                  30
Thr Arg Glu Ile Val Tyr Arg Asp Lys Leu Arg Tyr Thr Tyr Pro Thr
                35                  40                  45
Leu Ile Glu Arg Val Ala Arg Leu Ala Asn Val Leu Thr Asp Ala Gly
 50                  55                  60
Val Lys Ala Gly Asp Thr Val Ala Val Met Asp Trp Asp Ser His Arg
 65                  70                  75                  80
Tyr Leu Glu Cys Met Phe Ala Ile Pro Met Ile Gly Ala Val Ile His
                 85                  90                  95
Thr Ile Asn Val Arg Leu Ser Pro Glu Gln Ile Leu Tyr Thr Met Asn
                100                 105                 110
His Ala Glu Asp Arg Phe Val Leu Val Asn Ser Glu Phe Val Gly Leu
            115                 120                 125
Tyr Gln Ala Ile Ala Gly Gln Leu Thr Thr Val Asp Lys Thr Leu Leu
            130                 135                 140
Leu Thr Asp Gly Glu Ser Lys Thr Ala Glu Leu Pro Asn Leu Val Gly
145                 150                 155                 160
Glu Tyr Glu Thr Leu Leu Ala Ala Ala Ser Ala Gln Tyr Asp Phe Gln
                165                 170                 175
Asp Phe Asp Glu His Ser Val Ala Thr Thr Phe Tyr Thr Thr Gly Thr
            180                 185                 190
Thr Gly Asn Pro Lys Gly Val Tyr Phe Thr His Arg Gln Leu Val Leu
            195                 200                 205
His Thr Met Gly Val Ala Thr Ile Met Gly Ser Val Asp Ser Val Arg
            210                 215                 220
Leu Leu Gly Thr Asn Asp Val Tyr Met Pro Ile Thr Pro Met Phe His
225                 230                 235                 240
Val His Ala Trp Gly Leu Pro Tyr Val Ala Thr Met Leu Gly Leu Lys
                245                 250                 255
Gln Val Tyr Pro Gly Arg Tyr Asp Pro Glu Tyr Leu Val Glu Leu Trp
                260                 265                 270
Arg Lys Glu Lys Val Thr Phe Ser His Cys Val Pro Thr Ile Leu Gln
                275                 280                 285
Met Val Leu Asn Ala Lys Ala Ala Gln Asn Val Asp Phe Gly Gly Trp
            290                 295                 300
Lys Ile Val Ile Gly Gly Ser Ala Leu Asn Arg Thr Leu Tyr Glu Ala
305                 310                 315                 320
Ser Lys Ala Arg Gly Ile Gln Leu Thr Ala Ala Tyr Gly Met Ser Glu
                325                 330                 335
Thr Gly Pro Leu Val Ser Cys Ala His Leu Asn Glu Glu Leu Met Ala
            340                 345                 350
Gly Thr Glu Asp Glu Arg Thr Thr Tyr Arg Ile Lys Ala Gly Val Pro
            355                 360                 365
Gly Pro Leu Val Glu Ala Ala Ile Ile Asp Ser Asp Gly Asn Phe Leu
            370                 375                 380
Pro Ala Asp Gly Glu Ser Gln Gly Glu Leu Val Leu Arg Ala Pro Trp
385                 390                 395                 400
Leu Thr Glu Gly Tyr Tyr Asn Glu Pro Gln Lys Gly Ala Glu Leu Trp
                405                 410                 415
Ala Gly Gly Trp Met His Thr Gly Asp Val Ala Thr Leu Asp Ala Phe
            420                 425                 430
Gly Val Ile Asp Ile Arg Asp Arg Ile Lys Asp Val Ile Lys Thr Gly
            435                 440                 445
```

```
Gly Glu Trp Val Ser Ser Leu Ala Leu Glu Asp Leu Val Ser Arg His
            450                 455                 460

Pro Ala Val Arg Glu Val Ala Val Val Gly Ile Ala Asp Pro Gln Trp
465                 470                 475                 480

Gly Glu Arg Pro Phe Ala Leu Leu Val Val Arg Asp Gly His Met Ile
                485                 490                 495

Gly Ala Arg Glu Leu Lys Glu His Leu Lys Pro Phe Val Glu Leu Gly
            500                 505                 510

His Leu Ser Lys Trp Ala Ile Pro Ser Gln Ile Ala Val Val Thr Glu
            515                 520                 525

Ile Pro Lys Thr Ser Val Gly Lys Leu Asp Lys Lys Arg Ile Arg Ile
            530                 535                 540

Asp Ile Ile Glu Trp Gln Ala Asn Asn Ser Thr Phe Leu Ser Thr Leu
545                 550                 555                 560

<210> SEQ ID NO 101
<211> LENGTH: 560
<212> TYPE: PRT
<213> ORGANISM: Enterobacter cloacae

<400> SEQUENCE: 101

Met Leu Lys Thr Arg Leu Ile Pro Ala Ala Gly Ala Tyr Gln Tyr
1               5                   10                  15

Pro Leu Leu Ile Lys Ser Leu Met Leu Ser Gly Arg Arg Tyr Glu Lys
                20                  25                  30

Ser His Glu Ile Val Tyr Arg Asp Gln Leu Arg Tyr Ser Tyr Ala Thr
            35                  40                  45

Phe Asn Glu Arg Val Ala Arg Leu Ala Asn Val Leu Ser Glu Ala Gly
        50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Leu His
                85                  90                  95

Thr Ile Asn Ile Arg Leu Ser Pro Glu Gln Ile Leu Tyr Thr Met Asn
            100                 105                 110

His Ala Glu Asp Arg Phe Val Leu Val Asn Ser Glu Phe Val Pro Leu
        115                 120                 125

Tyr Gln Ala Val Ala Gly Gln Leu Ala Thr Val Glu Arg Thr Ile Leu
130                 135                 140

Leu Thr Asp Gly Ala Glu Lys Ser Ala Glu Leu Pro Gly Leu Val Gly
145                 150                 155                 160

Glu Tyr Glu Ser Leu Leu Ala Ala Ala Ser Pro Arg Tyr Asp Phe Pro
                165                 170                 175

Asp Phe Asp Glu Asn Ser Ile Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Leu Ala Met Ala Ser Thr Ile Gly Ser Leu Asp Ser Ile Arg
210                 215                 220

Leu Leu Gly Thr Ser Asp Val Tyr Met Pro Ile Thr Pro Met Phe His
225                 230                 235                 240

Val His Ala Trp Gly Thr Pro Tyr Val Ala Thr Met Leu Gly Val Lys
                245                 250                 255

Gln Val Tyr Pro Gly Arg Tyr Asp Pro Glu Leu Leu Val Glu Leu Trp
```

260                 265                 270
Lys Arg Glu Lys Val Thr Phe Ser His Cys Val Pro Thr Ile Leu Gln
                275                 280                 285

Met Val Met Asn Ala Arg Ala Ala Gln Gly Val Asp Phe Lys Gly Trp
        290                 295                 300

Lys Val Ile Ile Gly Gly Ser Ala Leu Asn Arg Ser Leu Tyr Glu Ala
305                 310                 315                 320

Ala Lys Ala Arg Gly Ile Gln Leu Thr Ala Ala Tyr Gly Met Ser Glu
                325                 330                 335

Thr Cys Pro Leu Ile Ser Cys Ala Tyr Leu Asn Asp Glu Leu Leu Ala
                340                 345                 350

Gly Ser Glu Asp Glu Arg Thr Thr Tyr Arg Ile Lys Ala Gly Val Pro
            355                 360                 365

Val Pro Leu Val Asp Ala Ala Ile Met Asp Glu Gln Gly Arg Phe Leu
        370                 375                 380

Pro Ala Asp Gly Glu Ser Gln Gly Glu Leu Val Leu Arg Ser Pro Trp
385                 390                 395                 400

Leu Thr Gln Gly Tyr Phe Arg Glu Pro Glu Arg Gly Glu Glu Leu Trp
                405                 410                 415

Arg Gly Gly Trp Met His Thr Gly Asp Val Ala Thr Leu Asp Gly Met
            420                 425                 430

Gly Phe Ile Glu Ile Arg Asp Arg Ile Lys Asp Val Ile Lys Thr Gly
        435                 440                 445

Gly Glu Trp Leu Ser Ser Leu Glu Leu Glu Asp Leu Ile Ser Arg His
    450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Val Arg Glu Gly Gln Gln Leu
                485                 490                 495

Asp Ala Arg Gly Leu Lys Glu His Leu Lys Pro Phe Val Glu Gln Gly
            500                 505                 510

Asn Ile Asn Lys Trp Ala Ile Pro Ser Gln Ile Ala Val Val Thr Asp
        515                 520                 525

Ile Pro Lys Thr Ser Val Gly Lys Leu Asp Lys Lys Arg Ile Arg Ile
530                 535                 540

Glu Ile Ala Gln Trp Gln Glu Ala Gly Ser Ala Phe Leu Ser Thr Val
545                 550                 555                 560

<210> SEQ ID NO 102
<211> LENGTH: 560
<212> TYPE: PRT
<213> ORGANISM: Acinetobacter baumannii

<400> SEQUENCE: 102

Met Leu Lys Thr Arg Leu Ile Pro Ala Ala Gly Ala Tyr Gln Tyr
1               5                   10                  15

Pro Leu Leu Ile Lys Ser Leu Met Leu Ser Gly Arg Arg Tyr Glu Lys
                20                  25                  30

Ser His Glu Ile Val Tyr Arg Asp Gln Val Arg Tyr Ser Tyr Ala Thr
            35                  40                  45

Phe Asn Glu Arg Val Ala Arg Leu Ala Asn Val Leu Ser Glu Ala Gly
        50                  55                  60

Val Lys Ala Gly Asp Thr Val Ala Val Met Asp Trp Asp Ser His Arg
65                  70                  75                  80

-continued

```
Tyr Leu Glu Cys Met Phe Ala Ile Pro Met Ile Gly Ala Val Leu His
                85                  90                  95
Thr Ile Asn Ile Arg Leu Ser Pro Glu Gln Ile Leu Tyr Thr Met Asn
           100                 105                 110
His Ala Glu Asp Arg Phe Val Leu Val Asn Ser Glu Phe Val Pro Leu
       115                 120                 125
Tyr Gln Ala Val Ala Gly Gln Leu Ala Thr Val Glu Arg Thr Ile Leu
   130                 135                 140
Leu Thr Asp Gly Ala Glu Lys Ser Ala Glu Leu Pro Gly Leu Val Gly
145                 150                 155                 160
Glu Tyr Glu Ser Leu Leu Ala Ala Ser Pro Arg Tyr Asp Phe Pro
               165                 170                 175
Asp Phe Asp Glu Asn Ser Ile Ala Thr Thr Phe Tyr Thr Thr Gly Thr
           180                 185                 190
Thr Gly Asn Pro Lys Gly Val Tyr Phe Ser His Arg Gln Leu Val Leu
       195                 200                 205
His Thr Leu Ala Met Ala Ser Thr Ile Gly Ser Leu Asp Ser Ile Arg
   210                 215                 220
Leu Leu Gly Thr Ser Asp Val Tyr Met Pro Ile Thr Pro Met Phe His
225                 230                 235                 240
Val His Ala Trp Gly Thr Pro Tyr Val Ala Thr Met Leu Gly Val Lys
               245                 250                 255
Gln Val Tyr Pro Gly Arg Tyr Asp Pro Glu Leu Leu Val Glu Leu Trp
           260                 265                 270
Lys Arg Glu Lys Val Thr Phe Ser His Cys Val Pro Thr Ile Leu Gln
       275                 280                 285
Met Val Met Asn Ala Arg Ala Ala Gln Gly Val Asp Phe Lys Gly Trp
   290                 295                 300
Lys Val Ile Ile Gly Gly Ser Ala Leu Asn Arg Ser Leu Tyr Glu Ala
305                 310                 315                 320
Ala Lys Ala Arg Gly Ile Gln Leu Thr Ala Ala Tyr Gly Met Ser Glu
               325                 330                 335
Thr Cys Pro Leu Ile Ser Cys Ala Tyr Leu Asn Asp Glu Leu Leu Ala
           340                 345                 350
Gly Ser Glu Asp Glu Arg Thr Thr Tyr Arg Ile Lys Ala Gly Val Pro
       355                 360                 365
Val Pro Leu Val Asp Ala Ala Ile Met Asp Glu Gln Gly Arg Phe Leu
   370                 375                 380
Pro Ala Asp Gly Glu Ser Gln Gly Glu Leu Val Leu Arg Ser Pro Trp
385                 390                 395                 400
Leu Thr Gln Gly Tyr Phe Arg Glu Pro Glu Arg Gly Glu Glu Leu Trp
               405                 410                 415
Arg Gly Gly Trp Met His Thr Gly Asp Val Ala Thr Leu Asp Gly Met
           420                 425                 430
Gly Phe Ile Glu Ile Arg Asp Arg Ile Lys Asp Val Ile Lys Thr Gly
       435                 440                 445
Gly Glu Trp Leu Ser Ser Leu Glu Leu Glu Asp Leu Ile Ser Arg His
   450                 455                 460
Pro Ala Val Arg Glu Val Ala Val Val Gly Val Pro Asp Pro Gln Trp
465                 470                 475                 480
Gly Glu Arg Pro Phe Ala Leu Leu Val Val Arg Glu Gly Gln Gln Leu
               485                 490                 495
Asp Ala Arg Gly Leu Lys Glu His Leu Lys Pro Phe Val Glu Gln Gly
```

```
                    500                 505                 510
Asn Ile Asn Lys Trp Ala Ile Pro Ser Gln Ile Ala Val Val Thr Asp
            515                 520                 525

Ile Pro Lys Thr Ser Val Gly Lys Leu Asp Lys Arg Ile Arg Ile
        530                 535                 540

Glu Ile Ala Gln Trp Gln Glu Ala Gly Ser Ala Phe Leu Ser Thr Val
545                 550                 555                 560

<210> SEQ ID NO 103
<211> LENGTH: 560
<212> TYPE: PRT
<213> ORGANISM: Streptococcus dysgalactiae

<400> SEQUENCE: 103

Met Leu Lys Thr Arg Leu Ile Pro Ala Ala Gly Ala Tyr Gln Tyr
1               5                   10                  15

Pro Leu Leu Ile Lys Ser Leu Met Leu Ser Gly Ser Arg Tyr Glu Lys
                20                  25                  30

Ser His Glu Ile Val Tyr Arg Asp Gln Val Arg Tyr Ser Tyr Ala Thr
            35                  40                  45

Phe Asn Glu Arg Val Ala Arg Leu Ala Asn Val Leu Ser Glu Ala Gly
50                  55                  60

Val Arg Ala Gly Asp Thr Val Ala Val Met Asp Trp Asp Ser His Arg
65                  70                  75                  80

Tyr Leu Glu Cys Met Phe Ala Ile Pro Met Ile Gly Ala Val Leu His
                85                  90                  95

Thr Ile Asn Ile Arg Leu Ser Pro Glu Gln Ile Leu Tyr Thr Met Asn
                100                 105                 110

His Ala Glu Asp Arg Phe Val Leu Val Asn Ser Glu Phe Val Pro Leu
            115                 120                 125

Tyr Gln Ala Val Ala Gly Gln Leu Ala Thr Val Glu Arg Thr Ile Leu
130                 135                 140

Leu Ser Asp Gly Ala Glu Lys Ser Ala Glu Leu Pro Gly Leu Val Gly
145                 150                 155                 160

Glu Tyr Glu Ser Leu Leu Ala Ala Ala Ser Pro Arg Tyr Asp Phe Pro
                165                 170                 175

Asp Phe Asp Glu Asn Ser Ile Ala Thr Thr Phe Tyr Thr Thr Gly Thr
            180                 185                 190

Thr Gly Asn Pro Lys Gly Val Tyr Phe Ser His Arg Gln Leu Val Leu
                195                 200                 205

His Thr Leu Ala Met Ala Ser Thr Ile Gly Ser Leu Asp Ser Ile Arg
            210                 215                 220

Leu Leu Gly Thr Ser Asp Val Tyr Met Pro Ile Thr Pro Met Phe His
225                 230                 235                 240

Val His Ala Trp Gly Thr Pro Tyr Val Ala Thr Met Leu Gly Val Lys
                245                 250                 255

Gln Val Tyr Pro Gly Arg Tyr Asp Pro Glu Leu Leu Val Glu Leu Trp
            260                 265                 270

Lys Arg Glu Lys Val Thr Phe Ser His Cys Val Pro Thr Ile Leu Gln
        275                 280                 285

Met Val Met Asn Ala Arg Ala Ala Gln Gly Val Asp Phe Arg Gly Trp
290                 295                 300

Lys Val Ile Ile Gly Gly Ser Ala Leu Asn Arg Ser Leu Tyr Glu Ala
305                 310                 315                 320
```

```
Ala Lys Ala Arg Gly Ile Gln Leu Thr Ala Ala Tyr Gly Met Ser Glu
            325                 330                 335

Thr Cys Pro Leu Ile Ser Cys Ala Tyr Leu Asn Asp Glu Leu Leu Ala
            340                 345                 350

Gly Ser Glu Asp Glu Arg Thr Thr Tyr Arg Ile Lys Ala Gly Val Pro
            355                 360                 365

Val Pro Leu Val Asp Ala Ala Ile Met Asp Glu Gln Gly Arg Phe Leu
370                 375                 380

Pro Ala Asp Gly Glu Ser Gln Gly Glu Leu Val Leu Arg Ser Pro Trp
385                 390                 395                 400

Leu Thr Gln Gly Tyr Phe Arg Glu Pro Glu Arg Gly Glu Glu Leu Trp
            405                 410                 415

Arg Gly Gly Trp Met His Thr Gly Asp Val Ala Thr Leu Asp Gly Met
            420                 425                 430

Gly Phe Ile Glu Ile Arg Asp Arg Ile Lys Asp Val Ile Lys Thr Gly
            435                 440                 445

Gly Glu Trp Leu Ser Ser Leu Glu Leu Glu Asp Leu Ile Ser Arg His
            450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Val Arg Glu Gly Gln Glu Leu
            485                 490                 495

Asp Ala Arg Gly Leu Lys Glu His Leu Lys Pro Phe Val Glu Gln Gly
            500                 505                 510

Asn Ile Asn Lys Trp Ala Ile Pro Ser Gln Ile Ala Ile Val Thr Asp
            515                 520                 525

Ile Pro Lys Thr Ser Val Gly Lys Leu Asp Lys Lys Arg Ile Arg Ile
530                 535                 540

Glu Ile Ala Gln Trp Gln Ala Gly Ser Ala Phe Leu Ser Thr Val
545                 550                 555                 560

<210> SEQ ID NO 104
<211> LENGTH: 558
<212> TYPE: PRT
<213> ORGANISM: Paucimonas lemoignei

<400> SEQUENCE: 104

Met Leu Gln Thr Arg Val Ile Ala Pro Asp Gly Ala Tyr Gln Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Ile Met Arg Tyr Thr Tyr Pro Glu
        35                  40                  45

Leu Val Glu Arg Val Ser Arg Leu Ala Asn Val Leu Thr Ala Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Val Pro Met Ile Gly Ala Val Ile His
                85                  90                  95

Thr Val Asn Val Arg Leu Ser Pro Glu Gln Ile Val Tyr Thr Met Asn
            100                 105                 110

His Ala Glu Asp Lys Phe Val Leu Val Asn Ser Glu Phe Val Gly Leu
        115                 120                 125

Tyr His Gly Ile Ala Gly His Leu Thr Thr Val Glu Lys Thr Leu Leu
    130                 135                 140
```

```
Leu Thr Asp Leu Pro Glu Lys Thr Ala Asp Leu Pro Asn Leu Val Gly
145                 150                 155                 160

Glu Tyr Glu Ser Leu Leu Ala Asp Ala Ser Pro Thr Tyr Glu Phe Glu
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Met Gly Val Ala Thr Ile Val Gly Ser Ala Glu Arg Leu Leu
    210                 215                 220

Gly Thr Asp Asp Val Tyr Met Pro Ile Thr Pro Met Phe His Val His
225                 230                 235                 240

Ala Trp Gly Met Pro Tyr Ala Ala Thr Met Leu Gly Ile Lys Gln Val
                245                 250                 255

Tyr Pro Gly Arg Tyr Asp Pro Glu Met Leu Val Ala Leu Trp Arg Asn
            260                 265                 270

Glu Lys Val Thr Phe Ser His Cys Val Pro Thr Ile Met Gln Met Val
            275                 280                 285

Leu Asn Cys Lys Ser Ala Gln Asp Met Asp Phe Ser Gly Trp Lys Ile
290                 295                 300

Ile Ile Gly Gly Ser Ser Leu Thr Arg Ser Leu Tyr Glu Ala Ala Lys
305                 310                 315                 320

Ala Arg Gly Ile Ala Leu Thr Gly Ala Tyr Gly Met Ser Glu Thr Gly
                325                 330                 335

Pro Leu Ile Ser Val Ala His Ile Asn Asp Gln Leu Arg Ala Gly Ser
            340                 345                 350

Glu Asp Glu Arg Val Thr Tyr Arg Ile Lys Ala Gly Val Pro Gly Ile
            355                 360                 365

Leu Val Asp Ala Ala Ile Val Asp Glu Asp Gly Asn Phe Leu Pro Ala
370                 375                 380

Asp Gly Glu Ser Met Gly Glu Leu Val Leu Arg Ala Pro Trp Leu Ser
385                 390                 395                 400

Glu Gly Tyr Phe Arg Glu Pro Gln Lys Gly Ala Glu Leu Trp Ala Gly
                405                 410                 415

Gly Trp Leu His Thr Gly Asp Val Ala Thr Leu Asp Ser Met Gly Val
            420                 425                 430

Ile Asp Ile Arg Asp Arg Ile Lys Asp Val Ile Lys Thr Gly Gly Glu
            435                 440                 445

Trp Ile Ser Ser Leu Ala Leu Glu Asp Leu Cys Ser Arg His Pro Gly
            450                 455                 460

Val Arg Glu Val Ala Val Val Gly Ile Ala Asp Pro Gln Trp Gly Glu
465                 470                 475                 480

Arg Pro Phe Ala Leu Leu Val Ala Arg Asp Gly His Ser Ile Asp Ala
                485                 490                 495

Lys Ser Leu Lys Glu His Leu Lys Pro Phe Val Glu Leu Gly His Ile
            500                 505                 510

Asn Lys Trp Ala Ile Pro His Gln Ile Ala Leu Val Thr Glu Ile Pro
            515                 520                 525

Lys Thr Ser Val Gly Lys Leu Asp Lys Lys Arg Met Arg Leu Asp Ile
            530                 535                 540

Val Glu Trp Gln Ser Thr Asn Ser Ala Phe Leu Ser Thr Leu
545                 550                 555
```

<210> SEQ ID NO 105
<211> LENGTH: 560
<212> TYPE: PRT
<213> ORGANISM: Streptococcus pneumoniae

<400> SEQUENCE: 105

```
Met Leu Gln Thr Arg Val Ile Lys Pro Ala Ala Asn Ala Tyr Gln Tyr
1               5                   10                  15

Pro Leu Leu Ile Lys Arg Leu Leu Ser Gly Val Arg Tyr Glu Arg
            20                  25                  30

Ser Arg Glu Ile Val Tyr Arg Asp Gln Leu Arg Tyr Asp Tyr Arg Thr
            35                  40                  45

Leu Asn Glu Arg Val Ala Arg Leu Ala Asn Val Leu Thr Ala Ala Gly
50                  55                  60

Val Lys Pro Gly Asp Thr Val Ala Val Met Asp Trp Asp Ser His Arg
65                  70                  75                  80

Tyr Leu Glu Cys Met Phe Ala Ile Pro Met Ile Gly Ala Val Val His
                85                  90                  95

Thr Ile Asn Val Arg Leu Ser Pro Asp Gln Ile Leu Tyr Thr Ile Asn
            100                 105                 110

His Ala Asp Asp Arg Phe Val Leu Val Asn Ser Glu Phe Val Pro Leu
        115                 120                 125

Tyr Gln Ala Ile Ala Gly Gln Leu Thr Thr Val Gln Lys Thr Leu Leu
130                 135                 140

Leu Thr Asp Gly Glu Ala Arg Asp Ala Gly Leu Pro Asp Cys Val Gly
145                 150                 155                 160

Glu Tyr Glu Ser Leu Leu Ala Asp Ala Ala Pro Ser Tyr Asp Phe Pro
                165                 170                 175

Asp Phe Asp Glu Asp Ser Val Ala Thr Thr Phe Tyr Thr Thr Gly Thr
            180                 185                 190

Thr Gly Asn Pro Lys Gly Val Tyr Phe Thr His Arg Gln Leu Val Leu
        195                 200                 205

His Thr Leu Ala Ala Val Thr Val Gly Cys Arg Glu Asn Pro Arg
210                 215                 220

Leu Met Gly Ser Val Asp Val Tyr Met Pro Ile Thr Pro Met Phe His
225                 230                 235                 240

Val His Ala Trp Gly Leu Pro Tyr Val Ala Thr Met Leu Gly Leu Lys
                245                 250                 255

Gln Val Tyr Pro Gly Arg Tyr Asp Pro Glu Tyr Leu Ile Asp Leu Trp
            260                 265                 270

Arg Arg Glu Gln Val Thr Phe Ser His Cys Val Pro Thr Ile Val Gln
        275                 280                 285

Met Leu Leu Asn Ala Lys Ala Gln Gly Thr Asp Phe Lys Gly Trp
290                 295                 300

Lys Ile Thr Ile Gly Gly Ser Ala Leu Thr Arg Gly Leu Tyr Asp Gln
305                 310                 315                 320

Ala Lys Ala Ser Gly Met Asn Leu Ile Ala Tyr Gly Met Ser Glu
                325                 330                 335

Thr Cys Pro Leu Ile Ser Gly Ala His Ile Asn Asp Glu Leu Leu Glu
            340                 345                 350

Ala Asp Glu Asp Thr Arg Ser Thr Phe His Leu Arg Ala Gly Val Pro
        355                 360                 365

Val Val Leu Val Asp Ala Ala Ile Gln Ala Ala Asp Gly Ser Phe Leu
370                 375                 380
```

```
Pro Ala Asp Gly Ala Ser Gln Gly Glu Leu Val Leu Arg Ala Pro Trp
385                 390                 395                 400

Leu Thr Gln Gly Tyr Tyr Asn Glu Pro Glu Lys Ser Glu Glu Leu Trp
            405                 410                 415

Ala Gly Gly Trp Leu His Thr Gly Asp Val Ala Val Ile Asp Glu Met
        420                 425                 430

Ala Asn Ile Glu Ile Arg Asp Arg Ile Lys Asp Val Ile Lys Thr Gly
            435                 440                 445

Gly Glu Trp Leu Ser Ser Leu Thr Leu Glu Gly Leu Ile Ser Arg His
450                 455                 460

Glu Ala Val Arg Asp Val Ala Val Val Gly Val Pro Asp Glu Arg Trp
465                 470                 475                 480

Gly Glu Arg Pro Phe Ala Leu Val Val Leu Gly Glu Gly Gln Glu Leu
            485                 490                 495

Asn Ala Glu Gln Leu Arg Asn Phe Leu Glu Pro Ala Val Ala Glu Gly
            500                 505                 510

His Ile Asn Lys Trp Ala Ile Pro Gln Gln Ile Ala Val Val Thr Glu
            515                 520                 525

Ile Pro Lys Thr Ser Val Gly Lys Leu Asp Lys Lys Arg Ile Arg Ser
530                 535                 540

Glu Leu Ala Arg Trp Gln Thr Glu Gly Val Ala Gln Ala Ser Arg
545                 550                 555                 560

<210> SEQ ID NO 106
<211> LENGTH: 569
<212> TYPE: PRT
<213> ORGANISM: Stenotrophomonas maltophilia

<400> SEQUENCE: 106

Met Leu Lys Thr Arg Leu Ile Thr Ser Ala Gln Asn Ala Pro Ala Tyr
1               5                   10                  15

Pro Leu Leu Ile Lys Ser Leu Leu Leu Ser Gly Ala Arg Tyr Glu Lys
            20                  25                  30

Gly Arg Glu Ile Val Tyr Arg Asp Gln Val Arg Tyr Ser Tyr Ala Thr
        35                  40                  45

Phe Asn Glu Arg Val Ala Arg Leu Ala Asn Ala Leu Thr Ala Ala Gly
    50                  55                  60

Val Arg Ala Gly Asp Thr Val Ala Val Met Asp Trp Asp Ser His Arg
65                  70                  75                  80

Tyr Leu Glu Cys Met Phe Ala Ile Pro Met Leu Gly Ala Val Leu His
            85                  90                  95

Thr Ile Asn Ile Arg Leu Ser Pro Glu Gln Ile Leu Tyr Thr Met Asn
            100                 105                 110

His Ala Glu Asp Arg Phe Val Leu Val Asn Ala Glu Phe Ala Gly Leu
        115                 120                 125

Tyr Gln Ser Val Ala Gly Gln Leu Thr Thr Val Glu Lys Thr Leu Leu
    130                 135                 140

Ile Ser Asp Thr Pro Glu Gln Ser Val Glu Leu Pro Ala Cys Val Gly
145                 150                 155                 160

Glu Tyr Glu Gln Leu Leu Ala Ala Ala Ser Pro Arg Tyr Asp Phe Glu
            165                 170                 175

Asp Phe Asp Glu Asn Ser Ile Ala Thr Thr Phe Tyr Thr Thr Gly Thr
            180                 185                 190

Thr Gly Asn Pro Lys Gly Val Tyr Phe Ser His Arg Gln Leu Val Leu
```

|   |   |   | 195 |   |   |   |   | 200 |   |   |   |   | 205 |   |   |
|---|---|---|---|---|---|---|---|---|---|---|---|---|---|---|---|

His Thr Leu Ala Met Ala Ala Thr Ile Gly Ser Leu Asp Ser Ile Arg
210                 215                 220

Leu Leu Gly Asn Ala Asp Val Tyr Met Pro Ile Thr Pro Met Phe His
225                 230                 235                 240

Val His Ala Trp Gly Thr Pro Tyr Val Ala Thr Met Leu Gly Ile Lys
            245                 250                 255

Gln Val Tyr Pro Gly Arg Tyr Asp Pro Glu Leu Leu Val Gln Leu Trp
        260                 265                 270

Gln Arg Glu Lys Val Thr Phe Ser His Cys Val Pro Thr Ile Leu Gln
    275                 280                 285

Met Ile Met Asn Ala Lys Ala Ala Gln Gly Val Asp Phe Asn Gly Trp
290                 295                 300

Lys Val Ile Ile Gly Gly Ser Ala Leu Asn Arg Ser Leu Tyr Glu Ala
305                 310                 315                 320

Ala Lys Ala Arg Gly Met Gln Leu Thr Ala Ala Tyr Gly Met Ser Glu
            325                 330                 335

Thr Cys Pro Leu Ile Ser Cys Ala Tyr Leu Asn Asp Asp Leu Leu Ala
        340                 345                 350

Gly Ser Glu Asp Glu Arg Thr Thr Tyr Arg Ile Lys Ala Gly Val Pro
    355                 360                 365

Val Pro Leu Val Asp Ala Ala Ile Met Asp Glu Glu Gly Arg Leu Leu
370                 375                 380

Pro Ala Asp Gly Glu Ser Gln Gly Glu Leu Val Leu Arg Ala Pro Trp
385                 390                 395                 400

Leu Thr Arg Gly Tyr Phe Arg Glu Pro Glu Lys Gly Glu Glu Leu Trp
            405                 410                 415

Ala Gly Gly Trp Met His Thr Gly Asp Val Ala Thr Ile Asp Gly Met
        420                 425                 430

Gly Phe Ile Asp Ile Arg Asp Arg Ile Lys Asp Val Ile Lys Thr Gly
    435                 440                 445

Gly Glu Trp Leu Ser Ser Leu Glu Leu Glu Asp Leu Ile Ser Arg His
450                 455                 460

Pro Ala Val Arg Glu Val Ala Val Val Gly Val Pro Asp Pro Gln Trp
465                 470                 475                 480

Gly Glu Arg Pro Phe Ala Leu Leu Val Leu Arg Asp Gly Gln Ala Leu
            485                 490                 495

Asp Ala Arg Ala Glu Gly Ala Pro Gln Ala Val Arg Gly Ala Gly Gln
        500                 505                 510

Tyr Gln Gln Val Gly Asp Ser Leu Ala Asp Arg Arg Cys Gln Arg Gly
    515                 520                 525

Ala Glu Asp Gln Arg Arg Gln Ala Arg Gln Glu Thr His Pro Pro Gly
530                 535                 540

His Arg Arg Leu Ala Glu Glu Arg Lys Arg Val Pro Val His Arg Leu
545                 550                 555                 560

Thr Pro Arg Asp Asn Glu Arg Leu Ser
            565

<210> SEQ ID NO 107
<211> LENGTH: 411
<212> TYPE: PRT
<213> ORGANISM: Cuphea palustris

<400> SEQUENCE: 107

```
Met Val Ala Ala Ala Ser Ser Ala Cys Phe Pro Val Pro Ser Pro
1               5                   10                  15

Gly Ala Ser Pro Lys Pro Gly Lys Leu Gly Asn Trp Ser Ser Leu
            20                  25                  30

Ser Pro Ser Leu Lys Pro Lys Ser Ile Pro Asn Gly Gly Phe Gln Val
            35                  40                  45

Lys Ala Asn Ala Ser Ala His Pro Lys Ala Asn Gly Ser Ala Val Thr
50                  55                  60

Leu Lys Ser Gly Ser Leu Asn Thr Gln Glu Asp Thr Leu Ser Ser Ser
65                  70                  75                  80

Pro Pro Pro Arg Ala Phe Phe Asn Gln Leu Pro Asp Trp Ser Met Leu
                85                  90                  95

Leu Thr Ala Ile Thr Thr Val Phe Val Ala Pro Glu Lys Arg Trp Thr
                100                 105                 110

Met Phe Asp Arg Lys Ser Lys Arg Pro Asn Met Leu Met Asp Ser Phe
                115                 120                 125

Gly Leu Glu Arg Val Val Gln Asp Gly Leu Val Phe Arg Gln Ser Phe
            130                 135                 140

Ser Ile Arg Ser Tyr Glu Ile Cys Ala Asp Arg Thr Ala Ser Ile Glu
145                 150                 155                 160

Thr Val Met Asn His Val Gln Glu Thr Ser Leu Asn Gln Cys Lys Ser
                165                 170                 175

Ile Gly Leu Leu Asp Asp Gly Phe Gly Arg Ser Pro Glu Met Cys Lys
                180                 185                 190

Arg Asp Leu Ile Trp Val Val Thr Arg Met Lys Ile Met Val Asn Arg
            195                 200                 205

Tyr Pro Thr Trp Gly Asp Thr Ile Glu Val Ser Thr Trp Leu Ser Gln
            210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Val Tyr Ala Met Met Asn
                245                 250                 255

Gln Lys Thr Arg Arg Phe Ser Lys Leu Pro His Glu Val Arg Gln Glu
            260                 265                 270

Phe Ala Pro His Phe Leu Asp Ser Pro Ala Ile Glu Asp Asn Asp
            275                 280                 285

Gly Lys Leu Gln Lys Phe Asp Val Lys Thr Gly Asp Ser Ile Arg Lys
            290                 295                 300

Gly Leu Thr Pro Gly Trp Tyr Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
                340                 345                 350

Cys Gly Arg Asp Ser Val Leu Glu Ser Val Thr Ser Met Asp Pro Ser
            355                 360                 365

Lys Val Gly Asp Arg Phe Gln Tyr Arg His Leu Leu Arg Leu Glu Asp
            370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr
                405                 410
```

```
<210> SEQ ID NO 108
<211> LENGTH: 378
<212> TYPE: PRT
<213> ORGANISM: Ulmus americana
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (374)..(374)
<223> OTHER INFORMATION: Xaa can be any naturally occurring amino acid

<400> SEQUENCE: 108
```

Gly Ser Gly Ala Leu Gln Val Lys Ala Ser Ser Gln Ala Pro Pro Lys
1               5                   10                  15

Leu Asn Gly Ser Asn Val Gly Leu Val Lys Ser Ser Gln Ile Val Lys
            20                  25                  30

Lys Gly Asp Asp Thr Thr Ser Pro Pro Ala Arg Thr Phe Ile Asn Gln
        35                  40                  45

Leu Pro Asp Trp Ser Met Leu Leu Ala Ala Ile Thr Thr Leu Phe Leu
    50                  55                  60

Ala Ala Glu Lys Gln Trp Met Met Leu Asp Trp Lys Pro Lys Arg Pro
65                  70                  75                  80

Asp Met Leu Val Asp Pro Phe Gly Leu Gly Arg Phe Val Gln Asp Gly
                85                  90                  95

Leu Val Phe Arg Asn Asn Phe Ser Ile Arg Ser Tyr Glu Ile Gly Ala
            100                 105                 110

Asp Arg Thr Ala Ser Ile Glu Thr Leu Met Asn His Leu Gln Glu Thr
        115                 120                 125

Ala Leu Asn His Val Lys Ser Val Gly Leu Leu Glu Asp Gly Leu Gly
    130                 135                 140

Ser Thr Arg Glu Met Ser Leu Arg Asn Leu Ile Trp Val Val Thr Lys
145                 150                 155                 160

Met Gln Val Ala Val Asp Arg Tyr Pro Thr Trp Gly Asp Glu Val Gln
                165                 170                 175

Val Ser Ser Trp Ala Thr Ala Ile Gly Lys Asn Gly Met Arg Arg Glu
            180                 185                 190

Trp Ile Val Thr Asp Phe Arg Thr Gly Glu Thr Leu Leu Arg Ala Thr
        195                 200                 205

Ser Val Trp Val Met Met Asn Lys Leu Thr Arg Arg Ile Ser Lys Ile
    210                 215                 220

Pro Glu Glu Val Trp His Glu Ile Gly Pro Ser Phe Ile Asp Ala Pro
225                 230                 235                 240

Pro Leu Pro Thr Val Glu Asp Asp Gly Arg Lys Leu Thr Arg Phe Asp
                245                 250                 255

Glu Ser Ser Ala Asp Phe Ile Arg Xaa Gly Leu Thr Pro Arg Trp Ser
            260                 265                 270

Asp Leu Asp Ile Asn Gln His Val Asn Val Lys Tyr Ile Gly Trp
        275                 280                 285

Leu Leu Glu Ser Ala Pro Pro Glu Ile His Glu Ser His Glu Ile Ala
    290                 295                 300

Ser Leu Thr Leu Glu Tyr Arg Arg Glu Cys Gly Arg Asp Ser Val Leu
305                 310                 315                 320

Asn Ser Ala Thr Lys Val Ser Asp Ser Ser Gln Leu Gly Lys Ser Ala
                325                 330                 335

Val Glu Cys Asn His Leu Val Arg Leu Gln Asn Gly Gly Glu Ile Val

```
                340             345             350
Lys Gly Arg Thr Val Trp Arg Pro Lys Arg Pro Leu Tyr Asn Asp Gly
            355                 360                 365

Ala Val Val Asp Val Xaa Ala Lys Thr Ser
        370                 375

<210> SEQ ID NO 109
<211> LENGTH: 419
<212> TYPE: PRT
<213> ORGANISM: Cuphea viscosissima

<400> SEQUENCE: 109

Met Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
            35                  40                  45

Lys Ala Asn Ala Ser Ala His Pro Lys Ala Asn Gly Ser Ala Val Asn
        50                  55                  60

Leu Lys Ser Gly Ser Leu Asn Thr Gln Glu Asp Thr Ser Ser Pro
65              70                  75                      80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
            115                 120                 125

Leu Lys Ser Ile Val Arg Asp Gly Leu Val Ser Arg His Ser Phe Ser
130             135                 140

Ile Arg Ser Tyr Glu Ile Gly Ala Asp Arg Thr Ala Ser Ile Glu Thr
145             150                 155                 160

Leu Met Asn His Leu Gln Glu Thr Thr Ile Asn His Cys Lys Ser Leu
                165                 170                 175

Gly Leu His Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
            195                 200                 205

Pro Thr Trp Gly Asp Thr Val Glu Ile Asn Thr Trp Phe Ser Gln Ser
        210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
            275                 280                 285

Lys Leu Arg Lys Phe Asp Val Lys Thr Gly Asp Ser Ile Arg Lys Gly
        290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335
```

-continued

```
Glu Thr Gln Glu Leu Cys Ser Leu Thr Val Tyr Arg Arg Glu Cys
                340                 345                 350

Gly Met Asp Ser Val Leu Glu Ser Val Thr Ala Val Asp Pro Ser Glu
                355                 360                 365

Asn Gly Gly Arg Ser Gln Tyr Lys His Leu Leu Arg Leu Glu Asp Gly
                370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser

<210> SEQ ID NO 110
<211> LENGTH: 246
<212> TYPE: PRT
<213> ORGANISM: Clostridium perfringens

<400> SEQUENCE: 110

Met Gly Lys Ala Tyr Glu Lys Val Tyr Glu Val Thr Tyr Gly Glu Thr
1               5                   10                  15

Asp Gly Arg Lys Asp Cys Arg Ile Thr Ser Met Met Asn Phe Phe Ser
                20                  25                  30

Asp Cys Cys Leu Ser Gln Glu Glu Lys Asn Ser Met Asn Tyr Ala Asp
                35                  40                  45

Asn Ser Ser Glu Thr Thr Trp Val Phe Phe Asp Tyr Glu Ile Ile Val
50                  55                  60

Asn Arg Tyr Pro Arg Tyr Arg Glu Lys Ile Lys Val Lys Thr Tyr Val
65                  70                  75                  80

Glu Ser Ile Arg Lys Phe Tyr Ser Asn Arg Val Phe Glu Ala Tyr Asp
                85                  90                  95

Met Asp Gly Ala Leu Val Ala Arg Ala Asp Val Leu Ala Phe Leu Ile
                100                 105                 110

Asn Lys Lys Thr Arg Arg Pro Ala Arg Ile Ser Asp Glu Glu Tyr Glu
                115                 120                 125

Ile His Gly Leu Ser Lys Glu Ser Ser Lys Leu Leu Arg Lys Lys Leu
                130                 135                 140

Asn Phe Glu Lys Phe Asp Lys Glu Asp Leu Glu Met Asn Phe His Ile
145                 150                 155                 160

Arg Tyr Leu Asp Ile Asp Leu Asn Met His Val Ser Asn Ile Lys Tyr
                165                 170                 175

Val Glu Trp Ile Leu Glu Thr Val Pro Val Asp Ile Val Leu Asn Tyr
                180                 185                 190

Lys Met Lys Lys Ile Lys Ile Lys Phe Glu Lys Glu Ile Thr Tyr Gly
                195                 200                 205

His Asn Val Ile Ile Lys Ser Lys Ile Lys Gly Glu Asp Glu Val
                210                 215                 220

Lys Val Leu His Lys Val Glu Asn Glu Glu Gly Glu Ser Ile Thr Leu
225                 230                 235                 240

Ala Glu Thr Tyr Trp Tyr
                245

<210> SEQ ID NO 111
<211> LENGTH: 238
<212> TYPE: PRT
<213> ORGANISM: Clostridium asparagiforme
```

```
<400> SEQUENCE: 111

Met Tyr Thr Phe Asp Ser Arg Val Arg Tyr Ser Glu Thr Asp Glu Glu
1               5                   10                  15

Gly Arg Leu Thr Val Thr Gly Ile Ile Asn Tyr Met Gln Asp Cys Ser
            20                  25                  30

Thr Phe His Ser Glu Asp Val Gly Val Gly Val Gly Tyr Leu Gly Glu
        35                  40                  45

His Arg Arg Ile Trp Leu Leu Ser Ser Trp Gln Ile Val Ile Asp Arg
    50                  55                  60

Tyr Pro Arg Leu Gly Glu Arg Leu Thr Val Gly Thr Trp His Asn Asp
65                  70                  75                  80

Phe Lys Gly Ile Tyr Gly Tyr Arg Asn Phe Val Leu Arg Asp Leu Asp
                85                  90                  95

Gly Asn Asp Cys Val Arg Ala Ala Ser Val Trp Phe Leu Tyr Asp Leu
            100                 105                 110

Glu Lys Glu Gln Pro Ile Arg Val Thr Gly Ala Asp Thr Asp Pro Tyr
        115                 120                 125

Gly Glu Pro Glu Pro Arg Leu Glu Leu Gly Lys Ala Pro Arg Lys Ile
    130                 135                 140

Pro Val Pro Glu His Leu Glu Ala Val Glu Pro Val Val Ala Arg
145                 150                 155                 160

His His Leu Asp Thr Asn His Val Asn Asn Ala Gln Tyr Val Glu
                165                 170                 175

Ile Ala Arg Glu Ala Val Pro Ala Gly Ile Thr Ile Arg Glu Ile Arg
            180                 185                 190

Ala Asp Tyr Lys Lys Ala Ala Leu Leu Gly Asp Val Ile Val Pro Arg
        195                 200                 205

Val Ala Cys Gly Gln Asp Lys Cys Tyr Thr Val Val Leu Gly Ser Glu
    210                 215                 220

Thr Gly Glu Ile Tyr Ala Val Val Trp Leu Arg Ala Glu Ala
225                 230                 235

<210> SEQ ID NO 112
<211> LENGTH: 238
<212> TYPE: PRT
<213> ORGANISM: Marvinbryantia formatexigens

<400> SEQUENCE: 112

Met Ile Tyr Met Ala Tyr Gln Tyr Arg Ser Arg Ile Arg Tyr Ser Glu
1               5                   10                  15

Ile Gly Glu Asp Lys Lys Leu Thr Leu Pro Gly Leu Val Asn Tyr Phe
            20                  25                  30

Gln Asp Cys Ser Thr Phe Gln Ser Glu Ala Leu Gly Ile Gly Leu Asp
        35                  40                  45

Thr Leu Gly Ala Arg Gln Arg Ala Trp Leu Leu Ala Ser Trp Lys Ile
    50                  55                  60

Val Ile Asp Arg Leu Pro Arg Leu Gly Glu Val Val Thr Glu Thr
65                  70                  75                  80

Trp Pro Tyr Gly Phe Lys Gly Phe Gln Gly Asn Arg Asn Phe Arg Met
                85                  90                  95

Leu Asp Gln Glu Gly His Thr Leu Ala Ala Ala Ser Val Trp Ile
            100                 105                 110

Tyr Leu Asn Val Glu Ser Gly His Pro Cys Arg Ile Asp Gly Asp Val
        115                 120                 125
```

```
Leu Glu Ala Tyr Glu Leu Glu Glu Leu Pro Leu Gly Pro Phe Ser
130                 135                 140

Arg Lys Ile Pro Val Pro Glu Ser Thr Glu Arg Asp Ser Phe Leu
145                 150                 155                 160

Val Met Arg Ser His Leu Asp Thr Asn His His Val Asn Asn Gly Gln
                165                 170                 175

Tyr Ile Leu Met Ala Glu Glu Tyr Leu Pro Glu Gly Phe Lys Val Lys
                180                 185                 190

Gln Ile Arg Val Glu Tyr Arg Lys Ala Val Leu His Asp Thr Ile
                195                 200                 205

Val Pro Phe Val Cys Thr Glu Pro Gln Arg Cys Thr Val Ser Leu Cys
210                 215                 220

Gly Ser Asp Glu Lys Pro Phe Ala Val Val Glu Phe Ser Glu
225                 230                 235

<210> SEQ ID NO 113
<211> LENGTH: 250
<212> TYPE: PRT
<213> ORGANISM: Streptococcus dysgalactiae

<400> SEQUENCE: 113

Met Gly Leu Ser Tyr Arg Glu Asp Ile Lys Leu Pro Phe Glu Leu Cys
1               5                   10                  15

Asp Val Lys Ser Asp Ile Lys Phe Pro Leu Leu Asp Tyr Cys Leu
                20                  25                  30

Thr Val Ser Gly Arg Gln Ser Ala Gln Leu Gly Arg Ser Asn Asp Tyr
                35                  40                  45

Leu Leu Glu Gln Tyr Gly Leu Ile Trp Ile Val Thr Asp Tyr Glu Ala
50                  55                  60

Thr Ile His Arg Leu Pro His Phe Gln Glu Thr Ile Thr Ile Glu Thr
65                  70                  75                  80

Lys Ala Leu Ser Tyr Asn Lys Phe Phe Cys Tyr Arg Gln Phe Tyr Ile
                85                  90                  95

Tyr Asp Gln Glu Gly Gly Leu Leu Val Asp Ile Leu Ala Tyr Phe Ala
                100                 105                 110

Leu Leu Asn Pro Asp Thr Arg Lys Val Ala Thr Ile Pro Glu Asp Leu
                115                 120                 125

Val Ala Pro Phe Glu Thr Asp Phe Val Lys Lys Leu His Arg Val Pro
130                 135                 140

Lys Met Pro Leu Leu Glu Gln Ser Ile Asp Arg Asp Tyr Tyr Val Arg
145                 150                 155                 160

Tyr Phe Asp Ile Asp Met Asn Gly His Val Asn Asn Ser Lys Tyr Leu
                165                 170                 175

Asp Trp Met Tyr Asp Val Leu Gly Cys Glu Phe Leu Lys Thr His Gln
                180                 185                 190

Pro Leu Lys Met Thr Leu Lys Tyr Val Lys Glu Val Ser Pro Gly Gly
                195                 200                 205

Gln Ile Thr Ser Ser Tyr His Leu Asp Gln Leu Thr Ser Tyr His Gln
                210                 215                 220

Ile Thr Ser Asp Gly Gln Leu Asn Ala Gln Ala Met Ile Glu Trp Arg
225                 230                 235                 240

Ala Ile Lys Gln Thr Glu Ser Glu Ile Asp
                245                 250

<210> SEQ ID NO 114
```

<211> LENGTH: 246
<212> TYPE: PRT
<213> ORGANISM: Lactobacillus brevis

<400> SEQUENCE: 114

Met Ala Ala Asn Glu Phe Ser Glu Thr His Arg Val Val Tyr Tyr Glu
1               5                   10                  15

Ala Asp Asp Thr Gly Gln Leu Thr Leu Ala Met Leu Ile Asn Leu Phe
            20                  25                  30

Val Leu Val Ser Glu Asp Gln Asn Asp Ala Leu Gly Leu Ser Thr Ala
        35                  40                  45

Phe Val Gln Ser His Gly Val Gly Trp Val Val Thr Gln Tyr His Leu
    50                  55                  60

His Ile Asp Glu Leu Pro Arg Thr Gly Ala Gln Val Thr Ile Lys Thr
65                  70                  75                  80

Arg Ala Thr Ala Tyr Asn Arg Tyr Phe Ala Tyr Arg Glu Tyr Trp Leu
                85                  90                  95

Leu Asp Asp Ala Gly Gln Val Leu Ala Tyr Gly Glu Gly Ile Trp Val
            100                 105                 110

Thr Met Ser Tyr Ala Thr Arg Lys Ile Thr Thr Ile Pro Ala Glu Val
        115                 120                 125

Met Ala Pro Tyr His Ser Glu Glu Gln Thr Arg Leu Pro Arg Leu Pro
    130                 135                 140

Arg Pro Asp His Phe Asp Glu Ala Val Asn Gln Thr Leu Lys Pro Tyr
145                 150                 155                 160

Thr Val Arg Tyr Phe Asp Ile Asp Gly Asn Gly His Val Asn Asn Ala
                165                 170                 175

His Tyr Phe Asp Trp Met Leu Asp Val Leu Pro Ala Thr Phe Leu Arg
            180                 185                 190

Ala His His Pro Thr Asp Val Lys Ile Arg Phe Glu Asn Glu Val Gln
        195                 200                 205

Tyr Gly His Gln Val Thr Ser Glu Leu Ser Gln Ala Ala Ala Leu Thr
    210                 215                 220

Thr Gln His Met Ile Lys Val Gly Asp Leu Thr Ala Val Lys Ala Thr
225                 230                 235                 240

Ile Gln Trp Asp Asn Arg
                245

<210> SEQ ID NO 115
<211> LENGTH: 261
<212> TYPE: PRT
<213> ORGANISM: Lactobacillus plantarum

<400> SEQUENCE: 115

Met Ala Thr Leu Gly Ala Asn Ala Ser Leu Tyr Ser Glu Gln His Arg
1               5                   10                  15

Ile Thr Tyr Tyr Glu Cys Asp Arg Thr Gly Arg Ala Thr Leu Thr Thr
            20                  25                  30

Leu Ile Asp Ile Ala Val Leu Ala Ser Glu Asp Gln Ser Asp Ala Leu
        35                  40                  45

Gly Leu Thr Thr Glu Met Val Gln Ser His Gly Val Gly Trp Val Val
    50                  55                  60

Thr Gln Tyr Ala Ile Asp Ile Thr Arg Met Pro Arg Gln Asp Glu Val
65                  70                  75                  80

Val Thr Ile Ala Val Arg Gly Ser Ala Tyr Asn Pro Tyr Phe Ala Tyr
                85                  90                  95

-continued

Arg Glu Phe Trp Ile Arg Asp Ala Asp Gly Gln Gln Leu Ala Tyr Ile
                100                 105                 110

Thr Ser Ile Trp Val Met Met Ser Gln Thr Thr Arg Ile Val Lys
            115                 120                 125

Ile Leu Pro Glu Leu Val Ala Pro Tyr Gln Ser Glu Val Val Lys Arg
130                 135                 140

Ile Pro Arg Leu Pro Arg Pro Ile Ser Phe Glu Ala Thr Asp Thr Thr
145                 150                 155                 160

Ile Thr Lys Pro Tyr His Val Arg Phe Phe Asp Ile Asp Pro Asn Arg
                165                 170                 175

His Val Asn Asn Ala His Tyr Phe Asp Trp Leu Val Asp Thr Leu Pro
                180                 185                 190

Ala Thr Phe Leu Leu Gln His Asp Leu Val His Val Asp Val Arg Tyr
            195                 200                 205

Glu Asn Glu Val Lys Tyr Gly Gln Thr Val Thr Ala His Ala Asn Ile
210                 215                 220

Leu Pro Ser Glu Val Ala Asp Gln Val Thr Thr Ser His Leu Ile Glu
225                 230                 235                 240

Val Asp Asp Glu Lys Cys Cys Glu Val Thr Ile Gln Trp Arg Thr Leu
                245                 250                 255

Pro Glu Pro Ile Gln
            260

<210> SEQ ID NO 116
<211> LENGTH: 231
<212> TYPE: PRT
<213> ORGANISM: Anaerococcus tetradius

<400> SEQUENCE: 116

Met Lys Phe Lys Lys Lys Phe Lys Ile Gly Arg Met His Val Asp Pro
1               5                   10                  15

Phe Asn Tyr Ile Ser Met Arg Tyr Leu Val Ala Leu Met Asn Glu Val
                20                  25                  30

Ala Phe Asp Gln Ala Glu Ile Leu Glu Lys Asp Ile Asp Met Lys Asn
            35                  40                  45

Leu Arg Trp Ile Ile Tyr Ser Trp Asp Ile Gln Ile Glu Asn Asn Ile
    50                  55                  60

Arg Leu Gly Glu Glu Ile Glu Ile Thr Thr Ile Pro Thr His Met Asp
65                  70                  75                  80

Lys Phe Tyr Ala Tyr Arg Asp Phe Ile Val Glu Ser Arg Gly Asn Ile
                85                  90                  95

Leu Ala Arg Ala Lys Ala Thr Phe Leu Leu Met Asp Ile Thr Arg Leu
            100                 105                 110

Arg Pro Ile Lys Ile Pro Gln Asn Leu Ser Leu Ala Tyr Gly Lys Glu
        115                 120                 125

Asn Pro Ile Phe Asp Ile Tyr Asp Met Glu Ile Arg Asn Asp Leu Ala
    130                 135                 140

Phe Ile Arg Asp Ile Gln Leu Arg Arg Ala Asp Leu Asp Asn Asn Phe
145                 150                 155                 160

His Ile Asn Asn Ala Val Tyr Phe Asp Leu Ile Lys Glu Thr Val Asp
                165                 170                 175

Ile Tyr Asp Lys Asp Ile Ser Tyr Ile Lys Leu Ile Tyr Arg Asn Glu
            180                 185                 190

Ile Arg Asp Lys Lys Gln Ile Gln Ala Phe Ala Arg Arg Glu Asp Lys

```
                195                 200                 205
Ser Ile Asp Phe Ala Leu Arg Gly Glu Asp Gly Arg Asp Tyr Cys Leu
        210                 215                 220

Gly Lys Ile Lys Thr Asn Val
225                 230

<210> SEQ ID NO 117
<211> LENGTH: 257
<212> TYPE: PRT
<213> ORGANISM: Bdellovibrio bacteriovorus

<400> SEQUENCE: 117

Met Thr Asn Ile Ser Asn Ser Pro Trp Val Glu Asn Phe His Ile Thr
1               5                   10                  15

Ser Leu Leu Val Asn Pro Leu Gly Arg Leu Gly Leu Tyr Gly Leu Leu
                20                  25                  30

Asn Leu Leu Gln Glu Thr Ala Trp Ile His Ala Glu Lys Met Gly Phe
            35                  40                  45

Gly Leu Leu Asp Met Glu Lys Gln Gly Leu Phe Trp Val Leu Thr Arg
        50                  55                  60

Gln Ser Leu Gln Met Lys Thr Trp Pro Arg Phe Gly Glu Asn Ile Gln
65                  70                  75                  80

Ile Gln Thr Trp Leu Arg Ala Pro Glu Gly Ala Phe Val Ala Arg Glu
                85                  90                  95

Phe Ala Ile Leu Asn Gln Ser Gly Glu Glu Ile Gly Leu Cys Ser Thr
            100                 105                 110

Ser Trp Leu Ala Leu Asp Arg Gln Ser Lys Lys Ile Leu Pro Ala Asp
        115                 120                 125

Asn Leu Arg Pro Trp Asp Gln Ile Ala His Ala Arg Ser Thr Gly Ile
    130                 135                 140

Asn Pro Glu Lys Ile Pro Val Thr Gly Thr Tyr Glu Lys Ile Ala Lys
145                 150                 155                 160

Tyr Arg Val Arg Asn Ser Asp Leu Asp Ile Asn Gln His Val Asn Asn
                165                 170                 175

Thr Lys Tyr Ala Gln Trp Ile Leu Asp Ala Ile Pro Tyr Asp Leu His
            180                 185                 190

Lys Ser Leu Lys Leu Asn Thr Tyr Ser Val Asn Phe Leu Ala Glu Thr
        195                 200                 205

His Leu Gly Asp Glu Val Glu Val His Arg Asn Cys Ser Ser Pro Asp
    210                 215                 220

Val Gln Leu Ala Ser His Gly Ala Ser Ala Tyr Lys Gly Leu Arg Val
225                 230                 235                 240

Gly Asp Glu Lys Val Leu Phe Thr Ala Val Leu Gly Trp Glu Lys Arg
                245                 250                 255

Lys

<210> SEQ ID NO 118
<211> LENGTH: 415
<212> TYPE: PRT
<213> ORGANISM: Cuphea viscosissima

<400> SEQUENCE: 118

Met Val Ala Thr Ala Ala Ser Ser Ala Phe Phe Pro Val Pro Ser Ala
1               5                   10                  15

Asp Thr Ser Ser Arg Pro Gly Lys Leu Gly Asn Gly Pro Ser Ser Phe
                20                  25                  30
```

Ser Pro Leu Lys Pro Lys Ser Ile Pro Asn Gly Gly Leu Gln Val Lys
            35                  40                  45

Ala Ser Ala Ser Ala Pro Pro Lys Ile Asn Gly Ser Ser Val Gly Leu
    50                  55                  60

Lys Ser Gly Gly Leu Lys Thr His Asp Asp Ala Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Ala Phe Leu Ala Ala Glu Lys Gln Trp Met Met Leu
                100                 105                 110

Asp Arg Lys Pro Lys Arg Leu Asp Met Leu Glu Asp Pro Phe Gly Leu
                115                 120                 125

Gly Arg Val Val Gln Asp Gly Leu Val Phe Arg Gln Asn Phe Ser Ile
130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Thr Ala Gly
                165                 170                 175

Leu Ser Asn Asp Gly Phe Gly Arg Thr Pro Glu Met Tyr Lys Arg Asp
                180                 185                 190

Leu Ile Trp Val Phe Ala Lys Met Gln Val Met Val Asn Arg Tyr Pro
                195                 200                 205

Thr Trp Gly Asp Thr Val Glu Val Asn Thr Trp Val Ala Lys Ser Gly
                210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg Glu Ile Glu
                260                 265                 270

Pro His Phe Val Asp Ser Ala Pro Val Ile Glu Asp Asp Arg Lys
                275                 280                 285

Leu Pro Lys Leu Asp Glu Lys Ser Ala Asp Ser Ile Arg Lys Gly Leu
                290                 295                 300

Thr Pro Arg Trp Asn Asp Leu Asp Val Asn Gln His Val Asn Asn Ala
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
                340                 345                 350

Arg Glu Ser Val Leu Glu Ser Leu Thr Ala Val Asp Pro Ser Gly Glu
                355                 360                 365

Gly Tyr Gly Ser Gln Phe Gln His Leu Leu Arg Leu Glu Asp Gly Gly
                370                 375                 380

Glu Ile Val Lys Gly Arg Thr Glu Trp Arg Pro Lys Asn Ala Gly Ile
385                 390                 395                 400

Asn Gly Val Val Pro Ser Glu Glu Ser Ser Pro Gly Asp Tyr Ser
                405                 410                 415

<210> SEQ ID NO 119
<211> LENGTH: 436
<212> TYPE: PRT
<213> ORGANISM: Arabidopsis thaliana -continued

```
<400> SEQUENCE: 119

Met Ala Val Leu Ser Ser Ala Asp Arg Ala Ser Asn Glu Lys Lys Val
1               5                   10                  15

Lys Ser Ser Tyr Phe Asp Leu Pro Pro Met Glu Met Ser Val Ala Phe
            20                  25                  30

Pro Gln Ala Thr Pro Ala Ser Thr Phe Pro Pro Cys Thr Ser Asp Tyr
        35                  40                  45

Tyr His Phe Asn Asp Leu Leu Thr Pro Glu Gln Ala Ile Arg Lys
    50                  55                  60

Lys Val Arg Glu Cys Met Glu Lys Glu Val Ala Pro Ile Met Thr Glu
65                  70                  75                  80

Tyr Trp Glu Lys Ala Glu Phe Pro Phe His Ile Thr Pro Lys Leu Gly
                85                  90                  95

Ala Met Gly Val Ala Gly Gly Ser Ile Lys Gly Tyr Gly Cys Pro Gly
            100                 105                 110

Leu Ser Ile Thr Ala Asn Ala Ile Ala Thr Ala Glu Ile Ala Arg Val
        115                 120                 125

Asp Ala Ser Cys Ser Thr Phe Ile Leu Val His Ser Ser Leu Gly Met
    130                 135                 140

Leu Thr Ile Ala Leu Cys Gly Ser Glu Ala Gln Lys Glu Lys Tyr Leu
145                 150                 155                 160

Pro Ser Leu Ala Gln Leu Asn Thr Val Ala Cys Trp Ala Leu Thr Glu
                165                 170                 175

Pro Asp Asn Gly Ser Asp Ala Ser Gly Leu Gly Thr Thr Ala Thr Lys
            180                 185                 190

Val Glu Gly Gly Trp Lys Ile Asn Gly Gln Lys Arg Trp Ile Gly Asn
        195                 200                 205

Ser Thr Phe Ala Asp Leu Leu Ile Ile Phe Ala Arg Asn Thr Thr Thr
    210                 215                 220

Asn Gln Ile Asn Gly Phe Ile Val Lys Lys Asp Ala Pro Gly Leu Lys
225                 230                 235                 240

Ala Thr Lys Ile Pro Asn Lys Ile Gly Leu Arg Met Val Gln Asn Gly
                245                 250                 255

Asp Ile Leu Leu Gln Asn Val Phe Val Pro Asp Glu Asp Arg Leu Pro
            260                 265                 270

Gly Val Asn Ser Phe Gln Asp Thr Ser Lys Val Leu Ala Val Ser Arg
        275                 280                 285

Val Met Val Ala Trp Gln Pro Ile Gly Ile Ser Met Gly Ile Tyr Asp
    290                 295                 300

Met Cys His Arg Tyr Leu Lys Glu Arg Lys Gln Phe Gly Ala Pro Leu
305                 310                 315                 320

Ala Ala Phe Gln Leu Asn Gln Gln Lys Leu Val Gln Met Leu Gly Asn
                325                 330                 335

Val Gln Ala Met Phe Leu Met Gly Trp Arg Leu Cys Lys Leu Tyr Glu
            340                 345                 350

Thr Gly Gln Met Thr Pro Gly Gln Ala Ser Leu Gly Lys Ala Trp Ile
        355                 360                 365

Ser Ser Lys Ala Arg Glu Thr Ala Ser Leu Gly Arg Glu Leu Leu Gly
    370                 375                 380

Gly Asn Gly Ile Leu Ala Asp Phe Leu Val Ala Lys Ala Phe Cys Asp
385                 390                 395                 400

Leu Glu Pro Ile Tyr Thr Tyr Glu Gly Thr Tyr Asp Ile Asn Thr Leu
                405                 410                 415
```

Val Thr Gly Arg Glu Val Thr Gly Ile Ala Ser Phe Lys Pro Ala Thr
            420                 425                 430

Arg Ser Arg Leu
        435

<210> SEQ ID NO 120
<211> LENGTH: 156
<212> TYPE: PRT
<213> ORGANISM: Pseudomonas aeruginosa

<400> SEQUENCE: 120

Met Ser Gln Val Gln Asn Ile Pro Tyr Ala Glu Leu Glu Val Gly Gln
1               5                   10                  15

Lys Ala Glu Tyr Thr Ser Ser Ile Ala Glu Arg Asp Leu Gln Leu Phe
            20                  25                  30

Ala Ala Val Ser Gly Asp Arg Asn Pro Val His Leu Asp Ala Ala Tyr
        35                  40                  45

Ala Ala Thr Thr Gln Phe Lys Glu Arg Ile Ala His Gly Met Leu Ser
    50                  55                  60

Gly Ala Leu Ile Ser Ala Ala Ile Ala Thr Val Leu Pro Gly Pro Gly
65                  70                  75                  80

Thr Ile Tyr Leu Gly Gln Thr Leu Arg Phe Thr Arg Pro Val Lys Leu
                85                  90                  95

Gly Asp Asp Leu Lys Val Glu Leu Glu Val Leu Glu Lys Leu Pro Lys
            100                 105                 110

Asn Arg Val Arg Met Ala Thr Arg Val Phe Asn Gln Ala Gly Lys Gln
        115                 120                 125

Val Val Asp Gly Glu Ala Glu Ile Met Ala Pro Glu Glu Lys Leu Ser
    130                 135                 140

Val Glu Leu Ala Glu Leu Pro Pro Ile Ser Ile Gly
145                 150                 155

<210> SEQ ID NO 121
<211> LENGTH: 288
<212> TYPE: PRT
<213> ORGANISM: Pseudomonas aeruginosa

<400> SEQUENCE: 121

Met Ala Leu Asp Pro Glu Val Leu Leu Asn Tyr Pro Ile Pro Glu Val
1               5                   10                  15

Arg Gln Arg Tyr Ser Arg Arg Asp Ser Ala Phe Tyr Ala Leu Ser Leu
            20                  25                  30

Gly Leu Gly Gly Asp Pro Leu Asp Glu Arg Gln Leu Ala Tyr Val Asp
        35                  40                  45

Pro Cys Arg Asp Leu Gln Ala Leu Pro Cys Met Ala Leu Val Leu Gly
    50                  55                  60

His Pro Gly Phe Trp Leu Gly Asn Pro Ala Thr Gly Val Asp Ala Leu
65                  70                  75                  80

Arg Leu Val His Gly Glu Gln Arg Leu Glu Trp Arg Arg Pro Leu Pro
                85                  90                  95

Ala Glu Gly Glu Val Ile Gly Arg Thr Arg Val Thr Gly Leu Val Asp
            100                 105                 110

Lys Gly Ala Asp Lys Gly Ala Leu Leu Tyr Ser Glu Lys Val Leu Ser
        115                 120                 125

Asp Ala Leu Ser Gly Glu Val Leu Ala Val Ala Arg Ser Thr Thr Phe
    130                 135                 140

-continued

Leu Arg Gly Asp Gly Gly Phe Gly Gly Ser Arg Gln Val Pro Glu Thr
145                 150                 155                 160

Pro His Arg Leu Pro Glu Arg Thr Pro Asp Leu Arg Leu Asp Leu Pro
            165                 170                 175

Thr Arg Pro Glu Gln Ala Leu Tyr Tyr Arg Leu Asn Gly Asp Asp Asn
        180                 185                 190

Pro Leu His Ala Glu Pro Ala Ala Leu Arg Ala Gly Phe Pro Arg
        195                 200                 205

Pro Ile Leu His Gly Leu Cys Thr Leu Gly Val Ala Phe His Ala Val
        210                 215                 220

Leu Arg Gly Leu Ala Asp Tyr Arg Ala Gly Gln Leu Gly His Leu Gln
225                 230                 235                 240

Val Arg Phe Ser Ala Pro Val Phe Pro Gly Glu Thr Leu Arg Thr Glu
            245                 250                 255

Met Trp Ser Asp Gly Ser Phe Arg Thr Arg Val Val Glu Arg Asp Val
            260                 265                 270

Val Val Leu Asp Asn Gly Arg Val Gly Pro Pro Glu Arg Pro Asp
        275                 280                 285

<210> SEQ ID NO 122
<211> LENGTH: 134
<212> TYPE: PRT
<213> ORGANISM: Aeromonas caviae

<400> SEQUENCE: 122

Met Ser Thr Gln Thr Leu Ala Val Gly Gln Lys Ala Arg Leu Thr Lys
1               5                   10                  15

Arg Phe Gly Pro Ala Glu Val Ala Ala Phe Ala Gly Leu Ser Glu Asp
            20                  25                  30

Phe Asn Pro Leu His Leu Asp Pro Asp Phe Ala Ala Thr Thr Val Phe
        35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Ser Ile Tyr Leu Gly Gln
65                  70                  75                  80

Ser Leu Gly Phe Lys Leu Pro Val Phe Val Gly Asp Glu Val Thr Ala
                85                  90                  95

Glu Val Glu Val Ile Ala Leu Arg Ser Asp Lys Pro Ile Ala Thr Leu
            100                 105                 110

Ala Thr Arg Ile Phe Thr Gln Gly Gly Ala Leu Ala Val Thr Gly Glu
        115                 120                 125

Ala Val Val Lys Leu Pro
    130

<210> SEQ ID NO 123
<211> LENGTH: 156
<212> TYPE: PRT
<213> ORGANISM: Enterobacter cloacae

<400> SEQUENCE: 123

Met Ser Gln Val Gln Asn Ile Pro Tyr Ala Glu Leu Glu Val Gly Gln
1               5                   10                  15

Lys Ala Glu Tyr Thr Ser Ser Ile Ala Glu Arg Asp Leu Gln Leu Phe
            20                  25                  30

Ala Ala Val Ser Gly Asp Arg Asn Pro Val His Leu Asp Ala Ala Tyr
        35                  40                  45

```
Ala Ala Thr Thr Gln Phe Lys Glu Arg Ile Ala His Gly Met Leu Ser
         50                  55                  60

Gly Ala Leu Ile Ser Ala Ala Ile Ala Thr Val Leu Pro Gly Pro Gly
 65                  70                  75                  80

Thr Ile Tyr Leu Gly Gln Thr Leu Arg Phe Thr Arg Pro Val Lys Leu
                 85                  90                  95

Gly Asp Asp Leu Lys Val Glu Leu Glu Val Leu Glu Lys Leu Pro Lys
                100                 105                 110

Asn Arg Val Arg Met Ala Thr Arg Val Phe Asn Gln Ala Gly Lys Gln
            115                 120                 125

Val Val Asp Gly Glu Ala Glu Ile Met Ala Pro Glu Glu Lys Leu Ser
        130                 135                 140

Val Glu Leu Ala Glu Leu Pro Pro Ile Ser Ile Gly
145                 150                 155
```

<210> SEQ ID NO 124
<211> LENGTH: 156
<212> TYPE: PRT
<213> ORGANISM: Streptococcus dysgalactiae

<400> SEQUENCE: 124

```
Met Ser Gln Val Gln Asn Ile Pro Tyr Ala Glu Leu Glu Val Gly Gln
 1               5                  10                  15

Lys Ala Glu Tyr Thr Ser Ser Ile Ala Glu Arg Asp Leu Gln Leu Phe
                20                  25                  30

Ala Glu Val Ser Gly Asp Arg Asn Pro Val His Leu Asp Ala Ala Tyr
            35                  40                  45

Ala Ala Thr Thr Gln Phe Lys Glu Arg Ile Ala His Gly Met Leu Ser
         50                  55                  60

Gly Ala Leu Ile Ser Ala Ala Ile Ala Thr Val Leu Pro Gly Pro Gly
 65                  70                  75                  80

Thr Ile Tyr Leu Gly Gln Thr Leu Arg Phe Thr Arg Pro Val Lys Leu
                 85                  90                  95

Gly Asp Asp Leu Arg Val Glu Leu Glu Val Leu Glu Lys Leu Pro Lys
                100                 105                 110

Asn Arg Val Arg Met Ala Thr Arg Val Phe Asn Gln Ala Gly Lys Gln
            115                 120                 125

Val Val Asp Gly Glu Ala Glu Ile Met Ala Pro Glu Asp Arg Leu Ser
        130                 135                 140

Val Glu Leu Ala Glu Leu Pro Pro Ile Ser Ile Gly
145                 150                 155
```

<210> SEQ ID NO 125
<211> LENGTH: 156
<212> TYPE: PRT
<213> ORGANISM: Streptococcus pneumoniae

<400> SEQUENCE: 125

```
Met Ser Thr Ile Ser Asn Thr Pro Tyr Ala Asp Leu Glu Val Gly Gln
 1               5                  10                  15

Gln Ala Ser Tyr Glu Lys His Val Glu Glu Lys Asp Ile Gln Leu Phe
                20                  25                  30

Ala Ala Met Ser Gly Asp Arg Asn Pro Val His Leu Asp Ala Glu Phe
            35                  40                  45

Ala Thr Gly Thr Leu Phe Lys Glu Arg Ile Ala His Gly Met Phe Ser
         50                  55                  60
```

```
Gly Ala Leu Ile Ser Ala Ala Val Ala Cys Thr Met Pro Gly Pro Gly
 65                  70                  75                  80

Thr Ile Tyr Leu Gly Gln Thr Met Lys Phe Thr Arg Pro Val Lys Ile
                 85                  90                  95

Asn Asp Thr Leu Thr Val Arg Leu Glu Ile Leu Glu Lys Leu Pro Lys
            100                 105                 110

Asn Arg Val Arg Ile Ala Thr Arg Val Phe Asn Gln Asn Asp Glu Leu
        115                 120                 125

Val Val Asp Gly Glu Ala Glu Val Leu Ala Pro Arg Lys Gln Glu Thr
    130                 135                 140

Val Glu Leu Lys Glu Leu Pro Pro Ile Ser Ile Gly
145                 150                 155
```

<210> SEQ ID NO 126
<211> LENGTH: 160
<212> TYPE: PRT
<213> ORGANISM: Lipotes vexillifer

<400> SEQUENCE: 126

```
Met His Leu Glu Met Thr Gln Val Thr Asn Thr Pro Tyr Glu Ala Leu
  1               5                  10                  15

Glu Val Gly Gln Thr Ala Ser Phe Ser Lys Thr Val Glu Glu Arg Asp
                 20                  25                  30

Ile Gln Leu Phe Ala Ala Met Ser Gly Asp His Asn Pro Val His Leu
             35                  40                  45

Asp Ala Glu Tyr Ala Lys Ala Thr Met Phe Lys Glu Arg Ile Ala His
         50                  55                  60

Gly Met Phe Ser Gly Ala Leu Ile Ser Ala Ala Val Ala Cys Glu Leu
 65                  70                  75                  80

Pro Gly Pro Gly Thr Ile Tyr Ile Gly Gln Gln Met Thr Phe Gln Lys
                 85                  90                  95

Pro Val Lys Ile Gly Asp Thr Leu Thr Val Arg Leu Glu Ile Leu Glu
            100                 105                 110

Lys Leu Pro Lys Phe Arg Val Arg Ile Ala Thr Arg Val Phe Asn Gln
        115                 120                 125

Arg Asp Glu Leu Val Val Asp Gly Glu Ala Glu Ile Leu Ala Pro Arg
    130                 135                 140

Lys Gln Gln Val Val Thr Leu Thr Glu Leu Pro Pro Ile Ser Ile Gly
145                 150                 155                 160
```

<210> SEQ ID NO 127
<211> LENGTH: 156
<212> TYPE: PRT
<213> ORGANISM: Paucimonas lemoignei

<400> SEQUENCE: 127

```
Met Thr Gln Val Thr Asn Thr Pro Tyr Glu Ala Leu Glu Val Gly Gln
  1               5                  10                  15

Thr Ala Ser Phe Ser Lys Thr Val Glu Glu Arg Asp Ile Gln Leu Phe
                 20                  25                  30

Ala Ala Met Ser Gly Asp His Asn Pro Val His Leu Asp Ala Glu Tyr
             35                  40                  45

Ala Ala Ser Thr Met Phe Lys Glu Arg Ile Ala His Gly Met Phe Ser
         50                  55                  60

Gly Ala Leu Ile Ser Ala Ala Val Ala Cys Glu Leu Pro Gly Pro Gly
 65                  70                  75                  80
```

```
Thr Ile Tyr Val Gly Gln Gln Met Thr Phe Gln Lys Pro Val Lys Ile
                85                  90                  95

Gly Asp Thr Leu Thr Val Arg Leu Glu Ile Leu Glu Lys Leu Pro Lys
            100                 105                 110

Phe Arg Val Arg Ile Ala Thr Arg Val Phe Asn Gln Arg Glu Glu Ile
        115                 120                 125

Val Val Asp Gly Glu Ala Glu Ile Ile Ala Pro Arg Lys Gln Gln Thr
    130                 135                 140

Val Thr Leu Thr Thr Leu Pro Ala Ile Ser Ile Gly
145                 150                 155

<210> SEQ ID NO 128
<211> LENGTH: 156
<212> TYPE: PRT
<213> ORGANISM: Unknown
<220> FEATURE:
<223> OTHER INFORMATION: Pantoea

<400> SEQUENCE: 128

Met Thr Gln Val Thr Asn Thr Pro Tyr Glu Ala Leu Glu Val Gly Gln
1               5                   10                  15

Lys Ala Glu Tyr Lys Lys Ser Val Glu Glu Arg Asp Ile Gln Leu Phe
            20                  25                  30

Ala Ala Met Ser Gly Asp His Asn Pro Val His Leu Asp Ala Glu Phe
        35                  40                  45

Ala Ala Lys Ser Met Phe Lys Glu Arg Ile Ala His Gly Met Phe Ser
    50                  55                  60

Gly Ala Leu Ile Ser Ala Ala Val Ala Cys Thr Leu Pro Gly Pro Gly
65                  70                  75                  80

Thr Ile Tyr Leu Gly Gln Gln Met Ser Phe Gln Lys Pro Val Lys Ile
                85                  90                  95

Gly Asp Ser Leu Thr Val Arg Leu Glu Ile Leu Glu Lys Leu Pro Lys
            100                 105                 110

Phe Lys Val Arg Ile Ala Thr Asn Val Tyr Asn Gln Asn Asp Glu Leu
        115                 120                 125

Val Val Glu Gly Val Ala Glu Ile Leu Ala Pro Arg Lys Gln Gln Thr
    130                 135                 140

Val Glu Leu Val Ser Pro Pro Asn Phe Val Ala Gly
145                 150                 155

<210> SEQ ID NO 129
<211> LENGTH: 157
<212> TYPE: PRT
<213> ORGANISM: Ventosimonas gracilis

<400> SEQUENCE: 129

Met Ser Asp Ser Leu Ser Asn Ile Pro Tyr Asp Glu Leu Gln Ile Gly
1               5                   10                  15

Gln Ser Ala Asn Tyr Gln Lys Thr Val Gly Glu Arg Asp Ile Gln Leu
            20                  25                  30

Phe Ala Ala Met Ser Gly Asp Cys Asn Pro Leu His Leu Asp Glu Asp
        35                  40                  45

Phe Ala Lys Thr Thr Met Phe Lys Gln Arg Ile Ala His Gly Met Phe
    50                  55                  60

Ser Gly Ala Leu Ile Ser Ala Val Ala Cys Glu Leu Pro Gly Pro
65                  70                  75                  80
```

Gly Thr Ile Tyr Val Gly Gln Thr Met Ser Phe Leu Lys Pro Val Lys
                    85                  90                  95

Leu Gly Asp Cys Leu Thr Val Arg Leu Glu Val Leu Glu Lys Leu Pro
                100                 105                 110

Lys Phe Arg Val Lys Ile Ala Thr Lys Val Leu Asn Gln His Glu Glu
                115                 120                 125

Leu Val Val Asp Gly Val Ala Glu Ile Ile Ala Pro Arg Lys Gln Gln
                130                 135                 140

Gln Val Leu Lys Val Asn Leu Pro Pro Val Thr Ile Gly
145                 150                 155

<210> SEQ ID NO 130
<211> LENGTH: 157
<212> TYPE: PRT
<213> ORGANISM: Aestuariirhabdus litorea

<400> SEQUENCE: 130

Met Ser Lys Leu Thr Asn Tyr Thr Phe Asp Glu Leu Ala Ile Gly Asp
1               5                   10                  15

Thr Ala Thr Phe Thr Arg Thr Leu Glu Glu Lys Asp Leu Ile Leu Phe
                20                  25                  30

Ala Ala Val Ser Gly Asp Ile Asn Pro Leu His Leu Asp Pro Glu Phe
                35                  40                  45

Ala Ser Thr Thr Pro Phe Lys Glu Arg Ile Ala His Gly Ala Trp Ser
            50                  55                  60

Gly Ser Leu Ile Ser Ala Ala Leu Ala Asn Val Met Pro Gly Pro Gly
65                  70                  75                  80

Thr Val Tyr Leu Gly Gln Ser Leu Lys Phe Gln Arg Pro Val Lys Leu
                85                  90                  95

Gly Asp Thr Leu Thr Val Gln Leu Glu Val Lys Glu Lys Gln Glu Arg
                100                 105                 110

Arg Asn Gln Val Thr Phe Ile Thr Gln Val Val Asn Gln Glu Gly Lys
                115                 120                 125

Thr Val Val Ser Gly Glu Ala Glu Val Met Ala Pro Lys Glu Lys Met
                130                 135                 140

Thr Leu Glu Ala Pro Ala Leu Pro Pro Ile Arg Ile Gly
145                 150                 155

<210> SEQ ID NO 131
<211> LENGTH: 161
<212> TYPE: PRT
<213> ORGANISM: Marinobacter mobilis

<400> SEQUENCE: 131

Met Ala Gln Asn Ser Lys Thr Leu Lys Asn Met Thr Tyr Asp Glu Leu
1               5                   10                  15

Ser Val Gly Asp Ser Ala Asp Phe Ser Arg Thr Leu Thr Glu Asp Glu
                20                  25                  30

Leu Val Leu Phe Ala Ala Val Ser Gly Asp Val Asn Pro Val His Leu
                35                  40                  45

Asp Ser Glu Phe Ala Ala Thr Thr Leu Phe Lys Glu Arg Ile Ala His
            50                  55                  60

Gly Met Trp Ser Gly Ser Leu Ile Ser Ala Ala Leu Ala Thr Thr Leu
65                  70                  75                  80

Pro Gly Pro Gly Thr Ile Tyr Leu Glu Gln Asn Leu Ala Phe Lys Arg
                85                  90                  95

```
Pro Val Lys Leu Gly Asp Thr Leu Thr Val Thr Leu Thr Val Lys Glu
            100                 105                 110

Lys Gln Pro Lys Asn Arg Val Val Ile Glu Cys Ala Val Arg Asn Gln
        115                 120                 125

Glu Gly Gln Gln Val Val Ser Gly Glu Ala Lys Val Met Ala Pro Thr
    130                 135                 140

Glu Ser Val Glu Leu Asp Ala Pro Thr Leu Pro Asn Ile Thr Ile Glu
145                 150                 155                 160

Arg

<210> SEQ ID NO 132
<211> LENGTH: 158
<212> TYPE: PRT
<213> ORGANISM: Hahella ganghwensis

<400> SEQUENCE: 132

Met Asp Val Leu Glu Asn Phe Thr Tyr Asp Glu Leu Asn Val Gly Asp
1               5                   10                  15

Thr Ala Thr Phe Thr Lys Thr Leu Thr Glu Glu Gln Ile Ile Leu Phe
            20                  25                  30

Ala Ala Val Ser Gly Asp Met Asn Pro Val His Leu Asp Pro Gln Tyr
        35                  40                  45

Ala Glu Thr Thr Val Phe Lys Glu Arg Ile Ala His Gly Met Trp Ser
    50                  55                  60

Gly Ala Leu Ile Ser Ala Ala Ile Ala Thr Val Leu Pro Gly Pro Gly
65                  70                  75                  80

Ser Ile Tyr Leu Glu Gln Ser Met Ala Phe Lys Arg Pro Val Lys Ile
                85                  90                  95

Asn Asp Thr Leu Thr Ala Lys Ile Thr Val Thr Glu Lys Leu Pro Lys
            100                 105                 110

Gly Arg Val Val Leu Ser Cys Glu Ile Phe Asn Gln Ser Asp Glu Leu
        115                 120                 125

Val Val Thr Gly Gln Ala Lys Val Ile Ala Pro Lys Asp Lys Ile Gln
    130                 135                 140

Ile Asp Lys Pro Glu Leu Pro Glu Ile Thr Ile Gly Ser Asn
145                 150                 155

<210> SEQ ID NO 133
<211> LENGTH: 288
<212> TYPE: PRT
<213> ORGANISM: Acinetobacter baumannii

<400> SEQUENCE: 133

Met Ala Leu Asp Pro Glu Val Leu Leu Asn Tyr Pro Ile Pro Glu Val
1               5                   10                  15

Arg Gln Arg Tyr Ser Arg Arg Asp Ser Ala Phe Tyr Ala Leu Ser Leu
            20                  25                  30

Gly Leu Gly Gly Asp Pro Leu Asp Glu Arg Gln Leu Ala Tyr Val Asp
        35                  40                  45

Pro Cys Arg Asp Leu Gln Ala Leu Pro Cys Met Ala Leu Val Leu Gly
    50                  55                  60

His Pro Gly Phe Trp Leu Gly Asn Pro Ala Thr Gly Val Asp Ala Leu
65                  70                  75                  80

Arg Leu Val His Gly Glu Gln Arg Leu Glu Trp Arg Arg Pro Leu Pro
                85                  90                  95

Ala Glu Gly Glu Val Ile Gly Arg Thr Arg Val Thr Gly Leu Val Asp
```

```
            100                 105                 110
Lys Gly Ala Asp Lys Gly Ala Leu Leu Tyr Ser Glu Lys Val Leu Ser
            115                 120                 125

Asp Ala Leu Ser Gly Glu Val Leu Ala Val Ala Arg Ser Thr Thr Phe
        130                 135                 140

Leu Arg Gly Asp Gly Gly Phe Gly Gly Ser Arg Gln Val Pro Glu Thr
145                 150                 155                 160

Pro His Arg Leu Pro Glu Arg Thr Pro Asp Leu Arg Leu Asp Leu Pro
                165                 170                 175

Thr Arg Pro Glu Gln Ala Leu Tyr Tyr Arg Leu Asn Gly Asp Asp Asn
            180                 185                 190

Pro Leu His Ala Glu Pro Ala Ala Leu Arg Ala Gly Phe Pro Arg
        195                 200                 205

Pro Ile Leu His Gly Leu Cys Thr Leu Gly Val Ala Phe His Ala Val
        210                 215                 220

Leu Arg Gly Leu Ala Asp Tyr Arg Ala Gly Gln Leu Gly His Leu Gln
225                 230                 235                 240

Val Arg Phe Ser Ala Pro Val Phe Pro Gly Glu Thr Leu Arg Thr Glu
                245                 250                 255

Met Trp Ser Asp Gly Ser Phe Arg Thr Arg Val Val Glu Arg Asp Val
            260                 265                 270

Val Val Leu Asp Asn Gly Arg Val Gly Pro Pro Gly Arg Pro Asp
            275                 280                 285

<210> SEQ ID NO 134
<211> LENGTH: 288
<212> TYPE: PRT
<213> ORGANISM: Enterobacter cloacae

<400> SEQUENCE: 134

Met Ala Leu Asp Pro Glu Val Leu Leu Asn Tyr Pro Ile Pro Glu Val
1               5                   10                  15

Arg Gln Arg Tyr Ser Arg Arg Asp Ser Ala Phe Tyr Ala Leu Thr Leu
                20                  25                  30

Gly Leu Gly Gly Asp Pro Leu Asp Glu Arg Gln Leu Val Tyr Val Asp
            35                  40                  45

Pro Cys Arg Asp Leu Gln Ala Leu Pro Cys Met Ala Leu Val Leu Gly
        50                  55                  60

His Pro Gly Phe Trp Leu Gly Asn Pro Ala Thr Gly Val Asp Ala Leu
65                  70                  75                  80

Arg Leu Val His Gly Glu Gln Arg Leu Glu Trp Arg Arg Pro Leu Pro
                85                  90                  95

Ala Glu Gly Glu Val Ile Gly Arg Thr Arg Val Thr Gly Leu Val Asp
            100                 105                 110

Lys Gly Ala Asp Lys Gly Ala Leu Leu Tyr Ser Glu Lys Val Leu Ser
        115                 120                 125

Asp Ala Leu Ser Gly Glu Val Leu Ala Val Ala Arg Ser Thr Thr Phe
    130                 135                 140

Leu Arg Gly Asp Gly Gly Phe Gly Gly Ser Arg Gln Val Pro Glu Thr
145                 150                 155                 160

Pro His Arg Leu Pro Glu Arg Ser Pro Asp Leu Arg Leu Asp Leu Pro
                165                 170                 175

Thr Arg Pro Glu Gln Ala Leu Tyr Tyr Arg Leu Asn Gly Asp Asp Asn
            180                 185                 190
```

```
Pro Leu His Ala Glu Pro Ala Ala Leu Arg Ala Gly Phe Pro Arg
        195                 200                 205

Pro Ile Leu His Gly Leu Cys Thr Leu Gly Val Ala Phe His Ala Val
    210                 215                 220

Leu Arg Gly Leu Ala Asp Tyr Arg Ala Glu Gln Leu Gly His Leu Gln
225                 230                 235                 240

Val Arg Phe Ser Ala Pro Val Phe Pro Gly Glu Thr Leu Arg Thr Glu
                245                 250                 255

Met Trp Ser Asp Gly Ser Phe Arg Thr Arg Val Val Glu Arg Asp Val
            260                 265                 270

Val Val Leu Asp Asn Gly Arg Val Gly Pro Pro Glu Arg Pro Asp
    275                 280                 285

<210> SEQ ID NO 135
<211> LENGTH: 288
<212> TYPE: PRT
<213> ORGANISM: Streptococcus dysgalactiae

<400> SEQUENCE: 135

Met Ala Leu Asp Pro Glu Val Leu Leu Asn Tyr Pro Ile Pro Glu Val
1               5                   10                  15

Arg Gln Arg Tyr Ser Arg Arg Asp Thr Ala Phe Tyr Ala Leu Ser Leu
            20                  25                  30

Gly Leu Gly Gly Asp Pro Leu Asp Glu Arg Gln Leu Ala Phe Val Asp
        35                  40                  45

Pro Arg Arg Glu Leu Arg Ala Leu Pro Cys Met Ala Leu Val Leu Gly
    50                  55                  60

His Pro Gly Phe Trp Leu Gly Arg Pro Asp Thr Gly Val Asp Ala Leu
65                  70                  75                  80

Arg Leu Val His Gly Glu Gln Arg Leu Glu Trp His Arg Pro Leu Pro
                85                  90                  95

Ala Glu Gly Glu Val Ile Gly Arg Thr Arg Val Thr Gly Leu Val Asp
            100                 105                 110

Lys Gly Ala Glu Lys Gly Ala Leu Leu Tyr Ser Glu Lys Val Leu Ser
        115                 120                 125

Asp Ala Leu Ser Gly Glu Val Leu Ala Val Ala His Ser Thr Thr Phe
    130                 135                 140

Leu Arg Gly Asp Gly Gly Cys Gly Gly Ser Arg Gln Val Ala Gln Ala
145                 150                 155                 160

Pro His Arg Leu Pro Glu Arg Ala Pro Asp Leu Gln Val Asp Leu Pro
                165                 170                 175

Thr Arg Pro Glu Gln Ala Leu Tyr Tyr Arg Leu Asn Gly Asp Asp Asn
            180                 185                 190

Pro Leu His Ala Glu Pro Val Ala Leu Arg Ala Gly Phe Pro Arg
        195                 200                 205

Pro Ile Leu His Gly Leu Cys Thr Leu Gly Val Ala Phe His Ala Leu
    210                 215                 220

Leu Arg Gly Leu Ala Asp Tyr Arg Ala Glu His Leu Gly Gln Leu Gln
225                 230                 235                 240

Val Arg Phe Ser Ala Pro Val Phe Pro Gly Glu Thr Leu Arg Thr Glu
                245                 250                 255

Met Trp Ser Asp Gly Ser Phe Arg Thr Arg Val Val Glu Arg Asp Arg
            260                 265                 270

Val Val Leu Asp Asn Gly Arg Ile Gly Ala Pro Arg Glu Arg Pro Asp
    275                 280                 285
```

-continued

```
<210> SEQ ID NO 136
<211> LENGTH: 259
<212> TYPE: PRT
<213> ORGANISM: Klebsiella pneumoniae

<400> SEQUENCE: 136
```

Met Ser Leu Gly Leu Gly Gly Asp Pro Leu Asp Glu Arg Gln Leu Ala
1               5                   10                  15

Tyr Val Asp Pro Cys Arg Asp Leu Gln Ala Leu Pro Cys Met Ala Leu
            20                  25                  30

Val Leu Gly His Pro Gly Phe Trp Leu Gly Asn Pro Ala Thr Gly Val
        35                  40                  45

Asp Ala Leu Arg Leu Val His Gly Glu Gln Arg Leu Glu Trp Arg Arg
    50                  55                  60

Pro Leu Pro Ala Glu Gly Glu Val Ile Gly Arg Thr Arg Val Thr Gly
65                  70                  75                  80

Leu Val Asp Lys Gly Ala Asp Lys Gly Ala Leu Leu Tyr Ser Glu Lys
                85                  90                  95

Val Leu Ser Asp Ala Leu Ser Gly Glu Val Leu Ala Val Ala Arg Ser
            100                 105                 110

Thr Thr Phe Leu Arg Gly Asp Gly Phe Gly Gly Ser Arg Gln Val
        115                 120                 125

Pro Glu Thr Pro His Arg Leu Pro Glu Arg Thr Pro Asp Leu Arg Leu
    130                 135                 140

Asp Leu Pro Thr Arg Pro Glu Gln Ala Leu Tyr Tyr Arg Leu Asn Gly
145                 150                 155                 160

Asp Asp Asn Pro Leu His Ala Glu Pro Ala Ala Ala Leu Arg Ala Gly
                165                 170                 175

Phe Pro Arg Pro Ile Leu His Gly Leu Cys Thr Leu Gly Val Ala Phe
            180                 185                 190

His Ala Val Leu Arg Gly Leu Ala Asp Tyr Arg Ala Gly Gln Leu Gly
        195                 200                 205

His Leu Gln Val Arg Phe Ser Ala Pro Val Phe Pro Gly Glu Thr Leu
    210                 215                 220

Arg Thr Glu Met Trp Ser Asp Gly Ser Phe Arg Thr Arg Val Val Glu
225                 230                 235                 240

Arg Asp Val Val Val Leu Asp Asn Gly Arg Val Gly Pro Pro Glu
                245                 250                 255

Arg Pro Asp

```
<210> SEQ ID NO 137
<211> LENGTH: 283
<212> TYPE: PRT
<213> ORGANISM: Tepidiphilus sp. J18

<400> SEQUENCE: 137
```

Met Ala Ile Asp Tyr His Lys Leu Leu Asn Phe Pro Ile Pro Glu Val
1               5                   10                  15

Arg Glu Arg Arg Thr Lys Arg Asp Ser Ala Phe Tyr Ala Leu Ser Ile
            20                  25                  30

Gly Leu Gly Gln Asp Pro Leu Asp Glu Arg Gln Leu Asp Phe Val Asp
        35                  40                  45

Pro Leu Arg Pro Gln Met Lys Thr Met Pro Ser Met Val Val Val Ile
    50                  55                  60

Gly His Pro Gly Phe Trp Leu Arg Asn Pro Glu Thr Gly Val Asp Ala
65                  70                  75                  80

Val Arg Leu Val His Gly Glu Gln Gly Phe Arg Ile His Arg Pro Leu
                85                  90                  95

Pro Val Glu Gly Glu Phe Val Gly Lys Thr Arg Val Thr Gly Leu Val
            100                 105                 110

Asp Lys Gly Ala Gly Lys Gly Ala Leu Leu Tyr Ser Glu Lys Glu Val
        115                 120                 125

Arg Gly Ser Asp Gly Thr Leu Tyr Ala Thr Ala Thr Ser Thr Thr Phe
130                 135                 140

Leu Arg Gly Asp Gly Gly Phe Gly Gly Pro Ser Gly Pro Val Lys Glu
145                 150                 155                 160

Pro His Pro Leu Pro Asp Thr Ala Pro Glu Leu His Leu Asp Leu Ser
                165                 170                 175

Thr Arg Pro Glu Gln Ala Leu Tyr Tyr Arg Leu Asn Gly Asp Asp Asn
            180                 185                 190

Pro Leu His Ser Asp Pro Ser Val Ala Ala Lys Ala Gly Phe Pro Arg
        195                 200                 205

Pro Ile Leu His Gly Leu Cys Thr Leu Gly Val Val Thr His Ala Leu
210                 215                 220

Ile Arg Thr Phe Ala Asp Tyr Asp Ala Thr Arg Leu Arg Ala Leu Asp
225                 230                 235                 240

Leu Arg Phe Ser Ala Pro Val Phe Pro Gly Glu Thr Ile Arg Thr Glu
                245                 250                 255

Met Trp Arg Asp Gly Ser Phe Arg Ala Arg Val Leu Glu Arg Asp Val
            260                 265                 270

Val Val Ile Asn Asn Gly Lys Ala Glu Phe Ala
        275                 280

<210> SEQ ID NO 138
<211> LENGTH: 283
<212> TYPE: PRT
<213> ORGANISM: Oceanibaculum indicum

<400> SEQUENCE: 138

Met Ala Ile Glu Tyr Glu Lys Leu Leu Asn Phe Pro Ile Pro Glu Val
1               5                   10                  15

Arg Gln His Leu Thr Lys Arg Asp Ser Val Phe Tyr Ala Leu Ser Val
                20                  25                  30

Gly Leu Gly Met Asp Pro Met Asp Glu Arg Gln Leu Asp Phe Val Asp
            35                  40                  45

His His Arg Glu Met Lys Ala Met Pro Ser Met Ala Val Val Leu Gly
        50                  55                  60

His Pro Gly Phe Trp Leu Arg Asn Pro Glu Thr Gly Val Asp Ala Val
65                  70                  75                  80

Arg Val Val His Gly Glu Gln Gly Ile Glu Ile His Lys Pro Leu Pro
                85                  90                  95

Val Glu Gly Ala Ile Ile Gly Thr Thr Arg Val Thr Gly Ile Val Asp
            100                 105                 110

Lys Gly Glu Gly Lys Gly Ala Leu Leu Tyr Ser Glu Lys Gln Val Arg
        115                 120                 125

Gly Ala Asp Gly Thr Leu Tyr Ala Thr Thr Arg Ser Thr Thr Phe Leu
130                 135                 140

Arg Gly Asp Gly Gly Phe Gly Gly Pro Ser Gly Pro Val Lys Pro Pro
145                 150                 155                 160

His Pro Val Pro Glu Gly Glu Pro Asp Met Val Val Asp Leu Pro Thr
            165                 170                 175

Arg Pro Glu Gln Ala Leu Tyr Tyr Arg Leu Asn Gly Asp Asp Asn Pro
            180                 185                 190

Leu His Ala Ser Pro Ser Ile Ala Ala Lys Ala Gly Phe Pro Arg Pro
            195                 200                 205

Ile Leu His Gly Leu Cys Thr Leu Gly Leu Val Thr His Ala Leu Ile
            210                 215                 220

Arg Ala Leu Ala Asn Tyr Asp Ala Ala Leu Lys Ser Leu Asp Leu
225                 230                 235                 240

Arg Phe Ser Ser Pro Val Tyr Pro Gly Glu Thr Ile Arg Thr Glu Ile
            245                 250                 255

Trp Arg Asp Gly Ala Phe Arg Ala Arg Leu Leu Glu Arg Asp Val Val
            260                 265                 270

Val Val Asn Asn Gly Lys Ala Val Ile His Gly
            275                 280

<210> SEQ ID NO 139
<211> LENGTH: 285
<212> TYPE: PRT
<213> ORGANISM: Acidibrevibacterium fodinaquatile

<400> SEQUENCE: 139

Met Ala Ile Asp Pro Glu Lys Leu Leu Asn Tyr Pro Ile Pro Glu Val
1               5                   10                  15

Arg Gln Gln Val Thr Gln Arg Asp Thr Ile Phe Tyr Ala Leu Ser Ile
            20                  25                  30

Gly Leu Gly Gln Asp Pro Met Asp Arg Arg Gln Leu Asp Phe Leu Asp
            35                  40                  45

His His Arg Ala Leu Lys Ala Phe Pro Ser Ile Ala Val Val Leu Gly
        50                  55                  60

His Pro Gly Phe Trp Ala Ala Arg Pro Asp Thr Gly Ile Asp Ala Val
65                  70                  75                  80

Arg Val Val His Gly Glu Gln Gly Ile Val Trp His His Pro Ile Pro
                85                  90                  95

Val Glu Gly Glu Ile Ile Gly Arg Thr Arg Ile Thr Gly Leu Ile Asp
            100                 105                 110

Lys Gly Ala Gly Lys Gly Ala Leu Met Tyr Ser Glu Lys Gln Val Ile
            115                 120                 125

Glu Ala Ala Ser Gly Lys Leu Leu Ala Thr Leu Thr Ser Thr Thr Phe
            130                 135                 140

Leu Arg Gly Asp Gly Gly Phe Gly Gly Pro Ser Gly Pro Val Lys Pro
145                 150                 155                 160

Val His Pro Val Pro Glu Arg Ala Pro Ala Leu Ser Leu Asp Leu Ala
            165                 170                 175

Thr Arg Pro Glu Gln Ala Leu Tyr Tyr Arg Leu Asn Gly Asp Asp Asn
            180                 185                 190

Pro Leu His Ala Asp Pro Asp Phe Ala Ala Arg Ala Gly Phe Pro Arg
            195                 200                 205

Pro Ile Leu His Gly Leu Cys Thr Leu Gly Val Val Cys His Ala Leu
            210                 215                 220

Leu Lys Thr Leu Cys Asp Tyr Asp Pro Ala Gly Leu Lys Glu Met Asp
225                 230                 235                 240

Leu Arg Phe Ser Ser Pro Val Tyr Pro Gly Glu Thr Ile Arg Thr Glu 245                 250                 255
Ile Trp Pro Glu Glu Gly Ala Phe Arg Ala Arg Val Val Glu Arg Asp
        260                 265                 270

Val Ile Val Val Asn Asn Gly Arg Val Val Arg Ala Arg
        275                 280                 285

<210> SEQ ID NO 140
<211> LENGTH: 291
<212> TYPE: PRT
<213> ORGANISM: Methylobacterium aquaticum

<400> SEQUENCE: 140

Met Ala Phe Thr Tyr Glu Ser Leu Met Ser His His Ile Pro Glu Val
1               5                   10                  15

Arg Gln Arg Leu Ser Lys Arg Asp Ser Val Leu Tyr Ala Leu Ser Val
            20                  25                  30

Gly Phe Gly Gln Asp Pro Leu Asp Thr Ser Gln Leu Glu Phe Val Asp
        35                  40                  45

Ala His Arg His Leu Lys Ala Val Pro Met Met Ser Val Val Leu Ala
    50                  55                  60

His Pro Gly Phe Trp Met Ala Asp Pro Ala Thr Gly Ile Asp Ala Val
65                  70                  75                  80

Arg Val Val His Gly Glu Gln Arg Ile Ala Met His Arg Pro Leu Pro
                85                  90                  95

Val Glu Gly Glu Val Ile Gly Thr Thr Arg Ile Thr Gly Leu Val Asp
            100                 105                 110

Lys Gly Glu Gly Arg Gly Ala Leu Met Tyr Ser Glu Lys Val Val Arg
        115                 120                 125

Asp Ala Glu Thr Gly Thr Leu Leu Ala Thr Thr Lys Ser Thr Thr Phe
    130                 135                 140

Leu Arg Gly Asn Gly Gly Phe Gly Gly Pro Pro Gly Pro Val Ala Glu
145                 150                 155                 160

Pro His Ser Pro Pro Glu Thr Pro Pro Asp Ser Val Val Glu Met Pro
                165                 170                 175

Thr Arg Pro Glu Gln Ala Leu Tyr Tyr Arg Leu Asn Gly Asp Asp Asn
            180                 185                 190

Pro Leu His Ala Asp Pro Ala Val Ala Ala Arg Ala Gly Phe Pro Arg
        195                 200                 205

Pro Ile Leu His Gly Leu Cys Thr Leu Gly Ile Val Gly His Ala Leu
    210                 215                 220

Leu Arg Val Leu Gly Asp Tyr Asp Ser Ala Arg Phe Arg Glu Leu Ala
225                 230                 235                 240

Met Arg Phe Ser Ala Pro Val Tyr Pro Gly Glu Thr Val Arg Val Glu
                245                 250                 255

Ile Trp Arg Asp Gly Ser Phe Arg Ala Arg Val Pro Glu Arg Asp Val
            260                 265                 270

Val Val Ile Asn Asn Gly Arg Ala Val Phe Ala Ala Pro Glu Glu Gly
        275                 280                 285

Ala Ala Arg
    290

<210> SEQ ID NO 141
<211> LENGTH: 283
<212> TYPE: PRT
<213> ORGANISM: Roseomonas cervicalis

<400> SEQUENCE: 141

Met Ile Asn His Glu Lys Leu Leu Asn Tyr Ala Ile Pro Glu Val Arg
1               5                   10                  15

Gln Arg Val Thr Pro Arg Asp Ala Val Leu Tyr Ala Leu Ser Ile Gly
            20                  25                  30

Phe Gly Gln Asp Pro Met Glu Arg Gln Ile Pro Phe Val Ser Thr
        35                  40                  45

His Arg Gly Pro Leu Val Val Pro Ala Met Ala Val Val Leu Gly His
    50                  55                  60

Pro Gly Phe Trp Leu Gly Arg Pro Asp Thr Gly Val Asp Ala Val Lys
65                  70                  75                  80

Leu Val His Gly Glu Gln Glu Ile Glu Leu His Ala Pro Ile Pro Ala
                85                  90                  95

Glu Gly Glu Val Ile Gly Gln Thr Arg Val Thr Gly Ile Val Asp Lys
            100                 105                 110

Gly Glu Gly Lys Gly Ala Leu Leu Tyr Ser Glu Lys Arg Leu Thr Asp
        115                 120                 125

Ala Ala Ser Gly Ala Leu Leu Ala Val Thr Arg Ser Thr Thr Phe Leu
    130                 135                 140

Arg Gly Asp Gly Gly Phe Gly Gly Pro Ser Gly Pro Val Arg Pro Pro
145                 150                 155                 160

Asn Pro Met Pro Glu Ser Ala Pro Asp Ile Thr Leu Asp Leu Pro Thr
                165                 170                 175

Arg Pro Glu Gln Ala Phe Tyr Tyr Arg Leu Asn Gly Asp Asp Asn Pro
            180                 185                 190

Leu His Thr Glu Pro Glu Val Ala Ala Arg Ala Gly Phe Pro Arg Pro
        195                 200                 205

Ile Leu His Gly Leu Cys Thr Leu Gly Val Val Thr His Ala Leu Leu
    210                 215                 220

Arg Glu Leu Cys Gly Tyr Asp Pro Ala Arg Leu Arg Ala Leu Ser Leu
225                 230                 235                 240

Arg Phe Ser Ala Pro Val Phe Pro Gly Glu Thr Ile Arg Thr Glu Ile
                245                 250                 255

Trp Arg Asp Gly Ala Phe Arg Ala Arg Val Val Glu Arg Asp Ile Ile
            260                 265                 270

Val Val Asn Asn Gly Lys Ala Glu Ile Ala Ala
        275                 280

<210> SEQ ID NO 142
<211> LENGTH: 280
<212> TYPE: PRT
<213> ORGANISM: Alcanivorax sp. 6-D-6

<400> SEQUENCE: 142

Met Ala Ile Asp Pro Gln His Leu Leu Asn Tyr Pro Ile Pro Glu Val
1               5                   10                  15

Arg Gln Thr Leu Thr Glu Lys Asp Thr Ala Phe Tyr Ala Leu Ser Val
            20                  25                  30

Gly Val Gly Thr Asp Pro Leu Asp Glu Lys Gln Leu Lys Phe Val Asp
        35                  40                  45

Ser Ala Arg Asp Phe Ser Ala Leu Pro Ser Ile Ala Val Val Leu Gly
    50                  55                  60

His Pro Gly Phe Trp Val Ala Arg Asp Asp Thr Gly Ile Asp Ala Val
65                  70                  75                  80

-continued

Arg Val Val His Gly Glu Gln Arg Ile Gln Trp His Lys Pro Leu Pro
            85                  90                  95

Val Ser Gly Glu Val Val Gly Asn Thr Arg Val Thr Gly Val Val Asp
           100                 105                 110

Lys Gly Asn Asn Ala Leu Met Tyr Ser Asp Lys Glu Leu Arg Asp Gly
           115                 120                 125

Asn Gly Asp Leu Leu Ala Thr Ala Gly Met Thr Thr Val Leu Arg Gly
           130                 135                 140

Gln Gly Gly Phe Gly Gly Asp Ser Glu Pro Leu His Ala Val His Thr
145                 150                 155                 160

Leu Pro Asp Ser Glu Pro Asp Ile Ser Val Asp Leu Pro Thr Arg Pro
                165                 170                 175

Glu Gln Ala Leu Tyr Tyr Arg Leu Asn Gly Asp Asp Asn Pro Leu His
                180                 185                 190

Ser Asn Pro Ala Thr Ala Glu Ala Ala Gly Tyr Pro Arg Pro Ile Leu
                195                 200                 205

His Gly Leu Cys Thr Leu Gly Val Val Phe His Ala Leu Phe Arg Glu
           210                 215                 220

Leu Val Asp Tyr Gln Glu Asp Arg Leu Lys Ala Met Ser Leu Arg Phe
225                 230                 235                 240

Ser Ser Pro Val Phe Pro Gly Glu Thr Ile Arg Thr Glu Ile Trp Arg
                245                 250                 255

Asp Gly Ser Phe Arg Ala Arg Val Glu Arg Asp Val Val Val
                260                 265                 270

Asn Asn Gly Lys Leu Asp Phe Val
           275                 280

<210> SEQ ID NO 143
<211> LENGTH: 134
<212> TYPE: PRT
<213> ORGANISM: Escherichia coli

<400> SEQUENCE: 143

Met Asn Thr Leu His Phe Glu Ile Gly Gln Lys Ala Ser Leu Thr Lys
1               5                   10                  15

Arg Phe Gly Ala Ala Glu Val Glu Ala Phe Ala Gly Leu Ser Glu Asp
            20                  25                  30

Phe Asn Pro Leu His Leu Asp Ser Ala Phe Ala Ala Thr Thr Pro Phe
        35                  40                  45

Glu Arg Pro Ile Val His Gly Met Leu Leu Ala Ser Leu Phe Ser Gly
    50                  55                  60

Leu Leu Gly Gln Gln Leu Pro Gly Lys Gly Thr Val Tyr Leu Gly Gln
65                  70                  75                  80

Ser Leu Ser Phe Lys Gln Pro Val Phe Val Gly Asp Glu Val Thr Ala
                85                  90                  95

Glu Val Glu Ile Ile Ala Met Arg Ser Asp Lys Pro Ile Ile Thr Leu
            100                 105                 110

Ala Thr Arg Ile Leu Ala Ala Gly Gly Ala Leu Ala Val Thr Gly Glu
        115                 120                 125

Ala Val Val Lys Val Gly
    130

<210> SEQ ID NO 144
<211> LENGTH: 136
<212> TYPE: PRT
<213> ORGANISM: Vibrio tapetis

<400> SEQUENCE: 144

Met Thr Leu Lys Val Gly Gln Val Ala Thr Ile Glu Lys Cys Leu Asp
1               5                   10                  15

Lys Asn Ser Val Ala Gln Phe Ala Thr Leu Ala Glu Asp Tyr Asn Pro
            20                  25                  30

Val His Leu Asp Glu Glu Phe Ala Ala Thr Thr Pro Phe Glu Arg Pro
        35                  40                  45

Ile Val His Gly Met Leu Ala Ser Ser Leu Val Ser Gly Ile Leu Ala
    50                  55                  60

Ser Lys Leu Pro Gly Ser Gly Ser Ile Tyr Leu Gly Gln Thr Leu Lys
65                  70                  75                  80

Phe Val Cys Pro Ile Phe Val Gly Glu Thr Ile Thr Ala Lys Val Glu
                85                  90                  95

Val Thr His Ile Arg Glu Asp Lys Pro Ile Ala Thr Leu Ala Thr Gln
            100                 105                 110

Ile Phe Asn Gln Ala Gly Glu Leu Ala Val Ser Gly Glu Ala Thr Val
        115                 120                 125

Arg Tyr Pro Val Val Asn Asn Glu
    130                 135

<210> SEQ ID NO 145
<211> LENGTH: 133
<212> TYPE: PRT
<213> ORGANISM: Shewanella halifaxensis

<400> SEQUENCE: 145

Met Ala Leu Glu Val Gly Gln Ser Ser Ala Ile Glu Lys Cys Leu Asp
1               5                   10                  15

Gln Glu Ser Val Val Gln Phe Ala Ser Leu Ala Glu Asp Tyr Asn Pro
            20                  25                  30

Val His Leu Asp Ala Lys Phe Ala Ala Ser Thr Pro Phe Glu Arg Pro
        35                  40                  45

Ile Val His Gly Met Leu Ala Ser Ser Leu Ile Ser Gly Leu Leu Ala
    50                  55                  60

Ser Glu Leu Pro Gly Ser Gly Thr Ile Tyr Leu Gly Gln Thr Leu Lys
65                  70                  75                  80

Phe Val Cys Pro Ile Tyr Val Gly Glu Thr Ile Thr Ala Lys Val Thr
                85                  90                  95

Val Lys His Ile Arg Glu Asp Lys Pro Ile Ala Thr Leu Ala Thr Gln
            100                 105                 110

Val Phe Asn Gln Asp Gly Lys Leu Ala Val Asp Gly Glu Ala Thr Val
        115                 120                 125

Arg Tyr Ile Val Gly
    130

<210> SEQ ID NO 146
<211> LENGTH: 140
<212> TYPE: PRT
<213> ORGANISM: Desulfobacterales bacterium SG8_35_2

<400> SEQUENCE: 146

Met Gly Asn Thr Phe Lys Val Gly Asp Lys Ala Phe Leu Ser Lys Ala
1               5                   10                  15

Phe Thr Glu Glu Glu Val Phe Gln Phe Ala Lys Ile Ser Ala Asp Arg
            20                  25                  30

Asn Pro Leu His Leu Asp Lys Asp Phe Gly Ser Ala Ser Ile Phe Gly
            35                  40                  45

Gln Arg Ile Val His Gly Met Leu Val Ala Ser Leu Phe Ser Gly Leu
 50                  55                  60

Ile Gly Met Glu Leu Pro Gly Pro Gly Ser Ile Tyr Leu Gly Gln Ser
 65                  70                  75                  80

Leu Ser Phe Lys Ala Pro Val Ala Ile Gly Glu Gln Val Thr Ala Ser
                85                  90                  95

Val Glu Ile Ile Lys Ile Arg Gln Asp Lys Pro Ile Ile Thr Leu Gln
               100                 105                 110

Thr Val Cys Ile Asn Ser Glu Gly Thr Ile Ala Ile Glu Gly Glu Ala
            115                 120                 125

Val Val Lys Val Ala Met Phe Ser Arg His Gly Asn
            130                 135                 140

<210> SEQ ID NO 147
<211> LENGTH: 141
<212> TYPE: PRT
<213> ORGANISM: Thiorhodococcus drewsii

<400> SEQUENCE: 147

Met Ala Arg Glu Leu Lys Ile Gly Asp Lys Ala Thr Ile Thr Arg Arg
 1                   5                  10                  15

Phe Ser Asp Ala Asp Val Arg Gln Phe Ala Glu Leu Ser Thr Asp His
                20                  25                  30

Asn Pro Ile His Leu Asp Pro Asp Tyr Ala Ala Glu Thr Gln Phe Lys
            35                  40                  45

Gln Arg Ile Val His Gly Ala Leu Val Gly Ser Leu Phe Ser Ala Leu
 50                  55                  60

Leu Gly Glu His Leu Pro Gly Asn Gly Ile Tyr Met Gly Gln Thr
 65                  70                  75                  80

Leu Gln Phe Lys Ala Pro Val Phe Leu Asp Met Glu Val Ile Ala Ser
                85                  90                  95

Val Glu Ile Thr Ser Ile His Glu Arg Lys Pro Ile Val Thr Leu Ser
               100                 105                 110

Thr Gln Cys Val Asp Ala Glu Gly Lys Thr Leu Ile Thr Gly Glu Ala
            115                 120                 125

Val Met Tyr Val Pro Trp Leu Lys Glu Ala Ala Ser Ala
            130                 135                 140

<210> SEQ ID NO 148
<211> LENGTH: 130
<212> TYPE: PRT
<213> ORGANISM: Ferrimonas senticii

<400> SEQUENCE: 148

Met Ser Leu Leu Val Gly Gln Ser Ala Ser Ile Thr Lys Val Phe Gly
 1                   5                  10                  15

Arg Asp Glu Val Ser Ala Phe Ala Asp Leu Ser Glu Asp Arg Asn Pro
                20                  25                  30

Val His Leu Asp Ala Asn Phe Ala Ala Gln Thr Pro Phe Lys Gln Pro
            35                  40                  45

Ile Val His Gly Met Leu Leu Ser Ser Leu Leu Ser Ala Leu Leu Gly
 50                  55                  60

Gln His Leu Pro Gly Glu Gly Thr Ile Tyr Leu Gly Gln Thr Leu Lys
 65                  70                  75                  80

```
Phe Val Arg Pro Val Tyr Val Gly Asp Ala Val Thr Ala Thr Val Thr
                85                  90                  95

Val Ser Asp Ile Arg Asp Asp Lys Pro Val Val Thr Leu Thr Thr Glu
            100                 105                 110

Val Phe Asp Lys His Gly Lys Pro Cys Val Gln Gly Glu Ala Val Val
        115                 120                 125

Arg Val
    130

<210> SEQ ID NO 149
<211> LENGTH: 135
<212> TYPE: PRT
<213> ORGANISM: Desulfatitalea sp. BRH_c12

<400> SEQUENCE: 149

Met Ala Gln Ala Leu His Val Gly Gln Gln Ala Ser Ile Lys Lys Ser
1               5                   10                  15

Phe Ser Ser Gly Glu Val Glu Ala Tyr Ala Asn Leu Ser Glu Asp Arg
            20                  25                  30

Asn Pro Ile His Leu Asp Glu Lys Ala Ala Glu Ser Val Phe Gly
        35                  40                  45

Arg Arg Val Val His Gly Met Leu Val Ser Ser Leu Phe Ser Ala Leu
    50                  55                  60

Leu Gly Gln His Leu Pro Gly Glu Gly Thr Ile Phe Leu Gly Leu Asp
65                  70                  75                  80

Ile Gln Phe Lys Gly Pro Val Phe Ile Gly Glu Val Thr Ala Phe
                85                  90                  95

Val Lys Ile Leu Thr Ile Arg Glu Asp Lys Pro Ile Val Thr Leu Arg
            100                 105                 110

Ala Trp Cys Glu Asn Ala Arg Gly Glu Thr Val Val Asp Gly Gln Ala
        115                 120                 125

Val Ala Lys Ala Val Leu Gln
    130             135

<210> SEQ ID NO 150
<211> LENGTH: 138
<212> TYPE: PRT
<213> ORGANISM: Thiofilum flexile

<400> SEQUENCE: 150

Met Pro Arg Glu Leu Lys Val Gly Asp Lys Val Ser Val Thr Arg Gln
1               5                   10                  15

Phe Thr Asp Gln Asp Val Arg Ile Phe Ala Asp Leu Ser Thr Asp His
            20                  25                  30

Asn Pro Val His Leu Asp Glu Ala Phe Ala Ala Thr Thr Gln Phe Lys
        35                  40                  45

Gln Arg Ile Val His Gly Met Leu Val Gly Ser Met Phe Ser Gly Leu
    50                  55                  60

Ile Gly Glu Glu Leu Pro Gly His Gly Ser Ile Tyr Met Thr Gln Asn
65                  70                  75                  80

Leu Asn Phe Lys Ala Pro Val Tyr Leu Asn Thr Asp Val Thr Ala Thr
                85                  90                  95

Val Glu Ile Thr Ser Ile Arg Glu Gly Lys Pro Ile Val Thr Leu Lys
            100                 105                 110

Thr Thr Cys Thr Asp Lys Asp Gly Lys Val Leu Ile Gln Gly Glu Ala
        115                 120                 125
```

Val Met Tyr Val Pro Trp Leu Lys Lys Ala
    130                 135

<210> SEQ ID NO 151
<211> LENGTH: 133
<212> TYPE: PRT
<213> ORGANISM: Spongiibacter sp. KMU-166

<400> SEQUENCE: 151

Met Asp Ile Gln Phe Glu Ile Gly Asn Thr Ala Thr Leu Ala Lys Thr
1               5                   10                  15

Phe Thr Glu Gly Asp Val Leu Gln Phe Ala Ser Leu Ser Glu Asp Arg
            20                  25                  30

Asn Pro Ile His Ile Asp Pro Glu Ala Gly Gly Ala Ser Val Phe Gly
        35                  40                  45

Ala Gln Val Val His Gly Met Leu Val Ala Ser Leu Ile Ser Gly Leu
    50                  55                  60

Leu Gly Leu His Leu Pro Gly Pro Gly Thr Ile Tyr Leu Gly Gln Asp
65                  70                  75                  80

Leu Lys Phe Lys Ala Pro Val Phe Ile Gly Asp Glu Ile Thr Ala Ile
                85                  90                  95

Val Glu Val Thr Ala Ile Arg Arg Asp Lys Pro Ile Ala Thr Leu Arg
            100                 105                 110

Thr Tyr Cys Val Asn Gln Lys Asp Thr Val Val Ile Asp Gly Val Ala
        115                 120                 125

Thr Val Lys Tyr Ala
    130

<210> SEQ ID NO 152
<211> LENGTH: 130
<212> TYPE: PRT
<213> ORGANISM: Hymenobacter sp. CCM 8763

<400> SEQUENCE: 152

Met Leu Glu Ile Gly Gln Lys Ala Arg Leu Ser Lys Thr Ile Thr Asp
1               5                   10                  15

Ala Asp Val Arg Ala Phe Ala Gln Leu Ser Leu Asp Thr Asn Pro Val
            20                  25                  30

His Leu Asp Glu Glu Tyr Ala Gln Ala Ser Leu Phe Gly Gln Arg Ile
        35                  40                  45

Ser His Gly Met Leu Tyr Gly Ser Leu Ile Ser Ala Val Leu Gly Thr
    50                  55                  60

Gln Leu Pro Gly Pro Gly Ala Ile Tyr Met Gly Gln Thr Phe Lys Phe
65                  70                  75                  80

Leu Lys Pro Val Phe Leu Asn Asp Thr Ile Thr Ala Glu Val Glu Val
                85                  90                  95

Leu Thr Leu Asn Glu Glu Lys His Ile Ala Thr Leu Gln Thr Thr Cys
            100                 105                 110

Val Asn Gln Asp Gly Lys Leu Val Leu Thr Gly Glu Ala Thr Met Lys
        115                 120                 125

Tyr Ala
    130

<210> SEQ ID NO 153
<211> LENGTH: 1671
<212> TYPE: PRT
<213> ORGANISM: Aspergillus parasiticus

<400> SEQUENCE: 153

```
Met Val Ile Gln Gly Lys Arg Leu Ala Ala Ser Ser Ile Gln Leu Leu
1               5                   10                  15

Ala Ser Ser Leu Asp Ala Lys Lys Leu Cys Tyr Glu Tyr Asp Glu Arg
            20                  25                  30

Gln Ala Pro Gly Val Thr Gln Ile Thr Glu Glu Ala Pro Thr Glu Gln
        35                  40                  45

Pro Pro Leu Ser Thr Pro Pro Ser Leu Pro Gln Thr Pro Asn Ile Ser
    50                  55                  60

Pro Ile Ser Ala Ser Lys Ile Val Ile Asp Asp Val Ala Leu Ser Arg
65                  70                  75                  80

Val Gln Ile Val Gln Ala Leu Val Ala Arg Lys Leu Lys Thr Ala Ile
                85                  90                  95

Ala Gln Leu Pro Thr Ser Lys Ser Ile Lys Glu Leu Ser Gly Gly Arg
            100                 105                 110

Ser Ser Leu Gln Asn Glu Leu Val Gly Asp Ile His Asn Glu Phe Ser
        115                 120                 125

Ser Ile Pro Asp Ala Pro Glu Gln Ile Leu Leu Arg Asp Phe Gly Asp
    130                 135                 140

Ala Asn Pro Thr Val Gln Leu Gly Lys Thr Ser Ser Ala Ala Val Ala
145                 150                 155                 160

Lys Leu Ile Ser Ser Lys Met Pro Ser Asp Phe Asn Ala Asn Ala Ile
                165                 170                 175

Arg Ala His Leu Ala Asn Lys Trp Gly Leu Gly Pro Leu Arg Gln Thr
            180                 185                 190

Ala Val Leu Leu Tyr Ala Ile Ala Ser Glu Pro Pro Ser Arg Leu Ala
        195                 200                 205

Ser Ser Ser Ala Ala Glu Glu Tyr Trp Asp Asn Val Ser Ser Met Tyr
    210                 215                 220

Ala Glu Ser Cys Gly Ile Thr Leu Arg Pro Arg Gln Asp Thr Met Asn
225                 230                 235                 240

Glu Asp Ala Met Ala Ser Ser Ala Ile Asp Pro Ala Val Val Ala Glu
                245                 250                 255

Phe Ser Lys Gly His Arg Arg Leu Gly Val Gln Gln Phe Gln Ala Leu
            260                 265                 270

Ala Glu Tyr Leu Gln Ile Asp Leu Ser Gly Ser Gln Ala Ser Gln Ser
        275                 280                 285

Asp Ala Leu Val Ala Glu Leu Gln Gln Lys Val Asp Leu Trp Thr Ala
    290                 295                 300

Glu Met Thr Pro Glu Phe Leu Ala Gly Ile Ser Pro Met Leu Asp Val
305                 310                 315                 320

Lys Lys Ser Arg Arg Tyr Gly Ser Trp Trp Asn Met Ala Arg Gln Asp
                325                 330                 335

Val Leu Ala Phe Tyr Arg Arg Pro Ser Tyr Ser Glu Phe Val Asp Asp
            340                 345                 350

Ala Leu Ala Phe Lys Val Phe Leu Asn Arg Leu Cys Asn Arg Ala Asp
        355                 360                 365

Glu Ala Leu Leu Asn Met Val Arg Ser Leu Ser Cys Asp Ala Tyr Phe
    370                 375                 380

Lys Gln Gly Ser Leu Pro Gly Tyr His Ala Ala Ser Arg Leu Leu Glu
385                 390                 395                 400

Gln Ala Ile Thr Ser Thr Val Ala Asp Cys Pro Lys Ala Arg Leu Ile
                405                 410                 415
```

-continued

Leu Pro Ala Val Gly Pro His Thr Thr Ile Thr Lys Asp Gly Thr Ile
            420                 425                 430

Glu Tyr Ala Glu Ala Pro Arg Gln Gly Val Ser Gly Pro Thr Ala Tyr
            435                 440                 445

Ile Gln Ser Leu Arg Gln Gly Ala Ser Phe Ile Gly Leu Lys Ser Ala
    450                 455                 460

Asp Val Asp Thr Gln Ser Asn Leu Thr Asp Ala Leu Leu Asp Ala Met
465                 470                 475                 480

Cys Leu Ala Leu His Asn Gly Ile Ser Phe Val Gly Lys Thr Phe Leu
                485                 490                 495

Val Thr Gly Ala Gly Gln Gly Ser Ile Gly Ala Gly Val Val Arg Leu
            500                 505                 510

Leu Leu Glu Gly Gly Ala Arg Val Leu Val Thr Thr Ser Arg Glu Pro
        515                 520                 525

Ala Thr Thr Ser Arg Tyr Phe Gln Gln Met Tyr Asp Asn His Gly Ala
    530                 535                 540

Lys Phe Ser Glu Leu Arg Val Val Pro Cys Asn Leu Ala Ser Ala Gln
545                 550                 555                 560

Asp Cys Glu Gly Leu Ile Arg His Val Tyr Asp Pro Arg Gly Leu Asn
                565                 570                 575

Trp Asp Leu Asp Ala Ile Leu Pro Phe Ala Ala Ser Asp Tyr Ser
            580                 585                 590

Thr Glu Met His Asp Ile Arg Gly Gln Ser Glu Leu Gly His Arg Leu
            595                 600                 605

Met Leu Val Asn Val Phe Arg Val Leu Gly His Ile Val His Cys Lys
        610                 615                 620

Arg Asp Ala Gly Val Asp Cys His Pro Thr Gln Val Leu Leu Pro Leu
625                 630                 635                 640

Ser Pro Asn His Gly Ile Phe Gly Gly Asp Gly Met Tyr Pro Glu Ser
                645                 650                 655

Lys Leu Ala Leu Glu Ser Leu Phe His Arg Ile Arg Ser Glu Ser Trp
            660                 665                 670

Ser Asp Gln Leu Ser Ile Cys Gly Val Arg Ile Gly Trp Thr Arg Ser
        675                 680                 685

Thr Gly Leu Met Thr Ala His Asp Ile Ile Ala Glu Thr Val Glu Glu
    690                 695                 700

His Gly Ile Arg Thr Phe Ser Val Ala Glu Met Ala Leu Asn Ile Ala
705                 710                 715                 720

Met Leu Leu Thr Pro Asp Phe Val Ala His Cys Glu Asp Gly Pro Leu
                725                 730                 735

Asp Ala Asp Phe Thr Gly Ser Leu Gly Thr Leu Gly Ser Ile Pro Gly
            740                 745                 750

Phe Leu Ala Gln Leu His Gln Lys Val Gln Leu Ala Ala Glu Val Ile
        755                 760                 765

Arg Ala Val Gln Ala Glu Asp Glu His Glu Arg Phe Leu Ser Pro Gly
    770                 775                 780

Thr Lys Pro Thr Leu Gln Ala Pro Val Ala Pro Met His Pro Arg Ser
785                 790                 795                 800

Ser Leu Arg Val Gly Tyr Pro Arg Leu Pro Asp Tyr Glu Gln Glu Ile
                805                 810                 815

Arg Pro Leu Ser Pro Arg Leu Glu Arg Leu Gln Asp Pro Ala Asn Ala
            820                 825                 830

-continued

Val Val Val Val Gly Tyr Ser Glu Leu Gly Pro Trp Gly Ser Ala Arg
         835             840             845

Leu Arg Trp Glu Ile Glu Ser Gln Gly Gln Trp Thr Ser Ala Gly Tyr
850             855             860

Val Glu Leu Ala Trp Leu Met Asn Leu Ile Arg His Val Asn Asp Glu
865             870             875             880

Ser Tyr Val Gly Trp Val Asp Thr Gln Thr Gly Lys Pro Val Arg Asp
             885             890             895

Gly Glu Ile Gln Ala Leu Tyr Gly Asp His Ile Asp Asn His Thr Gly
         900             905             910

Ile Arg Pro Ile Gln Ser Thr Ser Tyr Asn Pro Glu Arg Met Glu Val
         915             920             925

Leu Gln Glu Val Ala Val Glu Glu Asp Leu Pro Glu Phe Glu Val Ser
930             935             940

Gln Leu Thr Ala Asp Ala Met Arg Leu Arg His Gly Ala Asn Val Ser
945             950             955             960

Ile Arg Pro Ser Gly Asn Pro Asp Ala Cys His Val Lys Leu Lys Arg
             965             970             975

Gly Ala Val Ile Leu Val Pro Lys Thr Val Pro Phe Val Trp Gly Ser
             980             985             990

Cys Ala Gly Glu Leu Pro Lys Gly Trp Thr Pro Ala Lys Tyr Gly Ile
         995             1000            1005

Pro Glu Asn Leu Ile His Gln Val Asp Pro Val Thr Leu Tyr Thr
    1010            1015            1020

Ile Cys Cys Val Ala Glu Ala Phe Tyr Ser Ala Gly Ile Thr His
    1025            1030            1035

Pro Leu Glu Val Phe Arg His Ile His Leu Ser Glu Leu Gly Asn
    1040            1045            1050

Phe Ile Gly Ser Ser Met Gly Gly Pro Thr Lys Thr Arg Gln Leu
    1055            1060            1065

Tyr Arg Asp Val Tyr Phe Asp His Glu Ile Pro Ser Asp Val Leu
    1070            1075            1080

Gln Asp Thr Tyr Leu Asn Thr Pro Ala Ala Trp Val Asn Met Leu
    1085            1090            1095

Leu Leu Gly Cys Thr Gly Pro Ile Lys Thr Pro Val Gly Ala Cys
    1100            1105            1110

Ala Thr Gly Val Glu Ser Ile Asp Ser Gly Tyr Glu Ser Ile Met
    1115            1120            1125

Ala Gly Lys Thr Lys Met Cys Leu Val Gly Gly Tyr Asp Asp Leu
    1130            1135            1140

Gln Glu Glu Ala Ser Tyr Gly Phe Ala Gln Leu Lys Ala Thr Val
    1145            1150            1155

Asn Val Glu Glu Glu Ile Ala Cys Gly Arg Gln Pro Ser Glu Met
    1160            1165            1170

Ser Arg Pro Met Ala Glu Ser Arg Ala Gly Phe Val Glu Ala His
    1175            1180            1185

Gly Cys Gly Val Gln Leu Leu Cys Arg Gly Asp Ile Ala Leu Gln
    1190            1195            1200

Met Gly Leu Pro Ile Tyr Ala Val Ile Ala Ser Ser Ala Met Ala
    1205            1210            1215

Ala Asp Lys Ile Gly Ser Ser Val Pro Ala Pro Gly Gln Gly Ile
    1220            1225            1230

Leu Ser Phe Ser Arg Glu Arg Ala Arg Ser Ser Met Ile Ser Val

```
                  1235                1240                1245
        Thr Ser Arg Pro Ser Ser Arg Ser Ser Thr Ser Ser Glu Val Ser
                  1250                1255                1260

Asp Lys Ser Ser Leu Thr Ser Ile Thr Ser Ile Ser Asn Pro Ala
                  1265                1270                1275

Pro Arg Ala Gln Arg Ala Arg Ser Thr Thr Asp Met Ala Pro Leu
                  1280                1285                1290

Arg Ala Ala Leu Ala Thr Trp Gly Leu Thr Ile Asp Asp Leu Asp
                  1295                1300                1305

Val Ala Ser Leu His Gly Thr Ser Thr Arg Gly Asn Asp Leu Asn
                  1310                1315                1320

Glu Pro Glu Val Ile Glu Thr Gln Met Arg His Leu Gly Arg Thr
                  1325                1330                1335

Pro Gly Arg Pro Leu Trp Ala Ile Cys Gln Lys Ser Val Thr Gly
                  1340                1345                1350

His Pro Lys Ala Pro Ala Ala Trp Met Leu Asn Gly Cys Leu
                  1355                1360                1365

Gln Val Leu Asp Ser Gly Leu Val Pro Gly Asn Arg Asn Leu Asp
                  1370                1375                1380

Thr Leu Asp Glu Ala Leu Arg Ser Ala Ser His Leu Cys Phe Pro
                  1385                1390                1395

Thr Arg Thr Val Gln Leu Arg Glu Val Lys Ala Phe Leu Leu Thr
                  1400                1405                1410

Ser Phe Gly Phe Gly Gln Lys Gly Gly Gln Val Val Gly Val Ala
                  1415                1420                1425

Pro Lys Tyr Phe Phe Ala Thr Leu Pro Arg Pro Glu Val Glu Gly
                  1430                1435                1440

Tyr Tyr Arg Lys Val Arg Val Arg Thr Glu Ala Gly Asp Arg Ala
                  1445                1450                1455

Tyr Ala Ala Ala Val Met Ser Gln Ala Val Val Lys Ile Gln Thr
                  1460                1465                1470

Gln Asn Pro Tyr Asp Glu Pro Asp Ala Pro Arg Ile Phe Leu Asp
                  1475                1480                1485

Pro Leu Ala Arg Ile Ser Gln Asp Pro Ser Thr Gly Gln Tyr Arg
                  1490                1495                1500

Phe Arg Ser Asp Ala Thr Pro Ala Leu Asp Asp Ala Leu Pro
                  1505                1510                1515

Pro Pro Gly Glu Pro Thr Glu Leu Val Lys Gly Ile Ser Ser Ala
                  1520                1525                1530

Trp Ile Glu Glu Lys Val Arg Pro His Met Ser Pro Gly Gly Thr
                  1535                1540                1545

Val Gly Val Asp Leu Val Pro Leu Ala Ser Phe Asp Ala Tyr Lys
                  1550                1555                1560

Asn Ala Ile Phe Val Glu Arg Asn Tyr Thr Val Arg Glu Arg Asp
                  1565                1570                1575

Trp Ala Glu Lys Ser Ala Asp Val Arg Ala Ala Tyr Ala Ser Arg
                  1580                1585                1590

Trp Cys Ala Lys Glu Ala Val Phe Lys Cys Leu Gln Thr His Ser
                  1595                1600                1605

Gln Gly Ala Gly Ala Ala Met Lys Glu Ile Glu Ile Glu His Gly
                  1610                1615                1620

Gly Asn Gly Ala Pro Lys Val Lys Leu Arg Gly Ala Ala Gln Thr
                  1625                1630                1635
```

```
Ala Ala Arg Gln Arg Gly Leu Glu Gly Val Gln Leu Ser Ile Ser
    1640                1645                1650

Tyr Gly Asp Asp Ala Val Ile Ala Val Ala Leu Gly Leu Met Ser
    1655                1660                1665

Gly Ala Ser
    1670

<210> SEQ ID NO 154
<211> LENGTH: 1888
<212> TYPE: PRT
<213> ORGANISM: Aspergillus parasiticus

<400> SEQUENCE: 154

Met Gly Ser Val Ser Arg Glu His Glu Ser Ile Pro Ile Gln Ala Ala
1               5                   10                  15

Gln Arg Gly Ala Ala Arg Ile Cys Ala Ala Phe Gly Gly Gln Gly Ser
            20                  25                  30

Asn Asn Leu Asp Val Leu Lys Gly Leu Glu Leu Tyr Lys Arg Tyr
        35                  40                  45

Gly Pro Asp Leu Asp Glu Leu Leu Asp Val Ala Ser Asn Thr Leu Ser
50                  55                  60

Gln Leu Ala Ser Ser Pro Ala Ala Ile Asp Val His Glu Pro Trp Gly
65                  70                  75                  80

Phe Asp Leu Arg Gln Trp Leu Thr Thr Pro Glu Val Ala Pro Ser Lys
                85                  90                  95

Glu Ile Leu Ala Leu Pro Pro Arg Ser Phe Pro Leu Asn Thr Leu Leu
            100                 105                 110

Ser Leu Ala Leu Tyr Cys Ala Thr Cys Arg Glu Leu Glu Leu Asp Pro
        115                 120                 125

Gly Gln Phe Arg Ser Leu Leu His Ser Ser Thr Gly His Ser Gln Gly
    130                 135                 140

Ile Leu Ala Ala Val Ala Ile Thr Gln Ala Glu Ser Trp Pro Thr Phe
145                 150                 155                 160

Tyr Asp Ala Cys Arg Thr Val Leu Gln Ile Ser Phe Trp Ile Gly Leu
                165                 170                 175

Glu Ala Tyr Leu Phe Thr Pro Ser Ser Ala Ala Ser Asp Ala Met Ile
            180                 185                 190

Gln Asp Cys Ile Glu His Gly Glu Gly Leu Leu Ser Ser Met Leu Ser
        195                 200                 205

Val Ser Gly Leu Ser Arg Ser Gln Val Glu Arg Val Ile Glu His Val
    210                 215                 220

Asn Lys Gly Leu Gly Glu Cys Asn Arg Trp Val His Leu Ala Leu Val
225                 230                 235                 240

Asn Ser His Glu Lys Phe Val Leu Ala Gly Pro Pro Gln Ser Leu Trp
                245                 250                 255

Ala Val Cys Leu His Val Arg Arg Ile Arg Ala Asp Asn Asp Leu Asp
            260                 265                 270

Gln Ser Arg Ile Leu Phe Arg Asn Arg Lys Pro Ile Val Asp Ile Leu
        275                 280                 285

Phe Leu Pro Ile Ser Ala Pro Phe His Thr Pro Tyr Leu Asp Gly Val
    290                 295                 300

Gln Asp Arg Val Ile Glu Ala Leu Ser Ser Ala Ser Leu Ala Leu His
305                 310                 315                 320

Ser Ile Lys Ile Pro Leu Tyr His Thr Gly Thr Gly Ser Asn Leu Gln
```

```
              325                 330                 335
Glu Leu Gln Pro His Gln Leu Ile Pro Thr Leu Ile Arg Ala Ile Thr
                340                 345                 350

Val Asp Gln Leu Asp Trp Pro Leu Val Cys Arg Gly Leu Asn Ala Thr
                355                 360                 365

His Val Leu Asp Phe Gly Pro Gly Gln Thr Cys Ser Leu Ile Gln Glu
            370                 375                 380

Leu Thr Gln Gly Thr Gly Val Ser Val Ile Gln Leu Thr Thr Gln Ser
385                 390                 395                 400

Gly Pro Lys Pro Val Gly Gly His Leu Ala Ala Val Asn Trp Glu Ala
                405                 410                 415

Glu Phe Gly Leu Arg Leu His Ala Asn Val His Gly Ala Ala Lys Leu
                420                 425                 430

His Asn Arg Met Thr Thr Leu Leu Gly Lys Pro Pro Val Met Val Ala
            435                 440                 445

Gly Met Thr Pro Thr Thr Val Arg Trp Asp Phe Val Ala Ala Val Ala
450                 455                 460

Gln Ala Gly Tyr His Val Glu Leu Ala Gly Gly Tyr His Ala Glu
465                 470                 475                 480

Arg Gln Phe Glu Ala Glu Ile Arg Arg Leu Ala Thr Ala Ile Pro Ala
                485                 490                 495

Asp His Gly Ile Thr Cys Asn Leu Leu Tyr Ala Lys Pro Thr Thr Phe
            500                 505                 510

Ser Trp Gln Ile Ser Val Ile Lys Asp Leu Val Arg Gln Gly Val Pro
            515                 520                 525

Val Glu Gly Ile Thr Ile Gly Ala Gly Ile Pro Ser Pro Glu Val Val
530                 535                 540

Gln Glu Cys Val Gln Ser Ile Gly Leu Lys His Ile Ser Phe Lys Pro
545                 550                 555                 560

Gly Ser Phe Glu Ala Ile His Gln Val Ile Gln Ile Ala Arg Thr His
                565                 570                 575

Pro Asn Phe Leu Ile Gly Leu Gln Trp Thr Ala Gly Arg Gly Gly Gly
                580                 585                 590

His His Ser Trp Glu Asp Phe His Gly Pro Ile Leu Ala Thr Tyr Ala
            595                 600                 605

Gln Ile Arg Ser Cys Pro Asn Ile Leu Leu Val Gly Ser Gly Phe
            610                 615                 620

Gly Gly Gly Pro Asp Thr Phe Pro Tyr Leu Thr Gly Gln Trp Ala Gln
625                 630                 635                 640

Ala Phe Gly Tyr Pro Cys Met Pro Phe Asp Gly Val Leu Leu Gly Ser
                645                 650                 655

Arg Met Met Val Ala Arg Glu Ala His Thr Ser Ala Gln Ala Lys Arg
                660                 665                 670

Leu Ile Ile Asp Ala Gln Gly Val Gly Asp Ala Asp Trp His Lys Ser
            675                 680                 685

Phe Asp Glu Pro Thr Gly Gly Val Thr Val Asn Ser Glu Phe Gly
            690                 695                 700

Gln Pro Ile His Val Leu Ala Thr Arg Gly Val Met Leu Trp Lys Glu
705                 710                 715                 720

Leu Asp Asn Arg Val Phe Ser Ile Lys Asp Thr Ser Lys Arg Leu Glu
                725                 730                 735

Tyr Leu Arg Asn His Arg Gln Glu Ile Val Ser Arg Leu Asn Ala Asp
                740                 745                 750
```

```
Phe Ala Arg Pro Trp Phe Ala Val Asp Gly His Gly Gln Asn Val Glu
        755                 760                 765
Leu Glu Asp Met Thr Tyr Leu Glu Val Leu Arg Arg Leu Cys Asp Leu
    770                 775                 780
Thr Tyr Val Ser His Gln Lys Arg Trp Val Asp Pro Ser Tyr Arg Ile
785                 790                 795                 800
Leu Leu Leu Asp Phe Val His Leu Leu Arg Glu Arg Phe Gln Cys Ala
                805                 810                 815
Ile Asp Asn Pro Gly Glu Tyr Pro Leu Asp Ile Ile Val Arg Val Glu
                820                 825                 830
Glu Ser Leu Lys Asp Lys Ala Tyr Arg Thr Leu Tyr Pro Glu Asp Val
                835                 840                 845
Ser Leu Leu Met His Leu Phe Ser Arg Arg Asp Ile Lys Pro Val Pro
        850                 855                 860
Phe Ile Pro Arg Leu Asp Glu Arg Phe Glu Thr Trp Phe Lys Lys Asp
865                 870                 875                 880
Ser Leu Trp Gln Ser Glu Asp Val Glu Ala Val Ile Gly Gln Asp Val
                885                 890                 895
Gln Arg Ile Phe Ile Gln Gly Pro Met Ala Val Gln Tyr Ser Ile
                900                 905                 910
Ser Asp Asp Glu Ser Val Lys Asp Ile Leu His Asn Ile Cys Asn His
            915                 920                 925
Tyr Val Glu Ala Leu Gln Ala Asp Ser Arg Glu Thr Ser Ile Gly Asp
930                 935                 940
Val His Ser Ile Thr Gln Lys Pro Leu Ser Ala Phe Pro Gly Leu Lys
945                 950                 955                 960
Val Thr Thr Asn Arg Val Gln Gly Leu Tyr Lys Phe Glu Lys Val Gly
                965                 970                 975
Ala Val Pro Glu Met Asp Val Leu Phe Glu His Ile Val Gly Leu Ser
            980                 985                 990
Lys Ser Trp Ala Arg Thr Cys Leu Met Ser Lys Ser Val Phe Arg Asp
        995                 1000                1005
Gly Ser Arg Leu His Asn Pro Ile Arg Ala Ala Leu Gln Leu Gln
    1010                1015                1020
Arg Gly Asp Thr Ile Glu Val Leu Leu Thr Ala Asp Ser Glu Ile
    1025                1030                1035
Arg Lys Ile Arg Leu Ile Ser Pro Thr Gly Asp Gly Gly Ser Thr
    1040                1045                1050
Ser Lys Val Val Leu Glu Ile Val Ser Asn Asp Gly Gln Arg Val
    1055                1060                1065
Phe Ala Thr Leu Ala Pro Asn Ile Pro Leu Ser Pro Glu Pro Ser
    1070                1075                1080
Val Val Phe Cys Phe Lys Val Asp Gln Lys Pro Asn Glu Trp Thr
    1085                1090                1095
Leu Glu Glu Asp Ala Ser Gly Arg Ala Glu Arg Ile Lys Ala Leu
    1100                1105                1110
Tyr Met Ser Leu Trp Asn Leu Gly Phe Pro Asn Lys Ala Ser Val
    1115                1120                1125
Leu Gly Leu Asn Ser Gln Phe Thr Gly Glu Glu Leu Met Ile Thr
    1130                1135                1140
Thr Asp Lys Ile Arg Asp Phe Glu Arg Val Leu Arg Gln Thr Ser
    1145                1150                1155
```

```
Pro Leu Gln Leu Gln Ser Trp Asn Pro Gln Gly Cys Val Pro Ile
1160                1165                1170

Asp Tyr Cys Val Val Ile Ala Trp Ser Ala Leu Thr Lys Pro Leu
1175                1180                1185

Met Val Ser Ser Leu Lys Cys Asp Leu Leu Asp Leu Leu His Ser
1190                1195                1200

Ala Ile Ser Phe His Tyr Ala Pro Ser Val Lys Pro Leu Arg Val
1205                1210                1215

Gly Asp Ile Val Lys Thr Ser Ser Arg Ile Leu Ala Val Ser Val
1220                1225                1230

Arg Pro Arg Gly Thr Met Leu Thr Val Ser Ala Asp Ile Gln Arg
1235                1240                1245

Gln Gly Gln His Val Val Thr Val Lys Ser Asp Phe Phe Leu Gly
1250                1255                1260

Gly Pro Val Leu Ala Cys Glu Thr Pro Phe Glu Leu Thr Glu Glu
1265                1270                1275

Pro Glu Met Val Val His Val Asp Ser Glu Val Arg Arg Ala Ile
1280                1285                1290

Leu His Ser Arg Lys Trp Leu Met Arg Glu Asp Arg Ala Leu Asp
1295                1300                1305

Leu Leu Gly Arg Gln Leu Leu Phe Arg Leu Lys Ser Glu Lys Leu
1310                1315                1320

Phe Arg Pro Asp Gly Gln Leu Ala Leu Leu Gln Val Thr Gly Ser
1325                1330                1335

Val Phe Ser Tyr Ser Pro Asp Gly Ser Thr Thr Ala Phe Gly Arg
1340                1345                1350

Val Tyr Phe Glu Ser Glu Ser Cys Thr Gly Asn Val Val Met Asp
1355                1360                1365

Phe Leu His Arg Tyr Gly Ala Pro Arg Ala Gln Leu Leu Glu Leu
1370                1375                1380

Gln His Pro Gly Trp Thr Gly Thr Ser Thr Val Ala Val Arg Gly
1385                1390                1395

Pro Arg Arg Ser Gln Ser Tyr Ala Arg Val Ser Leu Asp His Asn
1400                1405                1410

Pro Ile His Val Cys Pro Ala Phe Ala Arg Tyr Ala Gly Leu Ser
1415                1420                1425

Gly Pro Ile Val His Gly Met Glu Thr Ser Ala Met Met Arg Arg
1430                1435                1440

Ile Ala Glu Trp Ala Ile Gly Asp Ala Asp Arg Ser Arg Phe Arg
1445                1450                1455

Ser Trp His Ile Thr Leu Gln Ala Pro Val His Pro Asn Asp Pro
1460                1465                1470

Leu Arg Val Glu Leu Gln His Lys Ala Met Glu Asp Gly Glu Met
1475                1480                1485

Val Leu Lys Val Gln Ala Phe Asn Glu Arg Thr Glu Glu Arg Val
1490                1495                1500

Ala Glu Ala Asp Ala His Val Glu Gln Glu Thr Thr Ala Tyr Val
1505                1510                1515

Phe Cys Gly Gln Gly Ser Gln Arg Gln Gly Met Gly Met Asp Leu
1520                1525                1530

Tyr Val Asn Cys Pro Glu Ala Lys Ala Leu Trp Ala Arg Ala Asp
1535                1540                1545

Lys His Leu Trp Glu Lys Tyr Gly Phe Ser Ile Leu His Ile Val
```

```
                 1550                1555                1560
Gln Asn Asn Pro Pro Ala Leu Thr Val His Phe Gly Ser Gln Arg
    1565                1570                1575
Gly Arg Arg Ile Arg Ala Asn Tyr Leu Arg Met Met Gly Gln Pro
    1580                1585                1590
Pro Ile Asp Gly Arg His Pro Pro Ile Leu Lys Gly Leu Thr Arg
    1595                1600                1605
Asn Ser Thr Ser Tyr Thr Phe Ser Tyr Ser Gln Gly Leu Leu Met
    1610                1615                1620
Ser Thr Gln Phe Ala Gln Pro Ala Leu Ala Leu Met Glu Met Ala
    1625                1630                1635
Gln Phe Glu Trp Leu Lys Ala Gln Gly Val Val Gln Lys Gly Ala
    1640                1645                1650
Arg Phe Ala Gly His Ser Leu Gly Glu Tyr Ala Ala Leu Gly Ala
    1655                1660                1665
Cys Ala Ser Phe Leu Ser Phe Glu Asp Leu Ile Ser Leu Ile Phe
    1670                1675                1680
Tyr Arg Gly Leu Lys Met Gln Asn Ala Leu Pro Arg Asp Ala Asn
    1685                1690                1695
Gly His Thr Asp Tyr Gly Met Leu Ala Ala Asp Pro Ser Arg Ile
    1700                1705                1710
Gly Lys Gly Phe Glu Glu Ala Ser Leu Lys Cys Leu Val His Ile
    1715                1720                1725
Ile Gln Gln Glu Thr Gly Trp Phe Val Glu Val Asn Tyr Asn
    1730                1735                1740
Ile Asn Ser Gln Gln Tyr Val Cys Ala Gly His Phe Arg Ala Leu
    1745                1750                1755
Trp Met Leu Gly Lys Ile Cys Asp Asp Leu Ser Cys His Pro Gln
    1760                1765                1770
Pro Glu Thr Val Glu Gly Gln Glu Leu Arg Ala Met Val Trp Lys
    1775                1780                1785
His Val Pro Thr Val Glu Gln Val Pro Arg Glu Asp Arg Met Glu
    1790                1795                1800
Arg Gly Arg Ala Thr Ile Pro Leu Pro Gly Ile Asp Ile Pro Tyr
    1805                1810                1815
His Ser Thr Met Leu Arg Gly Glu Ile Glu Pro Tyr Arg Glu Tyr
    1820                1825                1830
Leu Ser Glu Arg Ile Lys Val Gly Asp Val Lys Pro Cys Glu Leu
    1835                1840                1845
Val Gly Arg Trp Ile Pro Asn Val Val Gly Gln Pro Phe Ser Val
    1850                1855                1860
Asp Lys Ser Tyr Val Gln Leu Val His Gly Ile Thr Gly Ser Pro
    1865                1870                1875
Arg Leu His Ser Leu Leu Gln Gln Met Ala
    1880                1885

<210> SEQ ID NO 155
<211> LENGTH: 2051
<212> TYPE: PRT
<213> ORGANISM: Saccharomyces cerevisiae

<400> SEQUENCE: 155

Met Asp Ala Tyr Ser Thr Arg Pro Leu Thr Leu Ser His Gly Ser Leu
1               5                   10                  15
```

```
Glu His Val Leu Leu Val Pro Thr Ala Ser Phe Phe Ile Ala Ser Gln
                 20                  25                  30

Leu Gln Glu Gln Phe Asn Lys Ile Leu Pro Glu Pro Thr Glu Gly Phe
             35                  40                  45

Ala Ala Asp Asp Glu Pro Thr Thr Pro Ala Glu Leu Val Gly Lys Phe
 50                  55                  60

Leu Gly Tyr Val Ser Ser Leu Val Glu Pro Ser Lys Val Gly Gln Phe
 65                  70                  75                  80

Asp Gln Val Leu Asn Leu Cys Leu Thr Glu Phe Glu Asn Cys Tyr Leu
                 85                  90                  95

Glu Gly Asn Asp Ile His Ala Leu Ala Ala Lys Leu Leu Gln Glu Asn
                100                 105                 110

Asp Thr Thr Leu Val Lys Thr Lys Glu Leu Ile Lys Asn Tyr Ile Thr
            115                 120                 125

Ala Arg Ile Met Ala Lys Arg Pro Phe Asp Lys Lys Ser Asn Ser Ala
            130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Thr Leu Asp Ala Glu Lys Val
            195                 200                 205

Phe Thr Gln Gly Leu Asn Ile Leu Glu Trp Leu Glu Asn Pro Ser Asn
210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Val Thr Ala Lys Leu Leu
                245                 250                 255

Gly Phe Thr Pro Gly Glu Leu Arg Ser Tyr Leu Lys Gly Ala Thr Gly
                260                 265                 270

His Ser Gln Gly Leu Val Thr Ala Val Ala Ile Ala Glu Thr Asp Ser
            275                 280                 285

Trp Glu Ser Phe Phe Val Ser Val Arg Lys Ala Ile Thr Val Leu Phe
290                 295                 300

Phe Ile Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
            355                 360                 365

Ser Leu Val Asn Gly Ala Lys Asn Leu Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
                405                 410                 415

Ser Asn Arg Phe Leu Pro Val Ala Ser Pro Phe His Ser His Leu Leu
                420                 425                 430

Val Pro Ala Ser Asp Leu Ile Asn Lys Asp Leu Val Lys Asn Asn Val
```

```
            435                 440                 445
Ser Phe Asn Ala Lys Asp Ile Gln Ile Pro Val Tyr Asp Thr Phe Asp
450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
                    485                 490                 495

Lys Ala Thr His Ile Leu Asp Phe Gly Pro Gly Gly Ala Ser Gly Leu
                500                 505                 510

Gly Val Leu Thr His Arg Asn Lys Asp Gly Thr Gly Val Arg Val Ile
                515                 520                 525

Val Ala Gly Thr Leu Asp Ile Asn Pro Asp Asp Tyr Gly Phe Lys
530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                    565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
                595                 600                 605

Ala Thr Thr Asn Ala Gly Tyr Thr Ile Glu Leu Ala Gly Gly Gly Tyr
610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                    645                 650                 655

Phe Met Leu Gln Trp Gly Ile Pro Leu Ile Lys Glu Leu Arg Ser Lys
                    660                 665                 670

Gly Tyr Pro Ile Gln Phe Leu Thr Ile Gly Ala Gly Val Pro Ser Leu
                675                 680                 685

Glu Val Ala Ser Glu Tyr Ile Glu Thr Leu Gly Leu Lys Tyr Leu Gly
690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                    725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
                755                 760                 765

Ser Gly Phe Gly Ser Ala Asp Asp Thr Tyr Pro Tyr Leu Thr Gly Glu
770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                    805                 810                 815

Ala Lys Lys Cys Ile Ala Ala Cys Thr Gly Val Pro Asp Asp Lys Trp
                820                 825                 830

Glu Gln Thr Tyr Lys Lys Pro Thr Gly Gly Ile Val Thr Val Arg Ser
                835                 840                 845

Glu Met Gly Glu Pro Ile His Lys Ile Ala Thr Arg Gly Val Met Leu
850                 855                 860
```

```
Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
            900                 905                 910

Asp Leu Ala Thr Met Thr Tyr Glu Glu Val Ala Lys Arg Leu Val Glu
        915                 920                 925

Leu Met Phe Ile Arg Ser Thr Asn Ser Trp Phe Asp Val Thr Trp Arg
    930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
                965                 970                 975

Asp Glu Ala Ile Glu Lys Val Phe Asn Ala Tyr Pro Ala Ala Arg Glu
            980                 985                 990

Gln Phe Leu Asn Ala Gln Asp Ile Asp His Phe Leu Ser Met Cys Gln
        995                 1000                1005

Asn Pro Met Gln Lys Pro Val Pro Phe Val Pro Val Leu Asp Arg
    1010                1015                1020

Arg Phe Glu Ile Phe Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
    1100                1105                1110

Gln Val Asp Ser Ser Ser Val Ser Glu Asp Ser Ala Val Phe Lys
    1115                1120                1125

Ala Thr Ser Ser Thr Asp Glu Glu Ser Trp Phe Lys Ala Leu Ala
    1130                1135                1140

Gly Ser Glu Ile Asn Trp Arg His Ala Ser Phe Leu Cys Ser Phe
    1145                1150                1155

Ile Thr Gln Asp Lys Met Phe Val Ser Asn Pro Ile Arg Lys Val
    1160                1165                1170

Phe Lys Pro Ser Gln Gly Met Val Val Glu Ile Ser Asn Gly Asn
    1175                1180                1185

Thr Ser Ser Lys Thr Val Val Thr Leu Ser Glu Pro Val Gln Gly
    1190                1195                1200

Glu Leu Lys Pro Thr Val Ile Leu Lys Leu Leu Lys Glu Asn Ile
    1205                1210                1215

Ile Gln Met Glu Met Ile Glu Asn Arg Thr Met Asp Gly Lys Pro
    1220                1225                1230

Val Ser Leu Pro Leu Leu Tyr Asn Phe Asn Pro Asp Asn Gly Phe
    1235                1240                1245

Ala Pro Ile Ser Glu Val Met Glu Asp Arg Asn Gln Arg Ile Lys
    1250                1255                1260
```

-continued

| | | | | | | | | | | | |
|---|---|---|---|---|---|---|---|---|---|---|---|
|Glu|Met|Tyr|Trp|Lys|Leu|Trp|Ile|Asp|Glu|Pro|Phe|Asn|Leu|Asp|
| |1265| | | |1270| | | |1275| | |

Phe Asp Pro Arg Asp Val Ile Lys Gly Lys Asp Phe Glu Ile Thr
1280 1285 1290

Ala Lys Glu Val Tyr Asp Phe Thr His Ala Val Gly Asn Asn Cys
1295 1300 1305

Glu Asp Phe Val Ser Arg Pro Asp Arg Thr Met Leu Ala Pro Met
1310 1315 1320

Asp Phe Ala Ile Val Val Gly Trp Arg Ala Ile Ile Lys Ala Ile
1325 1330 1335

Phe Pro Asn Thr Val Asp Gly Asp Leu Leu Lys Leu Val His Leu
1340 1345 1350

Ser Asn Gly Tyr Lys Met Ile Pro Gly Ala Lys Pro Leu Gln Val
1355 1360 1365

Gly Asp Val Val Ser Thr Thr Ala Val Ile Glu Ser Val Val Asn
1370 1375 1380

Gln Pro Thr Gly Lys Ile Val Asp Val Val Gly Thr Leu Ser Arg
1385 1390 1395

Asn Gly Lys Pro Val Met Glu Val Thr Ser Ser Phe Phe Tyr Arg
1400 1405 1410

Gly Asn Tyr Thr Asp Phe Glu Asn Thr Phe Gln Lys Thr Val Glu
1415 1420 1425

Pro Val Tyr Gln Met His Ile Lys Thr Ser Lys Asp Ile Ala Val
1430 1435 1440

Leu Arg Ser Lys Glu Trp Phe Gln Leu Asp Asp Glu Asp Phe Asp
1445 1450 1455

Leu Leu Asn Lys Thr Leu Thr Phe Glu Thr Glu Thr Glu Val Thr
1460 1465 1470

Phe Lys Asn Ala Asn Ile Phe Ser Ser Val Lys Cys Phe Gly Pro
1475 1480 1485

Ile Lys Val Glu Leu Pro Thr Lys Glu Thr Val Glu Ile Gly Ile
1490 1495 1500

Val Asp Tyr Glu Ala Gly Ala Ser His Gly Asn Pro Val Val Asp
1505 1510 1515

Phe Leu Lys Arg Asn Gly Ser Thr Leu Glu Gln Lys Val Asn Leu
1520 1525 1530

Glu Asn Pro Ile Pro Ile Ala Val Leu Asp Ser Tyr Thr Pro Ser
1535 1540 1545

Thr Asn Glu Pro Tyr Ala Arg Val Ser Gly Asp Leu Asn Pro Ile
1550 1555 1560

His Val Ser Arg His Phe Ala Ser Tyr Ala Asn Leu Pro Gly Thr
1565 1570 1575

Ile Thr His Gly Met Phe Ser Ser Ala Ser Val Arg Ala Leu Ile
1580 1585 1590

Glu Asn Trp Ala Ala Asp Ser Val Ser Ser Arg Val Arg Gly Tyr
1595 1600 1605

Thr Cys Gln Phe Val Asp Met Val Leu Pro Asn Thr Ala Leu Lys
1610 1615 1620

Thr Ser Ile Gln His Val Gly Met Ile Asn Gly Arg Lys Leu Ile
1625 1630 1635

Lys Phe Glu Thr Arg Asn Glu Asp Asp Val Val Val Leu Thr Gly
1640 1645 1650

Glu Ala Glu Ile Glu Gln Pro Val Thr Thr Phe Val Phe Thr Gly

```
              1655                1660                1665
        Gln Gly Ser Gln Glu Gln Gly Met Gly Met Asp Leu Tyr Lys Thr
            1670                1675                1680

Ser Lys Ala Ala Gln Asp Val Trp Asn Arg Ala Asp Asn His Phe
            1685                1690                1695

Lys Asp Thr Tyr Gly Phe Ser Ile Leu Asp Ile Val Ile Asn Asn
            1700                1705                1710

Pro Val Asn Leu Thr Ile His Phe Gly Gly Glu Lys Gly Lys Arg
            1715                1720                1725

Ile Arg Glu Asn Tyr Ser Ala Met Ile Phe Glu Thr Ile Val Asp
            1730                1735                1740

Gly Lys Leu Lys Thr Glu Lys Ile Phe Lys Glu Ile Asn Glu His
            1745                1750                1755

Ser Thr Ser Tyr Thr Phe Arg Ser Glu Lys Gly Leu Leu Ser Ala
            1760                1765                1770

Thr Gln Phe Thr Gln Pro Ala Leu Thr Leu Met Glu Lys Ala Ala
            1775                1780                1785

Phe Glu Asp Leu Lys Ser Lys Gly Leu Ile Pro Ala Asp Ala Thr
            1790                1795                1800

Phe Ala Gly His Ser Leu Gly Glu Tyr Ala Ala Leu Ala Ser Leu
            1805                1810                1815

Ala Asp Val Met Ser Ile Glu Ser Leu Val Glu Val Val Phe Tyr
            1820                1825                1830

Arg Gly Met Thr Met Gln Val Ala Val Pro Arg Asp Glu Leu Gly
            1835                1840                1845

Arg Ser Asn Tyr Gly Met Ile Ala Ile Asn Pro Gly Arg Val Ala
            1850                1855                1860

Ala Ser Phe Ser Gln Glu Ala Leu Gln Tyr Val Val Glu Arg Val
            1865                1870                1875

Gly Lys Arg Thr Gly Trp Leu Val Glu Ile Val Asn Tyr Asn Val
            1880                1885                1890

Glu Asn Gln Gln Tyr Val Ala Ala Gly Asp Leu Arg Ala Leu Asp
            1895                1900                1905

Thr Val Thr Asn Val Leu Asn Phe Ile Lys Leu Gln Lys Ile Asp
            1910                1915                1920

Ile Ile Glu Leu Gln Lys Ser Leu Ser Leu Glu Glu Val Glu Gly
            1925                1930                1935

His Leu Phe Glu Ile Ile Asp Glu Ala Ser Lys Lys Ser Ala Val
            1940                1945                1950

Lys Pro Arg Pro Leu Lys Leu Glu Arg Gly Phe Ala Cys Ile Pro
            1955                1960                1965

Leu Val Gly Ile Ser Val Pro Phe His Ser Thr Tyr Leu Met Asn
            1970                1975                1980

Gly Val Lys Pro Phe Lys Ser Phe Leu Lys Lys Asn Ile Ile Lys
            1985                1990                1995

Glu Asn Val Lys Val Ala Arg Leu Ala Gly Lys Tyr Ile Pro Asn
            2000                2005                2010

Leu Thr Ala Lys Pro Phe Gln Val Thr Lys Glu Tyr Phe Gln Asp
            2015                2020                2025

Val Tyr Asp Leu Thr Gly Ser Glu Pro Ile Lys Glu Ile Ile Asp
            2030                2035                2040

Asn Trp Glu Lys Tyr Glu Gln Ser
            2045                2050
```

<210> SEQ ID NO 156
<211> LENGTH: 1887
<212> TYPE: PRT
<213> ORGANISM: Saccharomyces cerevisiae

<400> SEQUENCE: 156

```
Met Lys Pro Glu Val Glu Gln Glu Leu Ala His Ile Leu Leu Thr Glu
1               5                   10                  15

Leu Leu Ala Tyr Gln Phe Ala Ser Pro Val Arg Trp Ile Glu Thr Gln
                20                  25                  30

Asp Val Phe Leu Lys Asp Phe Asn Thr Glu Arg Val Val Glu Ile Gly
            35                  40                  45

Pro Ser Pro Thr Leu Ala Gly Met Ala Gln Arg Thr Leu Lys Asn Lys
        50                  55                  60

Tyr Glu Ser Tyr Asp Ala Ala Leu Ser Leu His Arg Glu Ile Leu Cys
65                  70                  75                  80

Tyr Ser Lys Asp Ala Lys Glu Ile Tyr Tyr Thr Pro Asp Pro Ser Glu
                85                  90                  95

Leu Ala Ala Lys Glu Glu Pro Ala Lys Glu Ala Pro Ala Pro Thr
                100                 105                 110

Pro Ala Ala Ser Ala Pro Ala Pro Ala Ala Ala Pro Ala Pro Val
            115                 120                 125

Ala Ala Ala Ala Pro Ala Ala Ala Ala Ala Glu Ile Ala Asp Glu Pro
130                 135                 140

Val Lys Ala Ser Leu Leu Leu His Val Leu Val Ala His Lys Leu Lys
145                 150                 155                 160

Lys Ser Leu Asp Ser Ile Pro Met Ser Lys Thr Ile Lys Asp Leu Val
                165                 170                 175

Gly Gly Lys Ser Thr Val Gln Asn Glu Ile Leu Gly Asp Leu Gly Lys
            180                 185                 190

Glu Phe Gly Thr Thr Pro Glu Lys Pro Glu Glu Thr Pro Leu Glu Glu
        195                 200                 205

Leu Ala Glu Thr Phe Gln Asp Thr Phe Ser Gly Ala Leu Gly Lys Gln
    210                 215                 220

Ser Ser Ser Leu Leu Ser Arg Leu Ile Ser Ser Lys Met Pro Gly Gly
225                 230                 235                 240

Phe Thr Ile Thr Val Ala Arg Lys Tyr Leu Gln Thr Arg Trp Gly Leu
                245                 250                 255

Pro Ser Gly Arg Gln Asp Gly Val Leu Leu Val Ala Leu Ser Asn Glu
            260                 265                 270

Pro Ala Ala Arg Leu Gly Ser Glu Ala Asp Ala Lys Ala Phe Leu Asp
        275                 280                 285

Ser Met Ala Gln Lys Tyr Ala Ser Ile Val Gly Val Asp Leu Ser Ser
    290                 295                 300

Ala Ala Ser Ala Ser Gly Ala Ala Gly Ala Gly Ala Ala Ala Gly Ala
305                 310                 315                 320

Ala Met Ile Asp Ala Gly Ala Leu Glu Glu Ile Thr Lys Asp His Lys
                325                 330                 335

Val Leu Ala Arg Gln Gln Leu Gln Val Leu Ala Arg Tyr Leu Lys Met
            340                 345                 350

Asp Leu Asp Asn Gly Glu Arg Lys Phe Leu Lys Glu Lys Asp Thr Val
        355                 360                 365

Ala Glu Leu Gln Ala Gln Leu Asp Tyr Leu Asn Ala Glu Leu Gly Glu
```

-continued

```
                370                 375                 380
        Phe Phe Val Asn Gly Val Ala Thr Ser Phe Ser Arg Lys Lys Ala Arg
        385                 390                 395                 400

Thr Phe Asp Ser Ser Trp Asn Trp Ala Lys Gln Ser Leu Leu Ser Leu
                            405                 410                 415

Tyr Phe Glu Ile Ile His Gly Val Leu Lys Asn Val Asp Arg Glu Val
                        420                 425                 430

Val Ser Glu Ala Ile Asn Ile Met Asn Arg Ser Asn Asp Ala Leu Ile
                    435                 440                 445

Lys Phe Met Glu Tyr His Ile Ser Asn Thr Asp Glu Thr Lys Gly Glu
                450                 455                 460

Asn Tyr Gln Leu Val Lys Thr Leu Gly Glu Gln Leu Ile Glu Asn Cys
        465                 470                 475                 480

Lys Gln Val Leu Asp Val Asp Pro Val Tyr Lys Asp Val Ala Lys Pro
                            485                 490                 495

Thr Gly Pro Lys Thr Ala Ile Asp Lys Asn Gly Asn Ile Thr Tyr Ser
                        500                 505                 510

Glu Glu Pro Arg Glu Lys Val Arg Lys Leu Ser Gln Tyr Val Gln Glu
                    515                 520                 525

Met Ala Leu Gly Gly Pro Ile Thr Lys Glu Ser Gln Pro Thr Ile Glu
                530                 535                 540

Glu Asp Leu Thr Arg Val Tyr Lys Ala Ile Ser Ala Gln Ala Asp Lys
        545                 550                 555                 560

Gln Asp Ile Ser Ser Ser Thr Arg Val Glu Phe Glu Lys Leu Tyr Ser
                            565                 570                 575

Asp Leu Met Lys Phe Leu Glu Ser Ser Lys Glu Ile Asp Pro Ser Gln
                        580                 585                 590

Thr Thr Gln Leu Ala Gly Met Asp Val Glu Asp Ala Leu Asp Lys Asp
                    595                 600                 605

Ser Thr Lys Glu Val Ala Ser Leu Pro Asn Lys Ser Thr Ile Ser Lys
                610                 615                 620

Thr Val Ser Ser Thr Ile Pro Arg Glu Thr Ile Pro Phe Leu His Leu
        625                 630                 635                 640

Arg Lys Lys Thr Pro Ala Gly Asp Trp Lys Tyr Asp Arg Gln Leu Ser
                            645                 650                 655

Ser Leu Phe Leu Asp Gly Leu Glu Lys Ala Ala Phe Asn Gly Val Thr
                        660                 665                 670

Phe Lys Asp Lys Tyr Val Leu Ile Thr Gly Ala Gly Lys Gly Ser Ile
                    675                 680                 685

Gly Ala Glu Val Leu Gln Gly Leu Leu Gln Gly Ala Lys Val Val
                690                 695                 700

Val Thr Thr Ser Arg Phe Ser Lys Gln Val Thr Asp Tyr Tyr Gln Ser
        705                 710                 715                 720

Ile Tyr Ala Lys Tyr Gly Ala Lys Gly Ser Thr Leu Ile Val Val Pro
                            725                 730                 735

Phe Asn Gln Gly Ser Lys Gln Asp Val Glu Ala Leu Ile Glu Phe Ile
                        740                 745                 750

Tyr Asp Thr Glu Lys Asn Gly Gly Leu Gly Trp Asp Leu Asp Ala Ile
                    755                 760                 765

Ile Pro Phe Ala Ala Ile Pro Glu Gln Gly Ile Glu Leu Glu His Ile
                770                 775                 780

Asp Ser Lys Ser Glu Phe Ala His Arg Ile Met Leu Thr Asn Ile Leu
        785                 790                 795                 800
```

```
Arg Met Met Gly Cys Val Lys Gln Lys Ser Ala Arg Gly Ile Glu
                805                 810                 815

Thr Arg Pro Ala Gln Val Ile Leu Pro Met Ser Pro Asn His Gly Thr
                820                 825                 830

Phe Gly Gly Asp Gly Met Tyr Ser Glu Ser Lys Leu Ser Leu Glu Thr
                835                 840                 845

Leu Phe Asn Arg Trp His Ser Glu Ser Trp Ala Asn Gln Leu Thr Val
    850                 855                 860

Cys Gly Ala Ile Ile Gly Trp Thr Arg Gly Thr Gly Leu Met Ser Ala
865                 870                 875                 880

Asn Asn Ile Ile Ala Glu Gly Ile Glu Lys Met Gly Val Arg Thr Phe
                885                 890                 895

Ser Gln Lys Glu Met Ala Phe Asn Leu Leu Gly Leu Leu Thr Pro Glu
                900                 905                 910

Val Val Glu Leu Cys Gln Lys Ser Pro Val Met Ala Asp Leu Asn Gly
                915                 920                 925

Gly Leu Gln Phe Val Pro Glu Leu Lys Glu Phe Thr Ala Lys Leu Arg
    930                 935                 940

Lys Glu Leu Val Glu Thr Ser Glu Val Arg Lys Ala Val Ser Ile Glu
945                 950                 955                 960

Thr Ala Leu Glu His Lys Val Val Asn Gly Asn Ser Ala Asp Ala Ala
                965                 970                 975

Tyr Ala Gln Val Glu Ile Gln Pro Arg Ala Asn Ile Gln Leu Asp Phe
                980                 985                 990

Pro Glu Leu Lys Pro Tyr Lys Gln Val Lys Gln Ile Ala Pro Ala Glu
                995                 1000                1005

Leu Glu Gly Leu Leu Asp Leu Glu Arg Val Ile Val Val Thr Gly
    1010                1015                1020

Phe Ala Glu Val Gly Pro Trp Gly Ser Ala Arg Thr Arg Trp Glu
    1025                1030                1035

Met Glu Ala Phe Gly Glu Phe Ser Leu Glu Gly Cys Val Glu Met
    1040                1045                1050

Ala Trp Ile Met Gly Phe Ile Ser Tyr His Asn Gly Asn Leu Lys
    1055                1060                1065

Gly Arg Pro Tyr Thr Gly Trp Val Asp Ser Lys Thr Lys Glu Pro
    1070                1075                1080

Val Asp Asp Lys Asp Val Lys Ala Lys Tyr Glu Thr Ser Ile Leu
    1085                1090                1095

Glu His Ser Gly Ile Arg Leu Ile Glu Pro Glu Leu Phe Asn Gly
    1100                1105                1110

Tyr Asn Pro Glu Lys Lys Glu Met Ile Gln Glu Val Ile Val Glu
    1115                1120                1125

Glu Asp Leu Glu Pro Phe Glu Ala Ser Lys Glu Thr Ala Glu Gln
    1130                1135                1140

Phe Lys His Gln His Gly Asp Lys Val Asp Ile Phe Glu Ile Pro
    1145                1150                1155

Glu Thr Gly Glu Tyr Ser Val Lys Leu Leu Lys Gly Ala Thr Leu
    1160                1165                1170

Tyr Ile Pro Lys Ala Leu Arg Phe Asp Arg Leu Val Ala Gly Gln
    1175                1180                1185

Ile Pro Thr Gly Trp Asn Ala Lys Thr Tyr Gly Ile Ser Asp Asp
    1190                1195                1200
```

-continued

```
Ile Ile Ser Gln Val Asp Pro Ile Thr Leu Phe Val Leu Val Ser
1205                1210                1215

Val Val Glu Ala Phe Ile Ala Ser Gly Ile Thr Asp Pro Tyr Glu
1220                1225                1230

Met Tyr Lys Tyr Val His Val Ser Glu Val Gly Asn Cys Ser Gly
1235                1240                1245

Ser Gly Met Gly Gly Val Ser Ala Leu Arg Gly Met Phe Lys Asp
1250                1255                1260

Arg Phe Lys Asp Glu Pro Val Gln Asn Asp Ile Leu Gln Glu Ser
1265                1270                1275

Phe Ile Asn Thr Met Ser Ala Trp Val Asn Met Leu Leu Ile Ser
1280                1285                1290

Ser Ser Gly Pro Ile Lys Thr Pro Val Gly Ala Cys Ala Thr Ser
1295                1300                1305

Val Glu Ser Val Asp Ile Gly Val Glu Thr Ile Leu Ser Gly Lys
1310                1315                1320

Ala Arg Ile Cys Ile Val Gly Gly Tyr Asp Asp Phe Gln Glu Glu
1325                1330                1335

Gly Ser Phe Glu Phe Gly Asn Met Lys Ala Thr Ser Asn Thr Leu
1340                1345                1350

Glu Glu Phe Glu His Gly Arg Thr Pro Ala Glu Met Ser Arg Pro
1355                1360                1365

Ala Thr Thr Thr Arg Asn Gly Phe Met Glu Ala Gln Gly Ala Gly
1370                1375                1380

Ile Gln Ile Ile Met Gln Ala Asp Leu Ala Leu Lys Met Gly Val
1385                1390                1395

Pro Ile Tyr Gly Ile Val Ala Met Ala Ala Thr Ala Thr Asp Lys
1400                1405                1410

Ile Gly Arg Ser Val Pro Ala Pro Gly Lys Gly Ile Leu Thr Thr
1415                1420                1425

Ala Arg Glu His His Ser Ser Val Lys Tyr Ala Ser Pro Asn Leu
1430                1435                1440

Asn Met Lys Tyr Arg Lys Arg Gln Leu Val Thr Arg Glu Ala Gln
1445                1450                1455

Ile Lys Asp Trp Val Glu Asn Glu Leu Glu Ala Leu Lys Leu Glu
1460                1465                1470

Ala Glu Glu Ile Pro Ser Glu Asp Gln Asn Glu Phe Leu Leu Glu
1475                1480                1485

Arg Thr Arg Glu Ile His Asn Glu Ala Glu Ser Gln Leu Arg Ala
1490                1495                1500

Ala Gln Gln Gln Trp Gly Asn Asp Phe Tyr Lys Arg Asp Pro Arg
1505                1510                1515

Ile Ala Pro Leu Arg Gly Ala Leu Ala Thr Tyr Gly Leu Thr Ile
1520                1525                1530

Asp Asp Leu Gly Val Ala Ser Phe His Gly Thr Ser Thr Lys Ala
1535                1540                1545

Asn Asp Lys Asn Glu Ser Ala Thr Ile Asn Glu Met Met Lys His
1550                1555                1560

Leu Gly Arg Ser Glu Gly Asn Pro Val Ile Gly Val Phe Gln Lys
1565                1570                1575

Phe Leu Thr Gly His Pro Lys Gly Ala Ala Gly Ala Trp Met Met
1580                1585                1590

Asn Gly Ala Leu Gln Ile Leu Asn Ser Gly Ile Ile Pro Gly Asn
```

```
            1595                1600                1605

Arg Asn Ala Asp Asn Val Asp Lys Ile Leu Glu Gln Phe Glu Tyr
    1610                1615                1620

Val Leu Tyr Pro Ser Lys Thr Leu Lys Thr Asp Gly Val Arg Ala
1625                1630                1635

Val Ser Ile Thr Ser Phe Gly Phe Gly Gln Lys Gly Gly Gln Ala
    1640                1645                1650

Ile Val Val His Pro Asp Tyr Leu Tyr Gly Ala Ile Thr Glu Asp
    1655                1660                1665

Arg Tyr Asn Glu Tyr Val Ala Lys Val Ser Ala Arg Glu Lys Ser
    1670                1675                1680

Ala Tyr Lys Phe Phe His Asn Gly Met Ile Tyr Asn Lys Leu Phe
    1685                1690                1695

Val Ser Lys Glu His Ala Pro Tyr Thr Asp Glu Leu Glu Glu Asp
    1700                1705                1710

Val Tyr Leu Asp Pro Leu Ala Arg Val Ser Lys Asp Lys Lys Ser
    1715                1720                1725

Gly Ser Leu Thr Phe Asn Ser Lys Asn Ile Gln Ser Lys Asp Ser
    1730                1735                1740

Tyr Ile Asn Ala Asn Thr Ile Glu Thr Ala Lys Met Ile Glu Asn
    1745                1750                1755

Met Thr Lys Glu Lys Val Ser Asn Gly Gly Val Gly Val Asp Val
    1760                1765                1770

Glu Leu Ile Thr Ser Ile Asn Val Glu Asn Asp Thr Phe Ile Glu
    1775                1780                1785

Arg Asn Phe Thr Pro Gln Glu Ile Glu Tyr Cys Ser Ala Gln Pro
    1790                1795                1800

Ser Val Gln Ser Ser Phe Ala Gly Thr Trp Ser Ala Lys Glu Ala
    1805                1810                1815

Val Phe Lys Ser Leu Gly Val Lys Ser Leu Gly Gly Gly Ala Ala
    1820                1825                1830

Leu Lys Asp Ile Glu Ile Val Arg Val Asn Lys Asn Ala Pro Ala
    1835                1840                1845

Val Glu Leu His Gly Asn Ala Lys Lys Ala Ala Glu Glu Ala Gly
    1850                1855                1860

Val Thr Asp Val Lys Val Ser Ile Ser His Asp Asp Leu Gln Ala
    1865                1870                1875

Val Ala Val Ala Val Ser Thr Lys Lys
    1880                1885

<210> SEQ ID NO 157
<211> LENGTH: 2051
<212> TYPE: PRT
<213> ORGANISM: Saccharomyces cerevisiae

<400> SEQUENCE: 157

Met Asp Ala Tyr Ser Thr Arg Pro Leu Thr Leu Ser His Gly Ser Leu
1               5                   10                  15

Glu His Val Leu Leu Val Pro Thr Ala Ser Phe Phe Ile Ala Ser Gln
                20                  25                  30

Leu Gln Glu Gln Phe Asn Lys Ile Leu Pro Glu Pro Thr Glu Gly Phe
            35                  40                  45

Ala Ala Asp Asp Glu Pro Thr Thr Pro Ala Glu Leu Val Gly Lys Phe
        50                  55                  60
```

```
Leu Gly Tyr Val Ser Ser Leu Val Glu Pro Ser Lys Val Gly Gln Phe
 65                  70                  75                  80

Asp Gln Val Leu Asn Leu Cys Leu Thr Glu Phe Glu Asn Cys Tyr Leu
                 85                  90                  95

Glu Gly Asn Asp Ile His Ala Leu Ala Ala Lys Leu Leu Gln Glu Asn
            100                 105                 110

Asp Thr Thr Leu Val Lys Thr Lys Glu Leu Ile Lys Asn Tyr Ile Thr
        115                 120                 125

Ala Arg Ile Met Ala Lys Arg Pro Phe Asp Lys Ser Asn Ser Ala
    130                 135                 140

Leu Phe Arg Ala Val Gly Glu Gly Asn Ala Gln Leu Val Ala Ile Phe
145                 150                 155                 160

Gly Gly Gln Gly Asn Thr Asp Asp Tyr Phe Glu Glu Leu Arg Asp Leu
                165                 170                 175

Tyr Gln Thr Tyr His Val Leu Val Gly Asp Leu Ile Lys Phe Ser Ala
            180                 185                 190

Glu Thr Leu Ser Glu Leu Ile Arg Thr Leu Asp Ala Glu Lys Val
        195                 200                 205

Phe Thr Gln Gly Leu Asn Ile Leu Glu Trp Leu Glu Asn Pro Ser Asn
210                 215                 220

Thr Pro Asp Lys Asp Tyr Leu Leu Ser Ile Pro Ile Ser Cys Pro Leu
225                 230                 235                 240

Ile Gly Val Ile Gln Leu Ala His Tyr Val Thr Ala Lys Leu Leu
                245                 250                 255

Gly Phe Thr Pro Gly Glu Leu Arg Ser Tyr Leu Lys Gly Ala Thr Gly
                260                 265                 270

His Ser Gln Gly Leu Val Thr Ala Val Ala Ile Ala Glu Thr Asp Ser
    275                 280                 285

Trp Glu Ser Phe Phe Val Ser Val Arg Lys Ala Ile Thr Val Leu Phe
        290                 295                 300

Phe Ala Gly Val Arg Cys Tyr Glu Ala Tyr Pro Asn Thr Ser Leu Pro
305                 310                 315                 320

Pro Ser Ile Leu Glu Asp Ser Leu Glu Asn Asn Glu Gly Val Pro Ser
                325                 330                 335

Pro Met Leu Ser Ile Ser Asn Leu Thr Gln Glu Gln Val Gln Asp Tyr
            340                 345                 350

Val Asn Lys Thr Asn Ser His Leu Pro Ala Gly Lys Gln Val Glu Ile
        355                 360                 365

Ser Leu Val Asn Gly Ala Lys Asn Leu Val Ser Gly Pro Pro Gln
370                 375                 380

Ser Leu Tyr Gly Leu Asn Leu Thr Leu Arg Lys Ala Lys Ala Pro Ser
385                 390                 395                 400

Gly Leu Asp Gln Ser Arg Ile Pro Phe Ser Glu Arg Lys Leu Lys Phe
            405                 410                 415

Ser Asn Arg Phe Leu Pro Val Ala Ser Pro Phe His Ser His Leu Leu
                420                 425                 430

Val Pro Ala Ser Asp Leu Ile Asn Lys Asp Leu Val Lys Asn Asn Val
        435                 440                 445

Ser Phe Asn Ala Lys Asp Ile Gln Ile Pro Val Tyr Asp Thr Phe Asp
    450                 455                 460

Gly Ser Asp Leu Arg Val Leu Ser Gly Ser Ile Ser Glu Arg Ile Val
465                 470                 475                 480

Asp Cys Ile Ile Arg Leu Pro Val Lys Trp Glu Thr Thr Thr Gln Phe
```

-continued

```
                485                 490                 495
Lys Ala Thr His Ile Leu Asp Phe Gly Pro Gly Gly Ala Ser Gly Leu
                500                 505                 510

Gly Val Leu Thr His Arg Asn Lys Asp Gly Thr Gly Val Arg Val Ile
                515                 520                 525

Val Ala Gly Thr Leu Asp Ile Asn Pro Asp Asp Tyr Gly Phe Lys
                530                 535                 540

Gln Glu Ile Phe Asp Val Thr Ser Asn Gly Leu Lys Lys Asn Pro Asn
545                 550                 555                 560

Trp Leu Glu Glu Tyr His Pro Lys Leu Ile Lys Asn Lys Ser Gly Lys
                565                 570                 575

Ile Phe Val Glu Thr Lys Phe Ser Lys Leu Ile Gly Arg Pro Pro Leu
                580                 585                 590

Leu Val Pro Gly Met Thr Pro Cys Thr Val Ser Pro Asp Phe Val Ala
                595                 600                 605

Ala Thr Thr Asn Ala Gly Tyr Thr Ile Glu Leu Ala Gly Gly Gly Tyr
                610                 615                 620

Phe Ser Ala Ala Gly Met Thr Ala Ala Ile Asp Ser Val Val Ser Gln
625                 630                 635                 640

Ile Glu Lys Gly Ser Thr Phe Gly Ile Asn Leu Ile Tyr Val Asn Pro
                645                 650                 655

Phe Met Leu Gln Trp Gly Ile Pro Leu Ile Lys Glu Leu Arg Ser Lys
                660                 665                 670

Gly Tyr Pro Ile Gln Phe Leu Thr Ile Gly Ala Gly Val Pro Ser Leu
                675                 680                 685

Glu Val Ala Ser Glu Tyr Ile Glu Thr Leu Gly Leu Lys Tyr Leu Gly
                690                 695                 700

Leu Lys Pro Gly Ser Ile Asp Ala Ile Ser Gln Val Ile Asn Ile Ala
705                 710                 715                 720

Lys Ala His Pro Asn Phe Pro Ile Ala Leu Gln Trp Thr Gly Gly Arg
                725                 730                 735

Gly Gly Gly His His Ser Phe Glu Asp Ala His Thr Pro Met Leu Gln
                740                 745                 750

Met Tyr Ser Lys Ile Arg Arg His Pro Asn Ile Met Leu Ile Phe Gly
                755                 760                 765

Ser Gly Phe Gly Ser Ala Asp Asp Thr Tyr Pro Tyr Leu Thr Gly Glu
                770                 775                 780

Trp Ser Thr Lys Phe Asp Tyr Pro Pro Met Pro Phe Asp Gly Phe Leu
785                 790                 795                 800

Phe Gly Ser Arg Val Met Ile Ala Lys Glu Val Lys Thr Ser Pro Asp
                805                 810                 815

Ala Lys Lys Cys Ile Ala Ala Cys Thr Gly Val Pro Asp Lys Trp
                820                 825                 830

Glu Gln Thr Tyr Lys Lys Pro Thr Gly Gly Ile Val Thr Val Arg Ser
                835                 840                 845

Glu Met Gly Glu Pro Ile His Lys Ile Ala Thr Arg Gly Val Met Leu
                850                 855                 860

Trp Lys Glu Phe Asp Glu Thr Ile Phe Asn Leu Pro Lys Asn Lys Leu
865                 870                 875                 880

Val Pro Thr Leu Glu Ala Lys Arg Asp Tyr Ile Ile Ser Arg Leu Asn
                885                 890                 895

Ala Asp Phe Gln Lys Pro Trp Phe Ala Thr Val Asn Gly Gln Ala Arg
                900                 905                 910
```

```
Asp Leu Ala Thr Met Thr Tyr Glu Glu Val Ala Lys Arg Leu Val Glu
        915                 920                 925

Leu Met Phe Ile Arg Ser Thr Asn Ser Trp Phe Asp Val Thr Trp Arg
    930                 935                 940

Thr Phe Thr Gly Asp Phe Leu Arg Arg Val Glu Glu Arg Phe Thr Lys
945                 950                 955                 960

Ser Lys Thr Leu Ser Leu Ile Gln Ser Tyr Ser Leu Leu Asp Lys Pro
            965                 970                 975

Asp Glu Ala Ile Glu Lys Val Phe Asn Ala Tyr Pro Ala Ala Arg Glu
                980                 985                 990

Gln Phe Leu Asn Ala Gln Asp Ile Asp His Phe Leu Ser Met Cys Gln
            995                1000                1005

Asn Pro Met Gln Lys Pro Val Pro Phe Val Pro Val Leu Asp Arg
    1010                1015                1020

Arg Phe Glu Ile Phe Phe Lys Lys Asp Ser Leu Trp Gln Ser Glu
    1025                1030                1035

His Leu Glu Ala Val Val Asp Gln Asp Val Gln Arg Thr Cys Ile
    1040                1045                1050

Leu His Gly Pro Val Ala Ala Gln Phe Thr Lys Val Ile Asp Glu
    1055                1060                1065

Pro Ile Lys Ser Ile Met Asp Gly Ile His Asp Gly His Ile Lys
    1070                1075                1080

Lys Leu Leu His Gln Tyr Tyr Gly Asp Asp Glu Ser Lys Ile Pro
    1085                1090                1095

Ala Val Glu Tyr Phe Gly Gly Glu Ser Pro Val Asp Val Gln Ser
    1100                1105                1110

Gln Val Asp Ser Ser Ser Val Ser Glu Asp Ser Ala Val Phe Lys
    1115                1120                1125

Ala Thr Ser Ser Thr Asp Glu Glu Ser Trp Phe Lys Ala Leu Ala
    1130                1135                1140

Gly Ser Glu Ile Asn Trp Arg His Ala Ser Phe Leu Cys Ser Phe
    1145                1150                1155

Ile Thr Gln Asp Lys Met Phe Val Ser Asn Pro Ile Arg Lys Val
    1160                1165                1170

Phe Lys Pro Ser Gln Gly Met Val Val Glu Ile Ser Asn Gly Asn
    1175                1180                1185

Thr Ser Ser Lys Thr Val Val Thr Leu Ser Glu Pro Val Gln Gly
    1190                1195                1200

Glu Leu Lys Pro Thr Val Ile Leu Lys Leu Leu Lys Glu Asn Ile
    1205                1210                1215

Ile Gln Met Glu Met Ile Glu Asn Arg Thr Met Asp Gly Lys Pro
    1220                1225                1230

Val Ser Leu Pro Leu Leu Tyr Asn Phe Asn Pro Asp Asn Gly Phe
    1235                1240                1245

Ala Pro Ile Ser Glu Val Met Glu Asp Arg Asn Gln Arg Ile Lys
    1250                1255                1260

Glu Met Tyr Trp Lys Leu Trp Ile Asp Glu Pro Phe Asn Leu Asp
    1265                1270                1275

Phe Asp Pro Arg Asp Val Ile Lys Gly Lys Asp Phe Glu Ile Thr
    1280                1285                1290

Ala Lys Glu Val Tyr Asp Phe Thr His Ala Val Gly Asn Asn Cys
    1295                1300                1305
```

```
Glu Asp Phe Val Ser Arg Pro Asp Arg Thr Met Leu Ala Pro Met
1310                 1315                1320

Asp Phe Ala Ile Val Val Gly Trp Arg Ala Ile Ile Lys Ala Ile
1325                 1330                1335

Phe Pro Asn Thr Val Asp Gly Asp Leu Leu Lys Leu Val His Leu
1340                 1345                1350

Ser Asn Gly Tyr Lys Met Ile Pro Gly Ala Lys Pro Leu Gln Val
1355                 1360                1365

Gly Asp Val Val Ser Thr Thr Ala Val Ile Glu Ser Val Val Asn
1370                 1375                1380

Gln Pro Thr Gly Lys Ile Val Asp Val Val Gly Thr Leu Ser Arg
1385                 1390                1395

Asn Gly Lys Pro Val Met Glu Val Thr Ser Ser Phe Phe Tyr Arg
1400                 1405                1410

Gly Asn Tyr Thr Asp Phe Glu Asn Thr Phe Gln Lys Thr Val Glu
1415                 1420                1425

Pro Val Tyr Gln Met His Ile Lys Thr Ser Lys Asp Ile Ala Val
1430                 1435                1440

Leu Arg Ser Lys Glu Trp Phe Gln Leu Asp Asp Glu Asp Phe Asp
1445                 1450                1455

Leu Leu Asn Lys Thr Leu Thr Phe Glu Thr Glu Thr Glu Val Thr
1460                 1465                1470

Phe Lys Asn Ala Asn Ile Phe Ser Ser Val Lys Cys Phe Gly Pro
1475                 1480                1485

Ile Lys Val Glu Leu Pro Thr Lys Glu Thr Val Glu Ile Gly Ile
1490                 1495                1500

Val Asp Tyr Glu Ala Gly Ala Ser His Gly Asn Pro Val Val Asp
1505                 1510                1515

Phe Leu Lys Arg Asn Gly Ser Thr Leu Glu Gln Lys Val Asn Leu
1520                 1525                1530

Glu Asn Pro Ile Pro Ile Ala Val Leu Asp Ser Tyr Thr Pro Ser
1535                 1540                1545

Thr Asn Glu Pro Tyr Ala Arg Val Ser Gly Asp Leu Asn Pro Ile
1550                 1555                1560

His Val Ser Arg His Phe Ala Ser Tyr Ala Asn Leu Pro Gly Thr
1565                 1570                1575

Ile Thr His Gly Met Phe Ser Ser Ala Ser Val Arg Ala Leu Ile
1580                 1585                1590

Glu Asn Trp Ala Ala Asp Ser Val Ser Ser Arg Val Arg Gly Tyr
1595                 1600                1605

Thr Cys Gln Phe Val Asp Met Val Leu Pro Asn Thr Ala Leu Lys
1610                 1615                1620

Thr Ser Ile Gln His Val Gly Met Ile Asn Gly Arg Lys Leu Ile
1625                 1630                1635

Lys Phe Glu Thr Arg Asn Glu Asp Asp Val Val Val Leu Thr Gly
1640                 1645                1650

Glu Ala Glu Ile Glu Gln Pro Val Thr Thr Phe Val Phe Thr Gly
1655                 1660                1665

Gln Gly Ser Gln Glu Gln Gly Met Gly Met Asp Leu Tyr Lys Thr
1670                 1675                1680

Ser Lys Ala Ala Gln Asp Val Trp Asn Arg Ala Asp Asn His Phe
1685                 1690                1695

Lys Asp Thr Tyr Gly Phe Ser Ile Leu Asp Ile Val Ile Asn Asn
```

```
                    1700                1705                 1710

Pro Val Asn Leu Thr Ile His Phe Gly Gly Glu Lys Gly Lys Arg
    1715                1720                 1725

Ile Arg Glu Asn Tyr Ser Ala Met Ile Phe Glu Thr Ile Val Asp
    1730                1735                 1740

Gly Lys Leu Lys Thr Glu Lys Ile Phe Lys Glu Ile Asn Glu His
    1745                1750                 1755

Ser Thr Ser Tyr Thr Phe Arg Ser Glu Lys Gly Leu Leu Ser Ala
    1760                1765                 1770

Thr Gln Phe Thr Gln Pro Ala Leu Thr Leu Met Glu Lys Ala Ala
    1775                1780                 1785

Phe Glu Asp Leu Lys Ser Lys Gly Leu Ile Pro Ala Asp Ala Thr
    1790                1795                 1800

Phe Ala Gly His Ser Leu Gly Glu Tyr Ala Ala Leu Ala Ser Leu
    1805                1810                 1815

Ala Asp Val Met Ser Ile Glu Ser Leu Val Glu Val Val Phe Tyr
    1820                1825                 1830

Arg Gly Met Thr Met Gln Val Ala Val Pro Arg Asp Glu Leu Gly
    1835                1840                 1845

Arg Ser Asn Tyr Gly Met Ile Ala Ile Asn Pro Gly Arg Val Ala
    1850                1855                 1860

Ala Ser Phe Ser Gln Glu Ala Leu Gln Tyr Val Val Glu Arg Val
    1865                1870                 1875

Gly Lys Arg Thr Gly Trp Leu Val Glu Ile Val Asn Tyr Asn Val
    1880                1885                 1890

Glu Asn Gln Gln Tyr Val Ala Ala Gly Asp Leu Arg Ala Leu Asp
    1895                1900                 1905

Thr Val Thr Asn Val Leu Asn Phe Ile Lys Leu Gln Lys Ile Asp
    1910                1915                 1920

Ile Ile Glu Leu Gln Lys Ser Leu Ser Leu Glu Glu Val Glu Gly
    1925                1930                 1935

His Leu Phe Glu Ile Ile Asp Glu Ala Ser Lys Lys Ser Ala Val
    1940                1945                 1950

Lys Pro Arg Pro Leu Lys Leu Glu Arg Gly Phe Ala Cys Ile Pro
    1955                1960                 1965

Leu Val Gly Ile Ser Val Pro Phe His Ser Thr Tyr Leu Met Asn
    1970                1975                 1980

Gly Val Lys Pro Phe Lys Ser Phe Leu Lys Lys Asn Ile Ile Lys
    1985                1990                 1995

Glu Asn Val Lys Val Ala Arg Leu Ala Gly Lys Tyr Ile Pro Asn
    2000                2005                 2010

Leu Thr Ala Lys Pro Phe Gln Val Thr Lys Glu Tyr Phe Gln Asp
    2015                2020                 2025

Val Tyr Asp Leu Thr Gly Ser Glu Pro Ile Lys Glu Ile Ile Asp
    2030                2035                 2040

Asn Trp Glu Lys Tyr Glu Gln Ser
    2045                2050

<210> SEQ ID NO 158
<211> LENGTH: 1887
<212> TYPE: PRT
<213> ORGANISM: Saccharomyces cerevisiae

<400> SEQUENCE: 158
```

```
Met Lys Pro Glu Val Glu Gln Glu Leu Ala His Ile Leu Leu Thr Glu
1               5                   10                  15

Leu Leu Ala Tyr Gln Phe Ala Ser Pro Val Arg Trp Ile Glu Thr Gln
            20                  25                  30

Asp Val Phe Leu Lys Asp Phe Asn Thr Glu Arg Val Val Glu Ile Gly
                35                  40                  45

Pro Ser Pro Thr Leu Ala Gly Met Ala Gln Arg Thr Leu Lys Asn Lys
        50                  55                  60

Tyr Glu Ser Tyr Asp Ala Leu Ser Leu His Arg Glu Ile Leu Cys
65                  70                  75                  80

Tyr Ser Lys Asp Ala Lys Glu Ile Tyr Tyr Thr Pro Asp Pro Ser Glu
                85                  90                  95

Leu Ala Ala Lys Glu Glu Pro Ala Lys Glu Glu Ala Pro Ala Pro Thr
                100                 105                 110

Pro Ala Ala Ser Ala Pro Ala Pro Ala Ala Ala Pro Ala Pro Val
            115                 120                 125

Ala Ala Ala Ala Pro Ala Ala Ala Ala Glu Ile Ala Asp Glu Pro
        130                 135                 140

Val Lys Ala Ser Leu Leu Leu His Val Leu Val Ala His Lys Leu Lys
145                 150                 155                 160

Lys Ser Leu Asp Ser Ile Pro Met Ser Lys Thr Ile Lys Asp Leu Val
                165                 170                 175

Gly Gly Lys Ser Thr Val Gln Asn Glu Ile Leu Gly Asp Leu Gly Lys
            180                 185                 190

Glu Phe Gly Thr Thr Pro Glu Lys Pro Glu Glu Thr Pro Leu Glu Glu
            195                 200                 205

Leu Ala Glu Thr Phe Gln Asp Thr Phe Ser Gly Ala Leu Gly Lys Gln
        210                 215                 220

Ser Ser Ser Leu Leu Ser Arg Leu Ile Ser Ser Lys Met Pro Gly Gly
225                 230                 235                 240

Phe Thr Ile Thr Val Ala Arg Lys Tyr Leu Gln Thr Arg Trp Gly Leu
                245                 250                 255

Pro Ser Gly Arg Gln Asp Gly Val Leu Leu Val Ala Leu Ser Asn Glu
            260                 265                 270

Pro Ala Ala Arg Leu Gly Ser Glu Ala Asp Ala Lys Ala Phe Leu Asp
        275                 280                 285

Ser Met Ala Gln Lys Tyr Ala Ser Ile Val Gly Val Asp Leu Ser Ser
        290                 295                 300

Ala Ala Ser Ala Ser Gly Ala Ala Gly Ala Gly Ala Ala Ala Gly Ala
305                 310                 315                 320

Ala Met Ile Asp Ala Gly Ala Leu Glu Glu Ile Thr Lys Asp His Lys
                325                 330                 335

Val Leu Ala Arg Gln Gln Leu Gln Val Leu Ala Arg Tyr Leu Lys Met
                340                 345                 350

Asp Leu Asp Asn Gly Glu Arg Lys Phe Leu Lys Glu Lys Asp Thr Val
                355                 360                 365

Ala Glu Leu Gln Ala Gln Leu Asp Tyr Leu Asn Ala Glu Leu Gly Glu
        370                 375                 380

Phe Phe Val Asn Gly Val Ala Thr Ser Phe Ser Arg Lys Lys Ala Arg
385                 390                 395                 400

Thr Phe Asp Ser Ser Trp Asn Trp Ala Lys Gln Ser Leu Leu Ser Leu
                405                 410                 415

Tyr Phe Glu Ile Ile His Gly Val Leu Lys Asn Val Asp Arg Glu Val
```

```
              420                 425                 430
Val Ser Glu Ala Ile Asn Ile Met Asn Arg Ser Asn Asp Ala Leu Ile
            435                 440                 445
Lys Phe Met Glu Tyr His Ile Ser Asn Thr Asp Glu Thr Lys Gly Glu
450                 455                 460
Asn Tyr Gln Leu Val Lys Thr Leu Gly Glu Gln Leu Ile Glu Asn Cys
465                 470                 475                 480
Lys Gln Val Leu Asp Val Asp Pro Val Tyr Lys Asp Val Ala Lys Pro
                485                 490                 495
Thr Gly Pro Lys Thr Ala Ile Asp Lys Asn Gly Asn Ile Thr Tyr Ser
                500                 505                 510
Glu Glu Pro Arg Glu Lys Val Arg Lys Leu Ser Gln Tyr Val Gln Glu
                515                 520                 525
Met Ala Leu Gly Gly Pro Ile Thr Lys Glu Ser Gln Pro Thr Ile Glu
                530                 535                 540
Glu Asp Leu Thr Arg Val Tyr Lys Ala Ile Ser Ala Gln Ala Asp Lys
545                 550                 555                 560
Gln Asp Ile Ser Ser Ser Thr Arg Val Glu Phe Glu Lys Leu Tyr Ser
                565                 570                 575
Asp Leu Met Lys Phe Leu Glu Ser Ser Lys Glu Ile Asp Pro Ser Gln
                580                 585                 590
Thr Thr Gln Leu Ala Gly Met Asp Val Glu Asp Ala Leu Asp Lys Asp
                595                 600                 605
Ser Thr Lys Glu Val Ala Ser Leu Pro Asn Lys Ser Thr Ile Ser Lys
                610                 615                 620
Thr Val Ser Ser Thr Ile Pro Arg Glu Thr Ile Pro Phe Leu His Leu
625                 630                 635                 640
Arg Lys Lys Thr Pro Ala Gly Asp Trp Lys Tyr Asp Arg Gln Leu Ser
                645                 650                 655
Ser Leu Phe Leu Asp Gly Leu Glu Lys Ala Ala Phe Asn Gly Val Thr
                660                 665                 670
Phe Lys Asp Lys Tyr Val Leu Ile Thr Gly Ala Gly Lys Gly Ser Ile
                675                 680                 685
Gly Ala Glu Val Leu Gln Gly Leu Leu Gln Gly Gly Ala Lys Val Val
                690                 695                 700
Val Thr Thr Ser Arg Phe Ser Lys Gln Val Thr Asp Tyr Tyr Gln Ser
705                 710                 715                 720
Ile Tyr Ala Lys Tyr Gly Ala Lys Gly Ser Thr Leu Ile Val Val Pro
                725                 730                 735
Phe Asn Gln Gly Ser Lys Gln Asp Val Glu Ala Leu Ile Glu Phe Ile
                740                 745                 750
Tyr Asp Thr Glu Lys Asn Gly Gly Leu Gly Trp Asp Leu Asp Ala Ile
                755                 760                 765
Ile Pro Phe Ala Ala Ile Pro Glu Gln Gly Ile Glu Leu Glu His Ile
                770                 775                 780
Asp Ser Lys Ser Glu Phe Ala His Arg Ile Met Leu Thr Asn Ile Leu
785                 790                 795                 800
Arg Met Met Gly Cys Val Lys Lys Gln Lys Ser Ala Arg Gly Ile Glu
                805                 810                 815
Thr Arg Pro Ala Gln Val Ile Leu Pro Met Ser Pro Asn His Gly Thr
                820                 825                 830
Phe Gly Gly Asp Gly Met Tyr Ser Glu Ser Lys Leu Ser Leu Glu Thr
                835                 840                 845
```

-continued

```
Leu Phe Asn Arg Trp His Ser Glu Ser Trp Ala Asn Gln Leu Thr Val
    850                 855                 860

Cys Gly Ala Ile Ile Gly Trp Thr Arg Gly Thr Gly Leu Met Ser Ala
865                 870                 875                 880

Asn Asn Ile Ile Ala Glu Gly Ile Glu Lys Met Gly Val Arg Thr Phe
                    885                 890                 895

Ser Gln Lys Glu Met Ala Phe Asn Leu Leu Gly Leu Leu Thr Pro Glu
                900                 905                 910

Val Val Glu Leu Cys Gln Lys Ser Pro Val Met Ala Asp Leu Asn Gly
            915                 920                 925

Gly Leu Gln Phe Val Pro Glu Leu Lys Glu Phe Thr Ala Lys Leu Arg
    930                 935                 940

Lys Glu Leu Val Glu Thr Ser Glu Val Arg Lys Ala Val Ser Ile Glu
945                 950                 955                 960

Thr Ala Leu Glu His Lys Val Val Asn Gly Asn Ser Ala Asp Ala Ala
                    965                 970                 975

Tyr Ala Gln Val Glu Ile Gln Pro Arg Ala Asn Ile Gln Leu Asp Phe
                980                 985                 990

Pro Glu Leu Lys Pro Tyr Lys Gln Val Lys Gln Ile Ala Pro Ala Glu
            995                1000                1005

Leu Glu Gly Leu Leu Asp Leu Glu Arg Val Ile Val Val Thr Gly
    1010                1015                1020

Phe Ala Glu Val Gly Pro Trp Gly Ser Ala Arg Thr Arg Trp Glu
    1025                1030                1035

Met Glu Ala Phe Gly Glu Phe Ser Leu Glu Gly Cys Val Glu Met
    1040                1045                1050

Ala Trp Ile Met Gly Phe Ile Ser Tyr His Asn Gly Asn Leu Lys
    1055                1060                1065

Gly Arg Pro Tyr Thr Gly Trp Val Asp Ser Lys Thr Lys Glu Pro
    1070                1075                1080

Val Asp Asp Lys Asp Val Lys Ala Lys Tyr Glu Thr Ser Ile Leu
    1085                1090                1095

Glu His Ser Gly Ile Arg Leu Ile Glu Pro Glu Leu Phe Asn Gly
    1100                1105                1110

Tyr Asn Pro Glu Lys Lys Glu Met Ile Gln Glu Val Ile Val Glu
    1115                1120                1125

Glu Asp Leu Glu Pro Phe Glu Ala Ser Lys Glu Thr Ala Glu Gln
    1130                1135                1140

Phe Lys His Gln His Gly Asp Lys Val Asp Ile Phe Glu Ile Pro
    1145                1150                1155

Glu Thr Gly Glu Tyr Ser Val Lys Leu Leu Lys Gly Ala Thr Leu
    1160                1165                1170

Tyr Ile Pro Lys Ala Leu Arg Phe Asp Arg Leu Val Ala Gly Gln
    1175                1180                1185

Ile Pro Thr Gly Trp Asn Ala Lys Thr Tyr Gly Ile Ser Asp Asp
    1190                1195                1200

Ile Ile Ser Gln Val Asp Pro Ile Thr Leu Phe Val Leu Val Ser
    1205                1210                1215

Val Val Glu Ala Phe Ile Ala Ser Gly Ile Thr Asp Pro Tyr Glu
    1220                1225                1230

Met Tyr Lys Tyr Val His Val Ser Glu Val Gly Asn Cys Ser Gly
    1235                1240                1245
```

```
Ser Ser Met Gly Gly Val Ser Ala Leu Arg Gly Met Phe Lys Asp
    1250                1255                1260

Arg Phe Lys Asp Glu Pro Val Gln Asn Asp Ile Leu Gln Glu Ser
    1265                1270                1275

Phe Ile Asn Thr Met Ser Ala Trp Val Asn Met Leu Leu Ile Ser
    1280                1285                1290

Ser Ser Gly Pro Ile Lys Thr Pro Val Gly Ala Cys Ala Thr Ser
    1295                1300                1305

Val Glu Ser Val Asp Ile Gly Val Glu Thr Ile Leu Ser Gly Lys
    1310                1315                1320

Ala Arg Ile Cys Ile Val Gly Gly Tyr Asp Asp Phe Gln Glu Glu
    1325                1330                1335

Gly Ser Phe Glu Phe Gly Asn Met Lys Ala Thr Ser Asn Thr Leu
    1340                1345                1350

Glu Glu Phe Glu His Gly Arg Thr Pro Ala Glu Met Ser Arg Pro
    1355                1360                1365

Ala Thr Thr Thr Arg Asn Gly Phe Met Glu Ala Gln Gly Ala Gly
    1370                1375                1380

Ile Gln Ile Ile Met Gln Ala Asp Leu Ala Leu Lys Met Gly Val
    1385                1390                1395

Pro Ile Tyr Gly Ile Val Ala Met Ala Ala Thr Ala Thr Asp Lys
    1400                1405                1410

Ile Gly Arg Ser Val Pro Ala Pro Gly Lys Gly Ile Leu Thr Thr
    1415                1420                1425

Ala Arg Glu His His Ser Ser Val Lys Tyr Ala Ser Pro Asn Leu
    1430                1435                1440

Asn Met Lys Tyr Arg Lys Arg Gln Leu Val Thr Arg Glu Ala Gln
    1445                1450                1455

Ile Lys Asp Trp Val Glu Asn Glu Leu Glu Ala Leu Lys Leu Glu
    1460                1465                1470

Ala Glu Glu Ile Pro Ser Glu Asp Gln Asn Glu Phe Leu Leu Glu
    1475                1480                1485

Arg Thr Arg Glu Ile His Asn Glu Ala Glu Ser Gln Leu Arg Ala
    1490                1495                1500

Ala Gln Gln Gln Trp Gly Asn Asp Phe Tyr Lys Arg Asp Pro Arg
    1505                1510                1515

Ile Ala Pro Leu Arg Gly Ala Leu Ala Thr Tyr Gly Leu Thr Ile
    1520                1525                1530

Asp Asp Leu Gly Val Ala Ser Phe His Gly Thr Ser Thr Lys Ala
    1535                1540                1545

Asn Asp Lys Asn Glu Ser Ala Thr Ile Asn Glu Met Met Lys His
    1550                1555                1560

Leu Gly Arg Ser Glu Gly Asn Pro Val Ile Gly Val Phe Gln Lys
    1565                1570                1575

Phe Leu Thr Gly His Pro Lys Gly Ala Ala Gly Ala Trp Met Met
    1580                1585                1590
```

```
Asn Gly Ala Leu Gln Ile Leu Asn Ser Gly Ile Ile Pro Gly Asn
    1595                1600                1605

Arg Asn Ala Asp Asn Val Asp Lys Ile Leu Glu Gln Phe Glu Tyr
    1610                1615                1620

Val Leu Tyr Pro Ser Lys Thr Leu Lys Thr Asp Gly Val Arg Ala
    1625                1630                1635

Val Ser Ile Thr Ser Phe Gly Phe Gly Gln Lys Gly Gly Gln Ala
    1640                1645                1650

Ile Val Val His Pro Asp Tyr Leu Tyr Gly Ala Ile Thr Glu Asp
    1655                1660                1665

Arg Tyr Asn Glu Tyr Val Ala Lys Val Ser Ala Arg Glu Lys Ser
    1670                1675                1680

Ala Tyr Lys Phe Phe His Asn Gly Met Ile Tyr Asn Lys Leu Phe
    1685                1690                1695

Val Ser Lys Glu His Ala Pro Tyr Thr Asp Glu Leu Glu Glu Asp
    1700                1705                1710

Val Tyr Leu Asp Pro Leu Ala Arg Val Ser Lys Asp Lys Lys Ser
    1715                1720                1725

Gly Ser Leu Thr Phe Asn Ser Lys Asn Ile Gln Ser Lys Asp Ser
    1730                1735                1740

Tyr Ile Asn Ala Asn Thr Ile Glu Thr Ala Lys Met Ile Glu Asn
    1745                1750                1755

Met Thr Lys Glu Lys Val Ser Asn Gly Gly Val Gly Val Asp Val
    1760                1765                1770

Glu Leu Ile Thr Ser Ile Asn Val Glu Asn Asp Thr Phe Ile Glu
    1775                1780                1785

Arg Asn Phe Thr Pro Gln Glu Ile Glu Tyr Cys Ser Ala Gln Pro
    1790                1795                1800

Ser Val Gln Ser Ser Phe Ala Gly Thr Trp Ser Ala Lys Glu Ala
    1805                1810                1815

Val Phe Lys Ser Leu Gly Val Lys Ser Leu Gly Gly Ala Ala
    1820                1825                1830

Leu Lys Asp Ile Glu Ile Val Arg Val Asn Lys Asn Ala Pro Ala
    1835                1840                1845

Val Glu Leu His Gly Asn Ala Lys Lys Ala Ala Glu Glu Ala Gly
    1850                1855                1860

Val Thr Asp Val Lys Val Ser Ile Ser His Asp Asp Leu Gln Ala
    1865                1870                1875

Val Ala Val Ala Val Ser Thr Lys Lys
    1880                1885
```

TRANSGENIC LAND PLANTS THAT EXPRESS A POLYHYDROXYALKANOATE SYNTHASE SEED SPECIFICALLY WITH CYTOSOLIC LOCALIZATION

TECHNICAL FIELD OF THE INVENTION

The invention is generally directed to transgenic land plants that express a polyhydroxyalkanoate synthase seed specifically, with cytosolic localization, and specifically to such transgenic land plants comprising: (a) a nucleic acid encoding the polyhydroxyalkanoate synthase; and (b) a seed-specific promoter operably linked to the nucleic acid, wherein: (i) the seed-specific promoter drives expression of the polyhydroxyalkanoate synthase in cytosol of cells of seeds of the transgenic land plant; (ii) the polyhydroxyalkanoate synthase comprises a catalytic domain; and (iii) the polyhydroxyalkanoate synthase does not comprise any sequence positioned to mediate translocation of the catalytic domain across any membrane of the cells, thereby resulting in the polyhydroxyalkanoate synthase being expressed seed specifically, with cytosolic localization.

BACKGROUND OF THE INVENTION

Polyhydroxyalkanoates (also termed "PHAs") are natural microbial carbon and energy storage polymers that can be produced from renewable resources, that accumulate intracellularly in the form of granules, and that are useful in a broad range of industrial, agricultural, and environmental applications. Polyhydroxyalkanoates can be produced as homopolymers, such as poly-3-hydroxybutyrate (also termed "polyhydroxybutyrate" or "PHB") and poly-4-hydroxybutyrate (also termed "P4HB"). Polyhydroxyalkanoates also can be produced as copolymers, such as poly(3-hydroxybutyrate-co-4-hydroxybutyrate) (also termed "P(3HB-co-4HB)"), poly(3-hydroxybutyrate-co-3-hydroxyvalerate) (also termed "P(3HB-co-3HV)"), poly(3-hydroxybutyrate-co-3-hydroxyhexanoate) (also termed "P(3HB-co-3HH)" or "PHBH"), and poly(3-hydroxybutyrate-co-5-hydroxyvalerate) (also termed "P(3HB-co-5HV)").

Polyhydroxyalkanoate synthases (also termed "PHA synthases," "PHB synthases," and/or "PhaC") catalyze polymerization of hydroxyacyl-CoAs to produce polyhydroxyalkanoates. A typical PHB biosynthetic pathway includes a beta-ketothiolase (also termed "PhaA") and an acetoacetyl-CoA reductase (also termed "PhaB"), along with the PhaC polyhydroxyalkanoate synthase. According to the typical pathway, the PhaA beta-ketothiolase catalyzes the conversion of two molecules of acetyl-CoA to acetoacetyl-CoA. The PhaB acetoacetyl-CoA reductase converts acetoacetyl-CoA to R-3-hydroxybutyryl-CoA. The PhaC polyhydroxyalkanoate synthase catalyzes enzymatic head to tail polymerization of R-3-hydroxybutyryl-CoA to produce PHB.

PHB is a high molecular weight polyester that, in purified form, has useful thermoplastic properties and is also biodegradable in a wide range of biologically active environments. Based on these attributes PHB and a range of PHB copolymers have been developed as biobased biodegradable plastics for industrial use. PHB can also be used as a feed supplement and has been shown to have nutritional value and/or prebiotic effects in studies with broiler chicks, sheep, pigs, fish, and prawns. PHB is also a useful growth substrate for denitrifying bacteria in aqueous environments where it is currently used commercially for denitrification in waste water treatment processes. The fact that the PHB polymer is high molecular weight and has a higher density than water means that the polymer acts in a controlled release manner where the denitrifying bacteria degrade the polymer. PHB can also be chemically converted to a range of industrial chemical intermediates including crotonic acid, butanol, and propylene.

Currently PHB is produced by microbial fermentation and is simply too expensive for large scale use in many commercial applications, but because it is a natural product of cellular metabolism, it is a very attractive candidate for production in genetically engineered crops. Production of PHB has already been demonstrated in a number of genetically engineered crop species (Snell, K. D. and Peoples, O. P., 2009, Biofuels, Bioprod Bioref 3, 456-467; Snell, K. D. and Peoples, O. P., 2013, Inform 24, 640-643; Snell, K. D., Singh, V. and Brumbley, S. M., 2015, Current Opinion in Biotechnology 32C, 68-75; Somleva, M. N., Peoples, O. P. and Snell, K. D., 2013, Plant Biotechnol J 11, 233-252), but to date this production approach has not been successful in developing a commercially viable production system. The reasons for this relate to the inability to achieve sufficiently high levels of the PHB polymer in the plant tissue with stability. When high levels of PHB polymer are produced, this impairs plant growth and/or seed germination (Malik et. al., 2015, Plant Biotechnol J 13, 675-688).

Extensive work has been performed to produce PHB in biomass crops such as maize, sugarcane, switchgrass, and tobacco (Snell, K. D., Singh, V. and Brumbley, S. M., 2015). Considerably less effort has been devoted to production of PHB in seeds, with efforts in *Brassica napus* (Houmiel et. al., 1999, Planta 209, 547-550; Valentin, et. al., 1999, Int J Biol Macromol 25, 303-306) and *Camelina sativa* (Malik et al., 2015) being the only examples reported to date where polymer production was demonstrated.

Seeds are natural stable storage sites for the large amounts of oil and proteins deposited by plants to nourish their offspring, the future seedling. The stability of seeds at ambient temperatures allows them to be stored prior to processing and makes these organs promising sites for production of novel bioproducts. Prior work has targeted the production of PHB to seed plastids (Houmiel et al., 1999; Malik et al., 2015; Valentin et al., 1999) to capture a portion of the high flux of acetyl-CoA within this organelle and divert it to polymer production. Up to 7.7% fresh weight (FW) was produced in such seeds of *B. napus* (Houmiel et al., 1999; Valentin et al., 1999) and up to 15.2% of the mature seed weight was obtained in such seeds of *Camelina* (Malik et. al., 2015). However, as the levels of PHB achieved in *Camelina* increased above 7% this resulted in significant impairment of seed germination, and in cases where germination was observed, the resulting seedlings showed impaired growth and often failed to develop into healthy mature plants. Naturally these issues would make it extremely challenging to produce sufficient seed for planting at a commercial scale.

An acetoacetyl-CoA synthase from *Streptomyces* sp., which converts malonyl-CoA and acetyl-CoA to acetoacetyl-CoA, can be used in PHB biosynthetic pathways as an alternative to the beta-ketothiolase to produce acetoacetyl-CoA (Okamura et al., Proc Natl Acad Sci USA, 2010, 107, 11265-11270). This enzyme, named NphT7, has been used successfully as a substitute for beta-ketothiolase to produce PHB in plastids of sugarcane producing up to 11.8% dry weight in sampled sugarcane leaves (McQualter et al., 2015, Plant Biotechnol J 13, 700-707). Overall, sugarcane plants containing the NphT7 protein as part of the PHB biosynthetic pathway produced polymer at levels greater than two times those observed in sugarcane engineered with polymer producing metabolic pathways using the thiolase (McQualter et al., 2015). NphT7 has a lower Km for its substrates compared to the thiolase (McQualter et al., 2015; Okamura et al., 2010), likely allowing it to more effectively compete for substrate for polymer synthesis. Field trials would need to be conducted, though, to determine the effect of the increased PHB production in plastids associated with NphT7 on agronomic traits (McQualter et al., 2015). The negative effect associated with production of PHB at high levels in plastids on seed germination would need to be addressed too.

PHB production in the cytosol of leaf tissue has been attempted previously too, but only with marginal success. For example, targeting polymer production to the cytosol of *Arabidopsis* resulted in plants exhibiting PHB yields only up to about ~0.2 µg/mg dry weight (Xing et al., 2014, Plant J 79, 270-284). Moreover, a strong negative correlation was observed between levels of PHB produced in rosette leaves and growth (Xing et al, 2014). Plants producing PHB to ~0.15 µg/mg dry weight exhibited a dwarf phenotype with a reduction of nearly 90% in fresh weight compared to wild-type plants (Xing et al, 2014). Plants producing PHB to ~0.2 µg/mg dry weight exhibited an even more severe impairment in growth (Xing et al, 2014). Co-expressing transgenes encoding ATP citrate lyase with the PHB genes alleviated the stunted growth to some degree, and yields of polymer increased slightly, for example from ~0.15 µg/mg to ~0.165 µg/mg dry weight (Xing et al, 2014). Yet, even with this co-expression yields of polymer were still very low, and the growth of the plants was still significantly impaired (Xing et al, 2014). The highest reported levels of cytosolic PHA obtained to date are 0.6% dry weight of poly(3-hydroxybutryate-co-3-hydroxyvalerate) containing 0.8 mol % of hydroxyvalerate produced in *Arabidopsis* (Matusmoto et al., 2005, Biomacromolecules 6, 2126-2130) and 0.34% dry weight PHB produced in cotton fibers (John and Keller, 1996, P Natl Acad Sci USA 93, 12768-12773), well below levels that would be needed for commercial applications.

Therefore, it is an object of the invention to provide healthy, transgenic plants that produce high levels of polyhydroxyalkanoates, such as, for example, PHB, in the cytosol of cells of seeds of the plants, without significant impairment of seed germination and/or maturation. It is another object to provide methods of making such transgenic plants that produce high levels of polyhydroxyalkanoates, such as PHB, in the cytosol of cells of seeds of the plants. It is still another object to provide transgenic oilseeds that contain high levels of polyhydroxyalkanoates, such as PHB, in the cytosol of cells of the oilseeds.

SUMMARY OF THE INVENTION

A transgenic land plant that expresses a polyhydroxyalkanoate synthase seed specifically, with cytosolic localization, is provided. The transgenic land plant comprises: (a) a nucleic acid encoding the polyhydroxyalkanoate synthase; and (b) a seed-specific promoter operably linked to the nucleic acid. The seed-specific promoter drives expression of the polyhydroxyalkanoate synthase in cytosol of cells of seeds of the transgenic land plant. The polyhydroxyalkanoate synthase comprises a catalytic domain. The polyhydroxyalkanoate synthase does not comprise any sequence positioned to mediate translocation of the catalytic domain across any membrane of the cells. This results in the polyhydroxyalkanoate synthase being expressed seed specifically, with cytosolic localization.

In some embodiments, the seed-specific promoter comprises one or more of a promoter from soybean oleosin isoform A gene or a promoter from soybean glycinin gene. Also in some embodiments, the seed-specific promoter comprises one or more of a promoter from the soybean oleosin isoform A gene of SEQ ID NO: 5 or a promoter from soybean glycinin gene of SEQ ID NO: 4.

In some embodiments, the catalytic domain comprises a G/S-X-C-X-G-G (SEQ ID NO: 59) PhaC box consensus sequence at positions 317-322, aspartate at position 480, and histidine at position 508, with numbering of the positions relative to PhaC of *Cupriavidus necator* of SEQ ID NO: 32. In some of these embodiments, (a) the catalytic domain further comprises proline at position 239, aspartate at position 254, serine at position 260, tryptophan at position 425, aspartate at position 428, asparagine at position 448, and glycine at position 507, with numbering of the positions relative to PhaC of *Cupriavidus necator* of SEQ ID NO: 32; and (b) the catalytic domain has at least 80% or higher sequence identity to one or more of the following: (i) Class I PhaC *Cupriavidus necator* of SEQ ID NO: 32 residues 201-589, *Chromobacterium violaceum* of SEQ ID NO: 33 residues 174-568, *Delftia acidovorans* of SEQ ID NO: 34 residues 204-630, *Aeromonas caviae* of SEQ ID NO: 35 residues 201-594, *Caulobacter vibrioides* of SEQ ID NO: 36 residues 203-587, *Zoogloea ramigera* of SEQ ID NO: 37 residues 190-576, *Azohydromonas latus* of SEQ ID NO: 38 residues 148-536, *Acinetobacter* sp. RA3849 of SEQ ID NO: 39 residues 206-590, *Burkholderia* sp. DSMZ 9242 of SEQ ID NO: 40 residues 236-625, *Nocardia corallina* of SEQ ID NO: 41 residues 178-561, *Rhodococcus ruber* of SEQ ID NO: 42 residues 176-562, or *Rhodospirillum rubrum* of SEQ ID NO: 43 residues 291-673; (ii) Class II PhaC of *Pseudomonas oleovorans* of SEQ ID NO: 44 residues 179-559, *Pseudomonas putida* of SEQ ID NO: 45 residues 179-560, or *Pseudomonas* sp. 61-3 of SEQ ID NO: 46 residues 183-567; (iii) Class III PhaC of *Allochromatium vinosum* of SEQ ID NO: 47 residues 33-355, *Thiocapsa pfennigii* of SEQ ID NO: 48 residues 35-357, *Arthrospira* sp. PCC 8005 of SEQ ID NO: 49 residues 46-373, *Cyanothece* sp. PCC 7425 of SEQ ID NO: 50 residues 35-366, or *Synechocystis* sp. PCC6803 of SEQ ID NO: 51 residues 48-378; or (iv) Class IV PhaC of *Bacillus cereus* of SEQ ID NO: 52 residues 35-361, *Bacillus megaterium* of SEQ ID NO: 53 residues 31-357, or *Bacillus bataviensis* of SEQ ID NO: 54 residues 31-355.

In some embodiments, the polyhydroxyalkanoate synthase comprises one or more of the following: (i) Class I PhaC of *Cupriavidus necator* of SEQ ID NO: 32, *Chromobacterium violaceum* of SEQ ID NO: 33, *Delftia acidovorans* of SEQ ID NO: 34, *Aeromonas caviae* of SEQ ID NO: 35, *Caulobacter vibrioides* of SEQ ID NO: 36, *Zoogloea ramigera* of SEQ ID NO: 37, *Azohydromonas latus* of SEQ ID NO: 38, *Acinetobacter* sp. RA3849 of SEQ ID NO: 39, *Burkholderia* sp. DSMZ 9242 of SEQ ID NO: 40, *Nocardia corallina* of SEQ ID NO: 41, *Rhodococcus ruber* of SEQ ID NO: 42, or *Rhodospirillum rubrum* of SEQ ID NO: 43; (ii) Class II PhaC of *Pseudomonas oleovorans* of SEQ ID NO: 44, *Pseudomonas putida* of SEQ ID NO: 45, or *Pseudomonas* sp. 61-3 of SEQ ID NO: 46; (iii) Class III PhaC of *Allochromatium vinosum* of SEQ ID NO: 47, *Thiocapsa pfennigii* of SEQ ID NO: 48, *Arthrospira* sp. PCC 8005 of SEQ ID NO: 49, *Cyanothece* sp. PCC 7425 of SEQ ID NO: 50, or *Synechocystis* sp. PCC6803 of SEQ ID NO: 51; or (iv) Class IV PhaC of *Bacillus cereus* of SEQ ID NO: 52, *Bacillus megaterium* of SEQ ID NO: 53, or *Bacillus bataviensis* of SEQ ID NO: 54. Also in some embodiments, the polyhydroxyalkanoate synthase comprises a hybrid PhaC of *Pseudomonas oleovarans/Zoogloea ramigera* of SEQ ID NO: 55.

In some embodiments, the polyhydroxyalkanoate synthase further comprises an endoplasmic reticulum targeting signal, the endoplasmic reticulum targeting signal being positioned to anchor the polyhydroxyalkanoate synthase to a membrane of endoplasmic reticulum of the cells with the catalytic domain remaining in the cytosol, thereby maintaining cytosolic localization of the polyhydroxyalkanoate synthase. In some of these embodiments, the endoplasmic reticulum targeting signal is positioned C-terminally with respect to the catalytic domain. Also in some of these embodiments, the endoplasmic reticulum targeting signal comprises an endoplasmic reticulum targeting signal of a cytochrome B5 isoform D protein. For example, in some of these embodiments the endoplasmic reticulum targeting signal comprises amino acids 108-140 of cytochrome B5 isoform D protein of *Arabidopsis thaliana* of SEQ ID NO: 58.

In some embodiments, the transgenic land plant further comprises one or more of a PhaA beta-ketothiolase or an NphT7 acetoacetyl-CoA synthetase.

In some embodiments, the transgenic land plant further comprises a PhaB acetoacetyl-CoA reductase.

In some embodiments, the transgenic land plant is one or more of a species, *Brassica napus, Brassica rapa, Brassica carinata, Brassica juncea, Camelina sativa*, a *Crambe* species, a *Jatropha* species, pennycress, *Ricinus communis*, a *Calendula* species, a *Cuphea* species, *Arabidopsis thaliana*, maize, soybean, a *Gossypium* species, sunflower, palm, coconut, safflower, peanut, *Sinapis alba*, sugarcane, flax, or tobacco.

In some embodiments, the transgenic land plant further comprises seeds, and the seeds comprise the polyhydroxyalkanoate synthase and a polyhydroxyalkanoate polymerized by the polyhydroxyalkanoate synthase.

In some of these embodiments, greater than 80% of the polyhydroxyalkanoate synthase expressed in the transgenic land plant is expressed in the seeds of the transgenic land plant. Also in some of these embodiments, greater than 80% of the polyhydroxyalkanoate synthase expressed in the seeds of transgenic land plant is localized in cytosol of the cells of the seeds. Also in some of these embodiments, greater than 80% of the polyhydroxyalkanoate polymerized by the polyhydroxyalkanoate synthase is localized in cytosol of the cells of the seeds. Also in some of these embodiments, the transgenic land plant produces the polyhydroxyalkanoate in the seeds to 2.0 to 20.0% of dry seed weight.

Also in some of these embodiments, the polyhydroxyalkanoate comprises one or more of 3-hydroxybutyrate monomers, 4-hydroxybutyrate monomers, 3-hydroxyvalerate monomers, 3-hydroxyhexanoate monomers, 5-hydroxyvalerate monomers, or saturated 3-hydroxyacid monomers with even-numbered carbon chains ranging from C6-C16. For example, in some of these embodiments, the polyhydroxyalkanoate comprises 3-hydroxybutyrate monomers. Also in some of these embodiments, the polyhydroxyalkanoate comprises one or more of poly-3-hydroxybutyrate, poly(3-hydroxybutyrate-co-4-hydroxybutyrate), poly(3-hydroxybutyrate-co-3-hydroxyvalerate), poly(3-hydroxybutyrate-co-3-hydroxhexanoate) and poly(3-hydroxybutyrate-co-5-hydroxyvalerate). For example, in some of these embodiments, the polyhydroxyalkanoate comprises poly-3-hydroxybutyrate.

Exemplary embodiments include the following:

Embodiment 1: A transgenic land plant that expresses a polyhydroxyalkanoate synthase seed specifically, with cytosolic localization, comprising: (a) a nucleic acid encoding the polyhydroxyalkanoate synthase; and (b) a seed-specific promoter operably linked to the nucleic acid, wherein: (i) the seed-specific promoter drives expression of the polyhydroxyalkanoate synthase in cytosol of cells of seeds of the transgenic land plant; (ii) the polyhydroxyalkanoate synthase comprises a catalytic domain; and (iii) the polyhydroxyalkanoate synthase does not comprise any sequence positioned to mediate translocation of the catalytic domain across any membrane of the cells, thereby resulting in the polyhydroxyalkanoate synthase being expressed seed specifically, with cytosolic localization.

Embodiment 2: The transgenic land plant according to embodiment 1, wherein the seed-specific promoter comprises one or more of a promoter from soybean oleosin isoform A gene or a promoter from soybean glycinin gene.

Embodiment 3: The transgenic land plant according to embodiment 1, wherein the seed-specific promoter comprises one or more of a promoter from the soybean oleosin isoform A gene of SEQ ID NO: 5 or a promoter from soybean glycinin gene of SEQ ID NO: 4.

Embodiment 4: The transgenic land plant according to any one of embodiments 1-3, wherein the catalytic domain comprises a G/S-X-C-X-G-G (SEQ ID NO: 59) PhaC box consensus sequence at positions 317-322, aspartate at position 480, and histidine at position 508, with numbering of the positions relative to PhaC of *Cupriavidus necator* of SEQ ID NO: 32.

Embodiment 5: The transgenic land plant according to embodiment 4, wherein: (a) the catalytic domain further comprises proline at position 239, aspartate at position 254, serine at position 260, tryptophan at position 425, aspartate at position 428, asparagine at position 448, and glycine at position 507, with numbering of the positions relative to PhaC of *Cupriavidus necator* of SEQ ID NO: 32; and (b) the catalytic domain has at least 80% or higher sequence identity to one or more of the following: (i) Class I PhaC *Cupriavidus necator* of SEQ ID NO: 32 residues 201-589, *Chromobacterium violaceum* of SEQ ID NO: 33 residues 174-568, *Delftia acidovorans* of SEQ ID NO: 34 residues 204-630, *Aeromonas caviae* of SEQ ID NO: 35 residues 201-594, *Caulobacter vibrioides* of SEQ ID NO: 36 residues 203-587, *Zoogloea ramigera* of SEQ ID NO: 37 residues 190-576, *Azohydromonas latus* of SEQ ID NO: 38 residues 148-536, *Acinetobacter* sp. RA3849 of SEQ ID NO: 39 residues 206-590, *Burkholderia* sp. DSMZ 9242 of SEQ ID NO: 40 residues 236-625, *Nocardia corallina* of SEQ ID NO: 41 residues 178-561, *Rhodococcus ruber* of SEQ ID NO: 42 residues 176-562, or *Rhodospirillum rubrum* of SEQ ID NO: 43 residues 291-673; (ii) Class II PhaC of *Pseudomonas oleovorans* of SEQ ID NO: 44 residues 179-559, *Pseudomonas putida* of SEQ ID NO: 45 residues 179-560, or *Pseudomonas* sp. 61-3 of SEQ ID NO: 46 residues 183-567; (iii) Class III PhaC of *Allochromatium vinosum* of SEQ ID NO: 47 residues 33-355, *Thiocapsa pfennigii* of SEQ ID NO: 48 residues 35-357, *Arthrospira* sp. PCC 8005 of SEQ ID NO: 49 residues 46-373, *Cyanothece* sp. PCC 7425 of SEQ ID NO: 50 residues 35-366, or *Synechocystis* sp. PCC6803 of SEQ ID NO: 51 residues 48-378; or (iv) Class IV PhaC of *Bacillus cereus* of SEQ ID NO: 52 residues 35-361, *Bacillus megaterium* of SEQ ID NO: 53 residues 31-357, or *Bacillus bataviensis* of SEQ ID NO: 54 residues 31-355.

Embodiment 6: The transgenic land plant according to any one of embodiments 1-5, wherein the polyhydroxyalkanoate synthase comprises one or more of the following: (i) Class I PhaC of *Cupriavidus necator* of SEQ ID NO: 32, *Chromobacterium violaceum* of SEQ ID NO: 33, *Delftia acidovorans* of SEQ ID NO: 34, *Aeromonas caviae* of SEQ ID NO: 35, *Caulobacter vibrioides* of SEQ ID NO: 36, *Zoogloea ramigera* of SEQ ID NO: 37, *Azohydromonas latus* of SEQ ID NO: 38, *Acinetobacter* sp. RA3849 of SEQ ID NO: 39, *Burkholderia* sp. DSMZ 9242 of SEQ ID NO: 40, *Nocardia corallina* of SEQ ID NO: 41, *Rhodococcus ruber* of SEQ ID NO: 42, or *Rhodospirillum rubrum* of SEQ ID NO: 43; (ii) Class II PhaC of *Pseudomonas oleovorans* of SEQ ID NO: 44, *Pseudomonas putida* of SEQ ID NO: 45, or *Pseudomonas* sp. 61-3 of SEQ ID NO: 46; (iii) Class III PhaC of *Allochromatium vinosum* of SEQ ID NO: 47, *Thiocapsa pfennigii* of SEQ ID NO: 48, *Arthrospira* sp. PCC 8005 of SEQ ID NO: 49, *Cyanothece* sp. PCC 7425 of SEQ ID NO: 50, or *Synechocystis* sp. PCC6803 of SEQ ID NO: 51; or (iv) Class IV PhaC of *Bacillus cereus* of SEQ ID NO: 52, *Bacillus megaterium* of SEQ ID NO: 53, or *Bacillus bataviensis* of SEQ ID NO: 54.

Embodiment 7: The transgenic land plant according to any one of embodiments 1-5, wherein the polyhydroxyalkanoate synthase comprises a hybrid PhaC of *Pseudomonas oleovarans/Zoogloea ramigera* of SEQ ID NO: 55.

Embodiment 8: The transgenic land plant according to any one of embodiments 1-7, wherein the polyhydroxyalkanoate synthase further comprises an endoplasmic reticulum targeting signal, the endoplasmic reticulum targeting signal being positioned to anchor the polyhydroxyalkanoate synthase to a membrane of endoplasmic reticulum of the cells with the catalytic domain remaining in the cytosol, thereby maintaining cytosolic localization of the polyhydroxyalkanoate synthase.

Embodiment 9: The transgenic land plant according to embodiment 8, wherein the endoplasmic reticulum targeting signal is positioned C-terminally with respect to the catalytic domain.

Embodiment 10: The transgenic land plant according to embodiment 8 or 9, wherein the endoplasmic reticulum targeting signal comprises an endoplasmic reticulum targeting signal of a cytochrome B5 isoform D protein.

Embodiment 11: The transgenic land plant according to embodiment 8 or 9, wherein the endoplasmic reticulum targeting signal comprises amino acids 108-140 of cytochrome B5 isoform D protein of *Arabidopsis thaliana* of SEQ ID NO: 58.

Embodiment 12: The transgenic land plant according to any one of claims 1-11, wherein the transgenic land plant further comprises one or more of a PhaA beta-ketothiolase or an NphT7 acetoacetyl-CoA synthetase.

Embodiment 13: The transgenic land plant according to any one of embodiments 1-12, wherein the transgenic land plant further comprises a PhaB acetoacetyl-CoA reductase.

Embodiment 14: The transgenic land plant according to any one of embodiments 1-13, wherein the transgenic land plant is one or more of a *Brassica* species, *Brassica napus*, *Brassica rapa, Brassica carinata, Brassica juncea, Camelina sativa*, a *Crambe* species, a *Jatropha* species, pennycress, *Ricinus communis*, a *Calendula* species, a *Cuphea* species, *Arabidopsis thaliana*, maize, soybean, a *Gossypium* species, sunflower, palm, coconut, safflower, peanut, *Sinapis alba*, sugarcane, flax, or tobacco.

Embodiment 15: The transgenic land plant according to any one of embodiments 1-14, wherein the transgenic land plant further comprises seeds, and the seeds comprise the polyhydroxyalkanoate synthase and a polyhydroxyalkanoate polymerized by the polyhydroxyalkanoate synthase.

Embodiment 16: The transgenic land plant according to embodiment 15, wherein greater than 80% of the polyhydroxyalkanoate synthase expressed in the transgenic land plant is expressed in the seeds of the transgenic land plant.

Embodiment 17: The transgenic land plant according to embodiment 15 or 16, wherein greater than 80% of the polyhydroxyalkanoate synthase expressed in the seeds of the transgenic land plant is localized in cytosol of the cells of the seeds.

Embodiment 18: The transgenic land plant according to any one of embodiments 15-17, wherein greater than 80% of the polyhydroxyalkanoate polymerized by the polyhydroxyalkanoate synthase is localized in cytosol of the cells of the seeds.

Embodiment 19: The transgenic land plant according to any one of embodiments 15-18, wherein the transgenic land plant produces the polyhydroxyalkanoate in the seeds to 2.0 to 20.0% of dry seed weight.

Embodiment 20: The transgenic land plant according to any one of embodiments 15-19, wherein the polyhydroxyalkanoate comprises one or more of 3-hydroxybutyrate monomers, 4-hydroxybutyrate monomers, 3-hydroxyvalerate monomers, 3-hydroxyhexanoate monomers, 5-hydroxyvalerate monomers, or saturated 3-hydroxyacid monomers with even-numbered carbon chains ranging from C6-C16.

Embodiment 21: The transgenic land plant according to any one of embodiments 15-19, wherein the polyhydroxyalkanoate comprises 3-hydroxybutyrate monomers.

Embodiment 22: The transgenic land plant according to any one of embodiments 15-21, wherein the polyhydroxyalkanoate comprises one or more of poly-3-hydroxybutyrate, poly(3-hydroxybutyrate-co-4-hydroxybutyrate), poly(3-hydroxybutyrate-co-3-hydroxyvalerate), poly(3-hydroxybutyrate-co-3-hydroxhexanoate) and poly(3-hydroxybutyrate-co-5-hydroxyvalerate).

Embodiment 23: The transgenic land plant according to any one of embodiments 15-21, wherein the polyhydroxyalkanoate comprises poly-3-hydroxybutyrate.

Gene systems, genetic constructs, and methods for producing the transgenic land plant also are disclosed. The transgenic land plant can produce and accumulate polyhydroxyalkanoates, such as PHB and/or copolymers, at concentrations of greater than 2% by weight of the plant, as discrete granular inclusions in the cytosol of plant cells. The result is stable plant cells, plant tissue, seeds, and fertile plants having high levels of polyhydroxyalkanoates, including PHB and/or copolymers, produced in the cell cytosol.

DETAILED DESCRIPTION OF THE INVENTION

Figure 1:
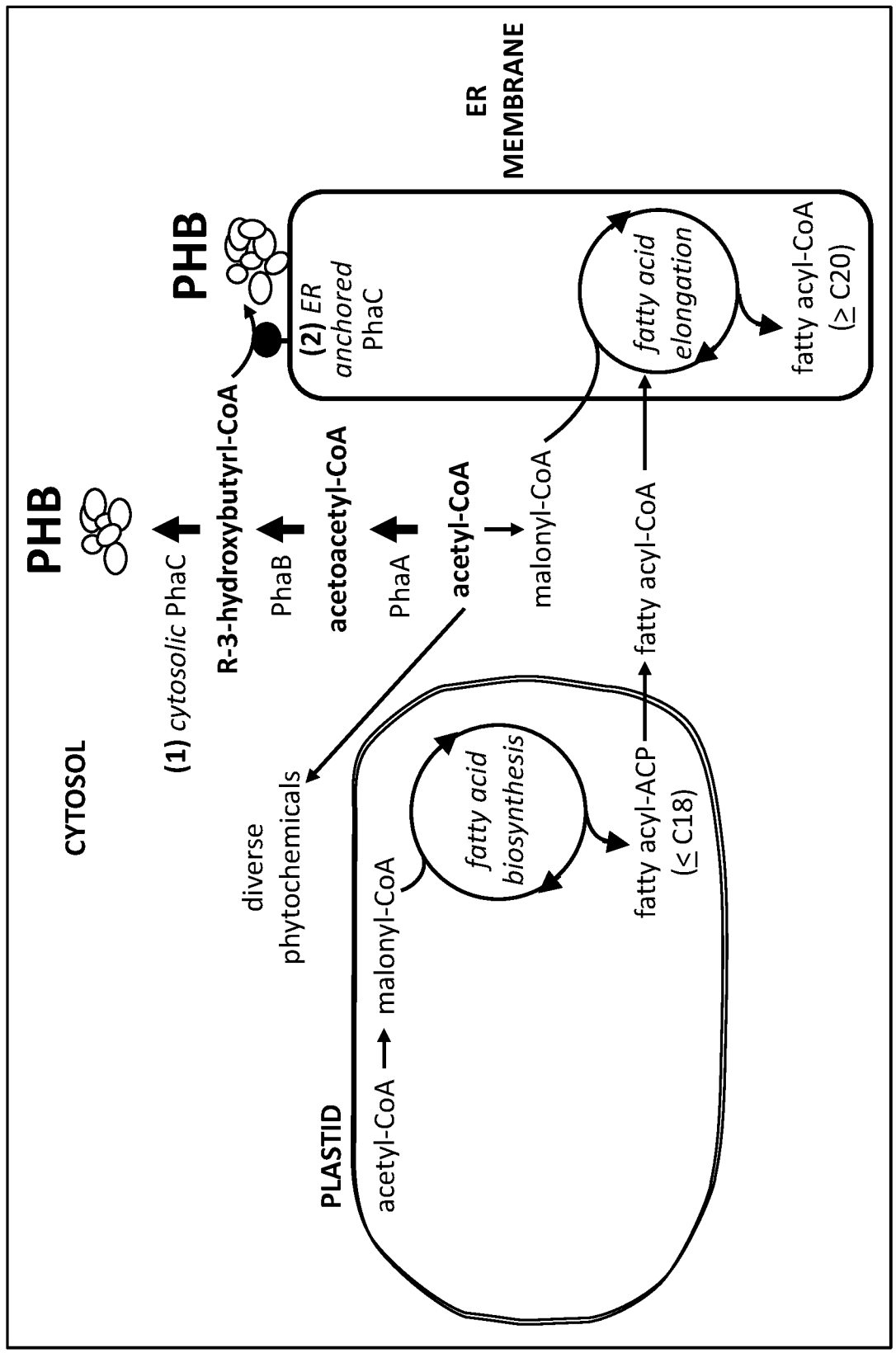
FIG. 1 shows an illustration of fatty acid biosynthesis and elongation in developing seeds and strategies for the PHB production of high levels of PHB in the cytosol. A portion of the acetyl-CoA in the cytosol that would otherwise be used for fatty acid elongation or synthesis of an array of other diverse phytochemicals (Xing et al., 2014, The Plant Journal for Cell and Molecular Biology 79:270-284) is captured by the transgene-encoded PHB biosynthesis pathway. Strategies in which PHA synthase (PhaC), the enzyme polymerizing substrate R-3-hydroxyacyl-CoA to polymer, is targeted to the cytosol or anchored to the ER membrane are shown. Acetyl-CoA in the cytosol is diverted to PHB formation by the expression of one or more transgenes encoding polypeptides having the activity of PhaA, a beta-ketothiolase capable of converting two molecules of acetyl-CoA to acetoacetyl-CoA, or alternatively, NphT7, an acetoacetyl-CoA synthase capable of converting acetyl-CoA and malonyl-CoA to acetoacetyl-CoA, and PhaB, an acetoacetyl-CoA reductase capable of converting acetoacetyl-CoA to R-3-hydroxybutyryl-CoA. Other abbreviations in the figure are as follows: ER, endoplasmic reticulum.

A transgenic land plant that expresses a polyhydroxyalkanoate synthase seed specifically, with cytosolic localization, is provided. The transgenic land plant comprises: (a) a nucleic acid encoding the polyhydroxyalkanoate synthase; and (b) a seed-specific promoter operably linked to the nucleic acid. The seed-specific promoter drives expression of the polyhydroxyalkanoate synthase in cytosol of cells of seeds of the transgenic land plant. The polyhydroxyalkanoate synthase comprises a catalytic domain. The polyhydroxyalkanoate synthase does not comprise any sequence positioned to mediate translocation of the catalytic domain across any membrane of the cells. This results in the polyhydroxyalkanoate synthase being expressed seed specifically, with cytosolic localization.

Without wishing to be bound by theory, it is believed that transgenic land plants that express a polyhydroxyalkanoate synthase seed specifically, with cytosolic localization, can capture and convert a substantial portion of carbon designated for fatty acid elongation to polyhydroxyalkanoate instead, and can do so without suffering a substantial detriment to growth. Surprisingly, the transgenic land plants can produce polyhydroxyalkanoates, such as PHB, in the cytosol of cells of their seeds in much higher amounts than had been achieved in previous efforts to accomplish cytosolic production of polyhydroxyalkanoates, and, importantly, can do so in some lines without the substantial impairments in growth that have been observed previously for production of polyhydroxyalkanoates to high levels in plastids and even at low levels in the cytosol. Also surprisingly, the transgenic land plants can transmit this trait to their progeny to at least $T_2$ generation seeds, and thus can stably maintain the trait to at least this extent. For example, as discussed below, the transgenic land plants can produce PHB at levels up to 4.5% of the mature seed weight in $T_2$ seeds. Additionally surprisingly, modifying the polyhydroxyalkanoate synthase such that the synthase is anchored to the cytoplasmic face of the endoplasmic reticulum (also termed "ER") membrane of cells of seeds of the transgenic land plants can allow the transgenic land plants to produce polyhydroxyalkanoates in their seeds to even higher levels, and can increase stability of maintenance of the trait. For example, also as discussed below, the transgenic land plants including a polyhydroxyalkanoate synthase modified to be anchored to the cytoplasmic face of the endoplasmic reticulum can produce PHB in homozygous $T_4$ seeds at levels up to 7.1% of the mature seed weight in a greenhouse and up to 10.2% of the mature seed weight in a controlled environmental chamber.

For context, previous work with plastid-based production of PHB in seeds was successful in producing high levels of polymer, reaching up to 15% of the mature seed weight, but cotyledons were chlorotic and a significant negative impact on seedling viability was observed (Malik et al., 2015). Prior attempts to produce PHB within the cytosol in leaves yielded only low levels of polymer, e.g. up to 0.61% dry weight (Matsumoto et al., 2005, Biomacromolecules 6, 2126-2130), and often produced stunted plant phenotypes despite many attempts including trials in *Arabidopsis* (Matsumoto et al., 2005; Poirier et al., 1992, Science 256, 520-523; Poirier et al., 1995, Nature Biotechnology 13, 142-150), cotton (Chowdhury and John, 1998, Thermochimica Acta 313, 43-53; John, 1998, Critical Reviews in Biotechnology 17, 185-208; John and Keller, 1996), rice (Endo et al., 2006, Plant Biotechnology 23, 99-109), tamarix (Endo et al., 2006), tobacco (Matsumoto et al., 2011, Journal of Bioscience and Bioengineering 111, 485-488; Nakashita et al., 2001, Plant Biotechnology 18, 289-293; Nakashita et al., 1999, Bioscience, Biotechnology, and Biochemistry, 63 870-874; Suzuki et al., 2002, Bioscience, Biotechnology, and Biochemistry 66, 2537-2542), and sugarcane (Petrasovits et al., 2007, Plant Biotechnology Journal 5, 162-172)). In *Arabidopsis*, an approximately 90% reduction in fresh weight was observed in some low level cytosolic PHB producers (Xing et al., 2014). This phenotype could be partially corrected upon overexpression of ATP citrate lyase, an enzyme that converts citrate and CoA to acetyl-CoA and oxaloacetate, possibly replenishing acetyl-CoA pools, however yields of PHB were not significantly improved (Xing et al., 2014). No efforts to produce PHB specifically in the cytosol of seeds have been reported.

As noted, surprisingly it has been determined that the transgenic land plants of the present application can produce polyhydroxyalkanoates in the cytosol of cells of their seeds in substantially higher amounts than had been achieved in previous efforts to accomplish production of polyhydroxyalkanoates in cytosol in leaves, and that the transgenic land plants can transmit this trait to at least $T_2$ generation seeds. Camelina seed oil contains multiple fatty acids that have a chain length≥20 carbon units that are formed by elongation of plastid-exported fatty acids using malonyl-CoA as a two carbon donor and an endoplasmic-reticulum-associated, multi-enzyme fatty acid elongase complex. With reference to FIG. 1, since the cytosol of seeds supplies malonyl-CoA, which can be obtained from acetyl-CoA and $CO_2$ via the cytosolic acetyl-CoA carboxylase, for these endoplasmic-reticulum-associated fatty acid elongation reactions (Li-Beisson et al., 2010, Acyl-Lipid Metabolism. In: The Arabidopsis Book 8:e0133. doi:10.1199/tab.0133), a greater pool of accessible substrate acetyl-CoA for production of PHB may be available in the cytosol of developing seeds than in leaves. Also with reference to FIG. 1, it was reasoned that targeting the PHB biosynthetic pathway, including PhaA beta-ketothiolase, PhaB acetoacetyl-CoA reductase, and PhaC polyhydroxyalkanoate synthase, to the cytosol could allow the capture and conversion of a portion of the carbon designated for fatty acid elongation to polymer. Thus, expression constructs for cytosolic production of PHB using strong seed-specific promoters were prepared and transformed into Camelina as described in the Examples.

It was expected that the expression constructs could be used to establish initial plant lines that would produce PHB in cytosol of their seeds and that could be used as a baseline for experiments to further modify metabolic pathways with the aim of increasing yields of PHB and alleviating impairment of growth. It was expected that the initial plant lines would produce only low levels of PHB, in view of previous results for cytosolic production of PHB in leaves, and would exhibit severe impairment of growth, also in view of the previous results.

Instead, surprisingly, results indicated that the initial plant lines can be used to produce substantial amounts of PHB even without further modification of metabolic pathways. Based on use of one of these expression constructs, pMBXS394, as noted above PHB levels of up to 4.5% of the mature seed weight were produced in $T_2$ seeds, and this was accomplished in some lines without substantial impairments in growth. These results represents a substantial improvement over prior approaches for producing polyhydroxyalkanoates in plants.

The results also suggested that this cytosolic PHB production exhibits some degree of instability beyond the $T_2$ generation seeds, though. In experiments involving these expression constructs PHB levels dropped in later generations, yielding a high of only 2.9% in $T_3$ seeds. This suggested room for further improvement.

An additional construct, pMBXS763, was made to anchor the polyhydroxyalkanoate synthase to the cytosolic face of the endoplasmic reticulum, with the aim of increasing yields of polyhydroxyalkanoates by localizing production of the polyhydroxyalkanoates to this discrete structure within the cytosol. An ER targeting signal had previously been used to increase the production of a novel protein, corresponding to human immunodeficiency virus protein Nef (negative factor) modified to include an ER targeting signal at its C-terminal end, in tobacco (Barbante et al., 2008, Plant Biotechnol J 6, 560-575). For that novel protein, the increase in production was suggested to have been based on increasing the stability of the protein or making the protein less susceptible to proteases.

Regarding polyhydroxyalkanoate synthase, it would not have been expected that increasing stability of the protein or making the protein less susceptible to proteases would have been necessary or beneficial to increase polyhydroxyalkanoate yields. This is because previous research suggests that factors other than polyhydroxyalkanoate synthase levels limit polyhydroxyalkanoate yields, and because negative correlations had been observed regarding polyhydroxyalkanoate levels and plant growth (see, e.g., Xing et al., 2014).

Instead, it was hypothesized that localizing production of polyhydroxyalkanoates to the cytosolic face of the endoplasmic reticulum, by localizing individual molecules of the synthase there over extended periods of time, might decrease potentially detrimental interactions between polyhydroxyalkanoates and other structure of the plant cells, and ultimately stabilize production of polyhydroxyalkanoates in the cells. As noted above, polyhydroxyalkanoates accumulate intracellularly in the form of granules. Polyhydroxyalkanoate synthases have been shown to bind granules of PHB (Gerngross et al., 1993, J. Bacteriol. 175, 5289-5293). Considering that negative correlations had been observed between polyhydroxyalkanoate levels and plant growth, and that polyhydroxyalkanoate synthases bind granules of PHB, it was hypothesized that targeting polyhydroxyalkanoate synthases to the endoplasmic reticulum might localize the granules there, specifically at the cytosolic face of the endoplasmic reticulum. It was further hypothesized that such targeting might promote initiation of synthesis of the polyhydroxyalkanoates there, and maintain localization of the resulting granules there, and that this in turn might alleviate negative effects of production of polyhydroxyalkanoates to high levels.

Figure 5:
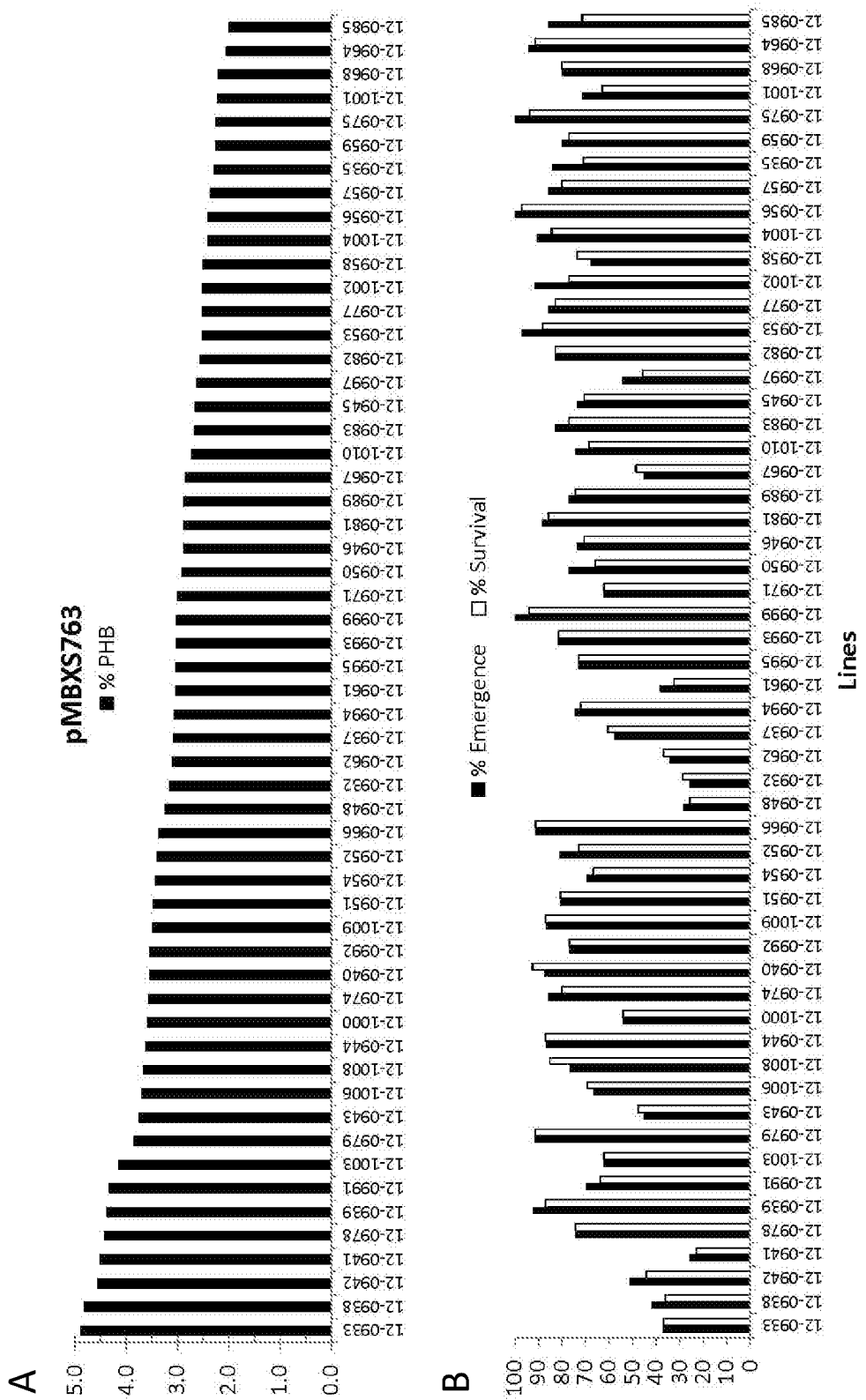
FIG. 5 shows bar graphs of (A) percent PHB content in $T_2$ seeds transformed with pMBXS763, and (B) percent emergence and survival of the seeds transformed with pMBXS763.
Figure 6:
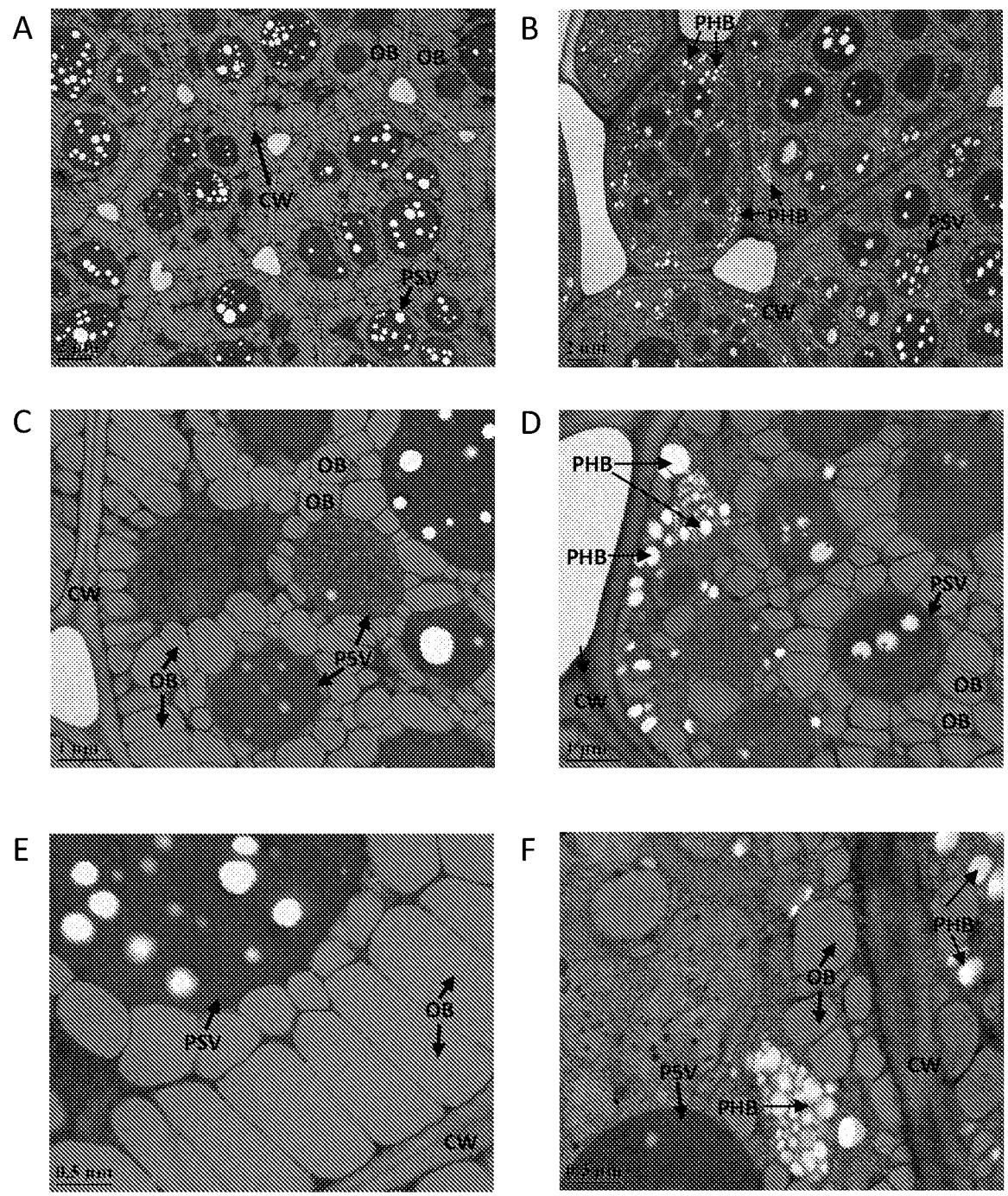
FIG. 6 shows transmission electron micrographs of imbibed seeds of (A, C, and E) WT43 and (B, D, and F) pMBXS394 line 12-0415. Longitudinal sections for analysis passed through the cotyledonary region. T2 seeds from pMBXS394 line 12-0415 contained 4.5% PHB. Seeds were imbibed for 5 hours before processing for TEM. Abbreviations are as follows: CW, cell wall; PSV, protein storage vesicles; OB, oil bodies; PHB, granules of PHB. Scale bars are provided at lower left of each image.
Figure 7:
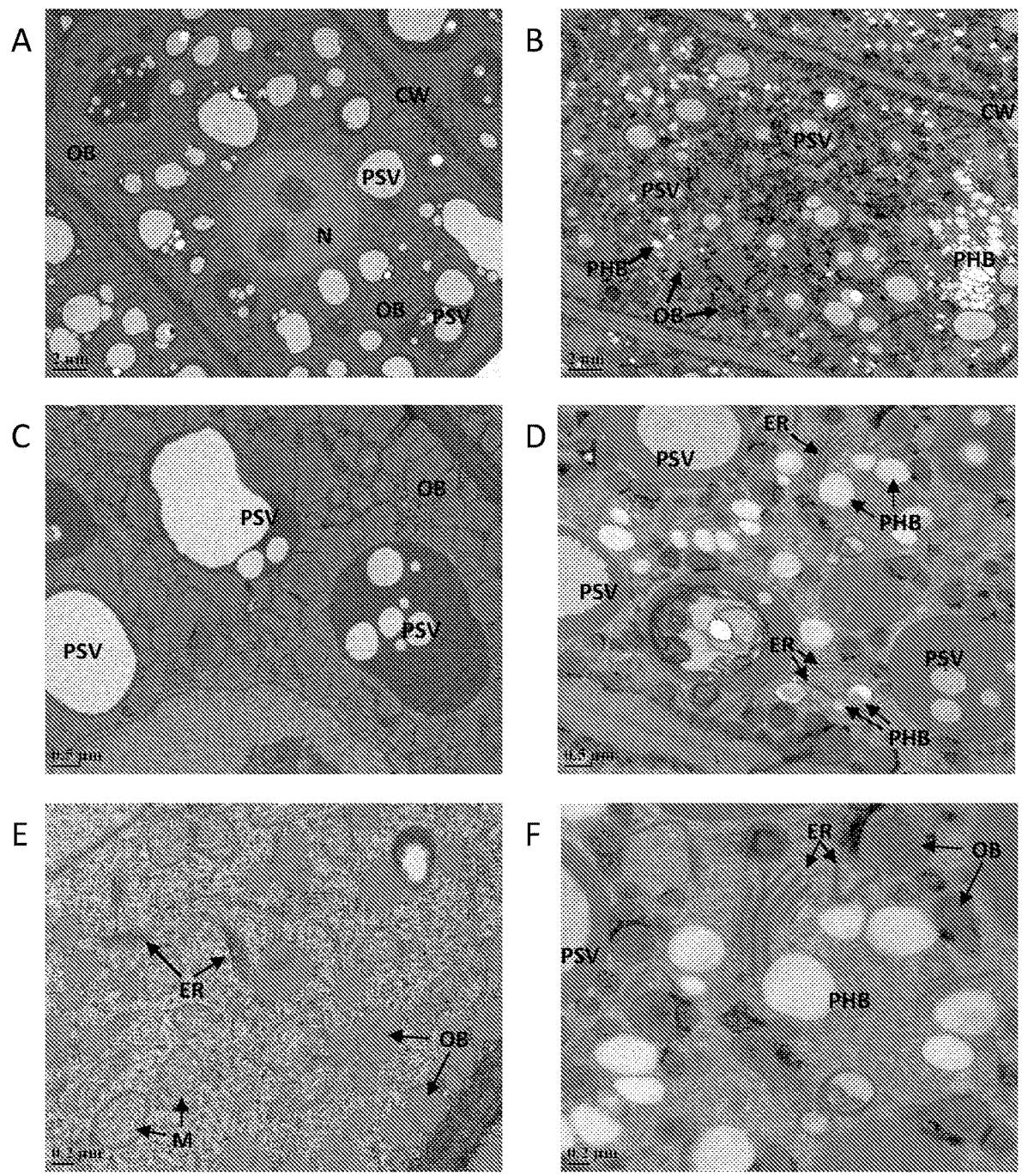
FIG. 7 shows transmission electron micrographs of imbibed seeds of (A, C, and E) WT43 and (B, D, and F) pMBXS763 line 12-0933. Longitudinal sections for analysis passed through the cotyledonary region. T2 seeds from pMBXS763 line 12-0933 contained 4.9% PHB in $T_2$ seeds. Seeds were imbibed for 5 hours before processing for TEM. Abbreviations are as follows: CW, cell wall; PSV, protein storage vesicles; OB, oil bodies; PHB, granules of PHB; ER, endoplasmic reticulum; M, mitochondria; N, nucleus. Scale bars are provided at lower left of each image.

Thus, the gene encoding polyhydroxyalkanoate synthase was modified to accomplish fusion of a C-terminal anchoring sequence for the endoplasmic reticulum at the C-terminal end of PHA synthase. Camelina plants were then transformed with the modified polyhydroxyalkanoate synthase gene and other genes of the PHB biosynthetic pathway. The corresponding ER targeted lines performed similarly to cytosolic lines with respect to yields of PHB. For example, the lines transformed with pMBXS394, in the $T_2$ generation, produced up to 4.9% PHB in $T_2$ seeds. Unlike the cytosolic lines, though, PHB production for ER targeted lines was found to be stable through multiple generations and in some lines polymer levels even increased in later generations. Thus, for example, in this case the top greenhouse grown line produced up to 7.1% PHB in homozygous $T_4$ seeds (FIGS. 5A-B).

Figure 9:
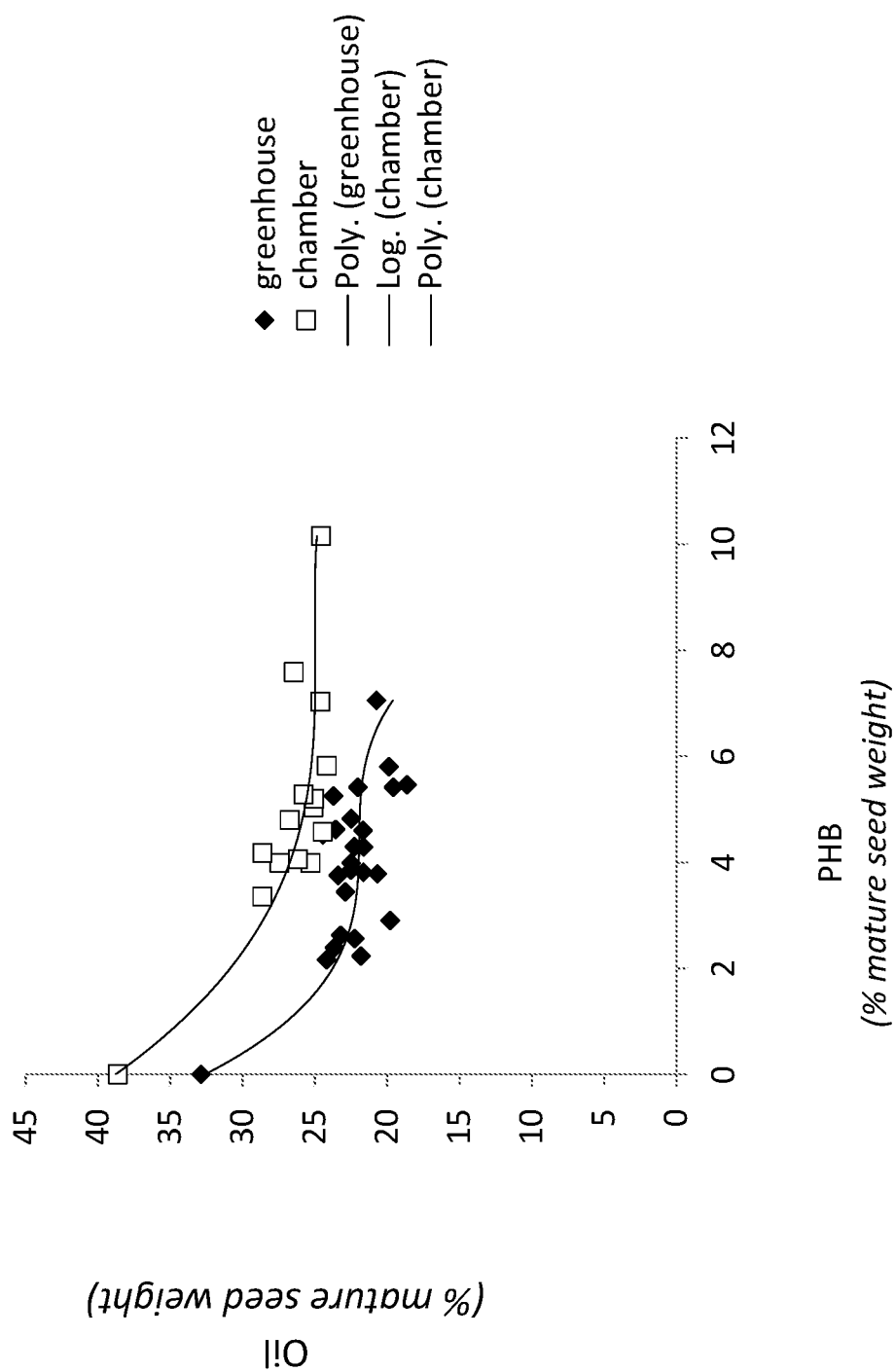
FIG. 9 shows a comparison of oil and PHB content in $T_4$ seeds of lines of pMBXS763 grown in the greenhouse or in a controlled environmental chamber. Chamber growth conditions are described in TABLE 8. Oil content for WT43 lines is 32.9±1.3% (n=8) for greenhouse growth and 38.6±0.7 (n=5) for chamber growth. A third order polynomial fit of data is shown.

As discussed in more detail below, further work with ER targeted lines was performed in a controlled environmental chamber programmed to simulate growth of lines in the field by varying the temperature cycle to reflect seasonal differences. This program included a low of 5° C. night/17° C. day during early simulated spring, a high of 20° C. night/25° C. day midway through the growth cycle, and a temperature of 11° C. night/24° C. day during later stages of development and harvest (TABLE 8). All transgenic and wild-type control WT43 *Camelina* lines thrived under these growth conditions and yielded significantly more seed compared to greenhouse growth of 18° C. night/22° C. day. Light conditions were essentially equivalent (900 µmoles/m$^{-2}$ s$^{-1}$) in the chamber and the greenhouse that was fitted with supplemental lights. PHB and fatty acid levels within harvested seeds of plants were also consistently higher in the chamber than in the greenhouse (FIG. 9). The best ER targeted PHB line produced up to 10.2% PHB in T$_4$ seeds when grown in the chamber (FIG. 9, TABLE 9).

Figure 4:
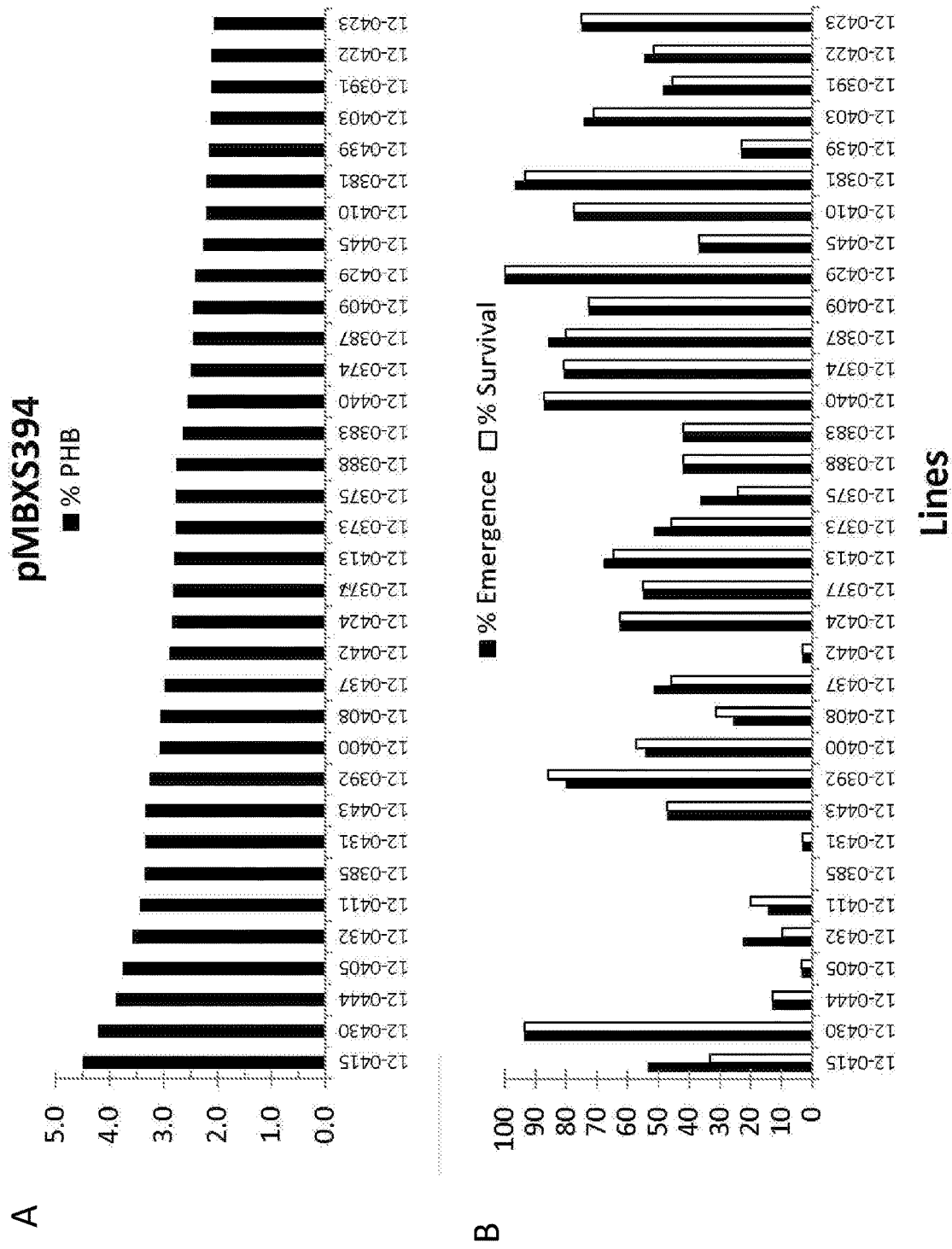
FIG. 4 shows bar graphs of (A) percent PHB content in $T_2$ seeds transformed with pMBXS394, and (B) percent emergence and survival for the seeds transformed with pMBXS394.
Figure 8:
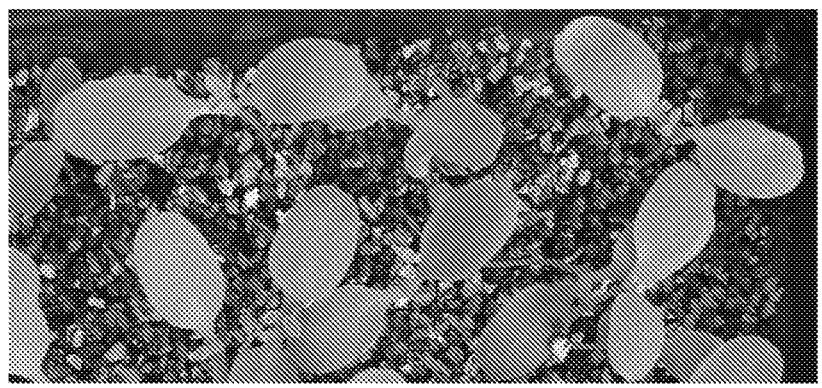
FIG. 8 shows phenotypes of $T_2$ seedlings germinated in soil at the fully expanded cotyledon stage with first true leaves emerging (seven day old seedlings) of (A) WT43, (B) pMBXS394 line 12-0415 containing 4.5% PHB in T2 seeds, and (C) pMBXS763 line 12-0939 containing 4.4% PHB in T2 seeds.
Figure 8:
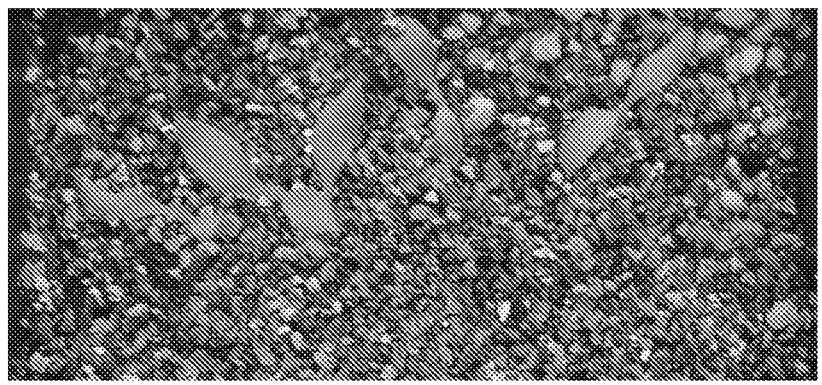
Figure 8:
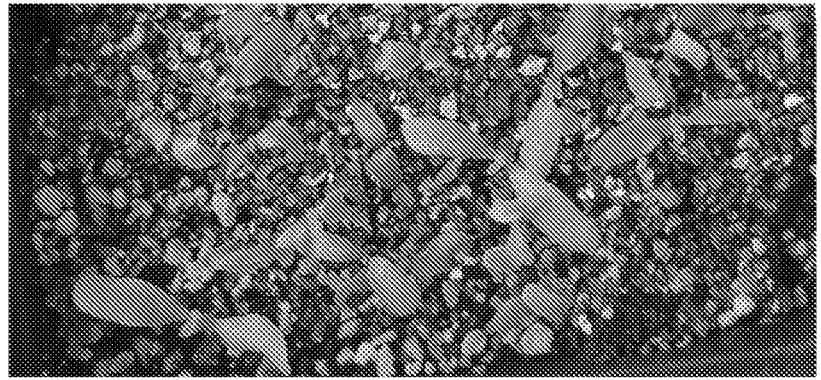

There were some differences in cotyledon phenotypes of cytosolic PHB producing lines in comparison to WT43 seedlings. The cotyledons of the WT43 control are rounded, whereas those of cytosolic PHB producing lines were narrow (FIG. 8). Depending on the line, the development of seedlings from PHB producing seeds was slower than that of WT43 control by 0-5 days. Light microscopy of thin sections of seedling cotyledons showed smaller cells in cytosolic and ER targeted lines as compared to the WT43 control. Intercellular spaces, which are typically observed in WT43, either were not apparent or were reduced in cytosolic and ER targeted lines. Survival of seedlings in soil varied by line and generation (FIG. 4(B), FIG. 5(B), and TABLE 9). Yet, the chlorotic phenotype observed with seed specific plastid PHB producers (Malik et al., 2015) was not observed and there was no visible difference in cotyledon greening in the large number of cytosolic and ER targeted lines evaluated for survival in soil. Also, the best ER targeted line, when grown in the controlled environmental chamber, had a 78% survival of T$_3$ seedlings yielding individual plants that produced T$_4$ seeds containing between 4.6 and 10.2% of the seed weight as PHB (TABLE 9).

Based on these results, it is believed that the transgenic land plants disclosed herein will be useful for producing polyhydroxyalkanoates, including PHB, commercially in a manner that is cost effective.

Thus, transgenic land plants, plant material, plant cells, and genetic constructs for synthesis of polyhydroxyalkanoates, such as PHB, are provided. In a preferred embodiment, the transgenic land plants are transgenic oilseed plants that synthesize PHB in the cytosol of cells in the seed. Host plants, plant tissue, and plant material have been engineered to express genes encoding enzymes in the biosynthetic pathway for PHB production such that polymer precursors are produced and polymerized in the cytosol to form the PHB polymer which accumulates as granular inclusions. Genes utilized include genes encoding enzymes for the PHB biosynthetic pathways, PhaA beta-ketothiolase enzyme, PhaB acetoacetyl-CoA reductase, and PhaC polyhydroxyalkanoate synthase. In some cases, a gene encoding NphT7, which is an acetoacetyl-CoA synthetase of the thiolase superfamily, can be used in place of the PhaA beta-ketothiolase enzyme. The genes can be introduced in the plant, plant tissue, or plant cell using conventional plant molecular biology techniques. Additional genetic modifications to the plants to increase the availability of the starting substrate acetyl-CoA, or cofactors such as NADPH, proteins to stabilize PHB granules, and/or transcription factors or other proteins to enhance carbon fixation, can also be carried out to increase the levels of PHB accumulated. The additional genetic modifications can include introducing additional transgenes through transformation and/or altering the activity of genes already present in the plants using genome editing.

As discussed in more detail below, in one embodiment methods and compositions are provided for producing transgenic oilseeds having PHB accumulated in the cytosolic compartment of the cells in the seed, for example greater than 2%, 3%, 4%, 5%, 7%, 10%, 12%, 15%, 20%, or greater of the total dry seed weight. The corresponding transgenic land plants have good seed germination and form healthy plantlets which grow into mature healthy fertile plants.

In another embodiment transgenic land plants and transgenic plant material are provided in which the transgene for the PHB synthase enzyme has been modified to add an ER targeting sequence such that the PHB synthase enzyme, when expressed in the seed cytosol, is anchored to the endoplasmic reticulum. An exemplary ER signal is a 33 amino acid sequence from the cytochrome B5 isoform D protein from *Arabidopsis thaliana* corresponding to DFVIKLLQFLVPLLILGLAFGIRYYTKTKAPSS (SEQ ID NO: 58 residues 108-140; amino acids 108-140 of sequence listed in NP_199692.1).

In still another embodiment the disclosed transgenic land plants and transgenic plant materials are provided including transgenes in addition to those encoding the PHB biosynthetic enzymes that increase the availability of acetyl-CoA, the primary metabolite necessary for PHA production, in the cytosol. In some of these embodiments the genes used to increase the availability of acetyl-CoA in the cytosol include genes designed to increase citrate synthase activity in the mitochondria and ATP citrate lyase activity (which catalyzes the conversion of citrate and CoA to acetyl-CoA and oxaloacetate) in the cytosol.

Methods and compositions for producing hybrid lines are also provided. Hybrid lines can be created by crossing lines containing one or more pathways to produce PHAs, for example a line with PHB genes crossed with a line containing the other gene(s) needed to complete the PHA biosynthetic pathway. Use of lines that possess cytoplasmic male sterility with the appropriate maintainer and restorer lines allows these hybrid lines to be produced efficiently.

Plants that are transformed include dicots or monocots. Preferred host plants are oilseed plants, but are not limited to members of the *Brassica* family including *B. napus*, *B. rapa*, *B. carinata* and *B. juncea* and other oilseeds including *Camelina sativa*, flax, *Crambe*, jatropha, pennycress, castor, *Calendula*, *Cuphea*, maize, soybean, cottonseed, sunflower, palm, coconut, safflower, peanut, mustards including *Sinapis alba*, and tobacco.

In other embodiments plant materials and plant parts of the transgenic plants are provided. The disclosed oilseeds can be used for the extraction of PHB biopolymer or as a source of PHB biopolymer based chemical intermediates. In some cases, the oil can be extracted from the seed and the remaining seed meal containing PHB can be used as a component of animal or aquaculture feed. In other cases, the oil can be extracted from the seed and the remaining seed meal containing PHB can be further processed to produce purified PHB and a protein meal useful in for example animal feed. In some examples it may be useful to combine the PHB producing lines with other input traits such as pest tolerance, herbicide resistance, nutritional proteins, other value-added co-products, or oils with modified profiles.

I. Definitions

Unless otherwise indicated, the disclosure encompasses all conventional techniques of plant breeding, microbiology, cell biology and recombinant DNA, which are within the skill of the art. See, e.g., Sambrook and Russell, Molecular Cloning: A Laboratory Manual, 3rd edition (2001); Current Protocols In Molecular Biology, F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993); Coligan, Dunn, Ploegh, Speicher and Wingfeld, eds. (1995) Current Protocols in Protein Science (John Wiley & Sons, Inc.); the series Methods in Enzymology (Academic Press, Inc.); and PCR 2: A Practical Approach (M. J. MacPherson, B. D. Hames and G. R. Taylor eds. (1995).

Unless otherwise noted, technical terms are used according to conventional usage. Definitions of common terms in molecular biology may be found in Lewin, Genes VII, published by Oxford University Press, 2000; Kendrew et al. (eds.), The Encyclopedia of Molecular Biology, published by Wiley-Interscience, 1999; and Robert A. Meyers (ed.), Molecular Biology and Biotechnology, a Comprehensive Desk Reference, published by VCH Publishers, Inc., 1995; Ausubel et al. (1987) Current Protocols in Molecular Biology, Green Publishing; Sambrook and Russell. (2001) Molecular Cloning: A Laboratory Manual 3rd. edition.

A number of terms used herein are defined and clarified in the following section.

The term "PHB" refers to poly-3-hydroxybutyrate, the homopolymer of 3-hydroxybutyric acid.

The term "PHB copolymer" encompasses copolymers of 3-hydroxybutyrate with other hydroxyacid monomers including, for example, 3-hydroxyvalerate, 3-hydroxyhexanoate, 3-hydroxyoctanoate, 4-hydroxybutyrate, 4-hydroxyvalerate, and 5-hydroxyvalerate. Such copolymers include, for example, poly-3-hydroxybutyrate-co-3-hydroxyvalerate, poly-3-hydroxybutyrate-co-3-hydroxyhexanoate, poly-3-hydroxybutyrate-co-3-hydroxyoctanoate, poly-3-hydroxybutyrate-co-4-hydroxybutyrate, poly-3-hydroxybutyrate-co-4-hydroxyvalerate and poly-3-hydroxybutyrate-co-5-hydroxyvalerate.

The term "PHBH" refers to the PHB copolymer poly-3-hydroxybutyrate-co-3-hydroxyhexanoate.

The term "PHA" refers to polyhydroxyalkanoates, which include PHB and the various PHB copolymers noted above, among others homopolymers and copolymers of hydroxyalkanoic acids.

The terms "PHA synthase" and "PHA polymerase" are used interchangeably and refer to the enzyme that catalyzes the formation of PHAs. The terms "PHB synthase" and "PHB polymerase" refer to PHA synthases that can catalyze the formation of PHB and/or PHB copolymers in particular.

As used herein, a "vector" is a replicon, such as a plasmid, phage, or cosmid, into which another DNA segment may be inserted so as to bring about the replication of the inserted segment. The vectors can be expression vectors.

As used herein, an "expression vector" is a vector that includes one or more expression control sequences.

As used herein, an "expression control sequence" is a DNA sequence that controls and regulates the transcription and/or translation of another DNA sequence. Plant cells are known to utilize promoters, polyadenylation signals, and enhancers.

As used herein an "expression cassette" is a DNA sequence that includes a promoter operable in a plant, the gene encoding a protein of interest and a polyadenylation sequence such that when the expression cassette is introduced into a plant cell genome it will express the protein of interest.

As used herein, "operably linked" means incorporated into a genetic construct so that expression control sequences effectively control expression of a coding sequence of interest.

As used herein, "transformed" and "transfected" encompass the introduction of a nucleic acid into a cell by a number of techniques known in the art.

"Plasmids" are designated by a lower case "p" preceded and/or followed by capital letters and/or numbers.

As used herein the term "heterologous" means from another host. The other host can be the same or different species.

The term "cell" refers to a membrane-bound biological unit capable of replication or division.

The term "construct" refers to a recombinant genetic molecule including one or more isolated polynucleotide sequences. Genetic constructs used for transgene expression in a host organism comprise, in the 5'-3' direction, the following: a promoter sequence; a nucleic acid sequence encoding the desired transgene product; and a termination sequence. The open reading frame may be oriented in either a sense or anti-sense direction. The construct may also comprise selectable marker gene(s) and other regulatory elements for expression.

The term "plant" is used in its broadest sense. It includes, but is not limited to, any species of woody, ornamental or decorative, crop or cereal, fruit or vegetable plant. It also refers to a plurality of plant cells that are largely differentiated into a structure that is present at any stage of a plant's development. Such structures include, but are not limited to, a fruit, shoot, stem, leaf, flower petal, seed etc.

The term "land plant" means a plant belonging to the plant subkingdom Embryophyta. The term "land plant" includes mature plants, seeds, shoots and seedlings, and parts, propagation material, plant organ tissue, protoplasts, callus and other cultures, for example cell cultures, derived from plants belonging to the plant subkingdom Embryophyta, and all other species of groups of plant cells giving functional or structural units, also belonging to the plant subkingdom Embryophyta. The term "mature plants" refers to plants at any developmental stage beyond the seedling. The term "seedlings" refers to young, immature plants at an early developmental stage.

"Plant tissue" refers to a group of plant cells organized into a structural and functional unit. Any tissue of a plant, whether in a plant or in culture, is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

The term "plant part" as used herein refers to a plant structure, a plant organ, or a plant tissue.

A "non-naturally occurring plant" refers to a plant that does not occur in nature without human intervention. Non-naturally occurring plants include transgenic plants and plants produced by non-transgenic means such as plant breeding.

The term "plant cell" refers to a structural and physiological unit of a plant, including a protoplast and a cell wall. The plant cell may be in the form of an isolated single cell or a cultured cell, or as a part of higher organized unit such as, for example, a plant tissue, a plant organ, or a whole plant.

The term "plant cell culture" refers to cultures of plant units such as, for example, protoplasts, cell culture cells, cells in plant tissues, pollen, pollen tubes, ovules, embryo sacs, zygotes and embryos at various stages of development.

The term "plant material" refers to leaves, stems, roots, flowers or flower parts, fruits, pollen, egg cells, zygotes, seeds, cuttings, cell or tissue cultures, or any other part or product of a plant.

A "plant organ" refers to a distinct and visibly structured and differentiated part of a plant such as a root, stem, leaf, flower bud, or embryo.

"Seed germination" refers to growth of an embryonic plant contained within a seed resulting in the formation and emergence of a seedling.

"Cotyledon" refers to the embryonic first leaves of a seedling.

"Early plantlet development" refers to growth of the cotyledon containing seedling to form a plantlet.

The term "non-transgenic plant" refers to a plant that has not been genetically engineered with heterologous nucleic acids. These non-transgenic plants can be the test or control plant when comparisons are made, including wild-type plants.

A "corresponding non-transgenic plant" refers to the plant prior to the introduction of heterologous nucleic acids. This plant can be the test plant or control plant, including wild type plants.

A "trait" refers to morphological, physiological, biochemical and physical characteristics or other distinguishing feature of a plant or a plant part or a cell or plant material. The term "trait modification" refers to a detectable change in a characteristic of a plant or a plant part or a plant cell induced by the expression of a polynucleotide or a polypeptide of the invention compared to a plant not expressing them, such as a wild type plant. Some trait modifications can be evaluated quantitatively, such as content of different metabolites, proteins, pigments, lignin, vitamins, starch, sucrose, glucose, fatty acids and other storage compounds, seed size and number, organ size and weight, total plant biomass, yield of seed and yield of genetically engineered products.

The term "with cytosolic localization" as used with reference to production of polyhydroxyalkanoate refers to producing the polyhydroxyalkanoate, preferably PHB, in the cytosol of a cell, such as a seed cell, and not in an organelle of the cell.

The term "ortholog," as used herein, means a polynucleotide sequence or polypeptide sequence possessing a high degree of homology, i.e. sequence relatedness, to a subject sequence and being a functional equivalent of the subject sequence, wherein the sequence that is orthologous is from a species that is different than that of the subject sequence. Homology may be quantified by determining the degree of identity and/or similarity between the sequences being compared.

As used herein, "percent homology" of two polynucleotide sequences or of two polypeptide sequences is the percent identity over the length of the entire sequence determined using the ALIGNX alignment function of the Vector NTI software package (Vector NTI Advance, Version 11.5.3, ThermoFisher), which uses the Clustal W algorithm. Default parameters of the program were used.

The percentage of sequence identity between two polypeptides can also be determined by making a pairwise sequence alignment. This can be done using EMBOSS Needle Pairwise Sequence Alignment (PROTEIN) tool using default settings (matrix: BLOSUM62; gap open: 10; gap extend: 0.5; output format: pair; end gap penalty: false; end gap open: 10; end gap extend: 0.5) (website: ebi.ac.uk/Tools/psa/emboss_needle/). This also can be done using other pairwise sequence alignment tools that are analogous.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Many other polypeptides will meet the same criteria.

II. Transgenic Plants

As noted above, the transgenic land plant expresses a polyhydroxyalkanoate synthase seed specifically, with cytosolic localization. The polyhydroxyalkanoate synthase comprises a catalytic domain.

A. Polyhydroxyalkanoate Synthases

A diverse range of polyhydroxyalkanoate synthases are suitable for expression in the transgenic land plant. Extensive biochemical studies, sequence comparisons, and structural analyses indicate that polyhydroxyalkanoate synthases include common structural features and structure-function correlations that can be used to identify polyhydroxyalkanoate synthases, distinguish them from other enzymes, and confirm their suitability.

Polyhydroxyalkanoate synthases have been identified from diverse microbial species (Mezzolla et al., 2018, Polymers 10, 910, doi:10:3390/polym10080910). Polyhydroxyalkanoate synthases have been grouped into four classes, designated Classes I-IV, based on their primary sequences, subunit compositions, and substrate specificities (Chek et al., 2017, Scientific Reports 7:5312, doi:10.1038/s41598-017-05509-4). Class I synthases include a single type of PhaC protein, form homodimers, and favor short-chain length monomers corresponding to C3-C5 carbon chain lengths. Class II synthases include two types of PhaC proteins, designated PhaC1 and PhaC2, form heterodimers, and favor medium-chain-length monomers corresponding to C6-C14 carbon chain lengths. Class III and Class IV synthases include two types of PhaC proteins, designated PhaC and PhaE or PhaC and PhaR, respectively, form heterodimers, and favor short-chain length monomers.

Polyhydroxyalkanoate synthases share a common structural feature corresponding to a catalytic domain (Wittenborn et al., 2016, Journal of Biochemistry 291, 25264-25277). Specifically, the Class I and Class II synthases include an N-terminal domain of unknown function and a C-terminal catalytic domain. Considering PhaC of *Cupriavidus necator* (previously termed *Alcaligenes eutrophus* and *Ralstonia eutropha*) of SEQ ID NO: 32, which is a well studied Class I synthase, the N-terminal domain corresponds to amino acid residues 1-200, and the C-terminal catalytic domain corresponds to amino acid residues 201-589. The catalytic domain of *Cupriavidus necator* has an α/β-hydrolase fold including a central mixed β-sheet flanked on both sides by α-helices. This structure is similar to that of lipases and had been predicted based on sequence similarity and threading models. The catalytic domains of other Class I and Class II synthases can be identified based on sequence alignments with PhaC of *Cupriavidus necator*, for example based on multiple sequence alignments using Clustal Omega (website: ebi.ac.uk/Tools/msa/clustalo/) with default settings. The Class III and Class IV synthases include only a short N-terminal sequence, also of unknown function, followed by a catalytic domain. Considering PhaC of *Allochromatium vinosum* of SEQ ID NO: 47, which is a well studied Class III synthase, the N-terminal sequence corresponds to amino acid residues 1-32, and the catalytic domain corresponds to amino acid residues 33-355. The catalytic domains of other Class III and Class IV synthases can be identified based on sequence alignments with PhaC of *Allochromatium vinosum*, also for example based on multiple sequence alignments using Clustal Omega.

Figure 2G:
FIG. 2A-N shows a Clustal Omega multiple sequence alignment of (i) Class I PhaC *Cupriavidus necator* (Accession: P23608.1; SEQ ID NO: 32), *Chromobacterium violaceum* (Accession: Q9ZHI2.2; SEQ ID NO: 33), *Delftia acidovorans* (Accession: BAA33155.1; SEQ ID NO: 34), *Aeromonas caviae* (Accession: BAA21815.1; SEQ ID NO: 35), *Caulobacter vibrioides* (Accession: AZH14788.1; SEQ ID NO: 36), *Zoogloea ramigera* (Accession: AAB06755.1; SEQ ID NO: 37), *Azohydromonas latus* (Accession: AAC83658.1; SEQ ID NO: 38), *Acinetobacter* sp. RA3849 (Accession: AAA99474.1; SEQ ID NO: 39), *Burkholderia* sp. DSMZ 9242 (Accession: AAF23364.1; SEQ ID NO: 40), *Nocardia corallina* (Accession: AAB94058.1; SEQ ID NO: 41), *Rhodococcus ruber* (Accession: CAA4703 5.1; SEQ ID NO: 42), and *Rhodospirillum rubrum* (Accession: AAD53179.1; SEQ ID NO: 43); (ii) Class II PhaC of *Pseudomonas oleovorans* (Accession: P26494.1; SEQ ID NO: 44), *Pseudomonas putida* (Accession: ADR62347.1; SEQ ID NO: 45), and *Pseudomonas* sp. 61-3 (Accession: BAA36198.1; SEQ ID NO: 46); (iii) Class III PhaC of *Allochromatium vinosum* (Accession: P45370.2; SEQ ID NO: 47), *Thiocapsa pfennigii* (Accession: CAA63797.1; SEQ ID NO: 48), *Arthrospira* sp. PCC 8005 (Accession: CDM92827.1; SEQ ID NO: 49), *Cyanothece* sp. PCC 7425 (Accession: ACL46371.1; SEQ ID NO: 50), and *Synechocystis* sp. PCC6803 (Accession: P73390.1; SEQ ID NO: 51); and (iv) Class IV PhaC of *Bacillus cereus* (Accession: AAW84266.2; SEQ ID NO: 52), *Bacillus megaterium* (Accession: AJI20472.1; SEQ ID NO: 53), and *Bacillus bataviensis* (Accession: EKN68787.1; SEQ ID NO: 54).

Polyhydroxyalkanoate synthases also share common structural features corresponding to a G/S-X-C-X-G-G (SEQ ID NO: 59) PhaC box consensus sequence, a conserved aspartate residue, and a conserved histidine residue within the catalytic domain (Wittenborn et al., 2016; Chek et al., 2017, Scientific Reports 7, 5312, doi:10.1038/s41598-017-05509-4). Considering PhaC of *Cupriavidus necator* of SEQ ID NO: 32, the PhaC box consensus sequence is located at positions 317-322, the conserved aspartate at position 480, and the conserved histidine at position 508 (FIG. 2A-N). According to a recently published mechanism for polyhydroxyalkanoate synthases, these enzymes catalyze polymerization of R-3-hydroxyacyl-CoAs at the cysteine of the PhaC box consensus sequence as a single active site that requires both covalent and noncovalent intermediates (Wittenborn et al., 2016). Structural studies indicate that the location of the cysteine of the PhaC box consensus sequence, the conserved aspartate residue, and the conserved histidine residue define the active site (Wittenborn et al., 2016). Biochemical and site-directed mutant studies indicate that these cysteine, aspartate, and histidine residues play crucial roles in catalysis, thus establishing structure-function correlations. The positions of the PhaC box consensus sequence, the conserved aspartate, and the conserved histidine in other Class I synthases, and in the Class II, Class III, and Class IV synthases, can be determined based on sequence alignments with PhaC of *Cupriavidus necator*, again for example based on multiple sequence alignments using Clustal Omega.

Polyhydroxyalkanoate synthases also share common structural features corresponding to additional conserved residues corresponding, in order from N-terminus to C-terminus, to a conserved proline residue, a conserved aspartate residue, a conserved serine residue, a conserved tryptophan residue, a conserved aspartate residue, a conserved asparagine residue, and a conserved glycine residue, also within the catalytic domain. Considering PhaC of *Cupriavidus necator* of SEQ ID NO: 32, the conserved proline is located at position 239, the conserved aspartate at position 254, the conserved serine at position 260, the conserved tryptophan at position 425, the conserved aspartate at position 428, the conserved asparagine at position 448, and the conserved glycine at position 507. The positions of these additional conserved residues in other Class I synthases, and in the Class II, Class III, and Class IV synthases, can be determined based on sequence alignments with PhaC of *Cupriavidus necator*, again for example based on multiple sequence alignments using Clustal Omega.

These common structural features and structure-function correlations, among others, can be used to identify polyhydroxyalkanoate synthases, distinguish them from other enzymes, and confirm their suitability.

Thus, suitable polyhydroxyalkanoate synthases include, for example, polyhydroxyalkanoate synthases that have been identified from natural sources, i.e. the diverse microbial species from which polyhydroxyalkanoate synthases have been identified to date.

Suitable polyhydroxyalkanoate synthases also include, for example, polyhydroxyalkanoate synthases that have been engineered to include modifications relative to naturally occurring polyhydroxyalkanoate synthases while maintaining the common structural features and structure-function correlations. This includes, for example, hybrid polyhydroxyalkanoate synthases, which have been engineered to include one or more portions of one polyhydroxyalkanoate synthase fused to one or more portions of another polyhydroxyalkanoate synthase. This also includes, for example, polyhydroxyalkanoate synthases that have been modified to include one or more other polypeptides fused at the N-terminus and/or C-terminus of the polyhydroxyalkanoate synthases. This also includes, for example, polyhydroxyalkanoate synthases that have been modified by minor truncations, e.g. of one, two, three, or more amino acids, at the N-terminus and/or C-terminus.

Thus, in some embodiments the catalytic domain comprises a G/S-X-C-X-G-G (SEQ ID NO: 59) PhaC box consensus sequence at positions 317-322, aspartate at position 480, and histidine at position 508, with numbering of the positions relative to PhaC of *Cupriavidus necator* of SEQ ID NO: 32.

In some of these embodiments, (a) the catalytic domain further comprises proline at position 239, aspartate at position 254, serine at position 260, tryptophan at position 425, aspartate at position 428, asparagine at position 448, and glycine at position 507, with numbering of the positions relative to PhaC of *Cupriavidus necator* of SEQ ID NO: 32; and (b) the catalytic domain has at least 80% or higher sequence identity to one or more of the following: (i) Class I PhaC *Cupriavidus necator* of SEQ ID NO: 32 residues 201-589, *Chromobacterium violaceum* of SEQ ID NO: 33 residues 174-568, *Delftia acidovorans* of SEQ ID NO: 34 residues 204-630, *Aeromonas caviae* of SEQ ID NO: 35 residues 201-594, *Caulobacter vibrioides* of SEQ ID NO: 36 residues 203-587, *Zoogloea ramigera* of SEQ ID NO: 37 residues 190-576, *Azohydromonas latus* of SEQ ID NO: 38 residues 148-536, *Acinetobacter* sp. RA3849 of SEQ ID NO: 39 residues 206-590, *Burkholderia* sp. DSMZ 9242 of SEQ ID NO: 40 residues 236-625, *Nocardia corallina* of SEQ ID NO: 41 residues 178-561, *Rhodococcus ruber* of SEQ ID NO: 42 residues 176-562, or *Rhodospirillum rubrum* of SEQ ID NO: 43 residues 291-673; (ii) Class II PhaC of *Pseudomonas oleovorans* of SEQ ID NO: 44 residues 179-559, *Pseudomonas putida* of SEQ ID NO: 45 residues 179-560, or *Pseudomonas* sp. 61-3 of SEQ ID NO: 46 residues 183-567; (iii) Class III PhaC of *Allochromatium vinosum* of SEQ ID NO: 47 residues 33-355, *Thiocapsa pfennigii* of SEQ ID NO: 48 residues 35-357, *Arthrospira* sp. PCC 8005 of SEQ ID NO: 49 residues 46-373, *Cyanothece* sp. PCC 7425 of SEQ ID NO: 50 residues 35-366, or *Synechocystis* sp. PCC6803 of SEQ ID NO: 51 residues 48-378; or (iv) Class IV PhaC of *Bacillus cereus* of SEQ ID NO: 52 residues 35-361, *Bacillus megaterium* of SEQ ID NO: 53 residues 31-357, or *Bacillus bataviensis* of SEQ ID NO: 54 residues 31-355.

In some embodiments, the polyhydroxyalkanoate synthase comprises one or more of the following: (i) Class I PhaC of *Cupriavidus necator* of SEQ ID NO: 32, *Chromobacterium violaceum* of SEQ ID NO: 33, *Delftia acidovorans* of SEQ ID NO: 34, *Aeromonas caviae* of SEQ ID NO: 35, *Caulobacter vibrioides* of SEQ ID NO: 36, *Zoogloea ramigera* of SEQ ID NO: 37, *Azohydromonas latus* of SEQ ID NO: 38, *Acinetobacter* sp. RA3849 of SEQ ID NO: 39, *Burkholderia* sp. DSMZ 9242 of SEQ ID NO: 40, *Nocardia corallina* of SEQ ID NO: 41, *Rhodococcus ruber* of SEQ ID NO: 42, or *Rhodospirillum rubrum* of SEQ ID NO: 43; (ii) Class II PhaC of Pseudomonas oleovorans of SEQ ID NO: 44, *Pseudomonas putida* of SEQ ID NO: 45, or *Pseudomonas* sp. 61-3 of SEQ ID NO: 46; (iii) Class III PhaC of *Allochromatium vinosum* of SEQ ID NO: 47, *Thiocapsa pfennigii* of SEQ ID NO: 48, *Arthrospira* sp. PCC 8005 of SEQ ID NO: 49, *Cyanothece* sp. PCC 7425 of SEQ ID NO: 50, or *Synechocystis* sp. PCC6803 of SEQ ID NO: 51; or (iv) Class IV PhaC of *Bacillus cereus* of SEQ ID NO: 52, *Bacillus megaterium* of SEQ ID NO: 53, or *Bacillus bataviensis* of SEQ ID NO: 54.

In some embodiments, the polyhydroxyalkanoate synthase comprises a hybrid PhaC of *Pseudomonas oleovarans/Zoogloea ramigera* of SEQ ID NO: 55.

B. Nucleic Acid Encoding the Polyhydroxyalkanoate Synthase and Seed-Specific Promoter As noted above, the transgenic land plant comprises a nucleic acid encoding the polyhydroxyalkanoate synthase. The transgenic land plant also comprises a seed-specific promoter operably linked to the nucleic acid.

The transgenic land plant can be made based on transformation of a host plant with a genetic construct including the nucleic acid encoding the polyhydroxyalkanoate synthase and the seed-specific promoter operably linked to the nucleic acid, or can be progeny of a host plant so transformed. The nucleic acid encoding the polyhydroxyalkanoate synthase is necessarily heterologous with respect to the host plant. This is because polyhydroxyalkanoate synthases do not occur naturally in land plants. The nucleic acid includes an open reading frame that encodes the polyhydroxyalkanoate synthase. In some embodiments, the nucleic acid corresponds to a sequence that occurs naturally in a microbe from which the polyhydroxyalkanoate synthase was identified, e.g. the nucleic acid can be identical to a sequence that occurs naturally in a microbe from which the polyhydroxyalkanoate synthase was identified. In some embodiments, the nucleic acid includes modifications relative to a sequence that occurs naturally in a microbe from which the polyhydroxyalkanoate synthase was identified, e.g. the nucleic acid can be codon-optimized for expression in plants.

The seed-specific promoter is a promoter that is active during seed development, such as promoters of seed storage proteins (see Thompson et al., 1989, BioEssays 10, 108-113). For dicots, seed-specific promoters include, but are not limited to, bean β-phaseolin, napin, β-conglycinin, soybean lectin, flax linin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1.

By the seed-specific promoter being operably linked to the nucleic acid encoding the polyhydroxyalkanoate synthase, it is meant that the nucleic acid is configured such that transcription of the nucleic acid is initiated from the seed-specific promoter and results in expression of the polyhydroxyalkanoate synthase. Accordingly, in the context of the transgenic land plant, the seed-specific promoter functions as a promoter of transcription of the nucleic acid sequence, and thus of expression of the polyhydroxyalkanoate synthase, such that the polyhydroxyalkanoate synthase is expressed during seed development, specifically in seeds.

This results in the polyhydroxyalkanoate synthase being expressed seed specifically.

In some embodiments, the seed-specific promoter comprises one or more of a promoter from soybean oleosin isoform A gene or a promoter from soybean glycinin gene. For example, in some embodiments, the seed-specific promoter comprises one or more of a promoter from the soybean oleosin isoform A gene of SEQ ID NO: 5 or a promoter from soybean glycinin gene of SEQ ID NO: 4.

In some embodiments, the nucleic acid encoding the polyhydroxyalkanoate synthase and the seed-specific promoter operably linked to the nucleic acid are present in nuclear genome of the transgenic land plant. This can be based, for example, on the transgenic land plant having been made based on integration of the nucleic acid encoding the polyhydroxyalkanoate synthase and the seed-specific promoter into nuclear DNA chromosomes of a corresponding host plant. This would be in contrast, for example, to integration into mitochondrial DNA or plastid DNA.

C. Genetic Constructs for Transformation

1. Vectors and Constructs

Suitable genetic constructs for the disclosed transgenic plants include expression cassettes for enzymes for production of the PHB biosynthetic pathway. In one embodiment, the construct contains an expression cassette where the following DNA sequence elements are operatively linked in the 5' to 3' direction, a seed-specific promoter that directs transcription of a nucleic acid sequence in the nucleus; a nucleic acid sequence encoding one of the PHB biosynthetic enzymes; and a 3' polyadenylation signal that increases levels of expression of transgenes. In one embodiment the construct contains multiple expression cassettes for multiple transgenes. As discussed in more detail below, in one embodiment the PHB synthase enzyme is modified such that it is attached to the endoplasmic reticulum (ER) in the cytosol of seed cells using appropriate ER-targeting signals.

DNA constructs useful in the methods described herein include transformation vectors capable of introducing transgenes into plants. The transgenes in the transgenic organism are preferably stable and inheritable. The heterologous nucleic acid fragment is integrated into the host genome.

Several plant transformation vector options are available, including those described in "Gene Transfer to Plants" (Potrykus, et al., eds.) Springer-Verlag Berlin Heidelberg New York (1995); "Transgenic Plants: A Production System for Industrial and Pharmaceutical Proteins" (Owen, et al., eds.) John Wiley & Sons Ltd. England (1996); and "Methods in Plant Molecular Biology: A Laboratory Course Manual" (Maliga, et al. eds.) Cold Spring Laboratory Press, New York (1995). Plant transformation vectors generally include one or more coding sequences of interest under the transcriptional control of 5' and 3' regulatory sequences, including a promoter, a transcription termination and/or polyadenylation signal, and a selectable or screenable marker gene. For the expression of two or more polypeptides from a single transcript, additional RNA processing signals and ribozyme sequences can be engineered into the construct (U.S. Pat. No. 5,519,164). This approach has the advantage of locating multiple transgenes in a single locus, which is advantageous in subsequent plant breeding efforts.

A transgene may be constructed to encode a series of enzyme activities separated by intein sequences such that on expression, two or more enzyme activities are expressed from a single promoter as described by Snell in U.S. Pat. No. 7,026,526 to Metabolix, Inc.

2. CRISPR/Cas Constructs

In some embodiments it may be possible to further increase levels of PHB polymers by modifying the activity of native plants genes. This can be accomplished using traditional transgenic techniques or by the more recently developed genome editing technologies. The advantage of using genome editing technologies is that the regulatory body in the United States views genome editing as an advanced plant breeding tool and may not regulate the technologies. Recent advances in genome editing technologies provide an opportunity to precisely remove genes or edit control sequences to significantly alter the expression levels of targeted genes. Plants engineered using this approach may be defined as non-regulated by USDA-APHIS providing the opportunity to continually improve the production of PHB by altering the activity of native plant genes to increase for example substrate or cofactor availability for PHB polymers produced in plants engineered with the PHB pathway. Given the timelines and costs associated with achieving regulatory approval for transgenic plants this approach enables a single regulatory filing instead of having to continuously file for regulatory approval for each subsequent genetic modification to improve PHB polymer production. One particular technology, CRISPR/Cas9 genome editing, has been receiving considerable attention in the scientific community as a way to edit the genomes of complex organisms including plants (Belhaj, K., 2013, Plant Methods 9, 39; Khandagale & Nadal, 2016, Plant Biotechnol Rep 10, 327). CRISPR is an acronym for clustered regulatory interspaced short palindromic repeat, and Cas9 is an abbreviation for CRISPR-associated protein. This technology is unique amongst genome editing technologies for its simplicity—a Cas9 nuclease and a single guide RNA (sgRNA) with homology to the modification target are the only components necessary for induction of targeted DNA cleavage. Other genome editing technologies, such as zinc finger nucleases and transcriptional activator-like effector nucleases (TALENS) require more complex protein engineering to bind the DNA sequence to enable editing. Examples of simultaneous CRISPR/Cas9 gene editing at multiple target sites, or multiplex genome editing, have been described for both mammalian cells and plants, and can be achieved by expressing one or more single guide RNAs (sgRNAs) to target multiple genome sites within the organism.

3. Herbicide Resistance and Insect Tolerance

The disclosed engineered plants for increased yield may have stacked input traits that include herbicide resistance and insect tolerance. For example, the transgenic plant can be engineered to be tolerant to the herbicide glyphosate and can be engineered to produce the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the genetically engineered plant (Suh, et al., 1993, J. M Plant Mol. Biol. 22, 195-205).

BT toxin is a protein that is lethal to many insects providing the plant that produces it protection against pests (Barton, et al., 1987, Plant Physiol. 85, 1103-1109). Other useful herbicide tolerance traits include but are not limited to tolerance to Dicamba by expression of the dicamba monoxygenase gene (Behrens et al, 2007, Science 316, 1185), tolerance to 2,4-D and 2,4-D choline by expression of a bacterial aad-1 gene that encodes for an aryloxyalkanoate dioxygenase enzyme (Wright et al., 2010, Proceedings of the National Academy of Sciences 107, 20240), glufosinate tolerance by expression of the bialophos resistance gene (bar) or the pat gene encoding the enzyme phosphinotricin acetyl transferase (Droge et al., 1992, Planta 187, 142), as well as genes encoding a modified 4-hydroxyphenylpyruvate dioxygenase (HPPD) that provides tolerance to the herbicides mesotrione, isoxaflutole, and tembotrione. (Siehl et al., 2014, Plant Physiol 166, 1162).

D. Cytosolic Localization

As noted above, the seed-specific promoter drives expression of the polyhydroxyalkanoate synthase in cytosol of cells of seeds of the transgenic land plant. Also, the polyhydroxyalkanoate synthase does not comprise any sequence positioned to mediate translocation of the catalytic domain across any membrane of the cells. This results in the polyhydroxyalkanoate synthase being expressed, not just seed specifically, but also with cytosolic localization.

This can be accomplished in various ways.

1. Polyhydroxyalkanoate Synthases that are Not Modified

For example, polyhydroxyalkanoate synthases identified from naturally occurring microbes do not appear to include any signal peptides or other sequences that would cause the polyhydroxyalkanoate synthases to be translocated across the endoplasmic reticulum membrane or otherwise to be targeted for delivery internal to plastids, mitochondria, or other organelles. Accordingly, expression of polyhydroxyalkanoate synthases that have not been modified to include any signal peptides or other sequences that would cause the polyhydroxyalkanoate synthases to be translocated across the endoplasmic reticulum membrane or otherwise to be targeted for delivery internal to plastids, mitochondria, or other organelles, wherein the expression is initiated from a seed-specific promoter present in the nuclear genome, as opposed for example to mitochondrial or plastid DNA, will result in cytosolic localization.

Thus, in some embodiments the polyhydroxyalkanoate synthase is expressed, not just seed specifically, but also with cytosolic localization, based on the polyhydroxyalkanoate synthase not having been modified to include any signal peptides or other sequences that would cause the polyhydroxyalkanoate synthase to be translocated across the endoplasmic reticulum membranes or otherwise to be targeted for delivery internal to plastids, mitochondria, or other organelles.

2. Targeting Polyhydroxyalkanoate Synthases to the Cytoplasmic Face of the Endoplasmic Reticulum Membrane Also for example, polyhydroxyalkanoate synthases can be modified such that, when they are expressed, they become anchored at the cytosolic face of the endoplasmic reticulum membrane of the cells of the seeds of the transgenic land plants. The polyhydroxyalkanoate synthases so anchored can be oriented such that the catalytic domain of the polyhydroxyalkanoate synthase remains in the cytosol of the cells. The polyhydroxyalkanoate synthases so anchored can remain soluble and active despite being attached to the ER membrane.

Specifically, ER targeting signals (also termed "attachment signals") have been identified that cause proteins to become anchored at the cytosolic face of the ER membrane (Barbante et al., 2008, Plant Biotechnology Journal 6, 560-575). An exemplary ER attachment signal is a 33 amino acid sequence from the cytochrome B5 isoform D protein from *Arabidopsis thaliana* corresponding to DFVIKLLQFLVPL-LILGLAFGIRYYTKTKAPSS (SEQ ID NO: 58 residues 108-140; amino acids 108-140 of sequence listed in NP_199692.1). According to Barbante et al. (2008), the mammalian ER isoform of cytochrome B5 is a type IV transmembrane polypeptide, also termed a TA protein. The mammalian ER isoform of cytochrome B5 includes a hydrophobic transmembrane domain near the C-terminus of the protein. Interestingly, expression of a modified version of the mammalian ER isoform of cytochrome B5 in plants demonstrated that the hydrophobic transmembrane domain accomplishes anchoring to the ER membrane, with the portion of the mammalian ER isoform of cytochrome B5 that is C-terminal of the transmembrane being localized in the lumen of the ER, and the portion that is N-terminal of the transmembrane remaining in the cytosol (Barbante et al., 2008). Without wishing to be bound by theory, it is believed that the 33 amino acid sequence from the cytochrome B5 isoform D protein from *Arabidopsis thaliana* noted above similarly can function as a transmembrane domain, such that modification of a polyhydroxyalkanoate synthase to include the 33 amino acid sequence at or near the C-terminus of the polyhydroxyalkanoate synthase, and thus at or near the C-terminal end of the catalytic domain of the polyhydroxyalkanoate synthase, followed by cytosolic expression of the polyhydroxyalkanoate synthase, results in anchoring of the polyhydroxyalkanoate synthase at the ER membrane, with the catalytic domain of the polyhydroxyalkanoate synthase remaining in the cytosol.

Figure 3:
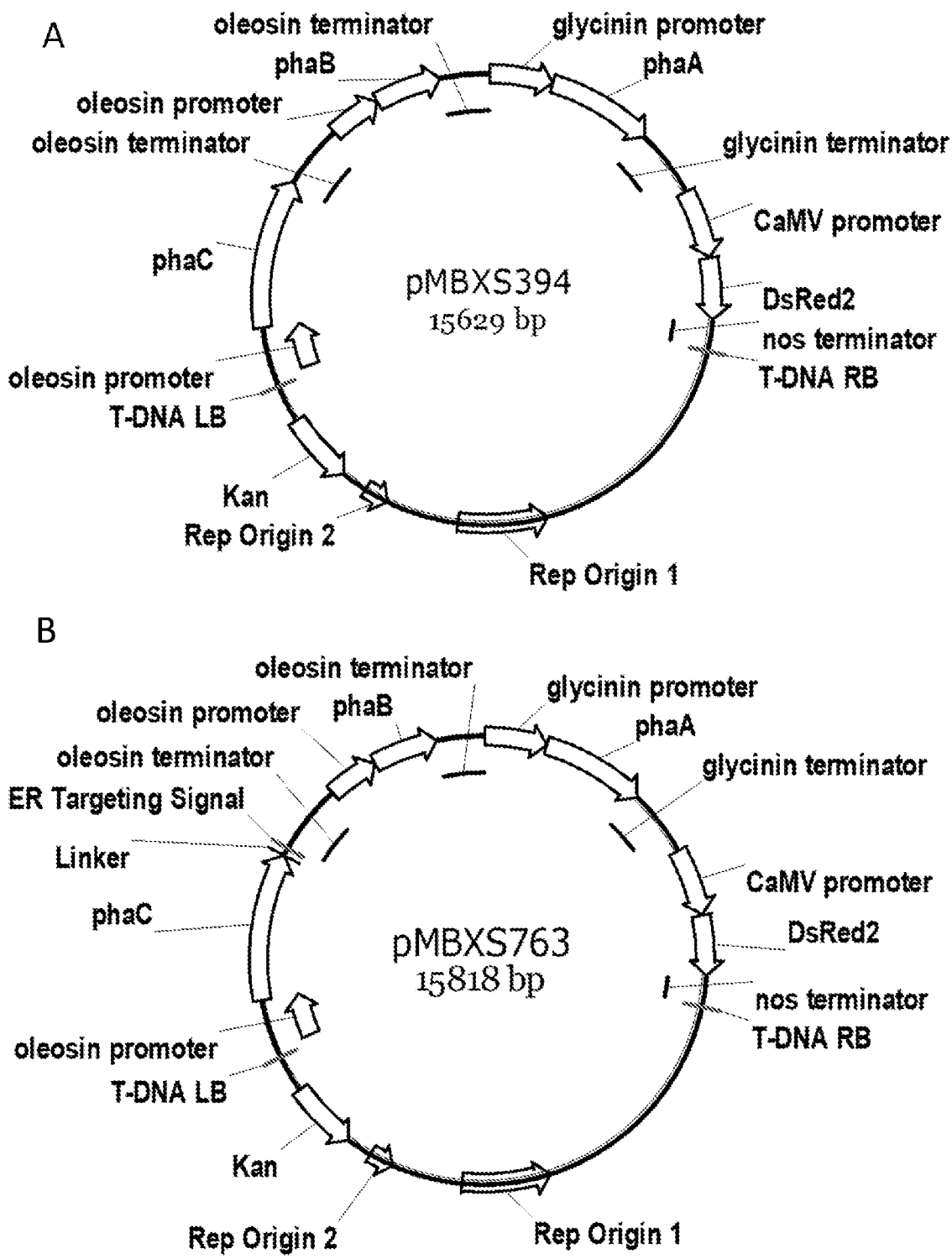
FIG. 3 shows maps for (A) pMBXS394 (SEQ ID NO: 29) and (B) pMBXS763 (SEQ ID NO: 30), which are transformation vectors designed for *Agrobacterium*-mediated transformation of dicots, including *Camelina*, to produce PHB in oilseeds. (A) The pMBXS394 vector is designed to produce PHB in the cytosol of oilseeds and contains the following expression cassettes: an expression cassette containing the promoter from the soybean oleosin isoform A gene (Rowley and Herman, 1997, Biochim Biophys Acta, 1345:1-4) operably linked to the phaC gene, a DNA fragment encoding a hybrid *Pseudomonas oleovorans/Zoogloea ramigera* PHA synthase (Huisman et al., 2001, U.S. Pat. No. 6,316,262; Kourtz et al., 2005, Plant Biotechnol J 3:435-447) operably linked to the 3' termination sequence from the soybean oleosin isoform A gene (Rowley and Herman, 1997); an expression cassette containing the promoter from the soybean oleosin isoform A gene operably linked to the phaB gene, a DNA fragment encoding a reductase from *Cupriavidus necator* (formerly called *Ralstonia eutropha*, Peoples and Sinskey, 1989, Mol Microbiol 3:349-357) operably linked to the 3' termination sequence from the soybean oleosin isoform A gene (Rowley and Herman, 1997); an expression cassette containing the promoter from the soybean glycinin (subunit G1) gene (Iida et al., 1995, Plant Cell Rep 14:539-544) operably linked to the phaA gene, a gene encoding the beta-ketothiolase from *C. necator* (Peoples and Sinskey, 1989) operably linked to the 3' termination sequence from the soybean glycinin (subunit G1) gene (Iida et al., 1995); an expression cassette containing the CaMV 35S promoter from the cauliflower mosaic virus (Odell et al., 1985, Nature, 313:810-812) operably linked to the DsRed2b gene, a 233 amino acid red fluorescent protein from the *Discosoma* genus of coral (Matz et al., 1999, Nat Biotechnol, 17:969-973) in which the first 225 amino acids are equivalent to Genbank EF451141 and the remaining sequence (amino acids 226-233) is VPMTRVSP (SEQ ID NO: 56), operably linked to the 3' termination sequence from the *Agrobacterium tumefaciens* nopaline synthase (nos) gene (Bevan et al., 1983, Nucleic Acids Res 11:369-385). (B) The pMBXS763 vector is designed to anchor the PHA synthase gene to the ER membrane. The vector is essentially equivalent to pMBXS394 with the exception of the PHA synthase gene which contains the DNA fragment encoding a hybrid *Pseudomonas oleovorans/Zoogloea ramigera* PHA synthase fused to an amino acid linker fused to a targeting signal to anchor the PhaC protein to the cytosolic face of the ER. The linker encodes the amino acid sequence VLAVAID-KRGGGGGSGGGGSGGGGSGGGGS (SEQ ID NO: 57), a sequence similar to previously published amino acid linkers for constructing fusion proteins at the C-terminus of a PHA synthase (Jahns and Rehm, 2009, Applied and Environmental Microbiology 75:5461-5466). The ER signal is a DNA fragment encoding a 33 amino acid sequence from the cytochrome B5 isoform D protein from *Arabidopsis thaliana* corresponding to DFVIKLLQFLVPLLILGLAF-GIRYYTKTKAPSS (SEQ ID NO: 58 residues 108-140; amino acids 108-140 of sequence listed in NP_199692.1) that has previously been shown to anchor proteins to the cytosolic face of the endoplasmic reticulum (Barbante et al., 2008, Plant Biotechnol J 6:560-575).

Other proteins known to be targeted to the ER include AtHsp90.7 or SHEPHERD (Song et al., 2009, Planta, 229, 955-964; Ishiguro et al., 2002, EMBO J. 21, 898-908). Pedrazzini (2009) lists several ER retained tail anchored proteins in plants (TABLE 3, Pedrazzini, 2009, J. Plant Biol. 52, 88-101). Kriechbaumer et al. (2009) also lists ER tail anchored proteins in *Arabidopsis* with experimentally determined localization (FIG. 3, Kriechbaumer et al., 2009, Traffic 10, 1753-1764). Additional ER targeting signals have also been reported (Denecke et al., 1992, EMBO J. 11, 2345-2355; Pagny et al., 1999, Journal of Experimental Biology 50, 157-164). Consensus sequences for ER targeting also have been identified by examining the sequences of native soluble ER-resident proteins that are collectively known as reticuloplasmins (Gomord and Faye, 1997, Plant Physiology and Biochemistry 34, 165-181). In plants two consensus tetrapeptides, HDEL (SEQ ID NO: 60) and KDEL (SEQ ID NO: 61), can be used as C-terminal extensions to target polypeptides for retention in the ER. Like for 33 amino acid sequence from the cytochrome B5 isoform D protein from *Arabidopsis thaliana*, it is believed that modification of a polyhydroxyalkanoate synthase to include a transmembrane domain and an ER targeting signal of one or more of these other proteins known to be targeted to the ER can similarly be used to anchor the polyhydroxyalkanoate synthase at the ER membrane, with the catalytic domain of the polyhydroxyalkanoate synthase remaining in the cytosol. For example, a transmembrane domain and one or more of these ER targeting signals may be operably linked at or near the C-terminus of a polyhydroxyalkanoate synthase to accomplish this.

Thus, in some embodiments the polyhydroxyalkanoate synthase is expressed, not just seed specifically, but also with cytosolic localization, based on the polyhydroxyalkanoate synthase comprising an endoplasmic reticulum targeting signal that causes the polyhydroxyalkanoate synthase to become anchored at the cytosolic face of the endoplasmic reticulum membrane.

For example, in some embodiments, the polyhydroxyalkanoate synthase further comprises an endoplasmic reticulum targeting signal, the endoplasmic reticulum targeting signal being positioned to anchor the polyhydroxyalkanoate synthase to a membrane of endoplasmic reticulum of the cells with the catalytic domain remaining in the cytosol, thereby maintaining cytosolic localization of the polyhydroxyalkanoate synthase. In some of these embodiments, the endoplasmic reticulum targeting signal is positioned C-terminally with respect to the catalytic domain. Also in some of these embodiments, the endoplasmic reticulum targeting signal comprises an endoplasmic reticulum targeting signal of a cytochrome B5 isoform D protein. Also in some of these embodiments, the endoplasmic reticulum targeting signal comprises amino acids 108-140 of cytochrome B5 isoform D protein of *Arabidopsis thaliana* of SEQ ID NO: 58.

E. Genes Useful for Polyhydroxybutyrate Synthesis in the Cytosol of Plant Cells

In a preferred embodiment, the products of the transgenes are enzymes and other factors required for production of a PHB biopolymer. For the PHB production pathway, a transgene encoding a protein having the enzymatic activity of a beta-ketothiolase to condense two molecules of acetyl-CoA to produce acetoacetyl-CoA is used. Alternatively, an acetoacetyl-CoA synthetase, such as the NphT7 from *Streptomyces* sp. (Okamura et al., Proc. Natl. Acad. Sci. USA, 2010, 107:11265-11270), can be used to convert malonyl-CoA and acetyl-CoA to acetoacetyl-CoA necessary for PHB synthesis. An acetoacetyl-CoA reductase required to reduce acetoacetyl-CoA to (D)-3-hydroxybutyryl-CoA and a PHB synthase to polymerize the (D)-3-hydroxybutyryl-CoA to produce the PHB polymer which accumulates as granular inclusion bodies complete the pathway. Useful genes are well known in the art (Snell and Peoples, 2002, Metab. Eng. 4, 29-40; Bohmert et. al., 2004, in Molecular Biology and Biotechnology of Plant Organelles. H. Daniell, C. D. Chase Eds., Kluwer Academic Publishers, Netherlands, pp. 559-585; Suriyamongkol et al., 2007, Biotechnol Adv 25, 148-175; and van Beilen et al., 2008, The Plant Journal 54, 684-701).

As discussed in more detail below, in some embodiments, the transgenic land plant further comprises one or more of a PhaA beta-ketothiolase or an NphT7 acetoacetyl-CoA synthetase.

Also in some embodiments, the transgenic land plant further comprises a PhaB acetoacetyl-CoA reductase.

1. Beta-Ketothiolases

The transgene can encode a thiolase. Beta-ketothiolase refers to an enzyme that can catalyze the conversion of acetyl CoA and an acyl CoA to a β-ketoacyl CoA, a reaction that is reversible. An example of such thiolases are PhaA from *Cupriavidus necator* (Accession J04987, Peoples, O. P. & Sinskey, A. J., 1989, J. Biol. Chem. 264 15293-15297), BktB from *Cupriavidus necator* (Slater et al., 1998, J Bacteriol. 180, 1979-87) and thiolases from the following *Rhizobium meliloti* (Accession RMU17226), *Z. ramigera* (Accession P07097), *Paracoccus denitrificans* (Accession D49362), *Burkholderia* sp. (Accession AF153086), *Alcaligenes latus* (Accession ALU47026), *Allochromatium vinosum* (Accession P45369), *Thiocystis violacea* (Accession P45363); *Pseudomonas* sp. strain 61-3 (Accession AB014757), *Acinetobacter* sp. strain RA3849 (Accession L37761) and *Synechocystis* sp. Strain PCC6803 (Taroncher-Oldenburg et al., 2000, Appl. Environ. Microbiol. 66, 4440-4448).

2. Acetoacetyl-CoA Synthases

The transgene(s) can encode an enzyme having acetoacetyl-CoA synthase activity. An acetoacetyl-CoA synthase activity converts malonyl-CoA plus acetyl-CoA to produce acetoacetyl-CoA (Okamura et al., 2010, Proc. Natl. Acad. Sci. USA 107, 11265-11270) described a novel acetoacetyl-CoA synthase encoded by the NphT7 gene of *Streptomyces* sp. The enzyme unidirectionally catalyzes the condensation of acetyl-CoA and malonyl-CoA to yield acetoacetyl-CoA, carbon dioxide, and free CoA. This enzyme has properties which may favor its use over the *C. necator* β-ketothiolase (PhaA) as a catalyst for acetoacetyl-CoA synthesis. PhaA favors thiolysis over synthesis of acetoacetyl-CoA (Davis et al., 1987, J Biol Chem 262, 82-89; reviewed in Snell et al., 2015, Current Opinion in Biotechnology 32C, 68-75), while NphT7-catalyzed acetoacetyl-CoA synthesis is essentially an energy-favored reaction and unidirectional (Okamura et al., 2010; reviewed in Snell et al., 2015). The PhaA β-ketothiolase has a published Km value for acetyl-CoA of between 0.39 and 1.1 mM (Haywood et al., 1988, FEMS Microbiol. Lett. 52, 91-96; Oeding and Schlegel, 1973, Biochem J. 134, 239-248) while NphT7 has a published Km value of 0.068 mM for acetyl-CoA and 0.028 mM for malonyl-CoA (Okamura et al., 2010). As such it has a higher affinity for acetyl-CoA and hence would compete more effectively for substrate under limiting conditions. Higher levels of PHB polymer have been produced in sugarcane chloroplasts using the acetoacetyl-CoA synthase in place of the beta-ketothiolase in engineered PHB biosynthetic pathways (McQualter et al., 2015, Plant Biotechnology Journal 13, 700-707). Acetoacetyl-CoA synthase may provide a similar advantage in cytosolic based PHB production. Homologs of the NphT7 useful for practicing the disclosed invention include: *Streptomyces*. sp K03988-1 and S. sp K03988-2, NphT7 homologs from *Streptomyces* sp. strain KO-3988 (Protein IDs, BAD86806 and BAE78983, respectively); *S. anulatus*, NphT7 homolog from *S. anulatus* strain 9663 (CAX48662); A. sp A40644, NphT7 homolog from *Actinoplanes* sp. strain A40644 (BAD07381); *M. ulcerans*, NphT7 homolog from *Mycobacterium ulcerans* Agy99 (YP_907152); and *M. marinum*, NphT7 homolog from *M. marinum* M (YP_001851502).

3. Acetoacetyl-CoA Reductases

The transgene can encode a reductase. A reductase refers to an enzyme that can reduce β-ketoacyl CoAs to R-3-OH-acyl CoAs, such as the NADH dependent reductase from *Chromatium vinosum* (Liebergesell, M., & Steinbuchel, A., 1992, Eur. J. Biochem. 209, 135-150), the NADPH dependent reductase from *Cupriavidus necator* (Accession J04987, Peoples, O. P. & Sinskey, A. J., 1989, J. Biol. Chem. 264, 15293-15297), the NADPH reductase from *Zoogloea ramigera* (Accession P23238; Peoples, O. P. & Sinskey, A. J., 1989, Molecular Microbiology 3, 349-357) or the NADPH reductase from *Bacillus megaterium* (U.S. Pat. No. 6,835,820), *Alcaligenes latus* (Accession ALU47026), *Rhizobium meliloti* (Accession RMU17226), *Paracoccus denitrificans* (Accession D49362), *Burkholderia* sp. (Accession AF153086), *Pseudomonas* sp. strain 61-3 (Accession AB014757), *Acinetobacter* sp. strain RA3849 (Accession L37761), *P. denitrificans*, (Accession P50204), and *Synechocystis* sp. Strain PCC6803 (Taroncher-Oldenburg et al., 2000, Appl. Environ. Microbiol. 66 4440-4448).

4. PHB Synthases

As discussed in detail above, examples of polyhydroxyalkanoate synthases that can be used include a polyhydroxyalkanoate synthase from *Cupriavidus necator* with short chain length specificity (Peoples, O. P. & Sinskey, A. J., 1989, J. Biol. Chem. 264, 15298-15303), or a two-subunit polyhydroxyalkanoate synthase such as the synthase from *Thiocapsa pfennigii* encoded by phaE and phaC (U.S. Pat. No. 6,011,144). Other useful PHA synthase genes have been isolated from, for example, *Alcaligenes latus* (Accession ALU47026), *Burkholderia* sp. (Accession AF153086), *Aeromonas caviae* (Fukui & Doi, 1997, J. Bacteriol. 179, 4821-30), *Acinetobacter* sp. strain RA3849 (Accession L37761), *Rhodospirillum rubrum* (U.S. Pat. No. 5,849,894), *Rhodococcus ruber* (Pieper & Steinbuechel, 1992, FEMS Microbiol. Lett. 96, 73-80), and *Nocardia corallina* (Hall et. al., 1998, Can. J. Microbiol. 44, 687-91), *Arthrospira* sp. PCC 8005 (Accessions ZP_07166315 and ZP_07166316), *Cyanothece* sp. PCC 7425 (Accessions ACL46371 and ACL46370) and *Synechocystis* sp. PCC6803 (Accession BAA17430; Hein et al., 1998, Archives of Microbiology 170, 162-170). Polyhydroxyalkanoate synthases with broad substrate specificity useful for producing copolymers of 3-hydroxybutyrate and longer chain length (from 6 to 14 carbon atoms) hydroxyacids have also been isolated from *Pseudomonas* sp. A33 (Lee et al., 1995, Appl. Microbiol. Biotechnol. 42, 901-909) and *Pseudomonas* sp. 61-3 (Accession AB014757; Kato et al., 1996, Appl. Microbiol. Biotechnol. 45, 363-370).

F. Exemplary Host Plants

Plants transformed in accordance with the present disclosure may be monocots or dicots. The transformation of suitable agronomic plant hosts using vectors for nuclear transformation can be accomplished with a variety of methods and plant tissues. Representative tissues for transformation of plants using these vectors described herein include protoplasts, cells, callus tissue, leaf discs, pollen, and meristems. Methods of transformation of some types of plants at the early flowering stage are also available. These methods using *Agrobacterium* infiltration of plants at early flowering stage, for example "floral dip" methods for *Camelina* (Lu and Kang, 2008, Plant Cell Reports 27, 273-278). Of particular interest are oilseed plants where the oil is accumulated in the seed and can account for greater than 5%, greater than 10%, greater than 15%, greater than 18%, greater than 25%, greater than 35%, greater than 50% by weight of the weight of dry seed. Oil crops encompass by way of example:

*Borago officinalis* (borage); *Camelina* (false flax); *Brassica* species such as *B. campestris, B. napus, B. rapa, B. carinata* (mustard, oilseed rape or turnip rape); *Sinapis alba; Cannabis sativa* (hemp); *Carthamus tinctorius* (safflower); *Cocos nucifera* (coconut); *Crambe abyssinica* (crambe); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Jatropha curcas* (jatropha); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Thlaspi caerulescens* (pennycress); *Triticum species* (wheat); *Zea mays* (maize), and various nut species such as, for example, walnut or almond. In many cases it is useful to use oilseed plants not normally used for food production or for export to other geographies. Preferred oilseeds include crops used as cover crops, examples of potentially useful cover crops include *Brassica carinata, Camelina sativa* (both spring and winter varieties), and *Thlaspi caerulescens* (Penny cress). Cover crops which produce oils comprising higher levels of long chain fatty acids in the oil may be preferred as they are expected to have useful levels of the acetyl-CoA precursor for the PHB polymers.

In a preferred embodiment, the transgenic plant is an oilseed plant. The transgenic oilseed plant synthesizes PHB in the cytosol of cells of the seed. Host plants, plant tissue, and plant material have been engineered to express genes encoding enzymes in the biosynthetic pathway for PHB production such that polymer precursors are produced and polymerized in the cytosol to form PHB which accumulates as granular inclusions. Genes utilized can include genes encoding enzymes for the PHB biosynthetic pathways, including PhaA beta-ketothiolase, PhaB acetoacetyl-CoA reductase, and PhaC PHA synthase. In some cases, a gene encoding NphT7, an acetoacetyl-CoA synthetase of the thiolase superfamily, can be used in place of PhaA beta-ketothiolase. The genes can be introduced in the plant, plant tissue, or plant cell using conventional plant molecular biology techniques. Additional genetic modifications to the plants to increase the availability of the starting substrate acetyl-CoA, or cofactors such as NADPH, proteins to stabilize PHB granules, and/or transcription factors or other proteins to enhance carbon fixation, can also be carried out to increase the levels of PHB accumulated. The additional genetic modifications can include introducing additional transgenes through transformation and/or altering the activity of genes already present in the plants using genome editing. One embodiment provides methods and compositions for producing transgenic oilseeds having PHB accumulated in the cytosolic compartment of the cells in the seed, for example greater than 2%, 3%, 4%, 5%, 7%, 10%, 12%, 15%, 20% or more of the total dry seed weight. The transgenic plants have good seed germination and form healthy plantlets which grow into mature healthy fertile plants.

Thus, in some embodiments the transgenic land plant is one or more of a *Brassica* species, *Brassica napus, Brassica rapa, Brassica carinata, Brassica juncea, Camelina sativa*, a *Crambe* species, a *Jatropha* species, pennycress, *Ricinus communis*, a *Calendula* species, a *Cuphea* species, *Arabidopsis thaliana*, maize, soybean, a *Gossypium* species, sunflower, palm, coconut, safflower, peanut, *Sinapis alba*, sugarcane, flax, or tobacco.

G. Additional Exemplary Embodiments of the Transgenic Land Plant

In some embodiments, the transgenic land plant further comprises seeds, and the seeds comprise the polyhydroxyalkanoate synthase and a polyhydroxyalkanoate polymerized by the polyhydroxyalkanoate synthase.

In some of these embodiments, greater than 80% of the polyhydroxyalkanoate synthase expressed in the transgenic land plant is expressed in the seeds of the transgenic land plant. Also in some of these embodiments, greater than 80% of the polyhydroxyalkanoate synthase expressed in the seeds of transgenic land plant is localized in cytosol of the cells of the seeds. Also in some of these embodiments, greater than 80% of the polyhydroxyalkanoate polymerized by the polyhydroxyalkanoate synthase is localized in cytosol of the cells of the seeds. Also in some of these embodiments, the transgenic land plant produces the polyhydroxyalkanoate in the seeds to 2.0 to 20.0% of dry seed weight.

Also in some of these embodiments, the polyhydroxyalkanoate comprises one or more of 3-hydroxybutyrate monomers, 4-hydroxybutyrate monomers, 3-hydroxyvalerate monomers, 3-hydroxyhexanoate monomers, 5-hydroxyvalerate monomers, or saturated 3-hydroxyacid monomers with even-numbered carbon chains ranging from C6-C16. For example, in some of these embodiments, the polyhydroxyalkanoate comprises 3-hydroxybutyrate monomers. Also in some of these embodiments, the polyhydroxyalkanoate comprises one or more of poly-3-hydroxybutyrate, poly(3-hydroxybutyrate-co-4-hydroxybutyrate), poly(3-hydroxybutyrate-co-3-hydroxyvalerate), poly(3-hydroxybutyrate-co-3-hydroxhexanoate) and poly(3-hydroxybutyrate-co-5-hydroxyvalerate). For example, in some of these embodiments, the polyhydroxyalkanoate comprises poly-3-hydroxybutyrate.

In some embodiments, the genes used to increase the availability of acetyl-CoA in the cytosol include genes designed to increase citrate synthase activity in the mitochondria and ATP citrate lyase activity (which catalyzes the conversion of citrate and CoA to acetyl-CoA and oxaloacetate) in the cytosol.

Methods and compositions for producing hybrid lines are also provided. Hybrid lines can be created by crossing lines containing one or more pathways to produce PHAs, for example a line with PHB genes crossed with a line containing the other gene(s) needed to complete the PHA biosynthetic pathway. Use of lines that possess cytoplasmic male sterility with the appropriate maintainer and restorer lines allows these hybrid lines to be produced efficiently.

Other embodiments provide plant material and plant parts of the transgenic plants. The disclosed oilseeds can be used for the extraction of PHB biopolymer or as a source of PHB biopolymer based chemical intermediates. In some cases, the oil can be extracted from the seed and the remaining seed meal containing PHB can be used as a component of animal or aquaculture feed. In other cases, the oil can be extracted from the seed and the remaining seed meal containing PHB can be further processed to produce purified PHB and a protein meal useful in, for example, animal feed. In some examples it may be useful to combine the PHB producing lines with other input traits such as pest tolerance, herbicide resistance, nutritional proteins, other value-added co-products, or oils with modified profiles.

III. Methods of Making Transgenic Plants

Transformation Protocols

Transformation protocols as well as protocols for introducing nucleotide sequences into plants are known in the art and may vary depending on the type of plant or plant cell targeted for transformation. Suitable methods of introducing nucleotide sequences into plant cells and subsequent insertion into the plant genome include microinjection (Crossway et al., 1986, Biotechniques 4, 320-334), electroporation (Riggs et al., 1986, Proc. Natl. Acad. Sci. USA 83, 5602-5606), *Agrobacterium*-mediated transformation (Townsend et al., U.S. Pat. No. 5,563,055; Zhao et al. WO US98/01268), direct gene transfer (Paszkowski et al., 1984, EMBO J. 3, 2717-2722), and ballistic particle acceleration (see, for example, Sanford et al., U.S. Pat. No. 4,945,050; Tomes et al., 1995, Plant Cell, Tissue, and Organ Culture: Fundamental Methods, ed. Gamborg and Phillips (Springer-Verlag, Berlin); and McCabe et al., 1988, Biotechnology 6, 923-926). Also see Weissinger et al., 1988, Ann. Rev. Genet. 22, 421-477; Sanford et al., 1987, Particulate Science and Technology 5, 27-37 (onion); Christou et al., 1988, Plant Physiol. 87, 671-674 (soybean); McCabe et al., 1988, Bio-Technology 6, 923-926 (soybean); Finer and McMullen, 1991, In Vitro Cell Dev. Biol. 27P, 175-182 (soybean); Singh et al., 1998, Theor. Appl. Genet. 96, 319-324 (soybean); Dafta et al., 1990, Biotechnology 8, 736-740 (rice); Klein et al., 1988, Proc. Natl. Acad. Sci. USA 85, 4305-4309 (maize); Klein et al., 1988, Biotechnology 6, 559-563 (maize); Tomes, U.S. Pat. No. 5,240,855; Buising et al., U.S. Pat. Nos. 5,322,783 and 5,324,646; Tomes et al., 1995, in Plant Cell, Tissue, and Organ Culture: Fundamental Methods, ed. Gamborg (Springer-Verlag, Berlin) (maize); Klein et al., 1988, Plant Physiol. 91, 440-444 (maize); Fromm et al., 1990, Biotechnology 8, 833-839 (maize); Hooykaas-Van Slogteren et al., 1984, Nature 311, 763-764; Bowen et al., U.S. Pat. No. 5,736,369 (cereals); Bytebier et al., 1987, Proc. Natl. Acad. Sci. USA 84, 5345-5349 (Liliaceae); De Wet et al., 1985, in The Experimental Manipulation of Ovule Tissues, ed. Chapman et al. (Longman, N.Y.), pp. 197-209 (pollen); Kaeppler et al., 1990, Plant Cell Reports 9, 415-418, and Kaeppler et al., 1992, Theor. Appl. Genet. 84, 560-566 (whisker-mediated transformation); D'Halluin et al. 1992, Plant Cell 4, 1495-1505 (electroporation); Li et al., 1993, Plant Cell Reports 12, 250-255, and Christou and Ford, 1995, Annals of Botany 75, 407-413 (rice); Osjoda et al., 1996, Nature Biotechnology 14, 745-750 (maize via *Agrobacterium tumefaciens*).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. (See, for example, U.S. Pat. No. 5,639,949). Alternatively, DNA fragments containing the transgene and the necessary regulatory elements for expression of the transgene can be excised from a plasmid and delivered to the plant cell using microprojectile bombardment-mediated methods. Nanoparticles or nanotubes capable of delivering biomolecules to plants can also be used (for review see Cunningham, 2018, Trends Biotechnol. 36, 882).

Methods for transforming plant protoplasts are available including transformation using polyethylene glycol (PEG), electroporation, and calcium phosphate precipitation (see for example Potrykus et al., 1985, Mol. Gen. Genet. 199, 183-188; Potrykus et al., 1985, Plant Molecular Biology Reporter 3, 117-128), Methods for plant regeneration from protoplasts have also been described (Evans et al., 1983, in Handbook of Plant Cell Culture, Vol 1, (Macmillan Publishing Co., New York); Vasil, I K, 1984, in Cell Culture and Somatic Cell Genetics (Academic, Orlando)).

Procedures for in planta transformation can be simple. Tissue culture manipulations and possible somaclonal variations are avoided and only a short time is required to obtain transgenic plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, The Plant J. 16, 735-743), transformation of germinating seeds (Feldmann & Marks, 1987, Mol. Gen. Genet. 208, 1-9), floral dip (Clough and Bent, 1998, Plant J. 16, 735-743), and floral spray (Chung et al., 2000, Transgenic Res. 9, 471-476). Other plants that have successfully been transformed by in planta methods include rapeseed and radish (vacuum infiltration, Ian and Hong, 2001, Transgenic Res., 10, 363-371; Desfeux et al., 2000, Plant Physiol. 123, 895-904), *Medicago truncatula* (vacuum infiltration, Trieu et al., 2000, Plant J. 22, 531-541), *Camelina* (floral dip, WO/2009/117555 to Nguyen et al.; Lu and Kang, 2008, Plant Cell Reports 27, 273-278), and wheat (floral dip, Zale et al., 2009, Plant Cell Rep. 28, 903-913). Genetic transformation procedures for several *Brassica* species including *B. napus*, *B. juncea*, *B. campestris* and *B. carinata* have recently been reviewed (Rani et al., 2013, Indian Journal of Agricultural Sciences 83, 367-373). In planta methods have also been used for transformation of germ cells in maize (pollen, Wang et al., 2001, Acta Botanica Sin. 43, 275-279; Zhang et al., 2005, Euphytica, 144, 11-22; pistils, Chumakov et al. 2006, Russian J. Genetics 42, 893-897; Mamontova et al. 2010, Russian J. Genetics 46, 501-504) and *Sorghum* (pollen, Wang et al. 2007, Biotechnol. Appl. Biochem. 48, 79-83). Molecular tools and systems for engineering Penny cress are described in detail by McGinn, et al., 2019, Plant Biotechnology Journal 17, 776-788.

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location. Alternatively, transformed plants may be selected on the basis of the presence of a new product or plant tissue compositional change produced as a result of the expression of the transgene(s). For example, in the case of the invention disclosed herein, the transformed plant expressing the PhbA, PhbB and PhbC genes can be screened for the level of PHB polymer produced in the seeds.

The cells that have been transformed may be grown into plants in accordance with conventional techniques. See, for example, McCormick et al., 1986, Plant Cell Reports 5, 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

In some scenarios, it may be advantageous to insert a multi-gene pathway into the plant by crossing of different lines, each expressing different transgenes encoding portions of the metabolic pathway, to produce hybrid plants in which the entire pathway has been reconstructed. Hybrid lines can be created by crossing a line containing one or more genes with a line containing the other gene(s) needed to complete a biosynthetic pathway. Use of lines that possess cytoplasmic male sterility (Esser, K. et al., 2006, Progress in Botany, Springer Berlin Heidelberg. 67, 31-52) with the appropriate maintainer and restorer lines allows these hybrid lines to be produced efficiently. Cytoplasmic male sterility systems are already available for some Brassicaceae species (Esser, K. et al., 2006, Progress in Botany, Springer Berlin Heidelberg. 67, 31-52). These Brassicaceae species can be used as gene sources to produce cytoplasmic male sterility systems for other oilseeds of interest such as for example *Camelina sativa, Brassica carinata* and Penny cress. Hybrid plants have significant yield advantages in field production and provide a means to protect the technology as planting of the seed progeny from hybrid plants results in significant yield impairment.

Plant Promoters

Plant promoters can be selected to control the expression of the transgene in different plant tissues or organelles or at different times during plant development for all of which methods are known to those skilled in the art (Gasser & Fraley, 1989, Science 244, 1293-1299). In one embodiment, promoters are selected from those of eukaryotic or synthetic origin that are known to yield high levels of expression in plants. In a preferred embodiment, promoters are selected from those that are known to provide high levels of expression in monocots. Also in a preferred embodiment a constitutive promoter is used to control the selectable marker gene and seed-preferred promoters and/or cob-preferred promoters are used to control the expression of the genes encoding the PhbA, PhbB and PhbC proteins. The seed preferred promoters and/or cob-preferred promoters controlling the expression of the phb genes may be the same or different promoters. Representative constitutive promoters are listed in TABLES 1 and 2. Representative seed-preferred promoters and cob-preferred promoters are listed in TABLES 3 and 4.

TABLE 1

Constitutive promoters useful for expression of genes in dicots.

| Gene/Promoter | Native organism of promoter | Gene ID* (SEQ ID NO) |
|---|---|---|
| CaMV 35S | Cauliflower mosaic virus | (SEQ ID NO: 12) |
| Hsp70 | Glycine max | Glyma.02G093200 (SEQ ID NO: 13) |
| Chlorophyll A/B Binding Protein (Cab5) | Glycine max | Glyma.08G082900 (SEQ ID NO: 14) |
| Pyruvate phosphate dikinase (PPDK) | Glycine max | Glyma.06G252400 (SEQ ID NO: 15) |

TABLE 1-continued

Constitutive promoters useful for expression of genes in dicots.

| Gene/Promoter | Native organism of promoter | Gene ID* (SEQ ID NO) |
|---|---|---|
| Actin | Glycine max | Glyma.19G147900 (SEQ ID NO: 16) |
| Hsp70 | Brassica napus | BnaA09g05860D |
| Chlorophyll A/B Binding Protein (Cab5) | Brassica napus | BnaA04g20150D |
| Pyruvate phosphate dikinase (PPDK) | Brassica napus | BnaA01g18440D |
| Actin | Brassica napus | BnaA03g34950D |

*Gene ID includes sequence information for coding regions as well as associated promoters. 5' UTRs, and 3' UTRs and are available at Phytozome (see JGI website phytozome.jgi.doe.gov/pz/portal.html).

TABLE 2

Constitutive promoters useful for expression of genes in monocots.

| Gene/ Promoter | Rice* | Maize* | Other |
|---|---|---|---|
| Hsp70 | LOC_Os05g38530 (SEQ ID NO: 17) | GRMZM2G310431 (SEQ ID NO: 18) | |
| Chlorophyll A/B Binding Protein (Cab5) | LOC_Os01g41710 (SEQ ID NO: 19) | AC207722.2_FG009 (SEQ ID NO: 20) GRMZM2G351977 (SEQ ID NO: 21) | |
| maize ubiquitin promoter/ maize ubiquitin intron (sequence listed in Genbank KT962835) | | (SEQ ID NO: 22) | |
| maize ubiquitin promoter/ maize ubiquitin intron (maize promoter and intron sequence with 99% identity to sequence in Genbank KT985051.1) | | (SEQ ID NO: 23) | |

TABLE 2-continued

Constitutive promoters useful for expression of genes in monocots.

| Gene/Promoter | Rice* | Maize* | Other |
|---|---|---|---|
| CaMV 35S | — | — | Cauliflower mosaic virus (SEQ ID NO: 12) |
| Pyruvate phosphate dikinase (PPDK) | LOC_Os05g33570 (SEQ ID NO: 24) | GRMZM2G306345 (SEQ ID NO: 25) | |
| Actin | LOC_Os03g50885 (SEQ ID NO: 26) | GRMZM2G047055 (SEQ ID NO: 27) | |
| Hybrid cab5/hsp70 intron promoter | N/A | SEQ ID NO: 28 | |

*Gene ID includes sequence information for coding regions as well as associated promoters, 5' UTRs, and 3' UTRs and are available at Phytozome (see JGI website phytozome.jgi.doe.gov/pz/portal.html).

TABLE 3

Seed-preferred promoters and cob-preferred promoters useful for expression of genes in dicots.

| Gene/Promoter | Expression | Native organism of promoter | Gene ID* (SEQ ID NO) |
|---|---|---|---|
| ADP-glucose pyrophosphorylase (AGPase) | Seed-specific | Glycine max | Glyma.04G011900 (SEQ ID NO: 1) |
| Glutelin C (GluC) | Seed-specific | Glycine max | Glyma.03G163500 (SEQ ID NO: 2) |
| β-fructofuranosidase insoluble isoenzyme 1 (CIN1) | Seed-specific | Glycine max | Glyma.17G227800 (SEQ ID NO: 3) |
| Glycinin (subunit G1) | Seed-specific | Glycine max | Glyma.03G163500 (SEQ ID NO: 4) |
| oleosin isoform A | Seed-specific | Glycine max | Glyma.16G071800 (SEQ ID NO: 5) |
| ADP-glucose pyrophosphorylase (AGPase) | Seed-specific | Brassica napus | BnaA06g40730D |
| Glutelin C (GluC) | Seed-specific | Brassica napus | BnaA09g50780D |
| β-fructofuranosidase insoluble isoenzyme 1 (CIN1) | Seed-specific | Brassica napus | BnaA04g05320D |
| Glycinin (subunit G1) | Seed-specific | Brassica napus | BnaA01g08350D |

TABLE 3-continued

Seed-preferred promoters and cob-preferred promoters useful for expression of genes in dicots.

| Gene/Promoter | Expression | Native organism of promoter | Gene ID* (SEQ ID NO) |
|---|---|---|---|
| oleosin isoform A | Seed-specific | Brassica napus | BnaC06g12930D |
| 1.7S napin (napA) | Seed-specific | Brassica napus | BnaA01g17200D |
| Sucrose synthase | Seed-specific | Arabidopsis thaliana | AT5G49190 (SEQ ID NO: 31) |
| MADS-Box | Cob-specific | Glycine max | Glyma.04G257100 (SEQ ID NO: 62) |
| MADS-Box | Cob-specific | Brassica napus | BnaA05g02990D |

*Gene ID includes sequence information for coding regions as well as associated promoters, 5' UTRs, and 3' UTRs and are available at Phytozome (see JGI website phytozome.jgi.doe.gov/pz/portal.html).

TABLE 4

Seed-preferred promoters and cob-preferred promoters useful for expression of genes in monocots, including maize and rice.

| Gene/Promoter | Expression | Rice* | Maize* |
|---|---|---|---|
| ADP-glucose pyrophosphorylase (AGPase) | Seed-specific | LOC_Os01g44220 (SEQ ID NO: 6) | GRMZM2G429899 (SEQ ID NO: 7) |
| Glutelin C (GluC) | Seed-specific | LOC_Os02g25640 (SEQ ID NO: 8) | |
| β-fructofuranosidase insoluble isoenzyme 1 (CIN1) | Seed-specific | LOC_Os02g33110 (SEQ ID NO: 9) | GRMZM2G139300 (SEQ ID NO: 10) |
| Maize TrpA promoter | Seed-specific | | GRMZM5G841619 (SEQ ID NO: 11) |
| MADS-Box | Cob-specific | LOC_Os12g10540 (SEQ ID NO: 63) | GRMZM2G160687 (SEQ ID NO: 64) |

*Gene ID includes sequence information for coding regions as well as associated promoters, 5' UTRs, and 3' UTRs and are available at Phytozome (see JGI website phytozome.jgi.doe.gov/pz/portal.html).

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, Nature 313, 810-812), rice actin (McElroy et al., 1990, Plant Cell 2, 163-171), ubiquitin (Christensen et al., 1989, Plant Mol. Biol. 12, 619-632; Christensen et al., 1992, Plant Mol. Biol. 18, 675-689), pEMU (Last et al., 1991, Theor. Appl. Genet. 81, 581-588), MAS (Velten et al., 1984, EMBO J. 3, 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Tissue-preferred promoters include those described by Van Ex et al., 2009, Plant Cell Rep. 28, 1509-1520; Yamamoto et al., 1997, Plant J. 12, 255-265; Kawamata et al., 1997, Plant Cell Physiol. 38, 792-803; Hansen et al., 1997, Mol. Gen. Genet. 254, 337-343; Russell et al., 1997, Transgenic Res. 6, 157-168; Rinehart et al., 1996, Plant Physiol. 112, 1331-1341; Van Camp et al., 1996, Plant Physiol. 112, 525-535; Canevascini et al., 1996, Plant Physiol. 112, 513-524; Yamamoto et al., 1994, Plant Cell Physiol. 35, 773-778; Lam, 1994, Results Probl. Cell Differ. 20, 181-196, Orozco et al., 1993, Plant Mol. Biol. 23, 1129-1138; Matsuoka et al., 1993, Proc. Natl. Acad. Sci. USA 90, 9586-9590, and Guevara-Garcia et al., 1993, Plant J. 4, 495-505. Such promoters can be modified, if necessary, for weak expression.

"Seed-preferred" promoters include both "seed-specific" promoters, as discussed above (those promoters active during seed development such as promoters of seed storage proteins), as well as "seed-germinating" promoters (those promoters active during seed germination). See Thompson et al., 1989, BioEssays 10, 108-113. Seed-specific promoters can be used to target gene expression to seeds in particular. Seed-specific promoters include promoters that are expressed in various tissues within seeds and at various stages of development of seeds. Seed-specific promoters can be absolutely specific to seeds, such that the promoters are only expressed in seeds, or can be expressed preferentially in seeds, e.g. at rates that are higher by 2-fold, 5-fold, 10-fold, or more, in seeds relative to one or more other tissues of a plant, e.g. stems, leaves, and/or roots, among other tissues. Seed-preferred promoters include, for example, Cim1 (cytokinin-induced message), cZ19B1 (maize 19 kDa zein), milps (myo-inositol-1-phosphate synthase), and ce1A (cellulose synthase), among others. Gamma-zein is a preferred endosperm-specific promoter. Glob-1 is a preferred embryo-specific promoter. Seed-specific promoters include, for example, seed-specific promoters of dicots and seed-specific promoters of monocots. For dicots, seed-specific promoters include, but are not limited to, bean β-phaseolin, napin, β-conglycinin, soybean oleosin 1, *Arabidopsis thaliana* sucrose synthase, flax conlinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1. The stage specific developmental promoter of the late embryogenesis abundant protein gene LEA has successfully been used to drive a recombination system for excision-mediated expression of a lethal gene at late embryogenesis stages in the seed terminator technology (U.S. Pat. No. 5,723,765 to Oliver et al.).

"Cob-preferred promoters" can be used to target gene expression to cob. Cob-preferred promoters include cob-specific promoters, such as MADS-Box promoters of soybean, *Brassica napus*, rice, and maize.

Expression Cassettes

Certain embodiments use transgenic plants or plant cells having multi-gene expression constructs harboring more than one promoter. The promoters can be the same or different.

Any of the described promoters can be used to control the expression of one or more of the genes of the invention, their homologs and/or orthologs as well as any other genes of interest in a defined spatiotemporal manner.

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra.

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

The coding sequence of the selected gene may be modified for optimal expression in the crop species of interest. Methods for modifying coding sequences to achieve optimal expression in a particular crop species are well known (Perlak et al., 1991, Proc. Natl. Acad. Sci. USA 88, 3324 and Koziel et al., 1993, Biotechnology 11, 194-200).

Plastid Targeting Sequences

Plastid targeting sequences are well known in the art and include, for example, the chloroplast small subunit of ribulose-1,5-bisphosphate carboxylase (Rubisco) (de Castro Silva Filho et al. *Plant Mol. Biol.* 30:769-780 (1996); Schnell et al. *J. Biol. Chem.* 266 (5):3335-3342 (1991)); 5-(enolpyruvyl)shikimate-3-phosphate synthase (EPSPS) (Archer et al. *J. Bioenerg. Biomemb.* 22 (6):789-810 (1990)); tryptophan synthase (Zhao et al. *J. Biol. Chem.* 270 (11):6081-6087 (1995)); plastocyanin (Lawrence et al. *J. Biol. Chem.* 272 (33):20357-20363 (1997)); chorismate synthase (Schmidt et al. J. Biol. Chem. 268 (36):27447-27457 (1993)); and the light harvesting chlorophyll a/b binding protein (LHBP) (Lamppa et al. *J. Biol. Chem.* 263:14996-14999 (1988)). See also Von Heijne et al. *Plant Mol. Biol. Rep.* 9:104-126 (1991); Clark et al. *J. Biol. Chem.* 264: 17544-17550 (1989); Della-Cioppa et al. *Plant Physiol.* 84:965-968 (1987); Romer et al. *Biochem. Biophys. Res. Commun.* 196:1414-1421 (1993); and Shah et al. *Science* 233:478-481 (1986). Alternative plastid targeting signals have also been described in the following: U.S. Pub. No. 2008/0263728; Miras, S. et al. (2002), J Biol Chem 277 (49): 47770-8; Miras, S. et al. (2007), J Biol Chem 282: 29482-29492.

Specific examples of using N-terminal plastid targeting sequences to target microbial proteins to plant plastids are disclosed for example by Malik et al., Plant Biotechnol. J., 13:675 (2015) and Petrasovits et al., Plant Biotechnol. J., 5:162 (2007).

Signal peptides (and the targeting nucleotide sequences encoding them) can be found in public databases such as the "Signal Peptide Website: An Information Platform for Signal Sequences and Signal Peptides." (website: signalpeptide.de); the "Signal Peptide Database" (website: proline.bic.nus.edu.sg/spdb/index.html) (Choo et al., *BMC Bioinformatics* 6:249 (2005) (available on website: biomedcentral.com/1471-2105/6/249/abstract); Predotar (website: urgi.versailles.inra.fr/predotar/predotar.html; predicts mitochondrial and plastid targeting sequences); SignalP (website: cbs.dtu.dk/services/SignalP/; predicts the presence and location of signal peptide cleavage sites in amino acid sequences from different organisms: Gram-positive prokaryotes, Gram-negative prokaryotes, and eukaryotes). The SignalP method incorporates a prediction of cleavage sites and a signal peptide/non-signal peptide prediction based on a combination of several artificial neural networks and hidden Markov models; and TargetP (website: cbs.dtu.dk/services/TargetP/) predicts the subcellular location of eukaryotic proteins, the location assignment being based on the predicted presence of any of the N-terminal presequences: chloroplast transit peptide (cTP), mitochondrial targeting peptide (mTP) or secretory pathway signal peptide (SP)). (See also, von Heijne, G., *Eur J Biochem* 133 (1) 17-21 (1983); Martoglio et al. *Trends Cell Biol* 8 (10):410-5 (1998); Hegde et al. *Trends Biochem Sci* 31 (10):563-71 (2006); Dultz et al. J Biol Chem 283 (15):9966-76 (2008); Emanuelsson et al. *Nature Protocols* 2 (4) 953-971 (2007); Zuegge et al. 280 (1-2):19-26 (2001); Neuberger et al. *J Mol Biol.* 328 (3):567-79 (2003); and Neuberger et al. *J Mol Biol.* 328 (3):581-92 (2003)).

Measurement of PHB Phenotypes

Individual plants within a population of transgenic plants that express recombinant gene(s) may have different levels of gene expression. The variable gene expression is due to multiple factors including multiple copies of the recombinant gene, chromatin effects, and gene suppression. Accordingly, a phenotype of the transgenic plant may be measured as a percentage of PHB in individual plants within a population.

The yield of a plant can be measured simply by weighing. The yield of seed from a plant can also be determined by weighing. The increase in seed weight from a plant can be due to a number of factors, including an increase in the number or size of the seed pods, an increase in the number of seed and/or an increase in the number of seed per plant. In the laboratory or greenhouse seed yield is usually reported as the weight of seed produced per plant and in a commercial crop production setting yield is usually expressed as weight per acre or weight per hectare.

Genetic Modification of Plant Genome

A recombinant DNA construct including a plant-expressible gene or other DNA of interest can be inserted into the genome of a plant by a suitable method. As discussed above, suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A genetically engineered plant can be produced by selection of transformed seeds or by selection of transformed plant cells and subsequent regeneration.

The present inventors have transformed plants with recombinant DNA molecules that encode heterologous metabolic enzymes in the nuclear genome. Transgenic plants and plant cells expressing the recombinant PHB pathway enzymes are selected on the basis of having higher content of PHB compared to wild type plants of the same species not comprising the recombinant metabolic enzymes.

In one embodiment, the transgenic plants are grown (e.g., in soil) and harvested. In one embodiment, above ground tissue is harvested separately from below ground tissue. Suitable above ground tissues include shoots, stems, leaves, flowers, grain, and seed. Exemplary below ground tissues include roots and root hairs. In one embodiment, whole plants are harvested and the above ground tissue is subsequently separated from the below ground tissue.

Transgenic plants can be selected by using a selectable marker. Genetic constructs may encode a selectable marker to enable selection of transformation events. There are many methods that have been described for the selection of transformed plants (for review see Miki et al., 2004, Journal of Biotechnology 107, 193-232, and references incorporated within). Selectable marker genes that have been used extensively in plants include the neomycin phosphotransferase gene nptII (U.S. Pat. Nos. 5,034,322, 5,530,196), hygromycin resistance gene (U.S. Pat. No. 5,668,298, Waldron et al., 1985, Plant Mol Biol 5, 103-108; Zhijian et al., 1995, Plant Sci 108, 219-227), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463,175; 7,045,684). Other suitable selectable markers include, but are not limited to, genes encoding resistance to chloramphenicol (Herrera Estrella et al., 1983, EMBO J. 2, 987-992), methotrexate (Herrera Estrella et al., 1983, Nature 303, 209-213; Meijer et al, 1991, Plant Mol Biol 16, 807-820); streptomycin (Jones et al., 1987, Mol Gen Genet 210, 86-91); bleomycin (Hille et al., 1990, Plant Mol Biol 7, 171-176); sulfonamide (Guerineau et al., 1990, Plant Mol Biol 15, 127-136); bromoxynil (Stalker et al., 1988, Science 242, 419-423); glyphosate (Shaw et al., 1986, Science 233, 478-481); phosphinothricin (DeBlock et al., 1987, EMBO J. 6, 2513-2518).

Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., 2004, Nat Biotechnol 22, 4558). European Patent Publication No. EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of transgenic plants.

Methods for positive selection using sorbitol dehydrogenase to convert sorbitol to fructose for plant growth have also been described (WO 2010/102293). Screenable marker genes include the beta-glucuronidase gene (Jefferson et al., 1987, EMBO J. 6, 3901-3907; U.S. Pat. No. 5,268,463) and native or modified green fluorescent protein gene (Cubitt et al., 1995, Trends Biochem. Sci. 20, 448-455; Pan et al., 1996, Plant Physiol. 112, 893-900).

Transformation events can also be selected through visualization of fluorescent proteins such as the fluorescent proteins from the nonbioluminescent *Anthozoa* species which include DsRed, a red fluorescent protein from the *Discosoma* genus of coral (Matz et al., 1999, Nat Biotechnol 17, 969-73). An improved version of the DsRed protein has been developed (Bevis and Glick, 2002, Nat Biotech 20, 83-87) for reducing aggregation of the protein.

Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004), Nat Biotech 22: 289-296). Improved versions of many of the fluorescent proteins have been made for various applications. It will be apparent to those skilled in the art how to use the improved versions of these proteins, including combinations, for selection of transformants.

Plastid Transformation

In some embodiments, genes encoding 6-phosphogluconate dehydratase (EDD) and 2-keto-3-deoxy-6-phosphogluconate aldolase (EDA) can be inserted into, and expressed directly from, the plastid genome. Genetic constructs used for plastid-encoded transgene expression in a host organism typically comprise in the 5'-3' direction, a left flank which mediates, together with the right flank, integration of the genetic construct into the target plastome; a promoter sequence; a sequence encoding a 5' untranslated region (5' UTR) containing a ribosome binding site; a sequence encoding a gene of interest, such as the genes disclosed herein; a 3' untranslated region (3' UTR); and a right flank. Plastid gene expression is regulated to a large extent at the post-transcriptional level and 5' and 3' UTRs have been shown to impact RNA stability and translation efficiency (Eibl et al., Plant J 19, 333-345 (1999)). Due to the prokaryotic nature of plastid expression systems, one or more transgenes may be arranged in an operon such that multiple genes are expressed from the same promoter. The promoter driving transcription of the operon may be located within the genetic construct, or alternatively, an endogenous promoter in the host plastome upstream of the transgene insertion site may drive transcription. In addition, the 3'UTR may be part of the right flank. The open reading frame may be oriented in either a sense or anti-sense direction. The construct may also comprise selectable marker gene(s) and other regulatory elements for expression.

Plastid-encoded expression can potentially yield high levels of expression due to the multiple copies of the plastome within a plastid and the presence of multiple plastids within the cell. Transgenic proteins have been observed to accumulate to 45% (De Cosa et al., *Nat. Biotechnol.* 19:71-74 (2001)) and >70% (Oey et al., *Plant J.* 57:436-445 (2009)) of the plant's total soluble protein. Since plastid DNA is maternally inherited in most plants, the presence of plastid-encoded transgenes in pollen is significantly reduced or eliminated, providing some level of gene containment in plants created by plastid transformation.

Stacked Input Traits

As noted above, the plants modified for producing PHB may have stacked input traits that include herbicide resistance and insect tolerance, for example a plant that is tolerant to the herbicide glyphosate and that produces the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the modified plant (Suh, et al., 1993, J. M Plant Mol. Biol. 22, 195-205). BT toxin is a protein that is lethal to many insects providing the plant that produces it protection against pests (Barton, et al., 1987, Plant Physiol. 85, 1103-1109). Other useful herbicide tolerance traits include but are not limited to tolerance to Dicamba by expression of the dicamba monoxygenase gene (Behrens et al, 2007, Science, 316, 1185), tolerance to 2,4-D and 2,4-D choline by expression of a bacterial aad-1 gene that encodes for an aryloxyalkanoate dioxygenase enzyme (Wright et al., 2010, Proc. Natl. Acad. Sci. USA 107, 20240), glufosinate tolerance by expression of the bialophos resistance gene (bar) or the pat gene encoding the enzyme phosphinotricin acetyl transferase (Droge et al., 1992, Planta 187, 142), as well as genes encoding a modified 4-hydroxyphenylpyruvate dioxygenase (HPPD) that provides tolerance to the herbicides mesotrione, isoxaflutole, and tembotrione (Siehl et al., 2014, Plant Physiol 166, 1162).

IV. Methods of Use

The disclosed genetic constructs can be used to produce industrial oilseed plants for high levels of PHB production. Specifically, PHB is produced in the cytosol of seed cells. The transgenic plants can be grown and the seed harvested. The oil can be extracted and the residual meal containing PHB can be used as animal feed. Alternatively the PHB can be isolated from the residual meal. The isolated PHB can be used in waste water treatment applications to reduce the levels of nitrates. The isolated PHB can be used for animal feed. The isolated PHB can be used in thermoplastic processing applications to produce renewable biodegradable replacements for petroleum-based plastics. The PHB-free meal can be used as a source of protein for animal feed or further processed for food applications.

The invention is further illustrated by the following non-limiting examples. Any variations in the exemplified compositions and methods that occur to the skilled artisan are intended to fall within the scope of the present invention.

EXAMPLES

Example 1. Design and Construction of Transformation Vectors pMBXS394 and pMBXS763 for Cytosolic Production of PHB in Plants To produce PHB in the cytosol of plants, transformation vectors pMBXS394 (FIG. 3(A), SEQ ID NO: 29) and pMBXS763 (FIG. 3(B), SEQ ID NO: 30) were constructed. These plasmids are derivatives of pCAMBIA binary vectors (Centre for Application of Molecular Biology to International Agriculture, Canberra, Australia) and were constructed using conventional molecular biology and cloning techniques. Expression cassettes for transgenes within these plasmids are listed in TABLE 5. The enzyme activities encoded by the transgenes, as well as their substrates and affiliated metabolic pathways are shown in FIG. 1.

TABLE 5

Plasmid Vectors Used to Transform Plants for Cytosolic PHB production in seeds.

| Vector* | Transgene Expression Cassettes | | | Marker Expression Cassette |
| --- | --- | --- | --- | --- |
| | 1 | 2 | 3 | |
| pMBXS394 (SEQ ID NO: 29) | pOle-phaC-tOle | pOle-phaB-tOle | pGyl-phaA-tGyl | CaMV35S-Dsred2b-nos |
| pMBXS763 (SEQ ID NO: 30) | pOle-phaC-ER-tOle | pOle-phaB-tOle | pGyl-phaA-tGyl | CaMV35S-Dsred2b-nos |

*Abbreviations are as follows:
pOle, promoter from the *Glycine max* oleosin isoform A gene; phaC, hybrid *Pseudomonas oleovorans/Zoogloea ramigera* PHA synthase;
tOle, terminator from the *Glycine max* oleosin isoform A gene;
ER, targeting signal to anchor the PhaC protein to the cytosolic face of the ER, phaB, reductase from *C. necator*;
pGyl, promoter from the soybean glycinin (subunit G1) gene;
phaA, a gene encoding the beta-ketothiolase from *C. necator*;
tGyl, 3' termination sequence from the soybean glycinin (subunit G1) gene;
CaMV 35S, promoter from the cauliflower mosaic virus;
DsRed2b gene, red fluorescent protein from the *Discosoma* genus of coral;
nos, 3' termination sequence from the *Agrobacterium tumefaciens* nopaline synthase gene.
See FIG. 3(A)-(B) for additional description of vectors.

The expression cassettes used in the construction of vectors pMBXS394 and pMBXS763 were as follows:

Vector pMBXS394 (SEQ ID NO: 29) contains an expression cassette for PHA synthase containing the promoter from the soybean oleosin isoform A gene (Rowley and Herman, 1997, Biochim. Biophys. Acta 1345, 1-4), a DNA fragment encoding a hybrid PHA synthase (U.S. Pat. No. 6,316,262) in which the first nine amino acids at the N-terminus of this synthase are derived from the *Pseudomonas oleovorans* phaC1 gene and the remainder of the synthase coding sequence is derived from *Zoogloea ramigera* phaC gene, and the 3' termination sequence from the soybean oleosin isoform A gene.

Vector pMBXS763 (SEQ ID NO: 30) contains: an expression cassette for an endoplasmic reticulum-targeted PHA synthase (PhaC-ER) containing the promoter from the soybean oleosin isoform A gene (Rowley and Herman, 1997, Biochim. Biophys. Acta 1345, 1-4); a DNA fragment encoding a hybrid PHA synthase (U.S. Pat. No. 6,316,262) in which the first nine amino acids at the N-terminus of this synthase are derived from the *Pseudomonas oleovorans* phaC1 gene and the remainder of the synthase coding sequence is derived from *Zoogloea ramigera* phaC gene; a DNA fragment encoding an amino acid linker with the sequence VLAVAID-KRGGGGGSGGGGSGGGGSGGGGS (SEQ ID NO: 57), a sequence similar to previously published amino acid linkers shown to enable translational fusions at the C-terminus of a PHA synthase (Jahns, A. C. & Rehm, B. H. A., 2009, Applied and Environmental Microbiology 75, 5461-5466); a DNA fragment encoding a 33 amino acid sequence encoding the 5 prime polar region-transmembrane domain-C-terminal polar region from the cytochrome B5 isoform D protein from *Arabidopsis thaliana* corresponding to DFVIKLLQFLVPLLILGLAFGIRYYTKTKAPSS (SEQ ID NO: 58 residues 108-140; amino acids 108-140 of sequence listed in NP_199692.1) that has previously been shown to anchor proteins to the cytosolic face of the endoplasmic reticulum (Barbante, A., 2008, Plant Biotechnology Journal 6, 560-575), and the 3' termination sequence from the soybean oleosin isoform A gene.

Both pMBXS394 and pMBX763 contain the same expression cassettes for the PhaA and PhaB enzymes.

PhaB: An expression cassette for acetoacetyl-CoA reductase containing the promoter from the soybean oleosin isoform A gene (Rowley and Herman, 1997, Biochim. Biophys. Acta 1345, 1-4), a DNA fragment encoding a NADPH dependent reductase (PhaB) from *C. necator* (Peoples, O & A. Sinskey, 1989, J. Biol. Chem. 264, 15293-15297), and the 3' termination sequence from the soybean oleosin isoform A gene. Mutated PhaB genes encoding an acetoacetyl-CoA reductase with higher specific activity as described by Matsumoto et al., 2013, Applied and Environmental Microbiology, 2013, 79, 6134-6139, may also be used.

PhaA: An expression cassette for thiolase containing the promoter from the soybean glycinin (gy1) gene (Iida et al., 1995, Plant Cell Reports 14, 539-544), the phaA gene encoding a 3-ketothiolase (PhaA) from *C. necator* (Peoples, O. & A. Sinskey, 1989, J. Biol. Chem. 264, 15293-15297), and a 3' termination sequence from the soybean glycinin gene.

Dsred2B: An expression cassette for DsRed, a protein that can be visualized in seeds by placing them in light of the appropriate wavelength, containing the promoter from the Cauliflower mosaic virus (CaMV), a DNA fragment encoding a 233 amino acid modified red fluorescent protein from *Discosoma* sp. (DsRed2B) (Matz et al., 1999, Nat Biotechnol 17, 969-73) in which the first 225 amino acids are equivalent to Genbank EF451141 and the remaining sequence (amino acids 226-233) is VPMTRVSP (SEQ ID NO: 56), and a termination sequence from the *Agrobacterium tumefaciens* nopaline synthase gene.

Maps illustrating the genes and plant expression elements for directing their expression in plants in the plasmid vectors pMBXS394 and pMBXS763 are shown in FIGS. 3A-B.

Example 2. Transformation of Genetic Constructs pMBXS394 and pMBXS763 into *Camelina sativa*

*C. sativa* line 10CS0043 (abbreviated WT43) was obtained from Agriculture and Agri-Food Canada and has been reported to have a larger seed size than other lines of *Camelina*. WT43 was grown in 6-inch pots in a greenhouse at 22/18° C. day/night and a photoperiod of 16 h under supplemental light intensity of 900 µmol $s^{-1}$ $m^{-2}$ during the day time.

Vectors pMBXS394 and pMBXS763 were transformed into *Camelina* as follows: Transformation constructs were inserted into *Agrobacterium iumefaciens* strain GV3101

(pMP90) and a single colony of GV3101(pMP90) containing the construct of interest was obtained from a freshly streaked plate and was inoculated into 5 mL LB medium. After overnight growth at 28° C., 2 mL of culture was transferred to a 500-mL flask containing 300 mL of LB and incubated overnight at 28° C. Cells were pelleted by centrifugation (6,000 rpm, 20 min), and diluted to an OD600 of ~0.8 with infiltration medium containing 5% sucrose and 0.05% (v/v) Silwet-L77 (Lehle Seeds, Round Rock, TX, USA). WT43 Camelina plants were transformed by "floral dip" methods (Lu and Kang, 2008, Plant Cell Rep, 27, 273). Pots containing plants at the flowering stage were placed inside a 460 mm height vacuum desiccator (Bel-Art, Pequannock, NJ, USA). Inflorescences were immersed into the Agrobacterium inoculum contained in a 500-ml beaker. A vacuum (85 kPa) was applied and held for 5 min. Plants were removed from the desiccator and were covered with plastic bags in the dark for 24 h at room temperature. Plants were removed from the bags and returned to normal growth conditions within the greenhouse for seed formation.

$T_1$ seeds of putative transformed lines were identified by visualization of the fluorescent protein DsRed expressed in transgenic seeds as follows: Fully mature seeds were harvested from transformed plants and placed in a desiccator with anhydrous calcium sulfate as desiccant for at least 2 days prior to screening. DsRed seeds were visually identified by fluorescent microscopy using a Nikon AZ100 microscope with a TRITC-HQ(RHOD)2 filter module (HQ545/30X, Q570LP, HQ610/75M). In an attempt to recover all lines and to determine maximum PHB production potential with cytosolic constructs, $T_1$ seeds were sterilized and germinated on half strength MS media (Murashige and Skoog, 1962, Physiologia Plantarum 15, 473-497) supplemented with 3% sucrose and 1 µM gibberellic acid ($GA_3$). This medium has previously allowed the rescue of seedlings obtained from high PHB producing Camelina seeds that may be compromised in their vigor (Malik et al., 2015, Plant Biotechnol J, 13, 675).

Results with genetic construct pMBXS394. After plating on half strength MS media, 79% of pMBXS394 DsRed positive seeds germinated and formed seedlings. These $T_1$ seedlings were transferred to soil and all plants grew normally, were healthy, and set normal seeds. $T_2$ seeds were harvested and a sample of DsRed positive seeds was picked from the segregating seed population and used to determine PHB content using a previously described simultaneous extraction and butanolysis procedure followed by gas chromatography (GC) that converts PHB polymer into butyl esters of monomeric units (Kourtz et al., 2007, Transgenic Res., 16, 759; Malik et al., 2015, Plant Biotechnol J, 13, 675). Calibration curves were made with purified PHB (Sigma-Aldrich). PHB levels were calculated as percent of mature seed weight. $T_2$ seeds from 56 of the 63 $T_1$ lines analyzed produced detectable levels of PHB (TABLE 6). The highest PHB level obtained was 4.5% of the mature seed weight (TABLE 6, FIG. 4(A)), a level significantly higher than the maximum level previously achieved in the cytosol of Arabidopsis biomass [0.6 polymer primarily composed of 3-hydroxybutyrate monomer with a small amount of 3-hydroxyvalerate monomer (Matsumoto et al., 2005)] or the fibers of cotton [0.34% dry weight PHB, (John and Keller, 1996)].

TABLE 6

Comparison of PHB production in $T_2$ seeds of WT43 transformed with pMBXS394 and pMBXS763.

| Genetic Construct | # of lines tested | # of PHB producing lines | Highest PHB producing line | Lowest PHB producing line[1] | Average PHB content[2] (% seed weight) |
|---|---|---|---|---|---|
| pMBXS394 (SEQ ID NO: 29) | 63 | 56 | 4.5 | 1.2 | 2.4 ± 0.8 |
| pMBXS763 (SEQ ID NO: 30) | 77 | 74 | 4.9 | 0.3 | 2.8 ± 1.0 |

[1]Lines producing 0% PHB were also isolated.
[2]Average PHB content is calculated from lines found to possess detectable levels of PHB in seeds.

$T_2$ seeds that contained PHB levels of 2% of the mature seed weight were germinated in soil and the emergence and survival of each line was determined (FIG. 4(B)) as follows:

Thirty DsRed seeds from an individual PHB line were planted in 6 inch pots filled with soil (Sunshine Mix #4 saturated with water containing NPK 20-20-20 fertilizer) and a top layer of vermiculite. The plants were grown in the greenhouse with supplemental lighting (16 h photoperiod, 22° C., typical light intensity of 900 µmol $s^{-1}$ $m^{-2}$ during day time). The pots were moistened daily with fertilized water (NPK-20-20-20). Percent emergence was determined one week after transfer of the seeds to pots. Survival was determined after one week under ambient greenhouse conditions. Percent emergence and survival were calculated based on 30 seeds. Lines were found to have varying levels of survival. While the top producing line containing 4.5% PHB had a survival of 33%, the second highest producing line containing 4.2% PHB had a survival of 93%. After germination, a cotyledon phenotype differing from the WT43 control was observed in most PHB producing lines. Cotyledons of Camelina WT43 are rounded whereas those of the transgenic cytosolic PHB producing lines were often narrow and elongated but were otherwise green and healthy.

Light microscopy was used to analyze structural differences in cotyledons of WT43 and pMBXS394. Fully expanded cotyledons were fixed in modified Karnovsky's fixative containing 2.5% glutaraldehyde and 2% paraformaldehyde in 0.1M phosphate buffer. Tissues were loaded into histology cassettes and dehydration of tissue was initiated manually in 50% and 70% ethanol. Subsequent dehydration and infiltration steps were performed in a LEICA TP1020-Automatic Tissue Processor through a gradual alcohol-toluene series (70%, 90%, 100% ethanol, 1:1 ethanol: toluene followed by toluene and then paraffin). Cotyledons were oriented and embedded in paraffin blocks. 7-10 µm thick sections were cut with a Leica RM2125 RTS microtome and placed on glass slides that were air dried overnight at 37° C. Staining with 1% Safranin O and 0.67% Fast Green FCF was performed according to a previously described protocol (Clark and Bartholomew, 1981, Williams & Wilkins, 32-33) with minor modifications. Sections were viewed and digitally photographed with a Zeiss AXIO Scope.A1 compound microscope equipped with an Optronics digital camera.

The typical elongation of cells in the palisade layer observed in WT43 controls was not visible in cotyledons of pMBXS394 PHB producing lines. In addition, intercellular spaces were significantly reduced in spongy and palisade mesophyll, if not absent, in PHB producing lines. Difficulties in cell elongation in PHB producing lines may help to explain the visibly narrower cotyledons.

Results with genetic construct pMBXS763. In an attempt to increase PHB levels beyond the 4.5% PHB obtained with transformation construct pMBXS394, construct pMBXS763 was used. Plant vector pMBXS763 contains the same expression cassettes for the PhaA, PhaB and DsRed2B genes as vector pMBXS394 with the exception that the PhaC expression cassette was replaced with the expression cassette PhaC-ER, encoding an ER-targeted PHA synthase designed to be targeted to the cytosolic face of the ER, as discussed in detail above (TABLE 5, FIG. 3(B)). The ER-targeted enzyme was employed in an attempt to localize the granules of PHB in a defined region of the cytosol. Construct pMBXS763 was transformed into *Camelina* WT43 and DsRed positive $T_1$ seeds were isolated. Seed from 77 $T_1$ lines were germinated and grown to produce $T_2$ seed. 74 of the 77 $T_1$ lines analyzed produced detectable levels of PHB. The PHB content of the highest producing line was 4.9% of seed weight (TABLE 6, FIG. 5(A)). The phenotypes of cotyledons of $T_2$ seedlings of pMBXS763 were narrower than WT43 but green and were similar to those obtained with pMBXS394 (FIG. 8).

Example 3. Seed-Specific Cytosolic PHB Production in Later Generations of Lines Transformed With pMBXS394 and pMBXS763

$T_2$ seeds of the most promising PHB producing lines from transformations of constructs pMBXS394 and pMBXS763, containing one or two copies of inserts and with good survival (FIG. 4 and FIG. 5), were propagated for additional generations to produce homozygous lines and to analyze the stability of polymer production. In lines of pMBXS394, PHB levels dropped from a high of 4.5% PHB in $T_2$ seeds to 2.9% PHB in $T_3$ seeds (TABLE 7). Some homozygous lines were isolated which contained up to 2.3% PHB. In contrast, PHB production in lines of pMBXS763 was generally stable and in some instances possessed higher levels of PHB than the previous generation (TABLE 7). Homozygous pMBXS763 lines were isolated that produced 9.1% and 6.8% PHB in $T_3$ seeds. Surprisingly, homozygous lines were much easier to isolate from lines transformed with pMBXS763.

The difference in PHB levels in pMBXS394 and pMBXS763 lines in later generations was an unexpected observation, since there was little observed difference in the growth of T1 lines and the level of PHB in T2 seeds. Because of their stable production of PHB, continued analysis proceeded with only lines from pMBXS763.

Several $T_3$ homozygous pMBXS763 lines were chosen for further propagation in 10-inch pots in the greenhouse and in a controlled environmental chamber. The controlled environmental chamber was set with variable conditions to simulate changes in temperature and day length that seedlings and plants would encounter during their life cycle in fields around Saskatoon, SK, Canada if planted in early May and harvested in late July (TABLE 8). During day hours, the maximum light capability of the controlled environmental chamber (800-900 µmol $s^{-1}$ $m^{-2}$) was used. For greenhouse growth, plants were subjected to 22° C. during the day (16 h day length) and 18° C. during the night under supplemental light intensities of 900 µmol $s^{-1}$ $m^{-2}$ during the day time.

$T_3$ siblings derived from the same $T_2$ lines performed differently when grown in the greenhouse than when in the controlled environmental chamber. In general, higher yields of seed and polymer were obtained in the controlled environmental chamber than in the greenhouse (TABLE 9). Maximum levels of PHB produced in the greenhouse were 7.1% whereas lines grown in the chamber produced PHB at levels up to 10.2% of the mature seed weight.

TABLE 7

PHB content in $T_2$ and $T_3$ seed of select lines transformed with pMBXS394 and pMBXS763.

| Genetic construct[a] | $T_1$ line | $T_2$ generation | | $T_3$ generation | | | |
|---|---|---|---|---|---|---|---|
| | | Copy number $T_1$ line | % PHB, bulk $T_2$ seed[b] | # lines tested | Range of PHB $T_3$ seed[b] | Avg PHB content[b,c] $T_3$ seed | Highest PHB content in homozygous line |
| pMBXS394 | 12-0415 | 1 | 4.5 | 10 | 0.5-2.9 | 1.8 ± 0.9 | 2.3 |
| | 12-0430 | 1 | 4.2 | 7 | 0.9-2.4 | 1.5 ± 0.6 | 1.7 |
| | 12-0424 | 1 | 2.8 | 5 | 1.0-2.9 | 1.5 ± 0.8 | na |
| pMBX763 | 12-0944 | 1 | 3.6 | 2 | 3.6-4.3 | 3.9 ± 0.5 | 4.3 |
| | 12-0950 | 1 | 2.9 | 3 | 2.3-5.3 | 3.6 ± 1.5 | 5.3 |
| | 12-0954 | 1 | 3.4 | 4 | 3.5-4.4 | 3.9 ± 0.4 | 4.4 |
| | 12-0962 | 2 | 3.1 | 8 | 1.5-9.1 | 4.1 ± 2.2 | 9.1 |
| | 12-0974 | 2 | 3.6 | 7 | 1.5-6.8 | 4.2 ± 1.7 | 6.8 |
| | 12-0992 | 1 | 3.5 | 2 | 3.5-3.7 | 3.6 ± 0.15 | 3.6 |
| | 12-0999 | 1 | 3.0 | 6 | 3.2-5.6 | 4.5 ± 1.0 | 5.6 |

[a]Genes in each construct are shown in TABLE 5.
[b]Units for PHB content are % mature seed weight.
[c]Average PHB content is calculated from lines containing detectable levels of PHB in seeds. All plants were grown in the greenhouse.

TABLE 8

Controlled environmental chamber growth conditions used in experiments designed to simulate spring planting.[1]

| Week | 1[2] | 2 | 3 | 4 | 5 | 6 | 7 | 8 | 9 | 10 | 11 | 12 | 13 |
|---|---|---|---|---|---|---|---|---|---|---|---|---|---|
| Days after seeding | 1-7 | 8-14 | 15-21 | 22-28 | 29-35 | 36-43 | 44-51 | 52-58 | 59-65 | 66-72 | 73-79 | 80-87 | 88-94 |
| Day length (h) | 15.25 | 15.5 | 15.75 | 16 | 16.25 | 16.5 | 16.75 | 16.75 | 16.5 | 16.25 | 16 | 16 | 16 |
| Day temp (° C.)[3] | 17 | 19 | 19 | 20 | 25 | 25 | 22 | 22 | 24 | 24 | 24 | 24 | 24 |
| Night temp (° C.) | 5 | 6 | 6 | 6 | 10 | 20 | 12 | 12 | 12 | 12 | 11 | 11 | 11 |

TABLE 8-continued

Controlled environmental chamber growth conditions used in experiments designed to simulate spring planting.[1]

| Week | 1[2] | 2 | 3 | 4 | 5 | 6 | 7 | 8 | 9 | 10 | 11 | 12 | 13 |
|---|---|---|---|---|---|---|---|---|---|---|---|---|---|
| Day Humidity (%) | 50 | 50 | 50 | 50 | 50 | 50 | 50 | 50 | 50 | 50 | 50 | 50 | 50 |
| Night Humidity (%) | 70 | 70 | 70 | 70 | 70 | 70 | 50 | 50 | 50 | 50 | 50 | 50 | 50 |

[1]Day time light levels ranged from 800 to 900 µmoles $m^{-2}$ $s^{-1}$.
[2]Week 1 assumed to start May 7th.
[3]Temperature settings in the controlled environmental chamber (CEC) were adapted from averages of weekly historical data between early May and late July for Saskatoon, Saskatchewan, Canada (data available at website:
climate.weather.gc.ca/climateData/almanac_e.html?StationID=3328&pageName=StationResults&Month=5&Day=8&stnSubmit=G).

TABLE 9

Growth of single copy $T_3$ homozygous lines of pMBXS763 showing high survival under greenhouse (GH) and controlled environmental chamber (CEC) conditions designed to simulate spring planting.

| $T_1$ line | Copy # $T_1$ line | % PHB, bulk $T_3$ seed[1] | Growth method | # of plants[2] | % emergence $T_3$ seedlings | % survival $T_3$ seedlings | $T_4$ PHB range[3] (%) | Avg $T_4$ seed yield[3] (g) | Avg $T_4$ 100 seed weight[3] (mg) |
|---|---|---|---|---|---|---|---|---|---|
| 12-0944 | 1 | 4.3 | GH | 8 | 86 | 80 | 2.9-5.3 | 8.6 ± 2.1 | 90 ± 2 |
|  |  |  | CEC | 5 | 83 | 69 | 4.0-7.0 | 18.6 ± 2.3 | 139 ± 4 |
| 12-0954 | 1 | 3.8 | GH | 8 | 33 | 36 | 2.3-4.3 | 8.1 ± 1.8 | 105 ± 1 |
|  |  |  | CEC | 5 | 50 | 47 | 4.6-6.1 | 15.2 ± 3.2 | 141 ± 1 |
| 12-0992 | 1 | 3.5 | GH | 8 | 86 | 86 | 3.9-7.1 | 8.2 ± 1.8 | 101 ± 2 |
|  |  |  | CEC | 4 | 81 | 78 | 4.6-10.2 | 14.7 ± 3.9 | 130 ± 5 |
| WT43 | — | — | GH | 8 | 92 | 94 | — | 8.5 ± 1.2 | 140 ± 2 |
|  |  |  | CEC | 5 | 97 | 97 | — | 17.8 ± 2.2 | 149 ± 4 |

[1]Units for PHB content are % mature seed weight.
[2]number of $T_3$ plants grown for analysis.
[3]$T_4$ bulk seed from individual plants.
Abbreviations are as follows.
AVG, average;
GH, greenhouse;
CEC, controlled environmental chamber;
WT43, wild-type control line.

Figure 10:
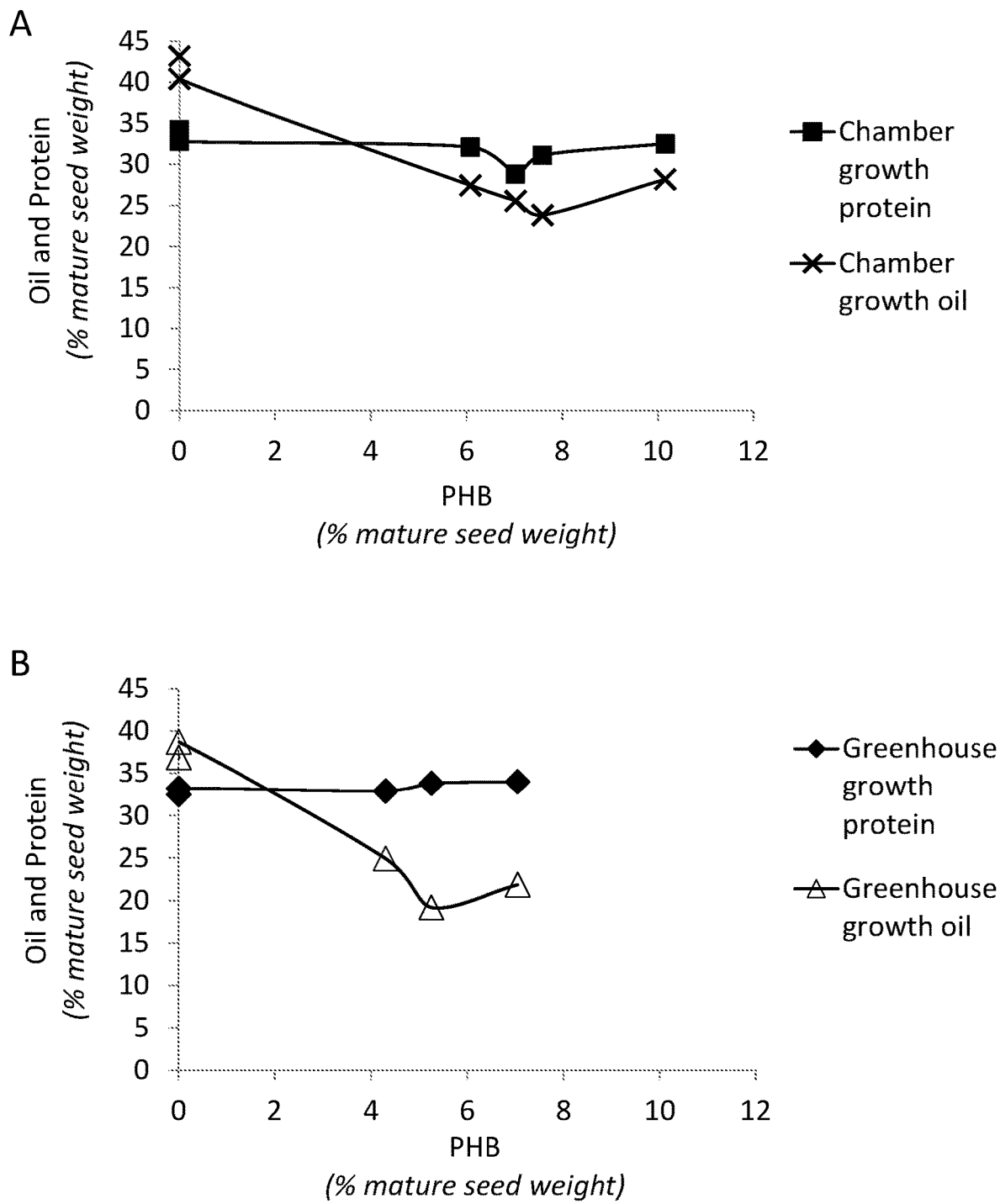
FIG. 10 shows scatter plots for comparison of protein, PHB, and oil content in select $T_4$ seeds of lines of pMBXS763 grown in (A) a controlled environmental growth chamber or (B) a greenhouse. Chamber growth conditions are described in TABLE 8. Data points show individual lines. Two WT43 control lines with 0% PHB were analyzed each for the chamber and greenhouse growth conditions.

The carbon partitioning in select $T_4$ seed samples of pMBXS763 was measured. For these experiments, plants were grown in the greenhouse and in a controlled environmental chamber under the conditions described in TABLE 8 and data are shown in FIGS. 9 and 10. A decrease in seed oil was observed upon PHB production. Plants grown in the controlled environmental chamber consistently contained more oil than plants grown in the greenhouse (FIG. 9). Total seed protein content remained essentially constant with PHB production (FIG. 10). In addition, there was not a significant difference in protein content in seeds harvested from chamber and greenhouse grown plants.

Example 4. Anchoring of PHA Synthase to the Endoplasmic Reticulum for Production of PHBH PHA synthase can be used for PHBH production. As discussed in the Examples above, anchoring the PHA synthase (PhaC) enzyme to the endoplasmic reticulum (ER) in the cytosol of *Camelina sativa* seeds resulted in significantly increased PHA accumulation compared to an unanchored PhaC. The C-terminus of the PhaC protein was modified with a sequence designed to "tail-anchor" it to the cytosolic face of the ER. The tail-anchor is described in Abell and Mullen, 2011, *Plant Cell Reports* 30:137-151, and Barbante et al., 2008, *Plant Biotechnol.* 1 6:560-575. Additionally, a linker was inserted at the C-terminus of the PhaC protein in order to fuse the PHA synthase protein to the ER anchor. The linker is described by Jahns and Rehm, 2009, *Appl. Environ. Microbiol.* 75:5461-5466. Therefore, in the subsequent examples set forth here, ER-anchored PhaC is referred to as "$PhaC_{ER}$."

To convert a PhaC protein into a $PhaC_{ER}$ protein, two sequences are appended at the C-terminus. First the linker sequence 5'-VLAVAID-KRGGGGGSGGGGSGGGGSGGGGS-3' (SEQ ID NO: 57); then the ER anchor sequence 5'-DFVIKLLQFLVPL-LILGLAFGIRYYTKTKAPSS—3' (SEQ ID NO: 58, amino acids 108-140; cytochrome B5 isoform D protein of *Arabidopsis thaliana*).

A further characteristic of the PHA synthase to be used for PHBH production is that it must accept 3-hydroxybutyryl-CoA and 3-hydroxyhexanoyl-CoA as substrates. A number of known PHA synthases meet this criterion. Among these are PHA synthases from *Aeromonas caviae* (Fukui et al., 1997, *J. Bacteriol.* 179:4821-4830; GenBank Accession No. BAA21815; SEQ ID NO: 35) and from *Chromobacterium violaceum* (Kolibachuk et al., 1999, *Appl. Environ. Microbiol.* 65:3561-3565; GenBank Accession No. Q9ZHI2; SEQ ID NO: 33).

Figure 11:
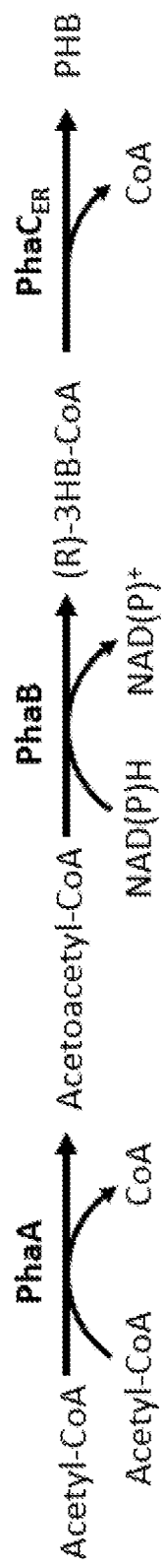
FIG. 11 shows the three-step PHB pathway. Abbreviations are as follows: PhaA, beta-ketothiolase; PhaB, acetoacetyl-CoA reductase; $PhaC_{ER}$, PHA synthase anchored to the endoplasmic reticulum; CoA, coenzyme A; NAD(P)H, reduced nicotinamide adenine dinucleotide (phosphate); $NAD(P)^+$, oxidized nicotinamide adenine dinucleotide (phosphate); 3HB, 3-hydroxybutyrate.

Example 5. PHB Production in the Cytosol of *Camelina* Seeds for Generation of PHBH An important component of any PHBH production strategy is the synthesis of poly(3-hydroxybutyrate), or PHB, which will make up the majority of the polymer. The enzymes and methods utilized to accomplish this will be the same for all subsequent examples. FIG. 11 shows that PHB is synthesized from acetyl-CoA by a three-step pathway that comprises the beta-ketothiolase (EC 2.3.1.9; PhaA), acetoacetyl-CoA reductase (EC 1.1.1.36; PhaB), and PHA synthase (EC 2.3.1.-; PhaC) proteins. For cytosolic production of PHBH, all three of these enzymes are to be expressed in the cytosol, with PHA synthase anchored to the ER as PhaC$_{ER}$. There are numerous sources of PhaA and PhaB enzymes, and selected lists of these are given in TABLE 10 and TABLE 11. It is important to note that plants generally already contain genes encoding PhaA proteins, and therefore these genes would not necessarily need to be imported from other organisms but rather could be modulated for suitable expression in the cytosol of the plant of interest by promoter alteration, addition of regulatory sequences, retransformation, etc.

TABLE 10

Sources of beta-ketothiolase (PhaA).

| Organism | Accession No. | Sequence |
| --- | --- | --- |
| Camelina sativa | XP_010482068 | SEQ ID NO: 65 |
| Oryza sativa | XP_015651167 | SEQ ID NO: 66 |
| Zea mays | XP_020399758 | SEQ ID NO: 67 |
| Brassica napus | XP_022569722 | SEQ ID NO: 68 |
| Glycine max | XP_003519682 | SEQ ID NO: 69 |
| Solanum tuberosum | XP_006353096 | SEQ ID NO: 70 |
| Saccharomyces cerevisiae | NP_015297 | SEQ ID NO: 71 |
| Cupriavidus necator H16 | CAJ92573 | SEQ ID NO: 72 |
| Synechocystis sp. PCC 6803 | BAA17882 | SEQ ID NO: 73 |
| Micrococcus luteus | ACS31435 | SEQ ID NO: 74 |

TABLE 11

Sources of acetoacetyl-CoA reductase (PhaB).

| Organism | Accession No. | Sequence |
| --- | --- | --- |
| Cupriavidus necator H16 | CAJ92574 | SEQ ID NO: 75 |
| Synechocystis sp. PCC 6803 | BAA17883 | SEQ ID NO: 76 |
| Bacillus megaterium | ADE68263 | SEQ ID NO: 77 |
| Xanthomonas campestris | CAP50185 | SEQ ID NO: 78 |
| Sinorhizobium meliloti | WP_003535773 | SEQ ID NO: 79 |
| Rhizobium etli | ABC92763 | SEQ ID NO: 80 |
| Rhodospirillum rubrum | WP_011388026 | SEQ ID NO: 81 |
| Azospirillum brasilense | CCD02124 | SEQ ID NO: 82 |
| Bacillus thuringiensis | AJG74649 | SEQ ID NO: 83 |
| Arthrospira platensis | BAI92197 | SEQ ID NO: 84 |

Example 6. PHBH Production in *Camelina* Seed Using the PhaG Pathway

Figure 12:
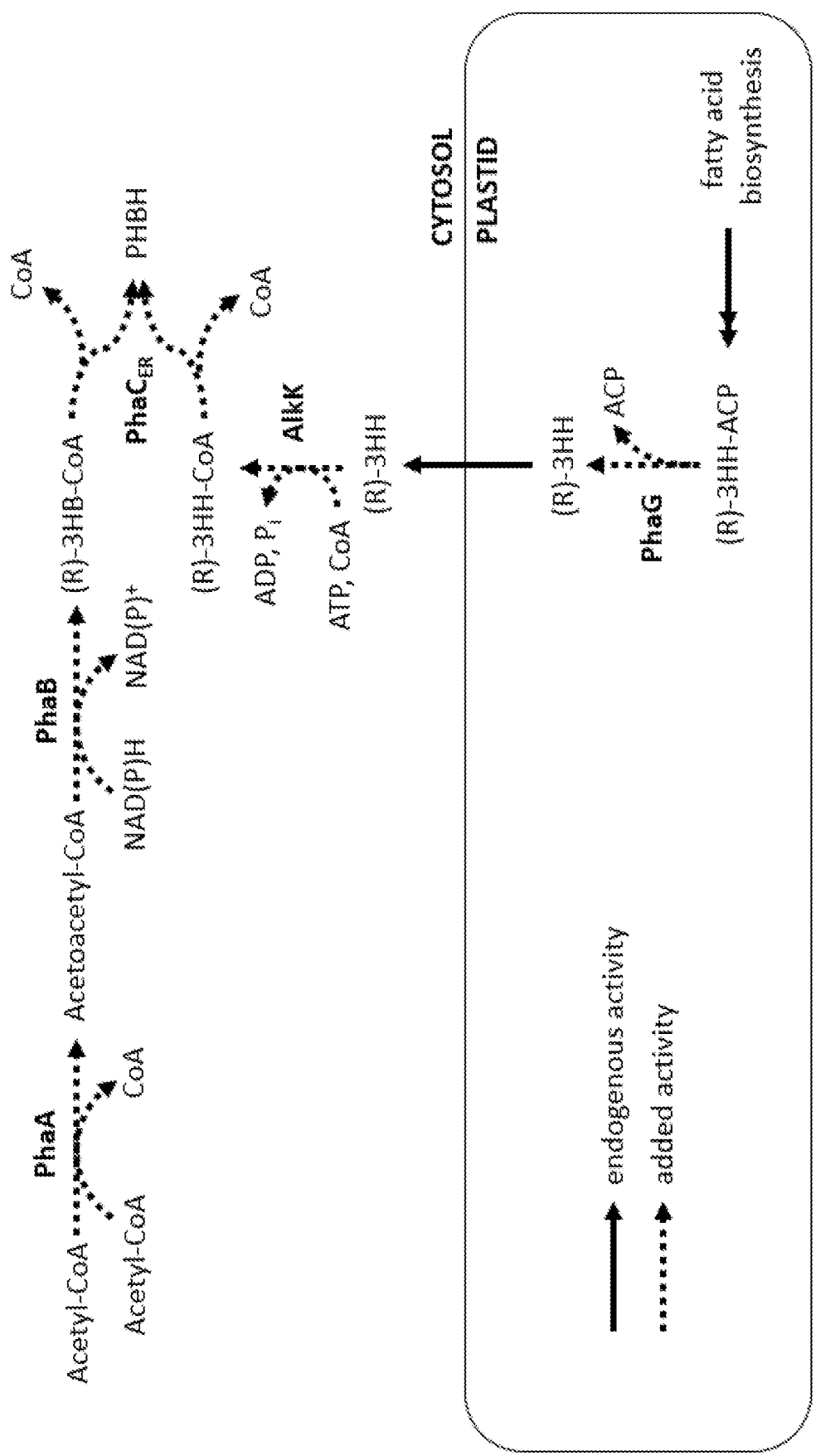
FIG. 12 shows the PhaG pathway to PHBH. Abbreviations are as follows: PhaA, beta-ketothiolase; PhaB, acetoacetyl-CoA reductase; $PhaC_{ER}$, PHA synthase anchored to endoplasmic reticulum; PhaG, hydroxyacyl-ACP thioesterase; AlkK, fatty acid-CoA ligase; CoA, coenzyme A; NAD(P)H, reduced nicotinamide adenine dinucleotide (phosphate); $NAD(P)^+$, oxidized nicotinamide adenine dinucleotide (phosphate); 3HB, 3-hydroxybutyrate; 3HH, 3-hydroxyhexanoate; ATP, adenosine triphosphate; ADP, adenosine diphosphate; Pi, orthophosphate; ACP, acyl carrier protein.

The PHB pathway consists of three enzymatic steps, encoded by the PhaA, PhaB, and PhaC proteins (FIG. 11). As previously described in Aquin et al., 2010, European patent EP 1334181B1, PHBH can be produced in the cytosol by employing a combination of the cytosolic PHB pathway, a plastidic hydroxyacyl-ACP thioesterase (PhaG) protein, and a cytosolic fatty acid-CoA ligase (AlkK) protein. This pathway is depicted in FIG. 12. In a preferred embodiment, a PhaC$_{ER}$ enzyme is used in order to increase polymer yield, and PhaG is targeted to the plastid as described in the section "PLASTID TARGETING SEQUENCES" above. Wang et al., 2011, *Appl. Environ. Microbiol.* 78:519-527 showed that the PhaG (PP_1408; SEQ ID NO: 85) and AlkK (PP_0763; SEQ ID NO: 86) proteins from *Pseudomonas putida* were sufficient to enable MCL PHA formation in *Escherichia coli* when coexpressed with a PHA synthase that could accept MCL substrates, making these suitable proteins for PHBH production in the plant. A BLAST search using PP_1408 or PP_0763 as the query generates hundreds of very similar proteins from Pseudomonadaceae; excluding that family results in other potential sources for these enzymes, selections of which are shown in TABLE 12 and TABLE 13.

TABLE 12

Sources of hydroxyacyl-ACP thioesterase (PhaG).

| Organism | Accession No. | E value | Sequence |
| --- | --- | --- | --- |
| Delftia acidovorans | AYM49080 | 0.0 | SEQ ID NO: 87 |
| Pantoea sp. Ap-967 | WP_167061760 | 0.0 | SEQ ID NO: 88 |
| Stenotrophomonas rhizophila | AXQ49510 | 0.0 | SEQ ID NO: 89 |
| Trinickia caryophylli | AAK71350 | 2e-170 | SEQ ID NO: 90 |
| Serratia sp. 18057 | WP_159962174 | 3e-148 | SEQ ID NO: 91 |
| Paucimonas lemoignei | SQF96561 | 5e-144 | SEQ ID NO: 92 |
| Streptococcus dysgalactiae subsp. equisimilis | VTS65778 | 5e-121 | SEQ ID NO: 93 |
| Enterobacter cloacae | SAJ14443 | 8e-121 | SEQ ID NO: 94 |
| Acinetobacter baumannii | SVK43159 | 2e-120 | SEQ ID NO: 95 |
| Nevskia soli | WP_029918804 | 5e-87 | SEQ ID NO: 96 |

TABLE 13

Sources of fatty acid-CoA ligase (AlkK).

| Organism | Accession No. | E value | Sequence |
| --- | --- | --- | --- |
| Stenotrophomonas rhizophila | AXQ46794 | 0.0 | SEQ ID NO: 97 |
| Pantoea sp. Cy-639 | NIF16511 | 0.0 | SEQ ID NO: 98 |
| Lipotes vexillifer | XP_007448630 | 0.0 | SEQ ID NO: 99 |
| Serratia sp. 18057 | WP_159962623 | 0.0 | SEQ ID NO: 100 |
| Enterobacter cloacae | SAI98381 | 0.0 | SEQ ID NO: 101 |
| Acinetobacter baumannii | SSU09518 | 0.0 | SEQ ID NO: 102 |
| Streptococcus dysgalactiae subsp. equisimilis | VTS35414 | 0.0 | SEQ ID NO: 103 |
| Paucimonas lemoignei | SQG00183 | 0.0 | SEQ ID NO: 104 |
| Streptococcus pneumoniae | CJL55150 | 0.0 | SEQ ID NO: 105 |
| Stenotrophomonas maltophila | KAF1051182 | 0.0 | SEQ ID NO: 106 |

Example 7. PHBH Production in *Camelina* Seed Using the PhaJ Pathway

Figure 13:
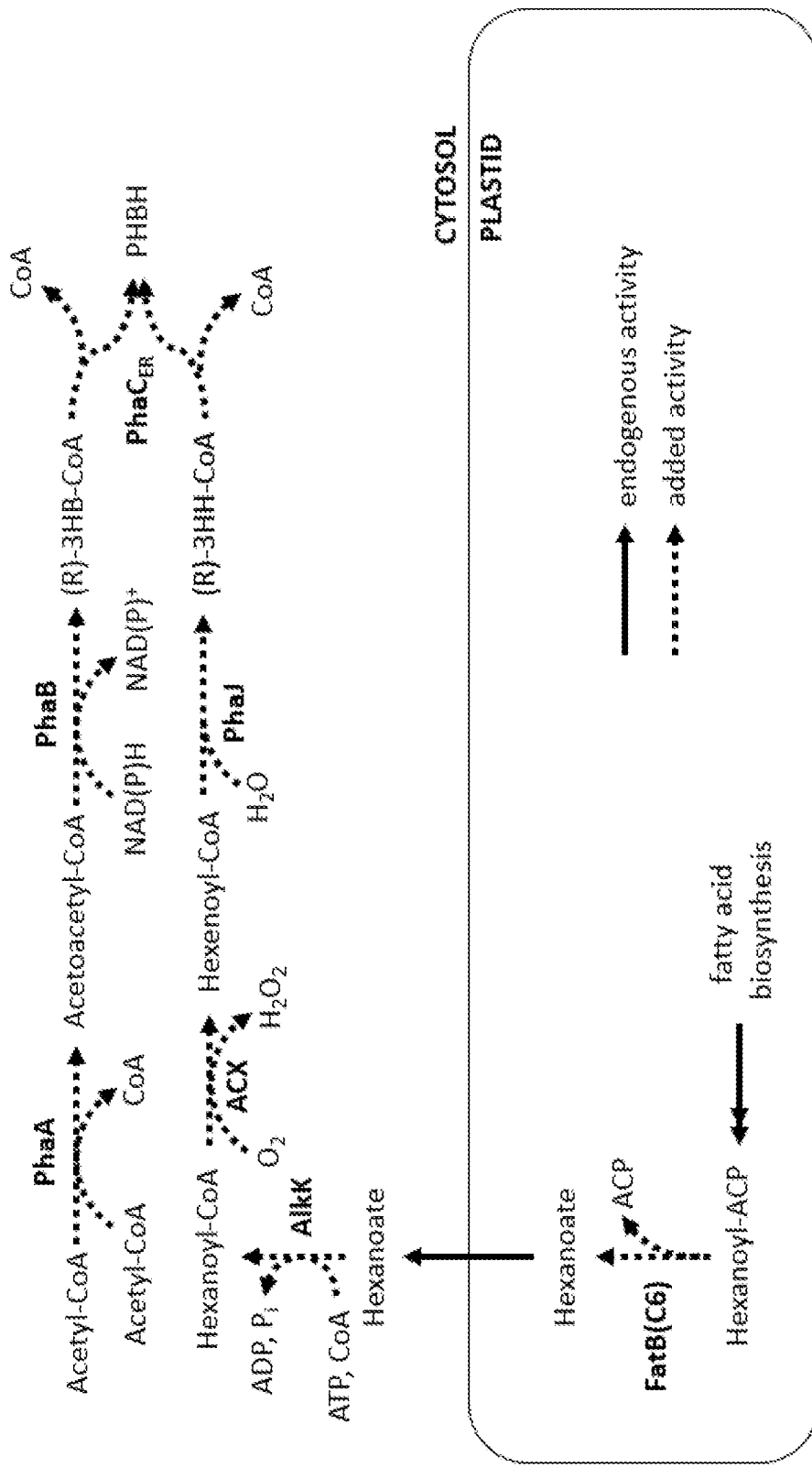
FIG. 13 shows the PhaJ pathway to PHBH. Abbreviations are as follows: PhaA, beta-ketothiolase; PhaB, acetoacetyl-CoA reductase; $PhaC_{ER}$, PHA synthase anchored to endoplasmic reticulum; AlkK, fatty acid-CoA ligase; ACX, acyl-CoA oxidase; PhaJ, R-specific enoyl-CoA hydratase; FatB (C6), thioesterase preferring 6-carbon substrates; CoA, coenzyme A; NAD(P)H, reduced nicotinamide adenine dinucleotide (phosphate); $NAD(P)^+$, oxidized nicotinamide adenine dinucleotide (phosphate); 3HB, 3-hydroxybutyrate; 3HH, 3-hydroxyhexanoate; ATP, adenosine triphosphate; ADP, adenosine diphosphate; Pi, orthophosphate; ACP, acyl carrier protein.

A second alternative for generation of the MCL comonomer is to use a medium-chain thioesterase within the plastid followed by fatty acid-CoA ligase (AlkK), acyl-CoA oxidase (ACX), and R-specific enoyl-CoA reductase (PhaJ) in the cytosol. This pathway is depicted in FIG. 13. There are a number of reported naturally occurring acyl-ACP thioesterases from both plants and bacteria with significant activity on MCL acyl-ACPs. A review of these was provided by Jing, 2013, doctoral thesis, Iowa State University, and TABLE 14 summarizes a selection of these.

TABLE 14

Naturally occurring thioesterases with significant activity on MCL-ACPs.

| | | | mol % of fatty acids* | |
|---|---|---|---|---|
| Organism | Accession No. | Sequence | C6:0 | C8:0 |
| Cuphea palustris | AAC49179 | SEQ ID NO: 107 | 0.2 | 97.5 |
| Ulmus americana | AAB71731 | SEQ ID NO: 108 | 0.4 | 44.2 |
| Cuphea viscosissima | AEM72522 | SEQ ID NO: 109 | 1.5 | 51.7 |
| Clostridium perfringens | ABG82470 | SEQ ID NO: 110 | 14.0 | 70.3 |
| Clostridium asparagiform | EEG55387 | SEQ ID NO: 111 | 4.5 | 26.0 |
| Bryantella formatexigens | EET61113 | SEQ ID NO: 112 | 20.4 | 31.8 |
| Streptococcus dysgalactiae | BAH81730 | SEQ ID NO: 113 | 13.2 | 29.9 |
| Lactobacillus brevis | ABJ63754 | SEQ ID NO: 114 | 13.7 | 55.5 |
| Lactobacillus plantarum | CAD63310 | SEQ ID NO: 115 | 11.0 | 68.0 |
| Anaerococcus tetradius | EEI82564 | SEQ ID NO: 116 | 1.4 | 86.7 |
| Bdellovibrio bacteriovorus | CAE80300 | SEQ ID NO: 117 | 0.9 | 36.9 |

*Liberated in *Escherichia coli* in vivo assays (Jing, 2013)

Furthermore, mutant acyl-ACP thioesterases are reported that have high specificity for MCL acyl-ACPs (Jing et al., 2018, *Nature Communications* 9:860-869). Chimeric derivatives of *Cuphea viscosissima* FatB1 and FatB2 have higher biases toward C6:0 substrates than either FatB1 or FatB2 individually. These include chimeras rTE48 (12.2 mol % C6:0, 23.8 mol % C8:0) and rTE52 (17.4 mol % C6:0, 31.0 mol % C8:0). Other FatB2 derivatives with multiple mutations have even higher biases towards C6:0 substrates, the best of which is CvB2MT1 (FatB2 V194F, SEQ ID NO: 118). Because the N-terminus of the FatB2 sequence given in Jing et al., 2018 is not complete, the first three amino acid residues from FatB1 were added to the partial sequence of FatB2 V194F based on the alignment of the two proteins to produce SEQ ID NO: 118, a likely functional CvB2MT1. The native ACX gene in the plant of interest is to be modified by removal of its peroxisomal targeting signal and expressed in the same plant separately from the native form. It is important to select an ACX protein that will accept substrates that include hexanoyl-CoA. For example, according to the UniProt database, in *Arabidopsis thaliana*, ACX1 will accept long- and medium-chain acyl-CoAs, whereas ACX2 accepts only C14 and higher. ACX3 uses C8 to C14 with a maximum at C12. ACX4, probably the most suitable for PHBH, is active on C4-C8 and has a $K_m$=8.3 µM for hexanoyl-CoA. A proteomic study of *Arabidopsis thaliana* showed that ACX4 is found only in the peroxisome (McBride et al., 2017, *Molec. Cell Proteomics* 16:1972-1979). The peroxisomal targeting signal of ACX4 is likely the C-terminal three amino acids SRL, and these would be removed to maintain ACX4 in the cytosol. The *A. thaliana* ACX4 protein (GenBank Accession No. NP_190752; SEQ ID NO: 119) can be utilized this way in other plants if the substrate specificity of their ACX proteins is not known. While R-specific enoyl-CoA hydratase (EC 4.2.1.119) appears as part of multifunctional enzyme complexes in eukaryotes, some bacteria contain a freestanding version known as PhaJ, generally used by these bacteria to liberate (R)-3-hydroxyacyl-CoAs from fatty acid beta-oxidation for the purpose of MCL PHA synthesis. The PhaJ protein PhaJ1 (GenBank Accession No. BAA92740; SEQ ID NO: 120) from *Pseudomonas aeruginosa* prefers C4-C6 substrates but will accept C8 to some degree, while PhaJ2 from this organism (GenBank Accession No. BAA92741; SEQ ID NO: 121) also accepts all three but prefers C8 (Tsuge et al., 2000, *FEMS Microbiol. Lett.* 184:193-198). The PhaJ from *Aeromonas caviae* (GenBank Accession No. SQH59475; SEQ ID NO: 122) has a similar substrate profile to *Pseudomonas aeruginosa* PhaJ1 (Fukui et al., 1998, *J. Bacteriol.* 180:667-673). Each of the three variants of PhaJ listed above was subjected to a BLAST search, and in each case a large number of very similar sequences from the same genus was generated. Therefore, each was run again with the provision that the same genus be excluded, and lists of candidate PhaJ proteins from other organisms were generated; selections from these lists are shown in TABLES 15-17.

TABLE 15

Sources of R-specific enoyl-CoA hydratase (PhaJ) selected from a BLAST search with *Pseudomonas aeruginosa* PhaJ1 as the query sequence.

| Organism | Accession No. | E value | Sequence |
|---|---|---|---|
| Enterobacter cloacae | SAJ33105 | 1e−108 | SEQ ID NO: 123 |
| Streptococcus dysgalactiae subsp. equisimilis | VTS33264 | 2e−106 | SEQ ID NO: 124 |
| Streptococcus pneumoniae | CJL23612 | 6e−78 | SEQ ID NO: 125 |
| Lipotes vexillifer | XP_007461728 | 6e−73 | SEQ ID NO: 126 |
| Paucimonas lemoignei | SQF99991 | 4e−72 | SEQ ID NO: 127 |
| Pantoea sp. Ap-967 | WP_167059635 | 2e−67 | SEQ ID NO: 128 |
| Ventosimonas gracilis | WP_068393436 | 2e−65 | SEQ ID NO: 129 |
| Aestuariirhabdus litorea | WP_164880862 | 5e−61 | SEQ ID NO: 130 |
| Marinobacter mobilis | WP_091812099 | 2e−58 | SEQ ID NO: 131 |
| Hahella ganghwensis | WP_020405163 | 2e−58 | SEQ ID NO: 132 |

TABLE 16

Sources of R-specific enoyl-CoA hydratase (PhaJ) selected from a BLAST search with *Pseudomonas aeruginosa* PhaJ2 as the query sequence.

| Organism | Accession No. | E value | Sequence |
|---|---|---|---|
| Acinetobacter baumannii | SCY02036 | 0.0 | SEQ ID NO: 133 |
| Enterobacter cloacae | SAJ28836 | 0.0 | SEQ ID NO: 134 |
| Streptococcus dysgalactiae subsp. equisimilis | VTS64847 | 0.0 | SEQ ID NO: 135 |
| Klebsiella pneumoniae | SVJ79134 | 0.0 | SEQ ID NO: 136 |
| Tepidiphilus sp. J18 | WP_142809208 | 5e−125 | SEQ ID NO: 137 |
| Oceanibaculum indicum | WP_008945501 | 1e−123 | SEQ ID NO: 138 |
| Acidibrevibacterium fodinaquatile | WP_114912109 | 4e−123 | SEQ ID NO: 139 |
| Methylobacterium aquaticum | WP_060850994 | 3e−122 | SEQ ID NO: 140 |
| Roseomonas cervicalis | WP_007004492 | 4e−122 | SEQ ID NO: 141 |
| Alcanivorax sp. 6-D-6 | WP_159661788 | 3e−120 | SEQ ID NO: 142 |

TABLE 17

Sources of R-specific enoyl-CoA hydratase (PhaJ) selected from a BLAST search with *Aeromonas caviae* PhaJ as the query sequence.

| Organism | Accession No. | E value | Sequence |
|---|---|---|---|
| *Escherichia coli* | MHO06761 | 5e-71 | SEQ ID NO: 143 |
| *Vibrio tapetis* | WP_102524434 | 9e-52 | SEQ ID NO: 144 |
| *Shewanella halifaxensis* | WP_012277084 | 5e-46 | SEQ ID NO: 145 |
| *Desulfobacterales* bacterium SG8_35_2 | KPK24020 | 8e-45 | SEQ ID NO: 146 |
| *Thiorhodococcus drewsii* | WP_007041994 | 1e-41 | SEQ ID NO: 147 |
| *Ferrimonas senticii* | WP_028116136 | 2e-41 | SEQ ID NO: 148 |
| *Desulfatitalea* sp. BRH_c12 | KJS32512 | 3e-40 | SEQ ID NO: 149 |
| *Thiofilum flexile* | WP_020558662 | 5e-40 | SEQ ID NO: 150 |
| *Spongibacter* sp. KMU-166 | WP_168448950 | 8e-40 | SEQ ID NO: 151 |
| *Hymenobacter* sp. CCM 8763 | WP_116941243 | 1e-38 | SEQ ID NO: 152 |

Figure 14:
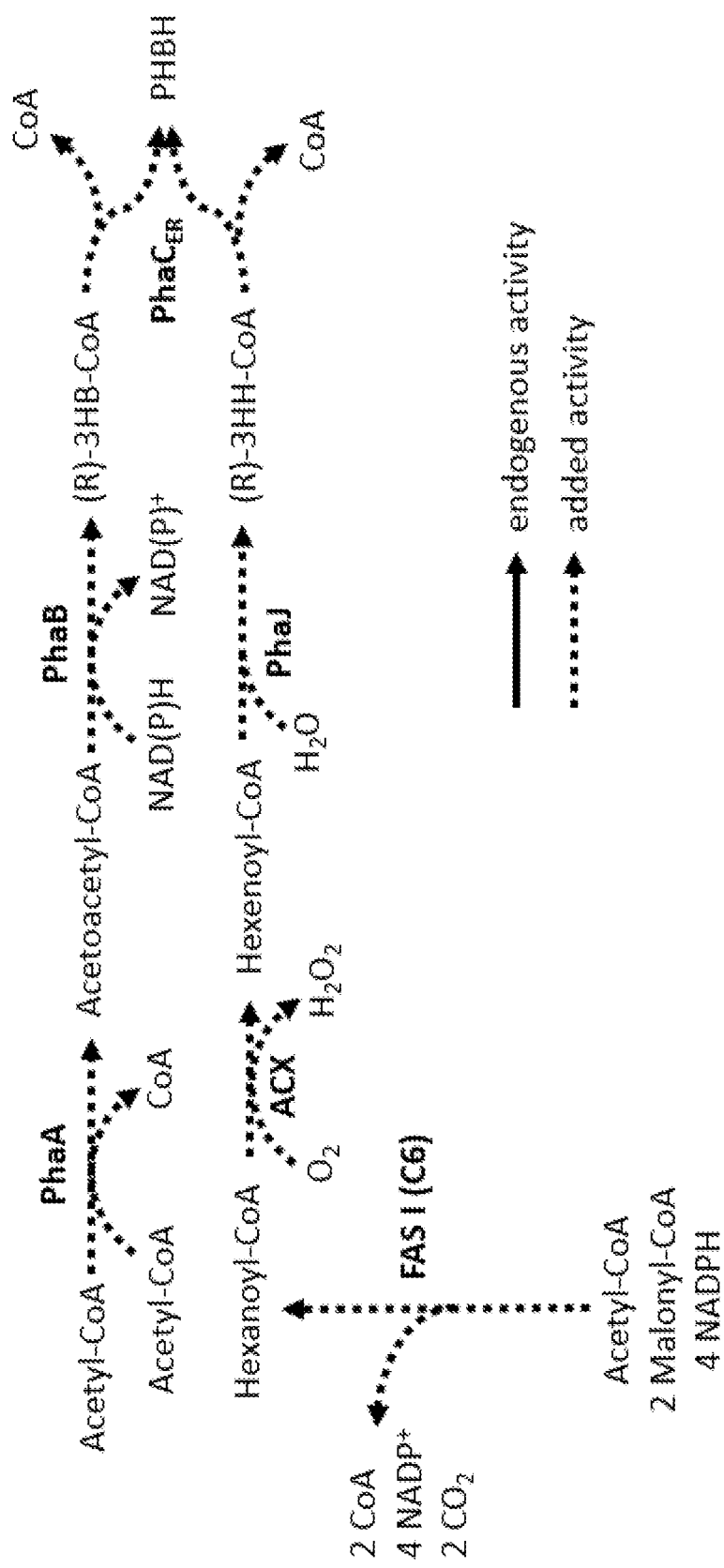
FIG. 14 shows the FAS I pathway to PHBH. Abbreviations are as follows: PhaA, beta-ketothiolase; PhaB, acetoacetyl-CoA reductase; $PhaC_{ER}$, PHA synthase anchored to endoplasmic reticulum; FAS I (C6), fatty acid synthase complex synthesizing hexanoyl-CoA; ACX, acyl-CoA oxidase; PhaJ, R-specific enoyl-CoA hydratase; CoA, coenzyme A; NAD(P)H, reduced nicotinamide adenine dinucleotide (phosphate); $NAD(P)^+$, oxidized nicotinamide adenine dinucleotide (phosphate); 3HB, 3-hydroxybutyrate; 3HH, 3-hydroxyhexanoate; ATP, adenosine triphosphate; ADP, adenosine diphosphate; Pi, orthophosphate; ACP, acyl carrier protein.

Example 8. PHBH Production in *Camelina* Seed Using the Cytosolic FAS Pathway It is possible to generate MCL fatty acids in the cytosol rather than relying on the plastid by reconstituting a fatty acid synthase (FAS) complex in the cytosol that produces MCL fatty acyl-CoAs, as depicted in FIG. 14. If hexanoyl-CoA is produced in the cytosol, it can be converted to (R)-3-hydroxyhexanoyl-CoA as in Example 7, with suitable ACX and PhaJ proteins expressed in the cytosol. Hitchman et al., 2001, *Bioorganic Chemistry* 29:293-307 reported a specialized FAS from *Aspergillus parasiticus* SU-1 whose end product is primarily hexanoic acid. It consists of two proteins, HexA (GenBank Accession No. AAL99898; SEQ ID NO: 153) and HexB (GenBank Accession No. AAL99899; SEQ ID NO: 154). The hexanoate remains covalently attached to the HexA-HexB complex and is released as hexanoyl-CoA (Yabe and Nakajima, 2004, *Appl. Microbiol. Biotechnol.* 64:745-755). BLAST searches using HexA and HexB as query sequences each generate a list of proteins nearly identical to the query sequence, all from *Aspergillus* species, followed by a steep dropoff from >90% identity to <60% identity, suggesting that hexanoate-specific proteins end at this cutoff. Mutants of *Saccharomyces cerevisiae* FAS I that produce primarily hexanoyl-CoA have been reported (Gajewski et al., 2017, *Nature Communications* 8:14650). The FAS I complex consists of the FAS1 (GenBank Accession No. NP_012739; SEQ ID NO: 155) and FAS2 (GenBank Accession No. NP_015093; SEQ ID NO: 156) proteins. The FAS1(I306A)-FAS2(G1250S) double mutant of FAS I was shown to produce primarily hexanoyl-CoA as its end product. These two mutated proteins are given as SEQ ID NO: 157 [FAS1(I306A)] and SEQ ID NO: 158 [FAS2(G1250S)]. Any of these hexanoyl-CoA-producing FAS systems can be expressed in the cytosol along with PhaA, PhaB, PhaC$_{ER}$, ACX, and PhaJ, to enable PHBH production in the cytosol.

Figure 15:
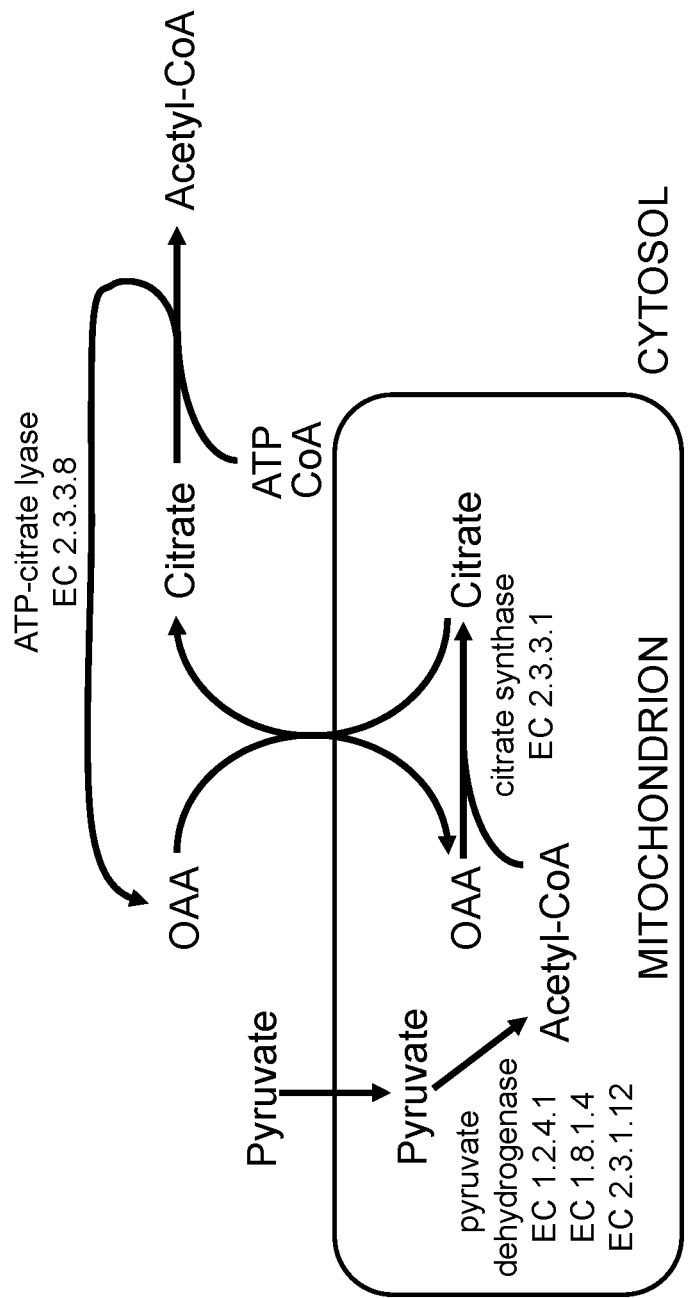
FIG. 15 shows a pathway for acetyl-CoA production using ATP-citrate lyase. Abbreviations: CoA, coenzyme A; ATP, adenosine triphosphate; OAA, oxaloacetate.

Example 9. Alternative Pathway for Acetyl-CoA Production to Take Advantage of High Flux Through Malate in Seeds A pathway for increasing acetyl-CoA production in the cytosol is shown in FIG. 15. This pathway overexpresses citrate synthase and/or ATP-citrate lyase (FIG. 15) to increase acetyl-CoA production. Increased expression of citrate synthase is expected to increase the concentration of citrate in the mitochondria, which can get transported to the cytosol through the use of the plant's native transport machinery. Increased ATP-citrate lyase activity converts the citrate to acetyl-CoA which can be used to increase polymer synthesis.

Figure 16:
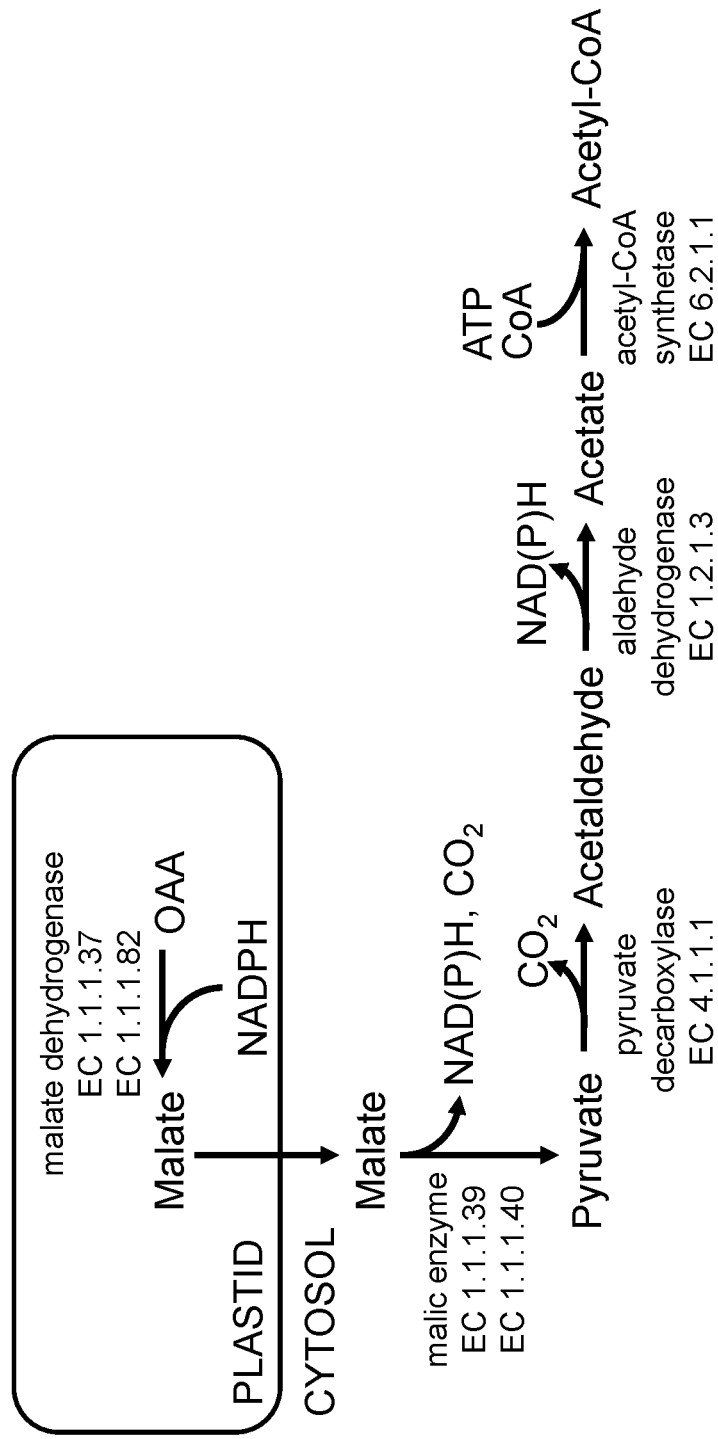
FIG. 16 shows an alternative pathway for acetyl-CoA production using endogenous malic enzyme, pyruvate decarboxylase, aldehyde dehydrogenase, and acetyl-CoA synthetase. Abbreviations: CoA, coenzyme A; ATP, adenosine triphosphate; OAA, oxaloacetate; NAD(P)H, reduced nicotinamide adenine dinucleotide (phosphate).

An alternative pathway for increasing acetyl-CoA is shown in FIG. 16 and can take advantage of what should be high flux through malate in many seeds, especially *Camelina*. This pathway consists of the endogenous cytosolic enzymes malic enzyme, pyruvate decarboxylase, aldehyde dehydrogenase, and acetyl-CoA synthetase to produce acetyl-CoA. This pathway is appealing because *Arabidopsis*, and probably *Camelina*, already contain all the genes in the seed to accomplish this conversion. Because *Camelina* uses an extraordinarily high flux through the oxidative pentose phosphate pathway (Carey et al., *Plant Physiology* 182, 493-506 (2020)), it is likely to already have a high cytosolic flux of malate, which would serve the function of delivering electrons to the mitochondrion for respiration or disposal. Combinations of the endogenous genes encoding cytosolic malic enzyme, pyruvate decarboxylase, acetaldehyde dehydrogenase, and/or acetyl-CoA synthetase can be upregulated in the plant of interest by promoter alteration, addition of regulatory sequences, retransformation, etc. to increase acetyl-CoA available for PHA production.

Unless defined otherwise, all technical and scientific terms used herein have the same meanings as commonly understood by one of skill in the art to which the disclosed invention belongs.

Those skilled in the art will recognize or be able to ascertain using no more than routine experimentation, many equivalents to the specific embodiments of the invention described herein. Such equivalents are intended to be encompassed by the following claims.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-60449US1-Sequence-Listing_ST25.txt", created Nov. 30, 2021, file size of 544,768 bytes, is hereby incorporated by reference.

What is claimed is:

1. A transgenic land plant that expresses a polyhydroxyalkanoate synthase seed specifically, with cytosolic localization, comprising:
   (a) a nucleic acid encoding the polyhydroxyalkanoate synthase; and
   (b) a seed-specific promoter operably linked to the nucleic acid,
   wherein:
   (i) the seed-specific promoter drives expression of the polyhydroxyalkanoate synthase in cytosol of cells of seeds of the transgenic land plant;
   (ii) the polyhydroxyalkanoate synthase comprises a catalytic domain; and
   (iii) the polyhydroxyalkanoate synthase does not comprise any sequence positioned to mediate translocation of the catalytic domain across any membrane of the cells, thereby resulting in the polyhydroxyalkanoate synthase being expressed seed specifically, with cytosolic localization; and
   (iv) the polyhydroxyalkanoate synthase further comprises an endoplasmic reticulum targeting signal, the endoplasmic reticulum targeting signal being positioned to anchor the polyhydroxyalkanoate synthase to a membrane of endoplasmic reticulum of the cells with the catalytic domain remaining in the cytosol, thereby maintaining cytosolic localization of the polyhydroxyalkanoate synthase.

2. The transgenic land plant according to claim 1, wherein the seed-specific promoter comprises one or more of a promoter from soybean oleosin isoform A gene or a promoter from soybean glycinin gene.

3. The transgenic land plant according to claim 1, wherein the seed-specific promoter comprises one or more of a promoter from the soybean oleosin isoform A gene of SEQ ID NO: 5 or a promoter from soybean glycinin gene of SEQ ID NO: 4.

4. The transgenic land plant according to claim 1, wherein the catalytic domain comprises a G/S-X-C-X-G-G (SEQ ID NO: 59) PhaC box consensus sequence at positions 317-322, aspartate at position 480, and histidine at position 508, with numbering of the positions relative to PhaC of *Cupriavidus necator* of SEQ ID NO: 32.

5. The transgenic land plant according to claim 4, wherein:
  (a) the catalytic domain further comprises proline at position 239, aspartate at position 254, serine at position 260, tryptophan at position 425, aspartate at position 428, asparagine at position 448, and glycine at position 507, with numbering of the positions relative to PhaC of *Cupriavidus necator* of SEQ ID NO: 32; and
  (b) the catalytic domain has at least 80% or higher sequence identity to one or more of the following:
    (i) Class I PhaC *Cupriavidus necator* of SEQ ID NO: 32 residues 201-589, Chromobacterium *violaceum* of SEQ ID NO: 33 residues 174-568, *Delftia acidovorans* of SEQ ID NO: 34 residues 204-630, *Aeromonas caviae* of SEQ ID NO: 35 residues 201-594, *Caulobacter vibrioides* of SEQ ID NO: 36 residues 203-587, *Zoogloea ramigera* of SEQ ID NO: 37 residues 190-576, *Azohydromonas latus* of SEQ ID NO: 38 residues 148-536, *Acinetobacter* sp. RA3849 of SEQ ID NO: 39 residues 206-590, *Burkholderia* sp. DSMZ 9242 of SEQ ID NO: 40 residues 236-625, *Nocardia corallina* of SEQ ID NO: 41 residues 178-561, *Rhodococcus ruber* of SEQ ID NO: 42 residues 176-562, or *Rhodospirillum rubrum* of SEQ ID NO: 43 residues 291-673;
    (ii) Class II PhaC of *Pseudomonas oleovorans* of SEQ ID NO: 44 residues 179-559, *Pseudomonas putida* of SEQ ID NO: 45 residues 179-560, or *Pseudomonas* sp. 61-3 of SEQ ID NO: 46 residues 183-567;
    (iii) Class III PhaC of *Allochromatium vinosum* of SEQ ID NO: 47 residues 33-355, *Thiocapsa pfennigii* of SEQ ID NO: 48 residues 35-357, *Arthrospira* sp. PCC 8005 of SEQ ID NO: 49 residues 46-373, *Cyanothece* sp. PCC 7425 of SEQ ID NO: 50 residues 35-366, or *Synechocystis* sp. PCC6803 of SEQ ID NO: 51 residues 48-378; or
    (iv) Class IV PhaC of *Bacillus cereus* of SEQ ID NO: 52 residues 35-361, *Bacillus megaterium* of SEQ ID NO: 53 residues 31-357, or *Bacillus bataviensis* of SEQ ID NO: 54 residues 31-355.

6. The transgenic land plant according to claim 1, wherein the polyhydroxyalkanoate synthase comprises one or more of the following:
  (i) Class I PhaC of *Cupriavidus necator* of SEQ ID NO: 32, Chromobacterium *violaceum* of SEQ ID NO: 33, *Delftia acidovorans* of SEQ ID NO: 34, *Aeromonas caviae* of SEQ ID NO: 35, *Caulobacter vibrioides* of SEQ ID NO: 36, *Zoogloea ramigera* of SEQ ID NO: 37, *Azohydromonas latus* of SEQ ID NO: 38, *Acinetobacter* sp. RA3849 of SEQ ID NO: 39, *Burkholderia* sp. DSMZ 9242 of SEQ ID NO: 40, *Nocardia corallina* of SEQ ID NO: 41, *Rhodococcus ruber* of SEQ ID NO: 42, or *Rhodospirillum rubrum* of SEQ ID NO: 43;
  (ii) Class II PhaC of *Pseudomonas oleovorans* of SEQ ID NO: 44, *Pseudomonas putida* of SEQ ID NO: 45, or *Pseudomonas* sp. 61-3 of SEQ ID NO: 46;
  (iii) Class III PhaC of *Allochromatium vinosum* of SEQ ID NO: 47, *Thiocapsa pfennigii* of SEQ ID NO: 48, *Arthrospira* sp. PCC 8005 of SEQ ID NO: 49, *Cyanothece* sp. PCC 7425 of SEQ ID NO: 50, or *Synechocystis* sp. PCC6803 of SEQ ID NO: 51; or
  (iv) Class IV PhaC of *Bacillus cereus* of SEQ ID NO: 52, *Bacillus megaterium* of SEQ ID NO: 53, or *Bacillus bataviensis* of SEQ ID NO: 54.

7. The transgenic land plant according to claim 1, wherein the polyhydroxyalkanoate synthase comprises a hybrid PhaC of *Pseudomonas oleovarans/Zoogloea ramigera* of SEQ ID NO: 55.

8. The transgenic land plant according to claim 1, wherein the endoplasmic reticulum targeting signal is positioned C-terminally with respect to the catalytic domain.

9. The transgenic land plant according to claim 1, wherein the endoplasmic reticulum targeting signal comprises an endoplasmic reticulum targeting signal of a cytochrome B5 isoform D protein.

10. The transgenic land plant according to claim 1, wherein the endoplasmic reticulum targeting signal comprises amino acids 108-140 of cytochrome B5 isoform D protein of *Arabidopsis thaliana* of SEQ ID NO: 58.

11. The transgenic land plant according to claim 1, wherein the transgenic land plant further comprises one or more of a PhaA beta-ketothiolase or an NphT7 acetoacetyl-CoA synthetase.

12. The transgenic land plant according to claim 1, wherein the transgenic land plant further comprises a PhaB acetoacetyl-CoA reductase.

13. The transgenic land plant according to claim 1, wherein the transgenic land plant is one or more of a *Brassica* species, *Brassica napus*, *Brassica rapa*, *Brassica carinata*, *Brassica juncea*, *Camelina sativa*, a *Crambe* species, a *Jatropha* species, pennycress, *Ricinus communis*, a *Calendula* species, a *Cuphea* species, *Arabidopsis thaliana*, maize, soybean, a *Gossypium* species, sunflower, palm, coconut, safflower, peanut, *Sinapis alba*, sugarcane, flax, or tobacco.

14. The transgenic land plant according to claim 1, wherein the transgenic land plant further comprises seeds, and the seeds comprise the polyhydroxyalkanoate synthase and a polyhydroxyalkanoate polymerized by the polyhydroxyalkanoate synthase.

15. The transgenic land plant according to claim 14, wherein greater than 80% of the polyhydroxyalkanoate synthase expressed in the transgenic land plant is expressed in the seeds of the transgenic land plant.

16. The transgenic land plant according to claim 14, wherein greater than 80% of the polyhydroxyalkanoate synthase expressed in the seeds of the transgenic land plant is localized in the cytosol of the cells of the seeds.

17. The transgenic land plant according to claim 14, wherein greater than 80% of the polyhydroxyalkanoate polymerized by the polyhydroxyalkanoate synthase is localized in the cytosol of the cells of the seeds.

18. The transgenic land plant according to claim 14, wherein the transgenic land plant produces the polyhydroxyalkanoate in the seeds to 2.0 to 20.0% of dry seed weight.

19. The transgenic land plant according to claim 14, wherein the polyhydroxyalkanoate comprises one or more of 3-hydroxybutyrate monomers, 4-hydroxybutyrate monomers, 3-hydroxyvalerate monomers, 3-hydroxyhexanoate monomers, 5-hydroxyvalerate monomers, or saturated 3-hydroxyacid monomers with even-numbered carbon chains ranging from C6-C16.

20. The transgenic land plant according to claim 14, wherein the polyhydroxyalkanoate comprises 3-hydroxybutyrate monomers.

21. The transgenic land plant according to claim 14, wherein the polyhydroxyalkanoate comprises one or more of poly-3-hydroxybutyrate, poly(3-hydroxybutyrate-co-4-hydroxybutyrate), poly(3-hydroxybutyrate-co-3-hydroxyvalerate), poly(3-hydroxybutyrate-co-3-hydroxhexanoate) and poly(3-hydroxybutyrate-co-5-hydroxyvalerate).

22. The transgenic land plant according to claim 14, wherein the polyhydroxyalkanoate comprises poly-3-hydroxybutyrate.

\* \* \* \* \*

UNITED STATES PATENT AND TRADEMARK OFFICE
CERTIFICATE OF CORRECTION

PATENT NO. : 12,305,179 B2
APPLICATION NO. : 17/596110
DATED : May 20, 2025
INVENTOR(S) : Meghna Malik et al.

It is certified that error appears in the above-identified patent and that said Letters Patent is hereby corrected as shown below:

In the Specification

Column 5; Line 28, "of a species, Brassica" should read --of a Brassica species, Brassica--

Column 46; Line 67, "Agrobacterium iumefaciens" should read --Agrobacterium tumefaciens--

Column 51; Line 64, "1 6:560-575. Additionally, a" should read --J. 6:560-575. Additionally, a--

Signed and Sealed this
Ninth Day of September, 2025

Coke Morgan Stewart
*Acting Director of the United States Patent and Trademark Office*